US012479837B2

(12) United States Patent
Plaunt et al.

(10) Patent No.: US 12,479,837 B2
(45) Date of Patent: Nov. 25, 2025

(54) REVERSIBLE DPP1 INHIBITORS AND USES THEREOF

(71) Applicant: Insmed Incorporated, Bridgewater, NJ (US)

(72) Inventors: Adam J. Plaunt, Bridgewater, NJ (US); Adrien Cerdan, Strasbourg (FR); Paola Ciapetti, Strasbourg (FR); Bastien Goegan, Strasbourg (FR)

(73) Assignee: Insmed Incorporated, Bridgewater, NJ (US)

( * ) Notice: Subject to any disclaimer, the term of this patent is extended or adjusted under 35 U.S.C. 154(b) by 0 days.

(21) Appl. No.: 19/088,795

(22) Filed: Mar. 24, 2025

(65) Prior Publication Data

US 2025/0223284 A1 Jul. 10, 2025

Related U.S. Application Data

(63) Continuation of application No. PCT/US2024/010555, filed on Jan. 5, 2024.

(60) Provisional application No. 63/485,243, filed on Feb. 15, 2023, provisional application No. 63/437,557, filed on Jan. 6, 2023.

(51) Int. Cl.

| | |
|---|---|
| ***C07D 413/12*** | (2006.01) |
| ***C07D 267/22*** | (2006.01) |
| ***C07D 413/14*** | (2006.01) |
| ***C07D 417/14*** | (2006.01) |
| ***C07D 491/107*** | (2006.01) |
| ***C07D 498/10*** | (2006.01) |

(52) U.S. Cl.

CPC ......... *C07D 413/12* (2013.01); *C07D 267/22* (2013.01); *C07D 413/14* (2013.01); *C07D 417/14* (2013.01); *C07D 491/107* (2013.01); *C07D 498/10* (2013.01)

(58) Field of Classification Search

CPC .. C07D 413/12; C07D 413/14; C07D 417/14; C07D 491/07; C07D 498/10; C07D 267/22

USPC .......................................................... 540/468

See application file for complete search history.

(56) References Cited

U.S. PATENT DOCUMENTS

| | | | |
|---|---|---|---|
| 8,552,034 | B2 | 10/2013 | Verwijs et al. |
| 8,871,783 | B2 | 10/2014 | Anderskewitz et al. |
| 8,877,775 | B2 | 11/2014 | Anderskewitz et al. |
| 8,889,708 | B2 | 11/2014 | Grauert et al. |
| 8,987,249 | B2 | 3/2015 | Anderskewitz et al. |
| 8,999,975 | B2 | 4/2015 | Grundl et al. |
| 9,073,869 | B2 | 7/2015 | Anderskewitz et al. |
| 9,440,960 | B2 | 9/2016 | Grauert et al. |
| 9,522,894 | B2 | 12/2016 | Lonn et al. |
| 9,540,373 | B2 | 1/2017 | Vintonyak et al. |
| 9,713,606 | B2 | 7/2017 | Anderskewitz et al. |
| 9,815,805 | B2 | 11/2017 | Lonn et al. |
| 9,856,228 | B2 | 1/2018 | Lauritzen et al. |
| 9,879,026 | B2 | 1/2018 | Vintonyak et al. |
| 10,238,633 | B2 | 3/2019 | Anderskewitz et al. |
| 10,287,258 | B2 | 5/2019 | Lonn et al. |
| RE47,636 | E | 10/2019 | Vintonyak et al. |
| 10,479,781 | B2 | 11/2019 | Lauritzen et al. |
| 10,669,245 | B2 | 6/2020 | Lonn et al. |
| 11,117,874 | B2 | 9/2021 | Lonn et al. |
| 11,655,221 | B2 | 5/2023 | Lönn et al. |
| 11,655,222 | B2 | 5/2023 | Lönn et al. |
| 11,655,223 | B2 | 5/2023 | Lönn et al. |
| 11,655,224 | B2 | 5/2023 | Lönn et al. |
| 11,667,615 | B2 | 6/2023 | Lonn et al. |
| 11,673,871 | B2 | 6/2023 | Lönn et al. |
| 11,673,872 | B2 | 6/2023 | Lönn et al. |
| 11,680,049 | B2 | 6/2023 | Lönn et al. |
| 11,773,069 | B2 | 10/2023 | Lönn et al. |
| 11,807,635 | B2 | 11/2023 | Li et al. |
| 11,814,359 | B2 | 11/2023 | Lönn et al. |

(Continued)

FOREIGN PATENT DOCUMENTS

| | | | |
|---|---|---|---|
| CN | 101945851 | A | 1/2011 |
| CN | 102574830 | A | 7/2012 |

(Continued)

OTHER PUBLICATIONS

Adkison, A. M. et al. (2002), "Dipeptidyl peptidase I activates neutrophil-derived serine proteases and regulates the development of acute experimental arthritis," J. Clin. Invest. 109(3):363-371.

(Continued)

*Primary Examiner* — Kahsay Habte

(74) *Attorney, Agent, or Firm* — Cooley LLP

(57) ABSTRACT

Provided herein are compounds of Formula (I), or pharmaceutically acceptable salts or deuterated forms thereof, wherein $R^0$, L and $R^1$ are defined herein. Also provided herein are pharmaceutical compositions comprising a compound of Formula (I) or pharmaceutically acceptable salt or deuterated form thereof, and methods of using a compound of Formula (I) or pharmaceutically acceptable salt or deuterated form thereof, e.g., in the treatment of a disease that is treatable by administration of a DPP1 inhibitor.

(I)

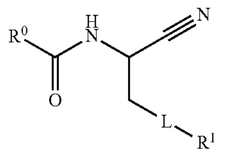

41 Claims, No Drawings

(56) References Cited

U.S. PATENT DOCUMENTS

| | | | |
|---|---|---|---|
| 11,998,553 | B2 | 6/2024 | Zhang |
| 12,054,465 | B2 | 8/2024 | Lönn |
| 12,059,424 | B2 | 8/2024 | Wikström et al. |
| 12,201,638 | B2 | 1/2025 | Wikström et al. |
| 2004/0063935 | A1 | 4/2004 | Yasuda et al. |
| 2008/0221093 | A1 | 9/2008 | Gege et al. |
| 2011/0201581 | A1 | 8/2011 | Furber et al. |
| 2011/0236367 | A1 | 9/2011 | Olsen et al. |
| 2012/0315271 | A1 | 12/2012 | Shelton et al. |
| 2012/0329775 | A1 | 12/2012 | Ford et al. |
| 2014/0275159 | A1 | 9/2014 | Anderskewitz et al. |
| 2015/0025058 | A1 | 1/2015 | Deutsch et al. |
| 2015/0105375 | A1 | 4/2015 | Anderskewitz et al. |
| 2015/0210655 | A1 | 7/2015 | Lonn et al. |
| 2015/0224199 | A1 | 8/2015 | De Weer et al. |
| 2015/0346203 | A1 | 12/2015 | Xu et al. |
| 2016/0061824 | A1 | 3/2016 | Hahn et al. |
| 2016/0324854 | A1 | 11/2016 | Finnie et al. |
| 2017/0027907 | A1 | 2/2017 | Legangneux et al. |
| 2017/0057938 | A1 | 3/2017 | Lonn et al. |
| 2018/0028541 | A1 | 2/2018 | Lonn et al. |
| 2018/0044328 | A1 | 2/2018 | Lauritzen et al. |
| 2018/0169017 | A1 | 6/2018 | Desai et al. |
| 2018/0251436 | A1 | 9/2018 | Lonn et al. |
| 2019/0091236 | A1 | 3/2019 | Lonn et al. |
| 2019/0167636 | A1 | 6/2019 | Anderskewitz et al. |
| 2019/0247400 | A1 | 8/2019 | Dipetrillo et al. |
| 2020/0017455 | A1 | 1/2020 | Lonn et al. |
| 2020/0138780 | A1 | 5/2020 | Anderskewitz et al. |
| 2020/0179398 | A1 | 6/2020 | Lonn et al. |
| 2020/0247765 | A1 | 8/2020 | Lonn et al. |
| 2020/0256866 | A1 | 8/2020 | Tirouvanziam |
| 2020/0390781 | A1 | 12/2020 | Dipetrillo et al. |
| 2021/0186931 | A1 | 6/2021 | Davidson et al. |
| 2021/0186984 | A1 | 6/2021 | Dipetrillo et al. |
| 2021/0238152 | A1 | 8/2021 | Lönn et al. |
| 2021/0252015 | A1 | 8/2021 | Zhang |
| 2021/0322438 | A1 | 10/2021 | Zhang |
| 2021/0369732 | A1 | 12/2021 | Wikström et al. |
| 2022/0133737 | A1 | 5/2022 | Lonn et al. |
| 2023/0025351 | A1 | 1/2023 | Lönn et al. |
| 2023/0028726 | A1 | 1/2023 | Lönn et al. |
| 2023/0033573 | A1 | 2/2023 | Lönn et al. |
| 2023/0062646 | A1 | 3/2023 | Lönn et al. |
| 2023/0069044 | A1 | 3/2023 | Lönn et al. |
| 2023/0085620 | A1 | 3/2023 | Lönn et al. |
| 2023/0115170 | A1 | 4/2023 | Lönn et al. |
| 2023/0116721 | A1 | 4/2023 | Lönn et al. |
| 2023/0250071 | A1 | 8/2023 | Lönn et al. |
| 2023/0278969 | A1 | 9/2023 | Lönn et al. |
| 2024/0041896 | A1 | 2/2024 | Lonn et al. |
| 2024/0059681 | A1 | 2/2024 | Li et al. |
| 2024/0083888 | A1 | 3/2024 | Hao et al. |
| 2024/0132455 | A1 | 4/2024 | Lönn et al. |
| 2024/0150335 | A1 | 5/2024 | Wu et al. |
| 2024/0226112 | A1 | 7/2024 | Usansky et al. |
| 2024/0252512 | A1 | 8/2024 | Wikström et al. |
| 2024/0336582 | A1 | 10/2024 | Lönn et al. |
| 2025/0101011 | A1 | 3/2025 | Ye et al. |

FOREIGN PATENT DOCUMENTS

| | | | |
|---|---|---|---|
| CN | 105026395 | A | 11/2015 |
| CN | 105612149 | A | 5/2016 |
| CN | 112920124 | A | 6/2021 |
| CN | 114106005 | A | 3/2022 |
| CN | 114591315 | A | 6/2022 |
| CN | 115925696 | A | 4/2023 |
| CN | 116332937 | A | 6/2023 |
| EP | 1317555 | B1 | 11/2007 |
| EP | 2840083 | A1 | 2/2015 |
| EP | 2970283 | B1 | 11/2020 |
| JP | 2006527704 | A | 12/2006 |
| JP | 2008501692 | A | 1/2008 |
| JP | 2008504307 | A | 2/2008 |
| JP | 2010540526 | A | 12/2010 |
| JP | 2011506421 | A | 3/2011 |
| JP | 2011522011 | A | 7/2011 |
| JP | 2012522764 | A | 9/2012 |
| JP | 2012526093 | A | 10/2012 |
| JP | 2016515576 | A | 5/2016 |
| JP | 2017503832 | A | 2/2017 |
| JP | 2019070029 | A | 5/2019 |
| JP | 2021046423 | A | 3/2021 |
| JP | 2022096662 | A | 6/2022 |
| TW | 201041889 | A | 12/2010 |
| WO | WO-9917777 | A1 | 4/1999 |
| WO | WO-0116108 | A2 | 3/2001 |
| WO | WO-0196285 | A1 | 12/2001 |
| WO | WO-02051831 | A1 | 7/2002 |
| WO | WO-03048123 | A1 | 6/2003 |
| WO | WO-2004076434 | A1 | 9/2004 |
| WO | WO-2004087153 | A2 | 10/2004 |
| WO | WO-2004106289 | A1 | 12/2004 |
| WO | WO-2004110988 | A1 | 12/2004 |
| WO | WO-2005106012 | A2 | 11/2005 |
| WO | WO-2005107762 | A2 | 11/2005 |
| WO | WO-2005120465 | A2 | 12/2005 |
| WO | WO-2006000228 | A2 | 1/2006 |
| WO | WO-2006020145 | A2 | 2/2006 |
| WO | WO-2007005668 | A2 | 1/2007 |
| WO | WO-2008109180 | A2 | 9/2008 |
| WO | WO-2008109181 | A2 | 9/2008 |
| WO | WO-2009026701 | A1 | 3/2009 |
| WO | WO-2009042187 | A1 | 4/2009 |
| WO | WO-2009074829 | A1 | 6/2009 |
| WO | WO-2009147238 | A1 | 12/2009 |
| WO | WO-2010077680 | A2 | 7/2010 |
| WO | WO-2010114405 | A2 | 10/2010 |
| WO | WO-2010128324 | A1 | 11/2010 |
| WO | WO-2010142985 | A1 | 12/2010 |
| WO | WO-2011154677 | A1 | 12/2011 |
| WO | WO-2012064715 | A1 | 5/2012 |
| WO | WO-2012119941 | A1 | 9/2012 |
| WO | WO-2013041497 | A1 | 3/2013 |
| WO | WO-2014091443 | A1 | 6/2014 |
| WO | WO-2014140075 | A1 | 9/2014 |
| WO | WO-2014140081 | A1 | 9/2014 |
| WO | WO-2014140091 | A1 | 9/2014 |
| WO | WO-2014151784 | A1 | 9/2014 |
| WO | WO-2014165303 | A1 | 10/2014 |
| WO | WO-2015032942 | A1 | 3/2015 |
| WO | WO-2015032943 | A1 | 3/2015 |
| WO | WO-2015032945 | A1 | 3/2015 |
| WO | WO-2015110826 | A1 | 7/2015 |
| WO | WO-2015175939 | A1 | 11/2015 |
| WO | WO-2016016242 | A1 | 2/2016 |
| WO | WO-2016038007 | A1 | 3/2016 |
| WO | WO-2016075240 | A1 | 5/2016 |
| WO | WO-2016139351 | A1 | 9/2016 |
| WO | WO-2018022978 | A1 | 2/2018 |
| WO | WO-2019157050 | A1 | 8/2019 |
| WO | WO-2019166626 | A1 | 9/2019 |
| WO | WO-2020018547 | A1 | 1/2020 |
| WO | WO-2020018551 | A1 | 1/2020 |
| WO | WO-2020247665 | A1 | 12/2020 |
| WO | WO-2022042591 | A1 | 3/2022 |
| WO | WO-2022117059 | A1 | 6/2022 |
| WO | WO-2022140516 | A1 | 6/2022 |
| WO | WO-2022166721 | A1 | 8/2022 |
| WO | WO-2022232420 | A1 | 11/2022 |
| WO | WO-2022232573 | A1 | 11/2022 |
| WO | WO-2023076615 | A1 | 5/2023 |
| WO | WO-2023134656 | A1 | 7/2023 |
| WO | WO-2023160541 | A1 | 8/2023 |
| WO | WO-2023160542 | A1 | 8/2023 |
| WO | WO-2023160579 | A1 | 8/2023 |
| WO | WO-2023236877 | A1 | 12/2023 |
| WO | WO-2023236879 | A1 | 12/2023 |
| WO | WO-2023243601 | A1 | 12/2023 |
| WO | WO-2024008680 | A1 | 1/2024 |
| WO | WO-2024026433 | A2 | 2/2024 |
| WO | WO-2024088307 | A1 | 5/2024 |
| WO | WO-2024094208 | A1 | 5/2024 |

(56) References Cited

FOREIGN PATENT DOCUMENTS

| | | | |
|---|---|---|---|
| WO | WO-2024148308 | A1 | 7/2024 |
| WO | WO-2024173556 | A2 | 8/2024 |
| WO | WO-2024192416 | A1 | 9/2024 |
| WO | WO-2025056038 | A1 | 3/2025 |
| WO | WO-2025059526 | A1 | 3/2025 |

OTHER PUBLICATIONS

Alpsoy, E. (Apr. 2005), "Behcet's Disease: Treatment of Mucocutaneous Lesions," Clinical and Experimental Rheumatology, vol. 23, No. 4, pp. 532-539.
Avci, D. (Feb. 2019), "Dipeptidyl Peptidase-4 Inhibitors and Inflammation: Dpp-4 Inhibitors Improve Mean Pleatelet vol. and Gamma Glutamyl Transferase Level," Journal of Biosciences and Medicines, vol. 7, No. 2, pp. 42-53.
Bae, S. et al. (Jul. 2012), "Elevated interleukin-32 expression in granulomatosis with polyangiitis," Rheumatology 2012;51:1979-1988.
Birmingham Vasculitis Activity Score (version 3), 1 page [No Date].
Birring, S. S. et al. (2003), "Development of a symptom specific health status measure for patients with chronic cough: Leicester Cough Questionnaire (LCQ)," Thorax; 58:339-343.
Bondebjerg, J et al. (2005), "Novel semicarbazide-derived inhibitors of human dipeptidyl peptidase I (hDPPI)," Bioorg Med Chem; 13:4408-4424.
Bondejberg, J. et al. (2006), "Dipeptidyl Nitriles as Human Dipeptidyl Peptidase 1 Inhibitors," Bioorg Med Chem Lett; 16:3614-3617.
Bragg, R. A. et al. (Sep. 2015), "Aortic Binding of AZD5248: Mechanistic Insight and Reactivity Assays to Support Lead Optimization," Chem Res Toxicol. Oct. 19, 2015;28(10):1991-1999.
Canonica, G. W. et al. (May 2020), "Chronic rhinosinusitis with nasal polyps impact in severe asthma patients: Evidences from the Severe Asthma Network Italy (SANI) registry," Respiratory Medicine, vol. 166, 105947, pp. 1-5.
Cartin-Ceba, R. et al. (Nov. 2012), "Rituximab for Remission Induction and Maintenance in Refractory Granulomatosis With Polyangiitis (Wegener's)," Arthritis & Rheumatism, vol. 64, No. 11, pp. 3770-3778.
Chalmers, J. D. et al. (2017), "Neutrophil Elastase Activity Is Associated with Exacerbations and Lung Function Decline in Bronchiectasis," Am J Respir Crit Care Med, 195(10):1384-1393.
Chalmers, J. D. et al. (Mar. 2014), "The Bronchiectasis Severity Index. An International Derivation and Validation Study," Am. J. Respir. Crit. Care Med., 189(5):576-585.
Chalmers, J. D. et al. (Nov. 2020), "Phase 2 Trial of the DPP-1 Inhibitor Brensocatib in Bronchiectasis," N Engl J Med ;383(22):2127-2137.
Clinical Trials Identifier: NCT03218917, ClinicalTrials.gov submitted on Aug. 15, 2017, 5 pages.
Clinical Trials Identifier: NCT03218917, ClinicalTrials.gov submitted on Aug. 20, 2018, 17 pages.
Clinical Trials Identifier: NCT03218917, ClinicalTrials.gov submitted on Dec. 11, 2020, 10 pages.
Clinical Trials Identifier: NCT03218917, ClinicalTrials.gov submitted on Dec. 17, 2018, 17 pages.
Clinical Trials Identifier: NCT03218917, ClinicalTrials.gov submitted on Dec. 17, 2019, 10 pages.
Clinical Trials Identifier: NCT03218917, ClinicalTrials.gov submitted on Dec. 4, 2019, 10 pages.
Clinical Trials Identifier: NCT03218917, ClinicalTrials.gov submitted on Dec. 8, 2018, 17 pages.
Clinical Trials Identifier: NCT03218917, ClinicalTrials.gov submitted on Feb. 11, 2019, 17 pages.
Clinical Trials Identifier: NCT03218917, ClinicalTrials.gov submitted on Feb. 12, 2019, 17 pages.
Clinical Trials Identifier: NCT03218917, ClinicalTrials.gov submitted on Feb. 5, 2018, 5 pages.
Clinical Trials Identifier: NCT03218917, ClinicalTrials.gov submitted on Jan. 14, 2019, 17 pages.
Clinical Trials Identifier: NCT03218917, ClinicalTrials.gov submitted on Jan. 28, 2019, 17 pages.
Clinical Trials Identifier: NCT03218917, ClinicalTrials.gov submitted on Jan. 3, 2019, 17 pages.
Clinical Trials Identifier: NCT03218917, ClinicalTrials.gov submitted on Jan. 31, 2019, 17 pages.
Clinical Trials Identifier: NCT03218917, ClinicalTrials.gov submitted on Jul. 12, 2017, 7 pages.
Clinical Trials Identifier: NCT03218917, ClinicalTrials.gov submitted on Jul. 30, 2018, 5 pages.
Clinical Trials Identifier: NCT03218917, ClinicalTrials.gov submitted on Mar. 28, 2019, 16 pages.
Clinical Trials Identifier: NCT03218917, ClinicalTrials.gov submitted on May 28, 2019, 10 pages.
Clinical Trials Identifier: NCT03218917, ClinicalTrials.gov submitted on Nov. 13, 2018, 17 pages.
Clinical Trials Identifier: NCT03218917, ClinicalTrials.gov submitted on Nov. 28, 2018, 17 pages.
Clinical Trials Identifier: NCT03218917, ClinicalTrials.gov submitted on Nov. 6, 2018, 17 pages.
Clinical Trials Identifier: NCT03218917, ClinicalTrials.gov submitted on Oct. 16, 2018, 17 pages.
Clinical Trials Identifier: NCT03218917, ClinicalTrials.gov submitted on Sep. 12, 2018, 17 pages.
Clinical Trials Identifier: NCT03218917, ClinicalTrials.gov submitted on Sep. 24, 2018, 17 pages.
Clinical Trials Identifier: NCT04594369. ClinicalTrials.gov submitted on Apr. 12, 2022, 33 pages.
Clinical Trials Identifier: NCT04594369. ClinicalTrials.gov submitted on Apr. 22, 2021, 14 pages.
Clinical Trials Identifier: NCT04594369. ClinicalTrials.gov submitted on Apr. 22, 2022, 32 pages.
Clinical Trials Identifier: NCT04594369. ClinicalTrials.gov submitted on Apr. 5, 2022, 32 pages.
Clinical Trials Identifier: NCT04594369. ClinicalTrials.gov submitted on Apr. 9, 2021, 13 pages.
Clinical Trials Identifier: NCT04594369. ClinicalTrials.gov submitted on Aug. 1, 2022, 32 pages.
Clinical Trials Identifier: NCT04594369. ClinicalTrials.gov submitted on Aug. 18, 2022, 32 pages.
Clinical Trials Identifier: NCT04594369. ClinicalTrials.gov submitted on Aug. 23, 2021, 24 pages.
Clinical Trials Identifier: NCT04594369. ClinicalTrials.gov submitted on Aug. 30, 2022, 32 pages.
Clinical Trials Identifier: NCT04594369. ClinicalTrials.gov submitted on Aug. 9, 2021, 23 pages.
Clinical Trials Identifier: NCT04594369. ClinicalTrials.gov submitted on Dec. 1, 2020, 6 pages.
Clinical Trials Identifier: NCT04594369. ClinicalTrials.gov submitted on Dec. 10, 2020, 6 pages.
Clinical Trials Identifier: NCT04594369. ClinicalTrials.gov submitted on Dec. 3, 2021, 28 pages.
Clinical Trials Identifier: NCT04594369. ClinicalTrials.gov submitted on Jul. 11, 2022, 32 pages.
Clinical Trials Identifier: NCT04594369. ClinicalTrials.gov submitted on Jul. 23, 2021, 21 pages.
Clinical Trials Identifier: NCT04594369. ClinicalTrials.gov submitted on Jul. 27, 2022, 32 pages.
Clinical Trials Identifier: NCT04594369. ClinicalTrials.gov submitted on Jul. 9, 2021, 21 pages.
Clinical Trials Identifier: NCT04594369. ClinicalTrials.gov submitted on Jun. 20, 2022, 32 pages.
Clinical Trials Identifier: NCT04594369. ClinicalTrials.gov submitted on Jun. 21, 2021, 19 pages.
Clinical Trials Identifier: NCT04594369. ClinicalTrials.gov submitted on Jun. 24, 2021, 19 pages.
Clinical Trials Identifier: NCT04594369. ClinicalTrials.gov submitted on Jun. 30, 2021, 20 pages.
Clinical Trials Identifier: NCT04594369. ClinicalTrials.gov submitted on Jun. 7, 2021, 19 pages.

(56) References Cited

OTHER PUBLICATIONS

Clinical Trials Identifier: NCT04594369. ClinicalTrials.gov submitted on Jun. 7, 2022, 32 pages.
Clinical Trials Identifier: NCT04594369. ClinicalTrials.gov submitted on Mar. 11, 2021, 9 pages.
Clinical Trials Identifier: NCT04594369. ClinicalTrials.gov submitted on Mar. 25, 2021, 11 pages.
Clinical Trials Identifier: NCT04594369. ClinicalTrials.gov submitted on Mar. 25, 2022, 34 pages.
Clinical Trials Identifier: NCT04594369. ClinicalTrials.gov submitted on Mar. 4, 2022, 32 pages.
Clinical Trials Identifier: NCT04594369. ClinicalTrials.gov submitted on May 13, 2022, 33 pages.
Clinical Trials Identifier: NCT04594369. ClinicalTrials.gov submitted on May 25, 2022, 31 pages.
Clinical Trials Identifier: NCT04594369. ClinicalTrials.gov submitted on Nov. 10, 2021, 29 pages.
Clinical Trials Identifier: NCT04594369. ClinicalTrials.gov submitted on Nov. 15, 2022, 30 pages.
Clinical Trials Identifier: NCT04594369. ClinicalTrials.gov submitted on Nov. 19, 2020, 6 pages.
Clinical Trials Identifier: NCT04594369. ClinicalTrials.gov submitted on Nov. 23, 2022, 30 pages.
Clinical Trials Identifier: NCT04594369. ClinicalTrials.gov submitted on Oct. 10, 2022, 31 pages.
Clinical Trials Identifier: NCT04594369. ClinicalTrials.gov submitted on Oct. 14, 2020, 6 pages.
Clinical Trials Identifier: NCT04594369. ClinicalTrials.gov submitted on Oct. 27, 2022, 31 pages.
Clinical Trials Identifier: NCT04594369. ClinicalTrials.gov submitted on Oct. 28, 2021, 29 pages.
Clinical Trials Identifier: NCT04594369. ClinicalTrials.gov submitted on Oct. 29, 2021, 29 pages.
Clinical Trials Identifier: NCT04594369. ClinicalTrials.gov submitted on Oct. 8, 2021, 28 pages.
Clinical Trials Identifier: NCT04594369. ClinicalTrials.gov submitted on Sep. 12, 2022, 31 pages.
Clinical Trials Identifier: NCT04594369. ClinicalTrials.gov submitted on Sep. 27, 2022, 31 pages.
Clinical Trials Identifier: NCT04594369. ClinicalTrials.gov submitted on Sep. 7, 2021, 25 pages.
Clinical Trials Identifier: NCT04817332. ClinicalTrials.gov submitted on Aug. 12, 2021, 8 pages.
Clinical Trials Identifier: NCT04817332. ClinicalTrials.gov submitted on Mar. 25, 2021, 8 pages.
Clinical Trials Identifier: NCT05090904. ClinicalTrials.gov submitted on Apr. 14, 2022, 6 pages.
Clinical Trials Identifier: NCT05090904. ClinicalTrials.gov submitted on Apr. 5, 2022, 6 pages.
Clinical Trials Identifier: NCT05090904. ClinicalTrials.gov submitted on Aug. 23, 2022, 7 pages.
Clinical Trials Identifier: NCT05090904. ClinicalTrials.gov submitted on Dec. 3, 2021, 6 pages.
Clinical Trials Identifier: NCT05090904. ClinicalTrials.gov submitted on Jul. 27, 2022, 7 pages.
Clinical Trials Identifier: NCT05090904. ClinicalTrials.gov submitted on Jul. 29, 2022, 7 pages.
Clinical Trials Identifier: NCT05090904. ClinicalTrials.gov submitted on Jul. 4, 2022, 7 pages.
Clinical Trials Identifier: NCT05090904. ClinicalTrials.gov submitted on Jun. 22, 2022, 7 pages.
Clinical Trials Identifier: NCT05090904. ClinicalTrials.gov submitted on Jun. 7, 2022, 7 pages.
Clinical Trials Identifier: NCT05090904. ClinicalTrials.gov submitted on Mar. 8, 2022, 6 pages.
Clinical Trials Identifier: NCT05090904. ClinicalTrials.gov submitted on May 13, 2022, 7 pages.
Clinical Trials Identifier: NCT05090904. ClinicalTrials.gov submitted on May 25, 2022, 7 pages.
Clinical Trials Identifier: NCT05090904. ClinicalTrials.gov submitted on Nov. 10, 2022, 7 pages.
Clinical Trials Identifier: NCT05090904. ClinicalTrials.gov submitted on Oct. 12, 2022, 7 pages.
Clinical Trials Identifier: NCT05090904. ClinicalTrials.gov submitted on Oct. 14, 2021, 5 pages.
Clinical Trials Identifier: NCT05090904. ClinicalTrials.gov submitted on Oct. 29, 2021, 5 pages.
Clinical Trials Identifier: NCT05090904. ClinicalTrials.gov submitted on Sep. 9, 2022, 7 pages.
Clinical Trials Identifier: NCT05344508. ClinicalTrials.gov submitted on Apr. 18, 2022, 3 pages.
Clinical Trials Identifier: NCT05344508. ClinicalTrials.gov submitted on Aug. 3, 2022, 3 pages.
Clinical Trials Identifier: NCT05344508. ClinicalTrials.gov submitted on Oct. 6, 2022, 3 pages.
Clinical Trials Identifier: NCT05355935. ClinicalTrials.gov submitted on Apr. 26, 2022, 6 pages.
Clinical Trials Identifier: NCT05355935. ClinicalTrials.gov submitted on Aug. 16, 2022, 6 pages.
Clinical Trials Identifier: NCT05355935. ClinicalTrials.gov submitted on Jul. 27, 2022, 6 pages.
Clinical Trials Identifier: NCT05355935. ClinicalTrials.gov submitted on Jul. 5, 2022, 6 pages.
Clinical Trials Identifier: NCT05355935. ClinicalTrials.gov submitted on Jun. 7, 2022, 6 pages.
Clinical Trials Identifier: NCT05355935. ClinicalTrials.gov submitted on May 16, 2022, 6 pages.
Clinical Trials Identifier: NCT05355935. ClinicalTrials.gov submitted on Oct. 19, 2022, 5 pages.
Clinical Trials Identifier: NCT05355935. ClinicalTrials.gov submitted on Sep. 9, 2022, 6 pages.
Clinical Trials Identifier: NCT05517525. ClinicalTrials.gov submitted on Aug. 24, 2022, 5 pages.
Clinical Trials Identifier: NCT05517525. ClinicalTrials.gov submitted on Nov. 7, 2022, 4 pages.
Clinical Trials Identifier: NCT05517525. ClinicalTrials.gov submitted on Oct. 17, 2022, 4 pages.
Clinical Trials Identifier: NCT05517525. ClinicalTrials.gov submitted on Sep. 21, 2022, 5 pages.
Dadoniene, J. et al. (2017), "Clinical characteristics and long-term survival differences of the ANCA-associated vasculitis group: a cross-sectional study of 27 patients," ACTA Medica Lituanica, vol. 24, No. 2, pp. 107-112.
Doyle, K. et al. (Oct. 2016), "Discovery of second generation reversible covalent DPP1 inhibitors leading to an Oxazepane Amidoacetonitrile based clinical candidate (AZD7986)," Journal of Medicinal Chemistry, 59(20):9457-9472.
Everts-Graber, J. et al. (2019), "Proteomic analysis of neutrophils in ANCA—associated vasculitis reveals a dysregulation in proteinase 3-associated proteins such as annexin-A1 involved in apoptotic cell clearance," Kidney International 96, 397-408; https://doi.org/10.1016/j.kint.2019.02.017.
Extended European Search Report for European Application No. 17195612.1, mailed Mar. 21, 2018, 5 pages.
Extended European Search Report for European Application No. 17835331.4, mailed Feb. 11, 2020, 8 pages.
Extended European Search Report for European Application No. 19751012.6, mailed Oct. 4, 2021, 7 pages.
Extended European Search Report for European Application No. 19837016.5, mailed Mar. 18, 2022, 10 pages.
Extended European Search Report for European Application No. 19838400.0, mailed Mar. 24, 2022, 9 pages.
Extended European Search Report for European Application No. 20173862.2, mailed Sep. 11, 2020, 7 pages.
Extended European Search Report for European Application No. 22796849.2 mailed Feb. 7, 2025, 10 pages.
Falk, R. J. et al. (Jun. 1990) "Anti-neutrophil cytoplasmic autoantibodies induce neutrophils to degranulate and produce oxygen radicals in vitro," Proc. Natl. Acad. Sci. USA, vol. 87, pp. 4115-4119.
Floris, A. et al. (Apr. 2016), "Using the Birmingham vasculitis activity score as a screening tool in patients with suspected vasculitis," i174, Poster Viewing III, Retrieved from the Internet: URL: https://

(56) References Cited

OTHER PUBLICATIONS academic.oup.com/rheumatology/article-abstract/55/suppl_1/1174/1795586, Retrieved from the Internet on Apr. 23, 2018, 1 page.
Furber, M. et al. (2014), "Cathepsin C Inhibitors: Property Optimization and Identification of a Clinical Candidate," Journal of Medicinal Chemistry, vol. 57, pp. 2357-2367.
Gardiner, P. et al. (2016), "Neutrophil maturation rate determines the effects of dipeptidyl peptidase 1 inhibition on neutrophil serine protease activity," Br J Pharmacol; 173:2390-401.
Geetha, D. et al. (2015), "Current therapy of granulomatosis with polyangiitis and microscopic polyangiitis: the role of rituximab," J Nephrol 28:17-27.
Gerald, L. B. et al. (Apr. 2009), "Changes in environmental tobacco smoke exposure and asthma morbidity among urban school children," Chest, vol. 135, No. 4, pp. 911-916.
Goeminne, P. C. et al. (Feb. 2014), "Mortality in non-cystic fibrosis bronchiectasis: A prospective cohort analysis," Respir. Med., 108(2):287-296.
Golchert, D. et al. (Sep. 2013), "Evaluation of some compression aids in tableting of roller compacted swellable core drug layer," Int J Pharm., 453(2):322-328.
Guarino, C. et al. (2017), "Prolonged pharmacological inhibition of cathepsin C results in elimination of neutrophil serine proteases," Biochem Pharmacol; 131:52-67.
Guay, D. et al. (2009), "Design and synthesis of dipeptidyl nitriles as potent, selective, and reversible inhibitors of cathepsin C," Bioorg Med Chem Lett; 19:5392-5396.
Guay, D. et al. (2010), "Therapeutic Utility and Medicinal chemistry of Cathepsin C Inhibitors," Curr Top Med Chem; 10:708-716.
Guillevin, L. et al. (Mar. 1999), "Microscopic Polyangiitis," Arthritis & Rheumatism, vol. 42, No. 3, pp. 421-430.
Insmed, (Feb. 2020), "Insmed Announces Positive Top-Line Results from Phase 2 WILLOW Study ofINS1007 in Patients with Non-Cystic Fibrosis Bronchiectasis," 5 pages.
Insmed, "Insmed Announces Worldwide License Agreement with AstraZeneca for Oral DPP1 Inhibitor," Oct. 2016, 3 pages.
Insmed, "Insmed Reports Third Quarter 2016 Financial Results and Provides Business Update," Nov. 2016, 11 pages.
International Preliminary Report on Patentability for International Application No. PCT/EP2019/055138 dated Sep. 10, 2020, 8 pages.
International Preliminary Report on Patentability for International Application No. PCT/US2021/064810, dated Jul. 6, 2023, 6 pages.
International Preliminary Report on Patentability for International Application No. PCT/US2022/027026, dated Nov. 9, 2023, 8 pages.
International Preliminary Report on Patentability for International Application No. PCT/US2023/062731 mailed Aug. 29, 2024, 6 pages.
International Search Report and Written Opinion for International Application No. PCT/CN2024/118880 mailed Nov. 21, 2024, 14 pages.
International Search Report and Written Opinion for International Application No. PCT/EP2019/055138, mailed Jul. 19, 2019, 11 pages.
International Search Report and Written Opinion for International Application No. PCT/GB2015/050155, mailed Mar. 6, 2015, 7 pages.
International Search Report and Written Opinion for International Application No. PCT/US2017/044343, mailed Oct. 12, 2017, 7 pages.
International Search Report and Written Opinion for International Application No. PCT/US2019/016844, mailed May 31, 2019, 10 pages.
International Search Report and Written Opinion for International Application No. PCT/US2019/042021, mailed Sep. 4, 2019, 7 pages.
International Search Report and Written Opinion for International Application No. PCT/US2019/042026, mailed Sep. 4, 2019, 7 pages.
International Search Report and Written Opinion for International Application No. PCT/US2021/064810, mailed Mar. 16, 2022, 8 pages.
International Search Report and Written Opinion for International Application No. PCT/US2022/026769, mailed Sep. 9, 2022, 15 pages.
International Search Report and Written Opinion for International Application No. PCT/US2022/027026, mailed Sep. 14, 2022, 11 pages.
International Search Report and Written Opinion for International Application No. PCT/US2022/048249, mailed Feb. 1, 2023, 8 pages.
International Search Report and Written Opinion for International Application No. PCT/US2023/062731, dated May 30, 2023, 32 pages.
International Search Report and Written Opinion for PCT Application No. PCT/US2023/071162 dated Feb. 21, 2024, 12 pages.
International Search Report and Written Opinion for PCT Application No. PCT/US2024/010555 dated Apr. 29, 2024, 13 pages.
International Search Report and Written Opinion for PCT Application No. PCT/US2024/020305 mailed Jul. 1, 2024, 12 pages.
International Search Report and Written Opinion for PCT Application No. PCT/US2024/046701 mailed Dec. 23, 2024, 11 pages.
Invitation to Pay Additional Fees for International Application No. PCT/US2022/026769, mailed Jun. 27, 2022, 3 pages.
Invitation to Pay Additional Fees for International Application No. PCT/US2022/027026, mailed Jul. 8, 2022, 2 pages.
Invitation to pay additional fees for International Application No. PCT/US2023/071162, dated Nov. 14, 2023, 2 pages.
Invitation to pay additional fees for International Application No. PCT/US2024/010555 dated Mar. 12, 2024, 2 pages.
Invitation to pay additional fees for International Application No. PCT/US2024/020305, dated May 15, 2024, 2 pages.
Invitation to pay additional fees for International Application No. PCT/US2024/046701, mailed Oct. 31, 2024, 2 pages.
Invitation to Pay Additional fees for International Application No. PCT/US2025/013490, mailed Mar. 25, 2025, 2 pages.
Jarrot, P-A et al. (Jul. 2016), "Review Pathogenesis of ANCA-associated vasculitis: An update," Autoimmunity Reviews, vol. 15, Issue 7, pp. 704-713.
Jenne, D. E. (Aug. 1990), "Wegener's autoantigen decoded," Nature, vol. 346, p. 520, 1 page.
Jennette, J. C. (2011), "Nomenclature and classification of vasculitis: lessons learned from granulomatosis with polyangiitis (Wegener's granulomatosis)," Clinical and Experimental Immunology, 164 (Suppl. 1), pp. 7-10.
Jones, B. E. et al. ( 2017), "Gene-Specific DNA Methylation Changes Predict Remission in Patients with ANCA-Associated Vasculitis," J Am Soc Nephrol 28: 1175-1187. doi: 10.1681/ASN.2016050548.
Kallenberg, C. G. M. et al. (Dec. 2006), "Mechanisms of Disease: pathogenesis and treatment of ANCA-associated vasculitides," Nature Clinical Practice Rheumatology, vol. 2, No. 12, pp. 661-670.
Karthik, V. V. (Jun. 2016), "Excipients Used in the Formulation of Tablets," Research and Reviews: Journal of chemistry, 5(2):143-154.
Kelly, M. G. et al. (Sep. 2003), "Bronchiectasis in secondary care: A comprehensive profile of a neglected disease," Eur. J. Intern. Med., 14(8):488-492.
Keogh, K. A. et al. (2006), "Rituximab for Refractory Wegener's Granulomatosis. Report of a Prospective, Open-Label Pilot Trial," Am J Respir Crit Care Med vol. 173. pp 180-187.
Kettritz, R. ( Jun. 2008), "Autoimmunity in kidney diseases," The Scandinavian Journal of Clinical & Laboratory Investigation, vol. 68, No. S241, 99-103.
Knopf, A. et al. (2015), "Clinical aspects of granulomatosis with polyangiitis affecting the head and neck," Eur Arch Otorhinolaryngol 272:185-193.
Kono, H., et al. (Oct. 2012), "The IL-1-dependent sterile inflammatory response has a substantial caspase-1-independent component that requires cathepsin C," The Journal of Immunology, vol. 189, No. 7, pp. 3734-3740.

(56) References Cited

OTHER PUBLICATIONS

Korkmaz, B. et al. (2013), "Neutrophil proteinase 3 and dipeptidyl peptidase I (cathepsin C)as pharmacological targets in granulomatosis with polyangiitis (Wegener granulomatosis)," Semin Immunopathol, 35:411-421.
Korkmaz, B. et al. (2018) "Therapeutic targeting of cathepsin C: from pathophysiology to treatment," Pharmacol Ther; 190:202-236.
Korkmaz, B. et al. (2019), "Structure-based design and in vivo anti-arthritic activity evaluation of a potent dipeptidyl cyclopropyl nitrile inhibitor of cathepsin C," Biochem Pharmacol ;164:349-367.
Korkmaz, B. et al. (2020), "Lung Protection by Cathepsin C Inhibition: A New Hope for COVID-19 and ARDS?" J Med Chem ;63:13258-13265. doi:10.1021/acs.jmedchem.0c00776.
Korkmaz, B. et al. (Dec. 2021), "Cathepsin C inhibition as a potential treatment strategy in cancer," Biochemical Pharmacology, 194:114803, 15 pages.
Korkmaz, B. et al. (Nov. 2010), "Neutrophil Elastase, Proteinase 3, and Cathepsin G as Therapeutic Targets in Human Diseases," Pharmacological Reviews, vol. 62, No. 4, pp. 726-759.
Laine, D. I. et al. (2010), "Discovery of novel cyanamide-based inhibitors of cathepsin C," ACS Med Chem Lett.;2(2):142-147.
Laine, D. I. et al. (2010), "Inhibitors of Cathepsin C (DPPI)," Expert Rev. Ther Pat; 20:497-506.
Li, J. et al. (2014), "Lubricants in Pharmaceutical Solid Dosage Forms", Lubricants, 2(1):21-43.
Lins, L. et al. (2016), "SF-36 total score as a single measure of health-related quality of life: Scoping review," SAGE Open Medicine, vol. 4:1-12.
Ludvigsson, J. W. et al. (2018), "Degradation caused by incompatibility between sodium stearyl fumarate (PRUV) and AZD7986 in the drug product," Journal of Pharmaceutical and Biomedical Analysis, 158:82-87.
Luqmani, R. A. et al. (1994), "Birmingham Vasculitis Activity Score (BVAS) in Systemic Necrotizing Vasculitis," Q. J. Med; 87:671-678.
Mayo Clinic, "Periodontitis," Oct. 19, 2021, 4 pages.
Mcshane, P. J. et al. (2013), "Non-cystic fibrosis bronchiectasis," Am J Respir Crit Care Med; 188(6):647-656. doi: 10.1164/rccm.201303-0411CI.
Methot, N. et al. (2008), "In Vivo Inhibition of Serine Protease Processing Requires a High Fractional Inhibition of Cathepsin C," Mol. Pharm; 73(6):1857-1865.
Methot, N. et al. (Jul. 2007), "Inhibition of the activation of multiple serine proteases with a cathepsin C inhibitor requires sustained exposure to prevent proenzyme processing," J. Biol. Chem., 282(29):20836-20846.
Miller, B. E. et al. (2017), "Epithelial desquamation observed in a Phase I study of an oral cathepsin C inhibitor (GSK2793660)," Br J Clin Pharmacol;83(12):2813-2820. doi:10.1111/bcp.13398.
Miller, M. R. et al. (2005), "Standardisation of spirometry," Eur. Respir. J; 26:319-338.
Mukhtyar, C. et al. (2009), "Modification and validation of the Birmingham Vasculitis Activity Score (version 3)," Ann Rheum Dis;68:1827-1832.
Murray, M. P. et al. (2009), "Sputum colour: a useful clinical tool in non-cystic fibrosis bronchiectasis," Eur Respir J; 34: 361-364.
Murray, M. P. et al. (2009), "Validation of the Leicester Cough Questionnaire in non-cystic fibrosis bronchiectasis," Eur Respir J; 34: 125-131.
National Center for Biotechnology Information (2025). PubChem Substance Record for SID 103924055, BDBM50011502, Source: BindingDB. Retrieved Apr. 7, 2025 from https://pubchem.ncbi.nlm.nih.gov/substance/103924055, 6 pages.
National Center for Biotechnology Information (2025). PubChem Substance Record for SID 311692964, SCHEMBL16932317, Source: SureChEMBL. Retrieved May 21, 2024 from https://pubchem.ncbi.nlm.nih.gov/substance/311692964, 7 pages.
National Center for Biotechnology Information (2025). PubChem Substance Record for SID 461766587, SID 461766587, Source: Patentscope (WIPO). Retrieved May 8, 2024 from https://pubchem.ncbi.nlm.nih.gov/substance/461766587, 6 pages.
Ochsenkuhn, T. et al. (Jan. 2018), "Ustekinumab as rescue treatment in therapy-refractory or -intolerant ulcerative colitis," Abstract P759, Abstracts of the 13th Congress of ECCO, Journal of Crohn's and Colitis, vol. 12, Supplement 1, p. S495, 1 page.
Pagnoux, C. et al. (2015), "Treatment of granulomatosis with polyangiitis (Wegener's)," Expert Review of Clinical Immunology, 11:3, 339-348.
Pagnoux, C. et al. (2016), "Optimal therapy and prospects for new medicines in eosinophilic granulomatosis with polyangiitis (Churg-Strauss syndrome)," Expert Review of Clinical Immunology, vol. 12, No. 10, pp. 1059-1067.
Palmer, R. et al. (2018), "Dipeptidyl Peptidase 1 Inhibitor AZD7986 Induces a Sustained, Exposure-Dependent Reduction in Neutrophil Elastase Activity in Healthy Subjects," Clin Pharmacol Ther; 104(6):1155-1164. doi:10.1002/cpt.1053.
Pham, C. T. (Jul. 2006), "Neutrophil serine proteases: specific regulators of inflammation," Nat. Rev. Immunol;6:541-550.
Popa, E. R. et al. (1999), "Differential B- and T-cell activation in Wegener's granulomatosis," J Allergy Clin Immunol ;103:885-894.
Pubchem, CID 134527801, "(2S)-2-[[Hydroxy-[(2S)-1,4-oxazepan-2-yl]methyl]amino]-3-[4-(3-methyl-2-oxo-1,3-benzoxazol-5-yl)phenyl]propanenitrile," Jun. 23, 2018, Retrieved from the Internet: URL: https://pubchem.ncbi.nlm.nih.gov/compound/134527801, 6 pages.
Rawn, S. et al. (2014), "Purpura, petechiae, and bullae as first signs of juvenile granulomatosis with polyangiitis," Eur J Pediatr 173:1685-1689.
Rehm, S. R. T. et al. (2019), "Premedication with a cathepsin C inhibitor alleviates early primary graft dysfunction in mouse recipients after lung transplantation," Sci Rep;9(1):9925-9933.
Rosati, M. G. et al. (Jan.-Feb. 2016), "Relationships among allergic rhinitis, asthma, and chronic rhinosinusitis," American Journal of Rhinology and Allergy, vol. 30, No. 1, pp. 44-47.
Schirmer, J. H. et al. (2016), "Clinical presentation and long-term outcome of 144 patients with microscopic polyangiitis in a monocentric German cohort," Rheumatology ;55:71-79.
Schreiber, A. et al. (Mar. 2012), "Neutrophil serine proteases promote IL-1B generation and injury in necrotizing crescentic glomerulonephritis," Journal of the American Society of Nephrology, vol. 23, No. 3, pp. 470-482.
Selga, D. et al. (2006), "Polyarteritis nodosa when applying the Chapel Hill nomenclature—a descriptive study on ten patients," Rheumatology; 45:1276-1281.
Shapiro, S. C. et al. (2016), "Inflammatory bowel disease mimicking granulomatosis with polyangiitis: a case report," Journal of Medical Case Reports 10:214, 5 pages.
Stenton (May 2008), "The MRC breathlessness scale" Occupational Med., 58:226-227.
Stockley, R. et al., (Feb. 2013), "Phase II study of a neutrophil elastase inhibitor (AZD9668) in patients with bronchiectasis," Respiratory Medicine, vol. 107, No. 4, pp. 524-533.
Stone, J. H. et al., (Apr. 2001), "A Disease-Specific Activity Index for Wegener's Granulomatosis," Arthritis & Rheumatism, vol. 44, No. 4, pp. 912-920.
Suka, M. et al. (2012), "Improvement in health-related quality of life in MPO-ANCA—associated vasculitis patients treated with cyclophosphamide plus prednisolone: an analysis of 18 months of follow-up data from the JMAAV study," Mod Rheumatol 22:877-884.
Suppiah, R. et al., (2011), "A cross-sectional study of the Birmingham Vasculitis Activity Score version 3 in systemic vasculitis," Rheumatology;50:899-905.
Trouvin, A.-P. et al. (2014), "Usefulness of monitoring of B cell depletion in rituximab-treated rheumatoid arthritis patients in order to predict clinical relapse: a prospective observational study," Clinical and Experimental Immunology, vol. 180, pp. 11-18.
U.S. National Library of Medicine, "History of Changes for Study: NCT02653872," Jul. 14, 2017, [Online], Retrieved from the Internet: URL:https://classic.clinicaltrials.gov/ct2/history/NCT02653872?V_6=View#StudyPageTop; 17 pages.

(56) References Cited

OTHER PUBLICATIONS

U.S. National Library of Medicine, "Randomized, Double-Blind, Placebo-Controlled, Parallel-Group, Multi-Center Study of Efficacy, Safety & Tolerability, and Pharmacokinetics of INS1007 Administered Daily for 24 Weeks in Non-Cystic Fibrosis Bronchiectasis—The Willow Study," Study NCT03218917 [online], Retrieved from the Internet: https://clinicaltrials.gov/ct2/history/NCT03218917?V_1=View#StudyPageTop , Jul. 2017, 8 pages.
Von Vietinghoff, S. et al., (2005), "Membrane proteinase 3 and Wegener's granulomatosis," Clinical Nephrology, vol. 64, No. 4, pp. 453-459.
Wang, J. et al. (2010), "Lubrication in tablet formulations," European Journal of Pharmaceutics and Biopharmaceutics, 75:1-15.
Wickremasinghe, M. et al. (2005), "Non-tuberculous mycobacteria in patients with bronchiectasis," Thorax, 60(12):1045-1051.
Yates, M. et al. (2016), "EULAR/ERA-EDTA recommendations for the management of ANCA-associated vasculitis," Ann Rheum Dis 75:1583-1594.
Zhang, J. et al. (2019), "INS1007, a Reversible Dipeptidyl Peptidase 1 Inhibitor, Ameliorates Interferon-alpha-Accelerated Lupus Nephritis in Mice," Abstract Review, 17th International Congress of Immunology. Abstract: A-1059-0027-00953, 1 page.
Zhang, J. et al. (2019), "The Reversible Dipeptidyl Peptidase 1 Inhibitor, INS1007, Decreases Surface Proteinase 3 Expression and Neutrophil Serine Protease Activities in Human Neutrophils," Rheumatology. 58(Supplement 2), p. ii24.
Banerjee, A. et al., "Development of potent and selective Cathepsin C inhibitors free of aortic binding liability by application of a conformational restriction strategy," Bioorg. Med. Chem. Lett., vol. 47, 128202, Jun. 2021, 7 pages.
Extended European Search Report for European Application No. 25150988.1 mailed May 27, 2025, 7 pages.
Huang, L-L et al., "3D-QSAR, molecular docking and molecular dynamics simulations of oxazepane amidoacetonitrile derivatives as novel DPPI inhibitors," Journal of Molecular Structure, vol. 1168, May 2018, pp. 223-233.
International Search Report and Written Opinion for International Application No. PCT/CN2025/082555 mailed May 30, 2025, 16 pages.
International search report and Written Opinion for International Application No. PCT/US2024/015802 mailed Jul. 9, 2024, 12 pages.
International Search Report and Written Opinion for PCT Application No. PCT/CN2025/075611 mailed May 8, 2025, 17 pages.
International Search Report and Written Opinion for PCT Application No. PCT/CN2025/075960 mailed Apr. 23, 2025, 13 pages.
International Search Report and Written Opinion for PCT Application No. PCT/US2025/013490 mailed Jun. 4, 2025, 12 pages.
Invitation to Pay Additional Fees for International Application No. PCT/US2024/015802 dated Apr. 15, 2024, 2 pages.
Invitation to Pay Additional Fees for International Application No. PCT/US2025/024417 mailed Jun. 16, 2025, 2 pages.
PubChem CID 169550959, Jan. 2024, 9 pages.
PubChem CID 61118902, Oct. 2012, 7 pages.
PubChem CID 63873324, Oct. 2012, 8 pages.
Registry RN 2781135-46-2, Jun. 2022, 8 pages.
International Preliminary Report on Patentability for International Application No. PCT/US2024/010555 mailed Jul. 17, 2025, 10 pages.
International Search Report and Written Opinion for PCT Application No. PCT/CN2025/088450 mailed Jul. 2, 2025, 13 pages.

REVERSIBLE DPP1 INHIBITORS AND USES THEREOF

CROSS-REFERENCE TO RELATED APPLICATIONS

This application is a continuation of International Application No. PCT/US2024/010555, filed Jan. 5, 2024, which claims priority to U.S. Provisional Application No. 63/437,557, filed Jan. 6, 2023, and U.S. Provisional Application No. 63/485,243, filed Feb. 15, 2023, the contents of which are hereby incorporated by reference in their entireties for all purposes.

BACKGROUND

Dipeptidyl peptidase 1 (DPP1; EC 3.4.14.1), also known as cathepsin C, is a lysosomal cysteine protease belonging to the papain family having a molecular weight of 200 kDa. DPP1 was first discovered by Gutman and Fruton in 1948 (J Biol Chem, 174, 851-858); however, the cDNA of the human enzyme was first described in 1995 (Paris et al. 1995, FEBS Lett, 369, 326-330). DPP1 is the only member of the papain family that is functional as a tetramer, consisting of four identical subunits. Each subunit is composed of an N-terminal fragment, a heavy chain and a light chain (Dolenc et al. 1995, *J Biol Chem,* 270, 21626-21631).

DPP1 is constitutively expressed in many tissues with highest levels in lung, kidney, liver and spleen. DPP1 catalyzes the removal of dipeptides from the N-terminal end of polypeptide substrates with broad specificity. Recent data suggest that besides being an important enzyme in lysosomal protein degradation, DPP1 also functions as a key enzyme in the activation of granule serine proteases in cytotoxic T-lymphocytes and natural killer cells (granzymes A and B), mast cells (chymase and tryptase) and neutrophils (cathepsin G, neutrophil elastase and proteinase-3).

Mast cells are found in many tissues but are present in greater numbers along the epithelial linings of the body, such as the skin, respiratory tract and gastrointestinal tract. In humans, two types of mast cells have been identified. The T-type, which expresses only tryptase, and the MC-type, which expresses both tryptase and chymase. In humans, the T-type mast cells are located primarily in alveolar tissue and intestinal mucosa while the TC-type cells predominate in skin and conjunctiva. Tryptase and chymase appear to be important mediators of allergic diseases, being involved in processes of inflammation, bronchoconstriction and mucus secretion.

Neutrophils play a critical role in host defense against invading pathogens. Neutrophils are produced in the bone marrow and are fully mature when released into the circulation to take up their role as the first line of cellular defense. Pro-inflammatory mediators and chemotactic attractants activate neutrophils and draw them to the site of infection, where they act to engulf bacteria by phagocytosis, assaulting them with an arsenal of anti-bacterial compounds that use both oxidative and non-oxidative methods of attack. The powerful serine protease, neutrophil elastase, is one of those anti-bacterial compounds that are clearly involved in destroying bacteria. Neutrophil elastase is released into the phagolysome surrounding the microorganism, which it proceeds to destroy. Neutrophil elastase is able to attack the outer membrane protein, OmpA, in gram-negative bacteria, helping to directly kill the pathogen by degrading its membrane, as well as enabling other anti-bacterial compounds to gain access to the pathogen. In addition, neutrophil elastase may help process other antibacterial compounds, converting them from inactive pro-peptides into their active states, such as for cathelicidin.

Yet neutrophil elastase can also cause problems for its host. It is one of the most destructive enzymes in the body, with the capability of degrading extracellular matrix proteins (including collagens, proteoglycan, fibronectin, platelet receptors, complement receptor, thrombomodulin, lung surfactant and cadherins) and key plasma proteins (including coagulation and complement factors, immunoglobulin, several proteases and protease inhibitors). Under physiological conditions, endogenous protease inhibitors, such as α1-antitrypsin, tightly regulate the activity of neutrophil elastase. However, at inflammatory sites, neutrophil elastase is able to evade regulation, and once unregulated it can induce the release of pro-inflammatory cytokines, such as interleukin-6 and interleukin-8, leading to acute lung injury. It can even impair host defense against infection by degrading phagocyte surface receptors and opsonins. Its negative role is illustrated by its involvement in the tissue destruction and inflammation that characterize numerous diseases, including hereditary emphysema, chronic obstructive pulmonary disease, cystic fibrosis, adult respiratory distress syndrome, ischemic-reperfusion injury and rheumatoid arthritis.

As such, there is a need in the art to provide novel DPP1 inhibitors in order to treat the aforementioned diseases, and others associated with DPP1 and neutrophil elastase.

SUMMARY

In embodiments, provided herein is a compound of formula (I)

(I)

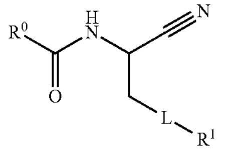

or a pharmaceutically acceptable salt or deuterated form thereof, wherein $R^0$ is

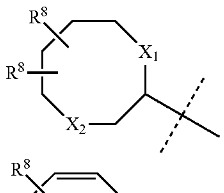,
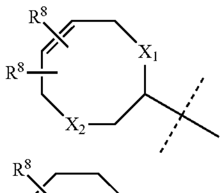,
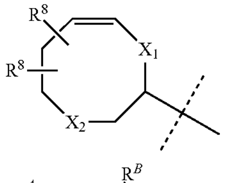,
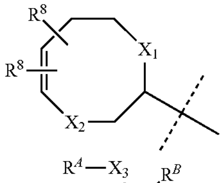, or
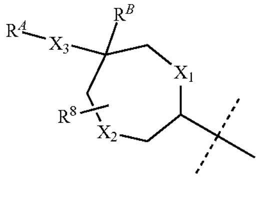,
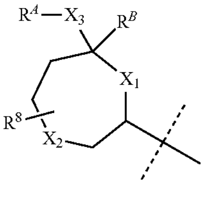;

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$, $X_3$ is O, S, NH, N($C_{1-6}$ alkyl), $CH_2O$;

$R^A$ is H, $C_{1-6}$ alkyl, $C_{1-6}$alkylene-carbocyclyl, $C_{1-6}$alkylene-heteroaryl, heteroaryl or carbocyclyl; and $R^B$ is $C_{1-6}$ alkyl, $C_{1-6}$haloalkyl, $C_{1-6}$ alkyl-OH, $C_{2-6}$alkenyl, cycloalkyl, $C_{1-6}$alkylene-carbocyclyl, $C_{1-6}$alkylene-aryl, $C_{1-6}$alkylene-heteroaryl, heteroaryl or carbocyclyl; or $R^A$ and $R^B$ are taken together to form a heterocyclyl;

L is aryl, heterocyclyl, heteroaryl, or

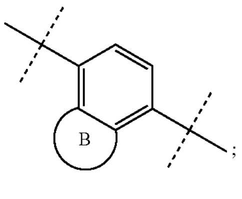

wherein L is independently substituted by 0-4 $R^{10}$ and wherein ring B is a carbocycle, or a heterocycle;

$R^1$ is

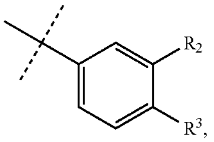
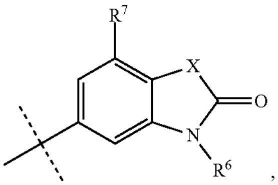
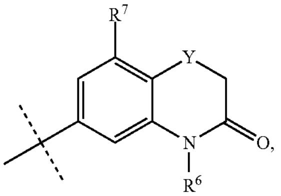
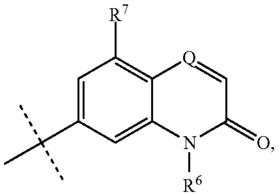
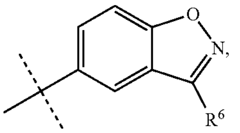
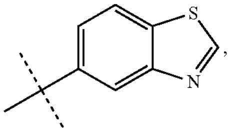
or
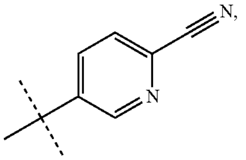
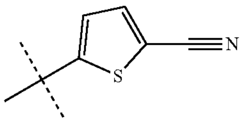
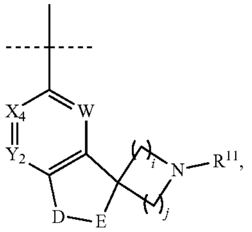
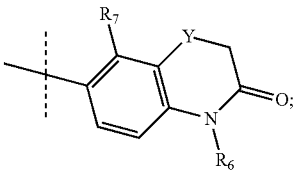

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O, S, or $CH_2$;

Q is CH or N;

$R^6$ is $C_{1-6}$ alkyl optionally substituted by 1, 2 or 3 F, or optionally substituted by OH, O $C_{1-6}$ alkyl, N($C_{1-6}$ alkyl)$_2$, N($C_{1-6}$ alkyl) ($C_{1-6}$alkylene-O—$C_{1-6}$ alkyl), cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, or $C_{1-6}$ alkylene-heteroaryl, halogenated $C_{1-6}$alkoxy, heteroaryl or carbocyclyl;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, N($C_{1-6}$ alkyl)$_2$, COOH, $COC_{1-6}$ alkyl, $COOC_{1-6}$ alkyl, $CON_{1-6}$ alkyl, CON($C_{1-6}$ alkyl)$_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$—O;

$R^{11}$ is H, $C_{1-6}$ alkyl, alkylene-O-alkyl, or heterocyclyl; and i and j are each independently 1, 2 or 3; provided that the sum of i+j is 2, 3 or 4.

In an aspect, the present disclosure provides a compound of formula (I):

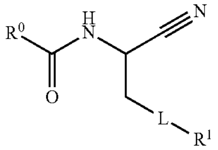
(I)

or a pharmaceutically acceptable salt or deuterated form thereof, wherein $R^0$ is

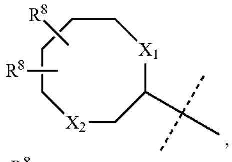
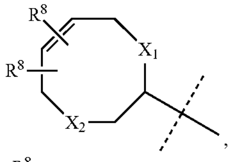
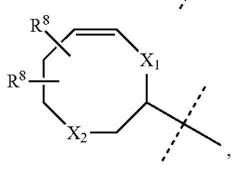
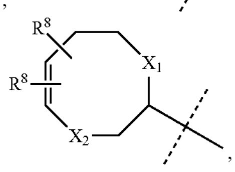
or

-continued

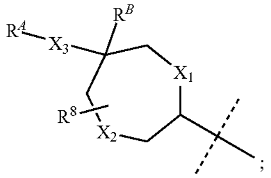

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, N($C_{1-6}$ alkyl), $OCH_2$, or $SCH_2$;

$R^A$ is H, $C_{1-6}$ alkyl, $C_{1-6}$alkylene-carbocyclyl, $C_{1-6}$alkylene-heteroaryl, heteroaryl or carbocyclyl; and $R^B$ is $C_{1-6}$ alkyl, $C_{1-6}$haloalkyl, $C_{1-6}$ alkyl-OH, $C_{2-6}$alkenyl, cycloalkyl, $C_{1-6}$alkylene-carbocyclyl, $C_{1-6}$alkylene-aryl, $C_{1-6}$alkylene-heteroaryl, heteroaryl or carbocyclyl; or $R^A$ and $R^B$ are taken together to form a heterocyclyl;

L is aryl, heterocyclyl, heteroaryl, or

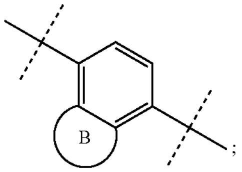

wherein L is independently substituted by 0-4 $R^{10}$ and wherein ring B is a carbocycle, or a heterocycle;

$R^1$ is

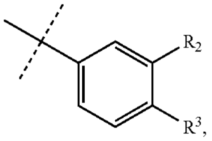

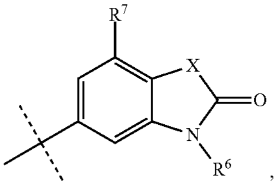

,

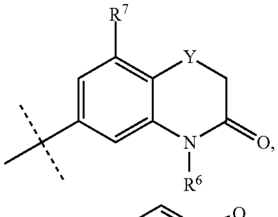

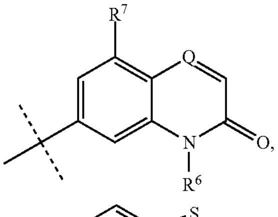

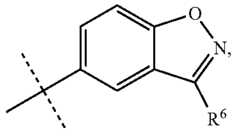

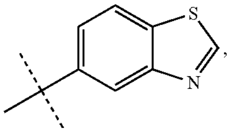

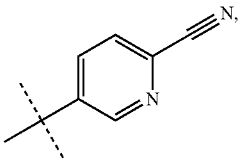

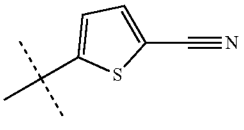

-continued

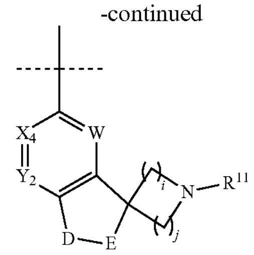

or

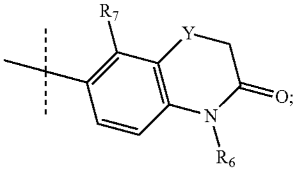

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O, S, or $CH_2$;

Q is CH or N;

$R^6$ is $C_{1-6}$ alkyl optionally substituted by 1, 2 or 3 F, or optionally substituted by OH, O $C_{1-6}$ alkyl, N($C_{1-6}$ alkyl)$_2$, N($C_{1-6}$ alkyl) ($C_{1-6}$alkylene-O—$C_{1-6}$ alkyl), cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, or $C_{1-6}$ alkylene-heteroaryl, halogenated $C_{1-6}$alkoxy, heteroaryl or carbocyclyl;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, N($C_{1-6}$ alkyl)$_2$, COOH, $COC_{1-6}$ alkyl, $COOC_{1-6}$ alkyl, $CON_{1-6}$ alkyl, CON($C_{1-6}$ alkyl)$_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$-0;

$R^{11}$ is H, $C_{1-6}$ alkyl, alkylene-O-alkyl, or heterocyclyl; and i and j are each independently 1, 2 or 3; provided that the sum of i+j is 2, 3 or 4.

In embodiments, the present disclosure provides a compound of Formula (I):

(I)

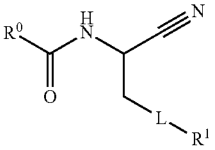

or a pharmaceutically acceptable salt or deuterated form thereof, wherein $R^0$ is

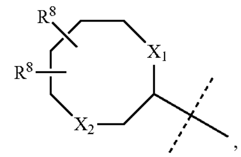,

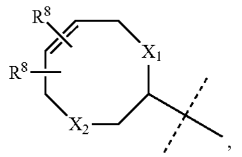,

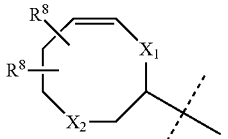,

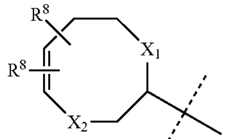, or

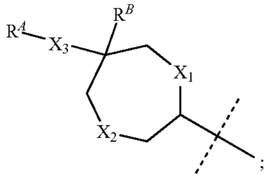;

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, or N($C_{1-6}$ alkyl);

$R^A$ is H, $C_{1-6}$ alkyl, $C_{1-6}$alkylene-carbocyclyl, $C_{1-6}$alkylene-heteroaryl, heteroaryl or carbocyclyl; and $R^B$ is $C_{1-6}$ alkyl, $C_{2-6}$alkenyl, cycloalkyl, $C_{1-6}$alkylene-carbocyclyl, $C_{1-6}$alkylene-aryl, $C_{1-6}$ alkylene-heteroaryl, heteroaryl or carbocyclyl; or $R^A$ and $R^B$ are taken together to form a heterocyclyl;

L is aryl, heterocyclyl, heteroaryl, or

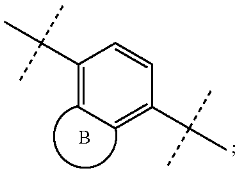;

wherein L is independently substituted by 0-4 $R^{10}$ and wherein ring B is a carbocycle, or a heterocycle;

$R^1$ is

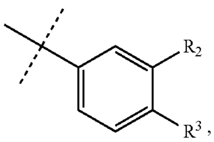,

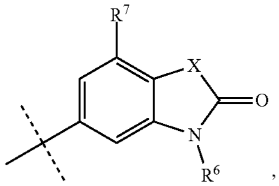,

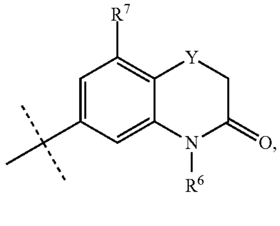,

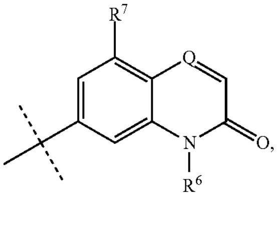,

-continued

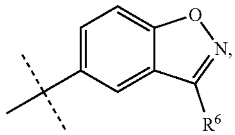,

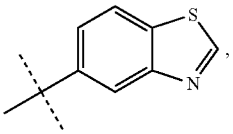,

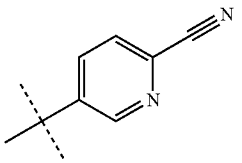,

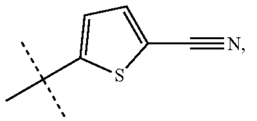, or

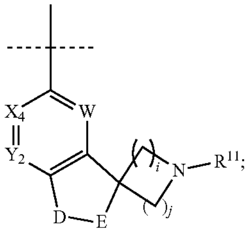;

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O or S;

Q is CH or N;

$R^6$ is $C_{1-6}$ alkyl optionally substituted by 1, 2 or 3 F, or optionally substituted by OH, O $C_{1-6}$ alkyl, N($C_{1-6}$ alkyl)$_2$, cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, or $C_{1-6}$ alkylene-heteroaryl, halogenated $C_{1-6}$alkoxy, heteroaryl or carbocyclyl;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, N($C_{1-6}$ alkyl)$_2$, COOH, $COC_{1-6}$ alkyl, $COOC_{1-6}$ alkyl, $CON_{1-6}$ alkyl, CON($C_{1-6}$ alkyl)$_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$—O;

$R^{11}$ is H, $C_{1-6}$ alkyl, alkylene-O-alkyl, or heterocyclyl; and i and j are each independently 1, 2 or 3; provided that the sum of i+j is 2, 3 or 4.

In one aspect, the present disclosure provides a compound of Formula (I):

(I)

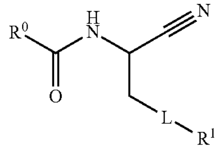

or a pharmaceutically acceptable salt or deuterated form thereof, wherein

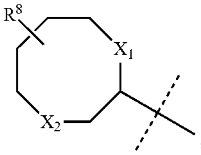
,
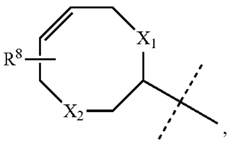
,

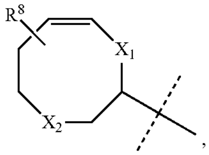
,
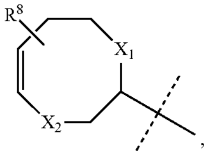
, or

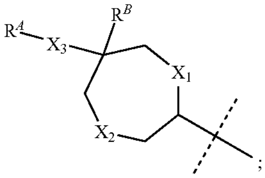
;

$R^0$ is $X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, or N($C_{1-6}$ alkyl);

$R^A$ is H, $C_{1-6}$ alkyl, $C_{1-6}$alkylene-carbocyclyl, or $C_{1-6}$alkylene-heteroaryl;

$R^B$ is $C_{1-6}$ alkyl, $C_{2-6}$alkenyl, $C_{1-6}$alkylene-carbocyclyl, or $C_{1-6}$alkylene-heteroaryl; or $R^A$ and $R^B$ are taken together to form a heterocyclyl;

L is aryl, heterocycle, heteroaryl, or

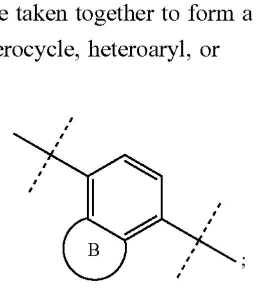
;

wherein L is independently substituted by 0-4 $R^{10}$, and wherein ring B is a carbocycle, a heterocycle or a heteroaryl;

$R^1$ is

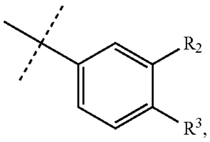
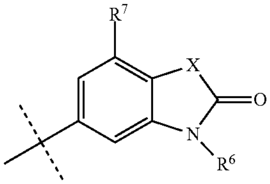
,

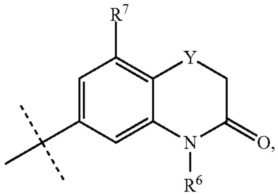
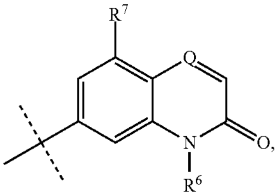

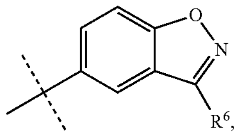
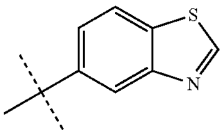
, or

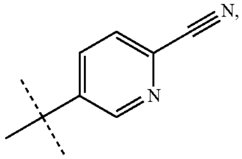
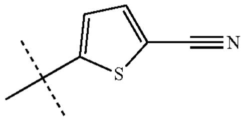

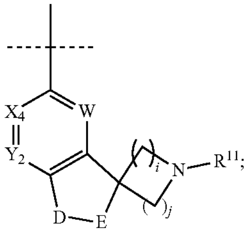

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl X is O, S, CHF, or $CF_2$;

Y is O or S;

Q is CH or N;

$R^6$ is $C_{1-6}$ alkyl, substituted by 1, 2 or 3 F, OH, $OC_{1-6}$ alkyl, N($C_{1-6}$ alkyl$)_2$, cycloalkyl, or heterocyclyl;

R is H, F, Cl, Br or $C_{1-6}$ alkyl;

$R^8$ and $R^{12}$ are independently H, OH, halogen, $NH_2$, COOH, unsubstituted $C_{1-6}$ alkyl, halogen, hydroxyl substituted $C_{1-6}$ alkyl, unsubstituted $C_{1-6}$alkoxy or halogenated $C_{1-6}$alkoxy;

each $R^{13}$ is independently H, F, Cl, Br, I or $C_{1-6}$ alkyl;

each $R^{10}$ is independently oxo, halogen, $C_{1-6}$ alkyl, $C_{1-6}$alkoxy, —S—$C_{1-6}$ alkyl, $C_{2-6}$ alkenyl, $C_{2-6}$ alkynyl, $C_{3-6}$ cycloalkyl, cyano, hydroxy, $NH_2$, —NH—$C_{1-6}$ alkyl, —N($C_{1-6}$ alkyl$)_2$, —COOH, —$COC_{1-6}$ alkyl, —$COOC_{1-6}$ alkyl, —$CON_{1-6}$ alkyl, —CON($C_{1-6}$ alkyl$)_2$, —$NHCOC_{1-6}$ alkyl, or heterocyclyl; wherein each alkyl, alkoxy, alkenyl, alkynyl, cycloalkyl, and heterocyclyl are independently optionally substituted with 1-3 substituents selected from halogen, cyano, hydroxyl, $NH_2$ and —COOH;

W, $X_4$ and $Y_2$ are each independently CH or N, with provided that a maximum of one of W, $X_4$ and $Y_2$ can be N;

D-E is N(H)—C(O), N($C_{1-6}$ alkyl)-C(O), $CH_2CH_2$, C(O)—O or $CH_2$—O;

$R^{11}$ is H, $C_{1-6}$ alkyl, -alkylene-O-alkyl, heterocyclyl; and i and j are each independently 1, 2 or 3; provided that the sum of i+j is 2, 3 or 4.

In embodiments, the present disclosure provides a compound of Formula (II):

(II)

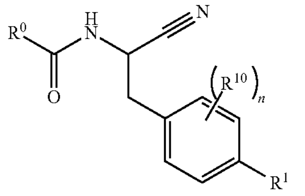

or a pharmaceutically acceptable salt or deuterated form thereof, wherein $R^0$ and $R^1$ are defined herein, n is 0 or 1, and $R^{10}$ is F.

In embodiments, the present disclosure provides a compound of Formula (III):

(III)

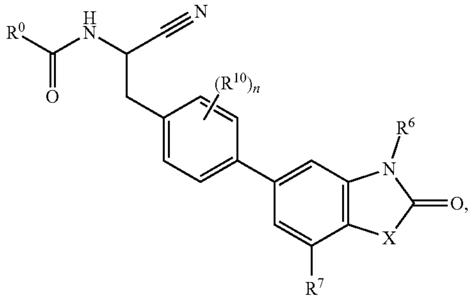

or a pharmaceutically acceptable salt or deuterated form thereof, wherein $R^0$, $R^6$, $R^7$, X, $R^{10}$ is F, and n is 0 or 1.

In embodiments, the present disclosure provides a compound of Formula (III-A):

(III-A)

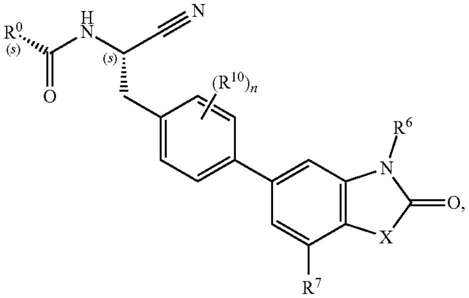

or a pharmaceutically acceptable salt or deuterated form thereof, wherein $R^0$, $R^6$, $R^7$, n, and X are defined as set forth above for Formula (III).

In embodiments, the present disclosure provides a compound of Formula (III-B):

(III-B)

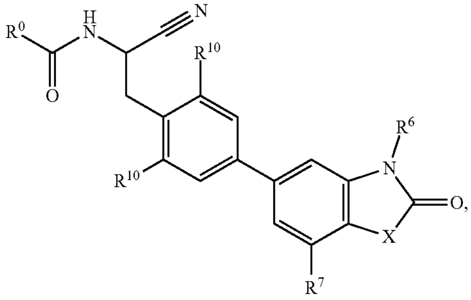

or a pharmaceutically acceptable salt or deuterated form thereof, wherein $R^0$, $R^6$, $R^7$ and X are defined herein and $R^{10}$ is —H or —F.

In embodiments, the present disclosure provides a pharmaceutical composition comprising a compound disclosed herein (e.g., a compound of Formula (I), (II) or (III), (III-A), or (III-B) or a pharmaceutically acceptable salt or deuterated form thereof), and a pharmaceutically acceptable adjuvant, diluent or carrier.

In yet another aspect of the disclosure, a method of treatment is provided. The method of treatment, in embodiments, comprises, administering to a subject in need thereof, a composition comprising an effective amount of a compound of Formula (I), (II) or (III), (III-A), or (III-B) or a pharmaceutically acceptable salt or deuterated form thereof.

The method of treatment, in embodiments, is a method of treating an obstructive disease of the airway, e.g., cystic fibrosis (CF), asthma or bronchiectasis (e.g., non-CF bronchiectasis). In another embodiment, the method of treatment is a method for treating chronic rhinosinusitis (CRS).

In some embodiments, the method of treatment is a method for treating hidradenitis suppurativa (HS).

In some embodiments, the method of treatment is a method for treating cancer.

In some embodiments, the method of treatment is a method of treating lupus nephritis.

In some embodiments, the method of treatment is a method of treating rheumatoid arthritis.

In some embodiments, the method of treatment is a method of treating inflammatory bowel disease (IBD).

DETAILED DESCRIPTION

Throughout this disclosure, various patents, patent applications and publications are referenced. The disclosures of these patents, Patent Applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

Listed below are definitions of various terms used in the specification and claims to describe the present disclosure.

Unless defined otherwise, all technical and scientific terms used in this disclosure have the same meanings as commonly understood by one of ordinary skill in the art to which this disclosure belongs.

The term "about" when immediately preceding a numerical value means a range encompassing said numerical value plus or minus an acceptable amount of variation in the art (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms below, as used herein, have the following meanings, unless indicated otherwise:

"Cyano" refers to the —CN radical.

"Hydroxy" or "hydroxyl" refers to the —OH radical.

"Oxo" refers to the =O substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_8$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkenyl group can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkynyl group can be optionally substituted.

"Alkoxy" refers to a radical of the formula —$OR_a$ where $R_a$ is an alkyl, alkenyl or alkynyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Aryl" refers to a hydrocarbon ring system radical comprising hydrogen, 6 to 18 carbon atoms and at least one aromatic ring. For purposes of this disclosure, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In embodiments where "L" is aryl, the aryl radical is a diradical. Unless stated otherwise specifically in the specification, the term "aryl" is meant to include aryl radicals that are optionally substituted.

"Aralkyl" or "arylalkyl" refers to a radical of the formula —$R_b$—$R_c$ where $R_b$ is an alkylene group as defined above and $R_c$ is one or more aryl radicals as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, e.g., having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, e.g., having from three to ten carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, e.g., having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" or "halogenated alkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkynyl group can be optionally substituted.

"Heterocyclyl" "heterocyclic ring" or "heterocycle" refers to a stable 3- to 20-membered non-aromatic or partially aromatic radical which consists of two to twelve carbon atoms and from one to six heteroatoms selected from nitrogen, oxygen or sulfur. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In embodiments where "L" is heterocyclyl, the heterocyclyl radical is a diradical. Unless stated otherwise specifically in the specification, a heterocyclyl group can be optionally substituted.

"Heteroaryl" refers to a 5- to 20-membered ring system radical comprising hydrogen atoms, one to thirteen carbon atoms, one to six heteroatoms selected from nitrogen, oxygen and sulfur, and at least one aromatic ring. For purposes of this disclosure, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophene (i.e. thienyl). In embodiments where "L" is heteroaryl, the heteroaryl radical is a diradical. Unless stated otherwise specifically in the specification, a heteroaryl group can be optionally substituted.

"The term "substituted" used herein means any of the above groups (i.e., alkyl, alkylene, alkenyl, alkenylene, alkynyl, alkynylene, alkoxy, alkylamino, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

"Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further includes any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

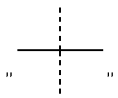

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

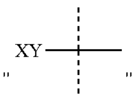

indicates that the chemical entity "XY" is bonded to another chemical entity via the point of attachment bond. Furthermore, the specific point of attachment to the non-depicted chemical entity can be specified by inference. For example, the compound $CH_3-R^L$, wherein $R^L$ is H or

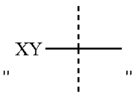

infers that when $R^L$ is "XY", the point of attachment bond is the same bond as the bond by which $R^L$ is depicted as being bonded to $CH_3$.

In embodiments, chemical groups within a chemical structure, such as formula (I) (e.g., any chemical groups in the definition of $R^0$, L, and $R^1$) can be present in more than a single orientation within the chemical structure. For example, it is understood that the group can be present in any possible orientation unless the context clearly limits the orientation of the group within the chemical structure to a particular orientation e.g., a $CH_2O$ group can be present in a $CH_2O$ orientation or $OCH_2$ orientation within the chemical structure.

In this specification, unless stated otherwise, the term "pharmaceutically acceptable" is used to characterize a moiety (e.g., a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

The term "pharmaceutically acceptable salt" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The compounds of the disclosure, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present disclosure is meant to include all such possible isomers, as well as their racemic and optically pure forms whether or not they are specifically depicted herein. Optically active (+) and (−), (R)- and(S)—, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

The term "treating" as used herein with regard to a patient, refers to improving at least one symptom of the patient's disorder. Treating can be improving, or at least partially ameliorating a disorder or an associated symptom of a disorder.

An "effective amount" means the amount compound or pharmaceutical formulation, that when administered to a patient for treating a state, disorder or condition is sufficient to effect such treatment.

The terms "subject," "individual," and "patient" are used interchangeably herein to refer to a vertebrate, such as a mammal. The mammal may be, for example, a mouse, a rat, a rabbit, a cat, a dog, a pig, a sheep, a horse, a non-human primate (e.g., cynomolgus monkey, chimpanzee), or a human.

Compounds

In one aspect of the present disclosure, a DPP1 inhibitor is provided, and the DPP1 inhibitor is a compound of Formula (I), (II), (III), (III-A), (III-B), or Table 1.

In embodiments, provided herein is a compound of formula (I)

(I)

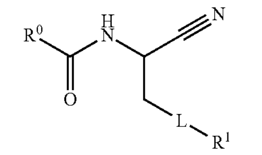

or a pharmaceutically acceptable salt or deuterated form thereof, wherein $R^0$ is

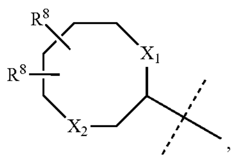

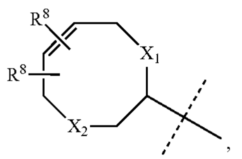

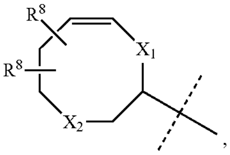

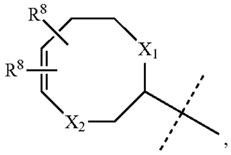

or

-continued

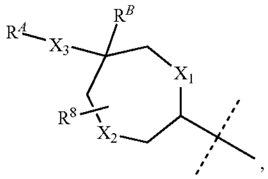

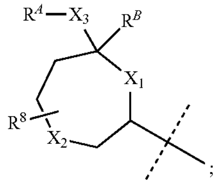

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, N($C_{1-6}$ alkyl), $CH_2O$;

$R^A$ is H, $C_{1-6}$ alkyl, $C_{1-6}$alkylene-carbocyclyl, $C_{1-6}$alkylene-heteroaryl, heteroaryl or carbocyclyl; and $R^B$ is $C_{1-6}$ alkyl, $C_{1-6}$haloalkyl, $C_{1-6}$ alkyl-OH, $C_{2-6}$alkenyl, cycloalkyl, $C_{1-6}$alkylene-carbocyclyl, $C_{1-6}$alkylene-aryl, $C_{1-6}$alkylene-heteroaryl, heteroaryl or carbocyclyl; or $R^A$ and $R^B$ are taken together to form a heterocyclyl;

L is aryl, heterocyclyl, heteroaryl, or

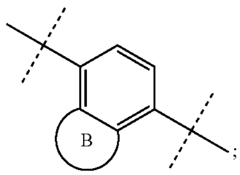

wherein L is independently substituted by 0-4 $R^{10}$ and wherein ring B is a carbocycle, or a heterocycle;

$R^1$ is

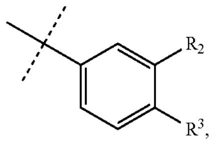

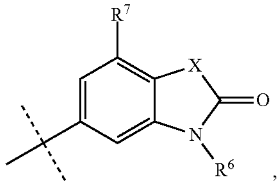

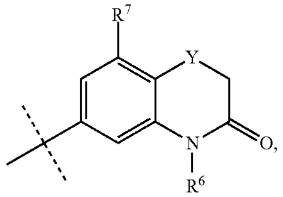

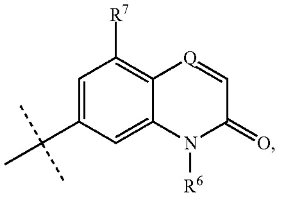

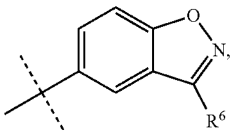

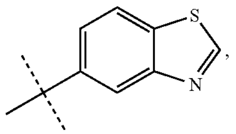

or

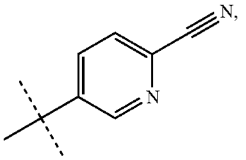

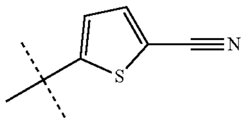

-continued

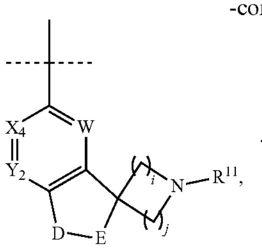

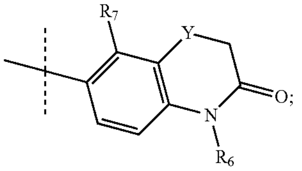

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O, S, or $CH_2$;

Q is CH or N;

$R^6$ is $C_{1-6}$ alkyl optionally substituted by 1, 2 or 3 F, or optionally substituted by OH, O $C_{1-6}$ alkyl, N($C_{1-6}$ alkyl)$_2$, N($C_{1-6}$ alkyl) ($C_{1-6}$alkylene-O—$C_{1-6}$ alkyl), cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, $C_{1-6}$alkylene-heteroaryl, halogenated $C_{1-6}$alkoxy, halogenated $C_{1-6}$ alkyl, heteroaryl or carbocyclyl;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, N($C_{1-6}$ alkyl)$_2$, COOH, $COC_{1-6}$ alkyl, $COOC_{1-6}$ alkyl, $CON_{1-6}$ alkyl, CON($C_{1-6}$ alkyl)$_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$-0;

$R^{11}$ is H, $C_{1-6}$ alkyl, alkylene-O-alkyl, or heterocyclyl; and i and j are each independently 1, 2 or 3; provided that the sum of i+j is 2, 3 or 4.

In an aspect, the present disclosure provides a compound of formula (I):

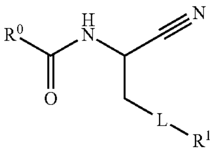

(I)

or a pharmaceutically acceptable salt or deuterated form thereof, wherein $R^0$ is

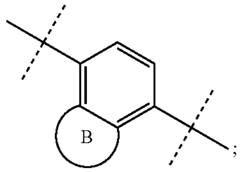

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, N($C_{1-6}$ alkyl), $OCH_2$, or $SCH_2$;

$R^A$ is H, $C_{1-6}$ alkyl, $C_{1-6}$alkylene-carbocyclyl, $C_{1-6}$alkylene-heteroaryl, heteroaryl or carbocyclyl; and $R^B$ is $C_{1-6}$ alkyl, $C_{1-6}$haloalkyl, $C_{1-6}$ alkyl-OH, $C_{2-6}$alkenyl, cycloalkyl, $C_{1-6}$alkylene-carbocyclyl, $C_{1-6}$alkylene-aryl, $C_{1-6}$alkylene-heteroaryl, heteroaryl or carbocyclyl; or $R^A$ and $R^B$ are taken together to form a heterocyclyl;

L is aryl, heterocyclyl, heteroaryl, or

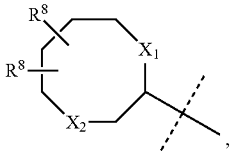

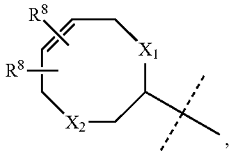

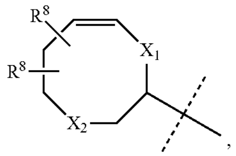

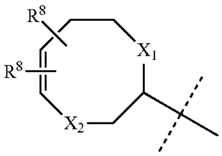

or

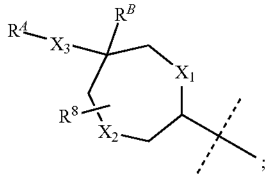

wherein L is independently substituted by 0-4 $R^{10}$ and wherein ring B is a carbocycle, or a heterocycle;

$R^1$ is

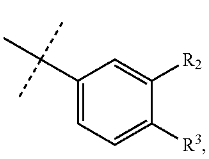

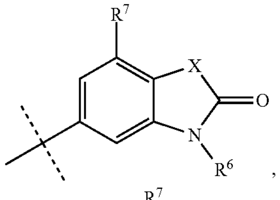

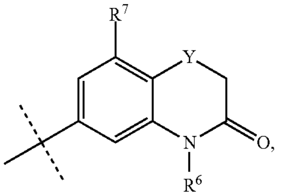

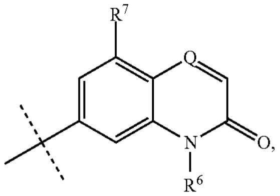

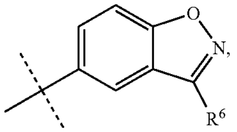

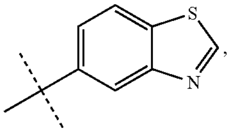

-continued

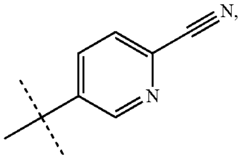

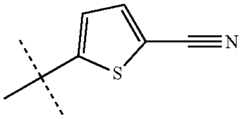

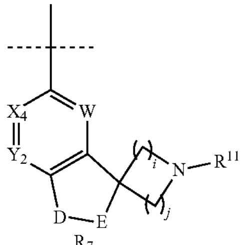

or

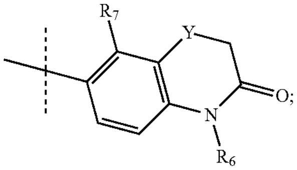

; or $R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O, S, or $CH_2$;

Q is CH or N;

$R^6$ is $C_{1-6}$ alkyl optionally substituted by 1, 2 or 3 F, or optionally substituted by OH, O $C_{1-6}$ alkyl, N($C_{1-6}$ alkyl)$_2$, N($C_{1-6}$ alkyl) ($C_{1-6}$alkylene-O—$C_{1-6}$ alkyl), cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, or $C_{1-6}$ alkylene-heteroaryl, halogenated $C_{1-6}$alkoxy, heteroaryl or carbocyclyl;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, N($C_{1-6}$ alkyl)$_2$, COOH, $COC_{1-6}$ alkyl, $COOC_{1-6}$ alkyl, $CON_{1-6}$ alkyl, CON($C_{1-6}$ alkyl)$_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$—O;

$R^{11}$ is H, $C_{1-6}$ alkyl, alkylene-O-alkyl, or heterocyclyl; and i and j are each independently 1, 2 or 3; provided that the sum of i+j is 2, 3 or 4.

In embodiments, the present disclosure provides a compound of formula (I)

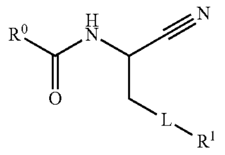

(I)

or a pharmaceutically acceptable salt or deuterated form thereof, wherein $R^0$ is

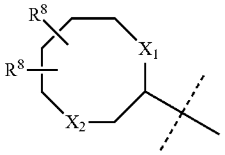

,

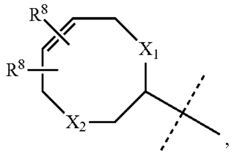

,

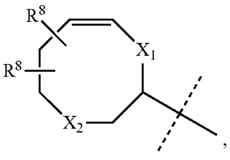

,

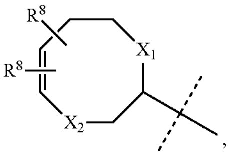

, or

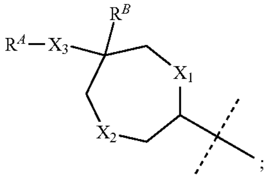

;

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, or N($C_{1-6}$ alkyl);

$R^A$ is H, $C_{1-6}$ alkyl, $C_{1-6}$alkylene-carbocyclyl, $C_{1-6}$alkylene-heteroaryl, heteroaryl or carbocyclyl; and $R^B$ is $C_{1-6}$ alkyl, $C_{2-6}$alkenyl, cycloalkyl, $C_{1-6}$alkylene-carbocyclyl, $C_{1-6}$alkylene-aryl, $C_{1-6}$ alkylene-heteroaryl, heteroaryl or carbocyclyl; or $R^A$ and $R^B$ are taken together to form a heterocyclyl;

L is aryl, heterocyclyl, heteroaryl, or

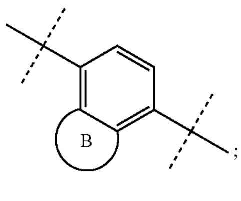

;

wherein L is independently substituted by 0-4 $R^{10}$ and wherein ring B is a carbocycle, or a heterocycle;

$R^1$ is

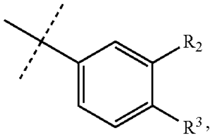

,

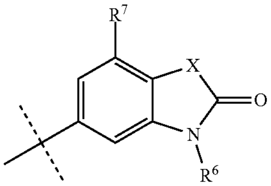

,

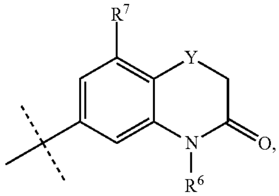

,

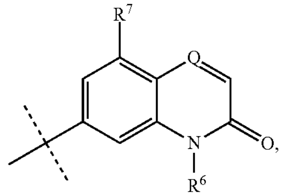

,

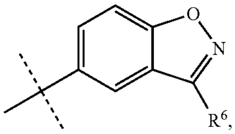

,

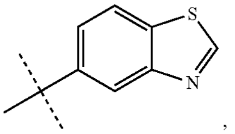

,

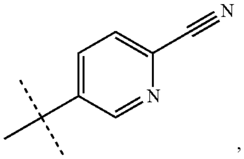

,

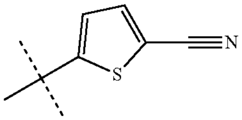

or

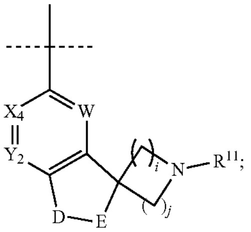

;

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O or S;

Q is CH or N;

$R^6$ is $C_{1-6}$ alkyl optionally substituted by 1, 2 or 3 F, or optionally substituted by OH, O $C_{1-6}$ alkyl, $N(C_{1-6}$ alkyl$)_2$, cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, or $C_{1-6}$ alkylene-heteroaryl, halogenated $C_{1-6}$alkoxy, heteroaryl or carbocyclyl;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, $N(C_{1-6}$ alkyl$)_2$, COOH, $COC_{1-6}$ alkyl, $COOC_{1-6}$ alkyl, $CON_{1-6}$ alkyl, $CON(C_{1-6}$ alkyl$)_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$—O;

$R^{11}$ is H, $C_{1-6}$ alkyl, alkylene-O-alkyl, or heterocyclyl; and i and j are each independently 1, 2 or 3; provided that the sum of i+j is 2, 3 or 4.

In embodiments, the present disclosure provides a compound of Formula (I):

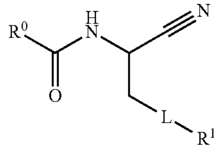

(I)

or a pharmaceutically acceptable salt or deuterated form thereof, wherein $R^0$ is

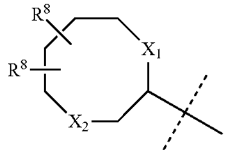

,

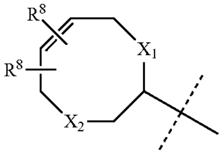

,

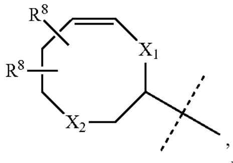

,

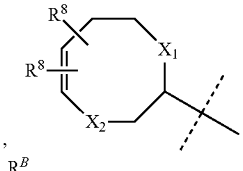

, or

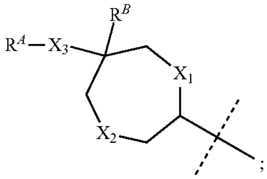

;

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, or N($C_{1-6}$ alkyl);

$R^A$ is H, $C_{1-6}$ alkyl, $C_{1-6}$alkylene-carbocyclyl, or $C_{1-6}$alkylene-heteroaryl; and $R^B$ is $C_{1-6}$ alkyl, $C_{2-6}$alkenyl, cycloalkyl, $C_{1-6}$alkylene-carbocyclyl, $C_{1-6}$alkylene-aryl, or $C_{1-6}$alkylene-heteroaryl; or $R^A$ and $R^B$ are taken together to form a heterocyclyl;

L is aryl, heterocyclyl, heteroaryl, or

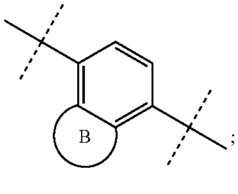

;

wherein L is independently substituted by 0-4 $R^{10}$ and wherein ring B is a carbocycle, or a heterocycle;

$R^1$ is

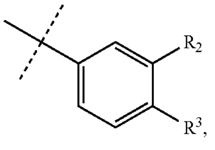

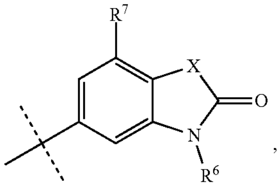

,

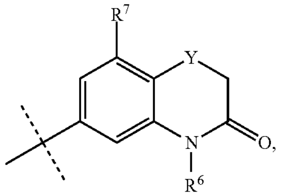

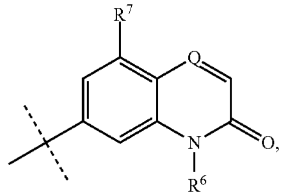

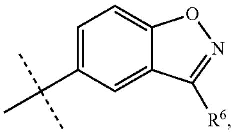

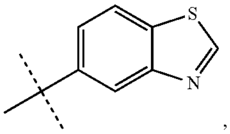

, or

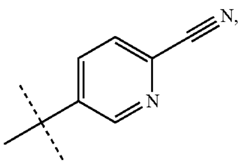

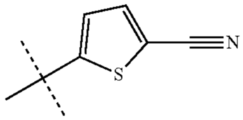

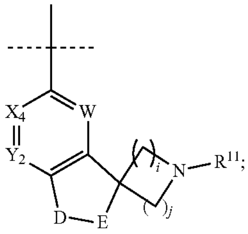

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O or S;

Q is CH or N;

$R^6$ is $C_{1-6}$ alkyl optionally substituted by 1, 2 or 3 F, or optionally substituted by OH, O $C_{1-6}$ alkyl, $N(C_{1-6}$ alkyl$)_2$, cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, or $C_{1-6}$ alkylene-heteroaryl, or halogenated $C_{1-6}$alkoxy;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, $N(C_{1-6}$ alkyl$)_2$, COOH, $COC_{1-6}$ alkyl, $COOC_{1-6}$ alkyl, $CON_{1-6}$ alkyl, $CON(C_{1-6}$ alkyl$)_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), $N(C_{1-6}$ alkyl)-C(O), $CH_2CH_2$, C(O)—O or $CH_2$—O;

$R^{11}$ is H, $C_{1-6}$ alkyl, alkylene-O-alkyl, or heterocyclyl; and i and j are each independently 1, 2 or 3; provided that the sum of i+j is 2, 3 or 4.

In embodiments, the present disclosure provides a compound of Formula (I), or a pharmaceutically acceptable salt or deuterated form thereof:

(I)

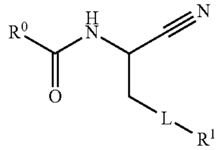

wherein $R^0$ is

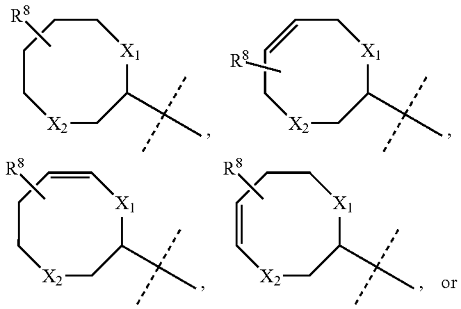

, or

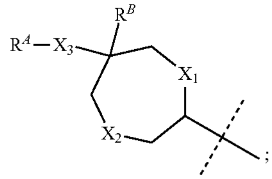

$X_1$ and $X_2$ are independently O, S, NH, $N(C_{1-6}$ alkyl), or $CR^{12}R^{13}$, wherein at least one of $X_1$ and $X_2$ are not $CR^{12}R^{13}$;

$X_3$ is O, S, NH, or $N(C_{1-6}$ alkyl);

$R^A$ is H, $C_{1-6}$ alkyl, $C_{1-6}$alkylene-carbocyclyl, or $C_{1-6}$alkylene-heteroaryl; and $R^B$ is $C_{1-6}$ alkyl, $C_{2-6}$alkenyl, $C_{1-6}$alkylene-carbocyclyl, or $C_{1-6}$alkylene-heteroaryl; or $R^A$ and $R^B$ are taken together to form a heterocyclyl;

L is aryl, heterocycle, heteroaryl, or

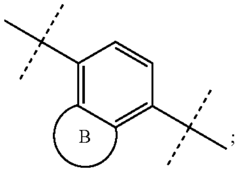

wherein L is independently substituted by 0-4 $R^{10}$, and wherein ring B is a carbocycle, a heterocycle (in embodiments, the heterocycle is not aromatic and contains 1-3 heteroatoms selected from N, S, and O; in embodiments, the heterocycle is a heteroaryl containing 1-3 heteroatoms selected from N, S, and O);

$R^1$ is

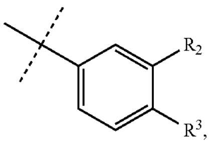

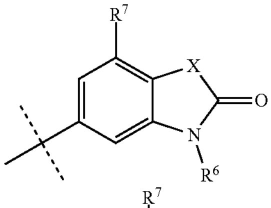

,

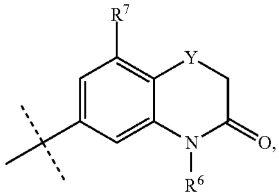

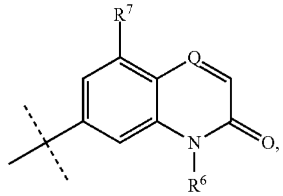

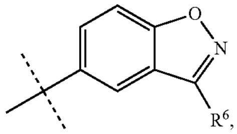

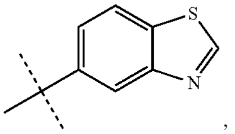

, or

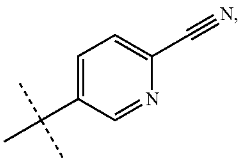

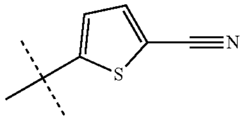

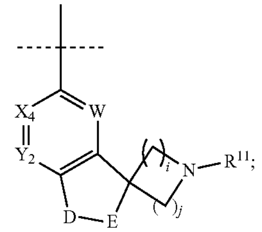

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O or S;

Q is CH or N;

$R^6$ is $C_{1-6}$ alkyl, wherein the $C_{1-6}$ alkyl is optionally substituted by 1, 2 or 3 F, OH, $OC_{1-6}$ alkyl, $N(C_{1-6}$ alkyl$)_2$, cycloalkyl, or heterocyclyl;

$R^7$ is H, F, Cl, Br, or $C_{1-6}$ alkyl;

$R^8$ and $R^{12}$ are independently H, OH, halogen, $NH_2$, COOH, unsubstituted $C_{1-6}$ alkyl, halogen, hydroxyl substituted $C_{1-6}$ alkyl, unsubstituted $C_{1-6}$alkoxy or halogenated $C_{1-6}$alkoxy;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, NH—$C_{1-6}$ alkyl, $N(C_{1-6}$ alkyl$)_2$, COOH, $COC_{1-6}$ alkyl, $COOC_{1-6}$ alkyl, $CON_{1-6}$ alkyl, $CON(C_{1-6}$ alkyl$)_2$, $NHCOC_{1-6}$ alkyl, or heterocyclyl; wherein each alkyl, alkoxy, alkenyl, alkynyl, cycloalkyl, and heterocyclyl are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$—O;

$R^{11}$ is H, $C_{1-3}$-alkyl, -alkylene-O-alkyl, or heterocyclyl; and i and j are each independently 1, 2 or 3; provided that the sum of i+j is 2, 3 or 4.

In embodiments, the present disclosure provides a compound of Formula (II):

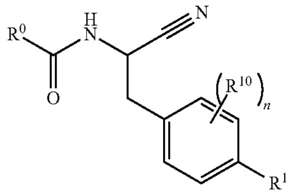

(II)

or a pharmaceutically acceptable salt or deuterated form thereof, wherein:

$R^0$ is

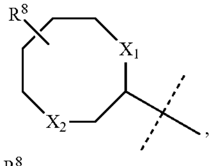

,

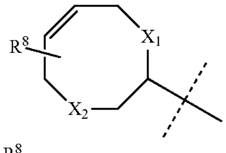

,

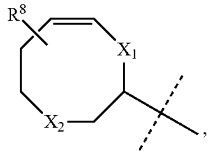

,

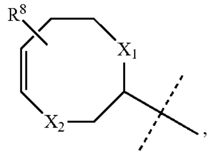

, or

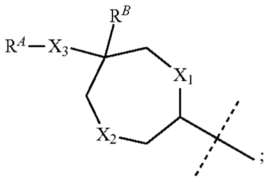

;

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, or N($C_{1-6}$ alkyl);

$R^A$ is H, $C_{1-6}$ alkyl, $C_{1-6}$alkylene-carbocyclyl, or $C_{1-6}$alkylene-heteroaryl; and $R^B$ is $C_{1-6}$ alkyl, $C_{2-6}$alkenyl, $C_{1-6}$alkylene-carbocyclyl, or $C_{1-6}$alkylene-heteroaryl; or $R^A$ and $R^B$ are taken together to form a heterocyclyl;

$R^1$ is

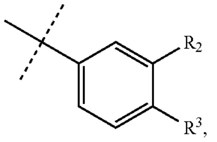

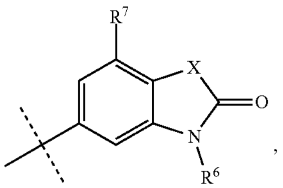

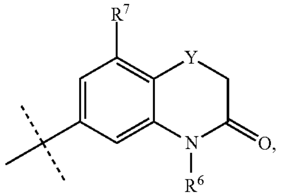

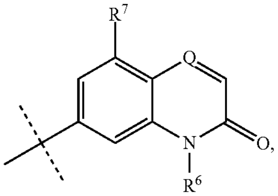

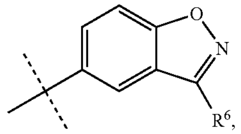

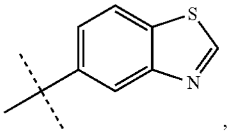

or

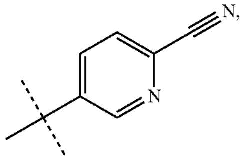

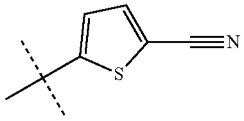

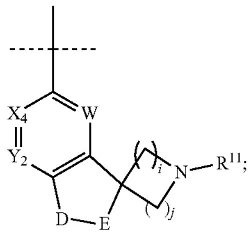

$R^2$ is H, F, Cl, Br, $OSO_2C_{1-6}$ alkyl, or $C_{1-6}$ alkyl;

$R^3$ is H, F, Cl, Br, CN, $CF_3$, $SO_2C_{1-6}$ alkyl, $CONH_2$ or $SO_2NR_4R^5$, wherein $R^4$ and $R^5$ together with the nitrogen atom to which they are attached form a azetidine, pyrrolidine or piperidine ring X is O, S or $CF_2$;

Y is O or S;

Q is CH or N;

$R^6$ is $C_{1-6}$ alkyl, wherein the $C_{1-6}$ alkyl is optionally substituted by 1, 2 or 3 F, OH, $OC_{1-6}$ alkyl, $N(C_{1-6}$ alkyl$)_2$, cycloalkyl, or heterocyclyl;

$R^7$ is H, F, Cl or $CH_3$;

$R^8$ and $R^{12}$ are independently H, OH, halogen, $NH_2$, COOH, unsubstituted $C_1$-$C_4$ alkyl, halogen, hydroxyl substituted $C_1$-$C_6$ alkyl, unsubstituted $C_1$-$C_6$ alkoxy or halogenated $C_1$-$C_6$alkoxy;

each $R^{13}$ is independently H, F, Cl, Br, I or $C_1$-$C_6$ alkyl;

$R^{10}$ is F, and n is 0 or 1;

W, $X_4$ and $Y_2$ are each independently is CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$—O;

$R^{11}$ is H, $C_{1-6}$ alkyl, $CH_3OCH_2CH_2$—, oxetanyl, tetrahydrofuranyl, 4-tetrahydropyranyl or 3-tetrahydropyranyl; and i and j are each independently 1, 2 or 3; provided that the sum of i+j is 2, 3 or 4.

In embodiments, the present disclosure provides a compound of Formula (III):

(III)

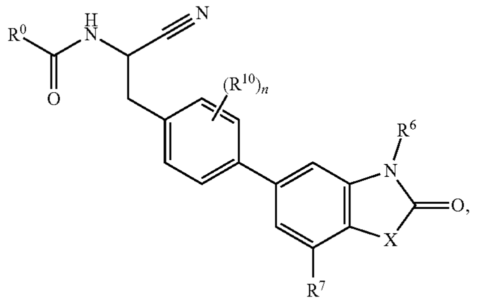

or a pharmaceutically acceptable salt thereof, wherein:

$R^0$ is

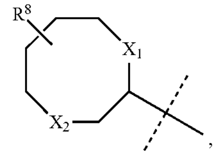

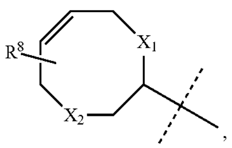

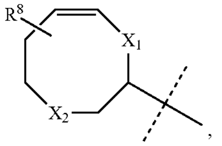

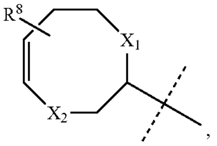

or

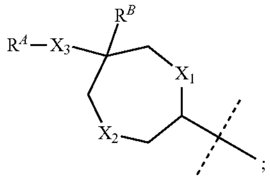

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, or N($C_{1-6}$ alkyl);

$R^A$ is H, $C_{1-6}$ alkyl, $C_{1-6}$alkylene-carbocyclyl, or $C_{1-6}$alkylene-heteroaryl; and $R^B$ is $C_{1-6}$ alkyl, $C_{2-6}$ alkenyl, $C_{1-6}$alkylene-carbocyclyl, or $C_{1-6}$alkylene-heteroaryl; or $R^A$ and $R^B$ are taken together to form a heterocyclyl;

X is O, S or $CF_2$;

$R^6$ is $C_{1-6}$ alkyl, wherein the $C_{1-6}$ alkyl is optionally substituted by 1, 2 or 3 F, OH, $OC_{1-6}$ alkyl, $N(C_{1-6}$ alkyl$)_2$, cycloalkyl, or heterocyclyl;

$R^7$ is H, F, Cl or $CH_3$;

$R^8$ and $R^{12}$ are independently H, OH, halogen, $NH_2$, COOH, unsubstituted $C_1$-$C_6$ alkyl, halogen, hydroxyl substituted $C_1$-$C_6$ alkyl, unsubstituted $C_1$-$C_6$ alkoxy or halogenated $C_1$-$C_6$ alkoxy;

each $R^{13}$ is independently H, F, Cl, Br, I or $C_1$-$C_6$ alkyl;

$R^{10}$ is F, and n is 0 or 1.

In embodiments, the present disclosure provides a compound of Formula (III-A):

(III-A)

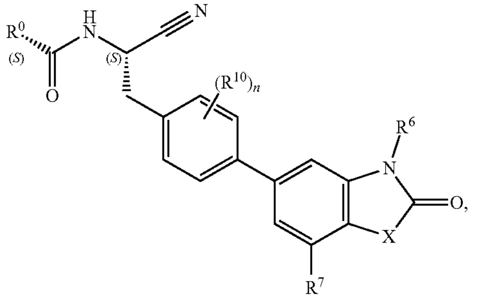

or a pharmaceutically acceptable salt or deuterated form thereof, wherein:

$R^0$ is

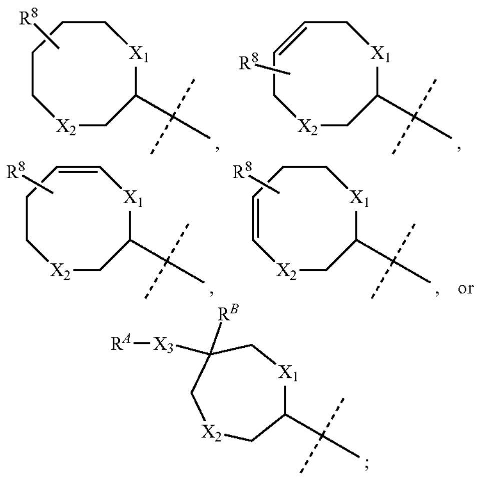

, or ;

$X_1$ and $X_2$ are independently O, S, NH, $N(C_{1-6}$ alkyl), or $CR^{12}R^{13}$, wherein at least one of $X_1$ and $X_2$ are not $CR^{12}R^{13}$;

$X_3$ is O, S, NH, or $N(C_{1-6}$ alkyl);

$R^A$ is H, $C_{1-6}$ alkyl, $C_{1-6}$alkylene-carbocyclyl, or $C_{1-6}$alkylene-heteroaryl; and $R^B$ is $C_{1-6}$ alkyl, $C_{2-6}$alkenyl, $C_{1-6}$alkylene-carbocyclyl, or $C_{1-6}$alkylene-heteroaryl; or $R^A$ and $R^B$ are taken together to form a heterocyclyl;

X is O, S or $CF_2$;

$R^6$ is $C_{1-6}$ alkyl, wherein the $C_{1-6}$ alkyl is optionally substituted by 1, 2 or 3 F, OH, $OC_{1-6}$ alkyl, $N(C_{1-6}$ alkyl$)_2$, cycloalkyl, or heterocyclyl;

$R^7$ is H, F, Cl or $CH_3$;

$R^8$ and $R^{12}$ are independently H, OH, halogen, $NH_2$, COOH, unsubstituted $C_1$-$C_4$ alkyl, halogen, hydroxyl substituted $C_1$-$C_4$ alkyl, unsubstituted $C_1$-$C_4$ alkoxy or halogenated $C_1$-$C_4$alkoxy;

each $R^{13}$ is independently H, F, Cl, Br, I or $C_1$-$C_6$ alkyl, $R^{10}$ is F, and n is 0 or 1.

In embodiments, the present disclosure provides a compound of Formula (III-B):

(III-B)

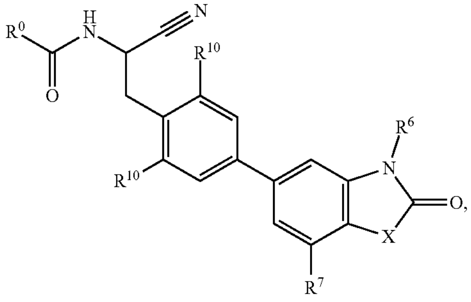

or a pharmaceutically acceptable salt or deuterated form thereof, wherein:

$R^0$ is

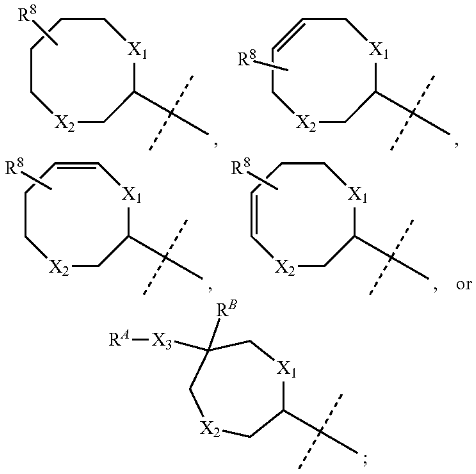

, or ;

$X_1$ and $X_2$ are independently O, S, NH, $N(C_{1-6}$ alkyl), or $CR^{12}R^{13}$, wherein at least one of $X_1$ and $X_2$ are not $CR^{12}R^{13}$;

$X_3$ is O, S, NH, or $N(C_{1-6}$ alkyl);

$R^A$ is H, $C_{1-6}$ alkyl, $C_{1-6}$alkylene-carbocyclyl, or $C_{1-6}$alkylene-heteroaryl; and $R^B$ is $C_{1-6}$ alkyl, $C_{2-6}$alkenyl, $C_{1-6}$alkylene-carbocyclyl, or $C_{1-6}$alkylene-heteroaryl; or $R^A$ and $R^B$ are taken together to form a heterocyclyl;

X is O, S or $CF_2$;

$R^6$ is $C_{1-6}$ alkyl, wherein the $C_{1-6}$ alkyl is optionally substituted by 1, 2 or 3 F, OH, $OC_{1-6}$ alkyl, $N(C_{1-6}$ alkyl$)_2$, cycloalkyl, or heterocyclyl;

$R^7$ is H, F, Cl or $CH_3$;

$R^8$ and $R^{12}$ are independently H, OH, halogen, $NH_2$, COOH, unsubstituted $C_1$-$C_4$ alkyl, halogen, hydroxyl substituted $C_1$-$C_4$ alkyl, unsubstituted $C_1$-$C_4$ alkoxy or halogenated $C_1$-$C_4$alkoxy;

each $R^{13}$ is independently H, F, Cl, Br, I or $C_1$-$C_6$ alkyl; and $R^{10}$ is F, and n is 0 or 1.

In some embodiments, the compound of Formula (III-B) is (III-B)

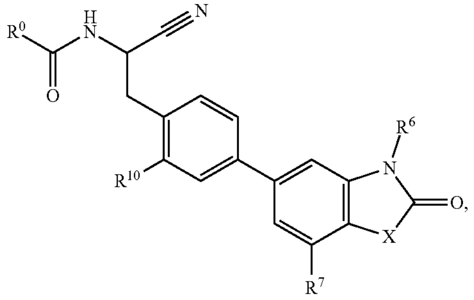

or a pharmaceutically acceptable salt or deuterated form thereof.

In embodiments of a compound of Formula (I), (II), (III), (III-A), or (III-B), or a pharmaceutically acceptable salt thereof, X is O, S CHF, or $CF_2$.

In embodiments of a compound of Formula (I), (II), (III), (III-A), or (III-B), or a pharmaceutically acceptable salt thereof, X is O, S or $CF_2$.

In embodiments of a compound of Formula (I), (II), (III), (III-A), or (III-B), or a pharmaceutically acceptable salt thereof, X is O.

In embodiments of a compound of Formula (I), (II), (III), (III-A), or (III-B), or a pharmaceutically acceptable salt thereof, X is S.

In embodiments of a compound of Formula (I), (II), (III), (III-A), or (III-B), or a pharmaceutically acceptable salt thereof, X is $CF_2$.

In embodiments of a compound of Formula (I), (II), (III), (III-A), or (III-B), or a pharmaceutically acceptable salt thereof, $R^0$ is

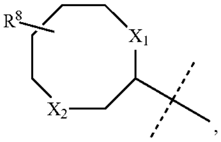,
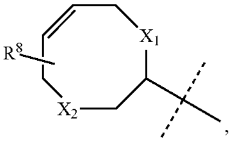,
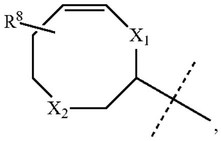,
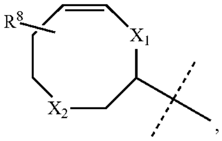,
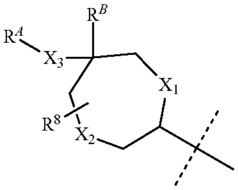, or
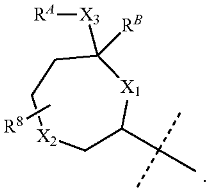.

In embodiments of a compound of Formula (I), (II), (III), (III-A), or (III-B), or a pharmaceutically acceptable salt thereof, $R^0$ is

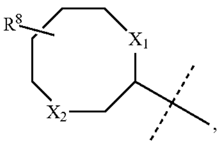,
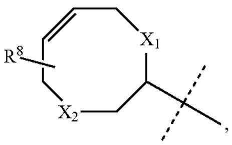,

-continued

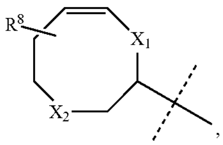,
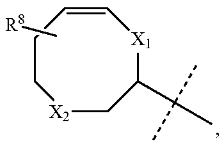, or
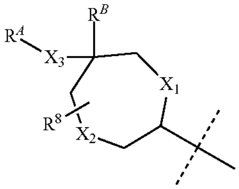,

In one embodiment of a compound of Formula (I), (II), (III), (III-A), or (III-B), or a pharmaceutically acceptable salt thereof, $R^0$ is

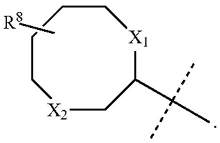.

In a further embodiment, $R^0$ is

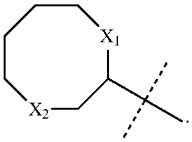.

In even a further embodiment, $R^0$ is

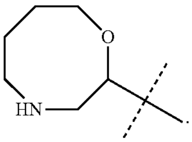.

In one embodiment of a compound of Formula (I), (II), (III), (III-A), or (III-B), or a pharmaceutically acceptable salt thereof, $R^0$ is

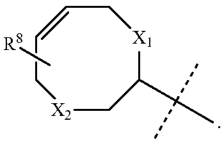.

In a further embodiment, $R^0$ is

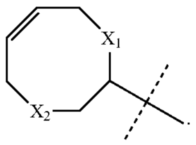

In even a further embodiment, $R^0$ is

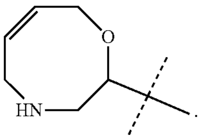

In another embodiment of a compound of Formula (I), (II), (III), (III-A), or (III-B), or a pharmaceutically acceptable salt thereof, $R^0$ is

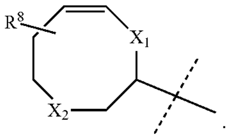

In a further embodiment, $R^0$ is

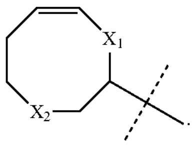

In even a further embodiment, $R^0$ is

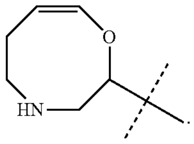

In another embodiment of a compounds of Formula (I), (II), (III), (III-A), or (III-B), or a pharmaceutically acceptable salt thereof, $R^0$ is

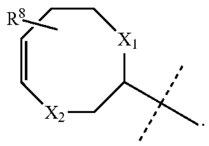

In a further embodiment, $R^0$ is

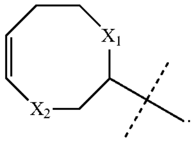

In even a further embodiment, $R^0$ is

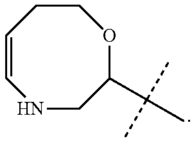

In some embodiments of a compound of Formula (I), (II), (III), (III-A), or (III-B), or a pharmaceutically acceptable salt thereof, $R^0$ is

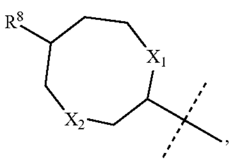

,

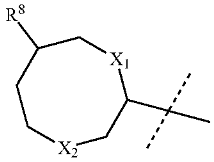

, or

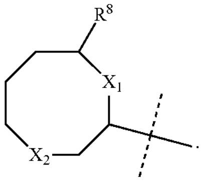

In some embodiments of a compound of Formula (I), (II), (III), (III-A), or (III-B), or a pharmaceutically acceptable salt thereof, $R^0$ is

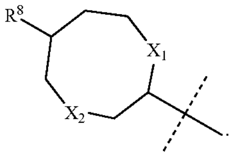

In some embodiments, $X_1$ is O and $X_2$ is NH. In some embodiments, $R^8$ is OH, unsubstituted $C_{1-6}$alkoxy, or O-cycloalkyl.

In some embodiments of a compound of Formula (I), (II), (III), (III-A), or (III-B), or a pharmaceutically acceptable salt thereof, $R^0$ is

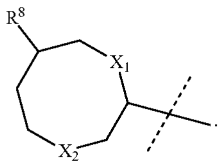

In some embodiments, $X_1$ is O and $X_2$ is NH. In some embodiments, $X_1$ is $CH_2$ and $X_2$ is NH. In some embodiments, $R^8$ is OH, unsubstituted $C_{1-6}$alkoxy, or O-cycloalkyl.

In some embodiments of a compound of Formula (I), (II), (III), (III-A), or (III-B), or a pharmaceutically acceptable salt thereof, $R^0$ is

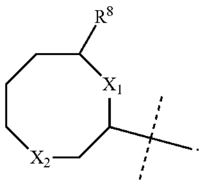

In some embodiments, $X_1$ is $CH_2$ and $X_2$ is NH. In some embodiments, $R^8$ is OH, unsubstituted $C_{1-6}$alkoxy, or O-cycloalkyl.

In embodiments of a compound of Formula (I), (II), (III), (III-A), or (III-B), or a pharmaceutically acceptable salt thereof, $R^0$ is

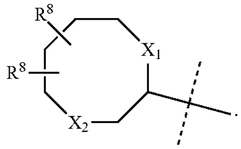

In embodiments of a compound of Formula (I), (II), (III), (III-A), or (III-B), or a pharmaceutically acceptable salt thereof, $R^0$ is

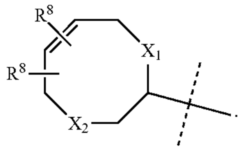

In embodiments of a compound of Formula (I), (II), (III), (III-A), or (III-B), or a pharmaceutically acceptable salt thereof, $R^0$ is

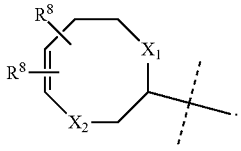

In embodiments of a compound of Formula (I), (II), (III), (III-A), or (III-B), or a pharmaceutically acceptable salt thereof, $R^0$ is

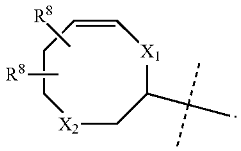

In embodiments of a compound of Formula (I), (II), (III), (III-A), or (III-B), or a pharmaceutically acceptable salt thereof, $R^0$ is

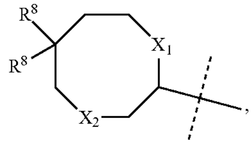, or 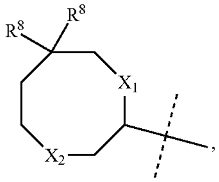, or

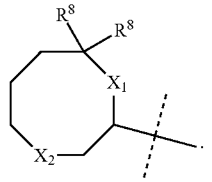

In embodiments of a compound of Formula (I), (II), (III), (III-A), or (III-B), or a pharmaceutically acceptable salt thereof, $R^0$ is

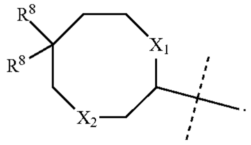

In embodiments, $X_1$ is O and $X_2$ is NH.

In embodiments of a compound of Formula (I), (II), (III), (III-A), or (III-B), or a pharmaceutically acceptable salt thereof, $R^0$ is

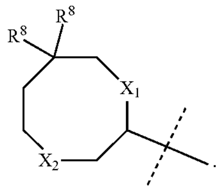

In embodiments, $X_1$ is O and $X_2$ is NH. In embodiments, $X_1$ is $CH_2$ and $X_2$ is NH.

In embodiments of a compound of Formula (I), (II), (III), (III-A), or (III-B), or a pharmaceutically acceptable salt thereof, $R^0$ is

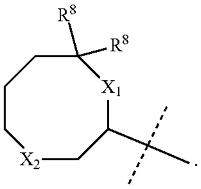

In embodiments, $X_1$ is $CH_2$ and $X_2$ is NH. In embodiments,

In yet another embodiment of a compound of Formula (I), (II), (III), (III-A), or (III-B), or a pharmaceutically acceptable salt thereof, $R^0$ is

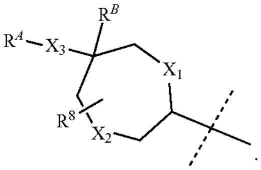

In an embodiment, $R^0$ is

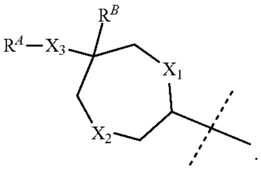

In a further embodiment, $R^0$ is

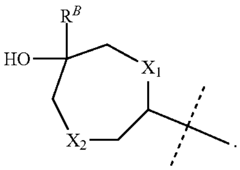

In even a further embodiment, $R^0$ is

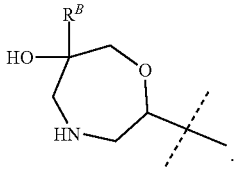

In even another embodiment of a compound of Formula (I), (II), (III), (III-A), or (III-B), or a pharmaceutically acceptable salt thereof, $R^0$ is

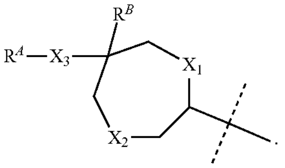

In a further embodiment, $R^0$ is

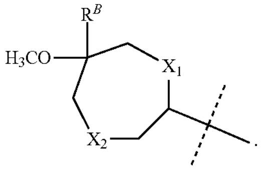

In even a further embodiment, $R^0$ is

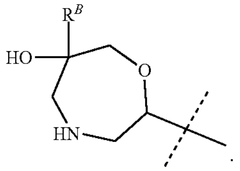

In another embodiment, $R^0$ is

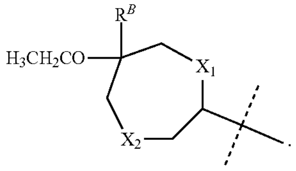

In a further embodiment, $R^0$ is

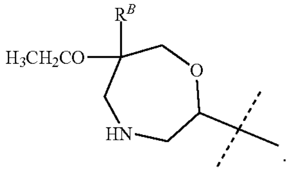

In embodiments of a compound of Formula (I), (II), (III), (III-A), or (III-B), or a pharmaceutically acceptable salt thereof, each $R^8$ is independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$ alkylene-carbocyclyl, or $C_{1-6}$alkylene-heteroaryl, halogenated $C_{1-6}$alkoxy, heteroaryl or carbocyclyl.

In embodiments of a compound of Formula (I), (II), (III), (III-A), or (III-B), or a pharmaceutically acceptable salt thereof, each $R^8$ is independently H, OH, halogen, $NH_2$, COOH, $C_{1-6}$ alkyl, $C_{1-6}$ alkyl-OH, $C_{1-6}$alkoxy, or halogenated $C_{1-6}$alkoxy.

In embodiments of a compound of Formula (I), (II), (III), (III-A), or (III-B), or a pharmaceutically acceptable salt thereof, each $R^8$ is independently H, OH, halogen, $NH_2$, COOH, unsubstituted $C_{1-6}$ alkyl, $C_{1-6}$ alkyl-OH, unsubstituted $C_{1-6}$alkoxy, or halogenated $C_{1-6}$ alkoxy.

In embodiments of a compound of Formula (I), (II), (III), (III-A), or (III-B), or a pharmaceutically acceptable salt thereof, each $R^8$ is independently OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$ alkylene-heteroaryl, halogenated $C_{1-6}$ alkyl or halogenated $C_{1-6}$alkoxy.

In embodiments, of a compound of Formula (I), (II), (III), (III-A), or (III-B), or a pharmaceutically acceptable salt thereof, each $R^8$ is independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, or halogenated $C_{1-6}$alkoxy, provided that one $R^8$ is not H.

In embodiments, of a compound of Formula (I), (II), (III), (III-A), or (III-B), or a pharmaceutically acceptable salt thereof, each $R^8$ is independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$ alkylene-heteroaryl, halogenated $C_{1-6}$ alkyl or halogenated $C_{1-6}$ alkoxy, provided that one $R^8$ is not H.

In embodiments of a compound of Formula (I), (II), (III), (III-A), or (III-B), or a pharmaceutically acceptable salt thereof, one $R^8$ is OH, unsubstituted $C_{1-6}$alkoxy, or O-cycloalkyl and the other $R^8$ is unsubstituted $C_{1-6}$ alkyl or cycloalkyl.

In embodiments of a compound of Formula (I), (II), (III), (III-A), or (III-B), or a pharmaceutically acceptable salt thereof, one $R^8$ is OH and the other $R^8$ is unsubstituted $C_{1-6}$ alkyl, halogenated $C_{1-6}$ alkyl, $C_{1-6}$ alkyl-OH, $C_{2-6}$alkenyl, or $C_{1-6}$ alkylene-heteroaryl.

In embodiments of a compound of Formula (I), (II), (III), (III-A), or (III-B), or a pharmaceutically acceptable salt thereof, each $R^8$ is independently OH, unsubstituted $C_{1-6}$ alkoxy, or O-cycloalkyl.

In embodiments of a compound of Formula (I), (II), (III), (III-A), or (III-B), or a pharmaceutically acceptable salt thereof, $R^8$ is independently OH or $CH_3$.

In embodiments of a compound of Formula (I), (II), (III), (III-A), or (III-B), or a pharmaceutically acceptable salt thereof, $R^{12}$ is H, OH, halogen, $NH_2$, COOH, unsubstituted $C_{1-4}$ alkyl, $C_{1-4}$ alkyl-OH, unsubstituted $C_{1-4}$alkoxy or halogenated $C_{1-4}$alkoxy.

In embodiments of a compound of Formula (I), (II), (III), (III-A), or (III-B), or a pharmaceutically acceptable salt thereof, $R^{12}$ is hydrogen.

In embodiments of a compound of Formula (I), (II), (III), (III-A), or (III-B), or a pharmaceutically acceptable salt thereof, $R^8$ is hydrogen, methoxy, ethoxy, or hydroxy.

In embodiments of a compound of Formula (I), (II), (III), (III-A), or (III-B), or a pharmaceutically acceptable salt thereof, $R^8$ is methoxy.

In embodiments of a compound of Formula (I), (II), (III), (III-A), or (III-B), or a pharmaceutically acceptable salt thereof, $R^8$ is OH.

In embodiments of a compound of Formula (I), (II), (III), (III-A), or (III-B), or a pharmaceutically acceptable salt thereof, $R^8$ is hydrogen.

In embodiments of a compound of Formula (I), (II), (III), (III-A), or (III-B), or a pharmaceutically acceptable salt thereof, $R^{13}$ is independently H, F, Cl, Br, I or $C_1$-$C_6$ alkyl.

In embodiments of a compound of Formula (I), (II), (III), (III-A), or (III-B), or a pharmaceutically acceptable salt thereof, $R^{13}$ is independently H, F, or $C_1$-$C_6$ alkyl.

In embodiments of a compound of Formula (I), (II), (III), (III-A), or (III-B), or a pharmaceutically acceptable salt thereof, $R^{13}$ is H.

In embodiments of a compound of Formula (I), (II), (III), (III-A), or (III-B), or a pharmaceutically acceptable salt thereof, $R^0$ is:

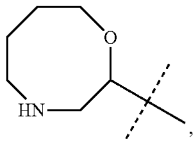,
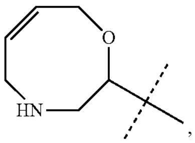,
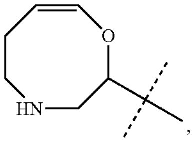, or
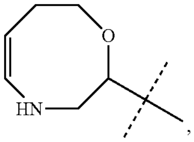,

In embodiments of a compound of Formula (I), (II), (III), (III-A), or (III-B), or a pharmaceutically acceptable salt thereof, $R^0$ is

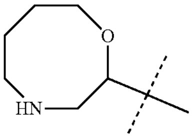,

In embodiments of a compound of Formula (I), (II), (III), (III-A), or (III-B), or a pharmaceutically acceptable salt thereof, $R^0$ is

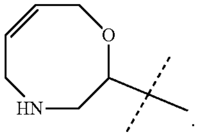.

In embodiments of a compound of Formula (I), (II), (III), (III-A), or (III-B), or a pharmaceutically acceptable salt thereof, $R^0$ is

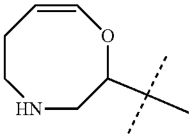,

In embodiments of a compound of Formula (I), (II), (III), (III-A), or (III-B), or a pharmaceutically acceptable salt thereof, $R^0$ is

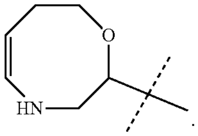.

In embodiments of a compound of Formula (I), (II), (III), (III-A), or (III-B), or a pharmaceutically acceptable salt thereof, $R^0$ is:

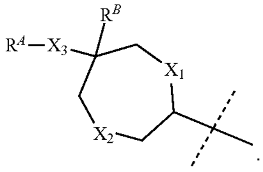

In embodiments of a compound of Formula (I), (II), (III), (III-A), or (III-B), or a pharmaceutically acceptable salt thereof, $X_1$ and $X_2$ are independently O, S, NH, N($C_{1-6}$ alkyl), or $CR^{12}R^{13}$, wherein at least one of $X_1$ and $X_2$ are not $CR^{12}R^{13}$. In embodiments, at least $X_1$ is O, S, NH, N($C_{1-6}$ alkyl).

In embodiments of a compound of Formula (I), (II), (III), (III-A), or (III-B), or a pharmaceutically acceptable salt thereof, $X_1$ and $X_2$ are independently O, S, or NH, N($C_{1-6}$ alkyl).

In embodiments of a compound of Formula (I), (II), (III), (III-A), or (III-B), or a pharmaceutically acceptable salt thereof, $X_1$ and $X_2$ are independently O or NH.

In embodiments of a compound of Formula (I), (II), (III), (III-A), or (III-B), or a pharmaceutically acceptable salt thereof, $R^0$ is:

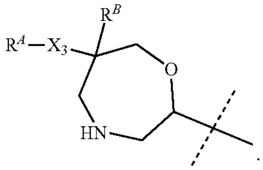

In embodiments of a compound of Formula (I), (II), (III), (III-A), or (III-B), or a pharmaceutically acceptable salt thereof, $R^A$ is H, $C_{1-6}$ alkyl, $C_{1-6}$alkylene-carbocyclyl, $C_{1-6}$ alkylene-heteroaryl, heteroaryl or carbocyclyl.

In embodiments of a compound of Formula (I), (II), (III), (III-A), or (III-B), or a pharmaceutically acceptable salt thereof, $R^A$ is H, $C_{1-6}$ alkyl, $C_{1-6}$alkylene-carbocyclyl, or $C_{1-6}$ alkylene-heteroaryl.

In one embodiment of a compound of Formula (I), (II), (III), (III-A), or (III-B), or a pharmaceutically acceptable salt thereof, $R^A$ is H, $C_{1-6}$ alkyl, $C_{1-6}$alkylene-carbocyclyl, or $C_{1-6}$alkylene-heteroaryl; and $R^B$ is $C_{1-6}$ alkyl, $C_{2-6}$alkenyl, $C_{1-6}$alkylene-carbocyclyl, or $C_{1-6}$ alkylene-heteroaryl; or $R^A$ and $R^B$ are taken together to form a heterocyclyl.

In another embodiment of a compound of Formula (I), (II), (III), (III-A), or (III-B), or a pharmaceutically acceptable salt thereof, $R^A$ is H or $C_{1-6}$ alkyl.

In even another embodiment of a compound of Formula (I), (II), (III), (III-A), or (III-B), or a pharmaceutically acceptable salt thereof, $R^A$ is H.

In yet another embodiment of a compound of Formula (I), (II), (III), (III-A), or (III-B), or a pharmaceutically acceptable salt thereof, $R^A$ is $C_{1-6}$ alkyl.

In one embodiment of a compound of Formula (I), (II), (III), (III-A), or (III-B), or a pharmaceutically acceptable salt thereof, $R^A$ is-$CH_3$.

In one embodiment of a compound of Formula (I), (II), (III), (III-A), or (III-B), or a pharmaceutically acceptable salt thereof, $R^A$ is butyl. In embodiments, $R^A$ is iso-butyl.

In one embodiment of a compound of Formula (I), (II), (III), (III-A), or (III-B), or a pharmaceutically acceptable salt thereof, $R^A$ is isopropyl.

In one embodiment of a compound of Formula (I), (II), (III), (III-A), or (III-B), or a pharmaceutically acceptable salt thereof, $R^AX_3$ and $R^B$ are taken together to form an oxetanyl, thietanyl, tetrahydrofuranyl. In embodiments, $R^AX_3$ and $R^B$ are taken together to form an oxetanyl. In embodiments, $R^AX_3$ and $R^B$ are taken together to form a thietanyl. In embodiments, $R^AX_3$ and $R^B$ are taken together to form a tetrahydrofuranyl.

In embodiments of the compounds of Formula (I), (II), (III), (III-A), or (III-B), or a pharmaceutically acceptable salt thereof, $R^0$ is

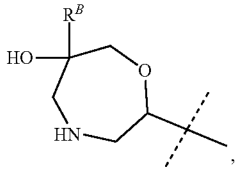
,
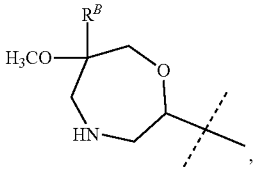
, or
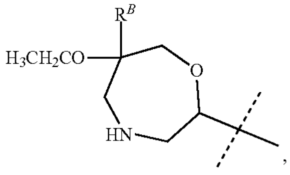
, and $R^B$ is methyl, ethyl, isopropyl,

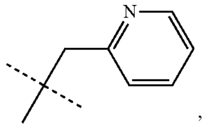
, or
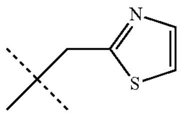
.

In another embodiment of a compound of Formula (I), (II), (III), (III-A), or (III-B), or a pharmaceutically acceptable salt thereof, $R^B$ is $C_{1-6}$ alkyl, $C_{1-6}$haloalkyl, $C_{1-6}$ alkyl-OH, $C_{2-6}$ alkenyl, cycloalkyl, $C_{1-6}$alkylene-carbocyclyl, $C_{1-6}$alkylene-aryl, $C_{1-6}$alkylene-heteroaryl, heteroaryl or carbocyclyl; or $R^A$ and $R^B$ are taken together to form a heterocyclyl.

In another embodiment of a compound of Formula (I), (II), (III), (III-A), or (III-B), or a pharmaceutically acceptable salt thereof, $R^B$ is $C_{1-6}$ alkyl, $C_{1-6}$haloalkyl, $C_{1-6}$ alkyl-OH, $C_{2-6}$alkenyl, cycloalkyl, $C_{1-6}$alkylene-carbocyclyl, $C_{1-6}$alkylene-aryl, $C_{1-6}$alkylene-heteroaryl, heteroaryl or carbocyclyl.

In another embodiment of a compound of Formula (I), (II), (III), (III-A), or (III-B), or a pharmaceutically acceptable salt thereof, $R^B$ is $C_{1-6}$ alkyl, $C_{2-6}$alkenyl, cycloalkyl, $C_{1-6}$ alkylene-carbocyclyl, $C_{1-6}$alkylene-aryl, $C_{1-6}$alkylene-heteroaryl, heteroaryl or carbocyclyl.

In another embodiment of a compound of Formula (I), (II), (III), (III-A), or (III-B), or a pharmaceutically acceptable salt thereof, $R^B$ is $C_{1-6}$ alkyl, $C_{2-6}$alkenyl, $C_{1-6}$alkylene-carbocyclyl, or $C_{1-6}$alkylene-heteroaryl.

In another embodiment of a compound of Formula (I), (II), (III), (III-A), or (III-B), or a pharmaceutically acceptable salt thereof, $R^B$ is $C_{1-6}$ alkyl, $C_{1-6}$haloalkyl, $C_{1-6}$ alkyl-OH, $C_{2-6}$alkenyl, cycloalkyl, $C_{1-6}$alkylene-carbocyclyl, $C_{1-6}$alkylene-aryl.

In embodiments of the compounds of Formula (I), (II), (III), (III-A), or (III-B), or a pharmaceutically acceptable salt thereof, $R^B$ is $C_{1-6}$ alkyl, $C_{2-6}$alkenyl, $C_{1-6}$alkylene-carbocyclyl, or $C_{1-6}$alkylene-heteroaryl.

In embodiments of the compounds of Formula (I), (II), (III), (III-A), or (III-B), or a pharmaceutically acceptable salt thereof, $R^B$ is $C_{1-6}$ alkyl, $C_{1-6}$alkylene-aryl or —$C_{1-6}$alkylene-5-6 membered heteroaryl.

In embodiments of the compounds of Formula (I), (II), (III), (III-A), or (III-B), or a pharmaceutically acceptable salt thereof, $R^B$ is $C_{1-6}$ alkyl.

In embodiments of the compounds of Formula (I), (II), (III), (III-A), or (III-B), or a pharmaceutically acceptable salt thereof, $R^B$ is $CF_3$.

In embodiments of the compounds of Formula (I), (II), (III), (III-A), or (III-B), or a pharmaceutically acceptable salt thereof, $R^B$ is isopropyl.

In embodiments of the compounds of Formula (I), (II), (III), (III-A), or (III-B), or a pharmaceutically acceptable salt thereof, $R^B$ is-$CH{=}CH_2$.

In embodiments of the compounds of Formula (I), (II), (III), (III-A), or (III-B), or a pharmaceutically acceptable salt thereof, $R^B$ is $CH_2OH$.

In embodiments of the compounds of Formula (I), (II), (III), (III-A), or (III-B), or a pharmaceutically acceptable salt thereof, $R^B$ is $CH_2$—$CH{=}CH_2$.

In embodiments of the compounds of Formula (I), (II), (III), (III-A), or (III-B), or a pharmaceutically acceptable salt thereof, $R^B$ is n-propyl.

In embodiments of the compounds of Formula (I), (II), (III), (III-A), or (III-B), $R^A$ and $R^B$ are taken together to form a heterocyclyl. In embodiments, the heterocyclyl is a 3- to 6-membered heterocyclyl. In embodiments, the heterocyclyl is oxetanyl, tetrahydrofuranyl, thietanyl, or tetrahydrothiophenyl.

In embodiments of the compounds of Formula (I), (II), (III), (III-A), or (III-B), $X_3$ is O, S, NH, N($C_{1-6}$ alkyl), $OCH_2$, $CH_2O$, $CH_2S$ or $SCH_2$.

In embodiments of the compounds of Formula (I), (II), (III), (III-A), or (III-B), $X_3$ is O, S, NH, N($C_{1-6}$ alkyl), $OCH_2$, or $SCH_2$.

In embodiments of the compounds of Formula (I), (II), (III), (III-A), or (III-B), or a pharmaceutically acceptable salt thereof, $X_3$ is O, S, NH, or N($C_{1-6}$ alkyl).

In embodiments of the compounds of Formula (I), (II), (III), (III-A), or (III-B), or a pharmaceutically acceptable salt thereof, $X_3$ is O, S, NH.

In embodiments of the compounds of Formula (I), (II), (III), (III-A), or (III-B), or a pharmaceutically acceptable salt thereof, $X_3$ is O.

In embodiments of the compounds of Formula (I), or a pharmaceutically acceptable salt thereof, L is aryl, heterocycle, heteroaryl, or

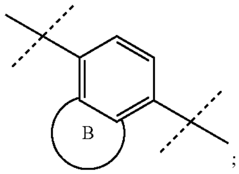

;

wherein L is independently substituted by 0-4 $R^{10}$ and wherein ring B is a carbocycle, a heterocycle or a heteroaryl.

In embodiments of the compounds of Formula (I), or a pharmaceutically acceptable salt thereof, L is aryl, heterocycle, heteroaryl, or

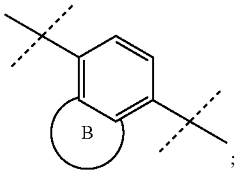

;

wherein L is independently substituted by 0-4 $R^{10}$ and wherein ring B is a carbocycle, a heterocycle containing 1-3 heteroatoms selected from N, S, and O or a heteroaryl containing 1-3 heteroatoms selected from N, S, and 0.

In embodiments of the compounds of Formula (I), or a pharmaceutically acceptable salt thereof, L is aryl, a heterocycle containing 1-3 heteroatoms selected from N, S, and O, a heteroaryl containing 1-3 heteroatoms selected from N, S, and O, or

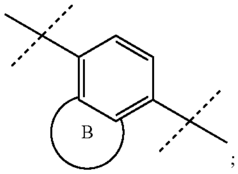

;

wherein L is independently substituted by 0-4 $R^{10}$ and wherein ring B is a carbocycle, a heterocycle containing 1-3 heteroatoms selected from N, S, and O or a heteroaryl containing 1-3 heteroatoms selected from N, S, and O.

In embodiments of the compounds of Formula (I), or a pharmaceutically acceptable salt thereof, L is aryl substituted by 0-4 $R^{10}$.

In embodiments of the compounds of Formula (I), or a pharmaceutically acceptable salt thereof, L is aryl substituted by zero (0) $R^{10}$.

In embodiments of the compounds of Formula (I), or a pharmaceutically acceptable salt thereof, L is aryl substituted by one (1) $R^{10}$.

In embodiments of the compounds of Formula (I), or a pharmaceutically acceptable salt thereof, L is aryl substituted by two (2) $R^{10}$. In embodiments of the compounds of Formula (I), L is aryl substituted by 3 $R^{10}$.

In embodiments of the compounds of Formula (I), or a pharmaceutically acceptable salt thereof, L is aryl substituted by four (4) $R^{10}$.

In embodiments of the compounds of Formula (I), or a pharmaceutically acceptable salt thereof, L is phenyl optionally substituted with fluoro. In a further embodiment of the compounds of Formula (I), L is phenyl and is substituted with fluoro.

In embodiments of the compounds of Formula (I), or a pharmaceutically acceptable salt thereof, $R^{10}$ is independently oxo, halogen, $C_{1-6}$ alkyl, $C_{1-6}$alkoxy, —S—$C_{1-6}$ alkyl, $C_{2-6}$alkenyl, $C_{2-6}$ alkynyl, $C_{3-6}$cycloalkyl, cyano, hydroxy, $NH_2$, —NH—$C_{1-6}$ alkyl, —N($C_{1-4}$ alkyl)$_2$, —COOH, —$COC_{1-6}$ alkyl, —$COOC_{1-6}$ alkyl, —$CON_{1-6}$ alkyl, —CON($C_{1-6}$ alkyl)$_2$, —$NHCOC_{1-6}$ alkyl, or a heterocycle; wherein each alkyl, alkoxy, alkenyl, alkynyl, cycloalkyl, and heterocyclic are independently optionally substituted with 1-3 substituents selected from halogen, cyano, hydroxyl, $NH_2$ and —COOH.

In embodiments of the compounds of Formula (I), or a pharmaceutically acceptable salt thereof, $R^{10}$ is independently oxo, halogen, $C_{1-6}$ alkyl, $C_{1-6}$alkoxy, —S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, —N($C_{1-4}$ alkyl)$_2$, —COOH, —COC$_{1-6}$ alkyl, —COOC$_{1-6}$ alkyl, —CON$_{1-6}$ alkyl, —CON($C_{1-6}$ alkyl)$_2$, —NHCOC$_{1-6}$ alkyl, or 4-7 membered heterocycle containing 1-3 heteroatoms selected from N, S, and O; wherein each alkyl, alkoxy, alkenyl, alkynyl, cycloalkyl, and heterocycle are independently optionally substituted with 1-3 substituents selected from halogen, cyano, hydroxyl, $NH_2$ and —COOH.

In embodiments of the compounds of Formula (I), or a pharmaceutically acceptable salt thereof, $R^{10}$ is independently halogen, $C_{1-4}$ alkyl, $C_{1-6}$alkoxy, —S—$C_{1-6}$ alkyl, cyano, hydroxy, $NH_2$, —NH—$C_{1-6}$ alkyl, —N($C_{1-6}$ alkyl)$_2$, —COOH, —COC$_{1-6}$ alkyl, —COOC$_{1-6}$ alkyl, —CON$_{1-6}$ alkyl, —CON($C_{1-6}$ alkyl)$_2$, or —NHCOC$_{1-6}$ alkyl; wherein each alkyl, and alkoxy are independently optionally substituted with 1-3 substituents selected from halogen, cyano, hydroxyl, $NH_2$ and —COOH.

In embodiments of the compounds of Formula (I), (II), (III), (III-A) or (III-B), or a pharmaceutically acceptable salt thereof, $R^{10}$ is halogen.

In embodiments of the compounds of Formula (II), (III), (III-A) or (III-B), or a pharmaceutically acceptable salt thereof, $R^{10}$ is fluoro.

In embodiments of the compounds of Formula (II), (III), or (III-A), or a pharmaceutically acceptable salt thereof, n is 0.

In embodiments of the compounds of Formula (II), (III), or (III-A), or a pharmaceutically acceptable salt thereof, n is 1.

In embodiments of the compounds of Formula (II), (III), or (III-A), or a pharmaceutically acceptable salt thereof, n is 1 and the $R^{10}$ substituent is in the position ortho to the $R^1$ substituent on the phenyl ring.

In embodiments of the compounds of Formula (II), (III), or (III-A), or a pharmaceutically acceptable salt thereof, n is 1 and the $R^{10}$ substituent is in the position meta to the $R^1$ substituent on the phenyl ring.

In embodiments of the compounds of Formula (I) or Formula (II), or a pharmaceutically acceptable salt thereof, $R^1$ is

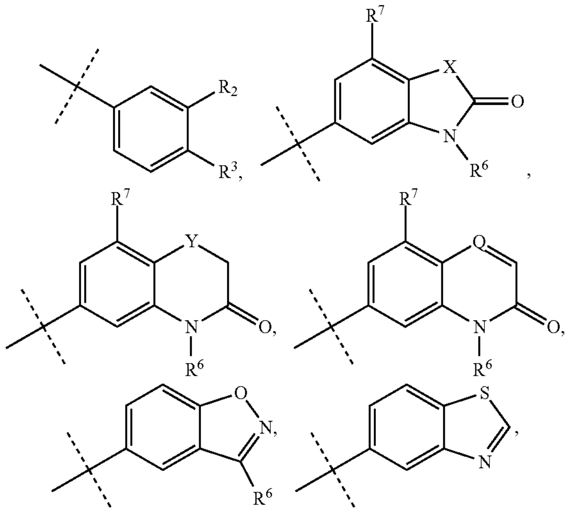

-continued

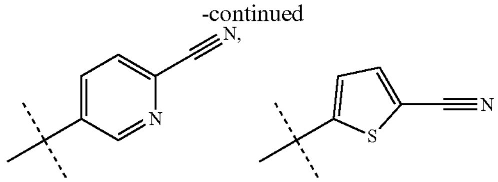

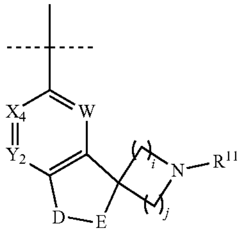

or

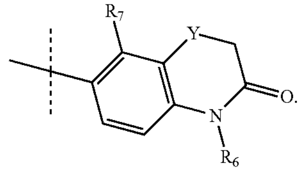

In embodiments of the compounds of Formula (I) or Formula (II), or a pharmaceutically acceptable salt thereof, $R^1$ is

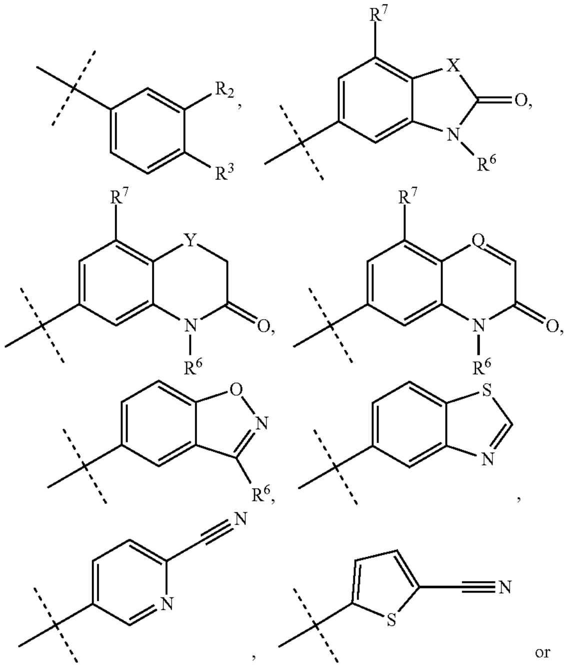

or

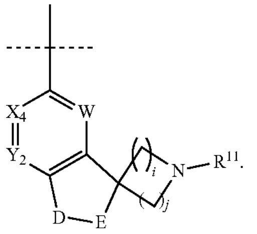

In embodiments of the compounds of Formula (I) or Formula (II), or a pharmaceutically acceptable salt thereof, $R^1$ is

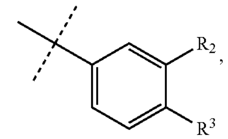

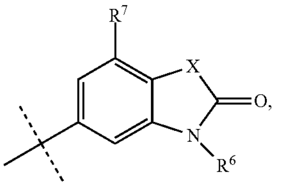

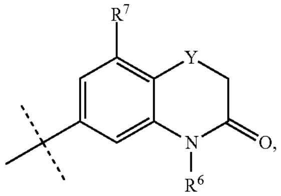

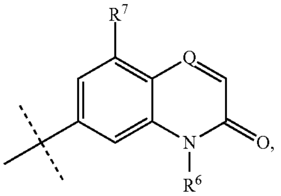

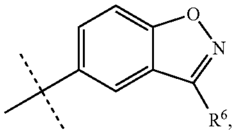

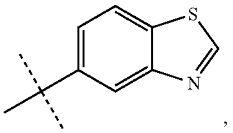

,

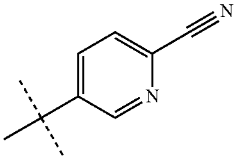

or

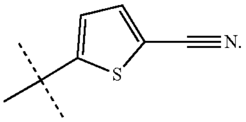

In embodiments of the compounds of Formula (I) or Formula (II), or a pharmaceutically acceptable salt thereof, $R^1$ is

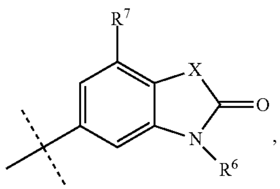

,

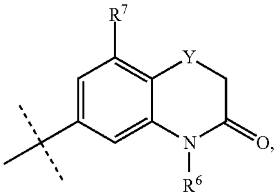

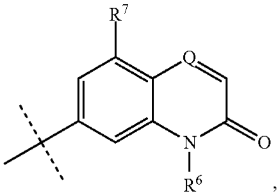

,

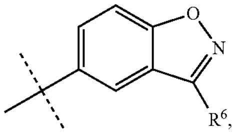

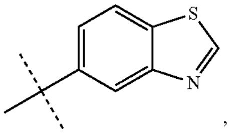

, or

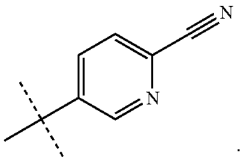

.

In embodiments of the compounds of Formula (I) or Formula (II), or a pharmaceutically acceptable salt thereof, $R^1$ is

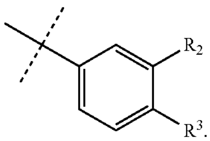

In embodiments of the compounds of Formula (I) or Formula (II), or a pharmaceutically acceptable salt thereof, $R^1$ is

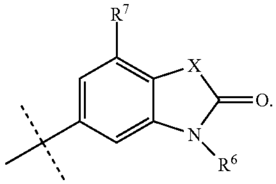

In embodiments of the compounds of Formula (I) or Formula (II), or a pharmaceutically acceptable salt thereof, $R^1$ is

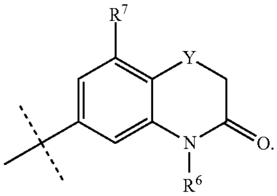

In embodiments of the compounds of Formula (I) or Formula (II), or a pharmaceutically acceptable salt thereof, $R^1$ is

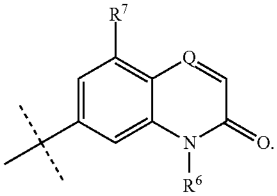

In embodiments of the compounds of Formula (I) or Formula (II), or a pharmaceutically acceptable salt thereof, $R^1$ is

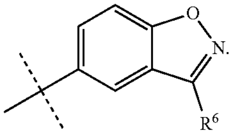

In embodiments of the compounds of Formula (I) or Formula (II), or a pharmaceutically acceptable salt thereof, $R^1$ is

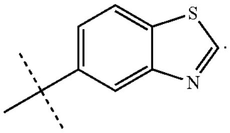

In embodiments of the compounds of Formula (I) or Formula (II), or a pharmaceutically acceptable salt thereof, $R^1$ is

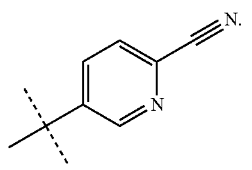

In embodiments of the compounds of Formula (I) or Formula (II), or a pharmaceutically acceptable salt thereof, $R^1$ is

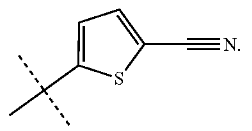

In embodiments of the compounds of Formula (I) or Formula (II), or a pharmaceutically acceptable salt thereof, $R^1$ is or

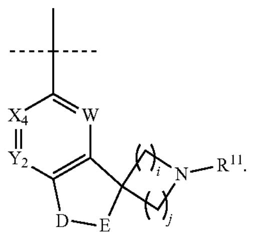

In embodiments of the compounds of Formula (I) or Formula (II), or a pharmaceutically acceptable salt or deuterated form thereof, $R^1$

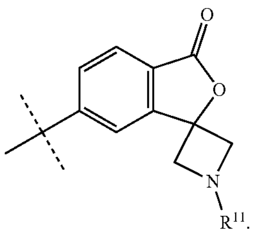

In embodiments of the compounds of Formula (I) or Formula (II), or a pharmaceutically acceptable salt or deuterated form thereof, $R^1$

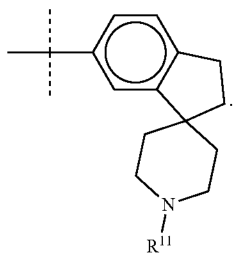

In embodiments of the compounds of Formula (I) or Formula (II), or a pharmaceutically acceptable salt thereof, $R^1$ is

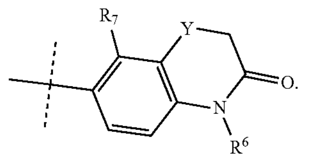

In embodiments of the compounds of Formula (I) or Formula (II), or a pharmaceutically acceptable salt thereof, $R^1$ is

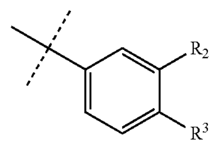

and $R^2$ is H, F, Cl, Br, $OSO_2C_{1-6}$ alkyl, or $C_{1-6}$ alkyl.

In embodiments of the compounds of Formula (I) or Formula (II), or a pharmaceutically acceptable salt thereof, $R^1$ is

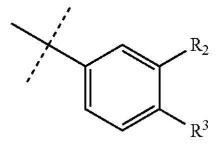

and $R^2$ is H, F, Cl or $C_{1-6}$ alkyl.

In embodiments of the compounds of Formula (I) or Formula (II), or a pharmaceutically acceptable salt thereof, $R^1$ is

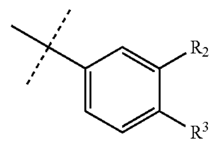

and $R^2$ is H, F or $C_{1-6}$ alkyl.

In embodiments of the compounds of Formula (I) or Formula (II), or a pharmaceutically acceptable salt thereof, $R^1$ is

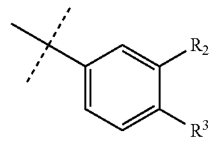

and $R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl.

In embodiments of the compounds of Formula (I) or Formula (II), or a pharmaceutically acceptable salt thereof, $R^1$ is

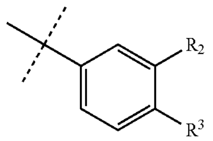

and $R^3$ is H, F, Cl, Br, CN, $CF_3$, $SO_2C_{1-6}$ alkyl, $CONH_2$ or $SO_2NR_4R^5$, wherein $R^4$ and $R^5$ together with the nitrogen atom to which they are attached form a heterocyclyl.

In embodiments of the compounds of Formula (I) or Formula (II), or a pharmaceutically acceptable salt thereof, $R^3$ is H, F, Cl, Br, CN, $CF_3$, $SO_2C_{1-6}$ alkyl, $CONH_2$ or $SO_2NR_4R^5$, wherein $R^4$ and $R^5$ together with the nitrogen atom to which they are attached form a azetidine, pyrrolidine or piperidine ring.

In embodiments of the compounds of Formula (I) or Formula (II), or a pharmaceutically acceptable salt thereof, $R^3$ is H, F, Cl, CN or $SO_2C_{1-6}$ alkyl.

In embodiments of the compounds of Formula (I) or Formula (II), or a pharmaceutically acceptable salt thereof, $R^3$ is H, F or CN.

In embodiments of the compounds of Formula (I) or Formula (II), or a pharmaceutically acceptable salt thereof, Y is O, S, or $CH_2$.

In embodiments of the compounds of Formula (I) or Formula (II), or a pharmaceutically acceptable salt thereof, Y is O or S.

In embodiments of the compounds of Formula (I) or Formula (II), or a pharmaceutically acceptable salt thereof, Q is CH or N.

In embodiments of the compounds of Formula (I) or Formula (II), or a pharmaceutically acceptable salt thereof, W, $X_4$ and $Y_2$ are each independently selected from CH and N, provided that that a maximum of one of W, $X_4$ and $Y_2$ can be N.

In embodiments of the compounds of Formula (I) or Formula (II), or a pharmaceutically acceptable salt thereof, D-E is selected from N(H)—C(O), N($C_{1-3}$-alkyl)-C(O), $CH_2CH_2$, C(O)—O and $CH_2$—O.

In embodiments of the compounds of Formula (I) or Formula (II), or a pharmaceutically acceptable salt thereof, D-E is N(H)—C(O), N($CH_3$)—C(O), $CH_2CH_2$, C(O)—O or $CH_2$—O.

In embodiments of the compounds of Formula (I) or Formula (II), or a pharmaceutically acceptable salt thereof, D-E is $CH_2$—O;

In embodiments of the compounds of Formula (I) or Formula (II), or a pharmaceutically acceptable salt thereof, $R^{11}$ is H, $C_{1-3}$ alkyl, alkylene-O-alkyl, or heterocyclyl.

In embodiments of the compounds of Formula (I) or Formula (II), or a pharmaceutically acceptable salt thereof, $R^{11}$ is H, alkylene-O-alkyl, or heterocyclyl.

In embodiments of the compounds of Formula (I) or Formula (II), or a pharmaceutically acceptable salt thereof, $R^{11}$ is H, $CH_3$, $CH_3OCH_2CH_2$, or heterocyclyl.

In embodiments of the compounds of Formula (I) or Formula (II), or a pharmaceutically acceptable salt thereof, $R^{11}$ is H, $CH_3OCH_2CH_2$, or heterocyclyl.

In embodiments of the compounds of Formula (I) or Formula (II), or a pharmaceutically acceptable salt thereof, $R^{11}$ is H, alkylene-O-alkyl, or oxetanyl, tetrahydrofuranyl, 4-tetrahydropyranyl or 3-tetrahydropyranyl.

In embodiments of the compounds of Formula (I) or Formula (II), or a pharmaceutically acceptable salt thereof, $R^{11}$ is H, $C_{1-3}$-alkyl, $CH_3OCH_2CH_2$, oxetanyl, tetrahydrofuranyl, 4-tetrahydropyranyl or 3-tetrahydropyranyl.

In embodiments of the compounds of Formula (I) or Formula (II), or a pharmaceutically acceptable salt thereof, $R^{11}$ is H, $CH_3$— or oxetanyl.

In embodiments of the compounds of Formula (I) or Formula (II), or a pharmaceutically acceptable salt thereof, $R^{11}$ is $CH_3$.

In embodiments of the compounds of Formula (I) or Formula (II), or a pharmaceutically acceptable salt thereof, i and j are each independently 1, 2 or 3; provided that the sum of i+j is 2, 3 or 4.

In embodiments of the compounds of Formula (I) or Formula (II), or a pharmaceutically acceptable salt thereof, $R^{11}$ is H, $CH_3$ or oxetanyl; W is CH or N; $X_4$ is CH or N; $Y_2$ is CH; provided that a maximum of one of W, X and Y can be N; D-E is selected from N($CH_3$)—C(O), $CH_2CH_2$, C(O)—O and $CH_2$—O; i is 1 or 2 and j is 1 or 2 provided that the sum of i+j is 2, 3 or 4.

In embodiments of the compounds of Formula (I), (II), (III), (III-A), or (III-B), or a pharmaceutically acceptable salt thereof, $R^6$ is $C_{1-6}$ alkyl, wherein the $C_{1-6}$ alkyl is optionally substituted by 1, 2 or 3 F, OH, $OC_{1-6}$ alkyl, N($C_{1-6}$ alkyl)$_2$, cycloalkyl, or heterocyclyl. In embodiments, cycloalkyl is cyclopropyl. In embodiments, heterocyclyl is tetrahydropyran.

In embodiments of the compounds of Formula (I), (II), (III), (III-A), or (III-B), or a pharmaceutically acceptable salt thereof, $R^6$ is $C_{1-6}$ alkyl wherein said $C_{1-6}$ alkyl is optionally substituted by 1, 2 or 3 F.

In embodiments of the compounds of Formula (I), (II), (III), (III-A), or (III-B), or a pharmaceutically acceptable salt thereof, $R^6$ is methyl or ethyl.

In embodiments of the compounds of Formula (I), (II), (III), (III-A), or (III-B), or a pharmaceutically acceptable salt thereof, $R^6$ is $CH_2CH_3$ or $CH_3$.

In embodiments of the compounds of Formula (I), (II), (III), (III-A), or (III-B), or a pharmaceutically acceptable salt thereof, $R^6$ is $CH_2CH_3$.

In embodiments of the compounds of Formula (I), (II), (III), (III-A), or (III-B), or a pharmaceutically acceptable salt thereof, $R^6$ is $CH_3$.

In embodiments of the compounds of Formula (I), (II), (III), (III-A), or (III-B), or a pharmaceutically acceptable salt thereof, $R^7$ is H, F, Cl or $CH_3$.

In embodiments of the compounds of Formula (I), (II), (III), (III-A), or (III-B), or a pharmaceutically acceptable salt thereof, $R^7$ is H.

In embodiments of the compounds of Formula (I), (II), (III), (III-A), or (III-B), or a pharmaceutically acceptable salt thereof, X is O, S or $CF_2$.

In embodiments of the compounds of Formula (I), (II), (III), (III-A), or (III-B), or a pharmaceutically acceptable salt thereof, X is O.

In embodiments of the compounds of Formula (I), or a pharmaceutically acceptable salt thereof, $R^1$ is

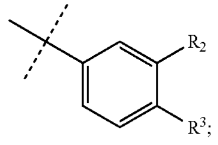

or a pharmaceutically acceptable salt thereof, $R^2$ is H, F, Cl, Br, $OSO_2C_{1-3}$ alkyl or $C_{1-3}$ alkyl; $R^3$ is selected from hydrogen, F, Cl, Br, CN, $CF_3$, $SO_2C_{1-3}$ alkyl, $CONH_2$ or $SO_2NR^4N^5$, wherein $R^4$ and $R^5$ together with the nitrogen atom to which they are attached form a azetidine, pyrrolidine or piperidine ring.

In embodiments of the compounds of Formula (I), or a pharmaceutically acceptable salt thereof, $R^1$ is

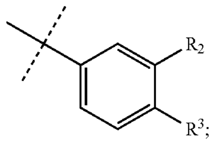

or a pharmaceutically acceptable salt thereof, $R^2$ is H, F, Cl or $C_{1-3}$ alkyl; $R^3$ is H, F, Cl, CN or $SO_2C_{1-3}$ alkyl.

In embodiments of the compounds described herein, or a pharmaceutically acceptable salt thereof, $R^1$ is

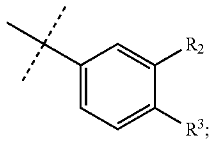

$R^2$ is H, F or $C_{1-3}$ alkyl; $R^3$ is H, F or CN.

In embodiments of the compounds of Formula (I), or a pharmaceutically acceptable salt thereof, $R^1$ is

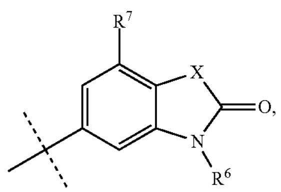
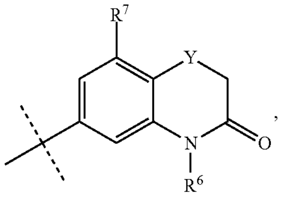
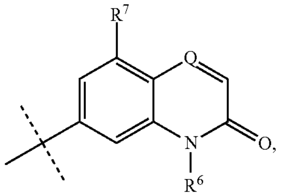
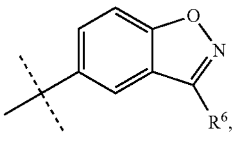
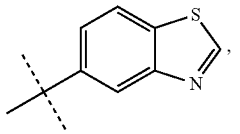
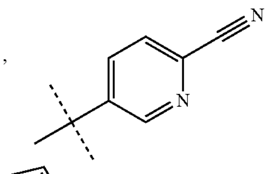

or

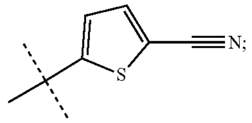

X is O, S or $CF_2$;

Y is O or S;

Q is CH or N;

$R^6$ is $C_{1-3}$ alkyl, optionally substituted by 1, 2 or 3 F, OH, $OC_{1-3}$ alkyl, $N(C_{1-3}$ alkyl$)_2$, cycloalkyl, or heterocyclyl;

$R^7$ is H, F, Cl or $CH_3$.

In embodiments of the compounds of Formula (I), or a pharmaceutically acceptable salt thereof, $R^1$ is

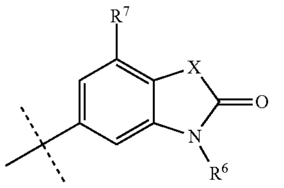

or

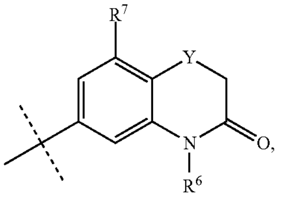

X is O, S or $CF_2$; Y is O or S; $R^6$ is $C_{1-3}$ alkyl, wherein said $C_{1-3}$ alkyl is optionally substituted by 1, 2 or 3 F, OH, $OC_{1-3}$ alkyl, $N(C_{1-3}$ alkyl$)_2$, cyclopropyl, or tetrahydropyran; $R^7$ is hydrogen, F, Cl or $CH_3$.

In embodiments of the compounds of Formula (I), (II), (III), (III-A), or (III-B), or a pharmaceutically acceptable salt thereof, $R^1$ is

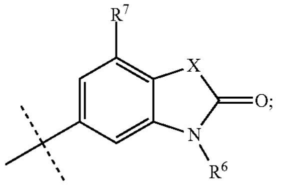

X is O, S or $CF_2$;

$R^6$ is $C_{1-3}$ alkyl, wherein said $C_{1-3}$ alkyl is optionally substituted by 1, 2 or 3 F;

$R^7$ is hydrogen, F, Cl or $CH_3$.

In embodiments of the compounds of Formula (I), (II), (III), (III-A), or (III-B), or a pharmaceutically acceptable salt thereof, $R^1$ is

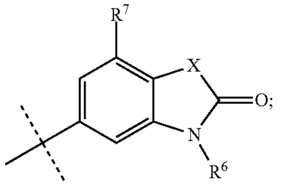

X is O;

$R^6$ is $C_{1-3}$ alkyl, wherein said $C_{1-3}$ alkyl is optionally substituted by 1, 2 or 3 F;

$R^7$ is hydrogen.

Another embodiment is a product obtainable by any of the processes or examples disclosed herein.

In embodiments, provided herein is a compound of Formula (I), (II) or (III), (III-A), or (III-B) or a stereoisomer thereof, or a pharmaceutically acceptable salt thereof.

In embodiments, provided herein is a pharmaceutically acceptable salt of a compound of Formula (I), (II) or (III), (III-A), or (III-B). Further embodiments of the disclosure relate to a deuterated compound of Formula (I), (II) or (III), (III-A), or (III-B), or a pharmaceutically acceptable salt thereof.

In embodiments, provided herein is a compound in Table 1, or a pharmaceutically acceptable salt thereof, or stereoisomer thereof.

In embodiments, provided herein is a compound in Table 1, or a pharmaceutically acceptable salt thereof.

In one embodiment, provided herein is a compound set forth in Table 1.

In some embodiments, provided herein is a pharmaceutically acceptable salt of a compound in Table 1.

TABLE 1

| Various compounds of the invention |
| --- |
| 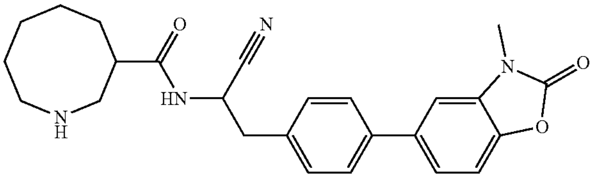 [SMILES: Cn1c(=O)oc2ccc(-c3ccc(CC(C#N)NC(=O)C4CCCCCNC4)cc3)cc21] |
| 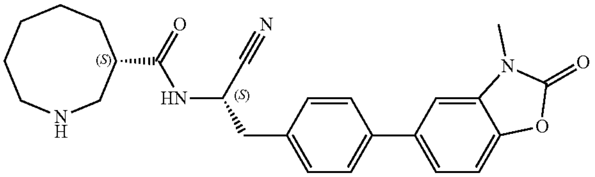 |
| 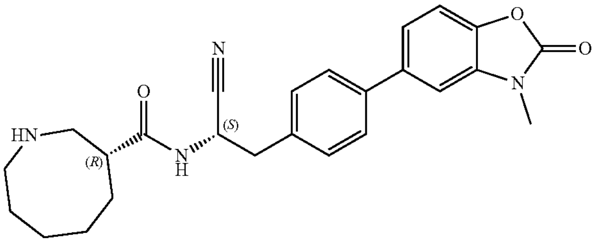 |
| 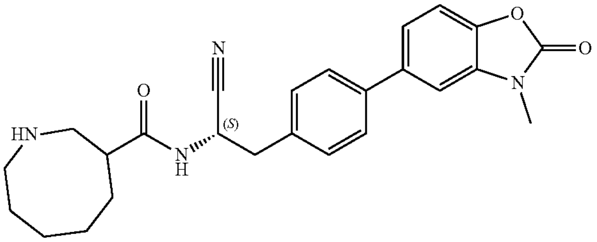 |
| 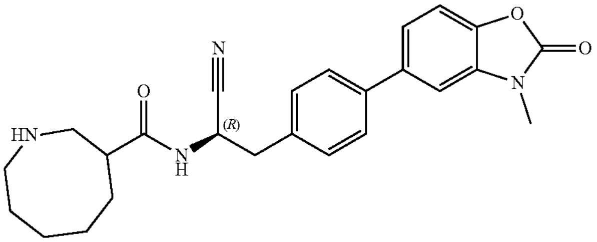 |
| 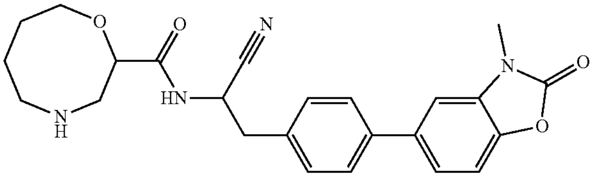 [SMILES: Cn1c(=O)oc2ccc(-c3ccc(CC(C#N)NC(=O)C4CNCCCCO4)cc3)cc21] |

TABLE 1-continued
| Various compounds of the invention |
| --- |
| 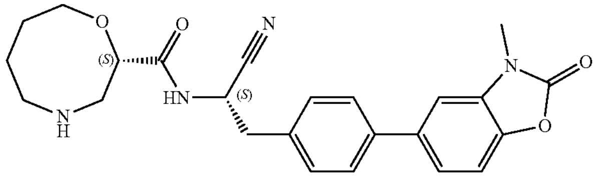 |
| 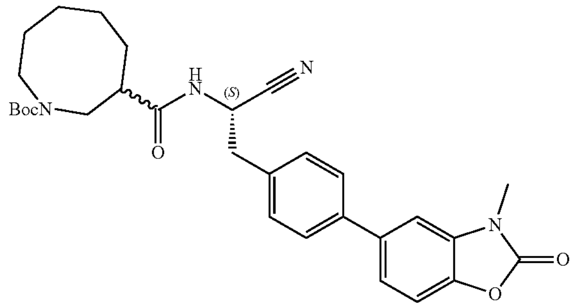 |
| 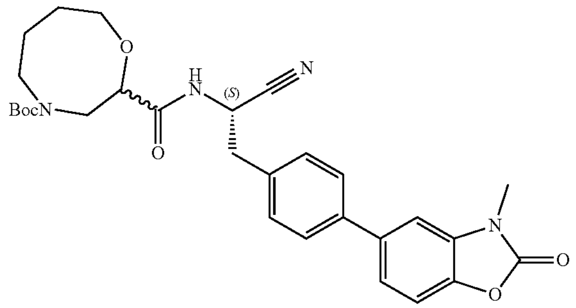 |
| 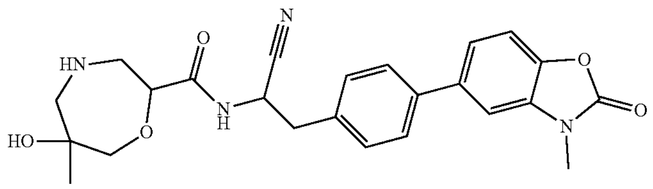 [SMILES: Cn1c(=O)oc2ccc(-c3ccc(CC(C#N)NC(=O)C4CNCC(C)(O)CO4)cc3)cc21] |
| 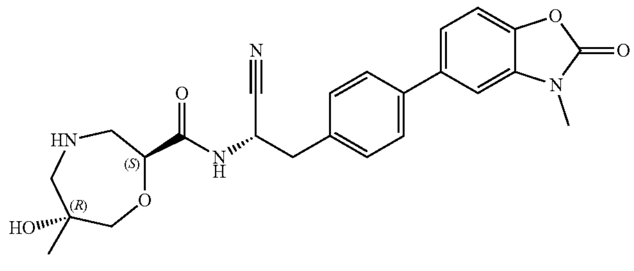 |
| 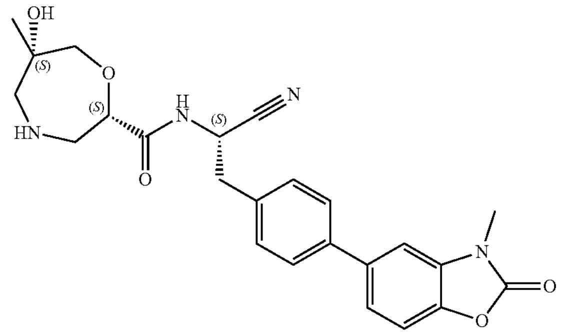 |

TABLE 1-continued
| Various compounds of the invention |
| --- |
| 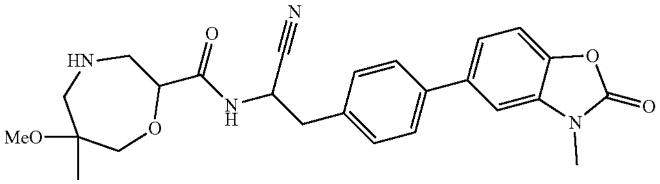 [SMILES: COC1(C)CNCC(C(=O)NC(C#N)Cc2ccc(-c3ccc4oc(=O)n(C)c4c3)cc2)OC1] |
| 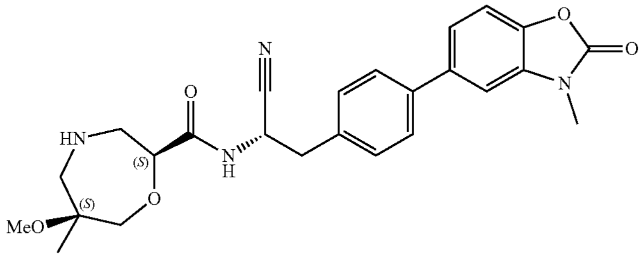 |
| 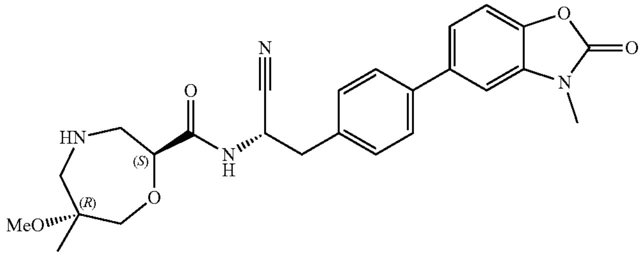 |
| 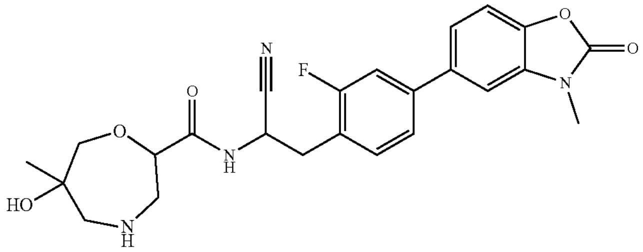 [SMILES: Cn1c(=O)oc2ccc(-c3ccc(CC(C#N)NC(=O)C4CNCC(C)(O)CO4)c(F)c3)cc21] |
| 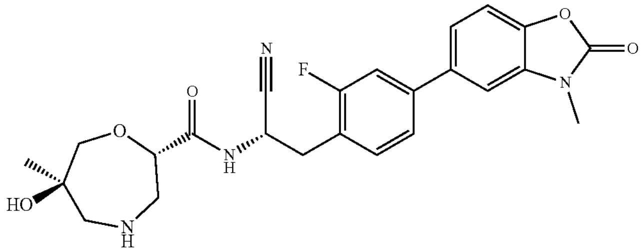 [SMILES: Cn1c(=O)oc2ccc(-c3ccc(C[C@@H](C#N)NC(=O)[C@@H]4CNC[C@@](C)(O)CO4)c(F)c3)cc21] |
| 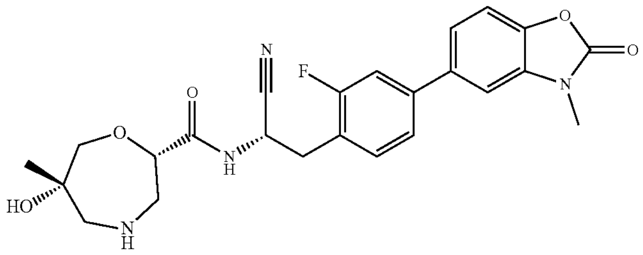 [SMILES: Cn1c(=O)oc2ccc(-c3ccc(C[C@@H](C#N)NC(=O)[C@@H]4CNC[C@](C)(O)CO4)c(F)c3)cc21] |

TABLE 1-continued
| Various compounds of the invention |
| --- |
| 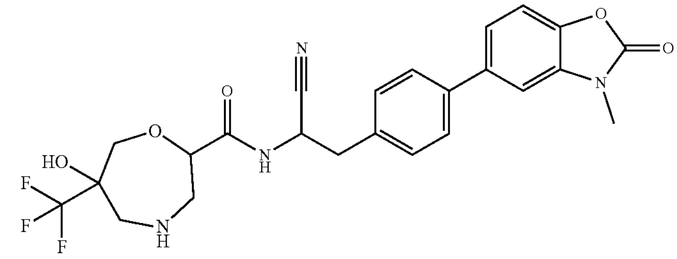 [SMILES: Cn1c(=O)oc2ccc(-c3ccc(CC(C#N)NC(=O)C4CNCC(O)(C(F)(F)F)CO4)cc3)cc21] |
| 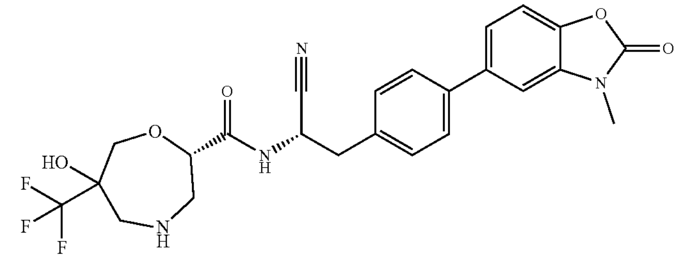 [SMILES: Cn1c(=O)oc2ccc(-c3ccc(C[C@@H](C#N)NC(=O)[C@@H]4CNCC(O)(C(F)(F)F)CO4)cc3)cc21] |
| 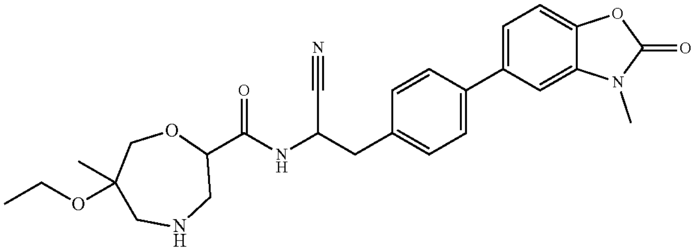 [SMILES: CCOC1(C)CNCC(C(=O)NC(C#N)Cc2ccc(-c3ccc4oc(=O)n(C)c4c3)cc2)OC1] |
| 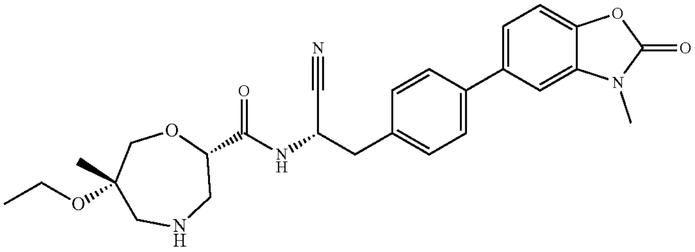 [SMILES: CCO[C@@]1(C)CNC[C@@H](C(=O)N[C@H](C#N)Cc2ccc(-c3ccc4oc(=O)n(C)c4c3)cc2)OC1] |
| 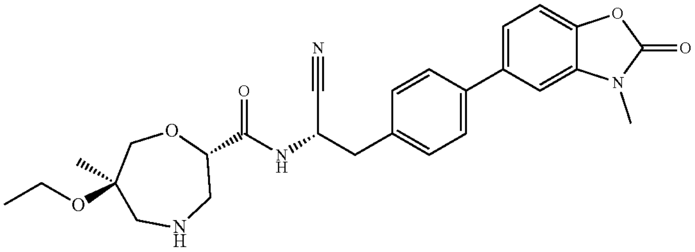 [SMILES: CCO[C@]1(C)CNC[C@@H](C(=O)N[C@H](C#N)Cc2ccc(-c3ccc4oc(=O)n(C)c4c3)cc2)OC1] |
| 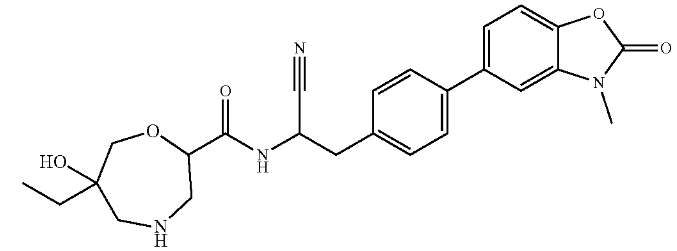 [SMILES: CCC1(O)CNCC(C(=O)NC(C#N)Cc2ccc(-c3ccc4oc(=O)n(C)c4c3)cc2)OC1] |

TABLE 1-continued
| Various compounds of the invention |
|---|
| 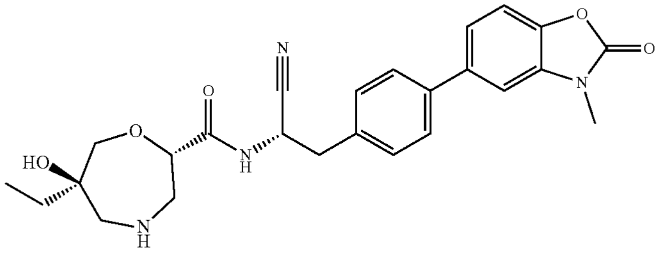 [SMILES: CC[C@@]1(O)CNC[C@@H](C(=O)N[C@H](C#N)Cc2ccc(-c3ccc4oc(=O)n(C)c4c3)cc2)OC1] |
| 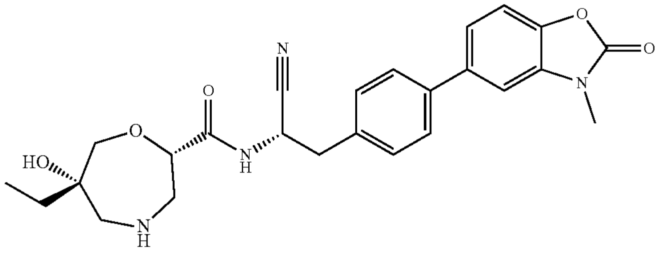 [SMILES: CC[C@]1(O)CNC[C@@H](C(=O)N[C@H](C#N)Cc2ccc(-c3ccc4oc(=O)n(C)c4c3)cc2)OC1] |
| 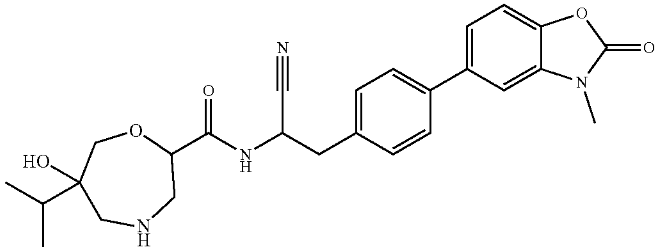 [SMILES: CC(C)C1(O)CNCC(C(=O)NC(C#N)Cc2ccc(-c3ccc4oc(=O)n(C)c4c3)cc2)OC1] |
| 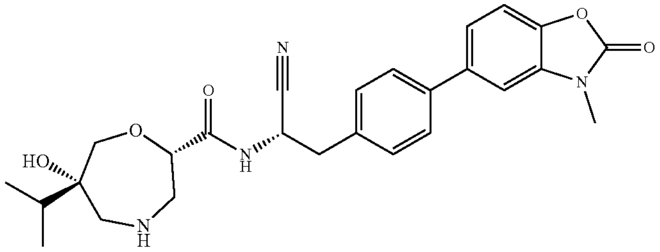 [SMILES: CC(C)[C@]1(O)CNC[C@@H](C(=O)N[C@H](C#N)Cc2ccc(-c3ccc4oc(=O)n(C)c4c3)cc2)OC1] |
| 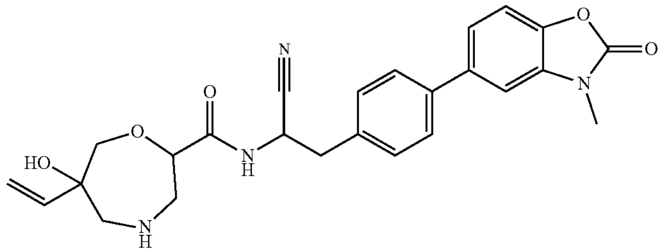 [SMILES: C=CC1(O)CNCC(C(=O)NC(C#N)Cc2ccc(-c3ccc4oc(=O)n(C)c4c3)cc2)OC1] |
| 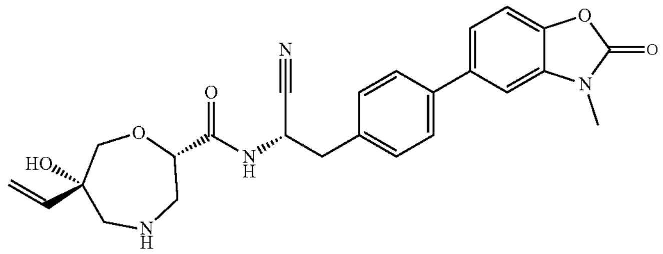 [SMILES: C=C[C@]1(O)CNC[C@@H](C(=O)N[C@H](C#N)Cc2ccc(-c3ccc4oc(=O)n(C)c4c3)cc2)OC1] |

TABLE 1-continued
| Various compounds of the invention |
| --- |
| 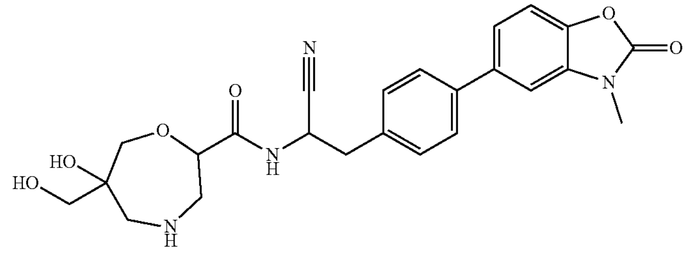 [SMILES: Cn1c(=O)oc2ccc(-c3ccc(CC(C#N)NC(=O)C4CNCC(O)(CO)CO4)cc3)cc21] |
| 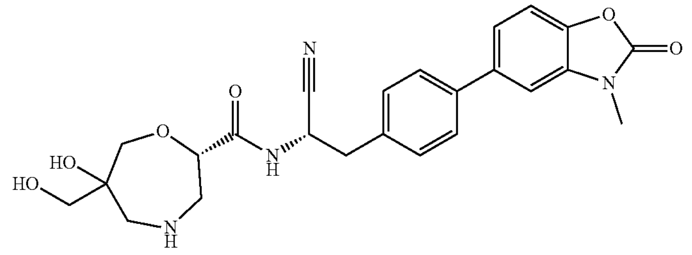 [SMILES: Cn1c(=O)oc2ccc(-c3ccc(C[C@@H](C#N)NC(=O)[C@@H]4CNCC(O)(CO)CO4)cc3)cc21] |
| 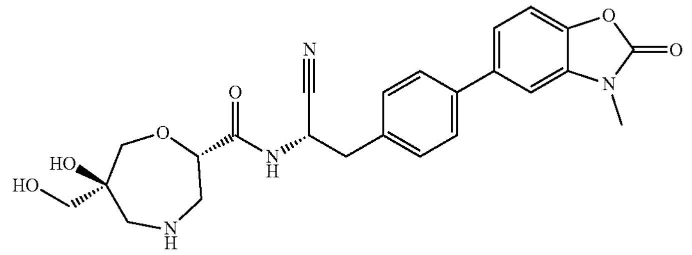 [SMILES: Cn1c(=O)oc2ccc(-c3ccc(C[C@@H](C#N)NC(=O)[C@@H]4CNC[C@](O)(CO)CO4)cc3)cc21] |
| 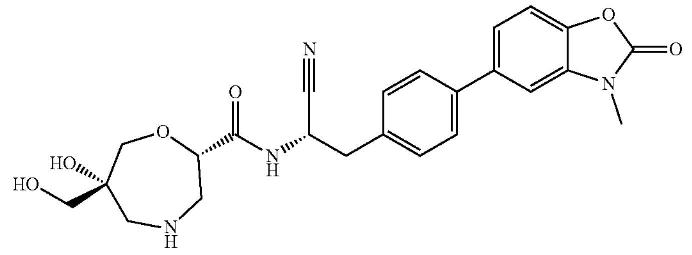 [SMILES: Cn1c(=O)oc2ccc(-c3ccc(C[C@@H](C#N)NC(=O)[C@@H]4CNC[C@@](O)(CO)CO4)cc3)cc21] |
| 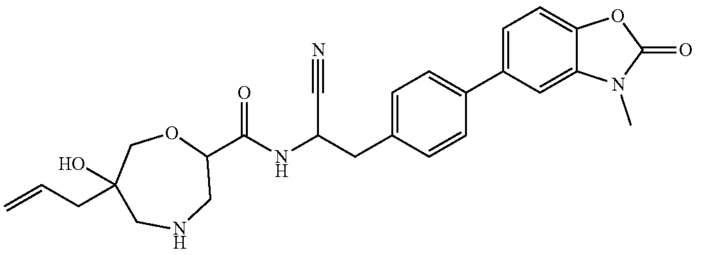 [SMILES: C=CCC1(O)CNCC(C(=O)NC(C#N)Cc2ccc(-c3ccc4oc(=O)n(C)c4c3)cc2)OC1] |
| 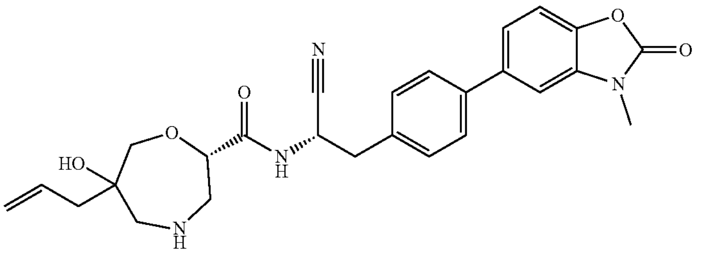 [SMILES: C=CCC1(O)CNC[C@@H](C(=O)N[C@H](C#N)Cc2ccc(-c3ccc4oc(=O)n(C)c4c3)cc2)OC1] |

TABLE 1-continued
| Various compounds of the invention |
| --- |
| 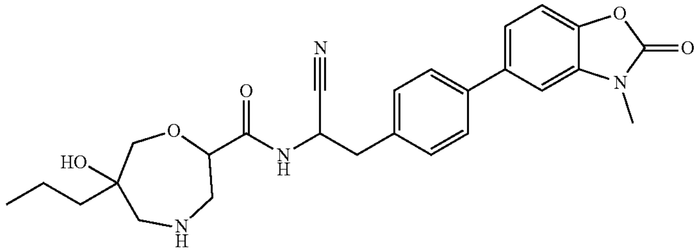 [SMILES: CCCC1(O)CNCC(C(=O)NC(C#N)Cc2ccc(-c3ccc4oc(=O)n(C)c4c3)cc2)OC1] |
| 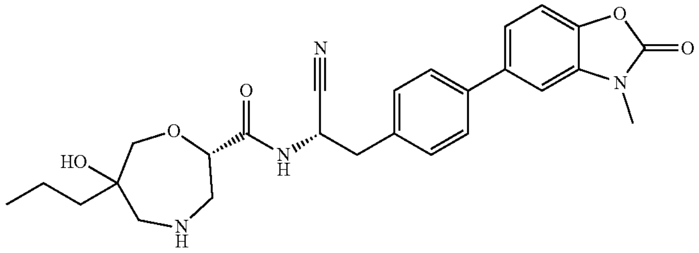 [SMILES: CCCC1(O)CNC[C@@H](C(=O)N[C@H](C#N)Cc2ccc(-c3ccc4oc(=O)n(C)c4c3)cc2)OC1] |
| 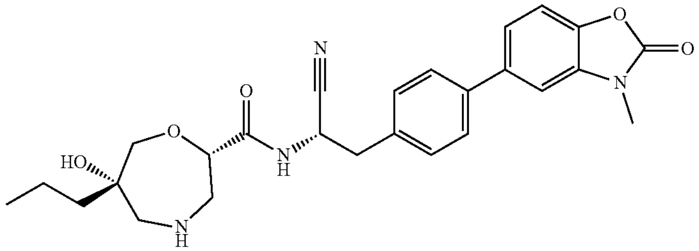 [SMILES: CCC[C@]1(O)CNC[C@@H](C(=O)N[C@H](C#N)Cc2ccc(-c3ccc4oc(=O)n(C)c4c3)cc2)OC1] |
| 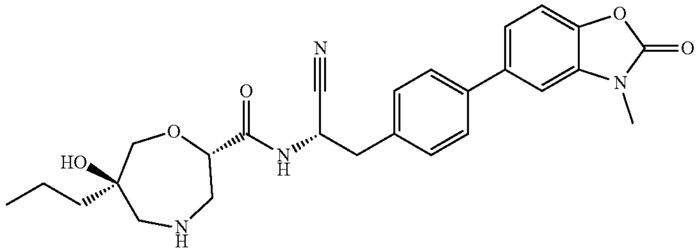 [SMILES: CCC[C@@]1(O)CNC[C@@H](C(=O)N[C@H](C#N)Cc2ccc(-c3ccc4oc(=O)n(C)c4c3)cc2)OC1] |
| 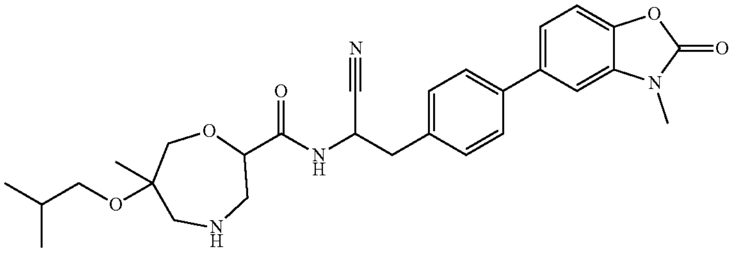 [SMILES: CC(C)COC1(C)CNCC(C(=O)NC(C#N)Cc2ccc(-c3ccc4oc(=O)n(C)c4c3)cc2)OC1] |
| 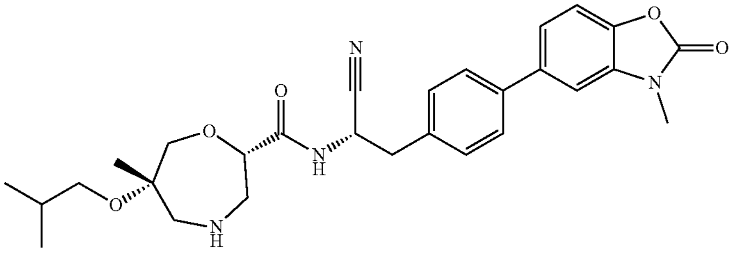 [SMILES: CC(C)CO[C@@]1(C)CNC[C@@H](C(=O)N[C@H](C#N)Cc2ccc(-c3ccc4oc(=O)n(C)c4c3)cc2)OC1] |

TABLE 1-continued
| Various compounds of the invention |
| --- |
| 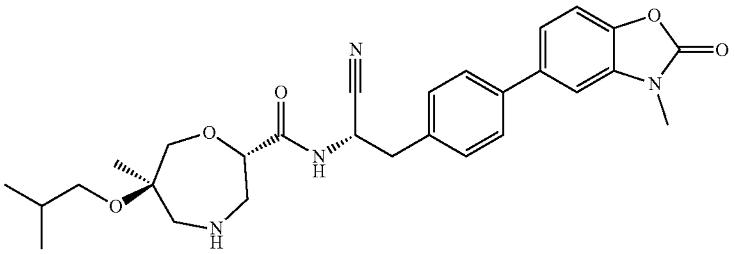 [SMILES: CC(C)CO[C@]1(C)CNC[C@@H](C(=O)N[C@H](C#N)Cc2ccc(-c3ccc4oc(=O)n(C)c4c3)cc2)OC1] |
| 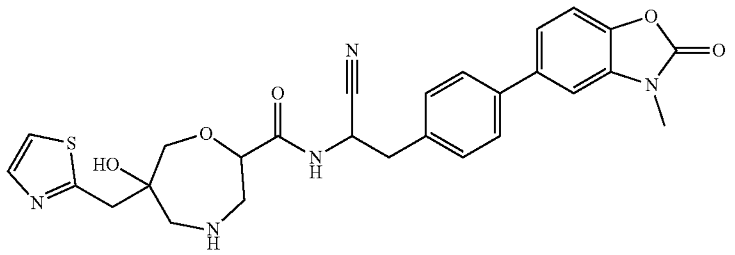 [SMILES: Cn1c(=O)oc2ccc(-c3ccc(CC(C#N)NC(=O)C4CNCC(O)(Cc5nccs5)CO4)cc3)cc21] |
| 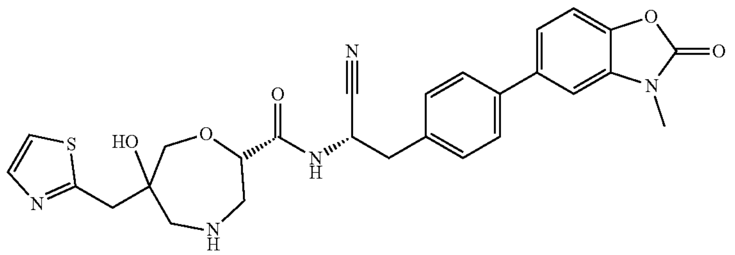 |
| 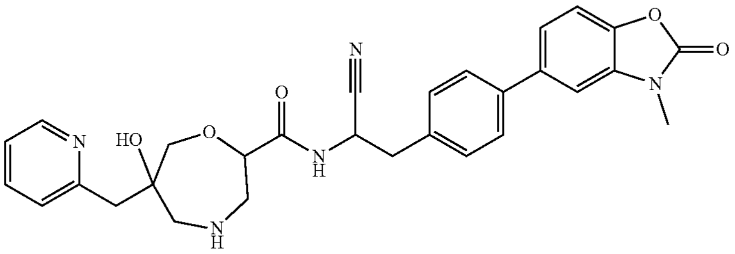 [SMILES: Cn1c(=O)oc2ccc(-c3ccc(CC(C#N)NC(=O)C4CNCC(O)(Cc5ccccn5)CO4)cc3)cc21] |
| 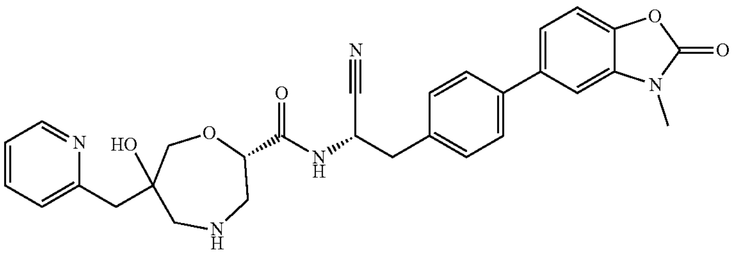 [SMILES: Cn1c(=O)oc2ccc(-c3ccc(C[C@@H](C#N)NC(=O)[C@@H]4CNCC(O)(Cc5ccccn5)CO4)cc3)cc21] |
| 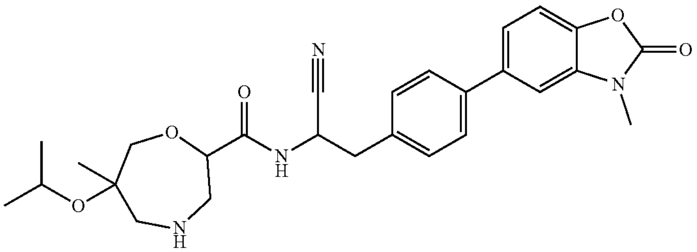 [SMILES: CC(C)OC1(C)CNCC(C(=O)NC(C#N)Cc2ccc(-c3ccc4oc(=O)n(C)c4c3)cc2)OC1] |

TABLE 1-continued
| Various compounds of the invention |
|---|
| 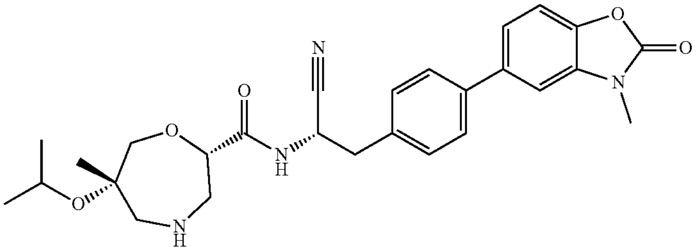 [SMILES: CC(C)O[C@@]1(C)CNC[C@@H](C(=O)N[C@H](C#N)Cc2ccc(-c3ccc4oc(=O)n(C)c4c3)cc2)OC1] |
| 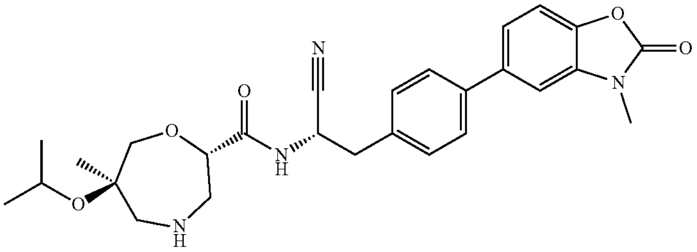 [SMILES: CC(C)O[C@]1(C)CNC[C@@H](C(=O)N[C@H](C#N)Cc2ccc(-c3ccc4oc(=O)n(C)c4c3)cc2)OC1] |
| 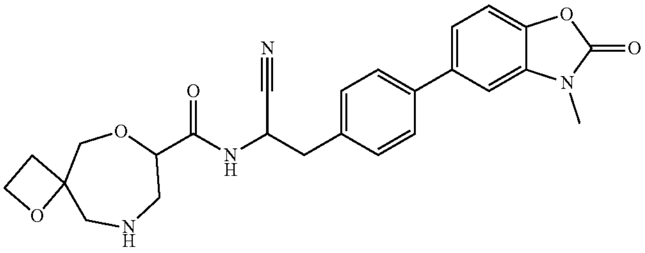 |
| 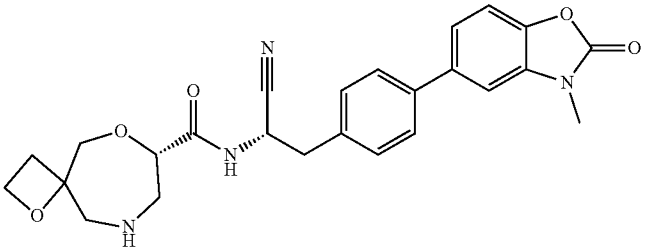 [SMILES: Cn1c(=O)oc2ccc(-c3ccc(C[C@@H](C#N)NC(=O)[C@@H]4CNCC5(CCO5)CO4)cc3)cc21] |
| 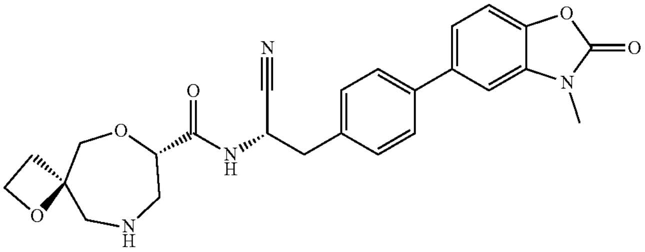 [SMILES: Cn1c(=O)oc2ccc(-c3ccc(C[C@@H](C#N)NC(=O)[C@@H]4CNC[C@]5(CCO5)CO4)cc3)cc21] |
| 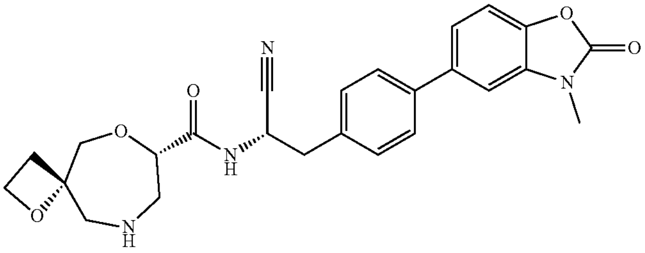 [SMILES: Cn1c(=O)oc2ccc(-c3ccc(C[C@@H](C#N)NC(=O)[C@@H]4CNC[C@@]5(CCO5)CO4)cc3)cc21] |

TABLE 1-continued
| Various compounds of the invention |
|---|
| 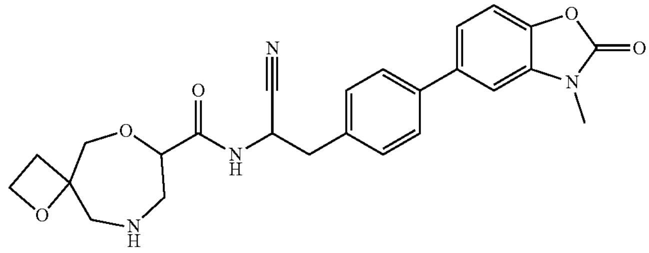 [SMILES: Cn1c(=O)oc2ccc(-c3ccc(CC(C#N)NC(=O)C4CNCC5(CCO5)CO4)cc3)cc21] |
| 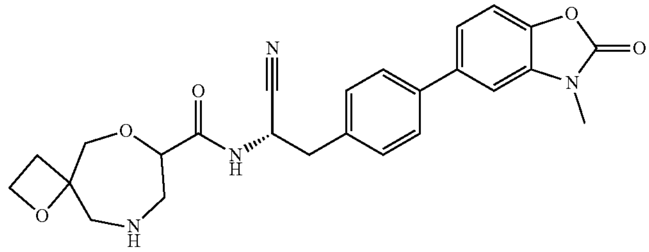 [SMILES: Cn1c(=O)oc2ccc(-c3ccc(C[C@@H](C#N)NC(=O)C4CNCC5(CCO5)CO4)cc3)cc21] |
| 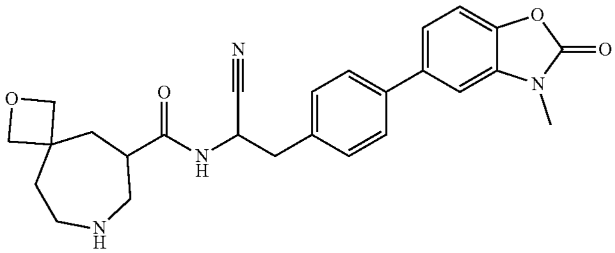 [SMILES: Cn1c(=O)oc2ccc(-c3ccc(CC(C#N)NC(=O)C4CNCCC5(COC5)C4)cc3)cc21] |
| 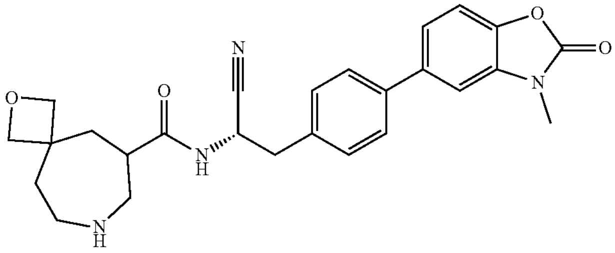 [SMILES: Cn1c(=O)oc2ccc(-c3ccc(C[C@@H](C#N)NC(=O)C4CNCCC5(COC5)C4)cc3)cc21] |
| 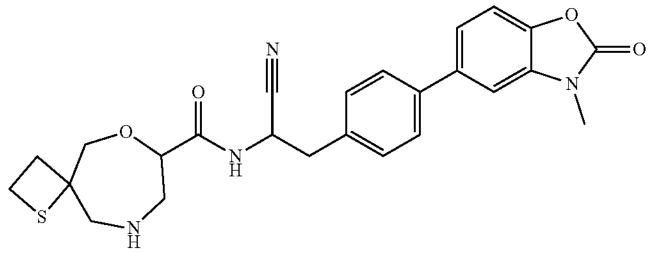 [SMILES: Cn1c(=O)oc2ccc(-c3ccc(CC(C#N)NC(=O)C4CNCC5(CCS5)CO4)cc3)cc21] |
| 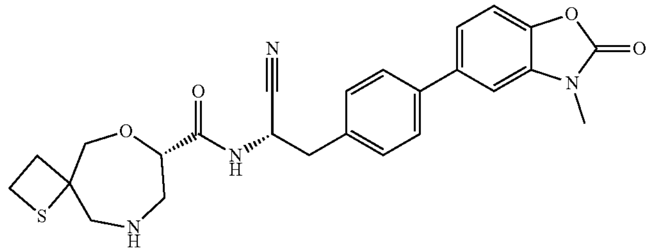 [SMILES: Cn1c(=O)oc2ccc(-c3ccc(C[C@@H](C#N)NC(=O)[C@@H]4CNCC5(CCS5)CO4)cc3)cc21] |

TABLE 1-continued
| Various compounds of the invention |
| --- |
| 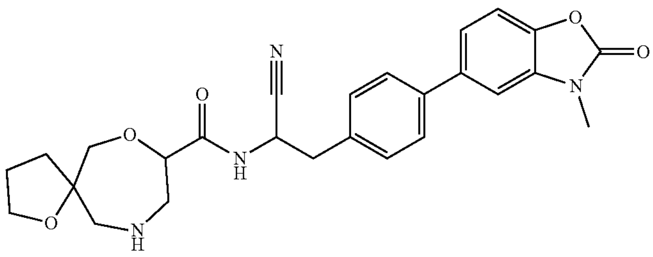 |
| 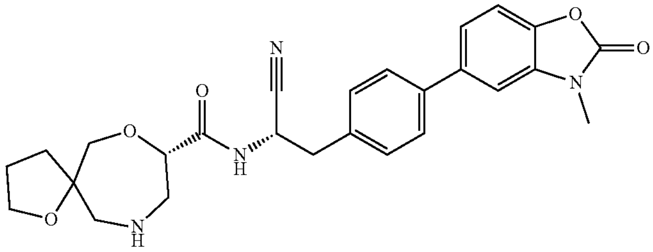 [SMILES: Cn1c(=O)oc2ccc(-c3ccc(C[C@@H](C#N)NC(=O)[C@@H]4CNCC5(CCCO5)CO4)cc3)cc21] |
| 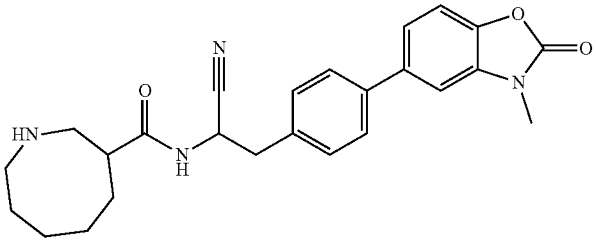 |
| 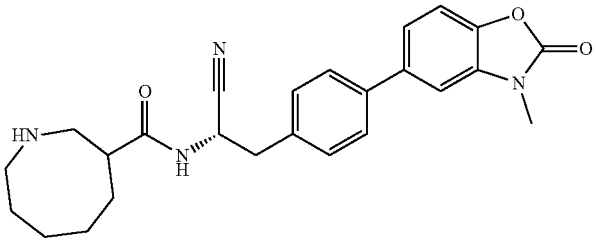 [SMILES: Cn1c(=O)oc2ccc(-c3ccc(C[C@@H](C#N)NC(=O)C4CCCCCNC4)cc3)cc21] |
| 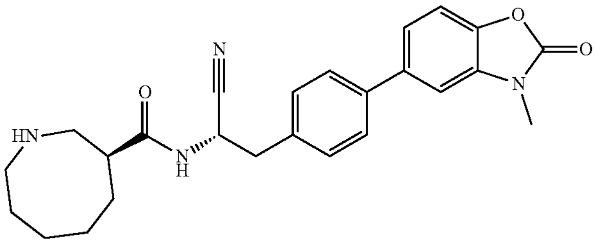 [SMILES: Cn1c(=O)oc2ccc(-c3ccc(C[C@@H](C#N)NC(=O)[C@H]4CCCCCNC4)cc3)cc21] |
| 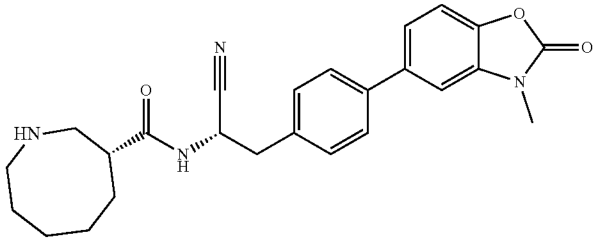 [SMILES: Cn1c(=O)oc2ccc(-c3ccc(C[C@@H](C#N)NC(=O)[C@@H]4CCCCCNC4)cc3)cc21]

TABLE 1-continued
| Various compounds of the invention |
|---|
| 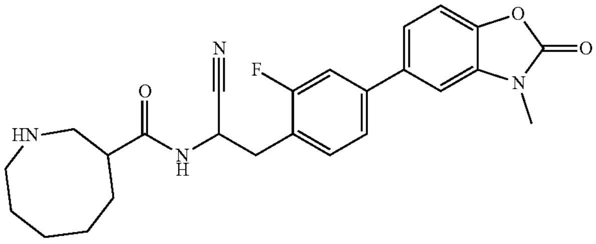 |
| 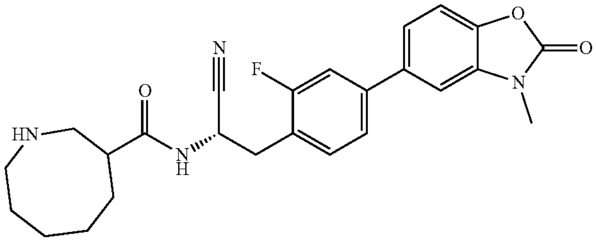 [SMILES: Cn1c(=O)oc2ccc(-c3ccc(C[C@@H](C#N)NC(=O)C4CCCCCNC4)c(F)c3)cc21] |
| 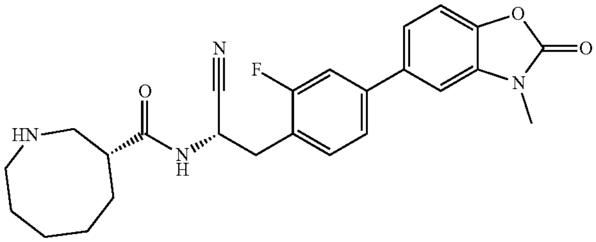 |
| 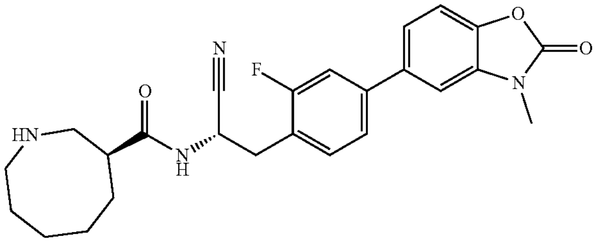 [SMILES: Cn1c(=O)oc2ccc(-c3ccc(C[C@@H](C#N)NC(=O)[C@H]4CCCCCNC4)c(F)c3)cc21] |
| 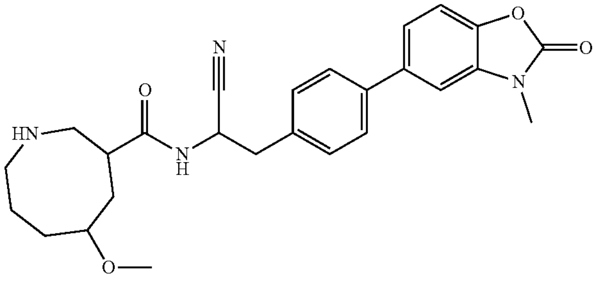 [SMILES: COC1CCCNCC(C(=O)NC(C#N)Cc2ccc(-c3ccc4oc(=O)n(C)c4c3)cc2)C1] |
| 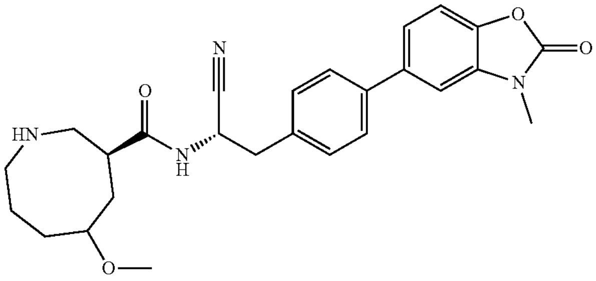 [SMILES: COC1CCCNC[C@@H](C(=O)N[C@H](C#N)Cc2ccc(-c3ccc4oc(=O)n(C)c4c3)cc2)C1] |

TABLE 1-continued
| Various compounds of the invention |
| --- |
| 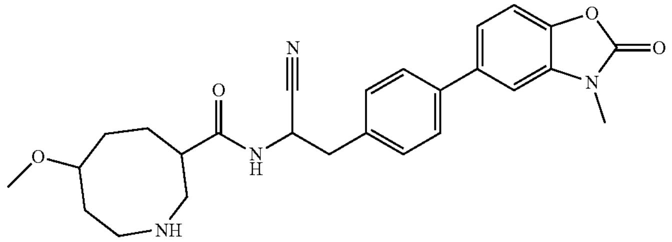 [SMILES: COC1CCNCC(C(=O)NC(C#N)Cc2ccc(-c3ccc4oc(=O)n(C)c4c3)cc2)CC1] |
| 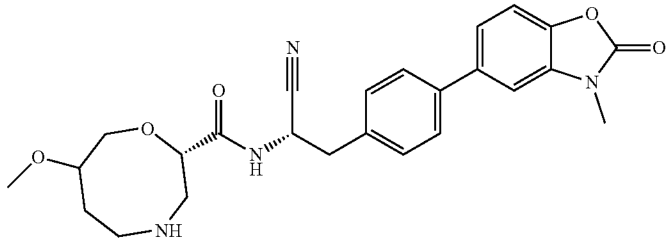 [SMILES: COC1CCNC[C@@H](C(=O)N[C@H](C#N)Cc2ccc(-c3ccc4oc(=O)n(C)c4c3)cc2)OC1] |
| 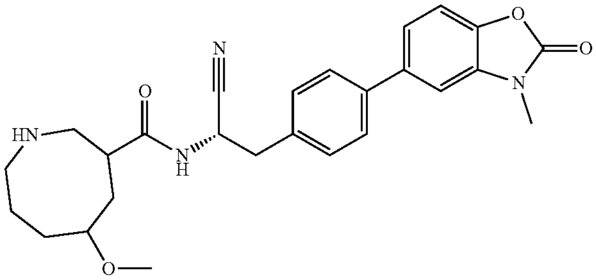 [SMILES: COC1CCCNCC(C(=O)N[C@H](C#N)Cc2ccc(-c3ccc4oc(=O)n(C)c4c3)cc2)C1] |
| 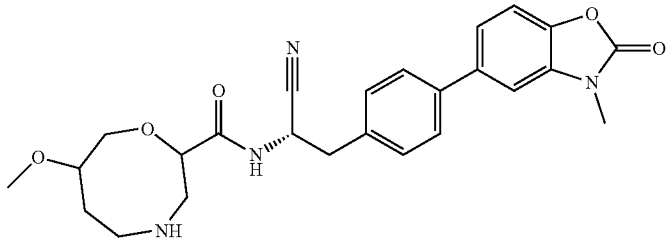 [SMILES: COC1CCNCC(C(=O)N[C@H](C#N)Cc2ccc(-c3ccc4oc(=O)n(C)c4c3)cc2)OC1] |
| 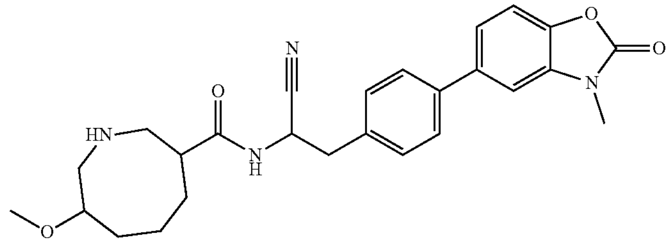 [SMILES: COC1CCCC(C(=O)NC(C#N)Cc2ccc(-c3ccc4oc(=O)n(C)c4c3)cc2)CNC1] |
| 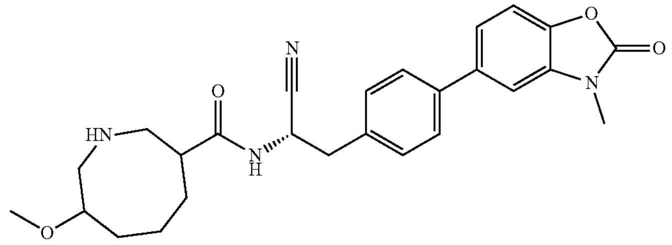 [SMILES: COC1CCCC(C(=O)N[C@H](C#N)Cc2ccc(-c3ccc4oc(=O)n(C)c4c3)cc2)CNC1] |

TABLE 1-continued
| Various compounds of the invention |
| --- |
| 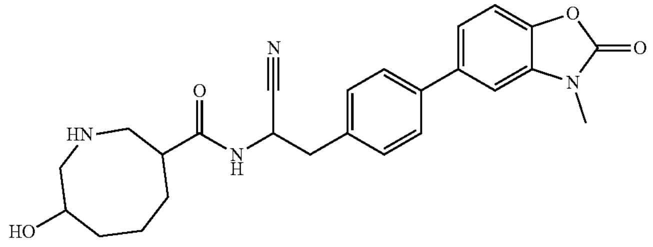 [SMILES: Cn1c(=O)oc2ccc(-c3ccc(CC(C#N)NC(=O)C4CCCC(O)CNC4)cc3)cc21] |
| 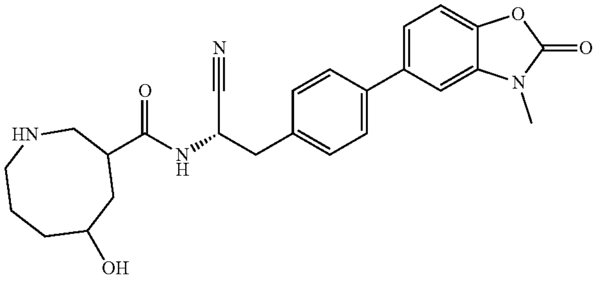 [SMILES: Cn1c(=O)oc2ccc(-c3ccc(C[C@@H](C#N)NC(=O)C4CNCCCC(O)C4)cc3)cc21] |
| 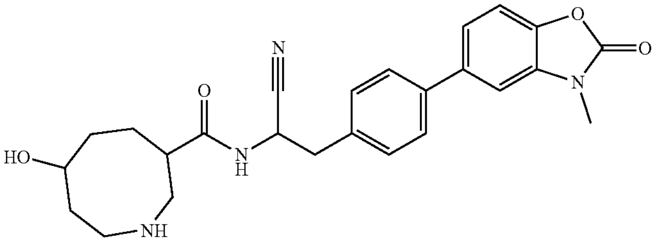 |
| 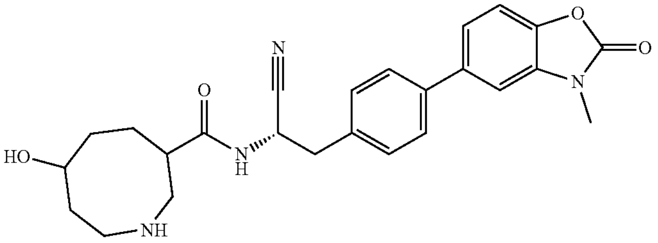 [SMILES: Cn1c(=O)oc2ccc(-c3ccc(C[C@@H](C#N)NC(=O)C4CCC(O)CCNC4)cc3)cc21] |
| 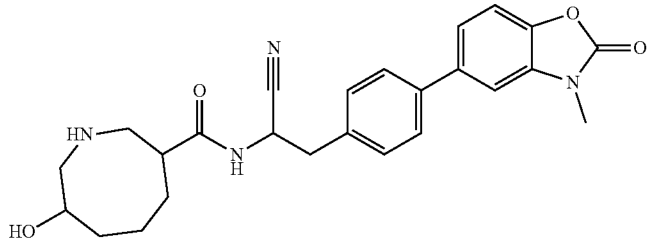 [SMILES: Cn1c(=O)oc2ccc(-c3ccc(CC(C#N)NC(=O)C4CCCC(O)CNC4)cc3)cc21] |
| 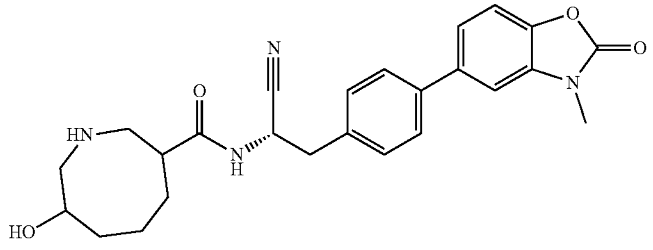 [SMILES: Cn1c(=O)oc2ccc(-c3ccc(C[C@@H](C#N)NC(=O)C4CCCC(O)CNC4)cc3)cc21] |

TABLE 1-continued
| Various compounds of the invention |
| --- |
| 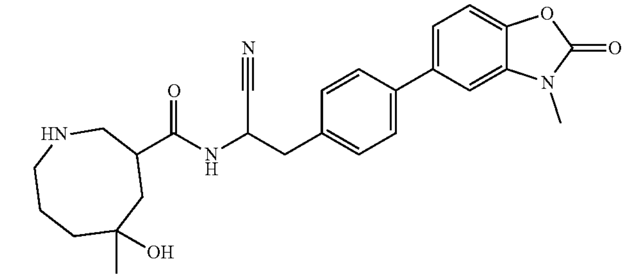 [SMILES: Cn1c(=O)oc2ccc(-c3ccc(CC(C#N)NC(=O)C4CNCCCC(C)(O)C4)cc3)cc21] |
| 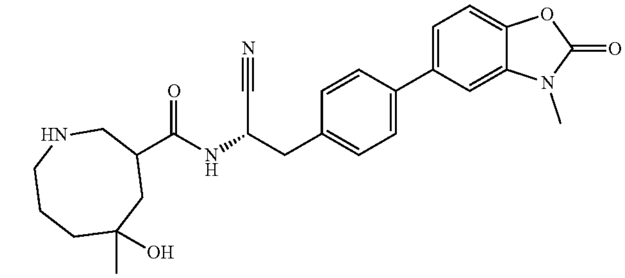 [SMILES: Cn1c(=O)oc2ccc(-c3ccc(C[C@@H](C#N)NC(=O)C4CNCCCC(C)(O)C4)cc3)cc21] |
| 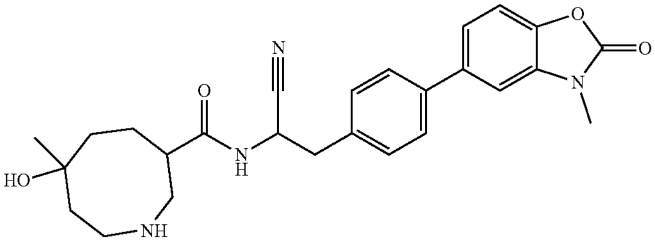 [SMILES: Cn1c(=O)oc2ccc(-c3ccc(CC(C#N)NC(=O)C4CCC(C)(O)CCNC4)cc3)cc21] |
| 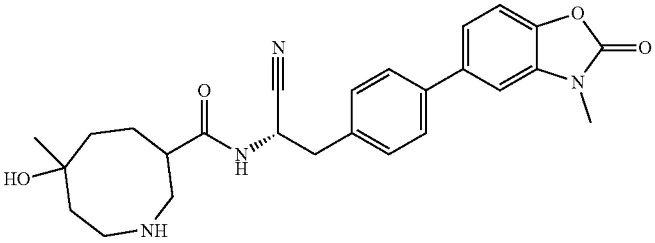 |
| 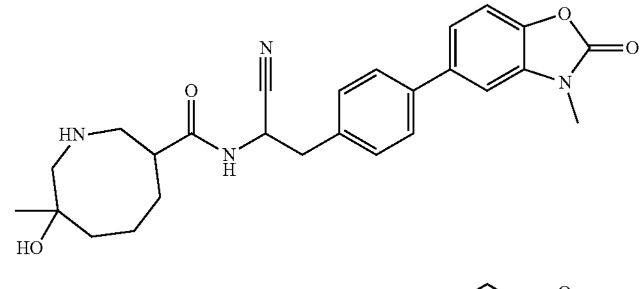 |
| 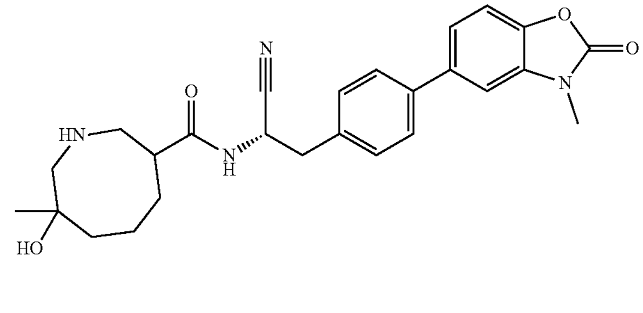 [SMILES: Cn1c(=O)oc2ccc(-c3ccc(C[C@@H](C#N)NC(=O)C4CCCC(C)(O)CNC4)cc3)cc21] |

TABLE 1-continued
| Various compounds of the invention |
| --- |
| 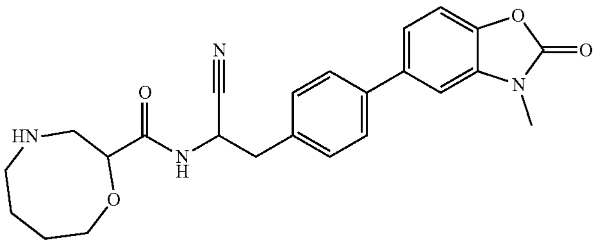 |
| 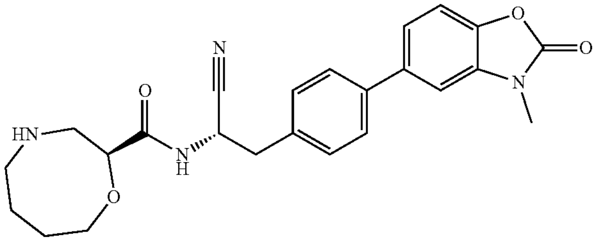 [SMILES: Cn1c(=O)oc2ccc(-c3ccc(C[C@@H](C#N)NC(=O)[C@@H]4CNCCCCO4)cc3)cc21] |
| 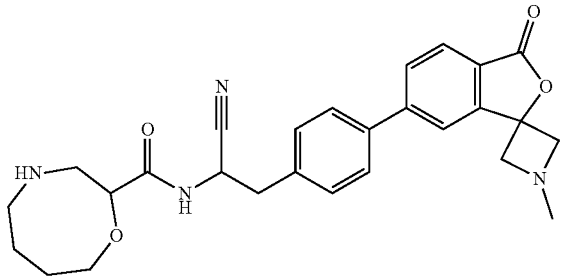 [SMILES: CN1CC2(C1)OC(=O)c1ccc(-c3ccc(CC(C#N)NC(=O)C4CNCCCCO4)cc3)cc12] |
| 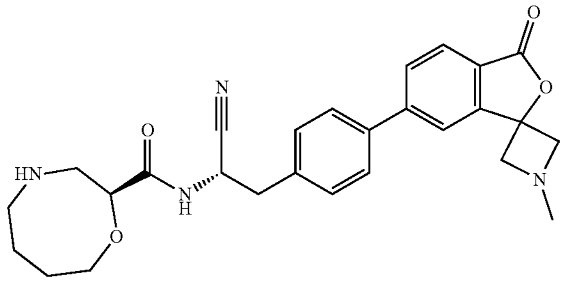 [SMILES: CN1CC2(C1)OC(=O)c1ccc(-c3ccc(C[C@@H](C#N)NC(=O)[C@@H]4CNCCCCO4)cc3)cc12] |
| 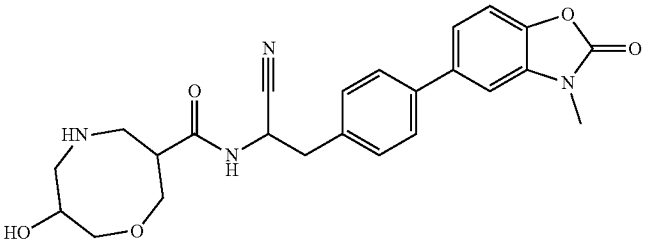 |
| 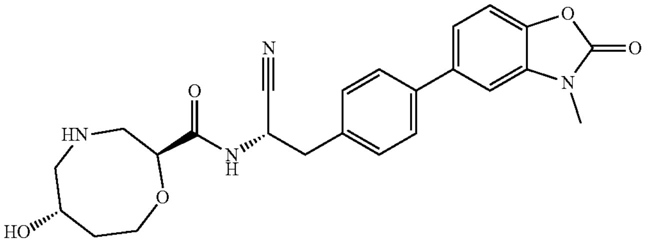 [SMILES: Cn1c(=O)oc2ccc(-c3ccc(C[C@@H](C#N)NC(=O)[C@@H]4CNC[C@@H](O)CCO4)cc3)cc21] |

TABLE 1-continued
| Various compounds of the invention |
|---|
| 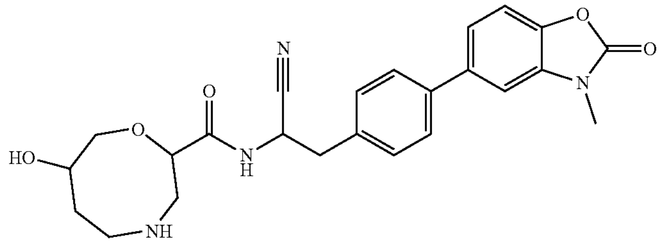 [SMILES: Cn1c(=O)oc2ccc(-c3ccc(CC(C#N)NC(=O)C4CNCCC(O)CO4)cc3)cc21] |
| 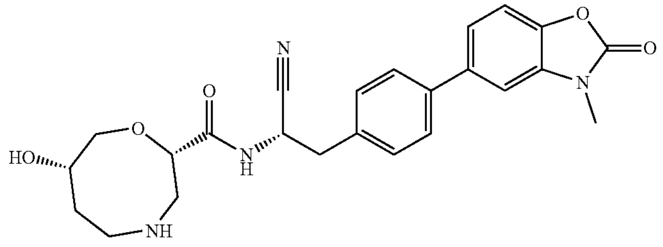 [SMILES: Cn1c(=O)oc2ccc(-c3ccc(C[C@@H](C#N)NC(=O)[C@@H]4CNCC[C@H](O)CO4)cc3)cc21] |
| 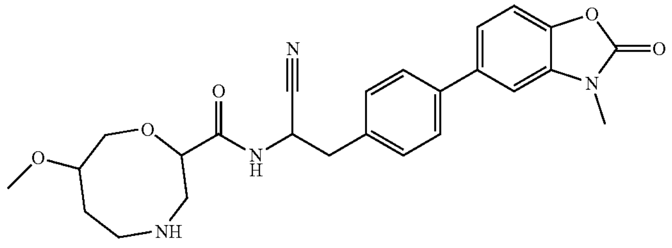 [SMILES: COC1CCNCC(C(=O)NC(C#N)Cc2ccc(-c3ccc4oc(=O)n(C)c4c3)cc2)OC1] |
| 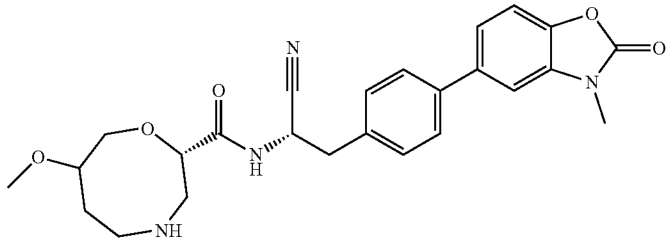 [SMILES: COC1CCNC[C@@H](C(=O)N[C@H](C#N)Cc2ccc(-c3ccc4oc(=O)n(C)c4c3)cc2)OC1] |
| 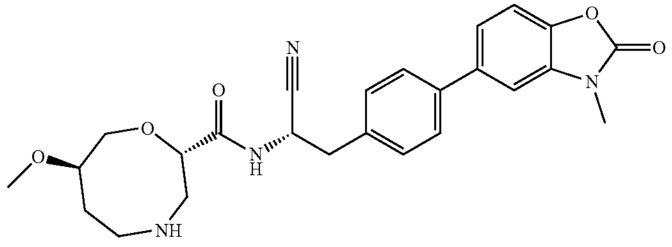 [SMILES: CO[C@@H]1CCNC[C@@H](C(=O)N[C@H](C#N)Cc2ccc(-c3ccc4oc(=O)n(C)c4c3)cc2)OC1] |
| 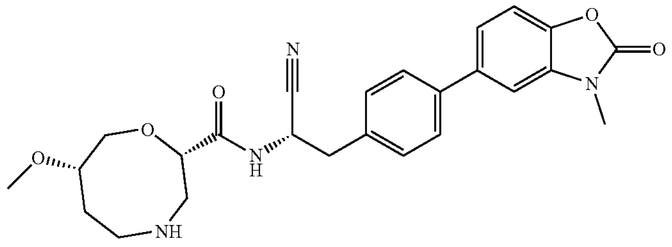 |

TABLE 1-continued
| Various compounds of the invention |
|---|
| 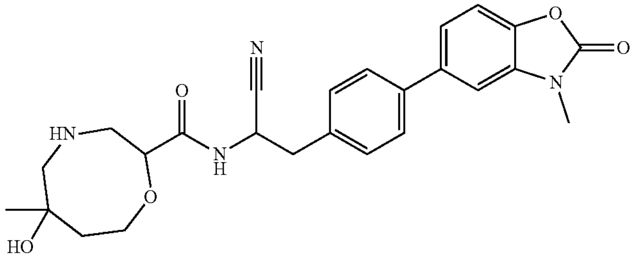 |
| 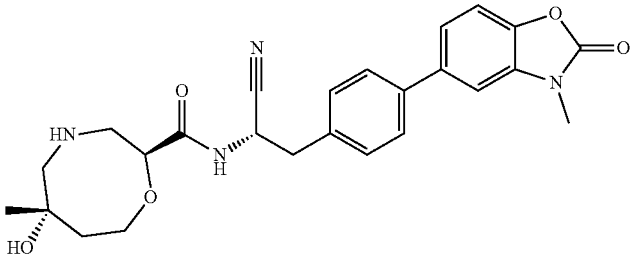 [SMILES: Cn1c(=O)oc2ccc(-c3ccc(C[C@@H](C#N)NC(=O)[C@@H]4CNC[C@@](C)(O)CCO4)cc3)cc21] |
| 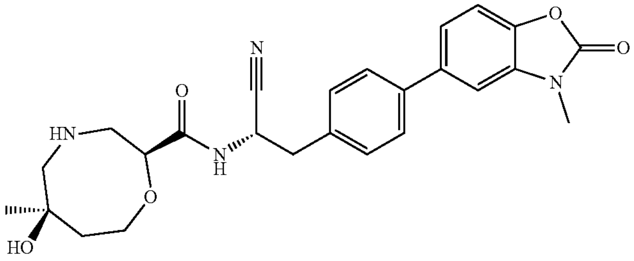 [SMILES: Cn1c(=O)oc2ccc(-c3ccc(C[C@@H](C#N)NC(=O)[C@@H]4CNC[C@](C)(O)CCO4)cc3)cc21] |
| 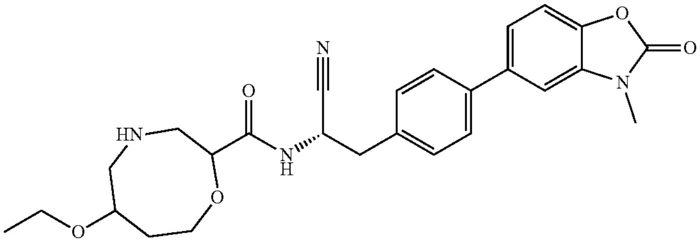 [SMILES: CCOC1CCOC(C(=O)N[C@H](C#N)Cc2ccc(-c3ccc4oc(=O)n(C)c4c3)cc2)CNC1] |
| 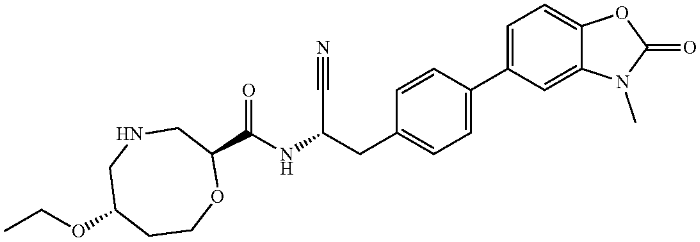 [SMILES: CCO[C@H]1CCO[C@H](C(=O)N[C@H](C#N)Cc2ccc(-c3ccc4oc(=O)n(C)c4c3)cc2)CNC1] |
| 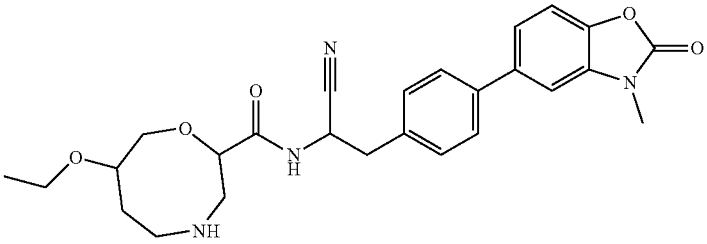 [SMILES: CCOC1CCNCC(C(=O)NC(C#N)Cc2ccc(-c3ccc4oc(=O)n(C)c4c3)cc2)OC1] |

TABLE 1-continued
| Various compounds of the invention |
|---|
| 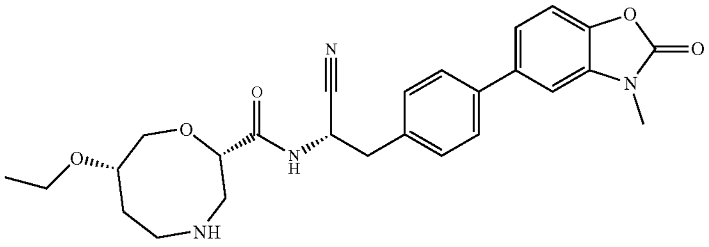 [SMILES: CCO[C@H]1CCNC[C@@H](C(=O)N[C@H](C#N)Cc2ccc(-c3ccc4oc(=O)n(C)c4c3)cc2)OC1] |
| 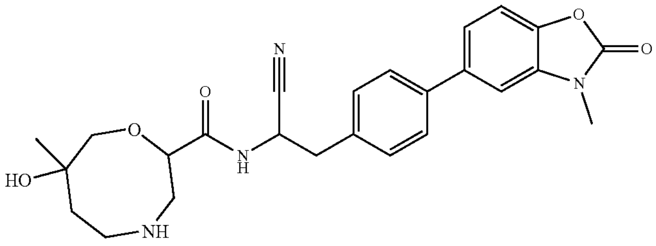 [SMILES: Cn1c(=O)oc2ccc(-c3ccc(CC(C#N)NC(=O)C4CNCCC(C)(O)CO4)cc3)cc21] |
| 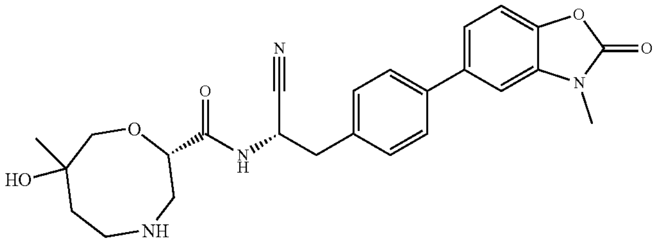 [SMILES: Cn1c(=O)oc2ccc(-c3ccc(C[C@@H](C#N)NC(=O)[C@@H]4CNCCC(C)(O)CO4)cc3)cc21] |
| 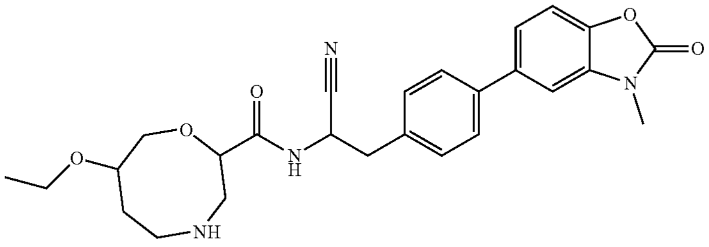 [SMILES: CCOC1CCNCC(C(=O)NC(C#N)Cc2ccc(-c3ccc4oc(=O)n(C)c4c3)cc2)OC1] |
| 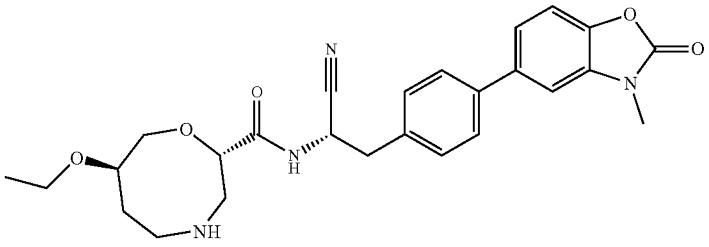 [SMILES: CCO[C@@H]1CCNC[C@@H](C(=O)N[C@H](C#N)Cc2ccc(-c3ccc4oc(=O)n(C)c4c3)cc2)OC1] |
| 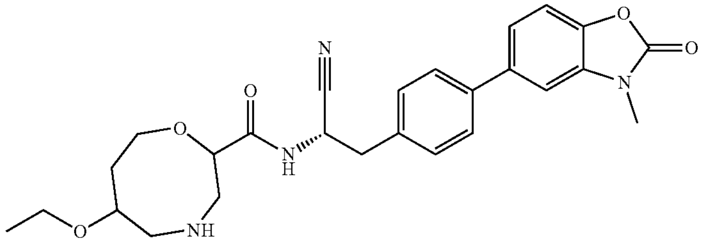 [SMILES: CCOC1CCOC(C(=O)N[C@H](C#N)Cc2ccc(-c3ccc4oc(=O)n(C)c4c3)cc2)CNC1] |

TABLE 1-continued
Various compounds of the invention
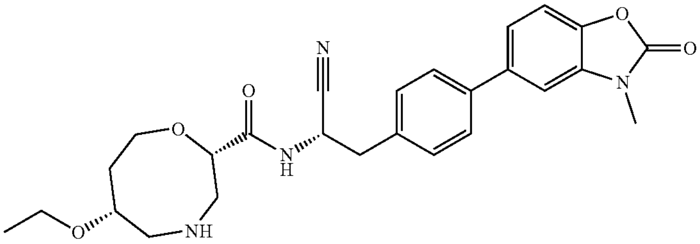 [SMILES: CCO[C@@H]1CCO[C@H](C(=O)N[C@H](C#N)Cc2ccc(-c3ccc4oc(=O)n(C)c4c3)cc2)CNC1]
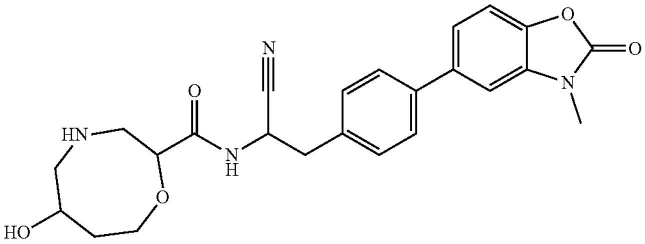 [SMILES: Cn1c(=O)oc2ccc(-c3ccc(CC(C#N)NC(=O)C4CNCC(O)CCO4)cc3)cc21]
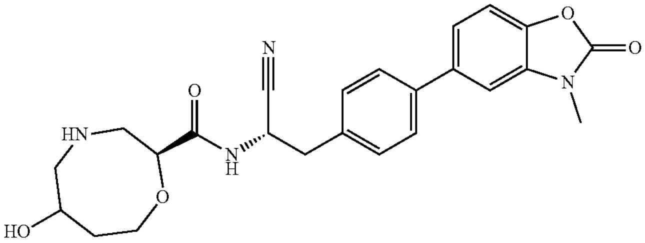 [SMILES: Cn1c(=O)oc2ccc(-c3ccc(C[C@@H](C#N)NC(=O)[C@@H]4CNCC(O)CCO4)cc3)cc21]
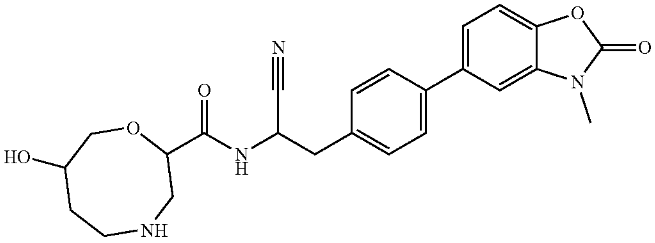 [SMILES: Cn1c(=O)oc2ccc(-c3ccc(CC(C#N)NC(=O)C4CNCCC(O)CO4)cc3)cc21]
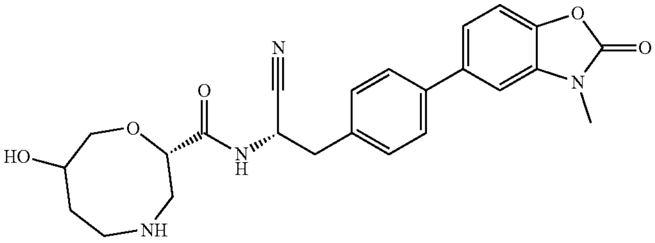
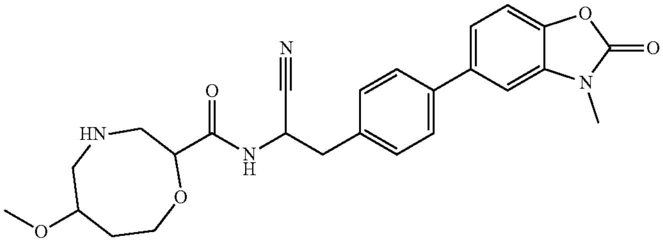

TABLE 1-continued
| Various compounds of the invention |
| --- |
| 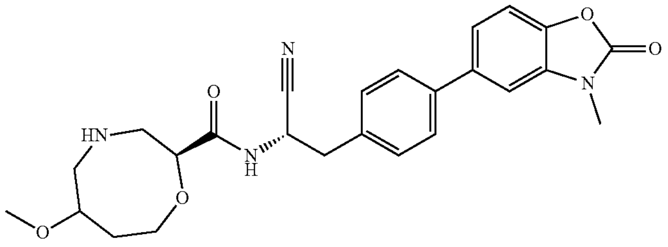 [SMILES: COC1CCO[C@H](C(=O)N[C@H](C#N)Cc2ccc(-c3ccc4oc(=O)n(C)c4c3)cc2)CNC1] |
| 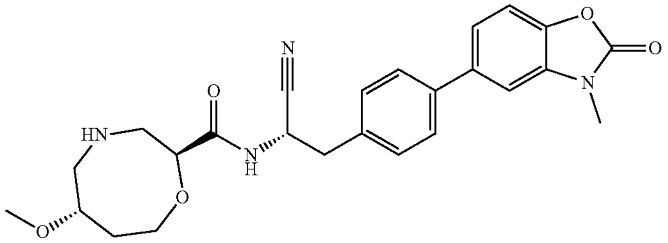 [SMILES: CO[C@H]1CCO[C@H](C(=O)N[C@H](C#N)Cc2ccc(-c3ccc4oc(=O)n(C)c4c3)cc2)CNC1] |
| 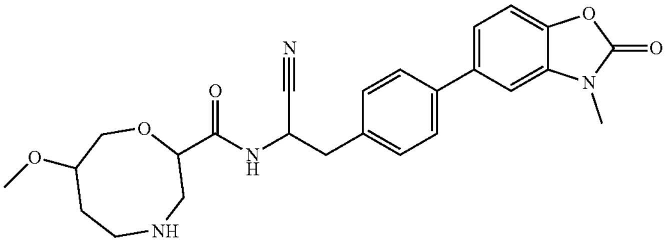 [SMILES: COC1CCNCC(C(=O)NC(C#N)Cc2ccc(-c3ccc4oc(=O)n(C)c4c3)cc2)OC1] |
| 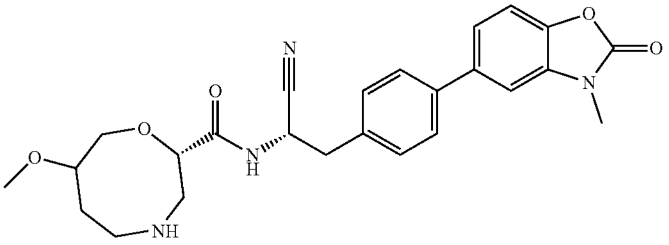 |
| 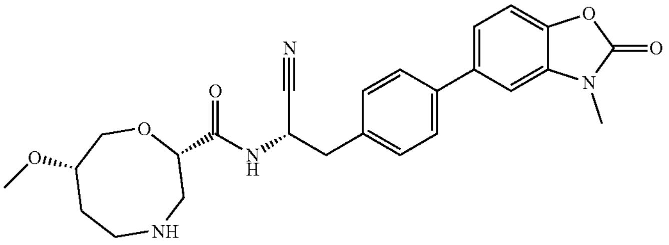 |
| 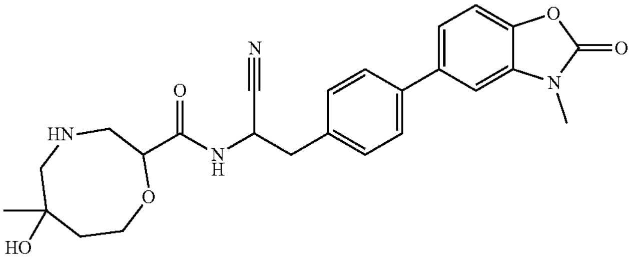 [SMILES: Cn1c(=O)oc2ccc(-c3ccc(CC(C#N)NC(=O)C4CNCC(C)(O)CCO4)cc3)cc21] |

TABLE 1-continued
| Various compounds of the invention |
|---|
| 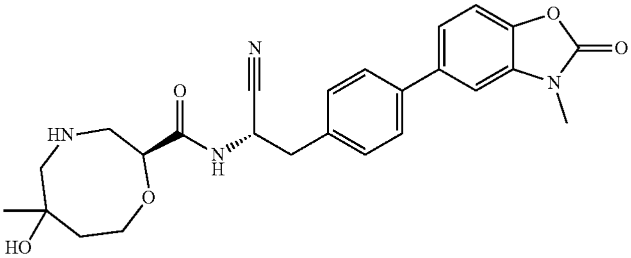 [SMILES: Cn1c(=O)oc2ccc(-c3ccc(C[C@@H](C#N)NC(=O)[C@@H]4CNCC(C)(O)CCO4)cc3)cc21] |
| 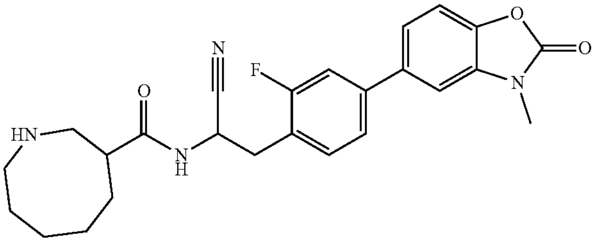 [SMILES: Cn1c(=O)oc2ccc(-c3ccc(CC(C#N)NC(=O)C4CCCCCNC4)c(F)c3)cc21] |
| 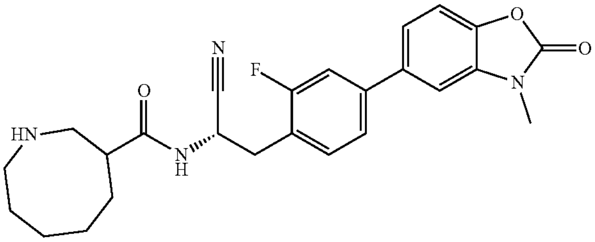 [SMILES: Cn1c(=O)oc2ccc(-c3ccc(C[C@@H](C#N)NC(=O)C4CCCCCNC4)c(F)c3)cc21] |
| 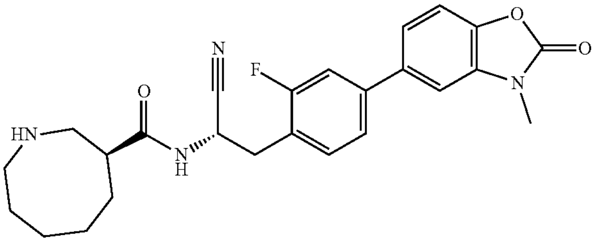 [SMILES: Cn1c(=O)oc2ccc(-c3ccc(C[C@@H](C#N)NC(=O)[C@H]4CCCCCNC4)c(F)c3)cc21] |
| 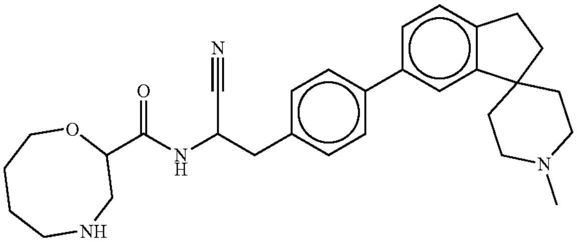 |
| 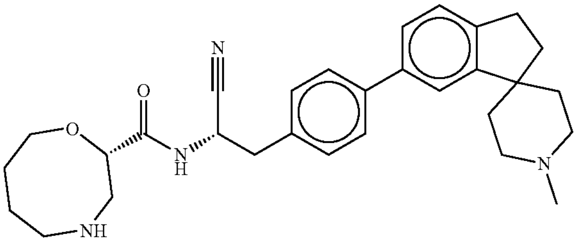 |

TABLE 1-continued
| Various compounds of the invention |
| --- |
| 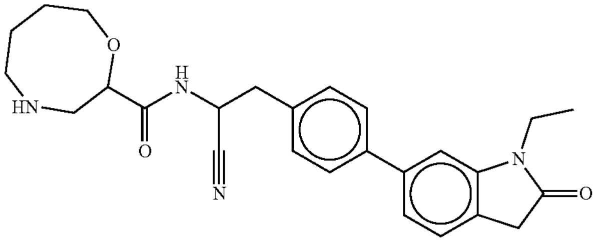 |
| 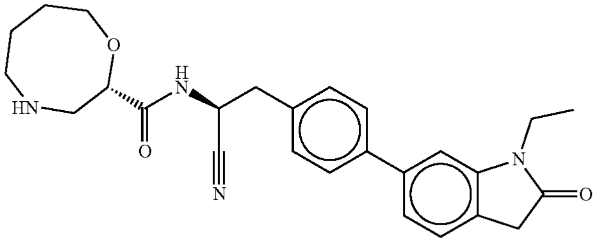 |
| 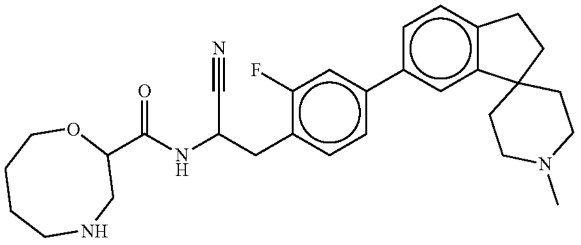 |
| 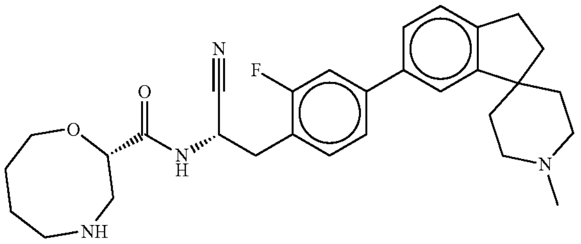 |
| 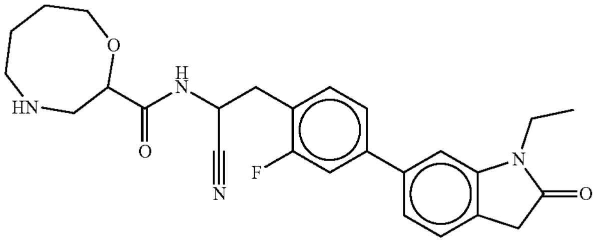 |
| 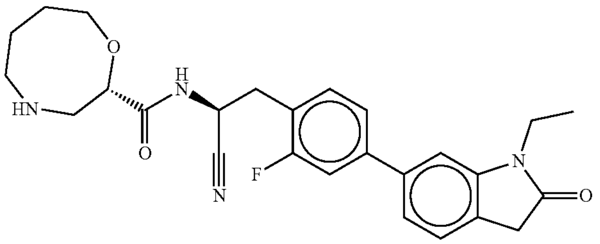 |

TABLE 1-continued
| Various compounds of the invention |
| --- |
| 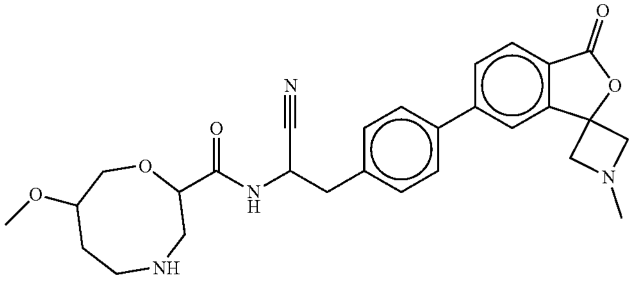 |
| 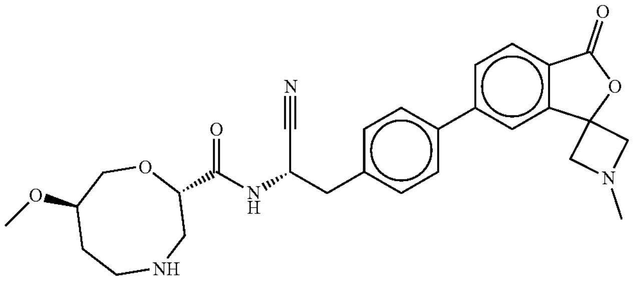 |
| 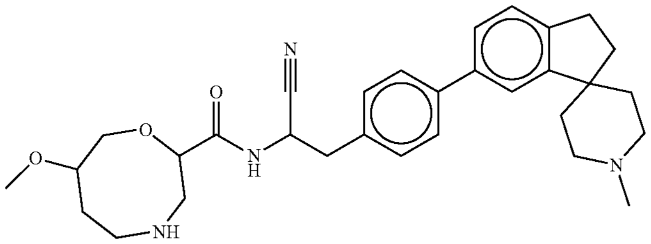 |
| 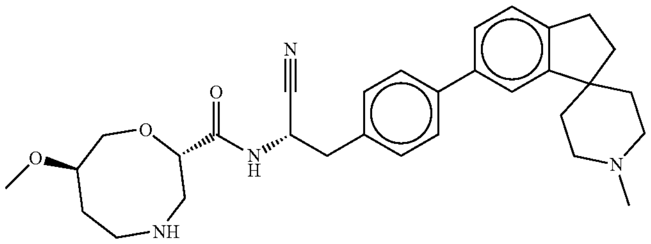 |
| 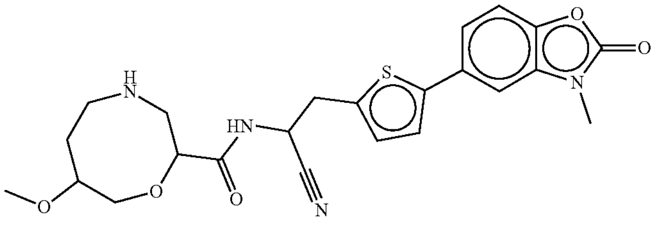 |
| 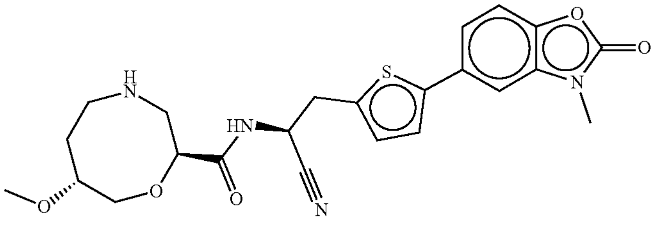 |

TABLE 1-continued
Various compounds of the invention
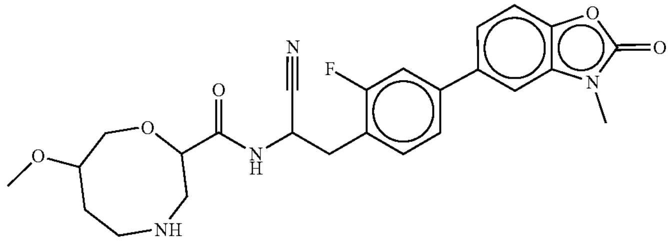
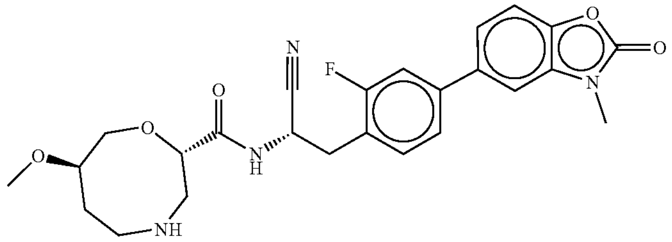
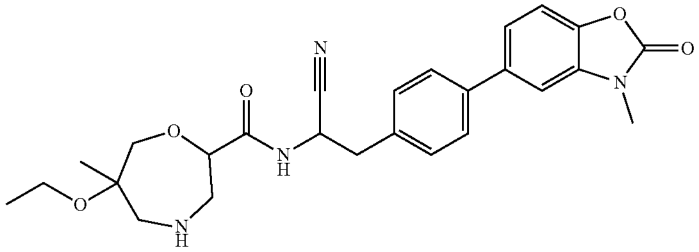
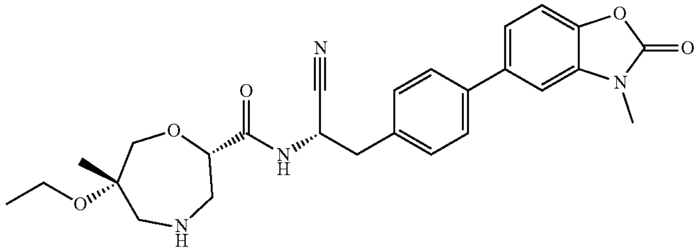 [SMILES: CCO[C@@]1(C)CNC[C@@H](C(=O)N[C@H](C#N)Cc2ccc(-c3ccc4oc(=O)n(C)c4c3)cc2)OC1]
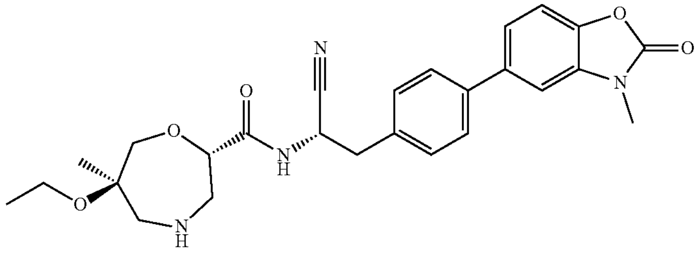 [SMILES: CCO[C@]1(C)CNC[C@@H](C(=O)N[C@H](C#N)Cc2ccc(-c3ccc4oc(=O)n(C)c4c3)cc2)OC1]
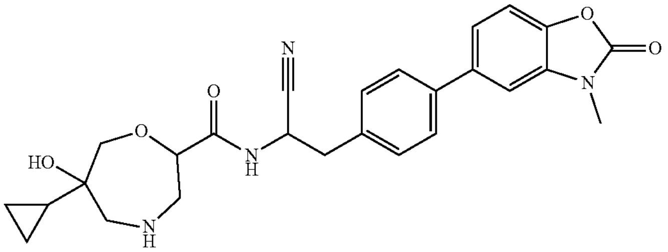 [SMILES: Cn1c(=O)oc2ccc(-c3ccc(CC(C#N)NC(=O)C4CNCC(O)(C5CC5)CO4)cc3)cc21]

TABLE 1-continued
| Various compounds of the invention |
|---|
| 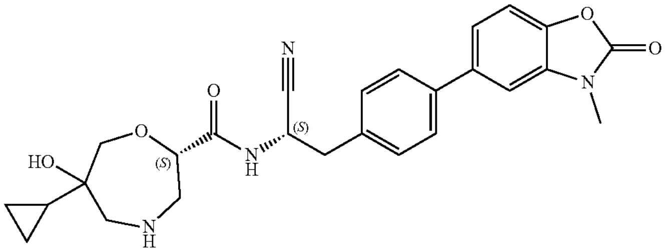 |
| 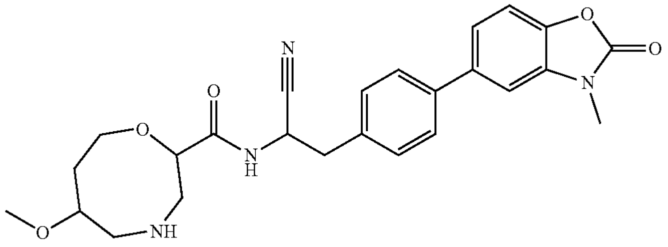 [SMILES: COC1CCOC(C(=O)NC(C#N)Cc2ccc(-c3ccc4oc(=O)n(C)c4c3)cc2)CNC1] |
| 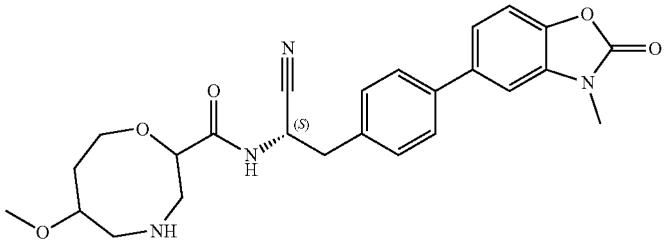 |
| 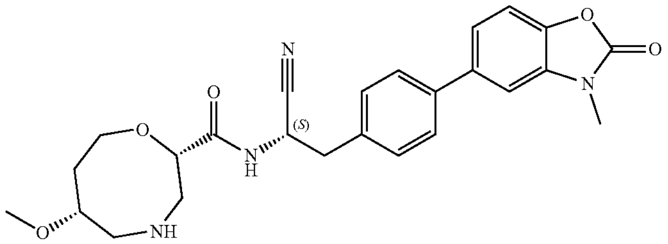 |
| 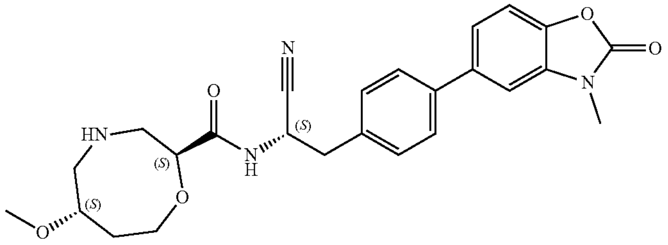 |
| 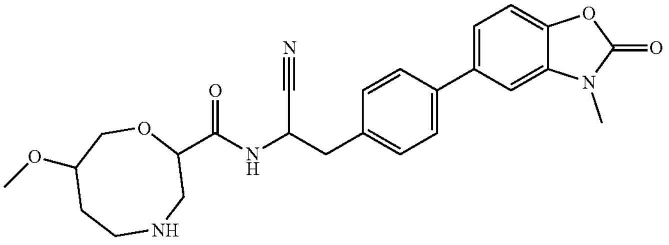 [SMILES: COC1CCNCC(C(=O)NC(C#N)Cc2ccc(-c3ccc4oc(=O)n(C)c4c3)cc2)OC1] |

TABLE 1-continued
| Various compounds of the invention |
| --- |
| 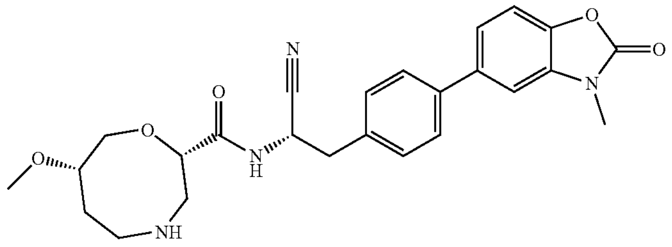 |
| 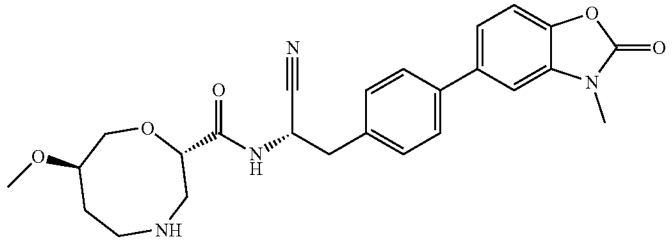 [SMILES: CO[C@@H]1CCNC[C@@H](C(=O)N[C@H](C#N)Cc2ccc(-c3ccc4oc(=O)n(C)c4c3)cc2)OC1] |
| 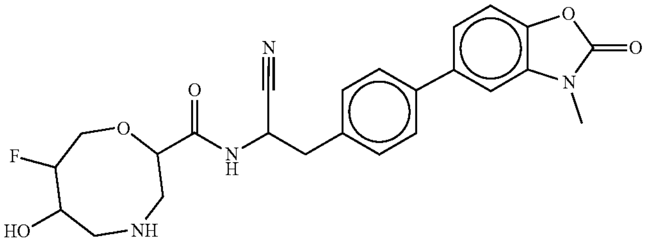 |
| 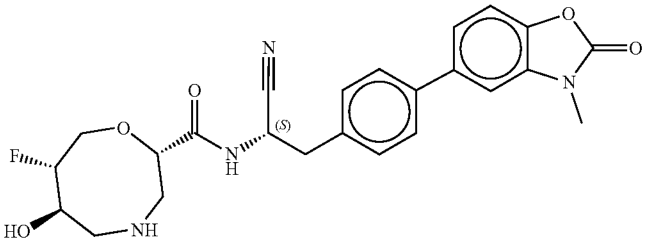 |
| 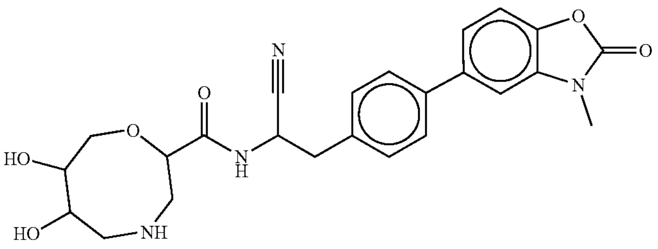 |
| 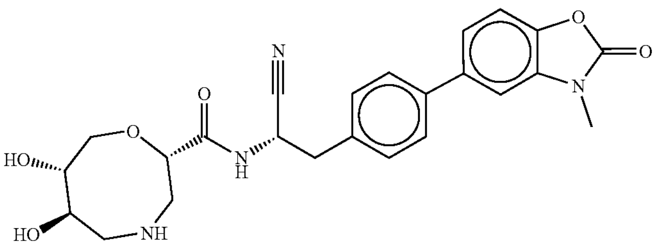 |

TABLE 1-continued
| Various compounds of the invention |
| --- |
| 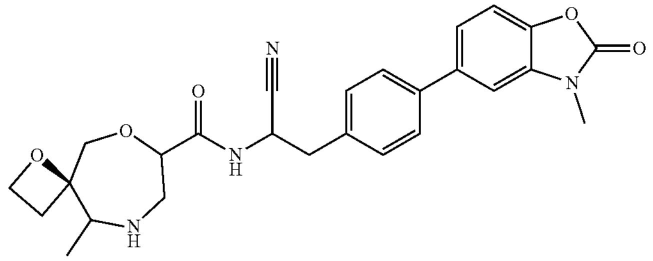 [SMILES: CC1NCC(C(=O)NC(C#N)Cc2ccc(-c3ccc4oc(=O)n(C)c4c3)cc2)OC[C@@]12CCO2] |
| 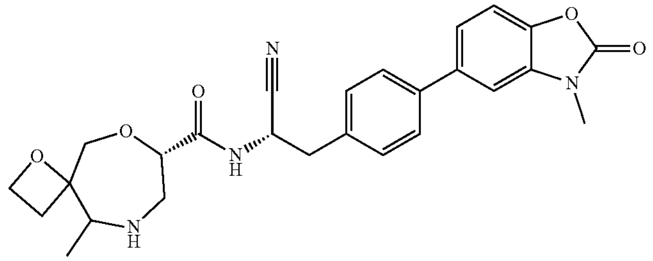 [SMILES: CC1NC[C@@H](C(=O)N[C@H](C#N)Cc2ccc(-c3ccc4oc(=O)n(C)c4c3)cc2)OCC12CCO2] |
| 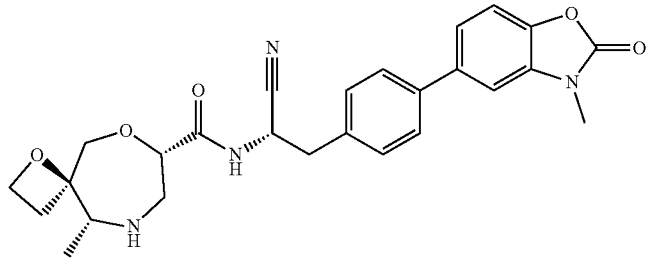 [SMILES: C[C@H]1NC[C@@H](C(=O)N[C@H](C#N)Cc2ccc(-c3ccc4oc(=O)n(C)c4c3)cc2)OC[C@@]12CCO2] |
| 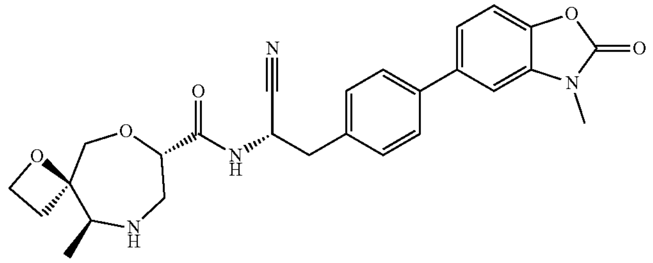 [SMILES: C[C@@H]1NC[C@@H](C(=O)N[C@H](C#N)Cc2ccc(-c3ccc4oc(=O)n(C)c4c3)cc2)OC[C@@]12CCO2] |
| 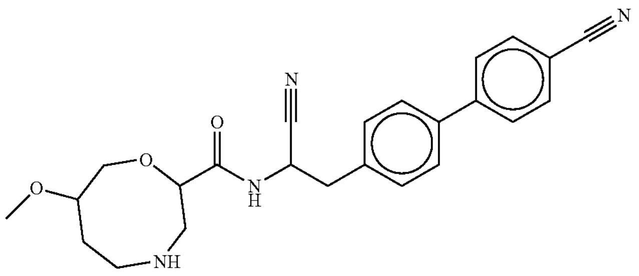 |

TABLE 1-continued
Various compounds of the invention
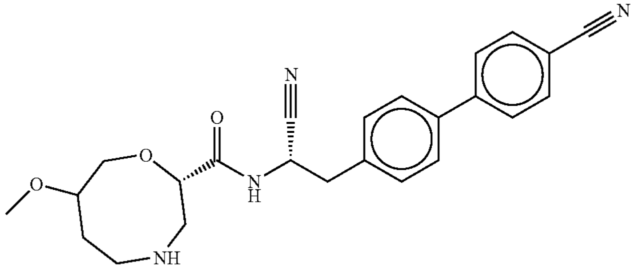
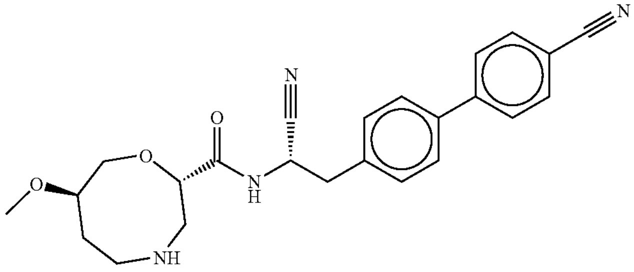
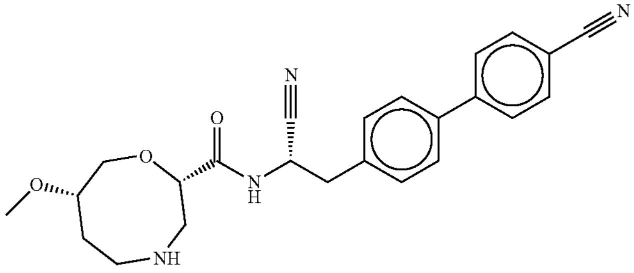
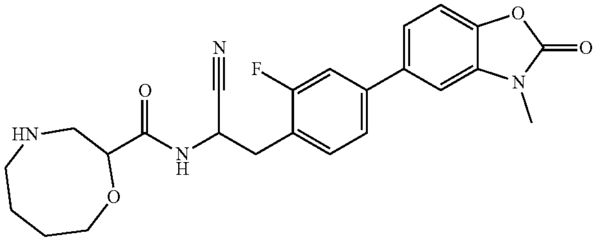 [SMILES: Cn1c(=O)oc2ccc(-c3ccc(CC(C#N)NC(=O)C4CNCCCCO4)c(F)c3)cc21]
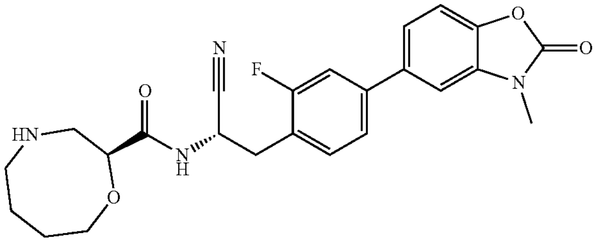 [SMILES: Cn1c(=O)oc2ccc(-c3ccc(C[C@@H](C#N)NC(=O)[C@@H]4CNCCCCO4)c(F)c3)cc21]
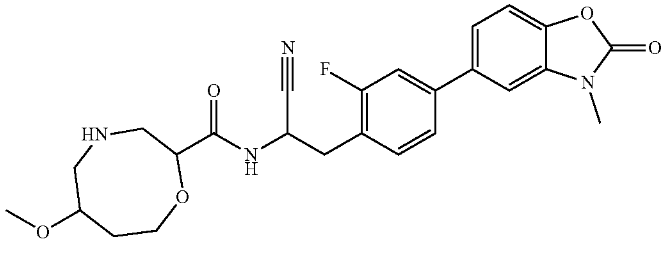 [SMILES: COC1CCOC(C(=O)NC(C#N)Cc2ccc(-c3ccc4oc(=O)n(C)c4c3)cc2F)CNC1]

TABLE 1-continued

| Various compounds of the invention |
|---|
| 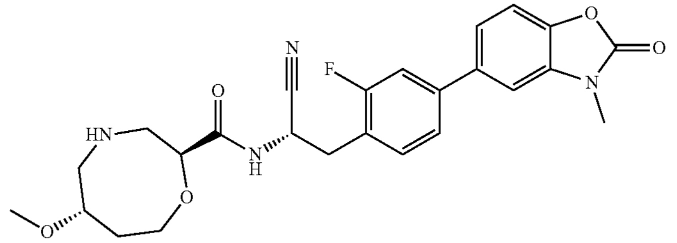 [SMILES: CO[C@H]1CCO[C@H](C(=O)N[C@H](C#N)Cc2ccc(-c3ccc4oc(=O)n(C)c4c3)cc2F)CNC1] |
| 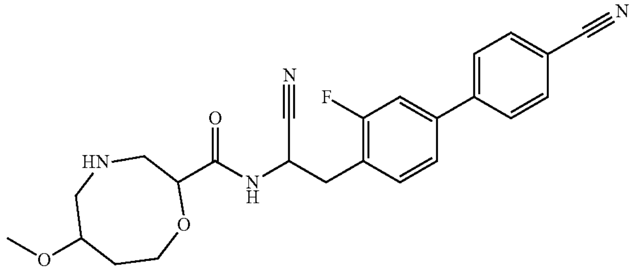 [SMILES: COC1CCOC(C(=O)NC(C#N)Cc2ccc(-c3ccc(C#N)cc3)cc2F)CNC1] |
| 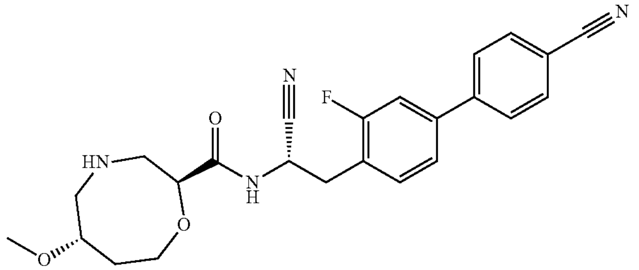 [SMILES: CO[C@H]1CCO[C@H](C(=O)N[C@H](C#N)Cc2ccc(-c3ccc(C#N)cc3)cc2F)CNC1] |
| 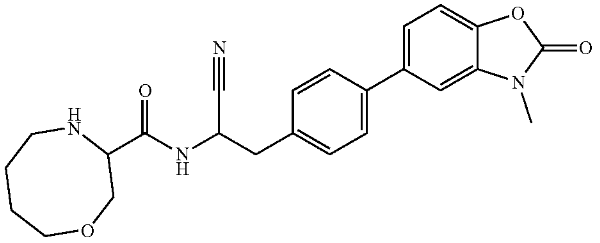 [SMILES: Cn1c(=O)oc2ccc(-c3ccc(CC(C#N)NC(=O)C4COCCCCN4)cc3)cc21] |
| 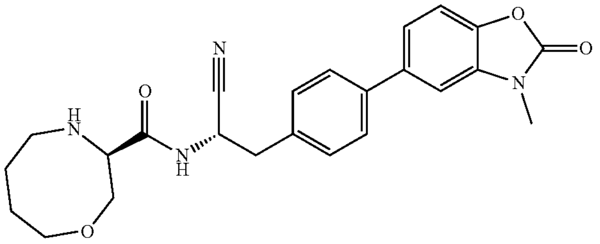 [SMILES: Cn1c(=O)oc2ccc(-c3ccc(C[C@@H](C#N)NC(=O)[C@H]4COCCCCN4)cc3)cc21] |

Compositions

The compounds of Formula (I), (II) or (III), (III-A), (III-B) or Table 1 or pharmaceutically acceptable salts thereof, or deuterated versions of the foregoing, may be used on their own but will generally be administered in the form of a pharmaceutical composition in which the Formula (I), (II) or (III), (III-A), (III-B) or Table 1 compound/salt (active ingredient) is in association with pharmaceutically acceptable adjuvant(s), diluents(s) or carrier(s). Conventional procedures for the selection and preparation of suitable pharmaceutical formulations are described in, for example, "Pharmaceuticals—The Science of Dosage Form Designs", M. E. Aulton, Churchill Livingstone, 2nd Ed. 2002.

In embodiments, the present disclosure provides pharmaceutical composition(s) comprising a compound of Formula (I), (II) or (III), (III-A), (III-B) or Table 1 or a pharmaceutically acceptable salt thereof, as hereinbefore defined in association with pharmaceutically acceptable adjuvant(s), diluent(s) or carrier(s).

The disclosure further provides a process for the preparation of a pharmaceutical composition of the disclosure which comprises mixing a compound of Formula (I), (II) or (III), (III-A), (III-B) or Table 1 or a pharmaceutically acceptable salt thereof, as hereinbefore defined with a pharmaceutically acceptable adjuvant(s), diluents(s) or carrier(s).

The pharmaceutical compositions may be administered topically (e.g., to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g., by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

For oral administration the compound of the disclosure may be admixed with adjuvant(s), diluent(s) or carrier(s), for example, lactose, saccharose, sorbitol, mannitol; starch, for example, potato starch, corn starch or amylopectin; cellulose derivative; binder, for example, gelatine or polyvinylpyrrolidone; disintegrant, for example cellulose derivative, and/or lubricant, for example, magnesium stearate, calcium stearate, polyethylene glycol, wax, paraffin, and the like, and then compressed into tablets. If coated tablets are required, the cores, prepared as described above, may be coated with a suitable polymer dissolved or dispersed in water or readily volatile organic solvent(s). Alternatively, the tablet may be coated with a concentrated sugar solution which may contain, for example, gum arabic, gelatine, talcum and titanium dioxide.

For the preparation of soft gelatine capsules, the compound of the disclosure may be admixed with, for example, a vegetable oil or polyethylene glycol. Hard gelatine capsules may contain granules of the compound using pharmaceutical excipients like the abovementioned excipients for tablets. Additionally, liquid or semisolid formulations of the compound of the disclosure may be filled into hard gelatine capsules.

Liquid preparations for oral application may be in the form of syrups, solutions or suspensions. Solutions, for example may contain the compound of the disclosure, the balance being sugar and a mixture of ethanol, water, glycerol and propylene glycol. Optionally such liquid preparations may contain coloring agents, flavoring agents, saccharine and/or carboxymethylcellulose as a thickening agent. Furthermore, other excipients known to those skilled in art may be used when making formulations for oral use.

Therapeutic Use

In embodiments, the compounds of Formula (I), (II) or (III), (III-A), (III-B) or Table 1 and their pharmaceutically acceptable salts, are DPP1 inhibitors, and thus may be used in any disease area where DPP1 plays a role. As such, in one aspect of the disclosure, a method of treatment is provided. The method of treatment, in one embodiment, comprises, administering to a subject in need thereof, a composition comprising an effective amount of a compound of Formula (I), (II) or (III), (III-A), (III-B) or Table 1 or a pharmaceutically acceptable salt of (I), (II) or (III), (III-A), (III-B) or Table 1. In embodiments, the composition is administered to the patient for an administration period.

In embodiments, a compound or composition of the present disclosure is administered to a patient in a method for treating a obstructive disease of the airway; chronic rhinosinusitis (CRS); hidradenitis suppurativa (HS); cancer (e.g., cancer metastasis); granulomatosis with polyangiitis (GPA); microscopic polyangiitis (MPA); giant cell arteritis; polyarteritis nodosa; anti-GBM disease (Goodpasture's); rheumatoid arthritis; lupus nephritis; systemic lupus erythematosus; systemic scleroderma; inflammatory bowel disease (IBD) (e.g., ulcerative colitis; Crohn's disease); diabetic nephropathy; diabetic neuropathy; diabetic retinopathy; diabetic ulcers; Duchenne muscular dystrophy; bronchiolitis obliterans; long covid)-prophylaxis of ILD; atopic dermatitis; pyoderma gangrenosum; sweet's syndrome; dermatomyositis/polymyositis; neutrophilic dermatoses; uveitis; Behcet's disease; thrombosis; bronchopulmonary dysplasia; amyotrophic lateral sclerosis; sickle cell anemia; psoriasis; ventilator-induced lung injury.

In embodiments, a compound or composition of the present disclosure is administered to a patient in a method for treating an obstructive disease of the airway. The obstructive disease of the airway, in one embodiment, is asthma (e.g., bronchial, allergic, intrinsic, extrinsic, exercise-induced, drug-induced (including aspirin and NSAID-induced and dust-induced asthma, both intermittent and persistent and of all severities) airway hyper-responsiveness, chronic obstructive pulmonary disease (COPD), bronchitis (e.g., infectious bronchitis, eosinophilic bronchitis), emphysema, cystic fibrosis (CF), bronchiectasis (e.g., non-CF bronchiectasis (NCFBE) and bronchiectasis associated with CF), cystic fibrosis; sarcoidosis; alpha-1 antitrypsin (A1AT) deficiency, farmer's lung and related diseases, hypersensitivity pneumonitis, interstitial lung disease, lung fibrosis (including idiopathic pulmonary fibrosis, cryptogenic fibrosing alveolitis, idiopathic interstitial pneumonias, fibrosis complicating anti-neoplastic therapy and chronic infection, including tuberculosis and aspergillosis and other fungal infections), complications of lung transplantation, vasculitic and thrombotic disorders of the lung vasculature, pulmonary hypertension (e.g., pulmonary arterial hypertension), antitussive activity including treatment of chronic cough associated with inflammatory and secretory conditions of the airways, iatrogenic cough, acute and chronic rhinitis including rhinitis medicamentosa, and vasomotor rhinitis; perennial and seasonal allergic rhinitis including rhinitis nervosa (hay fever), nasal polyposis; acute viral infection including the common cold, and infection due to a respiratory virus (e.g., respiratory syncytial virus, influenza, coronavirus (including SARS) and adenovirus), acute lung injury, acute respiratory distress syndrome (ARDS), as well as exacerbations of each of the foregoing respiratory tract disease states.

Cystic fibrosis (CF) is caused by abnormalities in the CF transmembrane conductance regulator protein, causing chronic lung infections (particularly with *Pseudomonas aeruginosa*) and excessive inflammation, and leading to bronchiectasis, declining lung function, respiratory insufficiency and quality of life. The inflammatory process is dominated by neutrophils that produce NE, as well as other destructive NSPs including CatG and PR3, that directly act upon extracellular matrix proteins and play a role in the host response to inflammation and infection (Dittrich et al., *Eur Respir J.* 2018; 51 (3)). The methods provided herein employ reversible inhibitors of DPP1. Without wishing to be bound by theory, it is thought that the compounds of Formula (I), (II), or (III), administered via the methods provided herein have beneficial effects via inhibiting the activation of NSPs and decreasing inflammation, which in turn leads to a decrease in pulmonary exacerbations, a decrease in the rate of pulmonary exacerbations, and/or an improvement in lung function (e.g., forced expiratory volume in 1 second [$FEV_1$]) in CF patients.

In one embodiment, a method is provided for treating CF comprising administering to a CF patient in need of treatment, a composition comprising an effective amount of a compound of Formula (I), (II), or (III), or a pharmaceutically acceptable salt thereof.

In one CF treatment method, a composition comprising an effective amount of a compound of Formula (I), (II), or (III), or a pharmaceutically acceptable salt thereof, is administered to a CF patient in need of treatment for an administration period. The method comprises improving the lung function of the patient during the administration period, as compared to the lung function of the patient prior to the administration period. The improvement in lung function in one embodiment, is measured by spirometry.

Improving the lung function of the patient, in one embodiment, comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC ($FEF_{(25-75\%)}$), as compared to the respective value prior to the administration period. Increasing, in one embodiment, is by about 5%, by about 10%, by about 15%, by about 20%, by about 25%, by about 30%, by about 35%, by about 40%, by about 45% or by about 50% of the respective value. Increasing, in one embodiment, is by at least about 5%, by at least about 10%, by at least about 15%, by at least about 20%, by at least about 25%, by at least about 30%, by at least about 35%, by at least about 40%, by at least about 45% or by at least about 50%. In yet another embodiment, the increasing is by about 5% to about 50%, by about 5% to about 40%, by about 5% to about 30% or by about 5% to about 20%. In even another embodiment, increasing is by about 10% to about 50%, by about 15% to about 50%, by about 20% to about 50%, or by about 25% to about 50%.

In one embodiment of a method provided herein, a composition comprising an effective amount of a compound of Formula (I), (II), or (III), or a pharmaceutically acceptable salt thereof, is administered to a bronchiectasis patient in need of treatment for an administration period. Bronchiectasis is considered a pathological endpoint that results from many disease processes and is a persistent or progressive condition characterized by dilated thick-walled bronchi. The symptoms vary from intermittent episodes of expectoration and infection localized to the region of the lung that is affected to persistent daily expectoration often of large volumes of purulent sputum. Bronchiectasis may be associated with other non-specific respiratory symptoms. The underlying pathological process of bronchiectasis, without wishing to be bound by theory, has been reported as damage to the airways which results from an event or series of events where inflammation is central to the process (Guideline for non-CF Bronchiectasis, Thorax, July 2010, V. 65 (Suppl 1), incorporated by reference herein in its entirety for all purposes).

Bronchiectasis is considered a pathological endpoint that results from many disease processes and is a persistent or progressive condition characterized by dilated thick-walled bronchi. The symptoms vary from intermittent episodes of expectoration and infection localized to the region of the lung that is affected to persistent daily expectoration often of large volumes of purulent sputum. Bronchiectasis may be associated with other non-specific respiratory symptoms. The underlying pathological process of bronchiectasis, without wishing to be bound by theory, has been reported as damage to the airways which results from an event or series of events where inflammation is central to the process (Guideline for non-CF Bronchiectasis, Thorax, July 2010, V. 65 (Suppl 1), incorporated by reference herein in its entirety for all purposes).

The methods provided herein employ reversible inhibitors of DPP1. Without wishing to be bound by theory, it is thought that the compounds of Formula (I), (II), or (III), administered via the methods provided herein have beneficial effects via decreasing inflammation and mucus hypersecretion, which in some embodiments, leads to a decrease in pulmonary exacerbations, a decrease in the rate of pulmonary exacerbations, and/or an improvement in lung function (cough, sputum production, and forced expiratory volume in 1 second [$FEV_1$]) in bronchiectasis patients. Without wishing to be bound by theory, it is thought that the methods provided herein modify bronchiectasis progression by reducing the accelerated rate of lung function decline or lung tissue destruction.

In one embodiment, the bronchiectasis is non-CF bronchiectasis.

In one embodiment, the method for treating bronchiectasis comprises improving lung function of the patient during the administration period, as compared to the lung function of the patient prior to the administration period.

A pulmonary exacerbation, in one embodiment, is characterized by three or more of the following symptoms exhibited for at least 48 hours by the patient: (1) increased cough; (2) increased sputum volume or change in sputum consistency; (3) increased sputum purulence; (4) increased breathlessness and/or decreased exercise tolerance; (5) fatigue and/or malaise; (6) hemoptysis. In a further embodiment, the three or more symptoms result in a physician's decision to prescribe an antibiotic(s) to the patient exhibiting the symptoms.

In one embodiment of a method for treating bronchiectasis, the method comprises decreasing the rate of pulmonary exacerbation in the subject, compared to the rate of pulmonary exacerbation experienced by the subject prior to the administration period of the composition, or compared to a control subject with bronchiectasis that is not subject to the method of treatment. In a further embodiment, the bronchiectasis is non-CF bronchiectasis.

In another aspect, a method for treating chronic rhinosinusitis (CRS) in a subject in need thereof is provided. The method comprises in one embodiment, administering to the subject for an administration period, a pharmaceutical composition comprising an effective amount of a compound of Formula (I), (II), or (III), or a pharmaceutically acceptable salt thereof.

The chronic rhinosinusitis is chronic rhinosinusitis without nasal polyps (CRSsNP), or chronic rhinosinusitis with nasal polyps (CRSwNP). In some embodiments, the chronic rhinosinusitis is chronic rhinosinusitis without nasal polyps (CRSsNP). In some embodiments, the chronic rhinosinusitis is chronic rhinosinusitis with nasal polyps (CRSwNP). In some embodiments, the chronic rhinosinusitis is refractory chronic rhinosinusitis. In some embodiments, the refractory chronic rhinosinusitis is refractory chronic rhinosinusitis without nasal polyps (CRSsNP). In some embodiments, the refractory chronic rhinosinusitis is refractory chronic rhinosinusitis with nasal polyps (CRSwNP).

In some embodiments, the subject exhibits one or more symptoms of CRS. In some embodiments, the one or more symptoms of CRS are: (a) nasal congestion; (b) nasal obstruction; (c) nasal discharge; (d) post-nasal drip; (e) facial pressure; (f) facial pain; (g) facial fullness; (h) reduced smell; (i) depression; (j) mucosal edema; (k) mucopurulent discharge; (1) obstruction of the middle meatus; (m)

mucosal changes within the ostiomeatal complex and sinuses; (n) rhinorrhea; or (o) any combinations thereof. In some embodiments, obstruction of the middle meatus is mucosal obstruction, edematous obstruction, or a combination thereof.

In some embodiments, the administration of the pharmaceutical composition reduces, diminishes the severity of, delays the onset of, or eliminates one or more symptoms of CRS. In some embodiments, the one or more symptoms of CRS are: (a) nasal congestion; (b) nasal obstruction; (c) nasal discharge; (d) post-nasal drip; (e) facial pressure; (f) facial pain; (g) facial fullness; (h) reduced smell; (i) depression; (j) mucosal edema; (k) mucopurulent discharge; (1) obstruction of the middle meatus; (m) mucosal changes within the ostiomeatal complex and sinuses; (n) rhinorrhea; (o) or any combinations thereof. In some embodiments, the administration of the pharmaceutical composition enhances sinus drainage.

In some embodiments, the methods comprise reducing a composite severity score of one or more symptoms of CRS. As used herein, the "composite severity score" is a quantitative measure of all the symptoms of CRS exhibited by the subject. In some embodiments, the composite severity score is a sum total of all the daily symptoms exhibited by the subject. In some embodiments, the composite severity score is reduced during or subsequent to the administration period, as compared to the composite severity score measured prior to the administration period. In some embodiments, the one or more symptoms of CRS exhibited by the subject may be any symptoms described herein or known in the art to be associated with CRS. In some embodiments, the one or more symptoms of CRS are: nasal congestion, reduced smell, rhinorrhea, or any combination thereof. In some embodiments, the rhinorrhea is anterior rhinorrhea. In some embodiments, the rhinorrhea is posterior rhinorrhea.

In some embodiments, the methods comprise decreasing the Sino-Nasal Outcome Test-22 (SNOT-22) score of the subject during the administration period or subsequent to the administration period, compared to the SNOT-22 score of the subject prior to the administration period. As used herein, "SNOT-22" is a patient-reported measure of outcome developed for use in CRS with or without nasal polyps and contains 22 individual questions. The questions cover a broad range of health and health-related quality of life problems including physical problems, functional limitations and emotional consequences. The theoretical range of the SNOT-22 score is 0-110, with lower scores implying a better health-related quality of life. Further details of SNOT-22 are provided in Hopkins, et al., *Clin. Otolaryngol.* 2009, 34, 447-454, and Kennedy, et al., *Ann Allergy Asthma Immunol.* 2013 October; 111 (4): 246-251, the contents of which are incorporated herein by reference in its entirety.

Hidradenitis suppurativa (HS) is a chronic relapsing inflammatory disorder. The symptoms include skin lesions that are often associated hair follicles, and may be painful, inflamed and/or swollen. In some cases, when the skin lesions heal, they can recur, and may lead to tunnels under the skin and progressive scarring. Since HS is a chronic condition, it can persist for many years and also, worsen over time, with serious effects on quality of life, physochological and emotional well-being. In fact, HS pateints have increased rates of anxiety and depression with a risk of suicide two and a half times that of the general population.

HS patients are categorized according to disease severity, termed Hurley staging, as mild (Stage I), moderate (Stage II), or severe (Stage III). Although more than 200,000 cases of HS are diagnosed in the U.S. per year, this disease can be difficult to diagnose and requires specialized care. HS may be mistaken for an infection, an ingrown hair or other conditions. Moreover, current treatment options are limited and lack efficacy.

In one aspect, a method of treating HS in a subject in need thereof is provided. The method comprises in one embodiment, administering to the subject for an administration period, a pharmaceutical composition comprising an effective amount of a compound of Formula (I), (II), or (III), or a pharmaceutically acceptable salt thereof. In a further embodiment, the method of treating HS comprises reducing neutrophilic inflammation in the subject.

The HS in one embodiment, is Hurley Stage I HS, Hurley Stage II HS or Hurley Stage III HS. In some embodiments, the HS is Hurley Stage I HS. In some embodiments, the HS is Hurley Stage II HS. In some embodiments, the HS is Hurley Stage III HS.

The disclosure provides methods of treating cancer in a subject in need thereof, comprising, administering to the subject, a pharmaceutical composition comprising an effective amount of any one of the compounds disclosed herein. The disclosure provides methods of treating cancer-induced pain in a subject having cancer, comprising, administering to the subject for an administration period, a pharmaceutical composition comprising an effective amount of any one of the compounds disclosed herein. In some embodiments, the cancer-induced pain is cancer-induced bone pain. The disclosure also provides methods of treating cancer-induced bone pain in a subject having cancer, comprising, administering to the subject for an administration period, a pharmaceutical composition comprising an effective amount of any one of the compounds disclosed herein.

In some embodiments, the cancer comprises a primary solid tumor. In some embodiments, the cancer is bladder cancer, lung cancer, brain cancer, ovarian cancer, pancreatic cancer, colorectal cancer, prostate cancer, liver cancer, hepatocellular carcinoma, kidney cancer, stomach cancer, skin cancer, fibroid cancer, lymphoma, virus-induced cancer, oropharyngeal cancer, testicular cancer, thymus cancer, thyroid cancer, melanoma, or bone cancer.

In some embodiments, the cancer is bladder cancer. In some embodiments, the cancer is lung cancer. In some embodiments, the cancer is brain cancer. In some embodiments, the cancer is ovarian cancer. In some embodiments, the cancer is pancreatic cancer. In some embodiments, the cancer is colorectal cancer. In some embodiments, the cancer is prostate cancer. In some embodiments, the cancer is liver cancer. In some embodiments, the cancer is hepatocellular carcinoma. In some embodiments, the cancer is kidney cancer. In some embodiments, the cancer is stomach cancer. In some embodiments, the cancer is skin cancer. In some embodiments, the cancer is fibroid cancer. In some embodiments, the cancer is lymphoma. In some embodiments, the cancer is virus-induced cancer. In some embodiments, the cancer is oropharyngeal cancer. In some embodiments, the cancer is testicular cancer. In some embodiments, the cancer is thymus cancer. In some embodiments, the cancer is thyroid cancer. In some embodiments, the cancer is melanoma. In some embodiments, the cancer is bone cancer. In some embodiments, the fibroid cancer is leiomyosarcoma.

In some embodiments, the breast cancer comprises ductal carcinoma, lobular carcinoma, medullary carcinoma, colloid carcinoma, tubular carcinoma, or inflammatory breast cancer. In some embodiments, the breast cancer comprises ductal carcinoma. In some embodiments, the breast cancer comprises lobular carcinoma. In some embodiments, the breast cancer comprises medullary carcinoma. In some embodiments, the breast cancer comprises colloid carcinoma. In some embodiments, the breast cancer comprises tubular carcinoma. In some embodiments, the breast cancer comprises inflammatory breast cancer.

In some embodiments, the breast cancer is triple-negative breast cancer. In some embodiments, the breast cancer does not respond to hormonal therapy or therapeutics that target the HER2 protein receptors.

In some embodiments, the lymphoma is Hodgkin's lymphoma, non-Hodgkin's lymphoma, diffuse large B-cell lymphoma, B-cell immunoblastic lymphoma, Natural Killer cell lymphoma, T-cell lymphoma, Burkitt lymphoma or Kaposi's Sarcoma. In some embodiments, the lymphoma is Hodgkin's lymphoma. In some embodiments, the lymphoma is non-Hodgkin's lymphoma. In some embodiments, the lymphoma is diffuse large B-cell lymphoma. In some embodiments, the lymphoma is B-cell immunoblastic lymphoma. In some embodiments, the lymphoma is Natural Killer cell lymphoma. In some embodiments, the lymphoma is T-cell lymphoma. In some embodiments, the lymphoma is Burkitt lymphoma. In some embodiments, the lymphoma is Kaposi's Sarcoma.

In some embodiments, the brain cancer is astrocytoma, anaplastic astrocytoma, glioblastoma multiforme, oligodendroglioma, ependymoma, meningioma, schwannoma, or medulloblastoma. In some embodiments, the brain cancer is astrocytoma. In some embodiments, the brain cancer is anaplastic astrocytoma. In some embodiments, the brain cancer is glioblastoma multiforme. In some embodiments, the brain cancer is oligodendroglioma. In some embodiments, the brain cancer is ependymoma. In some embodiments, the brain cancer is meningioma. In some embodiments, the brain cancer is schwannoma. In some embodiments, the brain cancer is medulloblastoma.

In some embodiments, the cancer is liquid tumor. In some embodiments, the liquid tumor is acute myeloid leukemia (AML), acute lymphoblastic leukemia, acute lymphocytic leukemia, acute promyelocytic leukemia, chronic myeloid leukemia, hairy cell leukemia, a myeloproliferative disorder, Natural Killer cell leukemia, blastic plasmacytoid dendritic cell neoplasm, chronic myelogenous leukemia (CML), mastocytosis, chronic lymphocytic leukemia (CLL), multiple myeloma (MM), or myelodysplastic syndrome (MDS). In some embodiments, the liquid tumor is acute myeloid leukemia (AML). In some embodiments, the liquid tumor is acute lymphoblastic leukemia. In some embodiments, the liquid tumor is acute lymphocytic leukemia. In some embodiments, the liquid tumor is acute promyelocytic leukemia. In some embodiments, the liquid tumor is chronic myeloid leukemia. In some embodiments, the liquid tumor is hairy cell leukemia. In some embodiments, the liquid tumor is a myeloproliferative disorder. In some embodiments, the liquid tumor is Natural Killer cell leukemia. In some embodiments, the liquid tumor is blastic plasmacytoid dendritic cell neoplasm. In some embodiments, the liquid tumor is chronic myelogenous leukemia (CML). In some embodiments, the liquid tumor is mastocytosis. In some embodiments, the liquid tumor is chronic lymphocytic leukemia (CLL). In some embodiments, the liquid tumor is multiple myeloma (MM). In some embodiments, the liquid tumor is myelodysplastic syndrome (MDS).

In some embodiments, the cancer is a pediatric cancer. In some embodiments, the pediatric cancer is neuroblastoma, Wilms tumor, rhabdomyosarcoma, retinoblastoma, osteosarcoma or Ewing sarcoma. In some embodiments, the pediatric cancer is neuroblastoma. In some embodiments, the pediatric cancer is Wilms tumor. In some embodiments, the pediatric cancer is rhabdomyosarcoma. In some embodiments, the pediatric cancer is retinoblastoma. In some embodiments, the pediatric cancer is osteosarcoma. In some embodiments, the pediatric cancer is Ewing sarcoma.

In some embodiments, the cancer is metastatic cancer. In some embodiments, the subject is at a risk for developing metastatic cancer. In some embodiments, the metastatic cancer comprises metastasis of breast cancer to the brain, bone, pancreas, lymph nodes, and/or liver. In some embodiments, the metastatic cancer comprises metastasis of bone cancer to the lung. In some embodiments, the metastatic cancer comprises metastasis of colorectal cancer to the peritoneum, the pancreas, the stomach, the lung, the liver, the kidney, and/or the spleen. In some embodiments, the metastatic cancer comprises metastasis of stomach cancer to the mesentery, the spleen, the pancreas, the lung, the liver, the adrenal gland, and/or the ovary. In some embodiments, the metastatic cancer comprises metastasis of leukemia to the lymph nodes, the lung, the liver, the hind limb, the brain, the kidney, and/or the spleen. In some embodiments, the metastatic cancer comprises metastasis of liver cancer to the intestine, the spleen, the pancreas, the stomach, the lung, and/or the kidney. In some embodiments, the metastatic cancer comprises metastasis of lymphoma to the kidney, the ovary, the liver, the bladder, and/or the spleen.

In some embodiments, the metastatic cancer comprises metastasis of hematopoietic cancer to the intestine, the lung, the liver, the spleen, the kidney, and/or the stomach. In some embodiments, the metastatic cancer comprises metastasis of melanoma to lymph nodes and/or the lung. In some embodiments, the metastatic cancer comprises metastasis of pancreatic cancer to the mesentery, the ovary, the kidney, the spleen, the lymph nodes, the stomach, and/or the liver. In some embodiments, the metastatic cancer comprises metastasis of prostate cancer to the lung, the pancreas, the kidney, the spleen, the intestine, the liver, the bone, and/or the lymph nodes. In some embodiments, the metastatic cancer comprises metastasis of ovarian cancer to the diaphragm, the liver, the intestine, the stomach, the lung, the pancreas, the spleen, the kidney, the lymph nodes, and/or the uterus. In some embodiments, the metastatic cancer comprises metastasis of myeloma to the bone.

In some embodiments, the metastatic cancer comprises metastasis of lung cancer to the bone, the brain, the lymph nodes, the liver, the ovary, and/or the intestine. In some embodiments, the metastatic cancer comprises metastasis of kidney cancer to the liver, the lung, the pancreas, the stomach, the brain, and/or the spleen. In some embodiments, the metastatic cancer comprises metastasis of bladder cancer to the bone, the liver and/or the lung. In some embodiments, the metastatic cancer comprises metastasis of thyroid cancer to the bone, the liver and/or the lung.

In some embodiments, the methods disclosed herein comprise treating cancer-induced bone pain (CIBP) in a subject having metastasis of a cancer to the bone. In some embodiments, the subject has metastasis of prostate cancer, breast cancer, lung cancer, or myeloma to the bone. In some embodiments, the subject is identified as having metastasis to the bone by the use of any one of the following methods: plain film radiography, computed tomography, technetium 99 m bone scan, magnetic resonance imaging, fluorodeoxyglucose positron emission tomography, fluorine positron emission tomography, and/or choline positron emission tomography, but is not yet feeling cancer-induced bone pain. In some embodiments, the subject is suffering from cancer-induced bone pain, which is indicative of metastasis of a previously treated or untreated primary tumor to the bone. In some embodiments, the cancer has metastasized to vertebrae, pelvis, long bones, or ribs.

In some embodiments, administration of the composition diminishes the severity of, delays the onset of, or eliminates a symptom of cancer. In some embodiments, the symptom of cancer is cancer-induced bone pain (CIBP). In some embodiments, the CIBP is neuropathic pain. In some embodiments, the CIBP is inflammatory pain. In some embodiments, the CIBP is spontaneous pain. In some embodiments, the symptom of cancer is nociceptive hypersensitivity. In some embodiments, the symptom of cancer is allodynia. In some embodiments, the allodynia is tactile allodynia. In some embodiments, the tactile allodynia is static mechanical allodynia. In some embodiments, the tactile allodynia is dynamic mechanical allodynia. In some embodiments, the subject has bone cancer or metastasis to the bone.

In yet another embodiment of the present disclosure, a method for treating lupus nephritis (LN) in a subject in need thereof is provided. The method comprises administering to the subject for an administration period, a pharmaceutical composition comprising an effective amount of a compound of Formula (I), (II), or (III), or a pharmaceutically acceptable salt thereof.

Rheumatoid arthritis (RA) is characterized by inflammation and thickening of the joint capsule, together with an effect on the underlying bone and cartilage. Currently, the cause of RA is unknown and no satisfactory cure for RA is available. While a number of therapeutic agents have been developed and utilized to alleviate pain and inflammation associated with the disease, such as disease-modifying anti-rheumatic drugs (DMARDs) and non-steroidal anti-inflammatory agents (NSAIDs), they often produce intolerable side effects. To addresses this and other needs, the present disclosure, in one embodiment, provides a method for treating RA using reversible inhibitors of DPP1 of Formula (I), (II), or (III). In one embodiment, a method of for treating RA in a subject in need thereof is provided, and comprises administering to the subject for an administration period, a pharmaceutical composition comprising an effective amount of a compound of Formula (I), (II), or (III), or a pharmaceutically acceptable salt thereof. In a further embodiment, the method comprises reducing neutrophilic inflammation in the subject.

Inflammatory bowel disease (IBD) is a group of inflammatory conditions that affect the colon and small intestine. The most common IBDs are Crohn's disease and ulcerative colitis. The present disclosure, in one embodiment, addresses the need for novel IBD therapies. Specifically, in one embodiment, a method for treating an inflammatory bowel disease (IBD) in a subject in need thereof is provided. The method comprises administering to the subject for an administration period, a pharmaceutical composition comprising an effective amount of a compound of Formula (I), or a pharmaceutically acceptable salt thereof.

In a further embodiment, the IBD is Crohn's disease or ulcerative colitis. In even a further embodiment, the method comprises reducing neutrophilic inflammation in the subject.

The length of the administration period in any given case may depend on the nature and severity of the condition being treated and/or prevented and be determined by the physician.

In one embodiment, the administration period starts at about the time of condition/disease diagnosis and continues for the lifetime of the patient.

Embodiments 1

Embodiment 1. A compound of formula (I)

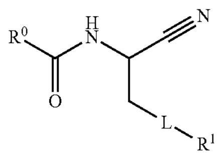

(I)

or a pharmaceutically acceptable salt or deuterated form thereof, wherein $R^0$ is

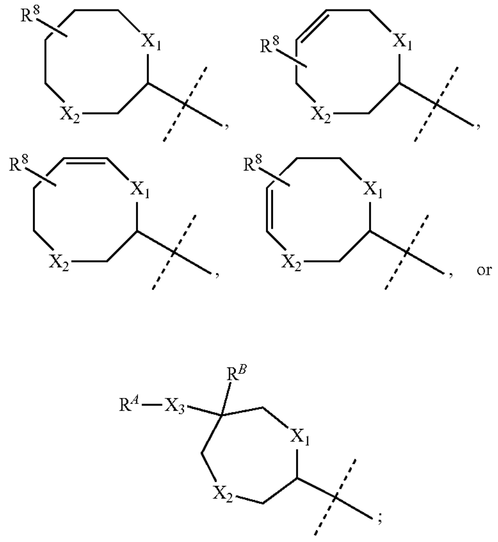

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, or N($C_{1-6}$ alkyl);

$R^A$ is H, $C_{1-6}$ alkyl, $C_{1-6}$alkylene-carbocyclyl, or $C_{1-6}$alkylene-heteroaryl; and $R^B$ is $C_{1-6}$ alkyl, $C_{2-6}$alkenyl, $C_{1-6}$alkylene-carbocyclyl, or $C_{1-6}$alkylene-heteroaryl; or $R^A$ and $R^B$ are taken together to form a heterocyclyl;

L is aryl, heterocycle, heteroaryl, or

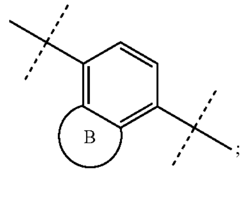

wherein L is independently substituted by 0-4 $R^{10}$ and wherein ring B is a carbocycle, or a heterocycle;

$R^1$ is

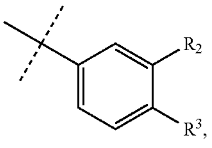

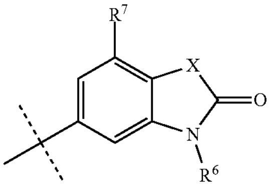

,

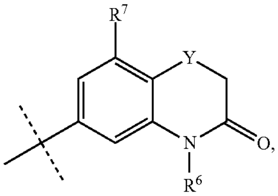

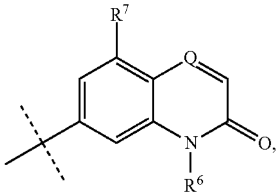

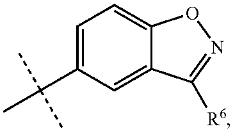

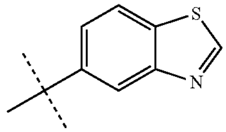

, or

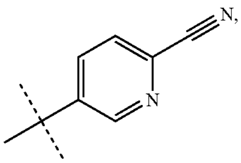

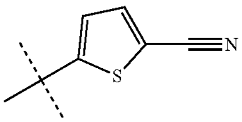

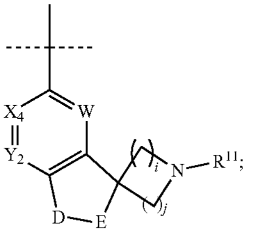

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O or S;

Q is CH or N;

$R^6$ is $C_{1-6}$ alkyl, wherein the $C_{1-6}$ alkyl is optionally substituted by 1, 2 or 3 F, or optionally substituted by one substituent selected from OH, O $C_{1-6}$ alkyl, N($C_{1-6}$ alkyl)$_2$, cycloalkyl, or heterocyclyl;

$R^7$ is H, F, Cl, Br, or $C_{1-6}$ alkyl;

$R^8$ and $R^{12}$ are independently H, OH, halogen, $NH_2$, COOH, unsubstituted $C_{1-6}$ alkyl, $C_{1-6}$ alkyl-OH, unsubstituted $C_{1-6}$alkoxy or halogenated $C_{1-6}$alkoxy;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, N($C_{1-6}$ alkyl)$_2$, COOH, $COC_{1-6}$ alkyl, $COOC_{1-6}$ alkyl, $CON_{1-6}$ alkyl, CON($C_{1-6}$ alkyl)$_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$—O;

$R^{11}$ is H, $C_{1-6}$ alkyl, alkylene-O-alkyl, or heterocyclyl; and i and j are each independently 1, 2 or 3; provided that the sum of i+j is 2, 3 or 4.

Embodiment 2. The compound of embodiment 1, wherein the compound is of Formula (II):

(II)

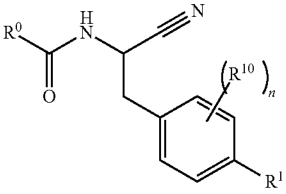

or a pharmaceutically acceptable salt or deuterated form thereof, wherein n is 0 or 1, and $R^{10}$ is F.

Embodiment 3. The compound of embodiment 1 or 2, or a pharmaceutically acceptable salt or deuterated form thereof, wherein, $R^1$ is

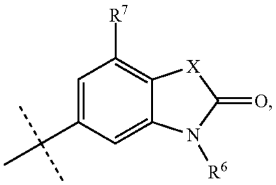

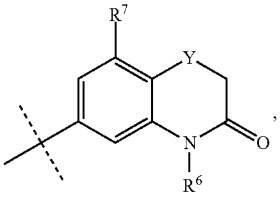

,

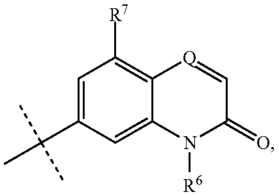

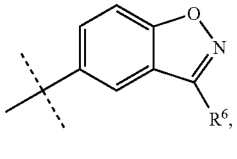

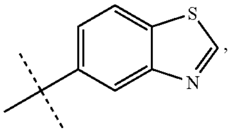

,

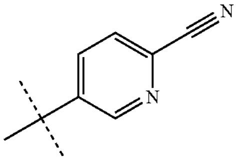

or

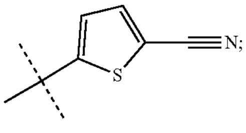

X is O, S or $CF_2$;

Y is O or S;

Q is CH or N;

$R^6$ is $C_{1-3}$ alkyl, wherein said $C_{1-3}$ alkyl is optionally substituted by 1, 2 or 3 F, OH, $OC_{1-3}$ alkyl, N($C_{1-3}$ alkyl)$_2$, cyclopropyl, or tetrahydropyran; and $R^7$ is H, F, Cl or $CH_3$.

Embodiment 4. The compound of embodiment 1 or 2, or a pharmaceutically acceptable salt or deuterated form thereof, wherein, $R^1$ is

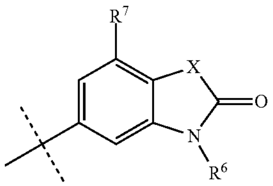

or

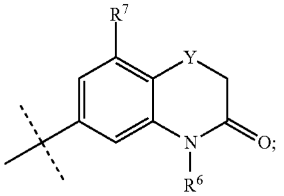

X is O, S or $CF_2$;

Y is O or S;

$R^6$ is $C_{1-3}$ alkyl, wherein said $C_{1-3}$ alkyl is optionally substituted by 1, 2 or 3 F, OH, $OC_{1-3}$ alkyl, $N(C_{1-3}$ alkyl$)_2$, cyclopropyl, or tetrahydropyran; and $R^7$ is H, F, Cl or $CH_3$.

Embodiment 5. The compound of embodiment 1 or 2, or a pharmaceutically acceptable salt or deuterated form thereof, wherein, $R^1$ is

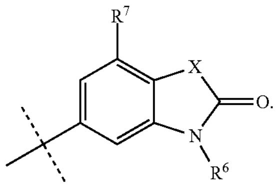

Embodiment 6. The compound of embodiment 5, or a pharmaceutically acceptable salt or deuterated form thereof, wherein, X is O; $R^6$ is $C_{1-3}$ alkyl; and $R^7$ is H.

Embodiment 7. The compound of embodiment 1 or 2, or a pharmaceutically acceptable salt or deuterated form thereof, wherein, $R^1$ is

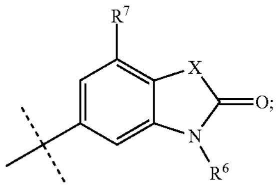

X is O;

$R^6$ is $C_{1-3}$ alkyl, wherein said $C_{1-3}$ alkyl is optionally substituted by 1, 2 or 3 F; and $R^7$ is H.

Embodiment 8. The compound of embodiment 1 or 2, or a pharmaceutically acceptable salt or deuterated form thereof, wherein,

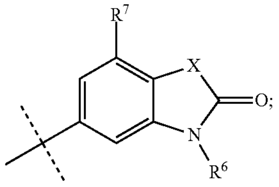

$R^1$ is
X is O;
$R^6$ is $C_{1-3}$ alkyl; and
$R^7$ is H.

Embodiment 9. The compound of embodiment 1 or 2, or a pharmaceutically acceptable salt or deuterated form thereof, wherein $R^1$ is

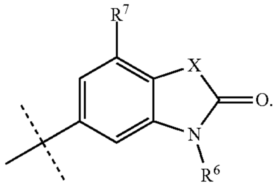

Embodiment 10. The compound of embodiment 1 or 2, or a pharmaceutically acceptable salt thereof, wherein $R^1$ is

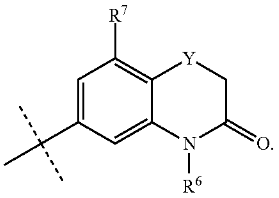

Embodiment 11. The compound of embodiment 1 or 2, or a pharmaceutically acceptable salt or deuterated form thereof, wherein $R^1$ is

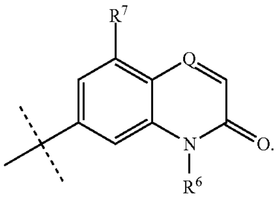

Embodiment 12. The compound of embodiment 1 or 2, or a pharmaceutically acceptable salt or deuterated form thereof, wherein $R^1$ is

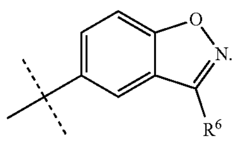

Embodiment 13. The compound of any one of embodiments 3-12, or a pharmaceutically acceptable salt or deuterated form thereof, wherein $R^6$ is methyl.

Embodiment 14. The compound of any one of embodiments 3-12, or a pharmaceutically acceptable salt or deuterated form thereof, wherein $R^6$ is ethyl.

Embodiment 15. The compound of any one of embodiments 3-12, or a pharmaceutically acceptable salt or deuterated form thereof, wherein $R^6$ is propyl.

Embodiment 16. The compound of embodiment 1 or 2, or a pharmaceutically acceptable salt or deuterated form thereof, wherein $R^1$ is

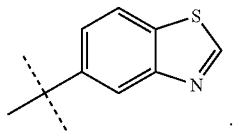

Embodiment 17. The compound of embodiment 1 or 2, or a pharmaceutically acceptable salt or deuterated form thereof, wherein $R^1$ is

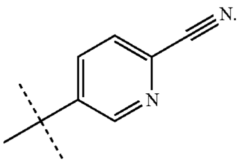

Embodiment 18. The compound of embodiment 1 or 2, or a pharmaceutically acceptable salt or deuterated form thereof, wherein $R^1$ is

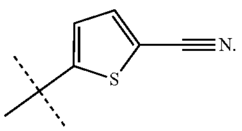

Embodiment 19. The compound of embodiment 1 or 2, wherein the compound is of Formula (III):

(III)

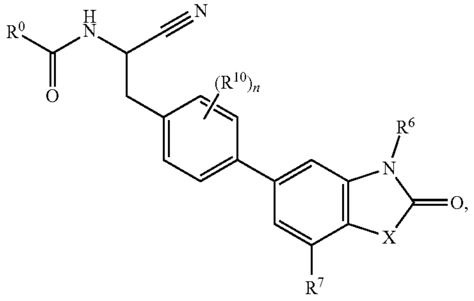

or a pharmaceutically acceptable salt or deuterated form thereof.

Embodiment 20. The compound of embodiment 1, wherein the compound is of Formula (III-A):

(III-A)

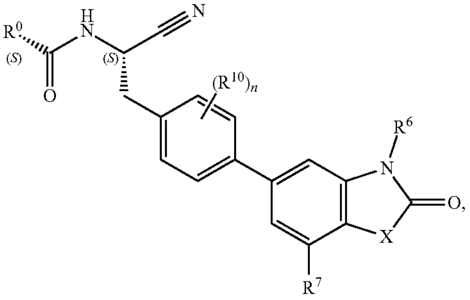

or a pharmaceutically acceptable salt or deuterated form thereof.

Embodiment 21. The compound of embodiment 1, wherein the compound is of Formula (III-B):

(III-B)

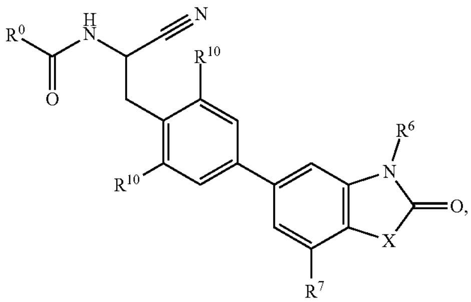

or a pharmaceutically acceptable salt or deuterated form thereof, wherein $R^{10}$ is —H or —F.

Embodiment 22. The compound of any one of embodiments 1-2 and 16-21, or a pharmaceutically acceptable salt or deuterated form thereof, wherein X is O.

Embodiment 23. The compound of any one of embodiments 1-22, or a pharmaceutically acceptable salt or deuterated form thereof, wherein $R^0$ is

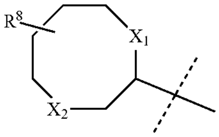

,

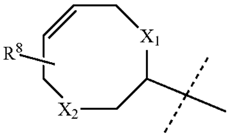

,

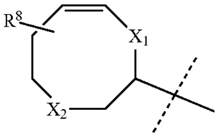

, or

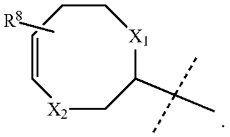

.

Embodiment 24. The compound of embodiment 23, or a pharmaceutically acceptable salt or deuterated form thereof, wherein $R^0$ is

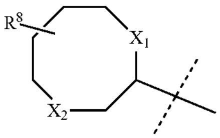

Embodiment 25. The compound of embodiment 23, or a pharmaceutically acceptable salt or deuterated form thereof, wherein $R^0$ is

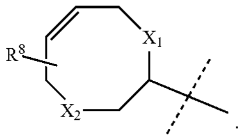

Embodiment 26. The compound of embodiment 23, or a pharmaceutically acceptable salt or deuterated form thereof, wherein $R^0$ is

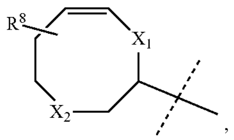

Embodiment 27. The compound of embodiment 23, or a pharmaceutically acceptable salt or deuterated form thereof, wherein $R^0$ is

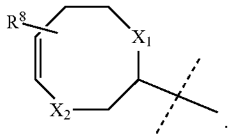

Embodiment 28. The compound of any one of embodiments 1-27, or a pharmaceutically acceptable salt or deuterated form thereof, wherein $R^8$ is methoxy.

Embodiment 29. The compound of any one of embodiments 1-27, or a pharmaceutically acceptable salt or deuterated form thereof, wherein $R^8$ is ethoxy.

Embodiment 30. The compound of any one of embodiments 1-27, or a pharmaceutically acceptable salt or deuterated form thereof, wherein $R^8$ is OH.

Embodiment 31. The compound of embodiment 23, or a pharmaceutically acceptable salt or deuterated form thereof, wherein $R^0$ is:

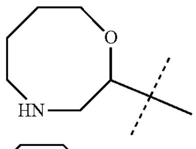
,
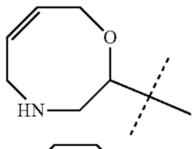
,
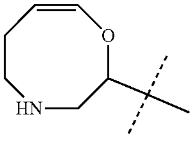
, or
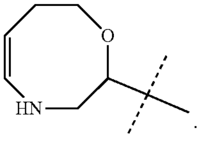
.

Embodiment 32. The compound of embodiment 31, or a pharmaceutically acceptable salt or deuterated form thereof, wherein $R^0$ is

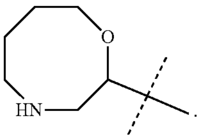

Embodiment 33. The compound of embodiment 31, or a pharmaceutically acceptable salt or deuterated form thereof, wherein $R^0$ is

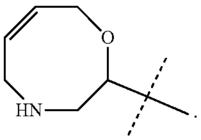

Embodiment 34. The compound of embodiment 31, or a pharmaceutically acceptable salt or deuterated form thereof, wherein $R^0$ is

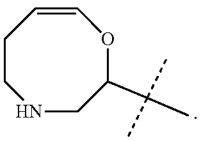

Embodiment 35. The compound of embodiment 31, or a pharmaceutically acceptable salt or deuterated form thereof, wherein $R^0$ is

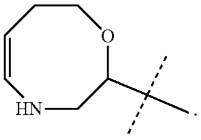

Embodiment 36. The compound of any one of embodiments 1-22, or a pharmaceutically acceptable salt or deuterated form thereof, wherein $R^0$ is

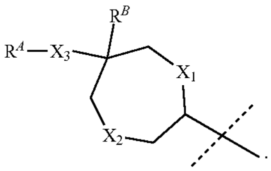

Embodiment 37. The compound of embodiment 36, or a pharmaceutically acceptable salt or deuterated form thereof, wherein $R^0$ is

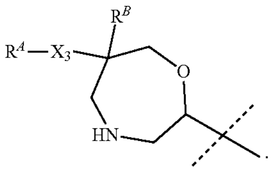

Embodiment 38. The compound of any one of embodiments 1-22 and 36-37, or a pharmaceutically acceptable salt or deuterated form thereof, wherein $R^A$ is H or $C_{1-6}$ alkyl.

Embodiment 39. The compound of embodiment 38, or a pharmaceutically acceptable salt or deuterated form thereof, wherein $R^A$ is H.

Embodiment 40. The compound of embodiment 38, or a pharmaceutically acceptable salt or deuterated form thereof, wherein $R^A$ is methyl.

Embodiment 41. The compound of any one of embodiments 1-22 and 36-40, or a pharmaceutically acceptable salt or deuterated form thereof, wherein $R^B$ is $C_{1-6}$ alkyl, $C_{2-6}$ alkenyl, $C_{1-6}$alkylene-carbocyclyl, or $C_{1-6}$alkylene-heteroaryl.

Embodiment 42. The compound of embodiment 41, or a pharmaceutically acceptable salt or deuterated form thereof, wherein $R^B$ is $C_{1-6}$ alkyl, $C_{1-6}$alkylene-aryl or —$C_{1-6}$ alkylene-5-6 membered heteroaryl.

Embodiment 43. The compound of embodiment 36, or a pharmaceutically acceptable salt or deuterated form thereof, wherein $R^0$ is

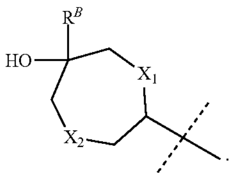

Embodiment 44. The compound of embodiment 36, or a pharmaceutically acceptable salt or deuterated form thereof, wherein $R^0$ is

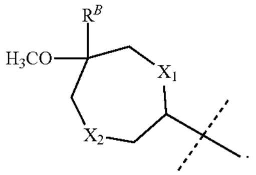

Embodiment 45. The compound of embodiment 36, or a pharmaceutically acceptable salt or deuterated form thereof, wherein $R^0$ is

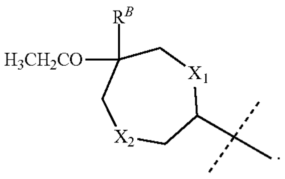

Embodiment 46. The compound of any one of embodiments 43-45, or a pharmaceutically acceptable salt or deuterated form thereof, wherein $R^B$ is methyl.

Embodiment 47. The compound of any one of embodiments 43-45, or a pharmaceutically acceptable salt or deuterated form thereof, wherein $R^B$ is ethyl.

Embodiment 48. The compound of embodiment 37, or a pharmaceutically acceptable salt or deuterated form thereof, wherein $R^0$ is

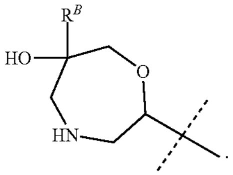

Embodiment 49. The compound of embodiment 37, or a pharmaceutically acceptable salt or deuterated form thereof, wherein $R^0$ is

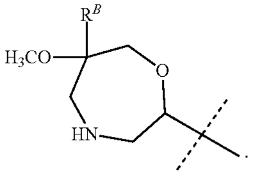

Embodiment 50. The compound of embodiment 37, or a pharmaceutically acceptable salt or deuterated form thereof, wherein $R^0$ is

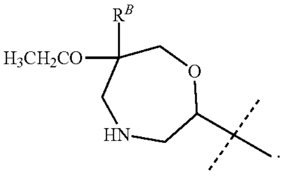

Embodiment 51. The compound of any one of embodiments 48-50, or a pharmaceutically acceptable salt or deuterated form thereof, wherein $R^B$ is methyl.

Embodiment 52. The compound of any one of embodiments 48-50, or a pharmaceutically acceptable salt or deuterated form thereof, wherein $R^B$ is ethyl.

Embodiment 53. The compound of any one of embodiments 1-6 and 36-42, or a pharmaceutically acceptable salt or deuterated form thereof, wherein $X_3$ is O.

Embodiment 54. The compound of any one of embodiments 1-2 and 23-53, or a pharmaceutically acceptable salt or deuterated form thereof, wherein $R^6$ is $C_1$-3 alkyl.

Embodiment 55. The compound of embodiment 40, or a pharmaceutically acceptable salt or deuterated form thereof, wherein $R^6$ is $CH_3$.

Embodiment 56. The compound of any one of embodiments 1-2 and 19-55, or a pharmaceutically acceptable salt or deuterated form thereof, wherein $R^7$ is H.

Embodiment 57. The compound of embodiment 1, or a pharmaceutically acceptable salt or deuterated form thereof, wherein the compound is selected from Table 1.

Embodiment 58. A pharmaceutical composition comprising an effective amount of a compound of any one of embodiments 1-57, or a pharmaceutically acceptable salt or deuterated form thereof and a pharmaceutically acceptable adjuvant, diluent or carrier.

Embodiment 59. A method for treating an obstructive disease of the airway in a patient in need thereof, comprising, administering to the patient an effective amount of a compound of any one of embodiments 1-57, or the composition of embodiment 58.

Embodiment 60. The method of embodiment 59, wherein the obstructive disease of the airway is asthma, chronic obstructive pulmonary disease (COPD), bronchitis, emphysema, cystic fibrosis (CF), bronchiectasis, sarcoidosis, alpha-1 antitrypsin (A1AT) deficiency, farmer's lung and related diseases, hypersensitivity pneumonitis, lung fibrosis, complications of lung transplantation, vasculitic and thrombotic disorders of the lung vasculature, pulmonary hypertension, antitussive activity including treatment of chronic cough associated with inflammatory and secretory conditions of the airways, iatrogenic cough, acute and chronic rhinitis including rhinitis medicamentosa, and vasomotor rhinitis; perennial and seasonal allergic rhinitis including rhinitis nervosa (hay fever), nasal polyposis; acute viral infection including the common cold, and infection due to a respiratory virus, acute lung injury, or acute respiratory distress syndrome (ARDS).

Embodiment 61. The method of embodiment 60, wherein the obstructive disease of the airway is asthma.

Embodiment 62. The method of embodiment 60, wherein the obstructive disease of the airway is acute respiratory distress syndrome (ARDS).

Embodiment 63. The method of embodiment 60, wherein the obstructive disease of the airway is bronchitis.

Embodiment 64. The method of embodiment 60, wherein the obstructive disease of the airway is lung fibrosis.

Embodiment 65. The method of embodiment 60, wherein the obstructive disease of the airway is emphysema.

Embodiment 66. The method of embodiment 60, wherein the obstructive disease of the airway is cystic fibrosis (CF).

Embodiment 67. The method of embodiment 60, wherein the obstructive disease of the airway is bronchiectasis.

Embodiment 68. The method of embodiment 60, wherein the obstructive disease of the airway is sarcoidosis.

Embodiment 69. The method of embodiment 60, wherein the obstructive disease of the airway is alpha-1 antitrypsin (A1AT) deficiency.

Embodiment 70. The method of embodiment 60, wherein the obstructive disease of the airway is farmer's lung.

Embodiment 71. The method of embodiment 60, wherein the obstructive disease of the airway is hypersensitivity pneumonitis.

Embodiment 72. The method of embodiment 60, wherein the obstructive disease of the airway is a complication of lung transplantation.

Embodiment 73. The method of embodiment 60, wherein the obstructive disease of the airway is a vasculitic or thrombotic disorder of the lung vasulature.

Embodiment 74. The method of embodiment 60, wherein the obstructive disease of the airway is pulmonary hypertension.

Embodiment 75. The method of embodiment 60, wherein the obstructive disease of the airway is iatrogenic cough.

Embodiment 76. The method of embodiment 60, wherein the obstructive disease of the airway is acute rhinitis.

Embodiment 77. The method of embodiment 60, wherein the obstructive disease of the airway is chronic rhinitis.

Embodiment 78. The method of embodiment 60, wherein the obstructive disease of the airway is rhinitis medicamentosa or vasomotor rhinitis.

Embodiment 79. The method of embodiment 60, wherein the obstructive disease of the airway is nasal polyposis.

Embodiment 80. The method of embodiment 60, wherein the obstructive disease of the airway is COPD.

Embodiment 81. The method of embodiment 61, wherein the asthma is bronchial, allergic, intrinsic, extrinsic, exercise-induced or drug-induced asthma.

Embodiment 82. The method of embodiment 63, wherein the bronchitis is infectious bronchitis or eosinophilic bronchitis.

Embodiment 83. The method of embodiment 64, wherein the lung fibrosis is idiopathic pulmonary fibrosis, cryptogenic fibrosing alveolitis, idiopathic interstitial pneumonia, or fibrosis complicating anti-neoplastic therapy or chronic infection.

Embodiment 84. The method of embodiment 67, wherein the bronchiectasis is non-cystic fibrosis bronchiectasis (NCFBE).

Embodiment 85. The method of embodiment 67, wherein the bronchiectasis is associated with cystic fibrosis.

Embodiment 86. The method of embodiment 74, wherein the pulmonary hypertension is pulmonary arterial hypertension.

Embodiment 87. A method for treating cystic fibrosis in a patient in need thereof, comprising, administering to the patient an effective amount of a compound of any one of embodiments 1-57, or the composition of embodiment 58.

Embodiment 88. The method of embodiment 87, wherein the treating comprises improving the lung function of the patient, as compared to the lung function of the patient prior to treatment.

Embodiment 89. The method of embodiment 88, wherein improving lung function of the patient comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC (FEF (25-75%)), as compared to the respective value for the patient prior treatment.

Embodiment 90. The method of embodiment 88 or 89, wherein the lung function is measured by spirometry.

Embodiment 91. A method for treating bronchiectasis in a patient in need thereof, comprising, administering to the patient, an effective amount of a compound of any one of embodiments 1-57, or the composition of embodiment 58.

Embodiment 92. The method of embodiment 91, wherein the bronchiectasis is non-cystic fibrosis bronchiectasis (NCFBE).

Embodiment 93. The method of embodiment 91, wherein the bronchiectasis is associated with cystic fibrosis.

Embodiment 94. The method of any one of embodiments 91-93, wherein treating comprises improving the lung function of the patient, as compared to the lung function of the patient prior to treatment.

Embodiment 95. The method of embodiment 94, wherein improving lung function of the patient comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC ($FEF_{(25-75\%)}$), as compared to the respective value for the patient prior to treatment.

Embodiment 96. The method of embodiment 94 or 95, wherein the lung function is measured by spirometry.

Embodiment 97. The method of any one of embodiments 91-96, wherein treating comprises decreasing the rate of pulmonary exacerbation, as compared to the rate of pulmonary exacerbation of the patient prior to treatment.

Embodiment 98. The method of any one of embodiments 91-97, wherein treating comprises increasing the time to first pulmonary exacerbation, as compared to an untreated patient.

Embodiment 99. The method of embodiment 86 or 87, wherein the pulmonary exacerbation is characterized by three or more of the following symptoms exhibited for at least 48 hours by the patient: (1) increased cough; (2) increased sputum volume or change in sputum consistency; (3) increased sputum purulence; (4) increased breathlessness and/or decreased exercise tolerance; (5) fatigue and/or malaise; (6) hemoptysis.

Embodiment 100. A method for treating chronic rhinosinusitis (CRS) in a patient in need thereof, comprising, administering to the patient, an effective amount of a compound of any one of embodiments 1-57, or the composition of embodiment 58.

Embodiment 101. The method of embodiment 100, wherein the chronic rhinosinusitis is chronic rhinosinusitis without nasal polyps (CRSsNP).

Embodiment 102. The method of embodiment 100, wherein the chronic rhinosinusitis is chronic rhinosinusitis with nasal polyps (CRSwNP).

Embodiment 103. The method of any one of embodiments 100-102, wherein the chronic rhinosinusitis is refractory chronic rhinosinusitis.

Embodiment 104. The method of any one of embodiments 100-103, wherein treating comprises reducing, diminishing the severity of, delaying the onset of, or eliminating one or more symptoms of CRS.

Embodiment 105. The method of embodiment 104, wherein the one or more symptoms of CRS is nasal congestion; nasal obstruction; nasal discharge; post-nasal drip; facial pressure; facial pain; facial fullness; reduced smell; depression; mucosal edema; mucopurulent discharge; obstruction of the middle meatus; mucosal changes within the ostiomeatal complex and sinuses; or rhinorrhea.

Embodiment 106. A method for treating hidradenitis suppurativa (HS) in a patient in need thereof, comprising, administering to the patient, an effective amount of a compound of any one of embodiments 1-57, or the composition of embodiment 58.

Embodiment 107. The method of embodiment 106, wherein the hidradenitis suppurativa (HS) is Hurley stage I.

Embodiment 108. The method of embodiment 106, wherein the hidradenitis suppurativa (HS) is Hurley stage II.

Embodiment 109. The method of embodiment 106, wherein the hidradenitis suppurativa (HS) is Hurley stage III.

Embodiment 110. A method for treating cancer in a patient in need thereof, comprising, administering to the patient, an effective amount of a compound of any one of embodiments 1-57, or the composition of embodiment 58.

Embodiment 111. The method of embodiment 110, wherein the cancer is a metastatic cancer.

Embodiment 112. The method of embodiment 111, wherein the metastatic cancer is breast to lung metastatic cancer.

Embodiment 113. The method of embodiment 111, wherein the metastatic cancer comprises metastasis of breast cancer to the brain, bone, pancreas, lymph nodes or liver.

Embodiment 114. The method of embodiment 111, wherein the metastatic cancer comprises metastasis of bone cancer to the lung.

Embodiment 115. The method of embodiment 111, wherein the metastatic cancer comprises metastasis of colorectal cancer to the peritoneum, the pancreas, the stomach, the lung, the liver, the kidney, or the spleen.

Embodiment 116. The method of embodiment 111, wherein the metastatic cancer comprises metastasis of stomach cancer to the mesentery, the spleen, the pancreas, the lung, the liver, the adrenal gland, or the ovary.

Embodiment 117. The method of embodiment 111, wherein the metastatic cancer comprises metastasis of liver cancer to the intestine, spleen, pancreas, stomach, lung, or the kidney.

Embodiment 118. The method of embodiment 111, wherein the metastatic cancer comprises metastasis of lymphoma to the kidney, ovary, liver, bladder, or the spleen.

Embodiment 119. A method for treating lupus nephritis in a patient in need thereof, comprising, administering to the patient, an effective amount of a compound of any one of embodiments 1-57, or the composition of embodiment 58.

Embodiment 120. A method for treating rheumatoid arthritis in a patient in need thereof, comprising, administering to the patient, an effective amount of a compound of any one of embodiments 1-57, or the composition of embodiment 58.

Embodiment 121. A method for treating inflammatory bowel disease (IBD) in a patient in need thereof, comprising, administering to the patient, an effective amount of a compound of any one of embodiments 1-57, or the composition of embodiment 58.

Embodiment 122. The method of embodiment 121, wherein the inflammatory bowel disease (IBD) is Crohn's disease.

Embodiment 123. The method of embodiment 121, wherein the inflammatory bowel disease (IBD) is ulcerative colitis.

Embodiment 124. A method for treating an anti-neutrophil cytoplasmic antibody (ANCA) associated vasculitis in a patient in need thereof, comprising, administering to the patient, an effective amount of a compound of any one of embodiments 1-57, or the composition of embodiment 58, wherein the ANCA associated disease is granulomatosis with polyangiitis (GPA); microscopic polyangiitis (MPA).

Embodiment 125. A method for treating a disease in a patient in need thereof comprising, administering to the patient, an effective amount of a compound of any one of embodiments 1-57, or the composition of embodiment 58, wherein the disease is giant cell arteritis, polyarteritis nodosa, anti-GBM disease (Goodpasture's), systemic scleroderma, diabetic nephropathy, diabetic neuropathy, diabetic retinopathy, diabetic ulcers, Duchenne muscular dystrophy, bronchiolitis obliterans, atopic dermatitis, pyoderma gangrenosum, sweet's syndrome, dermatomyositis/polymyositis, neutrophilic dermatoses, thrombosis, bronchopulmonary dysplasia, amyotrophic lateral sclerosis, sickle cell anemia, psoriasis, or a ventilator-induced lung injury.

Embodiments 2

Embodiment 1. A compound of formula (I)

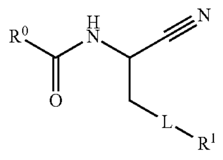

(I)

or a pharmaceutically acceptable salt or deuterated form thereof, wherein $R^0$ is

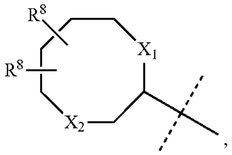

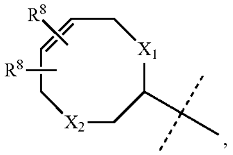

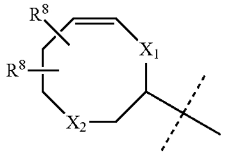

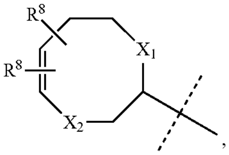

, or

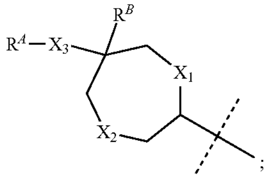

$X_1$ and $X_2$ are independently O, S, NH, N($C_{1-6}$ alkyl), or $CR^{12}R^{13}$, wherein at least one of $X_1$ and $X_2$ are not $CR^{12}R^{13}$;

$X_3$ is O, S, NH, or N($C_{1-6}$ alkyl);

$R^A$ is H, $C_{1-6}$ alkyl, $C_{1-6}$alkylene-carbocyclyl, $C_{1-6}$alkylene-heteroaryl, heteroaryl or carbocyclyl; and $R^B$ is $C_{1-6}$ alkyl, $C_{2-6}$alkenyl, cycloalkyl, $C_{1-6}$alkylene-carbocyclyl, $C_{1-6}$alkylene-aryl, $C_{1-6}$ alkylene-heteroaryl, heteroaryl or carbocyclyl; or $R^A$ and $R^B$ are taken together to form a heterocyclyl;

L is aryl, heterocyclyl, heteroaryl, or

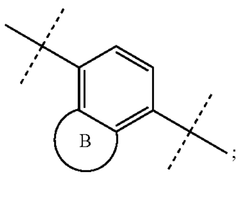

wherein L is independently substituted by 0-4 $R^{10}$ and wherein ring B is a carbocycle, or a heterocycle;

$R^1$ is

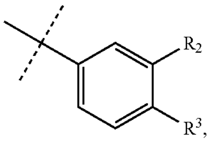

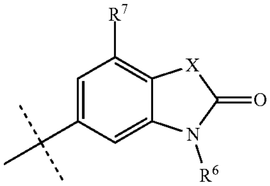

,

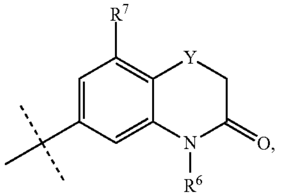

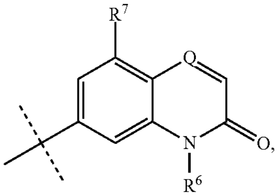

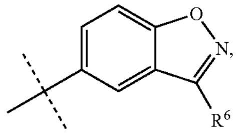

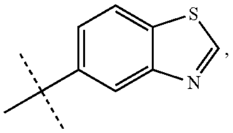

or

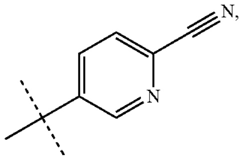

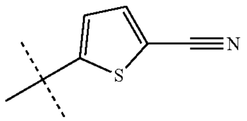

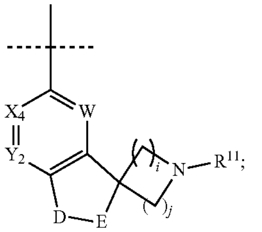

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$ or $SO_2NR_4R^5$, wherein $R^4$ and $R^5$ together with the nitrogen atom to which they are attached form a heterocyclyl;

X is O, S, CHF, or $CF_2$;

Y is O or S;

Q is CH or N;

$R^6$ is $C_{1-6}$ alkyl optionally substituted by 1, 2 or 3 F, or optionally substituted by OH, O $C_{1-6}$ alkyl, N($C_{1-6}$ alkyl)$_2$, cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, or $C_{1-6}$ alkylene-heteroaryl, halogenated $C_{1-6}$alkoxy, heteroaryl or carbocyclyl;

each $R^{13}$ is independently H, F, Cl, Br, I or $C_1$-$C_6$ alkyl;

each $R^{10}$ is independently oxo, halogen, $C_{1-6}$ alkyl, $C_{1-6}$alkoxy, S—$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, N($C_{1-6}$ alkyl)$_2$, COOH, $COC_{1-6}$ alkyl, $COOC_{1-6}$ alkyl, $CON_{1-6}$ alkyl, CON($C_{1-6}$ alkyl)$_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxyl, $NH_2$ and COOH;

W, $X_4$ and $Y_2$ are each independently CH or N, provided that a maximum of one of W, $X_4$ and $Y_2$ can be N;

D-E is N(H)—C(O), N($C_{1-6}$ alkyl)-C(O), $CH_2CH_2$, C(O)—O or $CH_2$-0;

$R^{11}$ is H, $C_{1-6}$ alkyl, alkylene-O-alkyl, or heterocyclyl; and i and j are each independently 1, 2 or 3; provided that the sum of i+j is 2, 3 or 4.

Embodiment 2. The compound of embodiment 1, wherein the compound is of Formula (II):

(II)

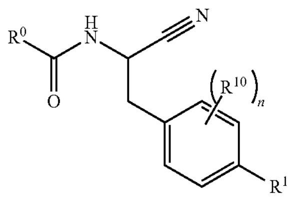

or a pharmaceutically acceptable salt or deuterated form thereof, wherein n is 0 or 1, and $R^{10}$ is halogen.

Embodiment 3. The compound of embodiment 2, or a pharmaceutically acceptable salt thereof, wherein the halogen is F.

Embodiment 4. The compound of embodiment 2 or 3, or a pharmaceutically acceptable salt thereof, wherein n is 0.

Embodiment 5. The compound of embodiment 2 or 3, or a pharmaceutically acceptable salt thereof, wherein n is 1.

Embodiment 6. The compound of any one of embodiments 1-5, or a pharmaceutically acceptable salt or deuterated form thereof, wherein, $R^1$ is

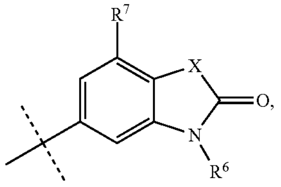
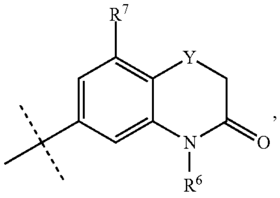
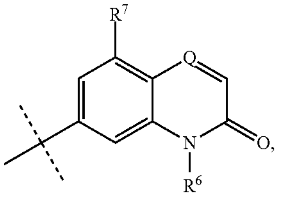
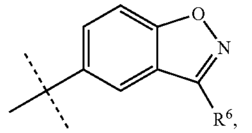
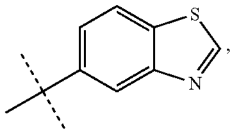
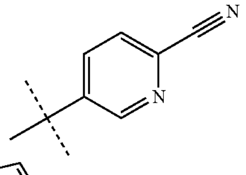
or
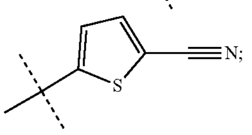

X is O, S or $CF_2$;

Y is O or S;

Q is CH or N;

$R^6$ is $C_{1-3}$ alkyl, wherein said $C_{1-3}$ alkyl is optionally substituted by 1, 2 or 3 F, OH, $OC_{1-3}$ alkyl, $N(C_{1-3}$ alkyl$)_2$, cyclopropyl, or tetrahydropyran; and $R^7$ is H, F, Cl or $CH_3$.

Embodiment 7. The compound of any one of embodiments 1-5, or a pharmaceutically acceptable salt or deuterated form thereof, wherein, $R^1$ is

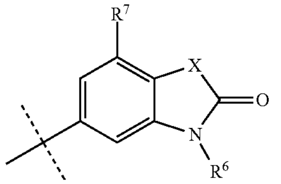
or
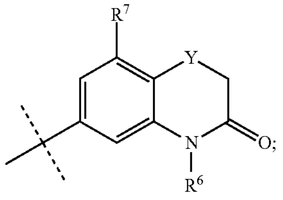

X is O, S or $CF_2$;

Y is O or S;

$R^6$ is $C_{1-3}$ alkyl, wherein said $C_{1-3}$ alkyl is optionally substituted by 1, 2 or 3 F, OH, $OC_{1-3}$ alkyl, $N(C_{1-3}$ alkyl$)_2$, cyclopropyl, or tetrahydropyran; and $R^7$ is H, F, Cl or $CH_3$.

Embodiment 8. The compound of any one of embodiments 1-5, or a pharmaceutically acceptable salt or deuterated form thereof, wherein, $R^1$ is

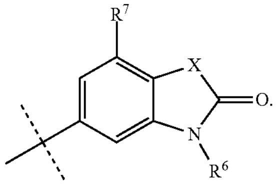

Embodiment 9. The compound of embodiment 8, or a pharmaceutically acceptable salt or deuterated form thereof, wherein, X is O; $R^6$ is $C_{1-3}$ alkyl; and $R^7$ is H.

Embodiment 10. The compound of any one of embodiments 1-5, or a pharmaceutically acceptable salt or deuterated form thereof, wherein, $R^1$ is

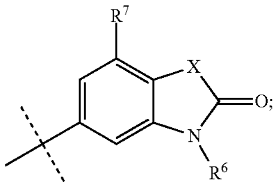

X is O;

$R^6$ is $C_{1-3}$ alkyl, wherein said $C_{1-3}$ alkyl is optionally substituted by 1, 2 or 3 F; and $R^7$ is H.

Embodiment 11. The compound of any one of embodiments 1-5, or a pharmaceutically acceptable salt or deuterated form thereof, wherein, $R^1$ is

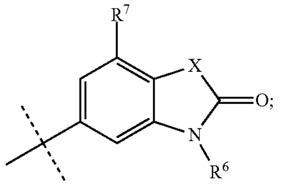

X is O;

$R^6$ is $C_{1-3}$ alkyl; and $R^7$ is H.

Embodiment 12. The compound of any one of embodiments 1-5, or a pharmaceutically acceptable salt or deuterated form thereof, wherein $R^1$ is

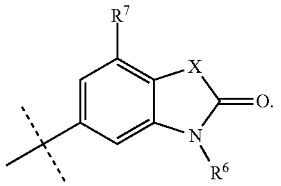

Embodiment 13. The compound of any one of embodiments 1-5, or a pharmaceutically acceptable salt thereof, wherein $R^1$ is

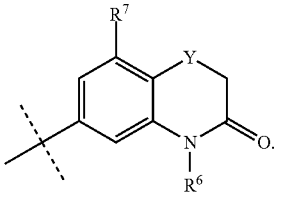

Embodiment 14. The compound of any one of embodiments 1-5, or a pharmaceutically acceptable salt or deuterated form thereof, wherein $R^1$ is

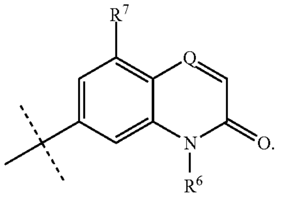

Embodiment 15. The compound of any one of embodiments 1-5, or a pharmaceutically acceptable salt or deuterated form thereof, wherein $R^1$ is

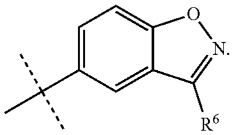

Embodiment 16. The compound of any one of embodiments 3-15, or a pharmaceutically acceptable salt or deuterated form thereof, wherein $R^6$ is methyl.

Embodiment 17. The compound of any one of embodiments 3-15, or a pharmaceutically acceptable salt or deuterated form thereof, wherein $R^6$ is ethyl.

Embodiment 18. The compound of any one of embodiments 3-15, or a pharmaceutically acceptable salt or deuterated form thereof, wherein $R^6$ is propyl.

Embodiment 19. The compound of any one of embodiments 1-5, or a pharmaceutically acceptable salt or deuterated form thereof, wherein $R^1$ is

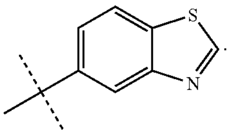

Embodiment 20. The compound of any one of embodiments 1-5, or a pharmaceutically acceptable salt or deuterated form thereof, wherein $R^1$ is

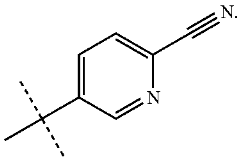

Embodiment 21. The compound of any one of embodiments 1-5, or a pharmaceutically acceptable salt or deuterated form thereof, wherein $R^1$ is

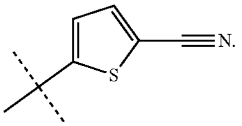

Embodiment 22. The compound of any one of embodiments 1-5, wherein the compound is of Formula (III):

(III)

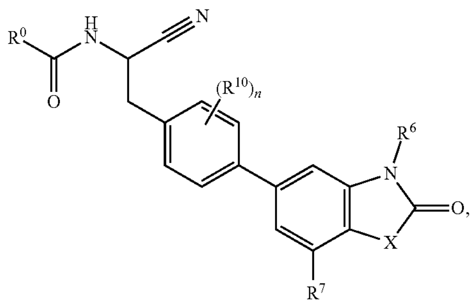

or a pharmaceutically acceptable salt or deuterated form thereof.

Embodiment 23. The compound of embodiment 1, wherein the compound is of Formula (III-A):

(III-A)

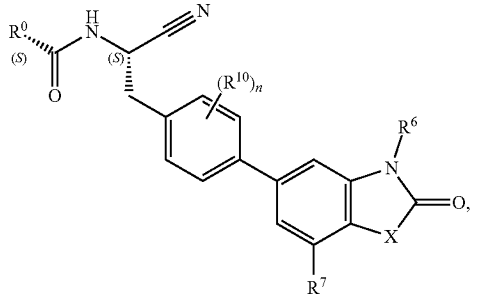

or a pharmaceutically acceptable salt or deuterated form thereof.

Embodiment 24. The compound of embodiment 22 or 23, wherein n is 0.

Embodiment 25. The compound of embodiment 22 or 23, wherein n is 1.

Embodiment 26. The compound of embodiment 1, wherein the compound is of Formula (III-B):

(III-B)

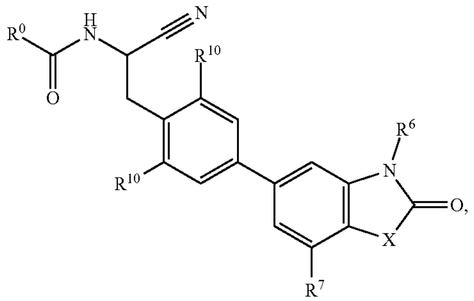

or a pharmaceutically acceptable salt or deuterated form thereof, wherein $R^{10}$ is —H or —F.

Embodiment 27. The compound of any one of embodiments 22-23 and 25-26, wherein $R^{10}$ is F.

Embodiment 28. The compound of any one of embodiments 1-5 and 16-27, or a pharmaceutically acceptable salt or deuterated form thereof, wherein X is O.

Embodiment 29. The compound of any one of embodiments 1-28, or a pharmaceutically acceptable salt or deuterated form thereof, wherein $R^0$ is

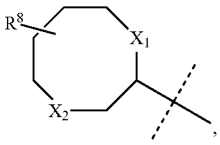
,
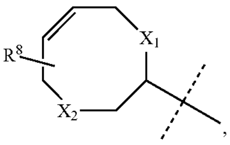
,
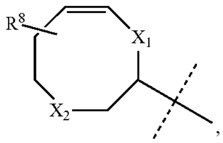
, or
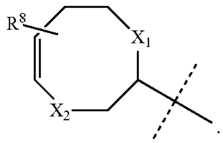

Embodiment 30. The compound of embodiment 29, or a pharmaceutically acceptable salt or deuterated form thereof, wherein $R^0$ is

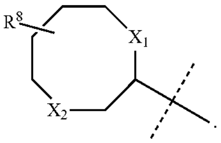

Embodiment 31. The compound of embodiment 29, or a pharmaceutically acceptable salt or deuterated form thereof, wherein $R^0$ is

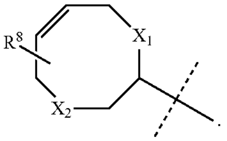

Embodiment 32. The compound of embodiment 29, or a pharmaceutically acceptable salt or deuterated form thereof, wherein $R^0$ is

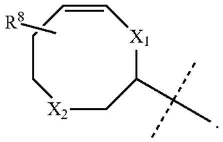

Embodiment 33. The compound of embodiment 29, or a pharmaceutically acceptable salt or deuterated form thereof, wherein $R^0$ is

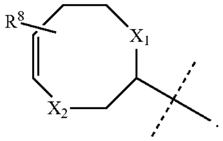

Embodiment 34. The compound of embodiment 30, or a pharmaceutically acceptable salt or deuterated form thereof, wherein $R^0$ is

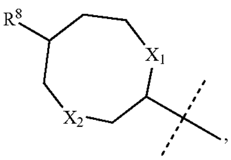
,
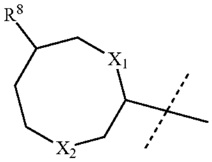
, or
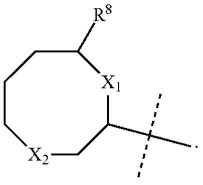

Embodiment 35. The compound of embodiment 34, or a pharmaceutically acceptable salt or deuterated form thereof, wherein $R^0$ is

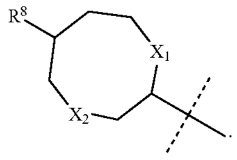

Embodiment 36. The compound of embodiment 34, or a pharmaceutically acceptable salt or deuterated form thereof, wherein $R^0$ is

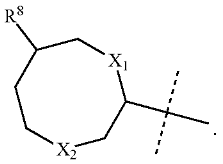

Embodiment 37. The compound of embodiment 34, or a pharmaceutically acceptable salt or deuterated form thereof, wherein $R^0$ is

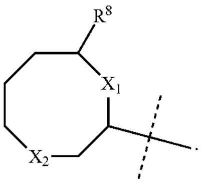

Embodiment 38. The compound of embodiment 35 or 36, wherein $X_1$ is O and $X_2$ is NH.

Embodiment 39. The compound of embodiment 36 or 37, wherein $X_1$ is $CH_2$ and $X_2$ is NH.

Embodiment 40. The compound of any one of embodiments 34-39, wherein one $R^8$ is OH, unsubstituted $C_{1-6}$alkoxy, or O-cycloalkyl.

Embodiment 41. The compound of any one of embodiments 1-40, or a pharmaceutically acceptable salt or deuterated form thereof, wherein each occurrence of $R^8$ is methoxy.

Embodiment 42. The compound of any one of embodiments 1-40, or a pharmaceutically acceptable salt or deuterated form thereof, wherein each occurrence of $R^8$ is ethoxy.

Embodiment 43. The compound of any one of embodiments 1-40, or a pharmaceutically acceptable salt or deuterated form thereof, wherein each occurrence of $R^8$ is OH.

Embodiment 44. The compound of any one of embodiments 1-28, or a pharmaceutically acceptable salt or deuterated form thereof, wherein $R^0$ is

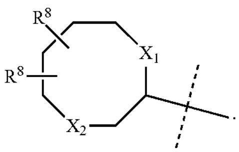

Embodiment 45. The compound of any one of embodiments 1-28, or a pharmaceutically acceptable salt or deuterated form thereof, wherein $R^0$ is

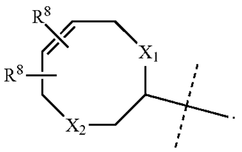

Embodiment 46. The compound of any one of embodiments 1-28, or a pharmaceutically acceptable salt or deuterated form thereof, wherein $R^0$ is

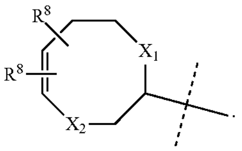

Embodiment 47. The compound of any one of embodiments 1-28, or a pharmaceutically acceptable salt or deuterated form thereof, wherein $R^0$ is

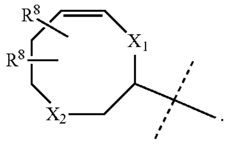

Embodiment 48. The compound of embodiment 44, or a pharmaceutically acceptable salt or deuterated form thereof, wherein $R^0$ is

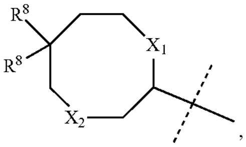

, or

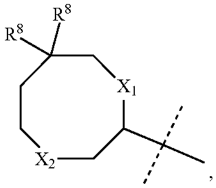

, or

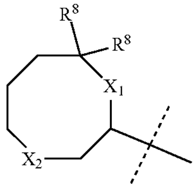

.

Embodiment 49. The compound of embodiment 48, or a pharmaceutically acceptable salt or deuterated form thereof, wherein $R^0$ is

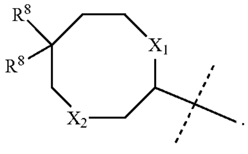

Embodiment 50. The compound of embodiment 48, or a pharmaceutically acceptable salt or deuterated form thereof, wherein $R^0$ is

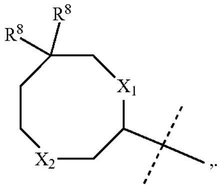

Embodiment 51. The compound of embodiment 48, or a pharmaceutically acceptable salt or deuterated form thereof, wherein $R^0$ is

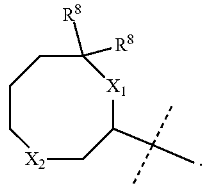

Embodiment 52. The compound of embodiment 49 or 50, wherein $X_1$ is O and $X_2$ is NH.

Embodiment 53. The compound of embodiment 50 or 51, wherein $X_1$ is $CH_2$ and $X_2$ is NH.

Embodiment 54. The compound of any one of embodiments 1-53, wherein each $R^8$ is independently H, OH, halogen, $NH_2$, COOH, $C_{1-6}$ alkyl, $C_{1-6}$ alkyl-OH, $C_{2-6}$alkenyl, $C_{1-6}$ alkoxy, O-cycloalkyl, cycloalkyl, or halogenated $C_{1-6}$alkoxy, provided that one $R^8$ is not H.

Embodiment 55. The compound of any one of embodiments 1-53, wherein each $R^8$ is independently OH, halogen, $NH_2$, COOH, $C_{1-6}$ alkyl, $C_{1-6}$ alkyl-OH, $C_{2-6}$alkenyl, $C_{1-6}$ alkoxy, O-cycloalkyl, cycloalkyl, or halogenated $C_{1-6}$alkoxy.

Embodiment 56. The compound of any one of embodiments 1-53, wherein each $R^8$ is independently OH or $C_{1-6}$alkoxy.

Embodiment 57. The compound of any one of embodiments 1-53, wherein each $R^8$ is $C_{1-6}$alkoxy.

Embodiment 58. The compound of any one of embodiments 1-53, wherein each $R^8$ is OH.

Embodiment 59. The compound of any one of embodiments 55-58, wherein the $C_{1-6}$alkoxy is methoxy or ethoxy.

Embodiment 60. The compound of any one of embodiments 55-58, wherein the $C_{1-6}$alkoxy is methoxy.

Embodiment 61. The compound of any one of embodiments 55-58, wherein the $C_{1-6}$alkoxy is ethoxy.

Embodiment 62. The compound of any one of embodiments 44-54, wherein one $R^8$ is OH, unsubstituted $C_{1-6}$alkoxy, or O-cycloalkyl and the other $R^8$ is unsubstituted $C_{1-6}$ alkyl or cycloalkyl.

Embodiment 63. The compound of embodiment 29, or a pharmaceutically acceptable salt or deuterated form thereof, wherein $R^0$ is:

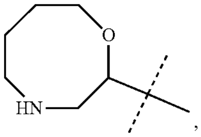

,

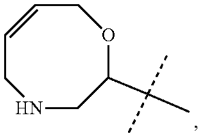

,

-continued

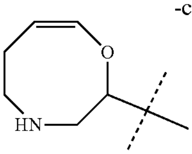

, or

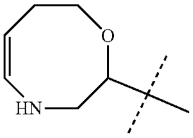

.

Embodiment 64. The compound of embodiment 63, or a pharmaceutically acceptable salt or deuterated form thereof, wherein $R^0$ is

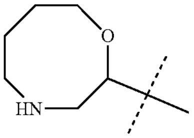

Embodiment 65. The compound of embodiment 63, or a pharmaceutically acceptable salt or deuterated form thereof, wherein $R^0$ is

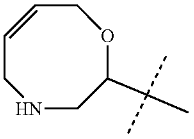

Embodiment 66. The compound of embodiment 63, or a pharmaceutically acceptable salt or deuterated form thereof, wherein $R^0$ is

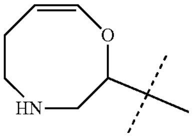

Embodiment 67. The compound of embodiment 63, or a pharmaceutically acceptable salt or deuterated form thereof, wherein $R^0$ is

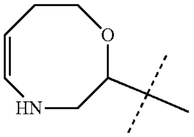

Embodiment 68. The compound of any one of embodiments 1-28, or a pharmaceutically acceptable salt or deuterated form thereof, wherein $R^0$ is

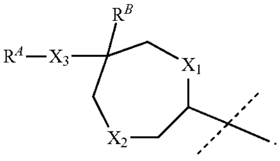

Embodiment 69. The compound of embodiment 68, or a pharmaceutically acceptable salt or deuterated form thereof, wherein $R^0$ is

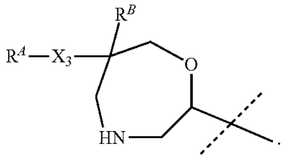

Embodiment 70. The compound of any one of embodiments 1-28 and 68-69, or a pharmaceutically acceptable salt or deuterated form thereof, wherein $R^A$ is H or $C_{1-6}$ alkyl.

Embodiment 71. The compound of embodiment 70, or a pharmaceutically acceptable salt or deuterated form thereof, wherein $R^A$ is H.

Embodiment 72. The compound of embodiment 70, or a pharmaceutically acceptable salt or deuterated form thereof, wherein $R^A$ is methyl.

Embodiment 73. The compound of any one of embodiments 1-28 and 68-72, or a pharmaceutically acceptable salt or deuterated form thereof, wherein $R^B$ is $C_{1-6}$ alkyl, $C_{2-6}$ alkenyl, $C_{1-6}$alkylene-carbocyclyl, or $C_{1-6}$alkylene-heteroaryl.

Embodiment 74. The compound of embodiment 73, or a pharmaceutically acceptable salt or deuterated form thereof, wherein $R^B$ is $C_{1-6}$ alkyl, $C_{1-6}$alkylene-aryl or —$C_{1-6}$ alkylene-5-6 membered heteroaryl.

Embodiment 75. The compound of embodiment 68, or a pharmaceutically acceptable salt or deuterated form thereof, wherein $R^0$ is

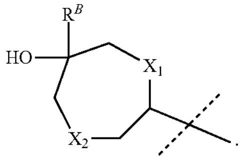

Embodiment 76. The compound of embodiment 68, or a pharmaceutically acceptable salt or deuterated form thereof, wherein $R^0$ is

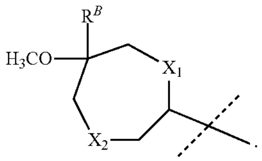

Embodiment 77. The compound of embodiment 68, or a pharmaceutically acceptable salt or deuterated form thereof, wherein $R^0$ is

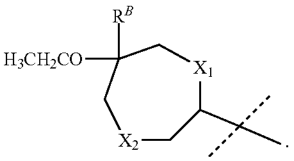

Embodiment 78. The compound of any one of embodiments 75-77, or a pharmaceutically acceptable salt or deuterated form thereof, wherein $R^B$ is methyl.

Embodiment 79. The compound of any one of embodiments 75-77, or a pharmaceutically acceptable salt or deuterated form thereof, wherein $R^B$ is ethyl.

Embodiment 80. The compound of embodiment 69, or a pharmaceutically acceptable salt or deuterated form thereof, wherein $R^0$ is

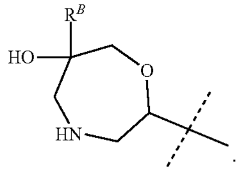

Embodiment 81. The compound of embodiment 69, or a pharmaceutically acceptable salt or deuterated form thereof, wherein $R^0$ is

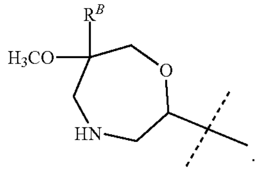

Embodiment 82. The compound of embodiment 69, or a pharmaceutically acceptable salt or deuterated form thereof, wherein $R^0$ is

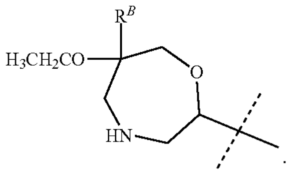

Embodiment 83. The compound of any one of embodiments 80-82, or a pharmaceutically acceptable salt or deuterated form thereof, wherein $R^B$ is methyl.

Embodiment 84. The compound of any one of embodiments 80-82, or a pharmaceutically acceptable salt or deuterated form thereof, wherein $R^B$ is ethyl.

Embodiment 85. The compound of any one of embodiments 80-82, or a pharmaceutically acceptable salt or deuterated form thereof, wherein $R^B$ is isopropyl.

Embodiment 86. The compound of any one of embodiments 80-82, or a pharmaceutically acceptable salt or deuterated form thereof, wherein $R^B$ is

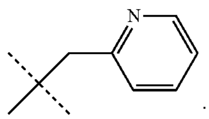

Embodiment 87. The compound of any one of embodiments 80-82, or a pharmaceutically acceptable salt or deuterated form thereof, wherein $R^B$ is

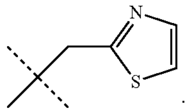

Embodiment 88. The compound of any one of embodiments 1-9 and 68-74, or a pharmaceutically acceptable salt or deuterated form thereof, wherein $X_3$ is O.

Embodiment 89. The compound of any one of embodiments 1-5 and 23-88, or a pharmaceutically acceptable salt or deuterated form thereof, wherein $R^6$ is $C_1$-3 alkyl.

Embodiment 90. The compound of embodiment 72, or a pharmaceutically acceptable salt or deuterated form thereof, wherein $R^6$ is $CH_3$.

Embodiment 91. The compound of any one of embodiments 1-5 and 22-90, or a pharmaceutically acceptable salt or deuterated form thereof, wherein $R^7$ is H.

Embodiment 92. The compound of embodiment 1, or a pharmaceutically acceptable salt or deuterated form thereof, wherein the compound is selected from Table 1.

Embodiment 93. A pharmaceutical composition comprising an effective amount of a compound of any one of embodiments 1-92, or a pharmaceutically acceptable salt or deuterated form thereof and a pharmaceutically acceptable adjuvant, diluent or carrier.

Embodiment 94. A method for treating an obstructive disease of the airway in a patient in need thereof, comprising, administering to the patient an effective amount of a compound of any one of embodiments 1-92, or the composition of embodiment 93.

Embodiment 95. The method of embodiment 94, wherein the obstructive disease of the airway is asthma, chronic obstructive pulmonary disease (COPD), bronchitis, emphysema, cystic fibrosis (CF), bronchiectasis, sarcoidosis, alpha-1 antitrypsin (A1AT) deficiency, farmer's lung and related diseases, hypersensitivity pneumonitis, lung fibrosis, complications of lung transplantation, vasculitic and thrombotic disorders of the lung vasculature, pulmonary hypertension, antitussive activity including treatment of chronic cough associated with inflammatory and secretory conditions of the airways, iatrogenic cough, acute and chronic rhinitis including rhinitis medicamentosa, and vasomotor rhinitis; perennial and seasonal allergic rhinitis including rhinitis nervosa (hay fever), nasal polyposis; acute viral infection including the common cold, and infection due to a respiratory virus, acute lung injury, or acute respiratory distress syndrome (ARDS).

Embodiment 96. The method of embodiment 95, wherein the obstructive disease of the airway is asthma.

Embodiment 97. The method of embodiment 95, wherein the obstructive disease of the airway is acute respiratory distress syndrome (ARDS).

Embodiment 98. The method of embodiment 95, wherein the obstructive disease of the airway is bronchitis.

Embodiment 99. The method of embodiment 95, wherein the obstructive disease of the airway is lung fibrosis.

Embodiment 100. The method of embodiment 95, wherein the obstructive disease of the airway is emphysema.

Embodiment 101. The method of embodiment 95, wherein the obstructive disease of the airway is cystic fibrosis (CF).

Embodiment 102. The method of embodiment 95, wherein the obstructive disease of the airway is bronchiectasis.

Embodiment 103. The method of embodiment 95, wherein the obstructive disease of the airway is sarcoidosis.

Embodiment 104. The method of embodiment 95, wherein the obstructive disease of the airway is alpha-1 antitrypsin (A1AT) deficiency.

Embodiment 105. The method of embodiment 95, wherein the obstructive disease of the airway is farmer's lung.

Embodiment 106. The method of embodiment 95, wherein the obstructive disease of the airway is hypersensitivity pneumonitis.

Embodiment 107. The method of embodiment 95, wherein the obstructive disease of the airway is a complication of lung transplantation.

Embodiment 108. The method of embodiment 95, wherein the obstructive disease of the airway is a vasculitic or thrombotic disorder of the lung vasulature.

Embodiment 109. The method of embodiment 95, wherein the obstructive disease of the airway is pulmonary hypertension.

Embodiment 110. The method of embodiment 95, wherein the obstructive disease of the airway is iatrogenic cough.

Embodiment 111. The method of embodiment 95, wherein the obstructive disease of the airway is acute rhinitis.

Embodiment 112. The method of embodiment 95, wherein the obstructive disease of the airway is chronic rhinitis.

Embodiment 113. The method of embodiment 95, wherein the obstructive disease of the airway is rhinitis medicamentosa or vasomotor rhinitis.

Embodiment 114. The method of embodiment 95, wherein the obstructive disease of the airway is nasal polyposis.

Embodiment 115. The method of embodiment 95, wherein the obstructive disease of the airway is COPD.

Embodiment 116. The method of embodiment 96, wherein the asthma is bronchial, allergic, intrinsic, extrinsic, exercise-induced or drug-induced asthma.

Embodiment 117. The method of embodiment 116, wherein the bronchitis is infectious bronchitis or eosinophilic bronchitis.

Embodiment 118. The method of embodiment 99, wherein the lung fibrosis is idiopathic pulmonary fibrosis, cryptogenic fibrosing alveolitis, idiopathic interstitial pneumonia, or fibrosis complicating anti-neoplastic therapy or chronic infection.

Embodiment 119. The method of embodiment 102, wherein the bronchiectasis is non-cystic fibrosis bronchiectasis (NCFBE).

Embodiment 120. The method of embodiment 102, wherein the bronchiectasis is associated with cystic fibrosis.

Embodiment 121. The method of embodiment 109, wherein the pulmonary hypertension is pulmonary arterial hypertension.

Embodiment 122. A method for treating cystic fibrosis in a patient in need thereof, comprising, administering to the patient an effective amount of a compound of any one of embodiments 1-92, or the composition of embodiment 93.

Embodiment 123. The method of embodiment 122, wherein the treating comprises improving the lung function of the patient, as compared to the lung function of the patient prior to treatment.

Embodiment 124. The method of embodiment 123, wherein improving lung function of the patient comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC ($FEF_{(25-75\%)}$), as compared to the respective value for the patient prior treatment.

Embodiment 125. The method of embodiment 123 or 124, wherein the lung function is measured by spirometry.

Embodiment 126. A method for treating bronchiectasis in a patient in need thereof, comprising, administering to the patient, an effective amount of a compound of any one of embodiments 1-92, or the composition of embodiment 93.

Embodiment 127. The method of embodiment 126, wherein the bronchiectasis is non-cystic fibrosis bronchiectasis (NCFBE).

Embodiment 128. The method of embodiment 126, wherein the bronchiectasis is associated with cystic fibrosis.

Embodiment 129. The method of any one of embodiments 126-128, wherein treating comprises improving the lung function of the patient, as compared to the lung function of the patient prior to treatment.

Embodiment 130. The method of embodiment 129, wherein improving lung function of the patient comprises increasing the patient's forced expiratory volume in 1 second ($FEV_1$), increasing the patient's forced vital capacity (FVC), increasing the patient's peak expiratory flow rate (PEFR), or increasing the patient's forced expiratory flow between 25% and 75% of FVC (FEF (25-75%)), as compared to the respective value for the patient prior to treatment.

Embodiment 131. The method of embodiment 129 or 130, wherein the lung function is measured by spirometry.

Embodiment 132. The method of any one of embodiments 126-131, wherein treating comprises decreasing the rate of pulmonary exacerbation, as compared to the rate of pulmonary exacerbation of the patient prior to treatment.

Embodiment 133. The method of any one of embodiments 126-132, wherein treating comprises increasing the time to first pulmonary exacerbation, as compared to an untreated patient.

Embodiment 134. The method of embodiment 121 or 122, wherein the pulmonary exacerbation is characterized by three or more of the following symptoms exhibited for at least 48 hours by the patient: (1) increased cough; (2) increased sputum volume or change in sputum consistency; (3) increased sputum purulence; (4) increased breathlessness and/or decreased exercise tolerance; (5) fatigue and/or malaise; (6) hemoptysis.

Embodiment 135. A method for treating chronic rhinosinusitis (CRS) in a patient in need thereof, comprising, administering to the patient, an effective amount of a compound of any one of embodiments 1-92, or the composition of embodiment 93.

Embodiment 136. The method of embodiment 135, wherein the chronic rhinosinusitis is chronic rhinosinusitis without nasal polyps (CRSsNP).

Embodiment 137. The method of embodiment 135, wherein the chronic rhinosinusitis is chronic rhinosinusitis with nasal polyps (CRSwNP).

Embodiment 138. The method of any one of embodiments 128-137, wherein the chronic rhinosinusitis is refractory chronic rhinosinusitis.

Embodiment 139. The method of any one of embodiments 125-130, wherein treating comprises reducing, diminishing the severity of, delaying the onset of, or eliminating one or more symptoms of CRS.

Embodiment 140. The method of embodiment 139, wherein the one or more symptoms of CRS is nasal congestion; nasal obstruction; nasal discharge; post-nasal drip; facial pressure; facial pain; facial fullness; reduced smell; depression; mucosal edema; mucopurulent discharge; obstruction of the middle meatus; mucosal changes within the ostiomeatal complex and sinuses; or rhinorrhea.

Embodiment 141. A method for treating hidradenitis suppurativa (HS) in a patient in need thereof, comprising, administering to the patient, an effective amount of a compound of any one of embodiments 1-92, or the composition of embodiment 93.

Embodiment 142. The method of embodiment 141, wherein the hidradenitis suppurativa (HS) is Hurley stage I.

Embodiment 143. The method of embodiment 141, wherein the hidradenitis suppurativa (HS) is Hurley stage II.

Embodiment 144. The method of embodiment 141, wherein the hidradenitis suppurativa (HS) is Hurley stage III.

Embodiment 145. A method for treating cancer in a patient in need thereof, comprising, administering to the patient, an effective amount of a compound of any one of embodiments 1-92, or the composition of embodiment 93.

Embodiment 146. The method of embodiment 145, wherein the cancer is a metastatic cancer.

Embodiment 147. The method of embodiment 146, wherein the metastatic cancer is breast to lung metastatic cancer.

Embodiment 148. The method of embodiment 146, wherein the metastatic cancer comprises metastasis of breast cancer to the brain, bone, pancreas, lymph nodes or liver.

Embodiment 149. The method of embodiment 146, wherein the metastatic cancer comprises metastasis of bone cancer to the lung.

Embodiment 150. The method of embodiment 146, wherein the metastatic cancer comprises metastasis of colorectal cancer to the peritoneum, the pancreas, the stomach, the lung, the liver, the kidney, or the spleen.

Embodiment 151. The method of embodiment 146, wherein the metastatic cancer comprises metastasis of stomach cancer to the mesentery, the spleen, the pancreas, the lung, the liver, the adrenal gland, or the ovary.

Embodiment 152. The method of embodiment 146, wherein the metastatic cancer comprises metastasis of liver cancer to the intestine, spleen, pancreas, stomach, lung, or the kidney.

Embodiment 153. The method of embodiment 146, wherein the metastatic cancer comprises metastasis of lymphoma to the kidney, ovary, liver, bladder, or the spleen.

Embodiment 154. A method for treating lupus nephritis in a patient in need thereof, comprising, administering to the patient, an effective amount of a compound of any one of embodiments 1-92, or the composition of embodiment 93.

Embodiment 155. A method for treating rheumatoid arthritis in a patient in need thereof, comprising, administering to the patient, an effective amount of a compound of any one of embodiments 1-92, or the composition of embodiment 93.

Embodiment 156. A method for treating inflammatory bowel disease (IBD) in a patient in need thereof, comprising, administering to the patient, an effective amount of a compound of any one of embodiments 1-92, or the composition of embodiment 93.

Embodiment 157. The method of embodiment 156, wherein the inflammatory bowel disease (IBD) is Crohn's disease.

Embodiment 158. The method of embodiment 156, wherein the inflammatory bowel disease (IBD) is ulcerative colitis.

Embodiment 159. A method for treating an anti-neutrophil cytoplasmic antibody (ANCA) associated vasculitis in a patient in need thereof, comprising, administering to the patient, an effective amount of a compound of any one of embodiments 1-92, or the composition of embodiment 93.

Embodiment 160. The method of embodiment 159, wherein the ANCA associated disease is granulomatosis with polyangiitis (GPA).

Embodiment 161. The method of embodiment 159, wherein the ANCA associated disease is microscopic polyangiitis (MPA).

Embodiment 162. A method for treating a disease in a patient in need thereof comprising, administering to the patient, an effective amount of a compound of any one of embodiments 1-92, or the composition of embodiment 93, wherein the disease is giant cell arteritis, polyarteritis nodosa, anti-GBM disease (Goodpasture's), systemic scleroderma, diabetic nephropathy, diabetic neuropathy, diabetic retinopathy, diabetic ulcers, Duchenne muscular dystrophy, bronchiolitis obliterans, atopic dermatitis, pyoderma gangrenosum, sweet's syndrome, dermatomyositis/polymyositis, neutrophilic dermatoses, thrombosis, bronchopulmonary dysplasia, amyotrophic lateral sclerosis, sickle cell anemia, psoriasis, or a ventilator-induced lung injury.

EXAMPLES

The present disclosure is further illustrated by reference to the following Examples. However, it should be noted that these Examples, like the embodiments described above, are illustrative and are not to be construed as restricting the scope of the disclosure in any way.

In embodiments, compounds of the present disclosure can be synthesized using the following methods. General reaction conditions are given, and reaction products can be purified by generally known methods including silica gel chromatography using various organic solvents such as hexane, dichloromethane, ethyl acetate, methanol and the like or preparative reverse phase high pressure liquid chromatography.

Representative Synthesis of Compounds of Formula (I)

Scheme 1: Representative synthesis of compounds of the disclosure

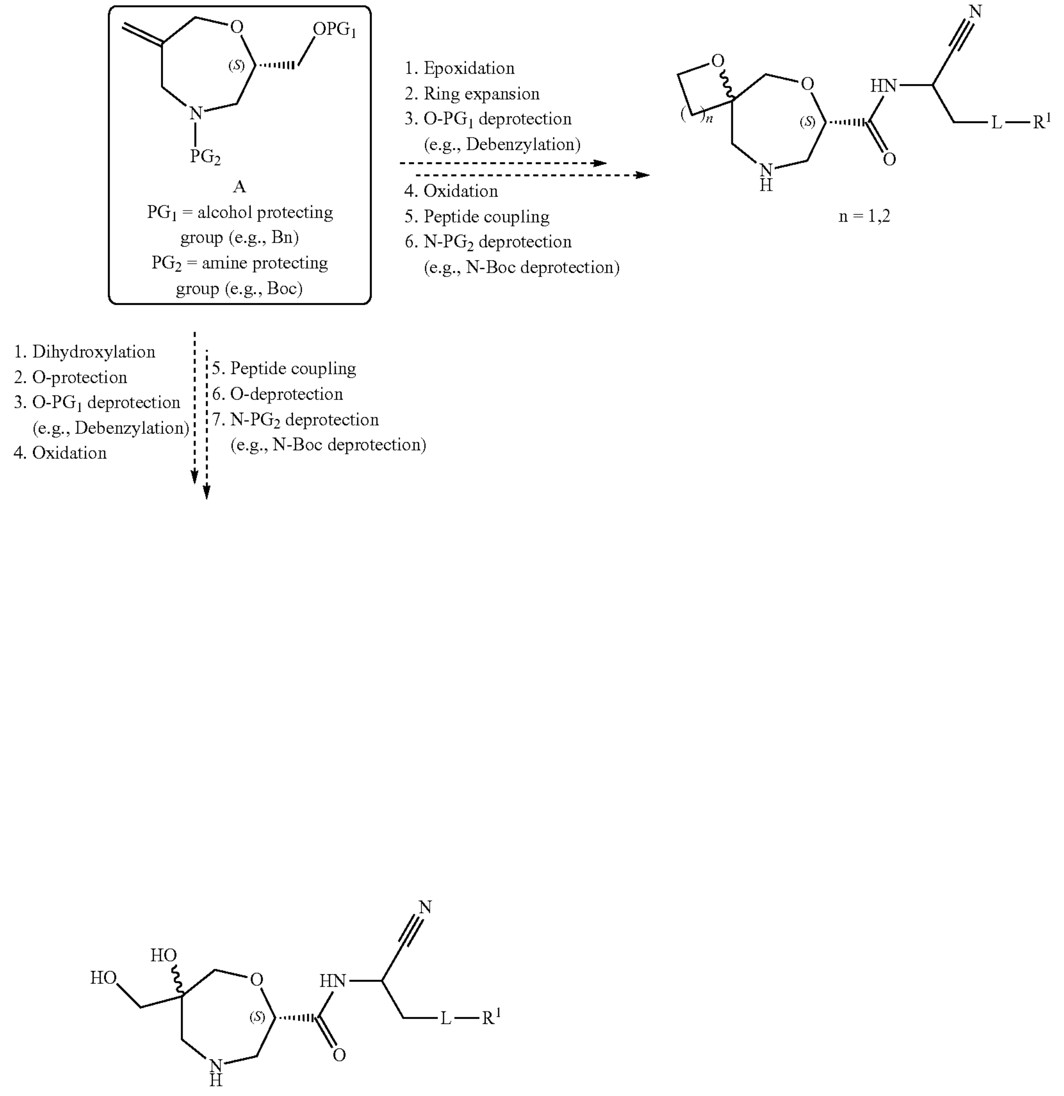

As shown in Scheme 1, compounds of the present disclosure, wherein L and $R^1$ are defined herein, can be prepared from compound A.

Scheme 2: Representative synthesis of compounds of the disclosure

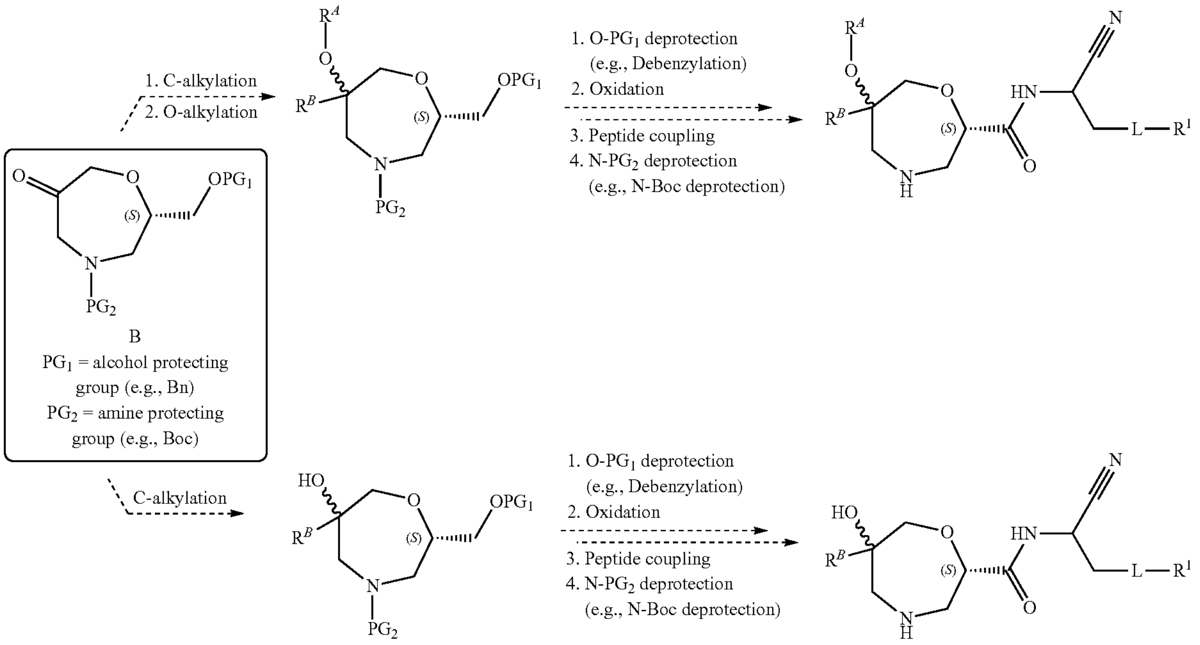

As shown in Scheme 2, compounds of the present disclosure, wherein $R^A$, $R^B$, L, and $R^1$ are defined herein, can be prepared from compound B.

Scheme 3: Representative synthesis of compounds of the disclosure

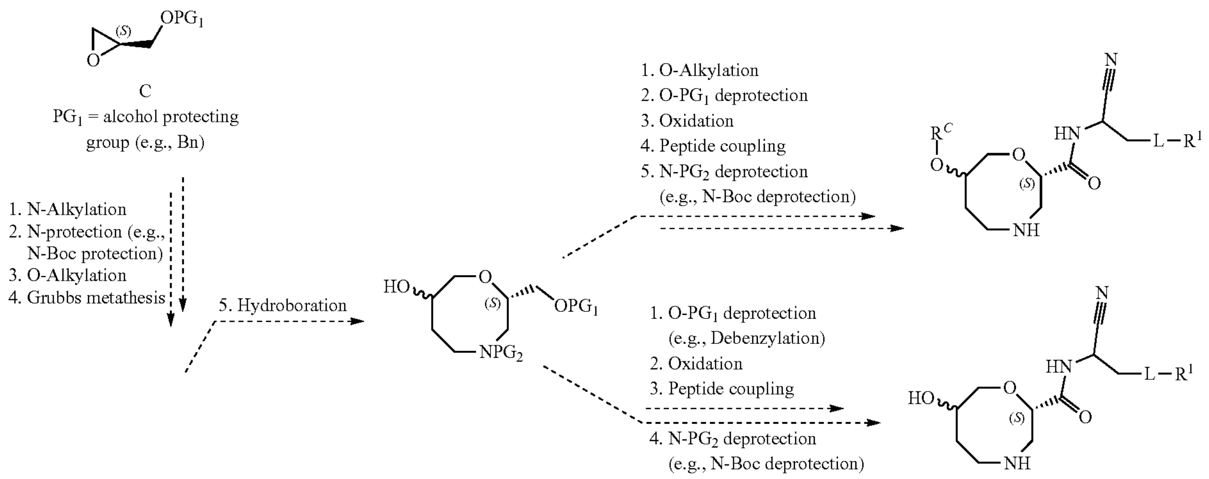

-continued

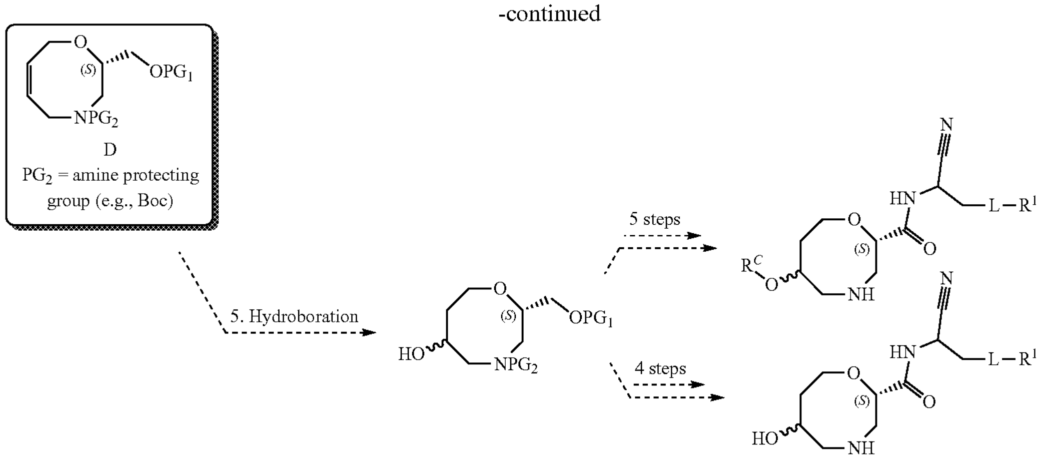

As shown in Scheme 3, compounds of the present disclosure, wherein L and $R^1$ are defined herein, and $R^C$ is $C_{1-6}$ alkyl, haloalkyl, or cycloalkyl can be prepared from compound D.

Scheme 4: Representative synthesis of compounds of the disclosure

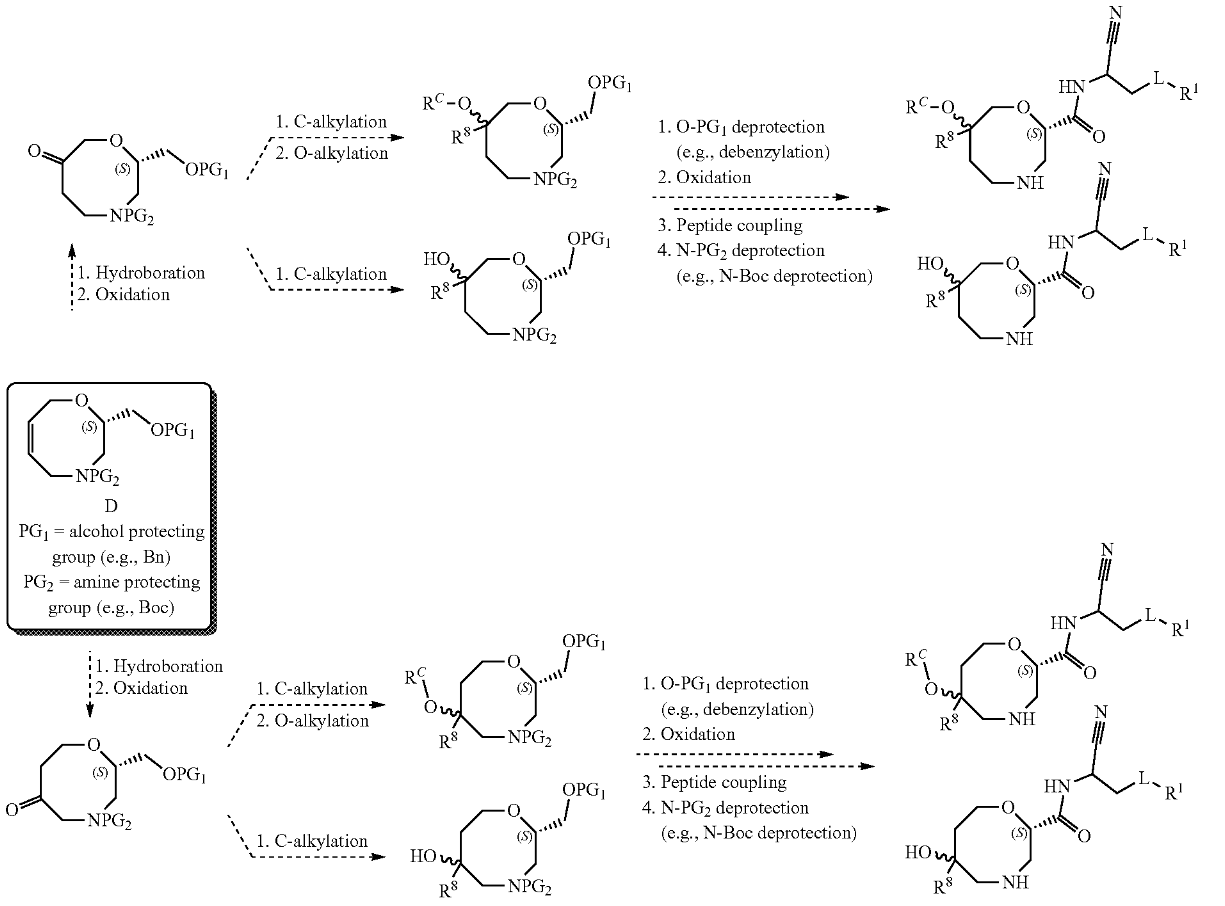

As shown in Scheme 4, compounds of the present disclosure, wherein $R^8$, L, and $R^1$ are defined herein, and $R^C$ is $C_{1-6}$ alkyl, haloalkyl, or cycloalkyl can be prepared from compound D.

Scheme 5: Representative synthesis of compounds of the disclosure
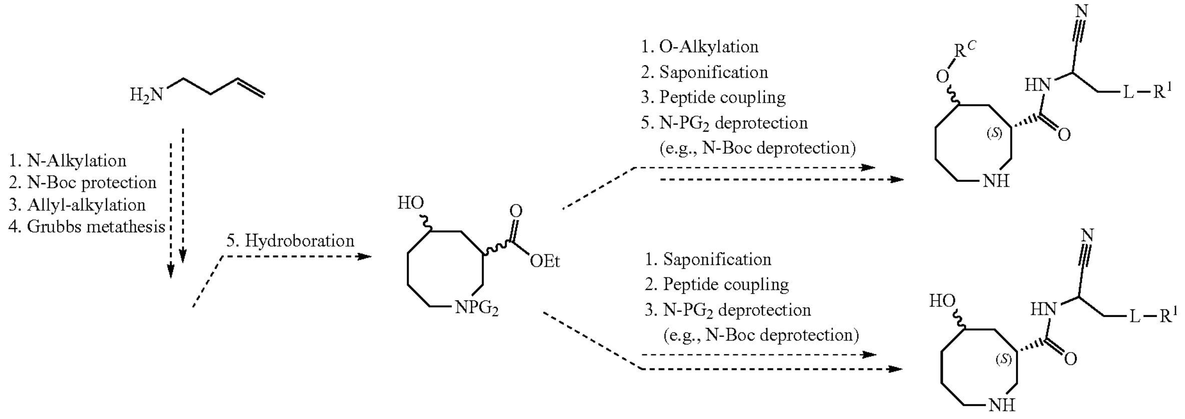
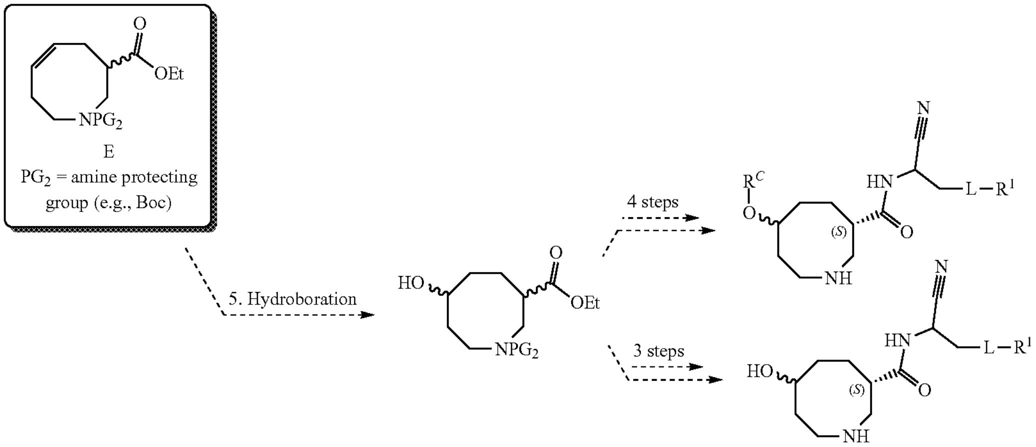
As shown in Scheme 5, compounds of the present disclosure, wherein L and $R^1$ are defined herein, and $R^C$ is $C_{1-6}$ alkyl, haloalkyl, or cycloalkyl can be prepared from compound E.

Scheme 6: Representative synthesis of compounds of the disclosure
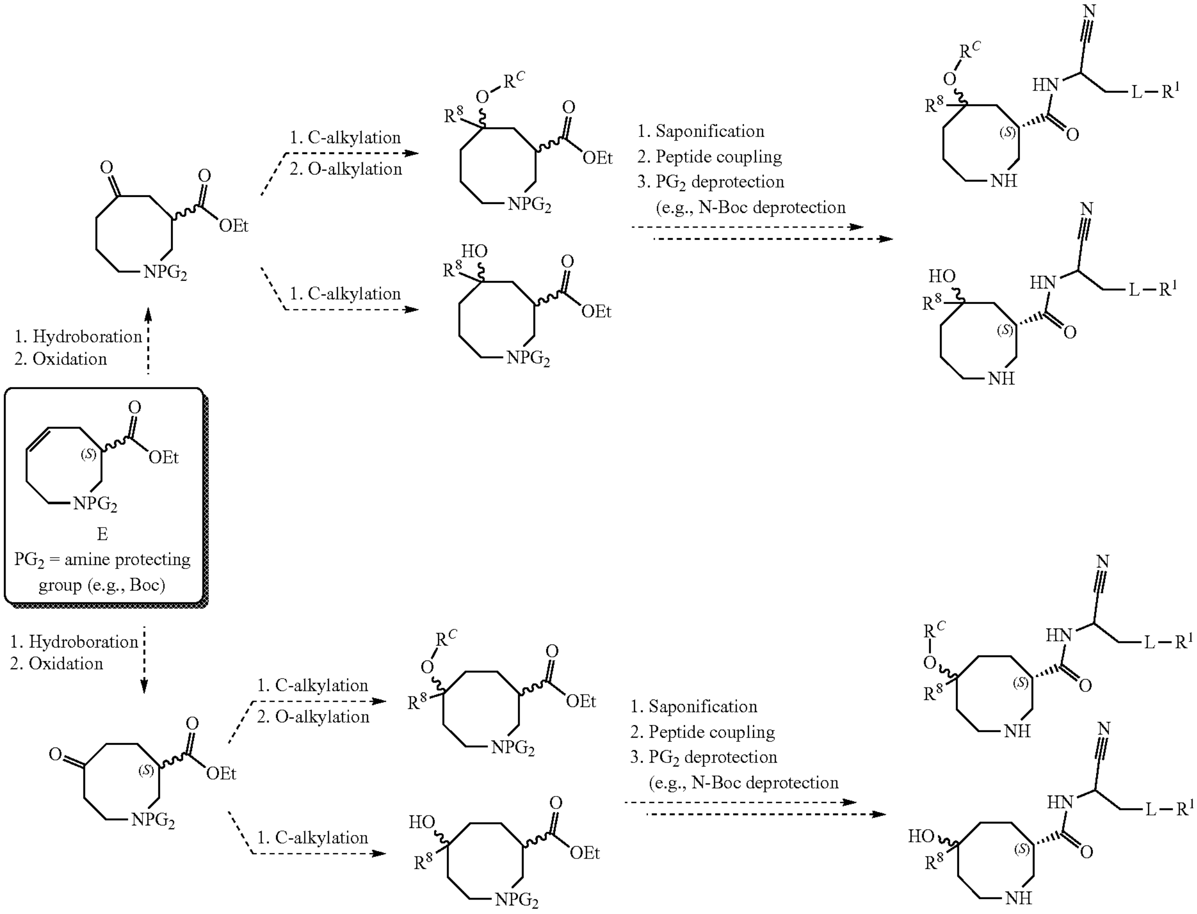
As shown in Scheme 6, compounds of the present disclosure, wherein $R^8$, L, and $R^1$ are defined herein, and $R^C$ is $C_{1-6}$ alkyl, haloalkyl, or cycloalkyl can be prepared from compound E.

Scheme 7: Representative synthesis of compounds of the disclosure
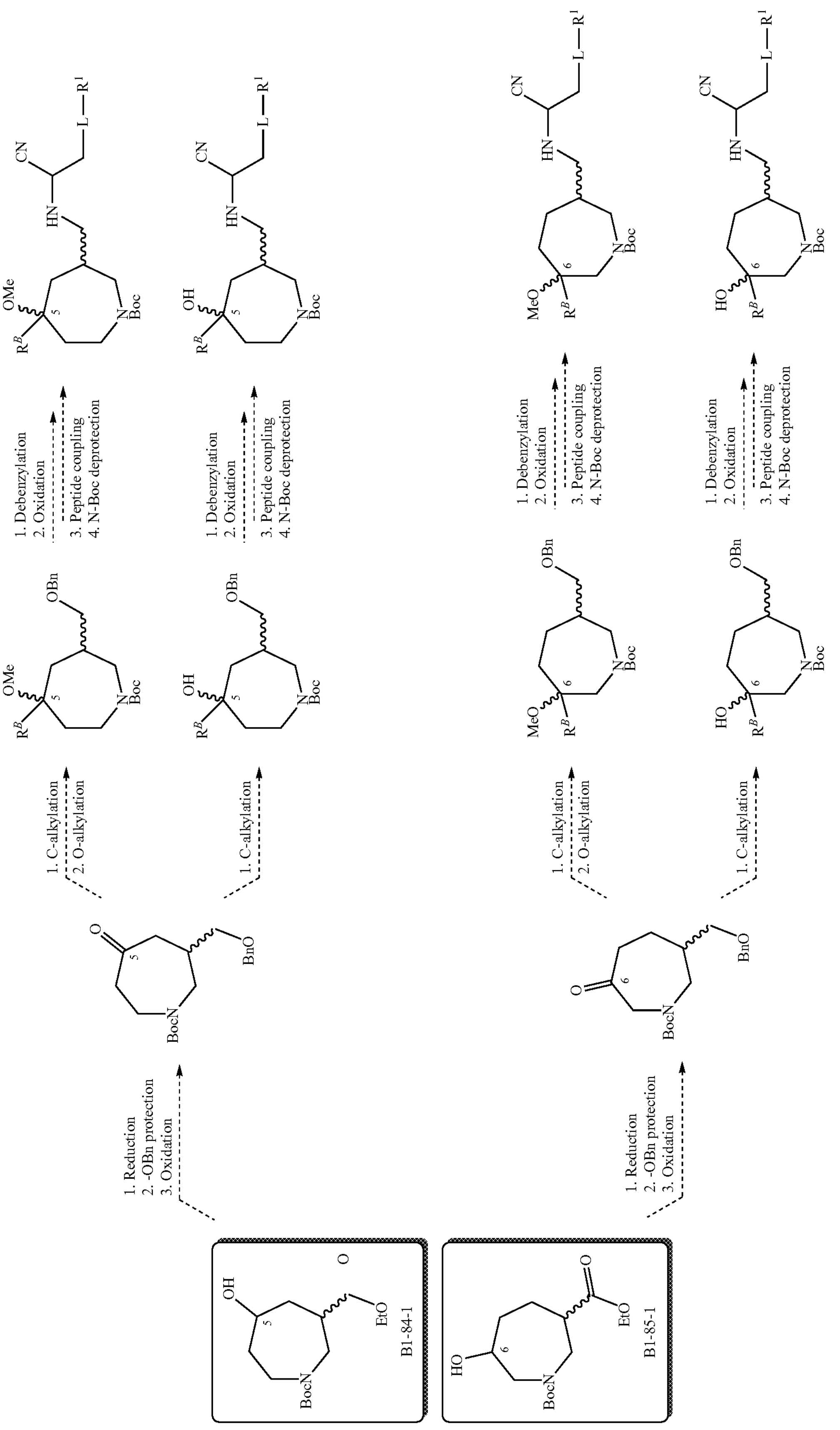
B1-84-1
B1-85-1

As shown in Scheme 7, compounds of the present disclosure, wherein $R^B$, L, and $R^1$ are defined herein can be prepared from compound B1-84-1 or B1-85-1.

General Experimental

1H Nmr Analysis:

1H-NMR spectra were recorded on a Bruker Ultrashield (400 MHZ). The multiplicity of a signal is designated by the following abbreviations: s, singlet; d, doublet; t, triplet; q, quartet; dd, doublet of doublets; dt, doublet of triplets; m, multiplet.

All observed coupling constants, J, are reported in Hertz (Hz).

Exchangeable protons are not always observed.

Lc/Ms Analysis:

LC/MS Method AN01_001_012:

LC-MS data was generated using a Waters Acquity system: TUV detector, SQD2 MS detector, Sedere SEDEX 80 (light scattering detector).

LC-MS method: reverse phase HPLC analysis

Column Agilent: Cortecs $C_{18}$

Solvent A: Water with Formic Acid (0.1% V/V)

Solvent B: Acetonitrile

Gradient table:

| Time (min) | Flow (mL/min) | % A | % B | Curve |
|---|---|---|---|---|
| 0 | 0.7 | 98 | 2 | initial |
| 2 | 0.7 | 0 | 100 | Linear |
| 2.5 | 0.7 | 0 | 100 | Linear |
| 2.6 | 0.7 | 98 | 2 | Linear |
| 5 | 0.7 | 98 | 2 | Linear |

LC/MS Method AN01_001_061:

LC-MS data was generated using a Waters Acquity UPLC Class I: Waters PDA eλ detector, Waters SQD2 MS detector, Sedere SEDEX 80 (light scattering detector).

LC-MS Method: Reverse Phase HPLC Analysis

Column Waters: Acquity UPLC CSH C18, length: 30 mm, Internal diameter: 2.1 mm, particle size: 1.7 µm Solvent A: Water with Formic Acid (0.1% V/V)

Solvent B: Acetonitrile

UV detection: 220 nm

Gradient table:

| Time (min) | Flow (mL/min) | % A | % B | Curve |
|---|---|---|---|---|
| 0 | 0.7 | 98 | 2 | initial |
| 0.45 | 0.7 | 98 | 2 | Linear |
| 1.90 | 0.7 | 0 | 100 | Linear |
| 2.60 | 0.7 | 0 | 100 | Linear |
| 2.70 | 0.7 | 98 | 2 | Linear |
| 3.50 | 0.7 | 98 | 2 | Linear |

LC/MS Method AN01_001_021:

LC-MS data was generated using a Waters 2695 e system: Waters PDA 2998 detector, Waters QDA detector (ESI), Sedere SEDEX 80 (light scattering detector).

LC-MS Method: Reverse Phase HPLC Analysis

Column Agilent: Poroshell, Length: 100 mm, Internal diameter: 4.6 mm, Particle size: 4 µm Solvent A: Water with TFA (0.1% V/V)

Solvent B: Acetonitrile

UV detection: 220 nm

Gradient table:

| Time (min) | Flow (mL/min) | % A | % B | Curve |
|---|---|---|---|---|
| 0 | 1 | 98 | 2 | initial |
| 2 | 1 | 98 | 2 | 6 |
| 12 | 1 | 0 | 100 | 6 |
| 15.4 | 1 | 0 | 100 | 6 |
| 16.7 | 1 | 98 | 2 | 6 |
| 18.4 | 1 | 98 | 2 | 6 |

LC/MS Method AN01_001_026:

LC-MS data was generated using a Waters Acquity system: TUV detector, SQD2 MS detector, Sedere SEDEX 80 (light scattering detector).

LC-MS Method: Reverse Phase HPLC Analysis

Column Agilent: Poroshell

Solvent A: Water with Formic Acid (0.1% V/V)

Solvent B: Acetonitrile

Gradient table:

| Time (min) | Flow (mL/min) | % A | % B | Curve |
|---|---|---|---|---|
| 0 | 1 | 98 | 2 | initial |
| 2 | 1 | 98 | 2 | 6 |
| 12 | 1 | 0 | 100 | 6 |
| 15.4 | 1 | 0 | 100 | 6 |
| 16.7 | 1 | 98 | 2 | 6 |
| 18.4 | 1 | 98 | 2 | 6 |

UV detection: 220 nm

LC/MS Method AN01_001_086:

LC-MS data was generated using a Waters Acquity UPLC Class I: Waters PDA eλ detector, Waters SQD2 MS detector, Sedere SEDEX 80 (light scattering detector).

LC-MS Method: Reverse Phase HPLC Analysis

Column Waters: Acquity Premier CSH C18, length: 100 mm, Internal diameter: 2.1 mm, particle size: 1.7 µm Solvent A: Water with Formic Acid (0.1% V/V)

Solvent B: Acetonitrile

UV detection: 220 nm

Gradient table:

| Time (min) | Flow (mL/min) | % A | % B | Curve |
|---|---|---|---|---|
| 0 | 0.4 | 98 | 2 | initial |
| 1.5 | 0.4 | 98 | 2 | Linear |
| 8.5 | 0.4 | 0 | 100 | Linear |
| 9.4 | 0.4 | 0 | 100 | Linear |
| 9.5 | 0.4 | 98 | 2 | Linear |
| 12 | 0.4 | 98 | 2 | Linear |

LC/MS Method AN01_001_087:

LC-MS data was generated using a Waters Acquity UPLC Class I: Waters PDA eλ detector, Waters SQD2 MS detector, Sedere SEDEX 80 (light scattering detector).

LC-MS Method: Reverse Phase HPLC Analysis

Column Waters: Acquity Premier CSH C18, length: 100 mm, Internal diameter: 2.1 mm, particle size: 1.7 µm Solvent A: Water with Formic Acid (0.1% V/V)

Solvent B: Acetonitrile

UV detection: 220 nm

Gradient table:

| Time (min) | Flow (mL/min) | % A | % B | Curve |
|---|---|---|---|---|
| 0 | 0.4 | 50 | 50 | initial |
| 1.5 | 0.4 | 50 | 50 | Linear |

-continued

| Time (min) | Flow (mL/min) | % A | % B | Curve |
|---|---|---|---|---|
| 8.5 | 0.4 | 0 | 100 | Linear |
| 9.4 | 0.4 | 0 | 100 | Linear |
| 9.5 | 0.4 | 50 | 50 | Linear |
| 12 | 0.4 | 50 | 50 | Linear |

LC/MS Method AN01_001_088:

LC-MS data was generated using a Waters Acquity UPLC Class I: Waters PDA eλ detector, Waters SQD2 MS detector, Sedere SEDEX 80 (light scattering detector).

LC-MS Method: Reverse Phase HPLC Analysis

Column Waters: Acquity Premier CSH C18, length: 100 mm, Internal diameter: 2.1 mm, particle size: 1.7 μm Solvent A: Water with TFA (0.1% V/V)

Solvent B: Acetonitrile

UV detection: 220 nm

Gradient table:

| Time (min) | Flow (mL/min) | % A | % B | Curve |
|---|---|---|---|---|
| 0 | 0.4 | 98 | 2 | initial |
| 1.5 | 0.4 | 98 | 2 | Linear |
| 8.5 | 0.4 | 0 | 100 | Linear |
| 9.4 | 0.4 | 0 | 100 | Linear |
| 9.5 | 0.4 | 98 | 2 | Linear |
| 12 | 0.4 | 98 | 2 | Linear |

Chiral SFC Purity Analysis Conditions

Column Details: ChiralPak OD-3 (4.6×100 mm)

Column Temperature: 35° C.

Flow Rate: 3.5 mL/min

Detector Wavelength: 220-410 nm

Injection Volume: 2 μL

BPR: 1500PSI

Isocratic Conditions: i-PrOH: $CO_2$, 30:70

General Synthetic Procedures

Procedure A—O-Bn Deprotection

To an argon-purged solution of protected alcohol (1 eq.) in EtOH (4.78 mL/mmol of protected alcohol) was added 10% Pd/C (0.1 eq.) at room temperature. The resulting mixture was purged with argon (×3) and then with $H_2$ (3×). The reaction mixture was stirred under an atmospheric pressure of $H_2$ at room temperature for 18 h. The reaction mixture was purged with argon, filtered on a pad of celite and rinsed with EtOH (3×5 mL). The filtrate was concentrated under reduced pressure to afford the expected compound.

Procedure B—Alcohol Oxidation into Carboxylic Acid

To a solution of alcohol derivative (1 eq.) in acetone (16.7 mL/mmol of alcohol) and sodium bromide (0.3 eq.) was added a saturated aqueous solution of $NaHCO_3$ (2.59 mL/mmol of alcohol) at room temperature. To the resulting mixture were added trichlorocyanuric acid (2.2 eq.) and 2,2,6,6-tetramethylpiperidine-1-oxyl (0.03 eq.) at 0° C. The reaction mixture was allowed to warm to room temperature and stirred for 18 h. Isopropanol (10 mL) was added at room temperature and the reaction mixture was stirred for 30 min. The reaction mixture was diluted with EtOAc (50 mL) and a saturated aqueous solution of $NaHCO_3$ (50 mL) was added. The two layers were separated, and the aqueous layer was washed with EtOAc (50 mL). The aqueous layer was then acidified with an aqueous solution of 3M HCl until pH ~1 and extracted with DCM (2×50 mL). The combined organic layers were dried over $Na_2SO_4$, filtered and concentrated under reduced pressure to afford the expected compound.

Procedure C—Peptide Coupling

To a solution of amine derivative (1 eq.) in anhydrous DMF (7.14 mL/mmol of amine) and carboxylic acid derivative (1.05 eq.) were added DIPEA (2.5 eq.) and TBTU (1.5 eq.) at room temperature under argon atmosphere. The reaction mixture was stirred at room temperature for 18 h. The reaction mixture was diluted with EtOAc (10 mL) and water (10 mL). The aqueous layer was extracted with EtOAc (2×10 mL) and the combined organic layers were washed with brine (3×10 mL), dried over $Na_2SO_4$, filtered and concentrated under reduced pressure. The crude was purified by flash chromatography over $SiO_2$ (see conditions for each compound) to afford the expected compound.

Procedure D—N-Boc Deprotection

To a preheated vial (50° C.) containing Boc protected amine derivative (1 eq.) was added formic acid (7.6 mL/mmol) also preheated at 50° C. The reaction mixture was stirred at 50° C. for 15 min. The reaction mixture was cooled back to room temperature and added dropwise into a cooled (0° C.) mixture of stirred aqueous solution of saturated $NaHCO_3$ (40 mL) and DCM (40 mL). The layers were separated, and the aqueous layer was extracted with DCM (2×40 mL). The combined organic layers were dried over $Na_2SO_4$, filtered and concentrated to under reduced pressure. The crude was purified by flash chromatography over $SiO_2$ and/or preparative HPLC (see conditions for each compound) to afford the expected compound.

Procedure E—O-Alkylation

To a solution of alcohol derivative (1 eq.) in anhydrous DMF (5.49 mL/mmol of alcohol derivative) and halogenalkyl e.g., iodomethane (2 eq.) was added NaH 60% in oil (1.1 eq.) at 0° C. under argon atmosphere. The resulting mixture was allowed to warm to room temperature and stirred for 22 h. The reaction mixture was quenched with a saturated aqueous solution of NH4Cl (10 mL) at room temperature. EtOAc (50 mL) and water (50 mL) were then added and the two layers were separated. The aqueous layer was extracted with EtOAc (2×50 mL) and the combined organic layers were dried over $Na_2SO_4$, filtered and concentrated under reduced pressure. The crude residue was purified by silica gel flash chromatography (see conditions for each compound) to afford the expected compound.

Procedure F (TBAF deprotection)

To a solution of O-TBDMS protected alcohol (1 eq.) in anhydrous THF (6.0 mL/mmol of protected alcohol) was added a 1M TBAF solution in THF (1.5 eq.) at 0° C. under argon atmosphere. The resulting mixture was allowed to warm to room temperature and stirred for 2 h. The reaction mixture was diluted with EtOAc (50 mL) and washed with brine (50 mL), dried over $Na_2SO_4$ and concentrated under reduced pressure. The crude was purified by flash chromatography over $SiO_2$ (see conditions for each compound) to afford the expected compound.

Procedure G—N-Boc Protection

To a solution of amine derivative (1 eq.) in DCM (4 mL/mmol of amine derivative) were added $Boc_2O$ (1.2 eq.) and $Et_3N$ (2 eq.) at room temperature. The resulting mixture was stirred at room temperature for 16 h. The reaction mixture was diluted with water (40 mL) and extracted with DCM (2×60 mL). The combined organic layers were washed with brine (30 mL), dried over $Na_2SO_4$, filtered and concentrated to dryness under reduced pressure. The crude residue was purified by silica gel flash chromatography (see conditions for each compound) to afford the expected compound.

Procedure H (Olefin Metathesis)

To a solution of diene (1 eq.) in DCM (63 mL/mmol) was added Benzylidene-bis (tricyclohexylphosphine)dichlororuthenium (0.1 eq.) at room temperature. The resulting mixture was stirred at 55° C. for 8 h. The reaction was concentrated to dryness under reduced pressure. The crude residue was purified by silica gel flash chromatography (see conditions for each compound) to afford the expected compound.

Procedure I (Hydroboration)

To an argon-purged solution of alkene derivative (1 eq.) in THF (2.5 mL/mmol) was added borane tetrahydrofuran complex solution 1M in THF (1 eq.) at 0° C. The resulting mixture was stirred at 0° C. for 2.5 h. Then, NaOH 3M in water (1 eq.) and $H_2O_2$ 33% in water (1 eq.) were added sequentially and the resulting mixture was stirred at 0° C. for 3.5 h. The reaction mixture was diluted with water (100 mL) and extracted with EtOAc (3×100 mL). The combined organic layers were washed with brine (100 mL), dried over $Na_2SO_4$, filtered and concentrated to dryness under reduced pressure. The crude residue was purified by silica gel flash chromatography (see conditions for each compound) to afford the expected compound.

Preparation of Key Intermediates

Preparation of Intermediates B1-46-1-(S)*& B1-46-1-(R)*

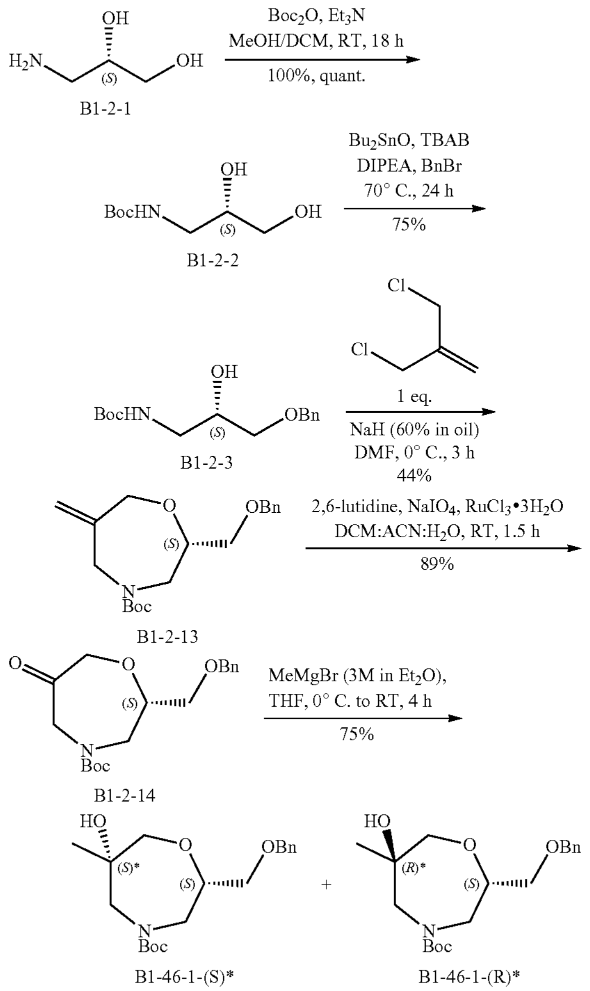

B1-2-1

B1-2-2

B1-2-3

B1-2-13

B1-2-14

B1-46-1-(S)* + B1-46-1-(R)* tert-butyl N-[(2S)-2,3-dihydroxypropyl]carbamate B1-2-2

To a solution of (2S)-3-aminopropane-1,2-diol (1 eq., 14.4 g, 158.1 mmol) and $Et_3N$ (1.01 eq., 22.2 mL, 159.6 mmol) in anhydrous MeOH (245 mL) was added a solution of $Boc_2O$ (1.2 eq., 41.4 g, 189.7 mmol) in anhydrous DCM (41 mL) at room temperature under argon atmosphere. The reaction mixture was stirred at room temperature for 18 h and then concentrated under reduced pressure to afford B1-2-2 as a pale yellow oil (30.2 g, quant.). The crude was considered quantitative and used as such.

LC/MS (AN01_001_012): Rt=1.69 min, non-UV active, $[M+Na]^+$=214.1.

tert-butyl N-[(2S)-3-(benzyloxy)-2-hydroxypropyl] carbamate B1-2-3

To a solution of B1-2-2 (1 eq., 1.72 g, 8.99 mmol), di(n-butyl) tin oxide (0.1 eq., 0.224 g, 0.899 mmol) and TBAB (0.3 eq., 0.870 g, 2.70 mmol) were added DIPEA (2 eq., 3.13 mL, 18.0 mmol) and BnBr (2 eq., 2.15 mL, 18.0 mmol) at room temperature under argon atmosphere. The reaction mixture was stirred at 70° C. for 6 h. The reaction mixture was concentrated under reduced pressure then taken into EtOAc (50 mL) and filtered over a pad of silica gel. The latter was rinsed with EtOAc (3×150 mL) and the filtrate was concentrated under reduced pressure. The resulting orange oil (4.46 g) was purified by silica gel flash chromatography (120 g, gradient: cyclohexane/EtOAc 100:0 to 50:50) to afford B1-2-3 as a pale-yellow oil (2.31 g, 75%) which was contaminated by the other-OBn regioisomer protected in position 2 (17 wt % by 1H NMR analysis).

LC/MS (AN01_001_012): Rt=2.28 min, 100%, $[M+Na]^+$= 304.1.

tert-butyl (2S)-2-[(benzyloxy)methyl]-6-methylidene-1,4-oxazepane-4-carboxylate B1-2-13

To a suspension of NaH 60% in oil (2.1 eq., 3.40 g, 85.1 mmol) in anhydrous DMF (72 mL) was added 3-chloro-2-chloromethyl-1-propene (1 eq., 4.69 mL, 40.5 mmol) at 0° C. The reaction mixture was stirred at 0° C. for 10 min, then a solution of B1-2-3 (1 eq., 11.4 g, 40.5 mmol) in anhydrous THF (50 mL) was added dropwise at 0° C. The reaction mixture was stirred at room temperature for 4 h. The reaction mixture was diluted with water (200 mL) and the aqueous layer was extracted with EtOAc (3×200 mL). The combined organic layers were washed with brine (200 mL), dried over $Na_2SO_4$, filtered and concentrated under reduced pressure. The crude residue was purified by silica gel flash chromatography (330 g, gradient: Cyclohexane/EtOAc from 100:0 to 90:10) to afford B1-2-13 as a colorless oil (5.93 g, 44%). LC/MS (AN01_001_012): Rt=2.73 min, 100%, $[M-C_4H_8+H]^+$=278.1.

tert-butyl (2S)-2-[(benzyloxy)methyl]-6-oxo-1,4-oxazepane-4-carboxylate B1-2-14

To a solution of B1-2-13 (1 eq., 2.10 g, 6.30 mmol) in a mixture of DCM (38 mL) and acetonitrile (38 mL) were added 2,6-lutidine (2 eq., 1.47 mL, 12.6 mmol), water (57 mL) and sodium periodate (4 eq., 5.39 g, 25.2 mmol) at room temperature. A solution of $RuCl_3{\cdot}3H_2O$ (0.035 eq., 57.6 mg, 0.220 mmol) in water (6.3 mL) was added dropwise forming a brown suspension. The reaction mixture was vigorously stirred at room temperature for 2 h. The reaction mixture was diluted with water (150 mL) and extracted with DCM (3×150 mL). The combined organic layers were washed with brine (150 mL), dried over $Na_2SO_4$, filtered and concentrated under reduced pressure. The crude residue was purified by silica gel flash chromatography (120 g, gradient: Cyclohexane/EtOAc from 100:0 to 85:15) to afford B1-2-14 as a colorless oil (1.88 g, 89%).

LC/MS (AN01_001_012): Rt=2.56 min, 100%, $[M+H]^+$=336.1.

tert-butyl (2S,6S*)-2-[(benzyloxy)methyl]-6-hydroxy-6-methyl-1,4-oxazepane-4-carboxylate B1-46-1-(S)*& tert-butyl (2S,6R*)-2-[(benzyloxy)methyl]-6-hydroxy-6-methyl-1,4-oxazepane-4-carboxylate B1-46-1-(R)*

To a solution of B1-2-14 (1 eq., 1.28 g, 3.82 mmol) in anhydrous THF (35 mL) was added a 3M solution of MeMgBr in $Et_2O$ (2.5 eq., 3.18 mL, 9.54 mmol) at 0° C. under argon atmosphere. The reaction mixture was allowed to warm to room temperature and stirred for 2 h. The reaction mixture was diluted with an aqueous saturated solution of $NH_4Cl$ (100 mL) and the aqueous layer was extracted with EtOAc (3×100 mL). The combined organic layers were washed with brine (100 mL), dried over $Na_2SO_4$, filtered and concentrated under reduced pressure. The crude residue was purified by silica gel flash chromatography (80 g, gradient: Cyclohexane/EtOAc from 100:0 to 70:30) to afford of B1-46-1-(S)*(0.650 g, 48%) and B1-46-1-(R)*(0.363 g, 27%) as colorless oils. The stereochemistry(S)*was arbitrarily assigned to the first eluted product by flash chromatography and then the second eluted product was assigned (R)*.

B1-46-1-(S)*: LC/MS (AN01_001_012): Rt=2.47 min, 100%, $[M-C_4H_8+H]^+$=296.2.

B1-46-1-(R)*: LC/MS (AN01_001_012): Rt=2.41 min, 100%, $[M-C_4H_8+H]^+$=296.2.

Preparation of Intermediates B1-84-1 and B1-85-1

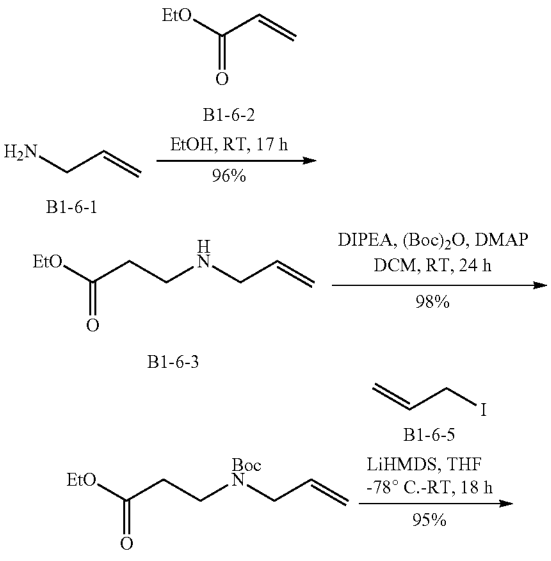

-continued

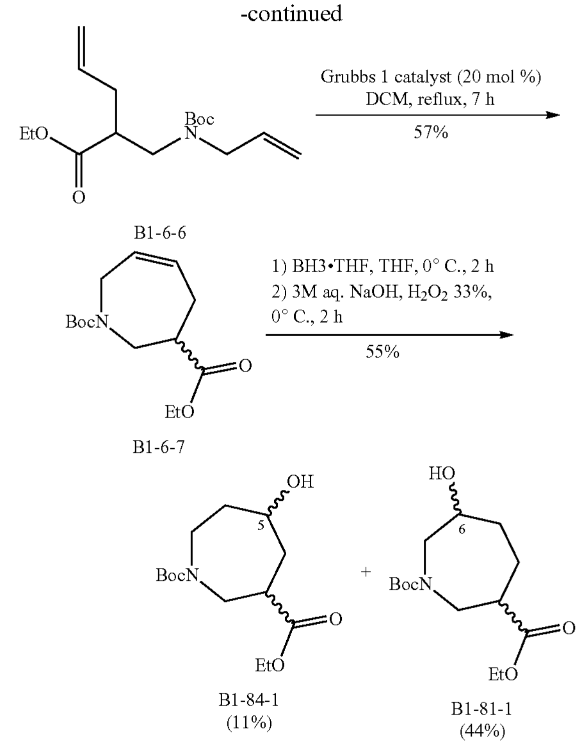

Ethyl 3-[(prop-2-en-1-yl)amino]propanoate B1-6-3

To an argon-purged solution of allylamine (1 eq., 2.5 g, 3.28 mL, 43.79 mmol) in EtOH (65 mL) was added ethyl acrylate (1 eq., 4.38 g, 4.76 mL, 43.79 mmol) and the resulting mixture was stirred at room temperature for 17 h. The reaction mixture was concentrated to dryness under reduced pressure affording B1-6-3 (6.58 g, 41.85 mmol, 95.59%) as a colorless oil. The crude was used as such for the next step without further purification.

LC/MS (AN01_001_012): Rt=1.67 min, ND, $[M+H]^+$=258.1.

ethyl 3-{[(tert-butoxy)carbonyl](prop-2-en-1-yl)amino}propanoate B1-6-4

To an argon-purged solution of B1-6-3 (1 eq., 6.58 g, 41.85 mmol) in DCM (65 mL) were added diisopropylamine (1 eq., 4.24 g, 5.92 mL, 41.85 mmol), $Boc_2O$ (1 eq., 9.13 g, 8.96 mL, 41.85 mmol) and DMAP (0.1 eq., 0.51 g, 4.19 mmol) at room temperature. The resulting mixture was stirred for 24 h. Then, the reaction mixture was diluted with water (100 mL) and extracted with DCM (2×100 mL). The combined organic layers were washed with brine (50 mL), dried over $Na_2SO_4$, filtered and concentrated to dryness under reduced pressure affording B1-6-4 (10.6 g, 41.19 mmol, 98%) as a yellow oil. The crude was used as such for the next step without further purification.

LC/MS (AN01_001_012): Rt=2.53 min, 100%, $[M-Boc+H]^+$=158.1.

ethyl 2-({[(tert-butoxy)carbonyl](prop-2-en-1-yl)amino}methyl) pent-4-enoate B1-6-6

To an argon-purged solution of B1-6-4 (1 eq., 1 g, 3.89 mmol) in THF (10 mL) was added LiHMDS 1M in THF (1.1 eq., 4.27 mL, 4.27 mmol) dropwise at −78° C. The resulting mixture was stirred at −78° C. for 1 h before the addition of allyl iodide (1.1 eq., 0.72 g, 0.39 mL, 4.27 mmol). The resulting mixture was warmed to room temperature and stirred for 18 h. The reaction mixture was diluted with water (50 mL) and extracted with EtOAc (3×50 mL). The combined organic layers were washed with brine (50 mL), dried over $Na_2SO_4$, filtered and concentrated to dryness under reduced pressure affording B1-6-6 (1.1 g, 95%) as an orange oil. The crude was used as such for the next step.

LC/MS (AN01_001_012): Rt=2.76 min, 100%, $[M-Boc+H]^+=198.1$.

1-tert-butyl 3-ethyl 2,3,4,7-tetrahydro-1H-azepine-1,3-dicarboxylate B1-6-7

To an argon-purged solution of B1-6-6 (1 eq., 1.1 g, 3.7 mmol) in DCM (200 mL) was added Benzylidene-bis (tricyclohexylphosphine)dichlororuthenium (0.1 eq., 0.305 g, 0.37 mmol) at room temperature. The resulting mixture was stirred at 55° C. for 7 h.

The reaction was concentrated to dryness under reduced pressure.

Residual Ruthenium Scavenger Procedure:

Crude material was solubilized in DCM (0.1 M) and 2-mercaptonicotinic acid (5 eq.) was added. The reaction mixture was heated and stirred at 60° C. for 1 h then was warmed back to RT and washed with sat. $NaHCO_3$ then water. The organic layer was concentrated under reduced pressure and the crude residue was purified by ELSD flash chromatography over silica gel (irregular SiOH, 50 μm, 80 g Interchim, dry loading (silica), mobile phase gradient: cyclohexane/EtOAc from 100/0 to 60/40 over 40 min) and co-evaporated with DCM to afford B1-6-7 (0.57 g, 2.098 mmol, 57%) as a black oil.

LC/MS (AN01_001_012): Rt=2.56 min, 82.71%, $[M-{}^tBu+H]^+=214.1$.

1-tert-butyl 3-ethyl 5-hydroxyazepane-1,3-Dicarboxylate B1-84-1 and 1-tert-butyl 3-ethyl 6-hydroxyazepane-1,3-dicarboxylate B1-85-1

Starting from B1-6-7 (1 eq., 673 mg, 2.5 mmol) and using general procedure I, B1-84-1 (82 mg, 0.28 mmol, 11%) and B1-85-1 (319 mg, 1.11 mmol, 44%) were obtained as colorless oils after purification by flash chromatography over silica gel (regular SiOH, 15 μm, 40 g, dry loading (silica), mobile phase gradient: Cyclo/EtOAc from 10/0 to 4/6 over 30 min) and co-evaporation with DCM. The C-6 and C-7 regioisomers were confirmed by 2D NMR analyses. An SFC analysis showed the presence of 2 pairs of enantiomers in B1-85-1 and one pair of enantiomers in B1-084-1 (see below):

B1-84-1 ($C_5$ regioisomer):

Chiral SFC analysis: Chiralpak (AD-3 4.6×100 mm, Mobile phase: CO2/(iPrOH+0.3% iPrNH2) 85/15): one pair of enantiomer (two products) at Rt=0.76 min and 0.98 min, 48.05 and 51.95%.

LC/MS (AN01_001_026): Rt=7.97 min, 91.2%, $[M-{}^tBu+H]^+=232.1$.

1H NMR (400 MHZ, DMSO) δ 4.69-4.60 (m, 1H), 4.16-4.01 (m, 2H), 3.98-3.87 (m, 1H), 3.64-3.41 (m, 2H), 3.37-3.28 (m, 1H), 3.24-3.11 (m, 1H), 3.07-2.91 (m, 1H), 1.89-1.79 (m, 1H), 1.78-1.55 (m, 3H), 1.48-1.31 (m, 9H), 1.19 (t, J=7.1 Hz, 3H).

B1-85-1 ($C_6$ regioisomer):

Chiral SFC analysis: Chiralpak (IG-3 4.6×100 mm, Mobile phase: CO2/(iPrOH+0.3% iPrNH2) 90/10): two pairs of enantiomers (4 products) at Rt=1.64, 1.95, 2.46 and 2.90 min, 31.84, 32.79, 16.57 and 18.80%.

LC/MS (AN01_001_026): Rt=8.00 and 8.14 min, 53.24 and 43.62%, $[M-{}^tBu+H]^+=232.1$.

1H NMR (400 MHZ, DMSO) δ 4.23-3.56 (m, 5H), 3.10 (dd, J=14.0, 10.7 Hz, 1H), 2.85-2.74 (m, 1H), 2.50-2.35 (m, 4H), 2.09-1.99 (m, 1H), 1.79-1.63 (m, 1H), 1.47-1.33 (m, 9H), 1.27-1.12 (m, 3H).

Preparation of Intermediates I1-2-1-(S)*and I1-3-1-(S)*as a mixture

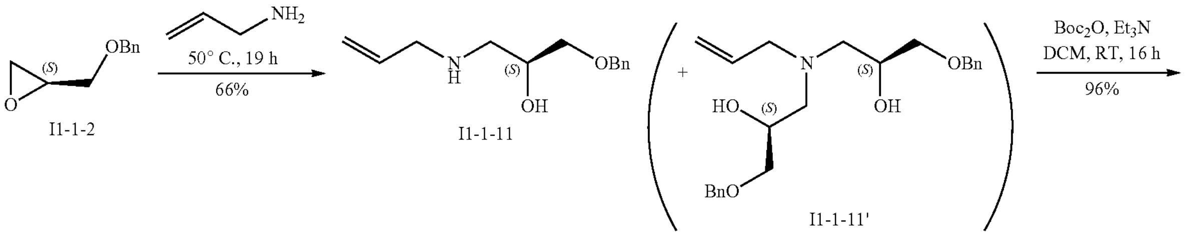

I1-1-2

I1-1-11

I1-1-11'

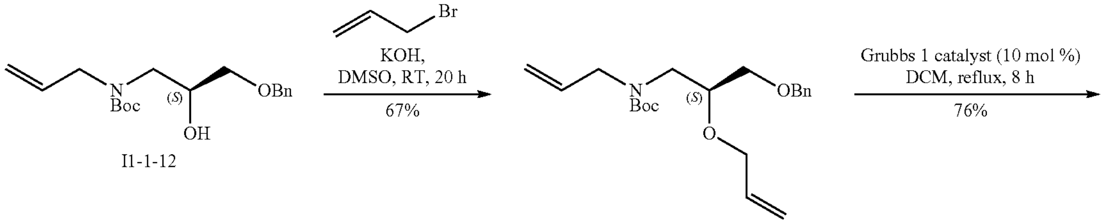

I1-1-12

I1-1-13

-continued

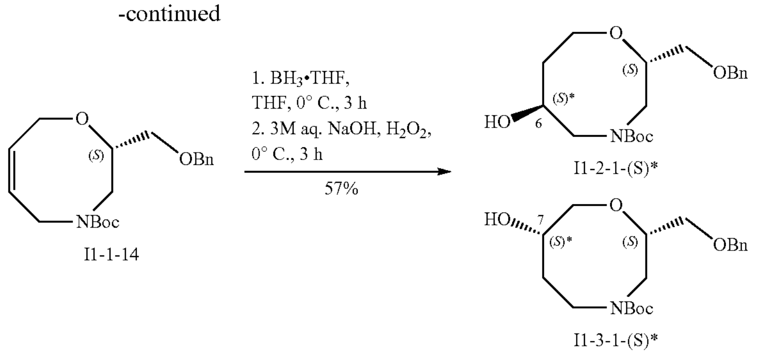

I1-1-14 I1-2-1-(S)* I1-3-1-(S)*

[(2S)-3-(benzyloxy)-2-hydroxypropyl](prop-2-en-1-yl)amine I1-1-11

To I1-1-2 (1 eq., 10 g, 9.26 mL, 60.9 mmol) was added allylamine (17.55 eq., 61.04 g, 80 mL, 1069.077 mmol) and the resulting mixture was stirred at 50° C. for 19 h. The reaction mixture was concentrated to dryness under reduced pressure affording Nov. 1, 2011 (13.5 g, 66%) as a yellow oil contaminated by 23% of I1-1-11'.

LC/MS (AN01_001_012): Rt=1.57 min, 91.2%, $[M+H]^+$= 222.1.

$^1$H NMR (400 MHZ, DMSO) δ 7.58-7.07 (m, 5H), 5.83 (ddt, J=17.2, 10.2, 5.7 Hz, 1H), 5.14 (dq, J=17.2, 1.8 Hz, 1H), 5.02 (ddt, J=10.3, 2.5, 1.4 Hz, 1H), 4.72 (s, 1H), 4.48 (s, 2H), 3.71 (dt, J=11.5, 5.3 Hz, 1H), 3.42-3.34 (m, 2H), 3.14 (dt, J=5.5, 1.2 Hz, 2H), 2.61-2.42 (m, 2H), 1.67 (s, 1H).

tert-butyl N-[(2S)-3-(benzyloxy)-2-hydroxypropyl]-N-(prop-2-en-1-yl) carbamate I1-1-12

Starting from I1-1-11 (1 eq., 2.6 g, 7.52 mmol) (containing ~75% mol of I1-1-11 and ~25% mol of I1-1-11') and using general procedure G, I1-1-12 was obtained as a yellowish oil (2.32 g, 96%) after purification by flash chromatography over silica gel (irregular SiOH, 50 μm, 80 g Interchim, dry loading (silica), mobile phase gradient: DCM/MeOH from 100/0 to 95/5 over 30 min) and co-evaporation with DCM.

LC/MS (AN01_001_012): Rt=2.56 min, 100%, $[M-Boc+H]^+$=222.1.

$^1$H NMR (400 MHZ, DMSO) δ 7.40-7.23 (m, 5H), 5.86-5.60 (m, 1H), 5.14-4.98 (m, 2H), 4.95-4.80 (m, 1H), 4.49 (s, 2H), 3.96-3.73 (m, 3H), 3.42-3.23 (m, 3H), 3.04-2.88 (m, 1H), 1.39-1.26 (m, 9H).

tert-butyl N-[(2S)-3-(benzyloxy)-2-(prop-2-en-1-yloxy)propyl]-N-(prop-2-en-1-yl) carbamate I1-1-13

To an argon-purged solution of Nov. 1, 2012 (1 eq., 3.0 g, 9.33 mmol) in DMSO (35 mL) were added KOH (2 eq., 1.047 g, 18.67 mmol), and allyl bromide (3 eq., 3.39 g, 2.44 mL, 28.00 mmol) at room temperature. The resulting mixture was stirred at room temperature for 20 h. The reaction mixture was diluted with water (200 mL) and extracted with EtOAc (2×200 mL). The combined organic layers were washed with brine (2×100 mL), dried over $Na_2SO_4$, filtered and concentrated to dryness under reduced. The crude was purified by flash chromatography over silica gel (irregular SiOH, 50 μm, 80 g Interchim, dry loading (silica), mobile phase gradient: cyclohexane/EtOAc from 100/0 to 85/15 over 25 min). The fractions containing the compound were combined, evaporated in vacuo and co-evaporated with DCM affording I1-1-13 (2.26 g, 67%) as a yellowish oil.

LC/MS (AN01_001_012): Rt=2.90 min, 100%, $[M-Boc+H]^+$=262.2.

$^1$H NMR (400 MHZ, DMSO) δ 7.40-7.24 (m, 5H), 5.93-5.79 (m, 1H), 5.81-5.64 (m, 1H), 5.30-5.19 (m, 1H), 5.16-4.99 (m, 3H), 4.50 (s, 2H), 4.15-4.05 (m, 1H), 4.04-3.94 (m, 1H), 3.90-3.73 (m, 2H), 3.74-3.64 (m, 1H), 3.53-3.39 (m, 2H), 3.31-3.22 (m, 1H), 3.20-3.10 (m, 1H), 1.37 (s, 9H).

tert-butyl (2S)-2-[(benzyloxy)methyl]-3,4,5,8-tetrahydro-2H-1,4-oxazocine-4-carboxylate I1-1-14

Starting from I1-1-13 (1 eq., 2.64 g, 7.29 mmol) and using general procedure H, I1-1-14 was obtained as a black gum (1.86 g, 76%) after purification by flash chromatography over silica gel (irregular SiOH, 50 μm, 25 g Interchim, dry loading (silica), mobile phase gradient: cyclohexane/EtOAc from 100/0 to 80/20 over 35 min) and co-evaporation with DCM.

LC/MS (AN01_001_012): Rt=2.72 min, 100%, $[M-Boc+H]^+$=234.1.

$^1$H NMR (400 MHZ, DMSO) δ 7.44-7.21 (m, 5H), 5.85-5.67 (m, 1H), 5.61-5.44 (m, 1H), 4.55-4.49 (m, 2H), 4.49-4.37 (m, 1H), 4.13-3.66 (m, 4H), 3.62-3.33 (m, 3H), 2.95-2.70 (m, 1H), 1.44-1.29 (m, 9H).

Mixture of tert-butyl (2S)-2-[(benzyloxy)methyl]-7-hydroxy-1,4-oxazocane-4-carboxylate and tert-butyl (2S)-2-[(benzyloxy)methyl]-6-hydroxy-1,4-oxazocane-4-carboxylate I1-2-1-(S)* & I1-3-1-(S)*

Starting from I1-1-14 (1 eq., 1 g, 3 mmol) and using general procedure I, a mixture of I1-2/3-1 (59:41, ratio from chiral SFC) was obtained as a brown oil (601 mg, 57%) after purification by ELSD flash chromatography over silica gel (regular SiOH, 15 μm, 40 g Interchim, dry loading (silica), mobile phase gradient: cyclohexane/EtOAc from 100/0 to 50/50 over 40 min.) and co-evaporation with DCM. (The position of C-6 and C-7 regioisomers were determined on the final compounds (2S,7S)—N—((S)-1-cyano-2-(4-(3-methyl-2-oxo-2,3-dihydrobenzo[d]oxazol-5-yl)phenyl) ethyl)-7-methoxy-1,4-oxazocane-2-carboxamide and (2S, 6S*)—N-[(1S)-1-cyano-2-[4-(3-methyl-2-oxo-2,3-dihydro-1,3-benzoxazol-5-yl)phenyl]ethyl]-6-methoxy-1,4-oxazocane-2-carboxamide).

Chiral SFC analysis: Chiralpak (OD-3 4.6×100 mm, Mobile phase: CO2/(MeOH+0.2% iPrNH2) 95/05): two products at Rt=5.09 and 6.31 min; 58.95 and 41.05%.

LC/MS (AN01_001_026): Rt=8.96 min, 96.3%, $[M-Boc+H]^+$=252.5.

$^1H$ NMR (400 MHZ, DMSO) δ 7.40-7.24 (m, 5H), 4.76-4.59 (m, 1H), 4.55-4.43 (m, 2H), 4.09-3.74 (m, 2H), 3.74-3.51 (m, 4H), 3.51-3.33 (m, 2H), 3.23-2.53 (m, 2H), 2.06-1.51 (m, 2H), 1.44-1.35 (m, 9H).

3.5 Preparation of Intermediates I1-2-1-(R)* & I1-3-1-(R)* as a Mixture

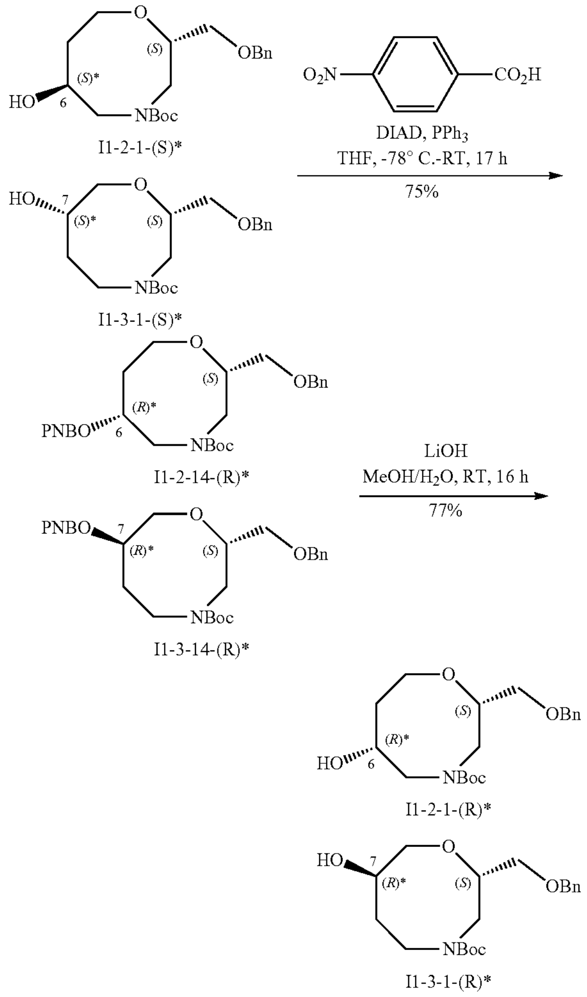

Mixture of tert-butyl (2S,6R*)-2-[(benzyloxy)methyl]-6-(4-nitrobenzoyloxy)-1,4-oxazocane-4-carboxylate and tert-butyl (2S,7R*)-2-[(benzyloxy)methyl]-6-(4-nitrobenzoyloxy)-1,4-oxazocane-4-carboxylate I1-2-14-(R)* & I1-3-14-(R)*

To solution of I1-2-1-(S)* & I1-3-1-(S)* (1 eq., 4 g, 10.65 mmol), triphenylphosphine (1.25 eq., 3.49 g, 13.32 mmol) and 4-nitro benzoic acid (1.5 eq., 2.67 g, 15.98 mmol) in THF (40 mL) was added a solution of DIAD (1.2 eq., 2.58 g, 2.53 mL, 12.78 mmol) in THF (20 mL) at −78° C. The reaction was warmed to RT and stirred for 18 h. The reaction mixture was diluted with water (150 mL) and extracted with EtOAc (3×150 mL). The combined organic layers were washed with brine (150 mL), dried over $Na_2SO_4$, filtered and concentrated to dryness under reduced pressure affording crude (13.7 g) as a brown oil. The crude was purified by flash chromatography over silica gel (irregular SiOH, 50 μm, 220 g Interchim, dry loading (silica), mobile phase gradient: cyclohexane/EtOAc from 100/0 to 60/40 over 45 min). The fractions containing compound were combined, evaporated in vacuo and co-evaporated with DCM affording I1-2-14-(R)* & I1-3-14-(R)* as a brown gum (4.00 g, 7.99 mmol, 75%).

LC/MS (AN01_001_026, ELSD): Rt=11.29 and 11.36 min, 11.46 and 83.91%, $[M-{}^*Bu+H]^+$=445.38.

$^1H$ NMR (400 MHZ, DMSO) δ 8.43-8.24 (m, 2H), 8.25-8.05 (m, 2H), 7.43-7.19 (m, 5H), 5.23-4.99 (m, 1H), 4.55-4.45 (m, 2H), 4.20-3.64 (m, 4H), 3.63-3.36 (m, 3H), 3.21-2.81 (m, 2H), 2.24-2.03 (m, 2H), 1.49-1.33 (m, 9H).

Mixture of tert-butyl (2S,6R*)-2-[(benzyloxy)methyl]-6-hydroxy-1,4-oxazocane-4-carboxylate and tert-butyl (2S, 7R*)-2-[(benzyloxy)methyl]-6-hydroxy-1,4-oxazocane-4-carboxylate I1-2-1-(R)* & I1-3-1-(R)*.

To a solution of mixture of I1-2-14-(R)* & I1-3-14-(R)* (1 eq., 5.77 g, 10.098 mmol) in MeOH (57 mL) and H2O (14 mL) was added lithium hydroxide monohydrate (2 eq., 0.85 g, 20.2 mmol) at RT and the reaction was stirred for 16 h. MeOH of the reaction mixture was removed under reduced pressure. The residue was diluted with an aq. sol. of $NaHCO_3$ (40 mL) and water (60 mL) (pH~10) and extracted with EtOAc (3×100 mL). The combined organic layers were washed with brine (100 mL), dried over $Na_2SO_4$, filtered and concentrated to dryness under reduced pressure affording crude (3.24 g) as a yellow gum. The crude was purified by flash chromatography over silica gel (irregular SiOH, 50 μm, 80 g Interchim, dry loading (silica), mobile phase gradient: DCM/MeOH from 100/0 to 90/10 over 40 min). The fractions containing compound were combined, evaporated in vacuo and co-evaporated with DCM affording I1-2-1-(R)* & I1-3-1-(R)* as a yellow oil (2.73 g, 77%).

LC/MS (AN01_001_026): Rt=8.79 and 9.53 min, 71.71 and 15.81%, $[M-Boc+H]^+$=252.50

$^1H$ NMR (400 MHZ, DMSO) δ 7.39-7.24 (m, 5H), 4.96-4.60 (m, 1H), 4.54-4.42 (m, 2H), 4.00-3.50 (m, 5H), 3.45-3.32 (m, 2H), 3.21-3.07 (m, 1H), 2.95-2.63 (m, 2H), 2.07-1.59 (m, 2H), 1.45-1.31 (m, 9H).

Example 1: Synthesis of (2S,6R*)—N—((S)-1-cyano-2-(4-(3-methyl-2-oxo-2,3-dihydrobenzo[d]oxazol-5-yl)phenyl)ethyl)-6-hydroxy-6-methyl-1,4-oxazepane-2-carboxamide & (2S,6S*)—N—((S)-1-cyano-2-(4-(3-methyl-2-oxo-2,3-dihydrobenzo[d]oxazol-5-yl)phenyl)ethyl)-6-hydroxy-6-methyl-1,4-oxazepane-2-carboxamide (Compound 2-A & Compound 2-B)

2-A

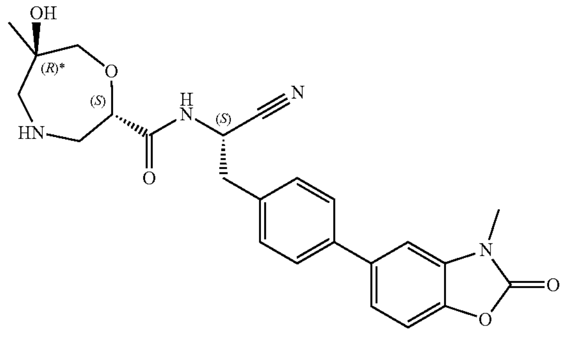

-continued

2-B

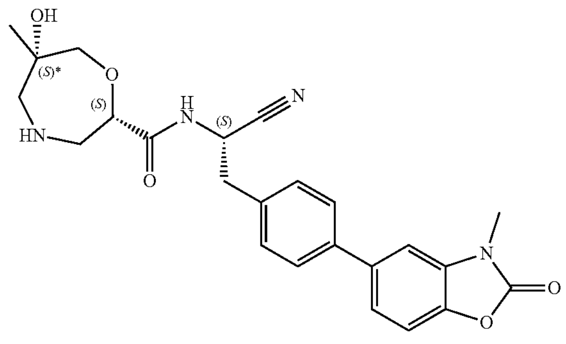

Part A: Synthetic Scheme for the Preparation of Intermediates B1-46-1-(S)* & B1-46-1-(R)*

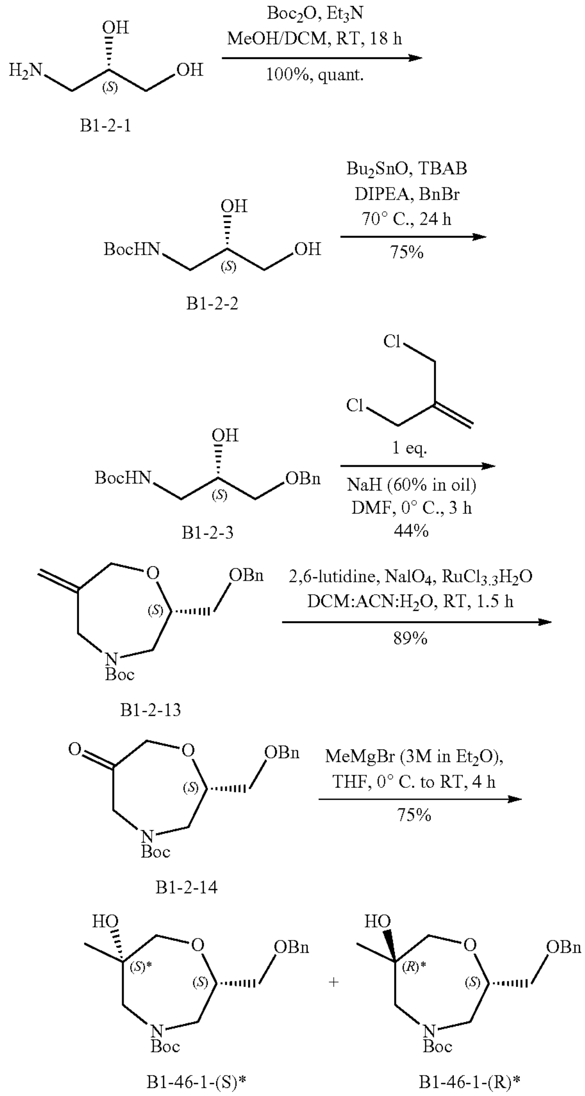

tert-butyl N-[(2S)-2,3-dihydroxypropyl]carbamate (B1-2-2)

B1-2-2

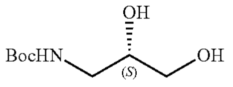

To a solution of (2S)-3-aminopropane-1,2-diol (1 eq., 14.4 g, 158.1 mmol) and $Et_3N$ (1.01 eq., 22.2 mL, 159.6 mmol) in anhydrous MeOH (245 mL) was added a solution of $Boc_2O$ (1.2 eq., 41.4 g, 189.7 mmol) in anhydrous DCM (41 mL) at room temperature under argon atmosphere. The reaction mixture was stirred at room temperature for 18 h and then concentrated under reduced pressure to afford B1-2-2 as a pale yellow oil (30.2 g, quant.). The crude was considered quantitative and used as such.

LC/MS (AN01_001_012): Rt=1.69 min, non-UV active, $[M+Na]^+$=214.1.

tert-butyl N-[(2S)-3-(benzyloxy)-2-hydroxypropyl] carbamate (B1-2-3)

B1-2-3

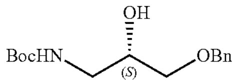

To a solution of B1-2-2 (1 eq., 1.72 g, 8.99 mmol), di(n-butyl) tin oxide (0.1 eq., 0.224 g, 0.899 mmol) and TBAB (0.3 eq., 0.870 g, 2.70 mmol) were added DIPEA (2 eq., 3.13 mL, 18.0 mmol) and BnBr (2 eq., 2.15 mL, 18.0 mmol) at room temperature under argon atmosphere. The reaction mixture was stirred at 70° C. for 6 h. The reaction mixture was concentrated under reduced pressure then taken into EtOAc (50 mL) and filtered over a pad of silica gel. The latter was rinsed with EtOAc (3×150 mL) and the filtrate was concentrated under reduced pressure. The resulting orange oil (4.46 g) was purified by silica gel flash chromatography (120 g, gradient: cyclohexane/EtOAc 100:0 to 50:50) to afford B1-2-3 as a pale-yellow oil (2.31 g, 75%) which was contaminated by the other-OBn regioisomer protected in position 2 (17 wt % by $^1H$ NMR analysis).

LC/MS (AN01_001_012): Rt=2.28 min, 100%, $[M+Na]^+$=304.1.

tert-butyl (2S)-2-[(benzyloxy)methyl]-6-methylidene-1,4-oxazepane-4-carboxylate I1-2-13

B1-2-13

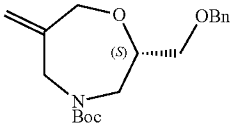

To a suspension of NaH 60% in oil (2.1 eq., 3.40 g, 85.1 mmol) in anhydrous DMF (72 mL) was added 3-chloro-2-chloromethyl-1-propene (1 eq., 4.69 mL, 40.5 mmol) at 0° C. The reaction mixture was stirred at 0° C. for 10 min, then a solution of B1-2-3 (1 eq., 11.4 g, 40.5 mmol) in anhydrous THF (50 mL) was added dropwise at 0° C. The reaction mixture was stirred at room temperature for 4 h. The reaction mixture was diluted with water (200 mL) and the aqueous layer was extracted with EtOAc (3×200 mL). The combined organic layers were washed with brine (200 mL), dried over $Na_2SO_4$, filtered and concentrated under reduced pressure. The crude residue was purified by silica gel flash chromatography (330 g, gradient: Cyclohexane/EtOAc from 100:0 to 90:10) to afford I1-2-13 as a colorless oil (5.93 g, 44%).

LC/MS (AN01_001_012): Rt=2.73 min, 100%, $[M-C4H8+H]^+$=278.1.

tert-butyl (2S)-2-[(benzyloxy)methyl]-6-oxo-1,4-oxazepane-4-carboxylate I1-2-14

B1-2-14

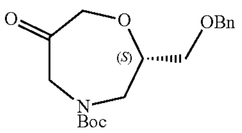

To a solution of I1-2-13 (1 eq., 2.10 g, 6.30 mmol) in a mixture of DCM (38 mL) and acetonitrile (38 mL) were added 2,6-lutidine (2 eq., 1.47 mL, 12.6 mmol), water (57 mL) and sodium periodate (4 eq., 5.39 g, 25.2 mmol) at room temperature. A solution of $RuCl_3 \cdot 3H_2O$ (0.035 eq., 57.6 mg, 0.220 mmol) in water (6.3 mL) was added dropwise forming a brown suspension. The reaction mixture was vigorously stirred at room temperature for 2 h. The reaction mixture was diluted with water (150 mL) and extracted with DCM (3×150 mL). The combined organic layers were washed with brine (150 mL), dried over $Na_2SO_4$, filtered and concentrated under reduced pressure. The crude residue was purified by silica gel flash chromatography (120 g, gradient: Cyclohexane/EtOAc from 100:0 to 85:15) to afford I1-2-14 as a colorless oil (1.88 g, 89%).

LC/MS (AN01_001_012): Rt=2.56 min, 100%, $[M+H]^+$=336.1.

tert-butyl (2S,6S*)-2-[(benzyloxy)methyl]-6-hydroxy-6-methyl-1,4-oxazepane-4-carboxylate B1-46-1-(S)* & tert-butyl (2S,6R*)-2-[(benzyloxy)methyl]-6-hydroxy-6-methyl-1,4-oxazepane-4-carboxylate B1-46-1-(R)*

B1-46-1-(S)*

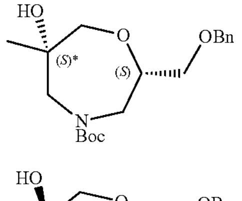

B1-46-1-(R)*

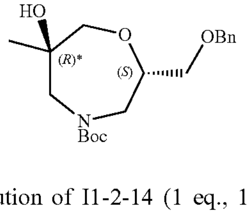

To a solution of I1-2-14 (1 eq., 1.28 g, 3.82 mmol) in anhydrous THF (35 mL) was added a 3M solution of MeMgBr in $Et_2O$ (2.5 eq., 3.18 mL, 9.54 mmol) at 0° C. under argon atmosphere. The reaction mixture was allowed to warm to room temperature and stirred for 2 h. The reaction mixture was diluted with an aqueous saturated solution of $NH_4Cl$ (100 mL) and the aqueous layer was extracted with EtOAc (3×100 mL). The combined organic layers were washed with brine (100 mL), dried over $Na_2SO_4$, filtered and concentrated under reduced pressure. The crude residue was purified by silica gel flash chromatography (80 g, gradient: Cyclohexane/EtOAc from 100:0 to 70:30) to afford of B1-46-1-(S)* (0.650 g, 48%) and B1-46-1-(R)* (0.363 g, 27%) as colorless oils. The stereochemistry(S)* was arbitrarily assigned to the first eluted product by flash chromatography and then the second eluted product was assigned (R)*.

B1-46-1-(S)*: LC/MS (AN01_001_012): Rt=2.47 min, 100%, $[M-C_4H_8+H]^+$=296.2.

B1-46-1-(R)*: LC/MS (AN01_001_012): Rt=2.41 min, 100%, $[M-C_4Hg+H]^+$=296.2.

Part B: General Strategy for the Synthesis of Compound 2-A & Compound 2-B

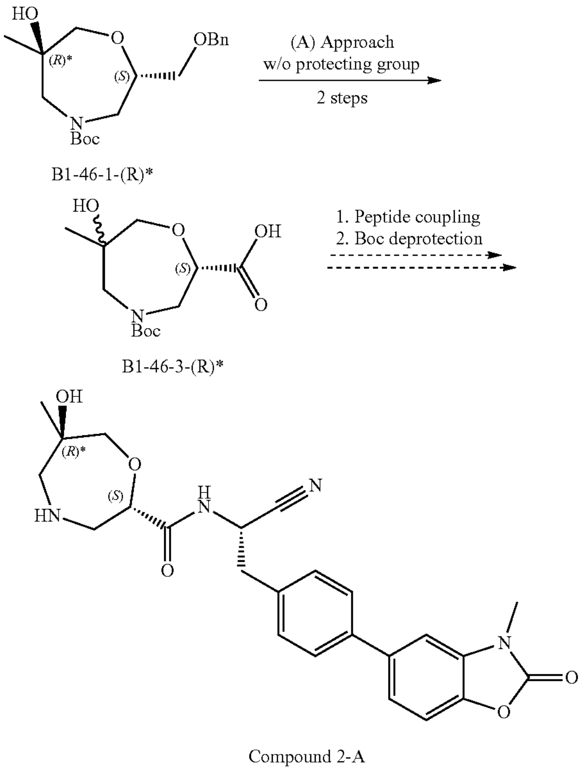

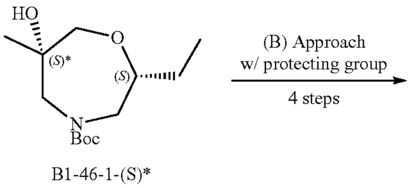

-continued

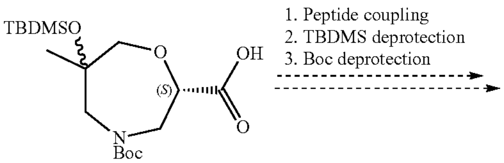

B1-46-5-(S)*

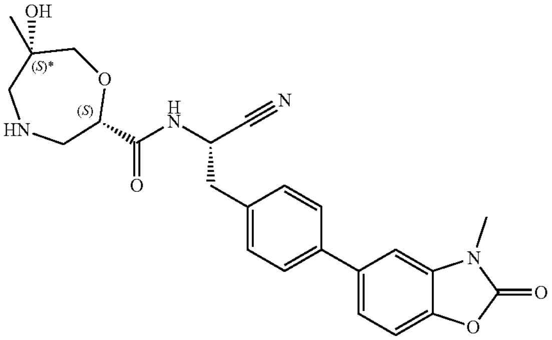

Compound 2-B

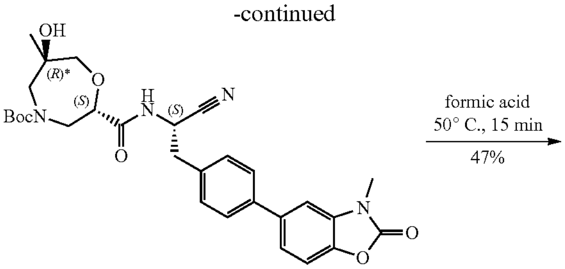

B1-46-4-(R)*

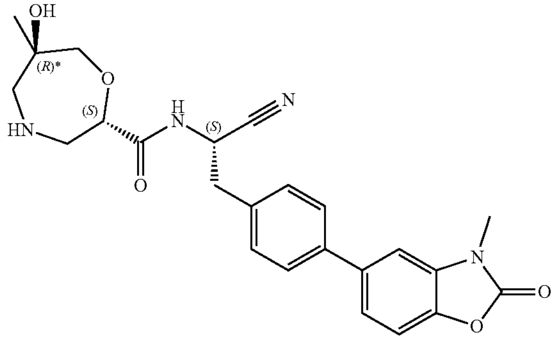

Compound 2-A

Synthetic Scheme for the Preparation of Compound 2-A: Approach (A) w/o Protecting Group

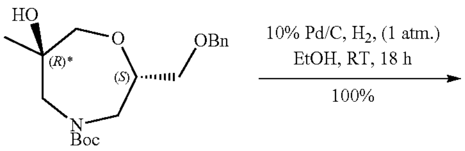

B1-46-1-(R)*

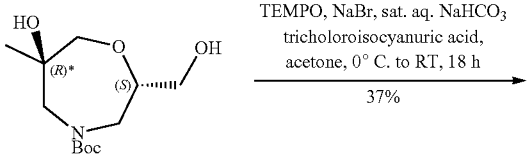

B1-46-2-(R)*

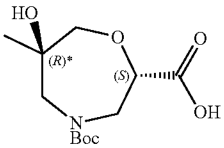

B1-46-3-(R)*

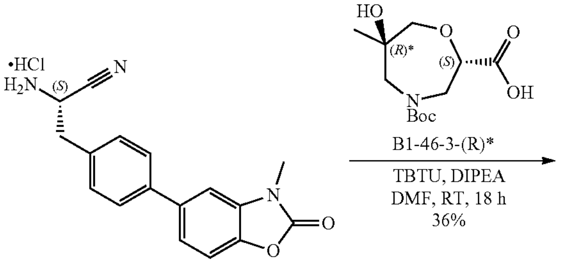

1 eq.
BB01 tert-butyl (2S,6R*)-6-hydroxy-2-(hydroxymethyl)-6-methyl-1,4-oxazepane-4-carboxylate B1-46-2-(R)*

B1-46-2-(R)*

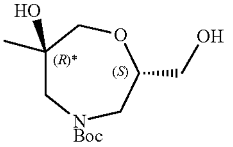

Starting from B1-46-1-(R)* (1 eq., 0.160 g, 0.455 mmol) and using general procedure A, B1-46-2-(R)* was obtained as a colorless oil (0.119 g, 100%).

LC/MS (AN01_001_012): Rt=1.83 min, non-UV active, $[M+Na]^+$=284.1.

(2S,6R*)-4-[(tert-butoxy) carbonyl]-6-hydroxy-6-methyl-1,4-oxazepane-2-carboxylic acid B1-46-3-(R)*

B1-46-3-(R)*

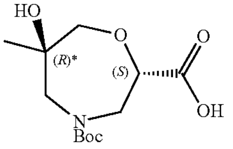

To a solution of B1-46-2-(R)* (1 eq., 0.110 g, 0.421 mmol) and sodium bromide (0.3 eq., 13.2 mg, 0.126 mmol) in acetone (7 mL) was added a saturated aqueous solution of $NaHCO_3$ (2 mL) at room temperature. To the resulting mixture were added trichlorocyanuric acid (2.2 eq., 0.215 mg, 0.926 mmol) and 2,2,6,6-tetramethylpiperidine-1-oxyl (0.03 eq., 1.97 mg, 0.0126 mmol) at 0° C. The reaction mixture was allowed to warm to room temperature and stirred for 18 h. Isopropanol (10 mL) was added at room temperature and the reaction mixture was stirred for 30 min. The reaction mixture was diluted with EtOAc (50 mL) and a saturated aqueous solution of $NaHCO_3$ (50 mL) was added. The two layers were separated, and the aqueous layer was washed with EtOAc (50 mL). The aqueous layer was then acidified with an aqueous solution of 3M HCl until pH ~1 and extracted with DCM (2×50 mL). The aqueous layer was further extracted with a mixture of $CHCl_3$/Isopropanol (8:2, 2×50 mL). The combined organic layers were dried over $Na_2SO_4$, filtered and concentrated under reduced pressure to afford B1-46-3-(R)* as a yellowish oil (42.6 mg, 37%).

LC/MS (AN01_001_012): Rt=1.83 min, non-UV active, $[M+Na]^+$=298.1.

tert-butyl (2S,6R*)-2-{[(1S)-1-cyano-2-[4-(3-methyl-2-oxo-2,3-dihydro-1,3-benzoxazol-5-yl)phenyl]ethyl]carbamoyl}-6-hydroxy-6-methyl-1,4-oxazepane-4-carboxylate B1-46-4-(R)*

B1-46-4-(R)*

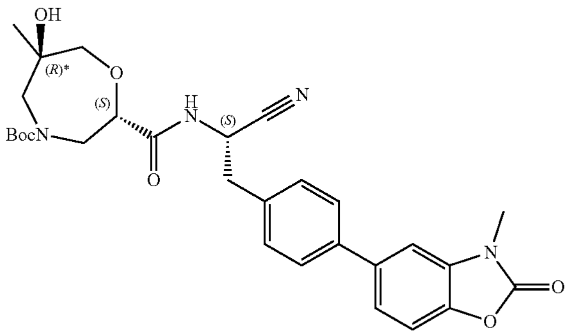

Starting from BB01 (1 eq., 45.6 mg, 0.138 mmol) and B1-46-3-(R)* (1.05 eq., 40.0 mg, 0.145 mmol), using general procedure C, B1-46-4-(R)* was obtained as a white solid (27.3 mg, 36%) after purification by silica gel flash chromatography (12 g, gradient: DCM/MeOH from 100:0 to 97:3).

LC/MS (AN01_001_012), Rt=2.37 min, 100%, $[M+Na]^+$=573.2.

(2S,6R*)—N-[(1S)-1-cyano-2-[4-(3-methyl-2-oxo-2,3-dihydro-1,3-benzoxazol-5-yl)phenyl]ethyl]-6-hydroxy-6-methyl-1,4-oxazepane-2-carboxamide (Compound 2-A)

Compound 2-A

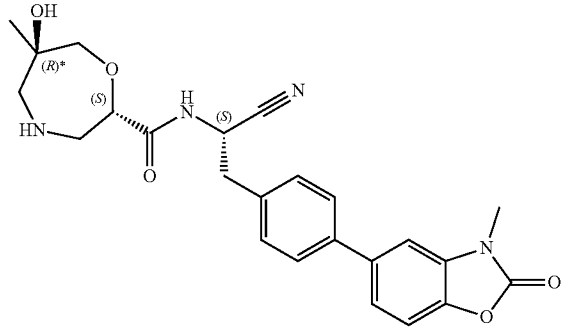

Starting from B1-46-4-(R)* (1 eq., 25.0 mg, 0.0454 mmol) using general procedure D, Compound 2-A was obtained as a white solid (9.70 mg, 47%) after purification by preparative HPLC (Eluant: Water+0.1% TFA/Acetonitrile, gradient: from 15 to 30% acetonitrile in water +0.1% TFA, column: XBridge C18 (30×150 (5 μm)), Flow Rate: 43 mL/min) and freeze-drying.

LC/MS (AN01_001_026): Rt=6.40 min, 99.5%, $[M+H]^+$=451.5.

$^1$H NMR (DMSO-$d_6$, 400 MHZ): δ ppm 8.68 (d, J=8.4 Hz, 1H), 7.65 (d, J=8.3 Hz, 2H), 7.59-7.54 (m, 1H), 7.43-7.35 (m, 4H), 5.02 (q, J=8.5 Hz, 1H), 4.55 (s, 1H), 3.99 (dd, J=7.8, 5.1 Hz, 1H), 3.60 (d, J=12.7 Hz, 1H), 3.49 (d, J=12.6 Hz, 1H), 3.40 (s, 3H), 3.25-3.14 (m, 2H), 3.02 (dd, J=14.1, 5.1 Hz, 1H), 2.62-2.45 (m, 4H), 0.98 (s, 3H).

Synthetic Scheme for the Preparation of Compound 2-B: Approach (B) with Protecting Group

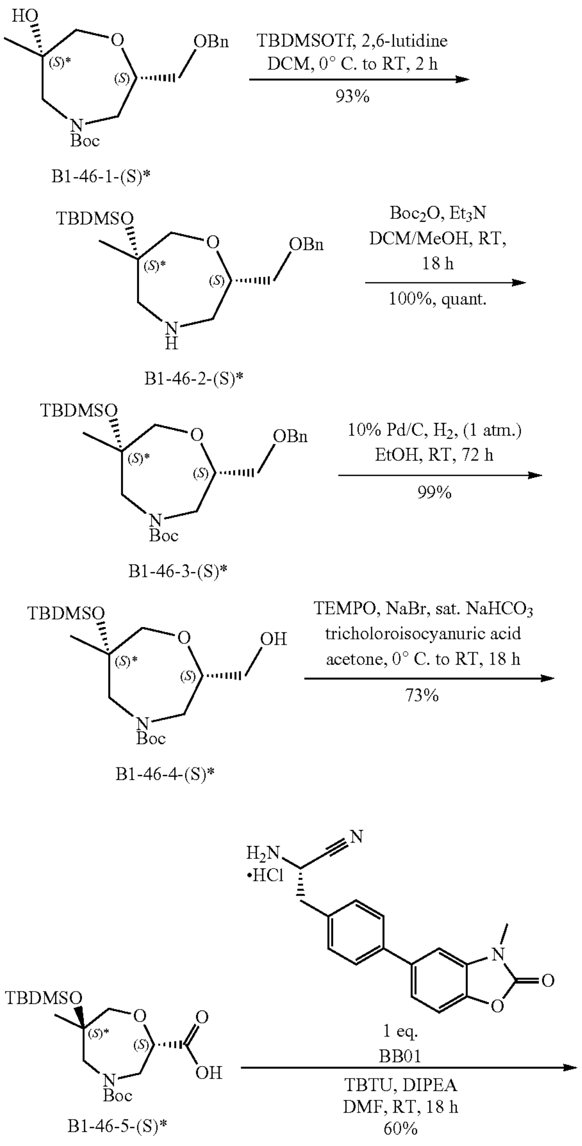

B1-46-1-(S)*

B1-46-2-(S)*

B1-46-3-(S)*

B1-46-4-(S)*

B1-46-5-(S)*

-continued

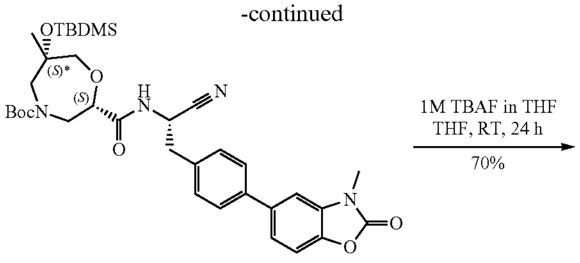

B1-46-6-(S)*

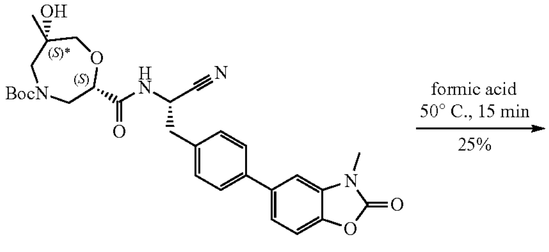

B1-46-7-(S)*

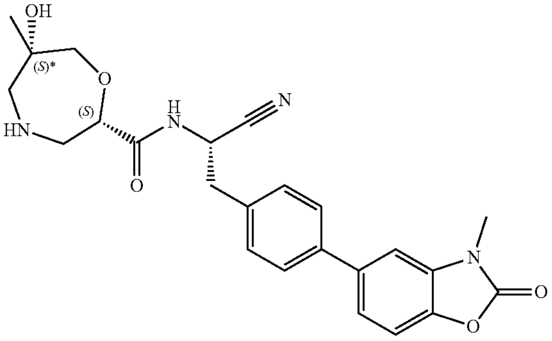

Compound 2-B

(2S,6S*)-2-[(benzyloxy)methyl]-6-[(tert-butyldimethylsilyl)oxy]-6-methyl-1,4-oxazepane B1-46-2-(S)*

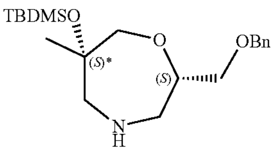

B1-46-2-(S)*

To a solution of B1-46-1-(S)* (1 eq., 0.320 g, 0.911 mmol) and 2,6-lutidine (2.5 eq., 0.265 mL, 2.28 mmol) in anhydrous DCM (3 mL) were added TBDMSOTf (1.5 eq., 0.310 mL, 1.37 mmol) and DMAP (0.05 eq., 5.56 mg, 0.0455 mmol) under argon atmosphere. The reaction mixture was stirred at room temperature for 6 h. The resulting mixture was diluted with DCM (50 mL) and water (50 mL). The two layers were separated and the aqueous layer was extracted with DCM (2×50 mL). The combined organic layers were dried over $Na_2SO_4$, filtered and concentrated under reduced pressure. The crude residue was purified by silica gel flash chromatography (40 g, gradient: cyclohexane/EtOAc from 100/0 to 50:50) to afford B1-46-2-(S)* as a pale-yellow oil (0.308 g, 93%).

LC/MS (AN01_001_012): Rt=2.30 min, 100%, $[M+H]^+$=366.3.

tert-butyl (2S,6S*)-2-[(benzyloxy)methyl]-6-[(tert-butyldimethylsilyl)oxy]-6-methyl-1,4-oxazepane-4-carboxylate B1-46-3-(S)*

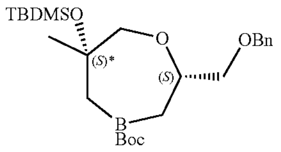

B1-46-3-(S)*

To a solution of B1-46-2-(S)* (1 eq., 0.305 g, 0.834 mmol) and $Et_3N$ (1.01 eq., 0.117 mL, 0.843 mmol) in anhydrous MeOH (1.3 mL) was added a solution of $Boc_2O$ (1.2 eq., 0.218 g, 1.00 mmol) in anhydrous DCM (0.25 mL) under argon atmosphere. The reaction mixture was stirred at room temperature for 18 h and then concentrated under reduced pressure to afford B1-46-3-(S)* as a colorless oil (0.389 g, quant.). The crude mixture was considered quantitative and used as such.

LC/MS (AN01_001_012): Rt=3.38 min, 100%, $[M+Na]^+$=488.3.

tert-butyl (2S,6S*)-6-[(tert-butyldimethylsilyl)oxy]-2-(hydroxymethyl)-6-methyl-1,4-oxazepane-4-carboxylate B1-46-4-(S)*

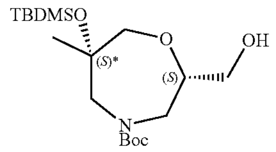

B1-46-4-(S)*

Starting from B1-46-3-(S)* (1 eq., 0.385 g, 0.827 mmol), using general procedure A, B1-46-4-(S)* was obtained as a colorless oil (0.306 g, 99%).

LC/MS (AN01_001_012): Rt=2.95 min, not UV active, $[M-C_4H_8+H]^+$=320.2.

(2S,6S*)-4-[(tert-butoxy) carbonyl]-6-[(tert-butyldimethylsilyl)oxy]-6-methyl-1,4-oxazepane-2-carboxylic acid B1-46-5-(S)*

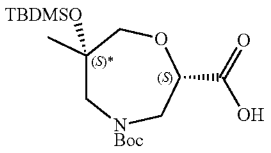

B1-46-5-(S)*

Starting from B1-46-4-(S)* (1 eq., 0.290 g, 0.772 mmol), using general procedure B, B1-46-5-(S)* was obtained as a yellowish oil (0.219 g, 73%).

LC/MS (AN01_001_012): Rt=2.84 min, not UV active, $[M+Na]^+$=412.2.

tert-butyl (2S,6S*)-6-[(tert-butyldimethylsilyl)oxy]-2-{[(1S)-1-cyano-2-[4-(3-methyl-2-oxo-2,3-dihydro-1,3-benzoxazol-5-yl)phenyl]ethyl]carbamoyl}-6-methyl-1,4-oxazepane-4-carboxylate B1-46-6-(S)*

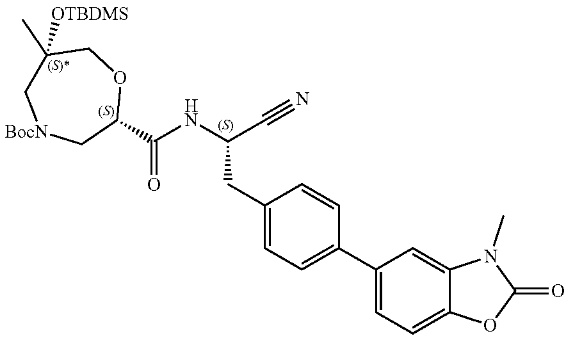

B1-46-6-(S)*

Starting from BB01 (1 eq., 0.173 g, 0.526 mmol) and B1-46-5-(S)* (1.05 eq., 0.215 g, 0.552 mmol), using general procedure C, B1-46-6-(S)* was obtained as an orange solid (0.209 g, 60%) after purification by silica gel flash chromatography (25 g, gradient: cyclohexane/EtOAc from 100:0 to 70:30).

LC/MS (AN01_001_012): Rt=3.08 min, 100%, $[M+Na]^+$=687.3.

tert-butyl (2S,6S*)-2-{[(1S)-1-cyano-2-[4-(3-methyl-2-oxo-2,3-dihydro-1,3-benzoxazol-5-yl)phenyl]ethyl]carbamoyl}-6-hydroxy-6-methyl-1,4-oxazepane-4-carboxylate B1-46-7-(S)*

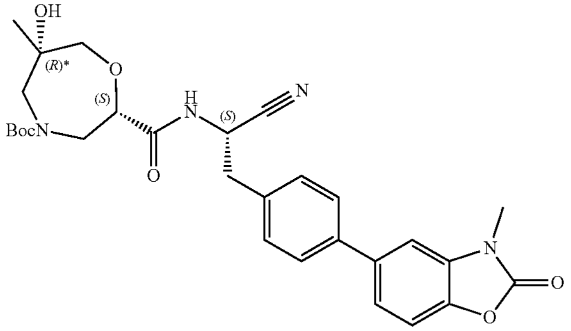

B1-46-7-(R)*

To a solution of B1-46-6-(S)* (1 eq., 0.200 g, 0.301 mmol) in anhydrous THF (1.85 mL) was added a 1M solution of TBAF in THF (1.5 eq., 0.451 mL, 0.451 mmol) at 0° C. under argon atmosphere. The reaction mixture was allowed to warm to room temperature and stirred for 24 h. The reaction mixture was diluted with EtOAc (30 mL) and washed with brine (30 mL). The organic layer was dried over $Na_2SO_4$, filtered and concentrated under reduced pressure. The crude residue was purified by silica gel flash chromatography (12 g, gradient: Cyclohexane/EtOAc from 100:0 to 25:75) to afford B1-46-7-(S)* as a colorless oil (0.116 g, 70%).

LC/MS (AN01_001_012): Rt=2.38 min, 100%, $[M+Na]^+$=573.2.

(2S,6S*)—N-[(1S)-1-cyano-2-[4-(3-methyl-2-oxo-2,3-dihydro-1,3-benzoxazol-5-yl)phenyl]ethyl]-6-hydroxy-6-methyl-1,4-oxazepane-2-carboxamide (Compound 2-B)

Compound 2-B

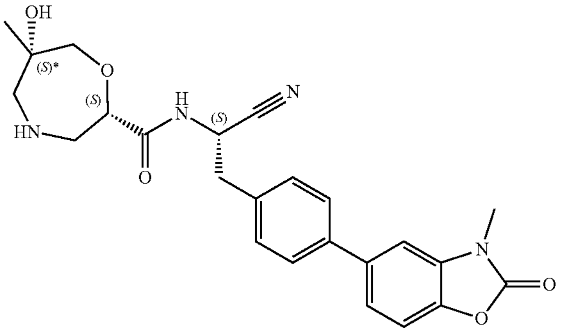

Starting from B1-46-7-(S)* (1 eq., 0.115 g, 0.209 mmol), using general procedure D, Compound 2B was obtained as a white solid (13.8 mg, 15%) after purification by silica gel flash chromatography (4 g, gradient: DCM/MeOH from 100:0 to 93:7) followed by preparative HPLC (Eluant: Water+0.1% TFA/Acetonitrile, gradient: from 20 to 35% of acetonitrile in water+0.1% TFA, column: XBridge C18 (30×150 (5 μm)), Flow Rate: 43 mL/min) and freeze-drying.

LC/MS (AN01_001_026): Rt=6.54 min, 100%, $[M+H]^+$=451.4.

$^1$H NMR (DMSO-$d_6$, 400 MHZ): 8 ppm 8.56 (d, J=8.4 Hz, 1H), 7.65 (d, J=8.3 Hz, 2H), 7.58-7.53 (m, 1H), 7.40-7.37 (m, 4H), 5.01 (q, J=8.7 Hz, 1H), 4.47 (s, 1H), 4.04 (dd, J=8.8, 4.4 Hz, 1H), 3.50-3.44 (m, 2H), 3.40 (s, 3H), 3.25-3.14 (m, 2H), 3.07 (dd, J=14.2, 4.4 Hz, 1H), 2.63 (d, J=13.7 Hz, 1H), 2.48-2.42 (m, 3H), 1.03 (s, 3H).

Example 2: Synthesis of (2S,6S*)—N—((S)-1-cyano-2-(4-(3-methyl-2-oxo-2,3-dihydrobenzo[d]oxazol-5-yl)phenyl)ethyl)-6-methoxy-6-methyl-1,4-oxazepane-2-carboxamide & (2S,6R*)—N—((S)-1-cyano-2-(4-(3-methyl-2-oxo-2,3-dihydrobenzo[d]oxazol-5-yl)phenyl)ethyl)-6-methoxy-6-methyl-1,4-oxazepane-2-carboxamide (Compound 3-A & Compound 3-B)

Compound 3-A

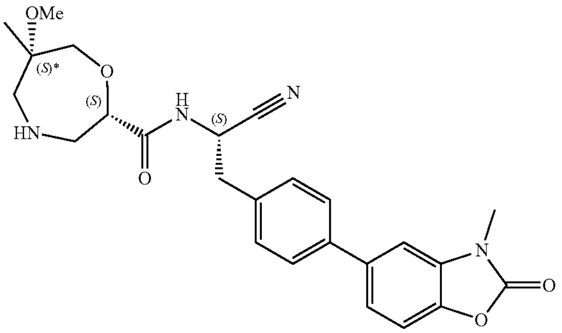

-continued

Compound 3-B

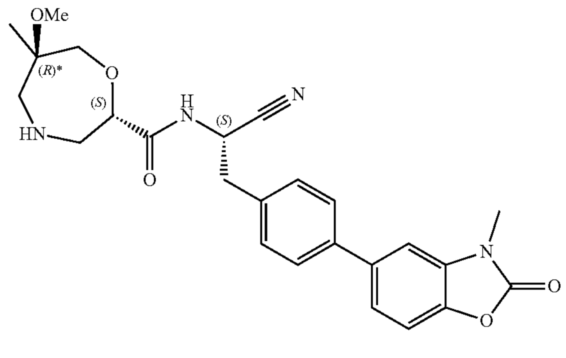

Synthetic Scheme for the Preparation of Compound 3-A

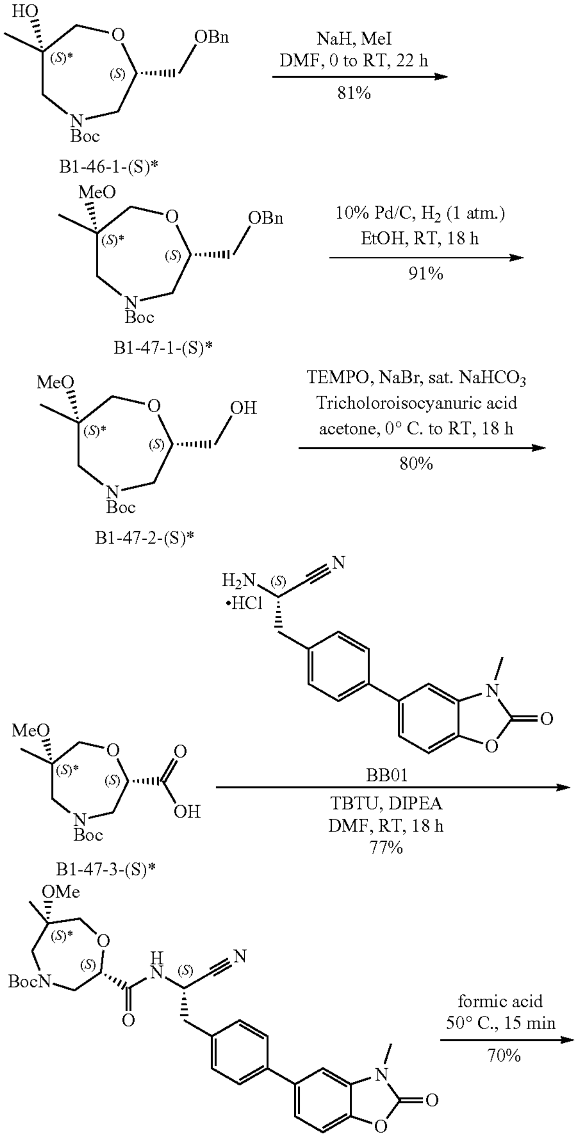

-continued

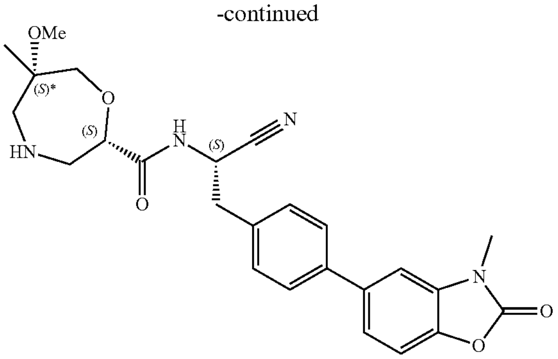

Compound 3-A tert-butyl (2S,6S*)-2-[(benzyloxy)methyl]-6-methoxy-6-methyl-1,4-oxazepane-4-carboxylate B1-47-1-(S)*

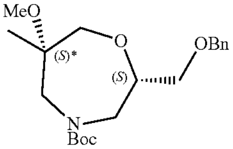

B1-47-1-(S)*

Starting from B1-46-1-(S)* (1 eq., 0.320 g, 0.910 mmol), using general procedure E, B1-47-1-(S)* was obtained as a colorless oil (0.268 g, 81%) after purification by silica gel flash chromatography (25 g, gradient: cyclohexane/EtOAc from 100:0 to 80:20).

LC/MS (AN01_001_012): Rt=2.65 min, 100%, $[M+Na]^+$=388.2.

tert-butyl (2S,6S*)-2-(hydroxymethyl)-6-methoxy-6-methyl-1,4-oxazepane-4-carboxylate B1-47-2-(S)*

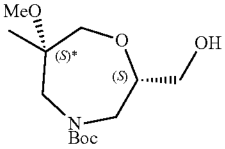

B1-47-2-(S)*

Starting from B1-47-1-(S)* (1 eq., 0.265 g, 0.725 mmol), using general procedure A, B1-47-2-(S)* was obtained as a colorless oil (0.181 g, 91%).

LC/MS (AN01_001_012): Rt=2.00 min, non-UV active, $[M+Na]^+$=298.2.

(2S,6S*)-4-[(tert-butoxy) carbonyl]-6-methoxy-6-methyl-1,4-oxazepane-2-carboxylic B1-47-3-(S)*

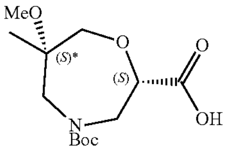

B1-47-3-(S)*

Starting from B1-47-2-(S)* (1 eq., 0.175 g, 0.636 mmol), using general procedure B, B1-47-3-(S)* was obtained as a white solid (0.147 g, 80%).

LC/MS (AN01_001_012): Rt=1.98 min, non-UV active, $[M+Na]^+$=312.1.

(2S,6S*)-2-{[(1S)-1-cyano-2-[4-(3-methyl-2-oxo-2,3-dihydro-1,3-benzoxazol-5yl)phenyl]ethyl]carbamoyl}-6-methoxy-6-methyl-1,4-oxazepane-4-carboxylate B1-47-4-(S)*

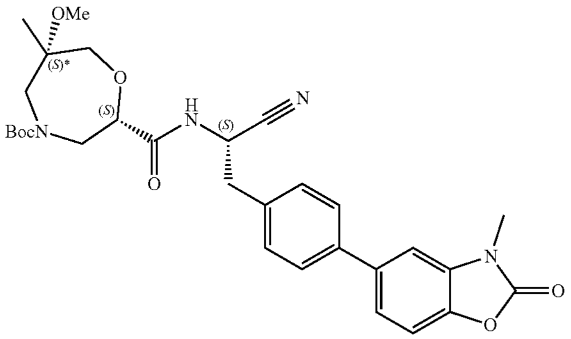

B1-47-4-(S)*

Starting from BB01 (1 eq., 0.157 g, 0.477 mmol) and B1-47-3-(S)* (1.05 eq., 0.145 g, 0.501 mmol), using general procedure C, B1-47-4-(S)* was obtained as an orange solid (0.209 g, 77%) after purification by silica gel flash chromatography (25 g, gradient: cyclohexane/EtOAc from 100:0 to 25:75).

LC/MS (AN01_001_012): Rt=2.51 min, 100%, $[M+Na]^+$=587.3.

(2S,6S*)—N-[(1S)-1-cyano-2-[4-(3-methyl-2-oxo-2,3-dihydro-1,3-benzoxazol-5-yl)phenyl]ethyl]-6-methoxy-6-methyl-1,4-oxazepane-2-carboxamide Compound 3-A Compound 3-A

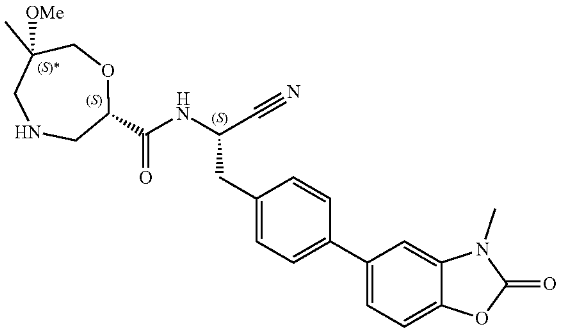

Starting from B1-47-4-(S)* (1 eq., 0.100 g, 0.170 mmol), using general procedure D, Compound 3-A was obtained as a white solid (55.3 mg, 70%) after purification by silica gel flash chromatography (4 g, gradient: DCM/MeOH from 100:0 to 95:5).

LC/MS (AN01_001_026): Rt=6.69 min, 99.8%, $[M+H]^+$=465.5.

$^1$H NMR (DMSO-$d_6$, 400 MHZ): 0 ppm 8.58 (d, J=8.4 Hz, 1H), 7.66 (d, J=8.2 Hz, 2H), 7.59-7.52 (m, 1H), 7.45-7.33 (m, 4H), 5.01 (q, J=8.7 Hz, 1H), 4.03 (dd, J=9.3, 4.0 Hz, 1H), 3.70 (d, J=12.5 Hz, 1H), 3.53 (d, J=12.5 Hz, 1H), 3.40 (s, 3H), 3.26-3.16 (m, 2H), 3.14 (s, 3H), 3.08 (dd, J=14.1, 4.3 Hz, 1H), 2.92 (d, J=14.4 Hz, 1H), 2.38 (dt, J=14.3, 4.8 Hz, 2H), 1.05 (s, 3H), one-NH signal is missing.

Synthetic Scheme for the Preparation of Compound 3-B

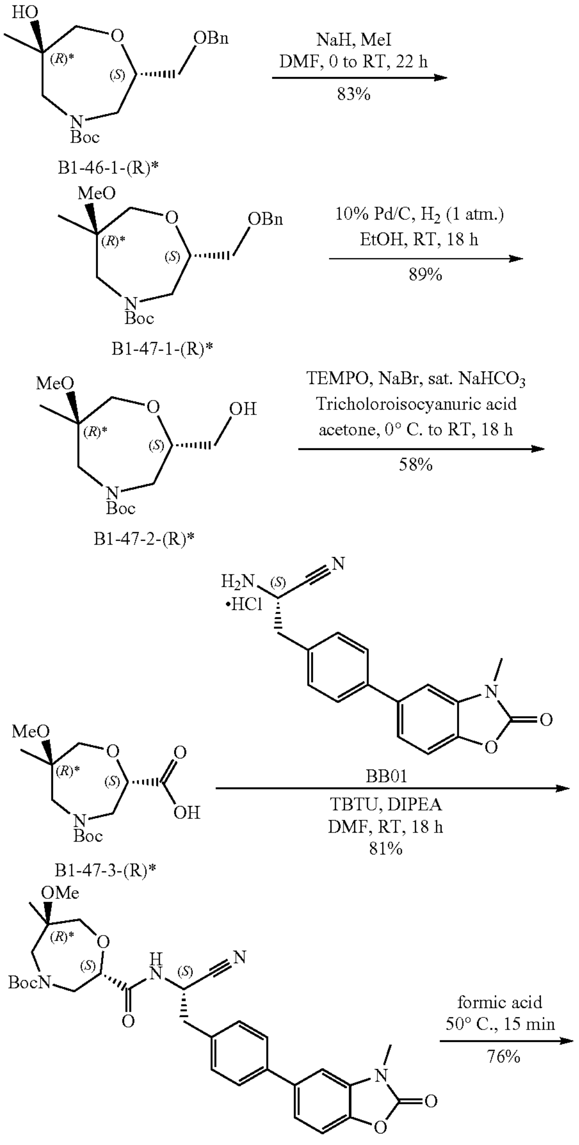

B1-46-1-(R)*

B1-47-1-(R)*

B1-47-2-(R)*

B1-47-3-(R)*

B1-47-4-(R)*

-continued

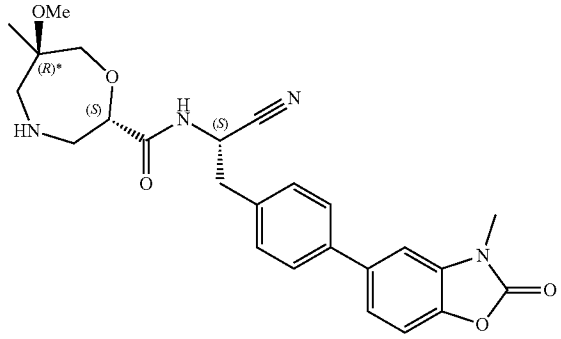

Compound 3-B tert-butyl (2S,6R*)-2-[(benzyloxy)methyl]-6-methoxy-6-methyl-1,4-oxazepane-4-carboxylate B1-47-1-(R)*

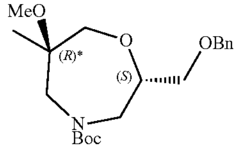

B1-47-1-(R)*

Starting from B1-46-1-(R)* (1 eq., 0.360 g, 1.02 mmol), using general procedure E, B1-47-1-(R)* was obtained as a colorless oil (0.311 g, 83%) after purification by silica gel flash chromatography (25 g, gradient: cyclohexane/EtOAc from 100:0 to 75:25).

LC/MS (AN01_001_012): Rt=2.65 min, 100%, $[M+Na]^+$=388.2.

tert-butyl (2S,6R*)-2-(hydroxymethyl)-6-methoxy-6-methyl-1,4-oxazepane-4-carboxylate B1-47-2-(R)*

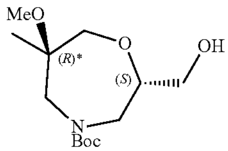

B1-47-2-(R)*

Starting from B1-47-1-(R)* (1 eq., 0.310 g, 0.848 mmol), using general procedure A, B1-47-2-(R)* was obtained as a colorless oil (0.208 g, 89%).

LC/MS (AN01_001_012): Rt=2.00 min, non-UV active, $[M+Na]^+$=298.1.

(2S,6R*)-4-[(tert-butoxy) carbonyl]-6-methoxy-6-methyl-1,4-oxazepane-2-carboxylic B1-47-3-(R)*

B1-47-3-(R)*

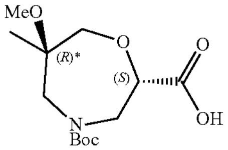

Starting from B1-47-2-(R)* (1 eq., 0.205 g, 0.744 mmol), using general procedure B, B1-47-3-(R)* was obtained as a white solid (0.124 g, 58%).

LC/MS (AN01_001_012): Rt=2.00 min, non-UV active, [M+Na]=312.1.

(2S,6R*)-2-{[(1S)-1-cyano-2-[4-(3-methyl-2-oxo-2,3-dihydro-1,3-benzoxazol-5yl)phenyl]ethyl]carbamoyl}-6-methoxy-6-methyl-1,4-oxazepane-4-carboxylate B1-47-4-(R)*

B1-47-4-(R)*

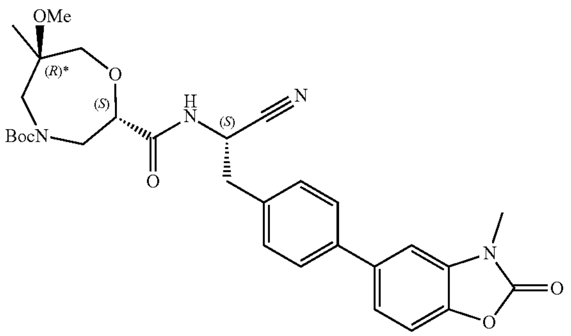

Starting from BB01 (1 eq., 0.130 g, 0.395 mmol) and B1-47-3-(R)* (1.05 eq., 0.120 g, 0.415 mmol), using general procedure C, B1-47-4-(R)* was obtained as an orange solid (0.181 g, 81%) after purification by silica gel flash chromatography (25 g, gradient: cyclohexane/EtOAc from 100:0 to 25:75).

LC/MS (AN01_001_012): Rt=2.53 min, 92%, $[M+Na]^+$=587.3.

(2S,6R*)—N-[(1S)-1-cyano-2-[4-(3-methyl-2-oxo-2,3-dihydro-1,3-benzoxazol-5-yl)phenyl]ethyl]-6-methoxy-6-methyl-1,4-oxazepane-2-carboxamide (Compound 3-B)

Compound 3-B

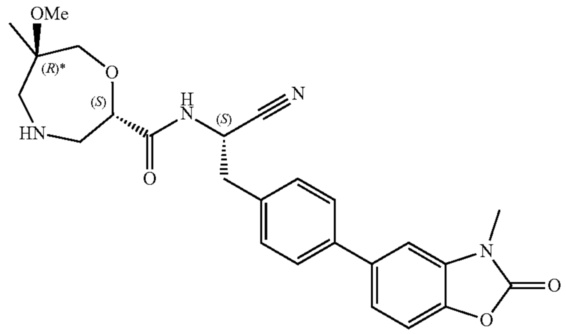

Starting from B1-47-4-(R)* (1 eq., 96.1 mg, 0.170 mmol), using general procedure D, Compound 3-B was obtained as a white solid (60.4 mg, 76%) after purification by flash chromatography over silica gel (4 g, gradient: DCM/MeOH from 100:0 to 95:5).

LC/MS (AN01_001_026): Rt=6.64 min, 99.4%, $[M+H]^+$=465.5.

$^1$H NMR (DMSO-$d_6$): δ ppm 8.57 (d, J=8.5 Hz, 1H), 7.65 (d, J=8.3 Hz, 2H), 7.59-7.54 (m, 1H), 7.44-7.32 (m, 4H), 5.01 (q, J=8.5 Hz, 1H), 3.95-3.91 (m, 2H), 3.43 (d, J=13.3 Hz, 1H), 3.40 (s, 3H), 3.26-3.14 (m, 5H), 3.08 (dd, J=13.6, 4.2 Hz, 1H), 2.69 (d, J=13.5 Hz, 1H), 2.64 (d, J=13.6 Hz, 1H), 2.36 (dd, J=13.6, 9.8 Hz, 1H), 0.99 (s, 3H), one-NH signal is missing.

Example 3: Synthesis of N—((S)-1-cyano-2-(4-(3-methyl-2-oxo-2,3-dihydrobenzo[d]oxazol-5-yl)phenyl)ethyl) azocane-3-carboxamide (Compound 1-A)

Compound 1-A

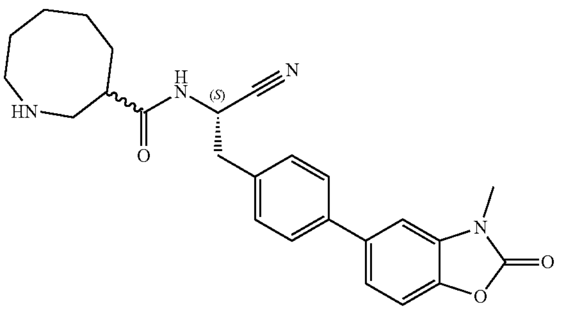

(mixture of diastereomers)

Synthetic Scheme for the Preparation of Compound 1-A

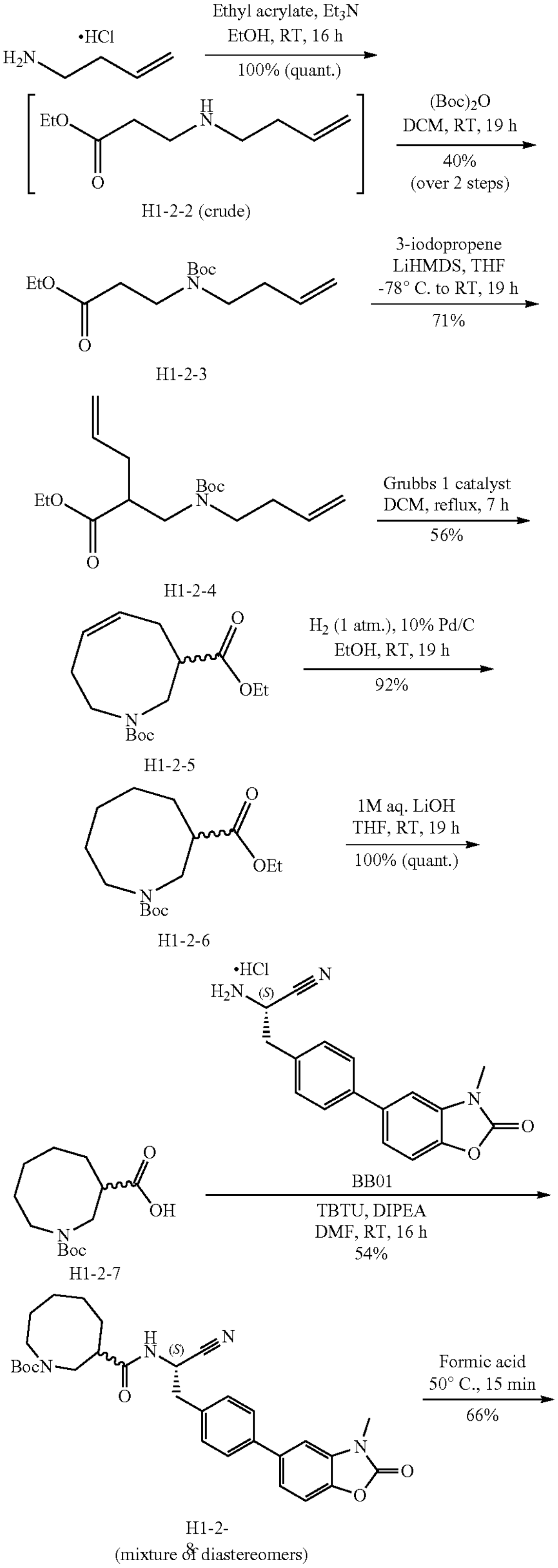

-continued

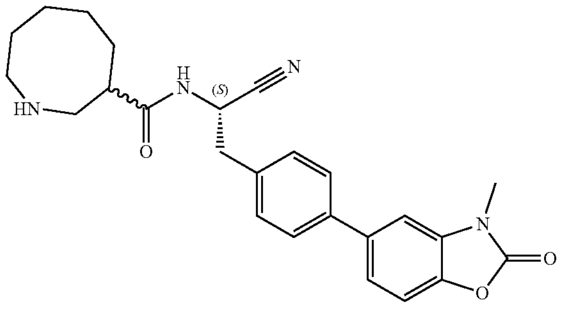

Compound 1-A
(mixture of diastereomers)

Ethyl 3-[(but-3-en-1-yl) [(tert-butoxy) carbonyl] amino]propanoate H1-2-3

H1-2-3

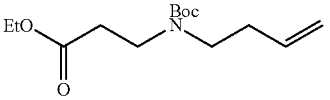

An argon-purged solution of but-3-en-1-amine hydrochloride H1-2-1 (1 eq., 1.99 g, 18.5 mmol) and triethylamine (1.05 eq., 2.70 mL, 19.4 mmol) in EtOH (28 mL) was stirred at room temperature for 30 min. Ethyl acrylate (1 eq., 2.01 mL, 18.5 mmol) was then added and the resulting mixture was stirred at room temperature for 17 h. The reaction mixture was concentrated under reduced pressure to afford a crude mixture containing H1-2-2 (4.88 g, estimated purity: 50%) as a colorless oil.

To an argon-purged solution of the crude mixture containing H1-2-2 (4.88 g, estimated purity: 50%, 14.2 mmol, 1 eq.) in DCM (30 mL) were added diisopropylamine (1.2 eq., 2.42 mL, 17.1 mmol), $Boc_2O$ (1.2 eq., 3.73 g, 17.1 mmol) and DMAP (0.1 eq., 0.170 g, 1.42 mmol) at room temperature. The resulting mixture was stirred at room temperature for 19 h. The reaction mixture was diluted with water (50 mL) and extracted with DCM (2×50 mL). The combined organic layers were washed with brine (25 mL), dried over $Na_2SO_4$, filtered and concentrated under reduced pressure. The resulting yellow oil was purified twice by silica gel flash chromatography ($1^{st}$ flash chromatography: 120 g, gradient: cyclohexane/EtOAc from 100:0 to 80:20; $2^{nd}$ flash chromatography: 40 g, gradient: cyclohexane/DCM from 80:20 to 0:100, then DCM/EtOAC from 100:0 to 80:20) to afford H1-2-3 as a colorless oil (1.99 g, 40% over 2 steps).

LC/MS (AN01_001_012): Rt=2.65 min, 100%, $[M-C_4H_8+H]$=216.2.

Ethyl 2-{[(but-3-en-1-yl) [(tert-butoxy) carbonyl] amino]methyl}pent-4-enoate H1-2-4

H1-2-4

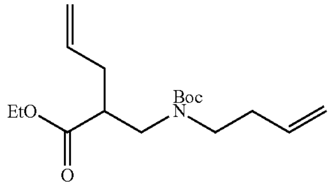

To an argon-purged solution of H1-2-3 (1 eq., 1.99 g, 7.33 mmol) in THF (20 mL) was added a 1M LiHMDS solution in THF (1.1 eq., 8.07 mL, 8.07 mmol) dropwise at −78° C. The resulting mixture was stirred at −78° C. for 1 h before the dropwise addition of allyl iodide (1.1 eq., 0.740 mL, 8.07 mmol). The resulting mixture was allowed to warm to room temperature and stirred for 15 h. The reaction mixture was cooled to −78° C. and a 1M LiHMDS solution in THF (0.2 eq., 1.47 mL, 1.47 mmol) was added dropwise at −78° C. The reaction was stirred at this temperature for 30 min before the dropwise addition of allyl iodide (0.2 eq., 0.135 mL, 1.47 mmol). The resulting mixture was allowed to warm to room temperature and stirred for 3 h. The reaction mixture was diluted with water (100 mL) and extracted with EtOAc (3×100 mL). The combined organic layers were washed with brine (100 mL), dried over $Na_2SO_4$, filtered and concentrated under reduced pressure. The resulting orange oil was purified by silica gel flash chromatography (80 g, gradient: cyclohexane/EtOAc from 100:0 to 80:20) to afford H1-2-4 as a yellow oil (1.62 g, 71%).

LC/MS (AN01_001_012): Rt=2.85 min, 100%, $[M-C_5H_8O_2+H]^+$=212.2.

1-tert-butyl 3-ethyl 1,2,3,4,7,8-hexahydroazocine-1,3-dicarboxylate H1-2-5

H1-2-5

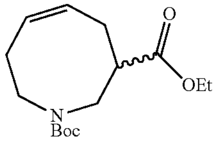

To an argon-purged solution of H1-2-4 (1 eq., 1.20 g, 3.85 mmol) in DCM (200 mL) was added benzylidene-bis(tricyclohexylphosphine)dichlororuthenium (0.1 eq., 0.318 g, 0.385 mmol) at room temperature. The resulting mixture was stirred and refluxed for 7 h. The reaction mixture was cooled to room temperature and concentrated under reduced pressure. The resulting black oil was purified by silica gel flash chromatography (80 g, gradient: cyclohexane/EtOAc from 100:0 to 80:20) to afford H1-2-5 as a black oil (0.613 g, 56%). LC/MS (AN01_001_012): Rt=2.67 min, 81%, $[M-C_4H_8+H]^+$=228.1.

1-tert-butyl 3-ethyl azocane-1,3-dicarboxylate H1-2-6

H1-2-6

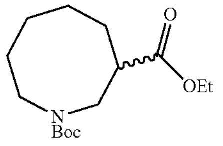

To an argon-purged solution of H1-2-5 (1 eq., 0.350 g, 1.24 mmol) in EtOH (6 mL) was added 10% Pd/C (0.2 eq., 0.263 g, 0.247 mmol) at room temperature. The resulting mixture was purged with argon (×3) and then with $H_2$ (3×). The reaction mixture was stirred under an atmospheric pressure of $H_2$ at room temperature for 19 h. The reaction mixture was purged with argon, filtered on a pad of celite and rinsed with EtOH (2×15 mL). The filtrate was concentrated under reduced pressure to afford H1-2-6 as a yellow oil (0.323 g, 92%).

LC/MS (AN01_001_012): Rt=2.73 min, non-UV active, $[M-C_4H_8+H]^+$=230.1.

1-[(tert-butoxy) carbonyl]azocane-3-carboxylic acid H1-2-7

H1-2-7

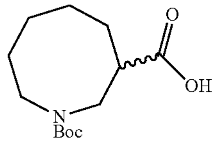

To a solution of H1-2-6 (1 eq., 0.323 g, 1.13 mmol) in THF (11 mL) was added a solution of LiOH (5 eq., 0.237 g, 5.66 mmol) in water (5.5 mL) at room temperature. The reaction mixture was stirred at room temperature for 19 h. The reaction mixture was poured dropwise into a stirred mixture of a 1M HCl aqueous solution (50 mL) and DCM (100 mL) at 0° C. The resulting mixture was stirred for 1 h (pH ~1) and the layers were separated. The aqueous layer was extracted with DCM (2×50 mL) and the combined organic layers were dried over $Na_2SO_4$, filtered and concentrated under reduced pressure to afford H1-2-7 as a yellow oil (0.291 g, 100%).

LC/MS (AN01_001_012): Rt=2.29 min, non-UV active, $[M+Na]^+$=280.2.

tert-butyl-3-{[(1S)-1-cyano-2-[4-(3-methyl-2-oxo-2,3-dihydro-1,3-benzoxazol-5-yl)phenyl]ethyl]carbamoyl}-azocane-1-carboxylate H1-2-8 (mixture of diastereomers)

H1-2-8

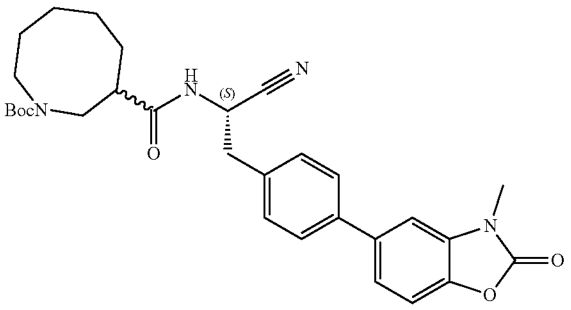

(mixture of diastereomers)

Starting from BB01 (1 eq., 0.150 g, 0.455 mmol) and H1-2-7 (1.05 eq., 0.145 g, 0.477 mmol), using general procedure C, H1-2-8 was obtained as a yellow gum (0.130 g, 54%) after purification by silica gel flash chromatography (25 g, cyclohexane/EtOAc from 100:0 to 50:50).

LC/MS (AN01_001_012): Rt=2.64 min, 100%, $[M+H]^+$=533.3.

N-[(1S)-1-cyano-2-[4-(3-methyl-2-oxo-2,3-dihydro-1,3-benzoxazol-5-yl)phenyl]ethyl]azocane-3-carboxamide Compound 1-A (mixture of diastereomers)

Compound 1-A

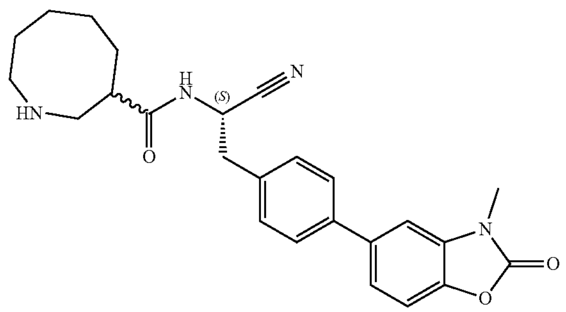

(mixture of diastereomers)

Starting from H1-2-8 (1 eq., 0.113 g, 0.212 mmol), using general procedure D, Compound 1-A was obtained as a white solid (35.4 mg, 39%) after purification by silica gel flash chromatography (12 g, DCM/MeOH from 100:0 to 80:20) and freeze-drying.

LC/MS (AN01_001_026): Rt=7.29 min, 97.8%, $[M+H]^+$=433.4.

$^1H$ NMR (DMSO-$d_6$, 400 MHZ): δ ppm 8.79-8.60 (m, 1H), 7.66 (dd, J=8.2, 2.9 Hz, 2H), 7.58-7.55 (m, 1H), 7.43-7.38 (m, 4H), 5.00-4.92 (m, 1H), 3.40 (s, 3H), 3.18-3.05 (m, 2H), 2.92-2.67 (m, 4H), 2.60-2.54 (m, 1H), 2.46-2.41 (m, 1H), 1.75-1.35 (m, 8H).

Example 4: Synthesis of(S)—N—((S)-1-cyano-2-(4-(3-methyl-2-oxo-2,3-dihydrobenzo[d]oxazol-5-yl) phenyl)ethyl)-1,4-oxazocane-2-carboxamide (Compound 4)

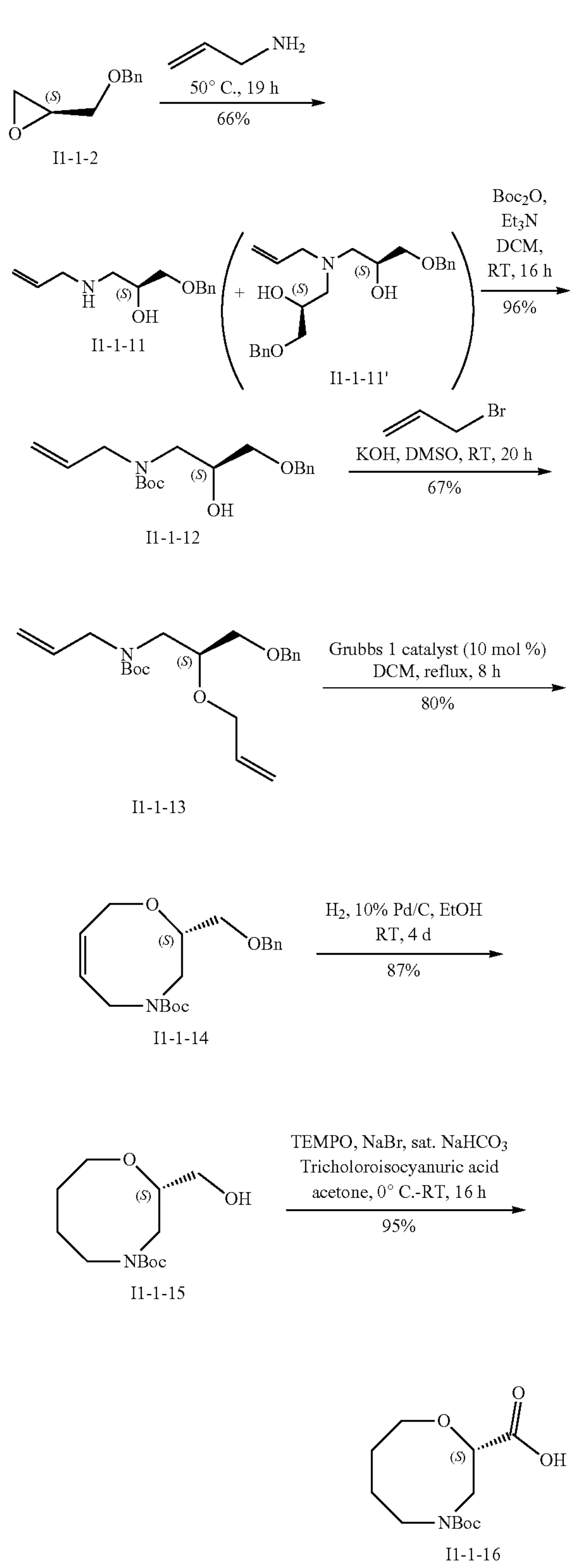

-continued

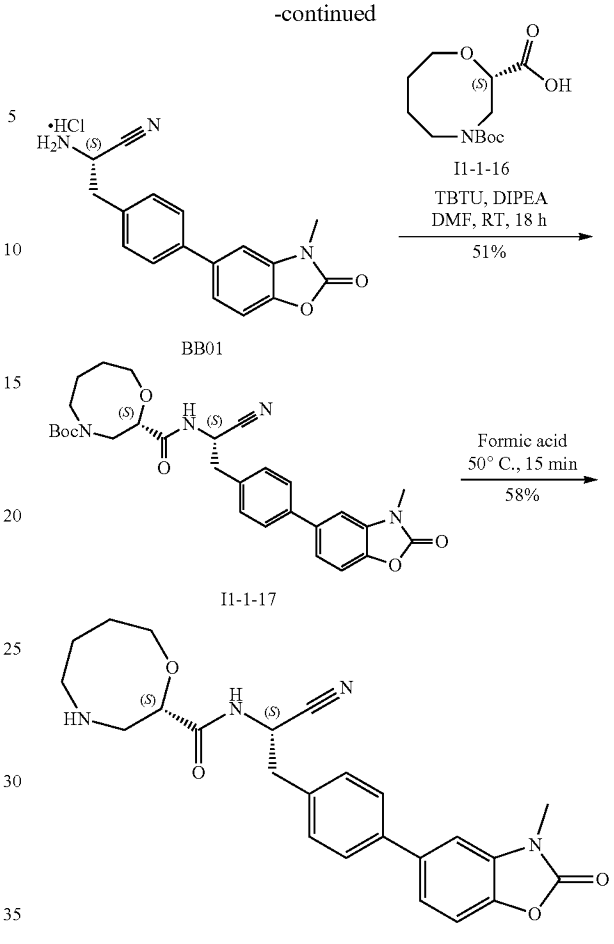

Compound 4

[(2S)-3-(benzyloxy)-2-hydroxypropyl](prop-2-en-1-yl)amine I1-1-11

To I-1-2 (1 eq., 10 g, 9.26 mL, 60.9 mmol) was added allylamine (17.55 eq., 61.04 g, 80 mL, 1069.077 mmol) and the resulting mixture was stirred at 50° C. for 19 h. The reaction mixture was concentrated to dryness under reduced pressure affording Nov. 1, 2011 (13.5 g, 66%) as a yellow oil contaminated by 23% of I1-1-11.

LC/MS (AN01_001_012): Rt=1.57 min, 91.2%, $[M+H]^+$=222.1.

$^1$H NMR (400 MHZ, DMSO) δ 7.58-7.07 (m, 5H), 5.83 (ddt, J=17.2, 10.2, 5.7 Hz, 1H), 5.14 (dq, J=17.2, 1.8 Hz, 1H), 5.02 (ddt, J=10.3, 2.5, 1.4 Hz, 1H), 4.72 (s, 1H), 4.48 (s, 2H), 3.71 (m, 1H), 3.47-3.25 (m, 2H), 3.14 (dt, J=5.7, 1.6 Hz, 2H), 2.57 (dd, J=11.8, 4.5 Hz, 1H), 2.45 (dd, J=11.8, 7.2 Hz, 1H), 1.67 (s, 1H).

tert-butyl N-[(2S)-3-(benzyloxy)-2-hydroxypropyl]-N-(prop-2-en-1-yl) carbamate I1-1-12

Starting from I1-1-11 (1 eq., 2.6 g, 7.52 mmol) (containing ~75% mol of I1-1-11 and ~25% mol of I1-1-11') and using general procedure G, Nov. 1, 2012 was obtained as a yellowish oil (2.32 g, 96%) after purification by flash chromatography over silica gel (irregular SiOH, 50 μm, 80 g Interchim, dry loading (silica), mobile phase gradient: DCM/MeOH from 100/0 to 95/5 over 30 min) and co-evaporation with DCM.

LC/MS (AN01_001_012): Rt=2.56 min, 100%, [M−Boc+H]$^+$=222.1.

$^1$H NMR (400 MHZ, DMSO) δ 7.39-7.23 (m, 5H), 5.73 (s, 1H), 5.21-4.95 (m, 2H), 4.88 (s, 1H), 4.48 (s, 2H), 4.02-3.66 (m, 3H), 3.38-3.20 (m, 3H), 2.97 (s, 1H), 1.36 (s, 9H).

tert-butyl N-[(2S)-3-(benzyloxy)-2-(prop-2-en-1-yloxy)propyl]-N-(prop-2-en-1-yl) carbamate I1-1-13

To an argon-purged solution of I1-1-12 (1 eq., 3 g, 9.33 mmol) in DMSO (12 mL) were added KOH (2 eq., 1.047 g, 18.67 mmol) and allyl bromide (3 eq., 3.39 g, 2.44 mL, 28.001 mmol) at RT. The resulting mixture was stirred at RT for 20 h. The reaction mixture was diluted with water (200 mL) and extracted with EtOAc (2×200 mL). The combined organic layers were washed with brine (2×100 mL), dried over $Na_2SO_4$, filtered and concentrated to dryness under reduced pressure affording crude (2.26 g) as a yellow oil. The crude was purified by flash chromatography over silica gel (irregular SiOH, 50 μm, 80 g Interchim, dry loading (silica), mobile phase gradient: cyclohexane/EtOAc from 100/0 to 85/15 over 25 min). The fractions containing compound were combined, evaporated in vacuo and co-evaporated with DCM affording I1-1-13 (2.26 g, 6.25 mmol, 66.98%) as a yellowish oil.

LC/MS (AN01_001_012): Rt=2.90 min, 100%, [M−Boc+H]$^+$=262.2.

$^1$H NMR (400 MHZ, DMSO) δ 7.47-7.18 (m, 5H), 5.85 (ddt, J=17.2, 10.5, 5.3 Hz, 1H), 5.73 (s, 1H), 5.24 (dq, J=17.3, 1.9 Hz, 1H), 5.17-4.97 (m, 3H), 4.49 (s, 2H), 4.09 (ddt, J=13.4, 5.1, 1.7 Hz, 1H), 3.99 (ddt, J=13.4, 5.5, 1.6 Hz, 1H), 3.75-3.85 (m, 2H), 3.72-3.61 (m, 1H), 3.48 (dd, J=10.6, 4.0 Hz, 1H), 3.42 (dd, J=10.6, 5.4 Hz, 1H), 3.26 (s, 1H), 3.15 (dd, J=14.4, 7.0 Hz, 1H), 1.37 (s, 9H).

tert-butyl (2S)-2-[(benzyloxy)methyl]-3,4,5,8-tetrahydro-2H-1,4-oxazocine-4-carboxylate I1-1-14

Starting from Nov. 1, 2013 (1 eq., 0.58 g, 1.59 mmol) and using general procedure H, I1-1-14 was obtained as a black gum (0.42 g, 80%) after purification by flash chromatography over silica gel (irregular SiOH, 50 μm, 25 g Interchim, dry loading (silica), mobile phase gradient: cyclohexane/EtOAc from 100/0 to 80/20 over 35 min) and co-evaporation with DCM.

LC/MS (AN01_001_012): Rt=2.72 min, 100%, [M−Boc+H]$^+$=234.1.

$^1$H NMR (400 MHZ, DMSO) δ 7.60-7.08 (m, 5H), 5.89-5.63 (m, 1H), 5.62-5.44 (m, 1H), 4.57-4.35 (m, 3H), 4.12-3.67 (m, 4H), 3.62-3.40 (m, 2H), 3.37 (dd, J=10.2, 6.0 Hz, 1H), 2.81 (ddd, J=64.1, 14.3, 9.4 Hz, 1H), 1.45-1.32 (m, 9H).

tert-butyl (2S)-2-(hydroxymethyl)-1,4-oxazocane-4-carboxylate IJan. 1, 2015

Starting from Nov. 1, 2014 (1 eq., 94 mg, 0.28 mmol) and using general procedure D, I1-1-15 was obtained as a yellowish gum (60 mg, 87%).

LC/MS (AN01_001_012): Rt=2.06 min, 100%, [M−Boc+H]$^+$=144.0.

$^1$H NMR (400 MHZ, DMSO) δ 4.75-4.44 (m, 1H), 3.97-3.56 (m, 3H), 3.52-3.27 (m, 3H), 3.26-3.15 (m, 1H), 3.02 (ddd, J=14.3, 11.1, 5.5 Hz, 1H), 2.53 (ddd, J=54.4, 14.4, 9.7 Hz, 1H), 1.96-1.76 (m, 1H), 1.69-1.42 (m, 3H), 1.40 (d, J=1.2 Hz, 9H).

(2S)-4-[(tert-butoxy) carbonyl]-1,4-oxazocane-2-carboxylic acid IJan. 1, 2016

Starting from Nov. 1, 2015 (1 eq., 60 mg, 0.24 mmol) and using general procedure E, IJan. 1, 2016 was obtained as a white solid (60.3 mg, 95%).

LC/MS (AN01_001_012): Rt=2.08 min, 65.5%, [M−H]−=258.0.

$^1$H NMR (400 MHZ, DMSO) § 12.63 (s, 1H), 4.12-3.75 (m, 3H), 3.68-3.44 (m, 2H), 3.12-2.73 (m, 2H), 1.94-1.76 (m, 1H), 1.68-1.45 (m, 3H), 1.41 (s, 9H).

tert-butyl (2S)-2-{[(1S)-1-cyano-2-[4-(3-methyl-2-oxo-2,3-dihydro-1,3-benzoxazol-5-yl)phenyl]ethyl]carbamoyl}-1,4-oxazocane-4-carboxylate I1-1-17

Starting from BB01 (1 eq., 72.67 mg, 0.22 mmol) and IJan. 1, 2016 (1.05 eq., 60 mg, 0.23 mmol), using general procedure B, I1-1-17 was obtained as an orange gum (60.2 mg, 51%) after purification by flash chromatography over silica gel (irregular SiOH, 50 μm, 12 g Interchim, dry loading (silica), mobile phase gradient: cyclohexane/EtOAc from 100/0 to 50/50 over 30 min) and co-evaporation with DCM.

LC/MS (AN01_001_012): Rt=2.58 min, 92.8%, [M−Boc+H]$^+$=435.1.

$^1$H NMR (400 MHZ, DMSO) δ 8.77 (d, J=8.7 Hz, 1H), 7.66 (dt, J=8.5, 2.0 Hz, 2H), 7.56 (s, 1H), 7.44-7.32 (m, 4H), 5.01 (p, J=7.9 Hz, 1H), 4.03-3.84 (m, 3H), 3.58 (s, 2H), 3.40 (s, 3H), 3.25-3.12 (m, 2H), 2.98 (ddd, J=42.9, 15.6, 5.2 Hz, 1H), 2.59-2.38 (m, 1H), 1.94-1.81 (m, 1H), 1.72-1.44 (m, 3H), 1.38 (s, 9H)

(2S)—N-[(1S)-1-cyano-2-[4-(3-methyl-2-oxo-2,3-dihydro-1,3-benzoxazol-5-yl)phenyl]ethyl]-1,4-oxazocane-2-carboxamide Starting from I1-1-17 (1 eq., 73.3 mg, 0.11 mmol) and using general procedure C, (2S)—N-[(1S)-1-cyano-2-[4-(3-methyl-2-oxo-2,3-dihydro-1,3-benzoxazol-5-yl)phenyl]ethyl]-1,4-oxazocane-2-carboxamide was obtained as a white solid (28.6 mg, 58%) after purification by flash chromatography over silica gel (regular SiOH, 15 μm, 12 g Interchim, dry loading (silica), mobile phase gradient: DCM/MeOH from 100/0 to 90/10 over 40 min), co-evaporation with DCM and freeze-drying using a mixture of ACN/water (1:10).

LC/MS (AN_01_001_021_DEDL): Rt=7.07 min, 99.6%, [M+H]$^+$=435.4.

$^1$H NMR (400 MHZ, DMSO) δ 8.64 (d, J=8.6 Hz, 1H), 7.72-7.60 (m, 2H), 7.57 (dd, J=1.6, 0.8 Hz, 1H), 7.45-7.30 (m, 4H), 5.00 (td, J=8.6, 7.3 Hz, 1H), 3.95 (td, J=9.1, 4.9 Hz, 1H), 3.89 (dd, J=9.6, 3.0 Hz, 1H), 3.65 (ddd, J=11.7, 6.2, 3.9 Hz, 1H), 3.40 (s, 3H), 3.25-3.12 (m, 2H), 2.98 (dd, J=14.0, 3.1 Hz, 1H), 2.93 (dt, J=5.0, 4.5 Hz, 1H), 2.62 (ddd, J=13.5, 8.5, 4.7 Hz, 1H), 2.27 (dd, J=14.0, 9.7 Hz, 1H), 1.94-1.80 (m, 1H), 1.64-1.45 (m, 3H), one missing proton (NH).

Example 5: Synthesis of (7S)—N—((S)-1-cyano-2-(4-(3-methyl-2-oxo-2,3-dihydrobenzo[d]oxazol-5-yl) phenyl)ethyl)-1,6-dioxa-9-azaspiro[3.6]decane-7-carboxamide (Compound 5)

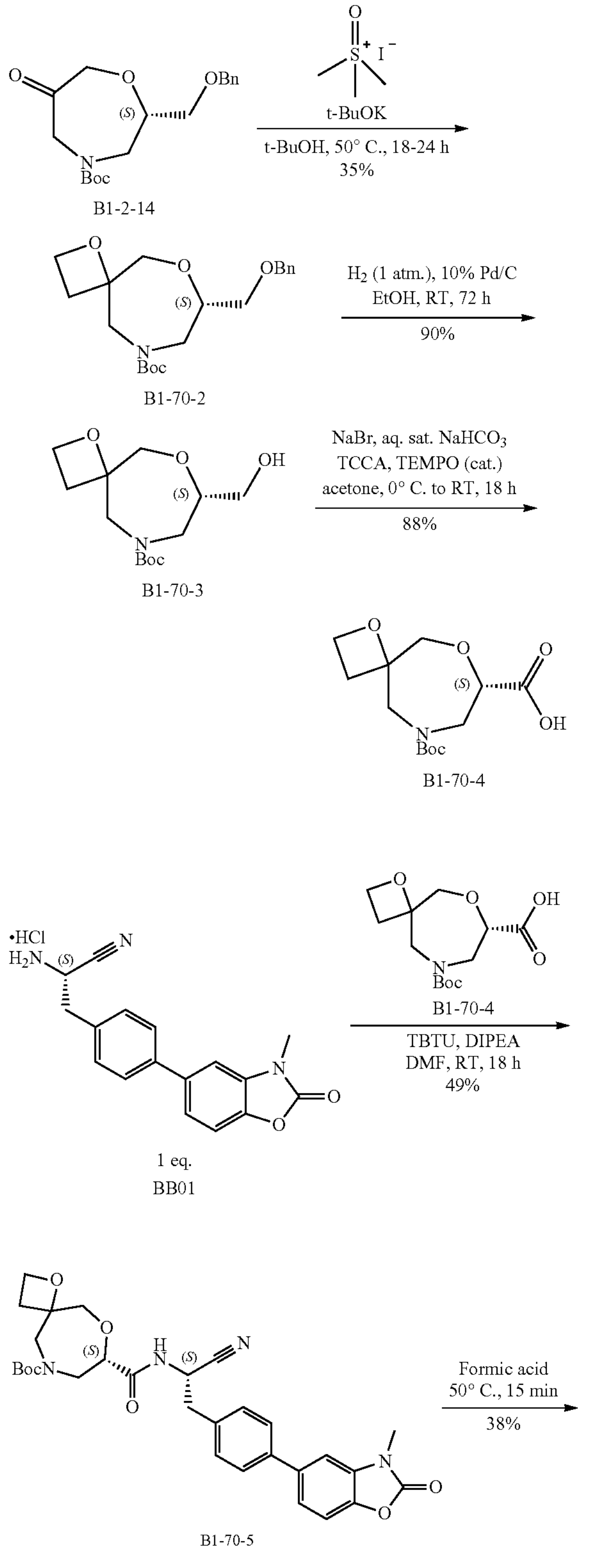

-continued

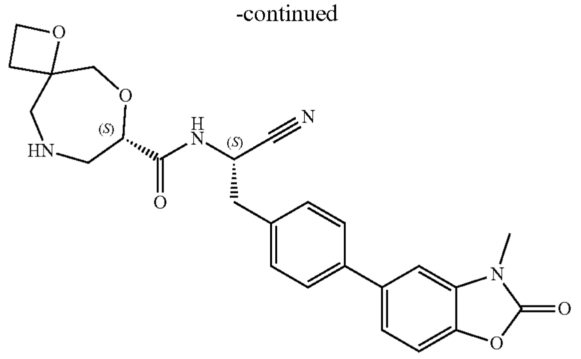

Compound 5 tert-butyl (7S)-7-[(benzyloxy)methyl]-1,6-dioxa-9-azaspiro[3.6]decane-9-carboxylate B1-70-2

To a solution of potassium tert-butoxide (2 eq., 162.6 mg, 1.45 mmol) in tert-butanol (2.43 mL) was added trimethylsulfoxonium iodide (2 eq., 318.88 mg, 1.45 mmol) at room temperature. The reaction mixture was stirred at 50° C. for 30 minutes. I1-2-14 (preparation previously described) (1 eq., 243 mg, 0.72 mmol) in tert-butanol (1.46 mL) was added and the reaction mixture was stirred for 18 h. The reaction mixture was quenched with water (25 mL) and extracted with EtOAc (3×25 mL). The combined organic layer was dried over $Na_2SO_4$, filtered and concentrated under reduced pressure. The crude was purified by flash chromatography over silica gel (50 μm, 12 g, Cyclohexane/EtOAc from 100/0 to 70/30 over 35 min) to afford B1-70-2 (92 mg, 35%) as a colorless oil.

LC/MS (AN01_001_012): Rt=2.61 min, 90.5%, $[M-Boc+H]^+$=264.6.

$^1H$ NMR (400 MHZ, DMSO) δ 7.40-7.24 (m, 5H), 4.48 (s, 2H), 4.41-4.29 (m, 2H), 4.30-3.89 (m, 2H), 3.79-3.57 (m, 2H), 3.49-3.44 (m, 1H), 3.46-3.40 (m, 1H), 3.36 (ddd, J=10.4, 7.6, 5.1 Hz, 1H), 3.14-2.56 (m, 2H), 2.47-2.17 (m, 2H), 1.46-1.31 (m, 9H).

tert-butyl (7S)-7-(hydroxymethyl)-1,6-dioxa-9-azaspiro[3.6]decane-9-carboxylate B1-70-3

Starting from B1-70-2 (1 eq., 130 mg, 0.36 mmol) and using general procedure D, B1-70-3 was obtained as a colorless oil (88 mg, 90%).

LC/MS (AN01_001_012): Rt=1.93 min, ND, $[M-Boc+H]^+$=174.2.

$^1H$ NMR (400 MHZ, DMSO) δ 4.74-4.67 (m, 1H), 4.39-4.27 (m, 2H), 4.27-3.93 (m, 2H), 3.89-3.55 (m, 2H), 3.50-3.33 (m, 2H), 3.30-3.21 (m, 1H), 3.13-2.58 (m, 2H), 2.46-2.20 (m, 2H), 1.59-1.21 (m, 9H).

(7S)-9-[(tert-butoxy) carbonyl]-1,6-dioxa-9-azaspiro [3.6]decane-7-carboxylic acid B1-70-4

Starting from B1-70-3 (1 eq., 130 mg, 0.36 mmol) and using general procedure E, B1-70-4 was obtained as a white solid (74.4 mg, 88%).

LC/MS (AN01_001_012): Rt=1.90 min, ND, $[M-Boc+H]^+$=188.1.

$^1H$ NMR (400 MHZ, DMSO) & 12.77 (s, 1H), 4.35 (t, J=7.8 Hz, 2H), 4.28-3.91 (m, 4H), 3.83-3.44 (m, 2H), 3.24-2.96 (m, 1H), 2.70-2.26 (m, 2H), 1.49-1.29 (m, 9H).

tert-butyl (7S)-7-{[(1S)-1-cyano-2-[4-(3-methyl-2-oxo-2,3-dihydro-1,3-benzoxazol-5-yl)phenyl]ethyl]carbamoyl}-1,6-dioxa-9-azaspiro[3.6]decane-9-carboxylate B1-70-57

Starting from BB01 (1 eq., 71.055 mg, 0.22 mmol) and B1-70-4 (1.05 eq., 65 mg, 0.23 mmol), using general procedure B, B1-70-5 was obtained as an orange solid (59 mg, 49%) after purification by flash chromatography over silica gel (50 μm, 12 g, cyclohexane/EtOAc from 80:20 to 20:80 over 45 min). A diastereomeric ratio of 65:35 was determined by LC/MS and $^1H$ NMR.

LC/MS (AN01_001_021_DEDL): Rt=9.33 min, 90.9%, $[M-{}^tBu+H]^+$=507.4.

$^1H$ NMR (400 MHZ, DMSO) δ 8.81 (dd, J=21.1, 8.4 Hz, 1H), 7.74-7.61 (m, 2H), 7.62-7.52 (m, 1H), 7.47-7.30 (m, 4H), 5.02 (q, J=8.1 Hz, 1H), 4.46-4.27 (m, 2H), 4.33-3.74 (m, 5H), 3.67-3.34 (m, 4H), 3.27-2.95 (m, 3H), 2.91-2.58 (m, 1H), 2.42 (t, J=7.9 Hz, 1H), 1.50-1.28 (m, 9H).

(7S)—N-[(1S)-1-cyano-2-[4-(3-methyl-2-oxo-2,3-dihydro-1,3-benzoxazol-5-yl)phenyl]ethyl]-1,6-dioxa-9-azaspiro[3.6]decane-7-carboxamide Starting from B1-70-5 (1 eq., 50 mg, 0.089 mmol) and using general procedure C, (7S)—N-[(1S)-1-cyano-2-[4-(3-methyl-2-oxo-2,3-dihydro-1,3-benzoxazol-5-yl)phenyl]ethyl]-1,6-dioxa-9-azaspiro[3.6]decane-7-carboxamide was obtained as a white solid (15.6 mg, 38%) after purification by flash chromatography over silica gel (15 μm, 4 g, DCM/MeOH from 100:0 to 95:05 over 40 min). A diastereomeric ratio of 65:35 was determined by LC/MS and 1H NMR.

LC/MS (AN_01_001_021_DEDL): Rt=6.98 & 7.07 min, 98.7%, $[M+H]^+$=463.4.

$^1H$ NMR (400 MHZ, DMSO) δ 8.63 (dd, J=11.2, 8.5 Hz, 1H), 7.71-7.61 (m, 2H), 7.57 (s, 1H), 7.46-7.32 (m, 4H), 5.08-4.94 (m, 1H), 4.39-4.25 (m, 2H), 4.09 (dd, J=75.9, 13.2 Hz, 1H), 3.92 (ddd, J=10.3, 6.3, 3.7 Hz, 1H), 3.75 (dd, J=34.9, 13.2 Hz, 1H), 3.40 (s, 3H), 3.26-3.13 (m, 3H), 3.14-3.00 (m, 1H), 2.74 (dd, J=15.6, 14.0 Hz, 1H), 2.48-2.21 (m, 4H).

Example 6: Preparation of (2S,6R)—N—((S)-1-cyano-2-(4-(3-methyl-2-oxo-2,3-dihydrobenzo[d]oxazol-5-yl)phenyl)ethyl)-6-ethyl-6-hydroxy-1,4-oxazepane-2-carboxamide (Compound 6)

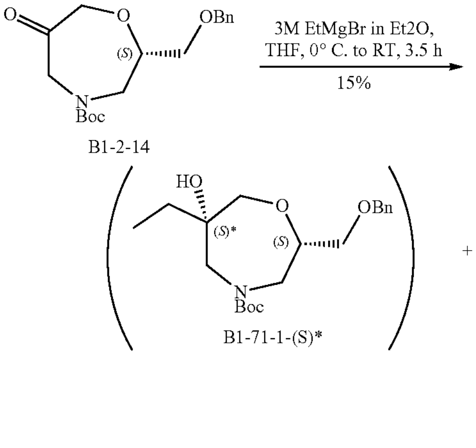

B1-2-14

B1-71-1-(S)*

+

-continued

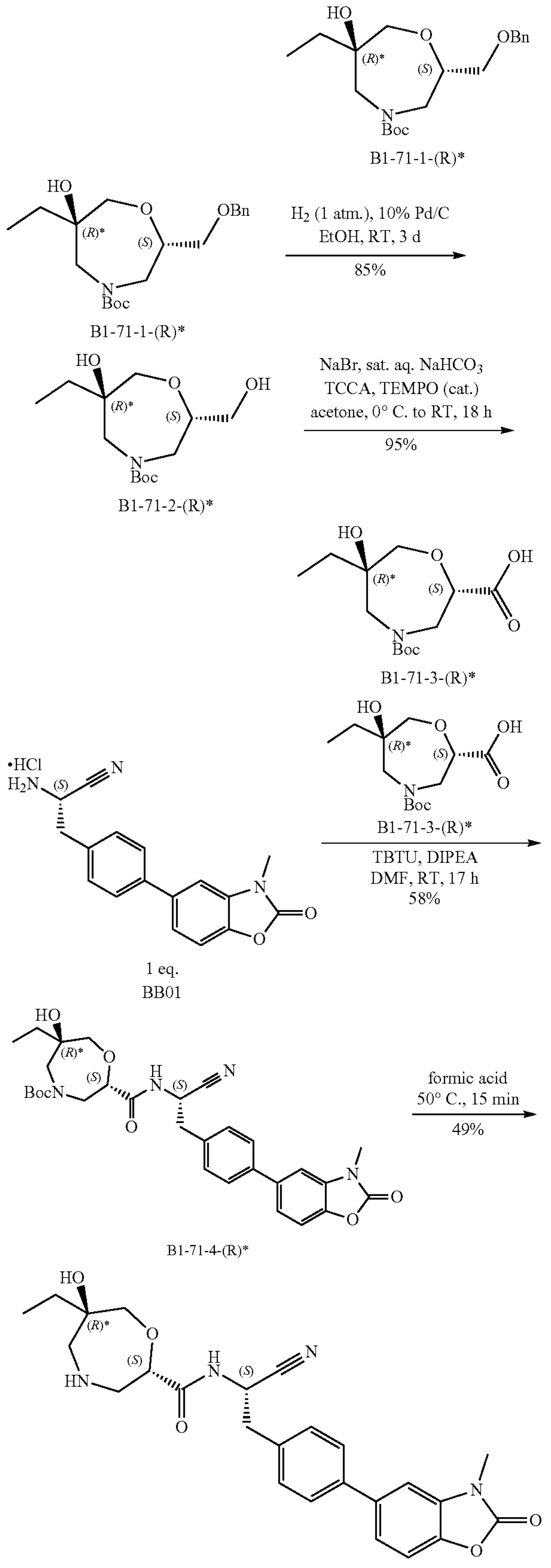

B1-71-1-(R)*

B1-71-1-(R)*

B1-71-2-(R)*

B1-71-3-(R)*

B1-71-3-(R)*

1 eq.
BB01

B1-71-4-(R)*

Compound 6 tert-butyl (2S,6R*)-2-[(benzyloxy)methyl]-6-ethyl-6-hydroxy-1,4-oxazepane-4-carboxylate B1-71-1-(R)*

To a solution of I1-2-14 (previously described) (1 eq., 992 mg, 2.96 mmol) in THF (28 mL) was added 3M Ethylmagnesium bromide in $Et_{20}$ (2.5 eq., 2.46 mL, 7.39 mmol) at 0° C. The reaction mixture was allowed to warm to room temperature and stirred for 2.5 h. The reaction mixture was cooled to 0° C. and additional 3M Ethylmagnesium bromide in $Et_{20}$ (0.8 eq., 0.79 mL, 2.37 mmol) was introduced dropwise. The resulting mixture was allowed to warm to room temperature and stirred for 1 h. The reaction mixture was quenched with a sat. aq. $NH_4Cl$ solution (75 mL) and diluted with EtOAc (100 mL). The layers were separated, and the aqueous layer was extracted with EtOAc (3×75 mL). The combined organic layers were washed with brine (150 mL), dried over $Na_2SO_4$, filtered and concentrated under reduced pressure. The crude was purified by flash chromatography over silica gel (15 μm, 40 g, Cyclohexane/EtOAc from 100:0 to 70:30 over 50 min, revealed with PMA) to afford impure B1-71-1-(R)* which was repurified by flash chromatography over silica gel (15 μm, 40 g, Cyclohexane/EtO Ac from 100:0 to 60:40 over 55 min, revealed with PMA) to afford B1-71-1-(R)* as a colorless oil (160 mg, 15%).

LC/MS (AN01_001_012): Rt=2.51 min, 100%, [M–Boc+H]$^+$=266.2.

$^1$H NMR (400 MHZ, DMSO) δ 7.39-7.23 (m, 5H), 4.48 (s, 2H), 4.34 (d, J=30.5 Hz, 1H), 3.76 (s, 1H), 3.60-3.33 (m, 5H), 3.25 (dd, J=15.5, 4.1 Hz, 2H), 3.19 (d, J=14.2 Hz, 1H), 1.47-1.33 (m, 11H), 0.85 (t, J=7.4 Hz, 3H).

tert-butyl (2S,6R*)-6-ethyl-6-hydroxy-2-(hydroxymethyl)-1,4-oxazepane-4-carboxylate B1-71-2-(R)*

Starting from B1-71-1-(R)* (1 eq., 212 mg, 0.58 mmol) and using general procedure D, B1-71-2-(R)* was obtained as a colorless oil (135 mg, 85%).

LC/MS (AN01_001_012): Rt=1.93 min, ND, [M–$^t$Bu+H]$^+$=220.1.

$^1$H NMR (400 MHZ, DMSO) & 4.69 (d, J=5.5 Hz, 1H), 4.40 (d, J=15.9 Hz, 1H), 4.01 (d, J=13.9 Hz, 1H), 3.79 (d, J=13.9 Hz, 1H), 3.65 (d, J=12.9 Hz, 1H), 3.56-3.37 (m, 2H), 3.35-3.27 (m, 1H), 3.23 (d, J=12.9 Hz, 1H), 3.17 (d, J=4.8 Hz, 1H), 2.99-2.70 (m, 2H), 1.42-1.20 (m, 10H), 0.85 (t, J=7.3 Hz, 3H).

(2S,6R*)-4-[(tert-butoxy) carbonyl]-6-ethyl-6-hydroxy-1,4-oxazepane-2-carboxylic acid B1-71-3-(R)*

Starting from B1-71-2-(R)* (1 eq., 129 mg, 0.47 mmol) and using general procedure E, B1-71-3-(R)* was obtained as a white solid (129 mg, 95%).

LC/MS (AN01_001_012): Rt=2.35 min, ND, [M–$^t$Bu+H]$^+$=234.0.

$^1$H NMR (400 MHZ, DMSO) § 12.79 (s, 1H), 4.52 (s, 1H), 4.23-4.14 (m, 1H), 4.11 (dd, J=14.1, 5.1 Hz, 1H), 3.77 (dd, J=20.0, 13.6 Hz, 1H), 3.64 (t, J=13.1 Hz, 1H), 3.42-3.04 (m, 2H), 2.74 (dd, J=17.7, 13.8 Hz, 1H), 1.40 (d, J=6.1 Hz, 11H), 0.92-0.77 (m, 3H).

tert-butyl (2S,6R*)-2-{[(1S)-1-cyano-2-[4-(3-methyl-2-oxo-2,3-dihydro-1,3-benzoxazol-5-yl)phenyl]ethyl]carbamoyl}-6-ethyl-6-hydroxy-1,4-oxazepane-4-carboxylate B1-71-4-(R)*

Starting from BB01 (1 eq., 135.69 mg, 0.41 mmol) and B1-71-3-(R)* (1.05 eq., 125 mg, 0.43 mmol) and using general procedure B, B1-71-4-(R)* was obtained as a light yellow solid (134 mg, 58%) after purification by flash chromatography over silica gel (regular SiOH, 50 μm, 25 g, dry loading (silica), mobile phase gradient: Cyclo/EtOAc from 70/30 to 30/70 over 45 min) and co-evaporation with DCM.

LC/MS (AN01_001_012): Rt=2.51 min, 76.8%, [M–$^t$Bu+H]$^+$=509.7.

$^1$H NMR (400 MHZ, DMSO) § 8.88 (d, J=8.4 Hz, 1H), 7.70-7.62 (m, 2H), 7.57 (s, 1H), 7.45-7.35 (m, 4H), 5.03 (q, J=8.1 Hz, 1H), 4.58 (s, 1H), 4.18-4.10 (m, 1H), 4.06-3.87 (m, 1H), 3.74 (d, J=14.4 Hz, 1H), 3.61-3.42 (m, 2H), 3.40 (s, 3H), 3.18 (t, J=6.6 Hz, 2H), 2.99-2.85 (m, 1H), 2.74 (d, J=14.0 Hz, 1H), 1.38 (d, J=10.9 Hz, 11H), 0.87 (t, J=7.3 Hz, 3H).

(2S,6R*)—N-[(1S)-1-cyano-2-[4-(3-methyl-2-oxo-2,3-dihydro-1,3-benzoxazol-5-yl)phenyl]ethyl]-6-ethyl-6-hydroxy-1,4-oxazepane-2-carboxamide Starting from B1-71-4-(R)* (1 eq., 130 mg, 0.23 mmol) and using general procedure C, (2S,6R*)—N-[(1S)-1-cyano-2-[4-(3-methyl-2-oxo-2,3-dihydro-1,3-benzoxazol-5-yl)phenyl]ethyl]-6-ethyl-6-hydroxy-1,4-oxazepane-2-carboxamide was obtained as a white solid (52 mg, 49%) after purification by flash chromatography over silica gel (irregular SiOH, 50 μm, 12 g Interchim, dry loading (silica), mobile phase gradient: DCM/MeOH from 100/00 to 90/10 over 30 min), co-evaporation with DCM and vacuum drying at 40° C. for 24 h.

LC/MS (AN_01_001_021_DEDL): Rt=7.00 min, 99.1%, [M+H]$^+$=465.4.

$^1$H NMR (400 MHZ, DMSO) & 8.68 (d, J=8.5 Hz, 1H), 7.72-7.61 (m, 2H), 7.60-7.54 (m, 1H), 7.49-7.30 (m, 4H), 5.07-4.96 (m, 1H), 4.36 (s, 1H), 3.97 (dd, J=8.1, 5.0 Hz, 1H), 3.60 (d, J=12.7 Hz, 1H), 3.52 (d, J=12.7 Hz, 1H), 3.40 (s, 3H), 3.26-3.13 (m, 2H), 3.03 (dd, J=13.9, 5.1 Hz, 1H), 2.65 (d, J=13.5 Hz, 1H), 2.58-2.51 (m, 2H), 2.45 (d, J=13.5 Hz, 1H), 1.43-1.26 (m, 2H), 0.82 (t, J=7.5 Hz, 3H).

Example 7: Preparation of(S)—N—((S)-1-cyano-2-(4-(3-methyl-2-oxo-2,3-dihydrobenzo[d]oxazol-5-yl)phenyl)ethyl) azocane-3-carboxamide (Compound 7-A) and (R)—N—((S)-1-cyano-2-(4-(3-methyl-2-oxo-2,3-dihydrobenzo[d]oxazol-5-yl)phenyl)ethyl) azocane-3-carboxamide (Compound 7-B)

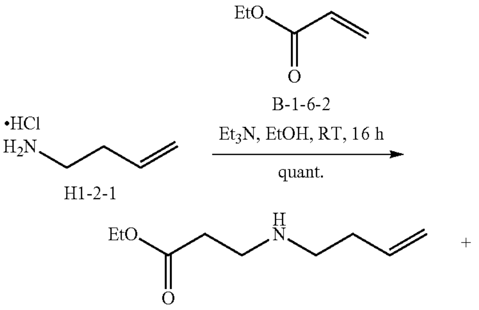

B-1-6-2

H1-2-1

H1-2-2

-continued

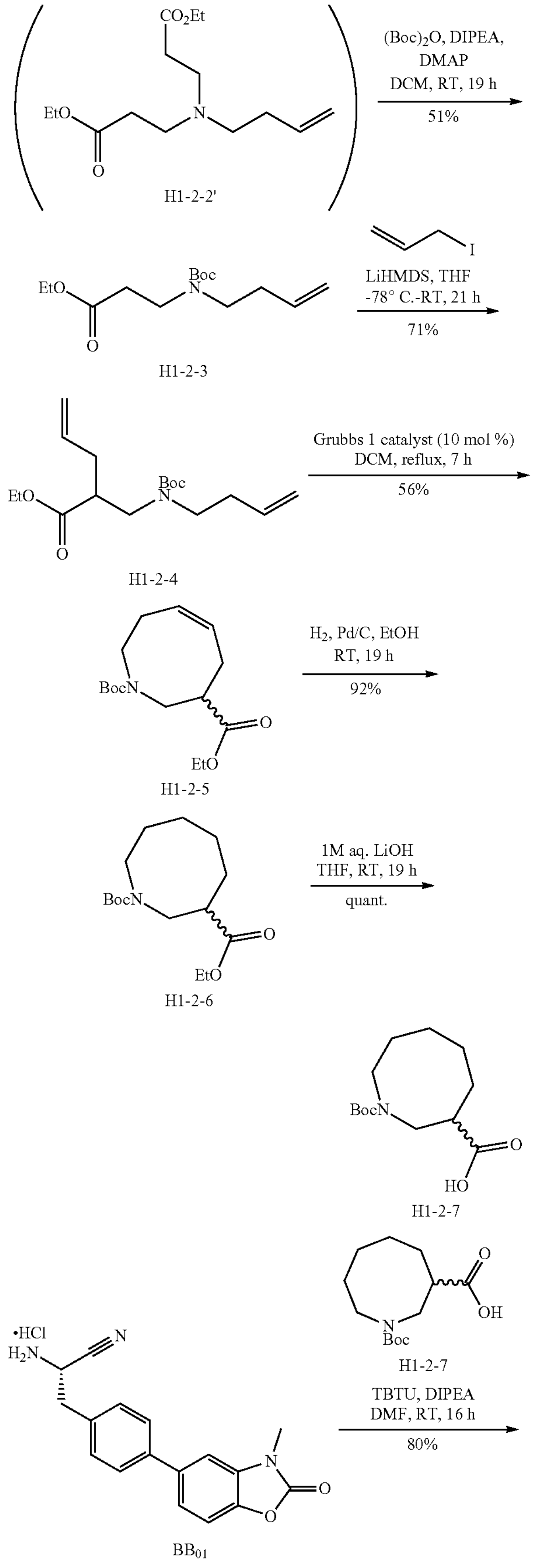

-continued

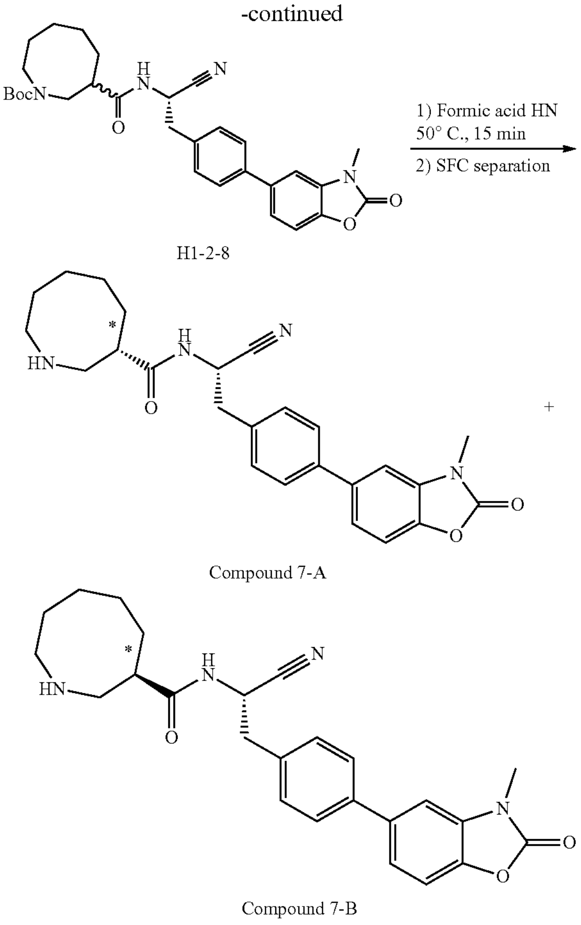

ethyl 3-[(but-3-en-1-yl)amino]propanoate H1-2-2

To an argon-purged solution of but-3-en-1-amine hydrochloride (1 eq., 1.99 g, 18.5 mmol) and triethylamine (1.05 eq., 1.97 g, 2.7 mL, 19.42 mmol) in EtOH (28 mL) was stirred at room temperature for 30 min. Then, ethyl acrylate (1 eq., 1.85 g, 2.013 mL, 18.5 mmol) was added and the resulting mixture was stirred at room temperature for 16 h. The reaction mixture was concentrated to dryness under reduced pressure to afford a 50:50 mixture of H1-2-2 and H1-2-2' (4.88 g, 18.5 mmol, quant.) as a colorless oil. The crude was used as such for the next step without further purification.

LC/MS (AN01_001_012): Rt=0.53 min, ND, $[M+H]^+$=172.1 ethyl 3-[(but-3-en-1-yl) [(tert-butoxy) carbonyl]amino]propanoate H1-2-3

To an argon-purged solution of H1-2-2 (1 eq., 4.88 g, 14.25 mmol) (containing ~50% mol of H1-2-2') in DCM (30 mL) were added diisopropylamine (1.2 eq., 1.73 g, 2.42 mL, 17.099 mmol), $Boc_2O$ (1.2 eq., 3.73 g, 3.66 mL, 17.099 mmol) and DMAP (0.1 eq., 0.17 g, 1.42 mmol) at room temperature. The resulting mixture was stirred for 19 h. The reaction mixture was diluted with water (50 mL) and extracted with DCM (2×50 mL). The combined organic layers were washed with brine (25 mL), dried over $Na_2SO_4$, filtered and concentrated to dryness under reduced pressure. The crude residue was purified by ELSD flash chromatographies over silica gel (1: irregular SiOH, 50 μm, 120 g Interchim, dry loading (silica), mobile phase gradient: cyclohexane/EtOAc from 100/0 to 80/20 over 45 min; 2: irregular SiOH, 50 μm, 40 g Interchim, dry loading (silica), mobile phase gradient: cyclohexane/DCM from 80/20 to 0/100 over 30 min then DCM/EtOAc from 100/0 to 80/20 over 20 min). The fractions containing the compound were combined, evaporated in vacuo and co-evaporated with DCM affording H1-2-3 (1.99 g, 7.33 mmol, 51% over 2 steps) as a colorless oil.

LC/MS (AN_01_001_012): Rt=2.64 min, 100%, $[M-Boc+H]^+$=172.1.

ethyl 2-{[(but-3-en-1-yl) [(tert-butoxy) carbonyl] amino]methyl}pent-4-enoate H1-2-4

To an argon-purged solution of H1-2-3 (1 eq., 1.99 g, 7.33 mmol) in THF (20 mL) was added LiHMDS 1M in THF (1.1 eq., 8.067 mL, 8.067 mmol) dropwise at −78° C. The resulting mixture was stirred at −78° C. for 1 h before the addition of allyl iodide (1.1 eq., 1.36 g, 0.74 mL, 8.067 mmol) dropwise. The resulting mixture was warmed to room temperature and stirred for 18 h. The reaction was cooled to −78° C. and LiHMDS 1M in THF (0.2 eq., 1.47 mL, 1.47 mmol) was added dropwise at −78° C. The reaction was stirred at this temperature for 30 min before the addition of allyl iodide (0.2 eq., 0.25 g, 0.13 mL, 1.47 mmol) dropwise. The resulting mixture was warmed to room temperature and stirred for 3 h. The reaction mixture was diluted with water (100 mL) and extracted with EtOAc (3×100 mL). The combined organic layers were washed with brine (100 mL), dried over $Na_2SO_4$, filtered and concentrated to dryness under reduced pressure. The crude residue was purified by ELSD flash chromatography over silica gel (regular SiOH, 15 μm, 80 g Interchim, dry loading (silica), mobile phase gradient: cyclohexane/EtOAc from 100/0 to 80/20 over 50 min). The fractions containing the compound were combined, evaporated in vacuo and co-evaporated with DCM affording H1-2-4 (1.62 g, 5.20 mmol, 71%) as a yellow oil.

LC/MS (AN_01_001_012): Rt=2.86 min, 100%, $[M-Boc+H]^+$=212.

1-tert-butyl 3-ethyl 1,2,3,4,7,8-hexahydroazocine-1,3-dicarboxylate H1-2-5

Starting from H1-2-4 (1 eq., 1.2 g, 3.85 mmol) in DCM (200 mL) and using general procedure H, H1-2-5 was obtained as a black oil (613 mg, 56%) after purification by flash chromatography over silica gel (irregular SiOH, 50 μm, 80 g Interchim, dry loading (silica), mobile phase gradient: cyclohexane/EtOAc from 100/0 to 80/20 over 45 min) and co-evaporation with DCM.

LC/MS (AN_01_001_012): Rt=2.67 min, 100%, $[M-Boc+H]^+$=184.11

1-tert-butyl 3-ethyl azocane-1,3-dicarboxylate H1-2-6

Starting from H1-2-5 (1 eq., 350 mg, 1.24 mmol) and using general procedure D, H1-2-6 was obtained as a yellow oil (323 mg, 92%).

LC/MS (AN_01_001_012): Rt=2.73 min, ND, $[M-{}^tBu+H]^+$=230.15

1-[(tert-butoxy) carbonyl]azocane-3-carboxylic acid H1-2-7

To an argon-purged solution of H1-2-6 (1 eq., 0.32 g, 1.13 mmol) in THF (11 mL) was added a solution of LiOH (5 eq., 0.24 g, 5.66 mmol) in water (5.5 mL) and the reaction mixture was stirred at RT for 19 h. The reaction was poured dropwise into a stirred aq. sol. of HCl 1M (50 mL) and DCM (100 mL) cooled to 0° C. The mixture was stirred 1 h (PH ~1). The layers were separated and the aqueous layer was extracted with DCM (2×50 mL). The combined organic layers were dried over $Na_2SO_4$, filtered and concentrated to dryness under reduced pressure affording crude H1-2-7 (0.29 g, 1.13 mmol, 100%) as a yellow oil.

LC/MS (AN01_001_012): Rt=2.29 min, ND, $[M-H]-$=256.1.

tert-butyl 3-{[(1S)-1-cyano-2-[4-(3-methyl-2-oxo-2,3-dihydro-1,3-benzoxazol-5-yl)phenyl]ethyl]carbamoyl}azocane-1-carboxylate H1-2-8

Starting from BB01 (1 eq., 150 mg, 0.45 mmol) and the mixture H1-2-7 (1 eq., 138.4 mg, 0.45 mmol), using general procedure B, was obtained H1-2-8 as an yellow gum (225 mg, 80%) after purification by flash chromatography over silica gel (irregular SiOH, 50 μm, 25 g Interchim, dry loading (silica), mobile phase gradient: cyclohexane/EtOAc from 90/10 to 50/50 over 25 min) and co-evaporation with DCM.

LC/MS (AN01_001_012): Rt=2.63 min, 100%, $[M-{}^tBu+H]^+$=477.2.

(3S*)—N-[(1S)-1-cyano-2-[4-(3-methyl-2-oxo-2,3-dihydro-1,3-benzoxazol-5-yl)phenyl]ethyl]azocane-3-carboxamide and (3R*)—N-[(1S)-1-cyano-2-[4-(3-methyl-2-oxo-2,3-dihydro-1,3-benzoxazol-5-yl)phenyl]ethyl]azocane-3-carboxamide.

Starting from H1-2-8 (1 eq., 230 mg, 0.36 mmol) and using general procedure C, a mixture of (3S*)—N-[(1S)-1-cyano-2-[4-(3-methyl-2-oxo-2,3-dihydro-1,3-benzoxazol-5-yl)phenyl]ethyl]azocane-3-carboxamide and (3R*)—N-[(1S)-1-cyano-2-[4-(3-methyl-2-oxo-2,3-dihydro-1,3-benzoxazol-5-yl)phenyl]ethyl]azocane-3-carboxamide was obtained as a yellow gum (134 mg, 85%) after purification by flash chromatography over silica gel (regular SiOH, 15 μm, 12 g Interchim, dry loading (silica), mobile phase gradient: DCM/MeOH from 100/0 to 80/20 over 60 min).

A SFC purification (Chiralpak OJ-3 (4.6×100 mm), 35° C., 35:65 MeOH: CO2 (0.3% v/v iPrNH2, 80 mL/min, 100 bar) afforded after freeze-drying (3S*)—N-[(1S)-1-cyano-2-[4-(3-methyl-2-oxo-2,3-dihydro-1,3-benzoxazol-5-yl)phenyl]ethyl]azocane-3-carboxamide (37.1 mg, 24%) and (3R*)—N-[(1S)-1-cyano-2-[4-(3-methyl-2-oxo-2,3-dihydro-1,3-benzoxazol-5-yl)phenyl]ethyl]azocane-3-carboxamide (36.2 mg, 23%) as white solids.

(3S*)—N-[(1S)-1-cyano-2-[4-(3-methyl-2-oxo-2,3-dihydro-1,3-benzoxazol-5-yl)phenyl]ethyl]azocane-3-carboxamide LC/MS (AN01_001_026_DEDL): Rt=7.26 min, 98.80%, $[M+H]^+$=433.4.

$^1H$ NMR (400 MHZ, DMSO) § 8.87-8.59 (m, 1H), 7.72-7.62 (m, 2H), 7.62-7.53 (m, 1H), 7.47-7.33 (m, 4H), 4.96 (q, J=7.7 Hz, 1H), 3.41 (s, 3H), 3.21-3.06 (m, 2H), 2.95-2.76 (m, 3H), 2.45 (s, 2H), 1.83-1.42 (m, 8H).

(3R*)—N-[(1S)-1-cyano-2-[4-(3-methyl-2-oxo-2,3-dihydro-1,3-benzoxazol-5-yl)phenyl]ethyl]azocane-3-carboxamide LC/MS (AN01_001_026_DEDL): Rt=7.29 min, 97.74%, $[M+H]^+$=433.4.

$^1$H NMR (400 MHZ, DMSO) δ 8.73 (d, J=7.9 Hz, 1H), 7.72-7.62 (m, 2H), 7.60-7.54 (m, 1H), 7.47-7.35 (m, 4H), 5.03-4.92 (m, 1H), 3.40 (d, J=3.5 Hz, 3H), 3.22-3.04 (m, 2H), 2.96-2.72 (m, 3H), 2.46 (t, J=1.9 Hz, 2H), 1.65-1.32 (m, 8H).

Example 8: Preparation of (2S,6S)—N—((S)-1-cyano-2-(4-(3-methyl-2-oxo-2,3-dihydrobenzo[d]oxazol-5-yl)phenyl)ethyl)-6-hydroxy-6-propyl-1,4-oxazepane-2-carboxamide (Compound 8)

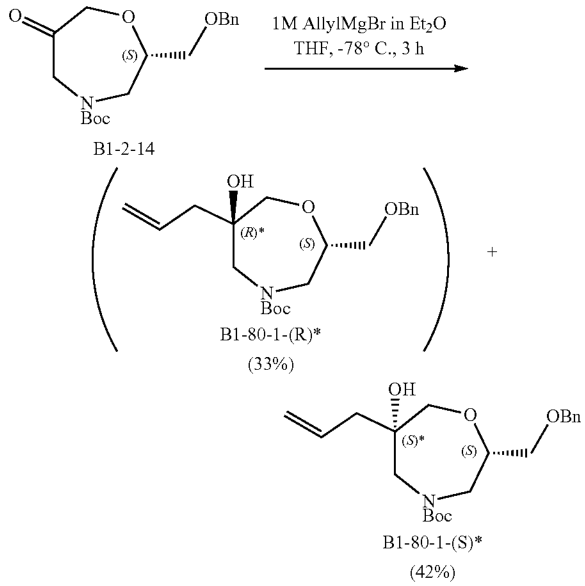

B1-2-14

B1-80-1-(R)*

(33%)

+

B1-80-1-(S)*

(42%)

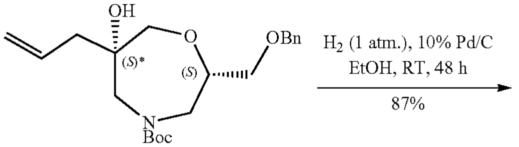

B1-80-1-(S)*

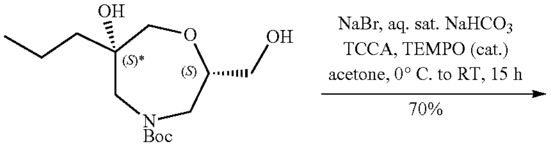

B1-81-1-(S)*

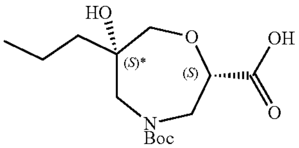

B1-81-2-(S)*

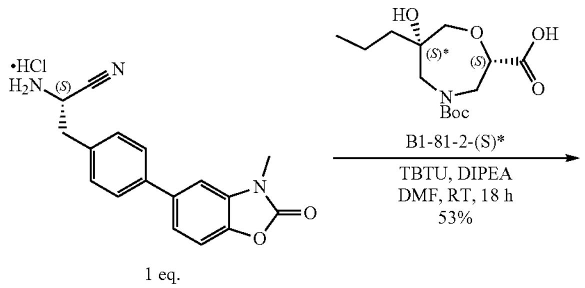

1 eq.
BB01

-continued

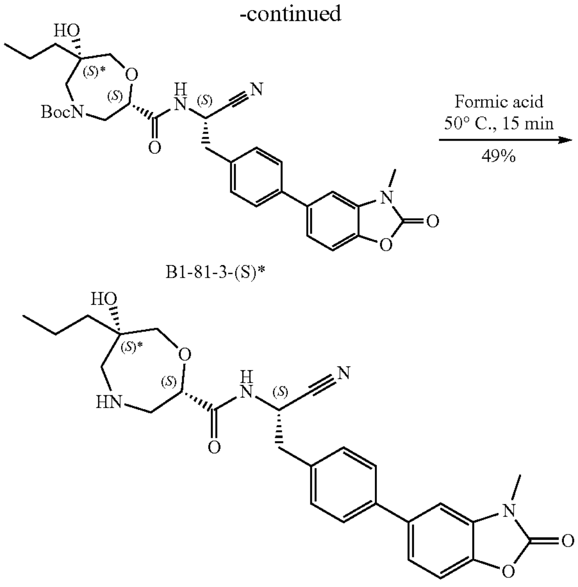

B1-81-3-(S)*

Compound 8 tert-butyl (2S,6S*)-2-[(benzyloxy)methyl]-6-hydroxy-6-(prop-2-en-1-yl)-1,4-oxazepane-4-carboxylate B1-80-1-(S)*

To a solution of B1-2-14) (1.0 eq., 500 mg, 1.49 mmol) (previously described) in THF (13.5 mL) was added 1M Allylmagnesium bromide in $Et_2O$ (3.0 eq., 4.47 mL, 4.47 mmol) at −78° C. The reaction mixture was stirred at −78° C. for 3 h. The reaction mixture was quenched with a sat. aq. $NH_4Cl$ solution (50 mL) and diluted with EtOAc (100 mL). The layers were separated and the aqueous layer was extracted with EtOAc (3×50 mL). The combined organic layers were washed with brine (150 mL), dried over $Na_2SO_4$, filtered and concentrated under reduced pressure. The crude was purified by flash chromatography over silica gel (15 μm, 25 g, Cyclohexane/EA from 100:0 to 75:25 over 40 min, revealed with PMA) to afford impure B1-71-1-(R)* which was repurified by flash chromatography over silica gel (15 μm, 40 g, Cyclohexane/EA from 100:0 to 6:4 over 55 min) to afford B1-80-1-(S)* as colorless oil (237 mg, 42%) and B1-80-1-(R)* as colorless oil (186 mg, 33%).

LC/MS (AN01_001_012): Rt=2.67 min, 100%, [M−Boc+H]$^+$=278.2.

$^1$H NMR (400 MHZ, DMSO) δ 7.41-7.21 (m, 5H), 5.94-5.78 (m, 1H), 5.11-4.96 (m, 2H), 4.59-4.41 (m, 3H), 3.82-3.71 (m, 1H), 3.65-3.50 (m, 2H), 3.49-3.33 (m, 3H), 3.31-3.15 (m, 3H), 2.24-2.09 (m, 2H), 1.47-1.29 (m, 9H).

tert-butyl (2S,6S*)-6-hydroxy-2-(hydroxymethyl)-6-propyl-1,4-oxazepane-4-carboxylate B1-81-1-(S)*

Starting from B1-80-1-(S)* (1 eq., 210 mg, 0.56 mmol) and using general procedure D, B1-81-1-(S)* was obtained as a colorless oil (140 mg, 87%).

LC/MS (AN01_001_012): Rt=2.07 min, ND, [M−$^t$Bu+H]$^+$=234.1.

$^1$H NMR (400 MHZ, DMSO) δ 4.71-4.55 (m, 1H), 4.41-4.22 (m, 2H), 3.62-3.50 (m, 2H), 3.50-3.34 (m, 2H), 3.30-3.12 (m, 4H), 1.57-1.19 (m, 13H), 0.94-0.74 (m, 3H).

(2S,6S*)-4-[(tert-butoxy) carbonyl]-6-hydroxy-6-propyl-1,4-oxazepane-2-carboxylic acid B1-81-2-(S)*

Starting from B1-81-1-(S)* (1 eq., 130 mg, 0.45 mmol) and using general procedure E, B1-81-2-(S)* was obtained as a white solid (95 mg, 70%).

LC/MS (AN01_001_012): Rt=2.07 min, ND, [M–H]–=302.1.

$^1$H NMR (400 MHZ, DMSO) & 12.59 (s, 1H), 4.40-4.23 (m, 1H), 4.23-3.99 (m, 1H), 3.84-3.68 (m, 1H), 3.67-3.54 (m, 1H), 3.53-3.38 (m, 1H), 3.37-3.25 (m, 2H), 3.20-3.12 (m, 2H), 1.46-1.19 (m, 13H), 0.93-0.79 (m, 3H).

tert-butyl (2S,6S*)-2-{[(1S)-1-cyano-2-[4-(3-methyl-2-oxo-2,3-dihydro-1,3-benzoxazol-5-yl)phenyl]ethyl]carbamoyl}-6-hydroxy-6-propyl-1,4-oxazepane-4-carboxylate B1-81-3-(S)*

Starting from BB01 (1 eq., 93.2 mg, 0.28 mmol) and B1-81-2-(S)* (1.05 eq., 90.0 mg, 0.30 mmol) and using general procedure B, B1-81-3-(S)* was obtained as an orange solid (90 mg, 53%) after purification by flash chromatography over silica gel (regular SiOH, 50 μm, 25 g, dry loading (silica), mobile phase gradient: Cyclo/EtOAc from 100:0 to 40:60).

LC/MS (AN01_001_012): Rt=2.56 min, 96%, [M–$^t$Bu+H]$^+$=523.2.

$^1$H NMR (400 MHZ, DMSO, presence of rotamers) δ 8.65 (m, 1H), 7.66 (d, J=7.8 Hz, 2H), 7.57 (s, 1H), 7.46-7.29 (m, 4H), 5.10-4.92 (m, 1H), 4.36 (d, J=15.8 Hz, 1H), 4.18 (dd, J=8.9, 4.7 Hz, 1H), 3.76 (dd, J=14.5, 4.8 Hz, 1H), 3.58 (t, J=12.0 Hz, 1H), 3.41 (s, 3H), 3.38-3.29 (m, 2H), 3.30-3.09 (m, 4H), 1.49-1.21 (m, 13H), 0.94-0.78 (m, 3H).

(2S,6S*)—N-[(1S)-1-cyano-2-[4-(3-methyl-2-oxo-2,3-dihydro-1,3-benzoxazol-5-yl)phenyl]ethyl]-6-hydroxy-6-propyl-1,4-oxazepane-2-carboxamide Starting from B1-81-3-(S)* (1 eq., 80.0 mg, 0.14 mmol) and using general procedure C, (2S,6S*)—N-[(1S)-1-cyano-2-[4-(3-methyl-2-oxo-2,3-dihydro-1,3-benzoxazol-5-yl)phenyl]ethyl]-6-hydroxy-6-propyl-1,4-oxazepane-2-carboxamide was obtained as a white solid (52 mg, 49%) after purification by flash chromatography over silica gel (irregular SiOH, 15 μm, 4 g Interchim, dry loading (silica), mobile phase gradient: DCM/MeOH from 100:0 to 90:10) and vacuum drying at 40° C. for 24 h.

LC/MS (AN_01_001_021_DEDL): Rt=7.43 min, 99.90%, [M+H]$^+$=479.44.

$^1$H NMR (400 MHZ, DMSO) δ 8.53 (d, J=8.5 Hz, 1H), 7.71-7.61 (m, 2H), 7.56 (t, J=1.2 Hz, 1H), 7.44-7.29 (m, 4H), 5.01 (td, J=8.7, 7.2 Hz, 1H), 4.31 (s, 1H), 4.01 (dd, J=9.4, 4.2 Hz, 1H), 3.50 (dd, J=44.7, 12.4 Hz, 2H), 3.40 (s, 3H), 3.27-3.13 (m, 2H), 3.09 (dd, J=14.0, 4.3 Hz, 1H), 2.63 (d, J=13.7 Hz, 1H), 2.49-2.44 (m, 2H), 2.39-2.32 (m, 1H), 1.36-1.23 (m, 4H), 0.90-0.77 (m, 3H).

Example 9: Preparation of (2S,6R)—N—((S)-1-cyano-2-(4-(3-methyl-2-oxo-2,3-dihydrobenzo[d]oxazol-5-yl)phenyl)ethyl)-6-hydroxy-6-propyl-1,4-oxazepane-2-carboxamide (Compound 9)

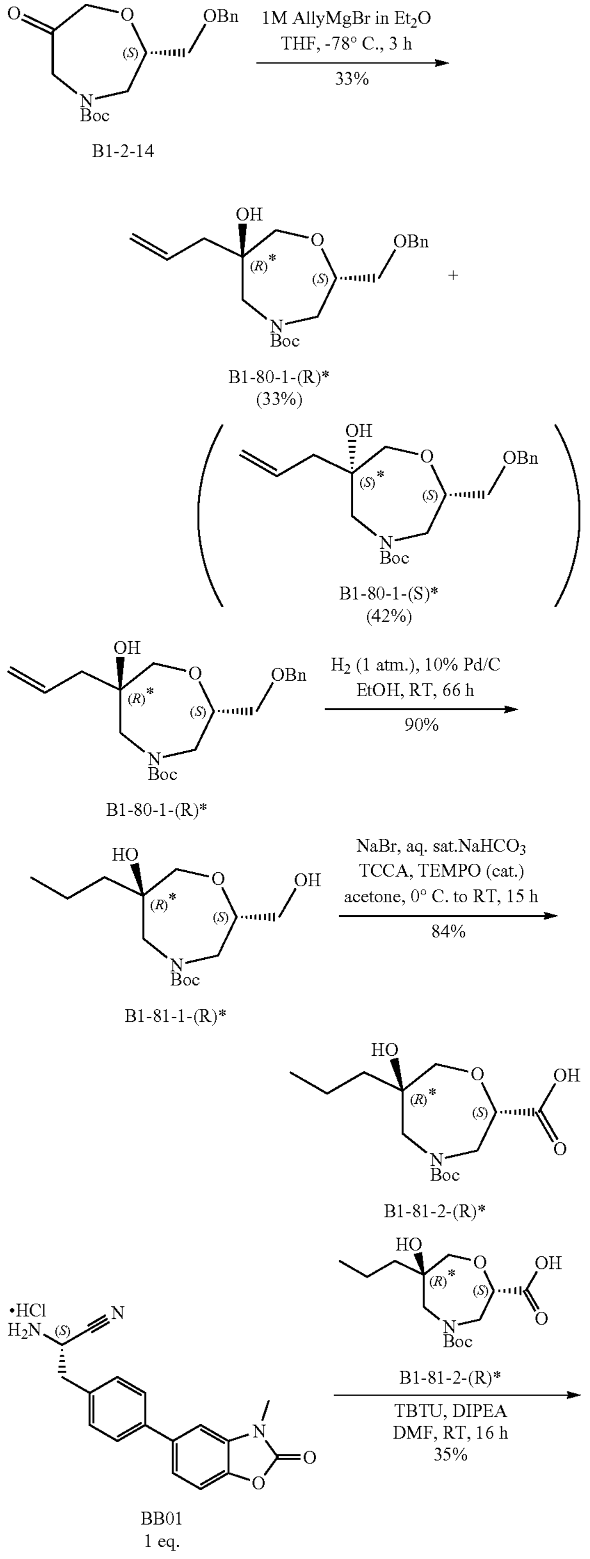

-continued

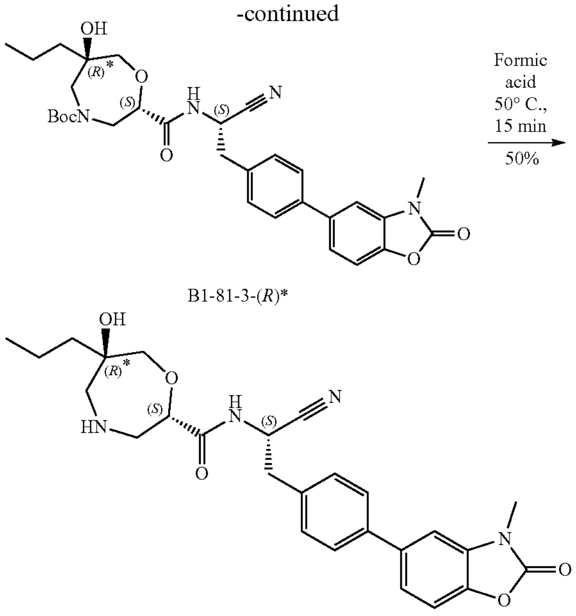

B1-81-3-(*R*)*

Compound 9 tert-butyl (2S,6R*)-2-[(benzyloxy)methyl]-6-hydroxy-6-(prop-2-en-1-yl)-1,4-oxazepane-4-carboxylate B1-80-1-(R)*

To a solution of I1-2-14 (1.0 eq., 500 mg, 1.49 mmol) (previously described) in THF (13.5 mL) was added 1M Allylmagnesium bromide in $Et_2O$ (3.0 eq., 4.47 mL, 4.47 mmol) at −78° C. The reaction mixture was stirred at −78° C. for 3 h. The reaction mixture was quenched with a sat. aq. $NH_4Cl$ solution (50 mL) and diluted with EtOAc (100 mL). The layers were separated and the aqueous layer was extracted with EtOAc (3×50 mL). The combined organic layers were washed with brine (150 mL), dried over $Na_2SO_4$, filtered and concentrated under reduced pressure. The crude was purified by flash chromatography over silica gel (15 μm, 25 g, Cyclohexane/EA from 100:0 to 75:25 over 40 min, revealed with PMA) to afford impure B1-71-1-(R)* which was repurified by flash chromatography over silica gel (15 μm, 40 g, Cyclohexane/EA from 100:0 to 6:4 over 55 min) to afford B1-80-1-(S)* as colorless oil (237 mg, 42%) and B1-80-1-(R)* as colorless oil (186 mg, 33%).

LC/MS (AN01_001_012): Rt=2.58 min, 100%, [M−$^t$Bu+H]$^+$=322.1

$^1$H NMR (400 MHZ, DMSO) δ 7.40-7.24 (m, 5H), 5.95-5.80 (m, 1H), 5.11-4.99 (m, 2H), 4.62 (d, J=16.8 Hz, 1H), 4.50 (s, 2H), 3.99-3.60 (m, 4H), 3.52-3.44 (m, 1H), 3.44-3.36 (m, 1H), 3.30-3.25 (m, 1H), 3.10-2.85 (m, 2H), 2.19-2.09 (m, 2H), 1.40 (s, 9H).

tert-butyl (2S,6R*)-6-hydroxy-2-(hydroxymethyl)-6-propyl-1,4-oxazepane-4-carboxylate B1-81-1-(R)*

Starting from B1-80-1-(R)* (1 eq., 210 mg, 0.56 mmol) and using general procedure D, B1-81-1-(R)* was obtained as a colorless oil (145 mg, 90%).

LC/MS (AN01_001_012): Rt=2.05 min, ND, [M−$^t$Bu+H]$^+$=234.1.

$^1$H NMR (400 MHZ, DMSO) δ 4.68 (t, J=5.6 Hz, 1H), 4.51-4.36 (m, 1H), 4.34 (t, J=5.1 Hz, 1H), 4.04-3.56 (m, 3H), 3.55-3.32 (m, 2H), 3.23 (d, J=12.9 Hz, 1H), 3.02-2.70 (m, 2H), 1.52-1.18 (m, 13H), 0.97-0.76 (m, 3H).

(2S,6R*)-4-[(tert-butoxy) carbonyl]-6-hydroxy-6-propyl-1,4-oxazepane-2-carboxylic acid B1-81-2-(R)*

Starting from B1-81-1-(R)* (1 eq., 145 mg, 0.50 mmol) and using general procedure E, B1-81-2-(R)* was obtained as a white solid (127 mg, 84%).

LC/MS (AN01_001_012): Rt=2.08 min, ND, [M−H]−=302.1.

tert-butyl (2S,6R*)-2-{[(1S)-1-cyano-2-[4-(3-methyl-2-oxo-2,3-dihydro-1,3-benzoxazol-5-yl)phenyl]ethyl]carbamoyl}-6-hydroxy-6-propyl-1,4-oxazepane-4-carboxylate B1-81-3-(R)*

Starting from BB01 (1 eq., 133 mg, 0.40 mmol) and B1-81-2-(S)* (1.05 eq., 128 mg, 0.42 mmol) and using general procedure B, B1-81-3-(R)* was obtained as a light yellow solid (81 mg, 35%) after purification by flash chromatography over silica gel (regular SiOH, 15 μm, 12 g, dry loading (silica), mobile phase gradient: Cyclo/EtOAc from 100:0 to 0:100).

LC/MS (AN01_001_012): Rt=2.53 min, 100%, [M−$^t$Bu+H]$^+$=523.15.

$^1$H NMR (400 MHZ, DMSO, presence of rotarmers) δ 8.87 (d, J=8.4 Hz, 1H), 7.72-7.63 (m, 2H), 7.61-7.53 (m, 1H), 7.49-7.34 (m, 4H), 5.03 (q, J=8.1 Hz, 1H), 4.65-4.52 (m, 1H), 4.20-4.09 (m, 1H), 4.08-3.98 (m, 1H), 3.95-3.74 (m, 1H), 3.76-3.68 (m, 1H), 3.62-3.46 (m, 1H), 3.40 (s, 3H), 3.26-3.12 (m, 2H), 3.07-2.85 (m, 1H), 2.82-2.71 (m, 1H), 1.52-1.27 (m, 13H), 0.94-0.76 (m, 3H).

(2S,6R*)—N-[(1S)-1-cyano-2-[4-(3-methyl-2-oxo-2,3-dihydro-1,3-benzoxazol-5-yl)phenyl]ethyl]-6-hydroxy-6-propyl-1,4-oxazepane-2-carboxamide Starting from B1-81-3-(R)* (1 eq., 87.0 mg, 0.15 mmol) and using general procedure C, (2S,6R*)—N-[(1S)-1-cyano-2-[4-(3-methyl-2-oxo-2,3-dihydro-1,3-benzoxazol-5-yl)phenyl]ethyl]-6-hydroxy-6-propyl-1,4-oxazepane-2-carboxamide was obtained as a white solid (36 mg, 50%) after purification by flash chromatography over silica gel (irregular SiOH, 50 μm, 4 g Interchim, dry loading (silica), mobile phase gradient: DCM/MeOH from 100:0 to 90:10) and vacuum drying at 40° C. for 24 h.

LC/MS (AN_01_001_021_DEDL): Rt=7.28 min, 97.98%, [M+H]=479.38.

$^1$H NMR (400 MHZ, DMSO) & 8.68 (d, J=8.5 Hz, 1H), 7.69-7.61 (m, 2H), 7.59-7.54 (m, 1H), 7.44-7.36 (m, 4H), 5.02 (td, J=8.5, 7.3 Hz, 1H), 4.38 (s, 1H), 3.97 (dd, J=8.0, 5.0 Hz, 1H), 3.64-3.49 (m, 2H), 3.40 (s, 3H), 3.25-3.13 (m, 2H), 3.02 (dd, J=14.0, 5.1 Hz, 1H), 2.64 (d, J=13.2 Hz, 1H), 2.58-2.51 (m, 3H), 1.39-1.20 (m, 4H), 0.91-0.80 (m, 3H).

Example 10: Preparation of (2S,6R)—N—((S)-1-cyano-2-(4-(3-methyl-2-oxo-2,3-dihydrobenzo[d]oxazol-5-yl)phenyl)ethyl)-6-isobutoxy-6-methyl-1,4-oxazepane-2-carboxamide (Compound 10)

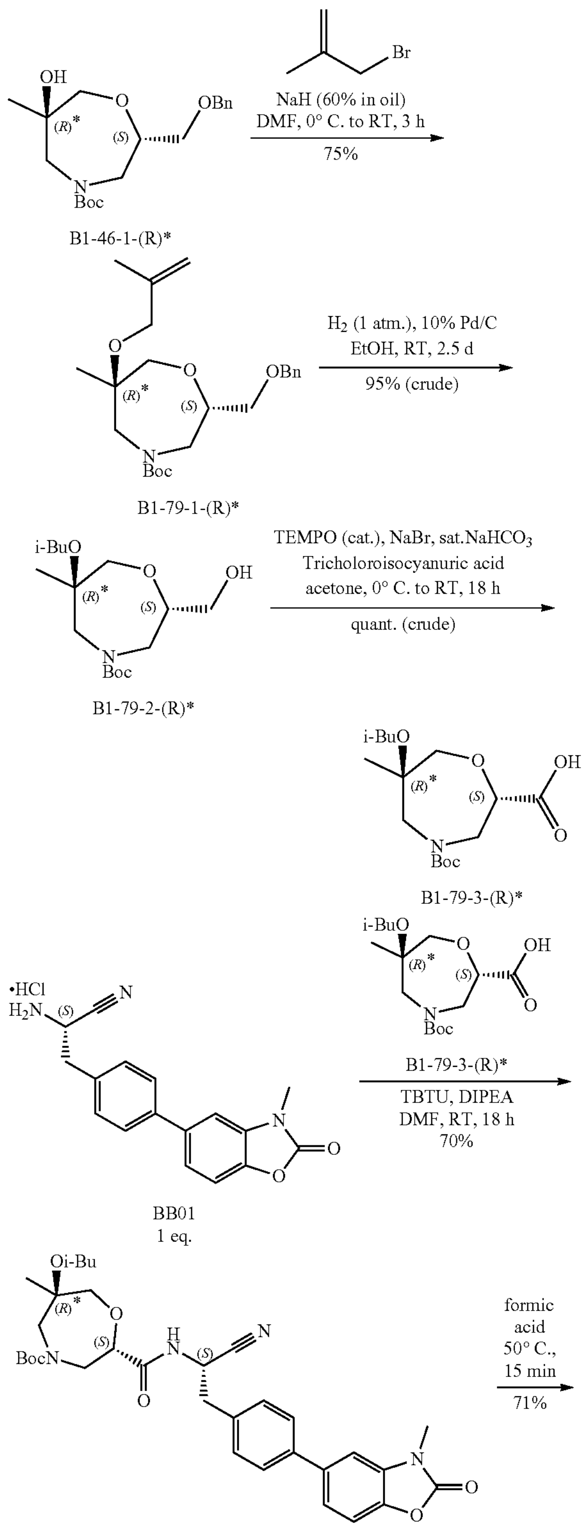

B1-46-1-(R)*

B1-79-1-(R)*

B1-79-2-(R)*

B1-79-3-(R)*

BB01
1 eq.

B1-79-4-(R)*

-continued

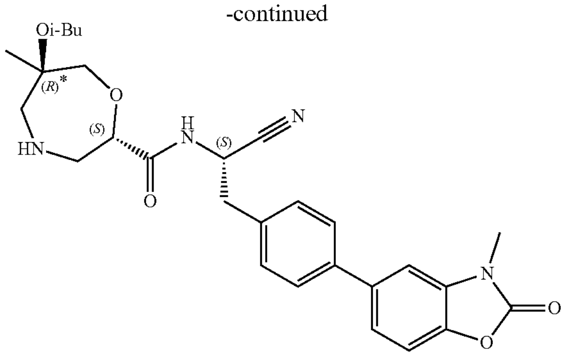

Compound 10 tert-butyl (2S,6R*)-2-[(benzyloxy)methyl]-6-methyl-6-[(2-methylprop-2-en-1-yl)oxy]-1,4-oxazepane-4-carboxylate B1-79-1-(R)*

Starting from B1-79-1-(R)* (1 eq., 273 mg, 0.780 mmol) (previously described) and 3-Bromo-2-methylpropene (2.5 eq., 262.18 mg, 0.2 mL, 1.94 mmol) using general procedure F, B1-79-1-(R)* was obtained as a colorless oil (235 mg, 75%) after purification by silica gel flash chromatography (50 μm, 25 g, Cyclohexane/EtOAc from 100:0 to 8:2 over 32 min, revealed with PMA).

LC/MS (AN01_001_012): Rt=2.95 min, 100%, $[M-{}^tBu+H]^+$=350.1.

tert-butyl (2S,6R*)-2-(hydroxymethyl)-6-methyl-6-(2-methylpropoxy)-1,4-oxazepane-4-carboxylate B1-79-2-(R)*

Starting from B1-47-1-(S)* (1 eq., 235 mg, 0.58 mmol), using general procedure D, B1-79-2-(R)* was obtained as a colorless oil (174 g, 95%).

LC/MS (AN01_001_012): Rt=2.00 min, non-UV active, $[M+H]^+$=262.1.

(2S,6R*)-4-[(tert-butoxy) carbonyl]-6-methyl-6-(2-methylpropoxy)-1,4-oxazepane-2-carboxylic acid B1-79-3-(R)*

Starting from B1-79-2-(R)* (1 eq., 176 mg, 0.55 mmol), using general procedure E, B1-79-3-(R)* was obtained as a colorless gum (184 mg, 100%).

LC/MS (AN01_001_012): Rt=2.46 min, non-UV active, [M−H]−=330.1.

tert-butyl (2S,6R*)-2-{[(1S)-1-cyano-2-[4-(3-methyl-2-oxo-2,3-dihydro-1,3-benzoxazol-5-yl)phenyl]ethyl]carbamoyl}-6-methyl-6-(2-methylpropoxy)-1,4-oxazepane-4-carboxylate B1-79-4-(R)*

Starting from BB01 (1 eq., 172.5 mg, 0.52 mmol) and B1-79-3-(R)* (1.05 eq., 0.182 mg, 0.55 mmol), using general procedure B, B1-79-4-(R)* was obtained as a light yellow solid (220 mg, 70%) after purification by silica gel flash chromatography ((regular SiOH, 50 μm, 24 g, dry loading (silica), mobile phase gradient: Cyclo/EtOAc from 10/0 to 5/5 over 50 min).

LC/MS (AN01_001_012): Rt=2.80 min, 100%, $[M-{}^tBu+H]^+$=551.2.

(2S,6R*)—N-[(1S)-1-cyano-2-[4-(3-methyl-2-oxo-2,3-dihydro-1,3-benzoxazol-5-yl)phenyl]ethyl]-6-methyl-6-(2-methylpropoxy)-1,4-oxazepane-2-carboxamide Starting from B1-79-4-(R)* (1 eq., 100 mg, 0.16 mmol), using general procedure C, 2S,6R*)—N-[(1S)-1-cyano-2-[4-(3-methyl-2-oxo-2,3-dihydro-1,3-benzoxazol-5-yl)phenyl]ethyl]-6-methyl-6-(2-methylpropoxy)-1,4-oxazepane-2-carboxamide was obtained as a white solid (59.0 mg, 71%) after purification by silica gel flash chromatography (irregular SiOH, 50 μm, 12 g Interchim, dry loading (silica), mobile phase gradient: DCM/MeOH from 10/0 to 9/1 over 30 min).

LC/MS (AN01_001_026): Rt=8.11 min, 98.3%, $[M+H]^+$=507.5.

$^1$H NMR (400 MHZ, DMSO) δ 8.55 (d, J=8.5 Hz, 1H), 7.66-7.60 (m, 2H), 7.57-7.54 (m, 1H), 7.42-7.35 (m, 4H), 5.05-4.95 (m, 1H), 3.96-3.86 (m, 2H), 3.43 (d, J=13.3 Hz, 1H), 3.40 (s, 3H), 3.24-3.16 (m, 3H), 3.15-3.05 (m, 2H), 2.75-2.60 (m, 2H), 2.36-2.26 (m, 1H), 1.69 (dt, J=13.2, 6.6 Hz, 1H), 1.00 (s, 3H), 0.88 (dd, J=6.7, 1.7 Hz, 7H).

Example 11: Preparation of a mixture of N-[(1S)-1-cyano-2-[4-(3-methyl-2-oxo-2,3-dihydro-1,3-benzoxazol-5-yl)phenyl]ethyl]-5-hydroxyazocane-3-carboxamide and N-[(1S)-1-cyano-2-[4-(3-methyl-2-oxo-2,3-dihydro-1,3-benzoxazol-5-yl)phenyl]ethyl]-6-hydroxyazocane-3-carboxamide (Compound 11)

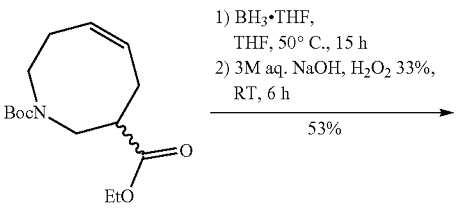

H1-2-5

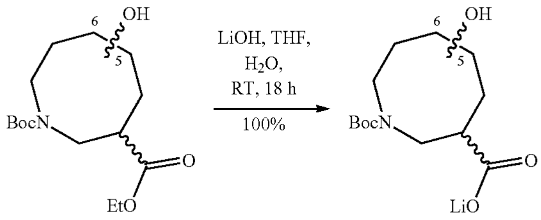

H1-3/4-1

H1-3/4-3

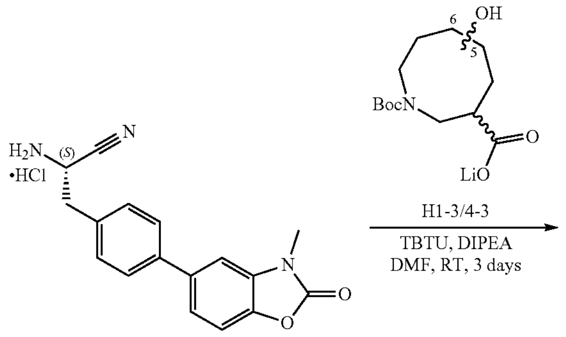

BB01

-continued

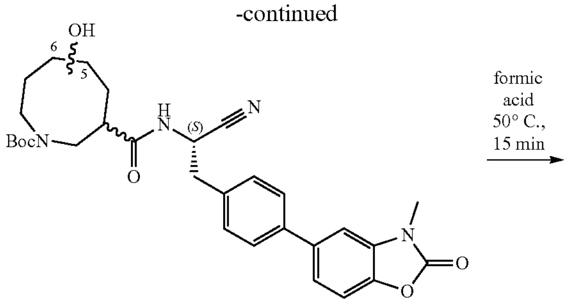

H1-3/4-4

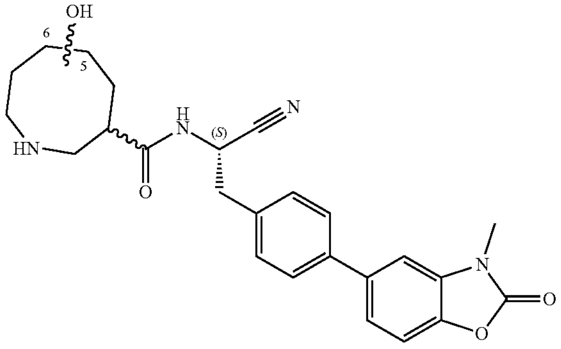

Compound 11
(mixture of regio-and diastereomers)

Mixture of 1-tert-butyl 3-ethyl 5-hydroxyazocane-1,3-dicarboxylate and 1-tert-butyl 3-ethyl 6-hydroxyazocane-1,3-dicarboxylate H1-3/4-1

Starting from H1-2-5 (1 eq., 1.41 g, 4.98 mmol) and using general procedure I, mixture of H1-3/4-1 (780 mg, 2.62 mmol, 53%) was obtained as a yellow gum after purification by flash chromatography over silica gel (regular SiOH, 15 μm, 40 g, dry loading (silica), mobile phase gradient: Cyclo/EtOAc from 10/0 to 0/10 over 50 min) and co-evaporation with DCM.

Chiral SFC analysis: Chiralpak (AD-3 4.6×100 mm, Mobile phase: CO2/(iPrOH+0.3% iPrNH2) 90/10): (eight products) at Rt=0.84, 1.07, 1.23, 1.34, 1.44, 1.71, 2.36 and 5.37 min; 21.6, 21.0, 2.14, 8.37, 3.54, 21.09, 1.88 and 20.33%.

LC/MS (AN01_001_026, ELSD): Rt=8.09 and 8.18 min, 52.4 and 47.4%, $[M-{}^tBu+H]^+$=246.2

Mixture of 1-tert-butyl 3-lithio 5-hydroxyazocane-1,3-dicarboxylate and 1-tert-butyl 3-lithio 6-hydroxyazocane-1,3-dicarboxylate H1-3/4-3

To an argon-purged solution of H1-3/4-1 (1 eq., 75.1 mg, 0.25 mmol) in THF (2.5 mL) was added a solution of LiOH (1 eq., 10.46 mg, 0.25 mmol) in H2O (0.3 mL) and the reaction mixture was stirred at RT for 17 h. The reaction mixture was concentrated to dryness under reduced pressure and co-evaporated with THE affording crude H1-3/4-3 as an off-white solid (76.3 mg, 100%) which was used as such without further purification.

LC/MS (AN01_001_012): Not UV active, Rt=1.88 min, ND, $[M-Li+H]^+$=272.1.

Mixture of tert-butyl 3-{[(1S)-1-cyano-2-[4-(3-methyl-2-oxo-2,3-dihydro-1,3-benzoxazol-5-yl)phenyl]ethyl]carbamoyl}-5-hydroxyazocane-1-carboxylate and tert-butyl 3-{[(1S)-1-cyano-2-[4-(3-methyl-2-oxo-2,3-dihydro-1,3-benzoxazol-5-yl)phenyl]ethyl]carbamoyl}-6 hydroxyazocane-1-carboxylate H1-3/4-4

Starting from BB01 (1 eq., 78.0 mg, 0.24 mmol) and H1-3/4-3 (1.05 eq., 69.4 mg, 0.25 mmol), using general procedure B, H1-3/4-4 was obtained as a yellowish solid (69.0 mg, 53%) after purification by silica gel flash chromatography ((regular SiOH, 15 µm, 12 g, dry loading (silica), mobile phase gradient: DCM/EtOAc from 80/20 to 0/100 over 40 min).

LC/MS (AN01_001_026): Rt=8.73 and 9.06 min, 48.9 and 47.0%, $[M-{}^{t}Bu+H]^+$=493.39.

Mixture of N-[(1S)-1-cyano-2-[4-(3-methyl-2-oxo-2,3-dihydro-1,3-benzoxazol-5-yl)phenyl]ethyl]-5-hydroxyazocane-3-carboxamide and N-[(1S)-1-cyano-2-[4-(3-methyl-2-oxo-2,3-dihydro-1,3-benzoxazol-5-yl)phenyl]ethyl]-6-hydroxyazocane-3-carboxamide.

Starting from H1-3/4-4 (1 eq., 62.7 mg, 0.11 mmol), using general procedure C, mixture of regio- and diastereomers of N-[(1S)-1-cyano-2-[4-(3-methyl-2-oxo-2,3-dihydro-1,3-benzoxazol-5-yl)phenyl]ethyl]-5-hydroxyazocane-3-carboxamide and N-[(1S)-1-cyano-2-[4-(3-methyl-2-oxo-2,3-dihydro-1,3-benzoxazol-5-yl)phenyl]ethyl]-6-hydroxyazocane-3-carboxamide was obtained as a white solid (18.5 mg, 36%) after purification by preparative HPLC (Eluant:Water+0.1% TFA/Acetonitrile; Gradient: from 20 to 35% acetonitrile in water+0.1% TFA; Column: XBridge C18 (30×150 (5 µm)); Flow Rate: 43 mL/min). The fractions containing the compound were combined and ACN was evaporated in vacuo. The resulting solution containing water was basified and extracted with DCM (3×200 mL). The combined organic layers were dried over $Na_2SO_4$, filtered, concentrated to dryness under reduced pressure and the resulting solid was freeze-dried.

Chiral SFC analysis: Chiralpak (AD-3 4.6×100 mm, Mobile phase: CO2/(iPrOH+0.3% iPrNH2) 90/10): (seven products) at Rt=4.15, 4.93, 5.31, 5.61, 6.19, 6.84 and 7.46 min; 14.35, 16.49, 2.52, 1.30, 30.38, 4.25 and 29.9%.

LC/MS (AN01_001_026): Rt=6.82 and 6.95 min, 36.49 and 59.94%, $[M+H]^+$=449.45.

$^1$H NMR (400 MHZ, DMSO) δ 8.85-8.54 (m, 1H), 7.72-7.50 (m, 3H), 7.48-7.24 (m, 4H), 5.06-4.82 (m, 1H), 3.95-3.53 (m, 1H), 3.40 (s, 3H), 3.19-3.02 (m, 2H), 2.92-2.54 (m, 5H), 2.45-2.34 (m, 1H), 1.92-1.25 (m, 7H).

Example 12: Preparation of (2S,6S)—N—((S)-1-cyano-2-(4-(3-methyl-2-oxo-2,3-dihydrobenzo[d]oxazol-5-yl)phenyl)ethyl)-6-isobutoxy-6-methyl-1,4-oxazepane-2-carboxamide (Compound 12)

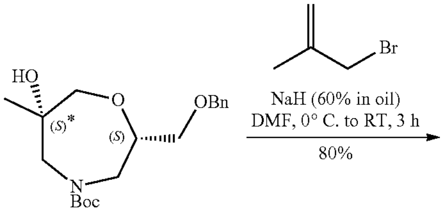

B1-46-1-(S)*

-continued

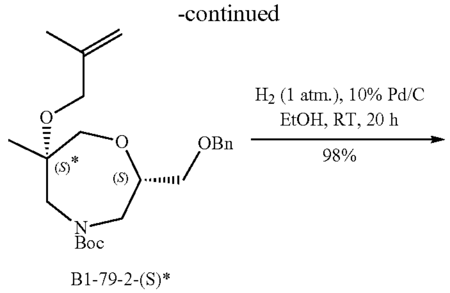

B1-79-2-(S)*

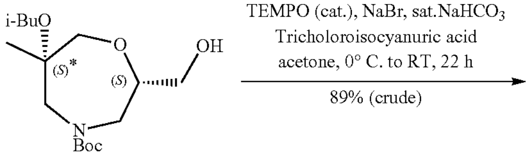

B1-79-3-(S)*

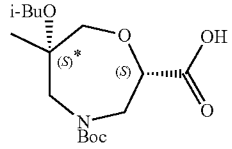

B1-79-4-(S)*

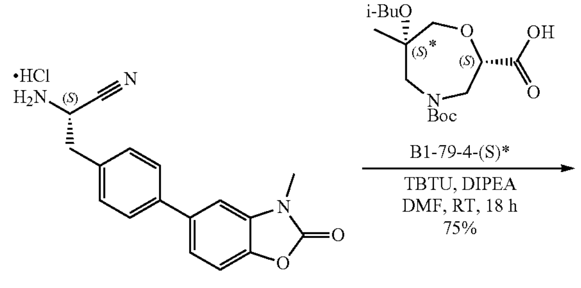

BB01
1 eq.

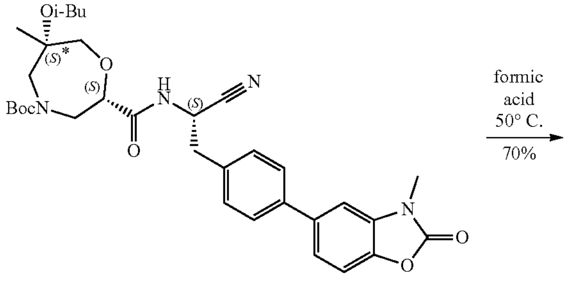

B1-79-5-(S)*

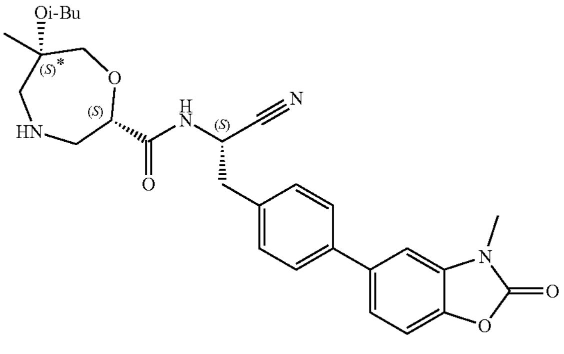

Compound 12 tert-butyl (2S,6S*)-2-[(benzyloxy)methyl]-6-methyl-6-[(2-methylprop-2-en-1-yl)oxy]-1,4-oxazepane-4-carboxylate B1-79-2-(S)*

Starting from B1-46-1-(S)* (1 eq., 164 mg, 0.47 mmol) (previously described) and 3-Bromo-2-methylpropene (2.5 eq., 157.5 mg, 0.12 mL, 1.17 mmol) using general procedure F, B1-79-2-(S)* was obtained as a colorless oil (151.4 mg, 80%) after purification by silica gel flash chromatography ((50 μm, 25 g, Cyclohexane/EtOAC from 100:0 to 8:2 over 32 min, revealed with PMA).

LC/MS (AN01_001_012): Rt=2.95 min, 100%, [M−Boc+H]$^+$=306.17.

tert-butyl (2S,6S*)-2-(hydroxymethyl)-6-methyl-6-(2-methylpropoxy)-1,4-oxazepane-4-carboxylate B1-79-3-(S)*

Starting from B1-79-2-(S)* (1 eq., 194 Mg, 0.48 mmol), using general procedure D, B1-79-3-(S)* was obtained as a colorless oil (149 mg, 98%).

LC/MS (AN01_001_012): Rt=2.46 min, non-UV active, [M−$^t$Bu+H]$^+$=262.1.

(2S,6S*)-4-[(tert-butoxy) carbonyl]-6-methyl-6-(2-methylpropoxy)-1,4-oxazepane-2-carboxylic acid B1-79-4-(S)*

Starting from B1-79-3-(S)* (1 eq., 141 mg, 0.44 mmol), using general procedure E, B1-79-4-(S)* was obtained as a colorless gum (131 mg, 89%).

LC/MS (AN01_001_012): Rt=2.42 min, 100%, [M−H]−=330.1.

tert-butyl (2S,6S*)-2-{[(1S)-1-cyano-2-[4-(3-methyl-2-oxo-2,3-dihydro-1,3-benzoxazol-5-yl)phenyl]ethyl]carbamoyl}-6-methyl-6-(2-methylpropoxy)-1,4-oxazepane-4-carboxylate B1-79-5-(S)*

Starting from BB01 (1 eq., 120.4 mg, 0.36 mmol) and B1-79-4-(S)* (1.05 eq., 127 mg, 0.38 mmol), using general procedure B, B1-79-5-(S)* was obtained as an yellow solid (167 mg, 75%) after purification by silica gel flash chromatography (50 μm, 40 g, cyclohexane/EtOAc from 100:0 to 20:80 over 42 min).

LC/MS (AN01_001_012): Rt=2.81 min, 100%, [M−Boc+H]=507.2.

(2S,6S*)—N-[(1S)-1-cyano-2-[4-(3-methyl-2-oxo-2,3-dihydro-1,3-benzoxazol-5-yl)phenyl]ethyl]-6-methyl-6-(2-methylpropoxy)-1,4-oxazepane-2-carboxamide Starting from B1-79-5-(S)* (1 eq., 80 mg, 0.13 mmol), using general procedure C, (2S,6S*)—N-[(1S)-1-cyano-2-[4-(3-methyl-2-oxo-2,3-dihydro-1,3-benzoxazol-5-yl)phenyl]ethyl]-6-methyl-6-(2-methylpropoxy)-1,4-oxazepane-2-carboxamide was obtained as a white solid (55 mg, 70%) after purification by silica gel flash chromatography (50 μm, 12 g, gradient: DCM/MeOH from 100:0 to 80:20 over 42 min).

LC/MS (AN01_001_026): Rt=8.08 min, 99.72%, [M+H]$^+$=507.5.

$^1$H NMR (400 MHZ, DMSO) δ 8.56 (d, J=8.5 Hz, 1H), 7.69-7.61 (m, 2H), 7.59-7.53 (m, 1H), 7.44-7.32 (m, 4H), 5.05-4.96 (m, 1H), 4.02 (dd, J=9.2, 4.0 Hz, 1H), 3.70 (d,

J=12.3 Hz, 1H), 3.53 (d, J=12.3 Hz, 1H), 3.40 (s, 3H), 3.26-3.03 (m, 5H), 2.90 (d, J=14.2 Hz, 1H), 2.44-2.27 (m, 3H), 1.65 (hept, J=6.7 Hz, 1H), 1.07 (s, 3H), 0.84 (d, J=6.7 Hz, 6H).

Example 13: Preparation of (2S,6S)—N—((S)-1-cyano-2-(4-(3-methyl-2-oxo-2,3-dihydrobenzo[d]oxazol-5-yl)phenyl)ethyl)-6-hydroxy-6-(hydroxymethyl)-1,4-oxazepane-2-carboxamide (Compound 13)

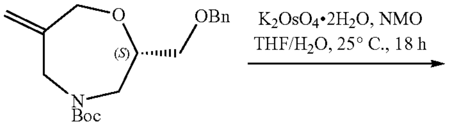

B1-2-13

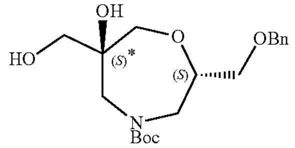

+

B1-78-1-(S)*
24%

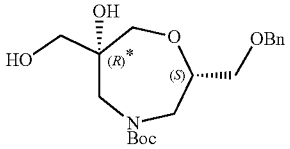

B1-78-1-(R)*
36% tert-butyl (2S,6R*)-2-[(benzyloxy)methyl]-6-hydroxy-6-(hydroxymethyl)-1,4-oxazepane-4-carboxylate B1-78-1-(R)* and tert-butyl (2S,6S*)-2-[(benzyloxy)methyl]-6-hydroxy-6-(hydroxymethyl)-1,4-oxazepane-4-carboxylate B1-78-1-(S)*

To a solution of I1-2-13 (1 eq., 820 mg, 2.46 mmol) (previously prepared) in a mixture of THF (13.67 mL) and water (4.56 mL) were added successively potassium osmate (VI) dihydrate (0.1 eq., 90.61 mg, 0.25 mmol) and NMO (1.5 eq., 432.15 mg, 3.69 mmol) at room temperature. The resulting mixture was stirred for 18 h at room temperature.

The reaction mixture was diluted with water (40 mL) and EtOAc (75 mL). The layers were separated and the aqueous layer was extracted with EtOAc (3×75 mL). The combined organic layers were washed with a sat. aq. $Na_2SO_3$ solution (2×100 mL) then with brine (75 mL), dried over $Na_2SO_4$, filtered and concentrated under reduced pressure. The resulting crude was purified by flash chromatography over silica gel (15 μm, 25 g, Cyclohexane/EtOAc from 100:0 to 2:8 over 36 min, revealed with PMA) to afford B1-78-1-(S*) (124 mg, 24%) and B1-78-1-(R*) (156 mg, 36%) as colorless oils. The stereochemistry of both diastereomers was assigned arbitrarily.

LC/MS (AN01_001_021): Rt=9.19 min, 79.3%, [M−Boc+H]$^+$=268.08

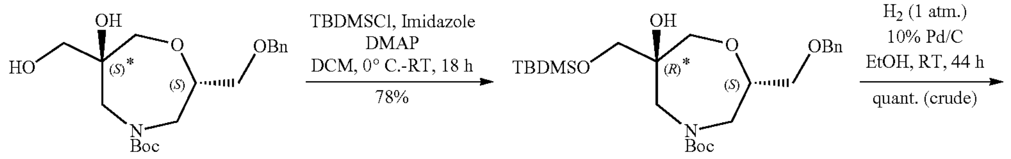
B1-78-1-(S)* B1-78-3-(R)*
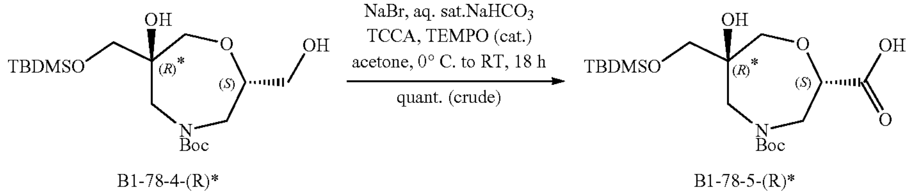
B1-78-4-(R)* B1-78-5-(R)*
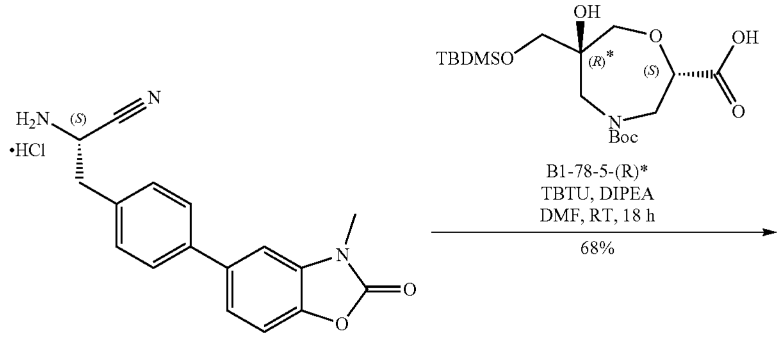
BB01
1 eq.
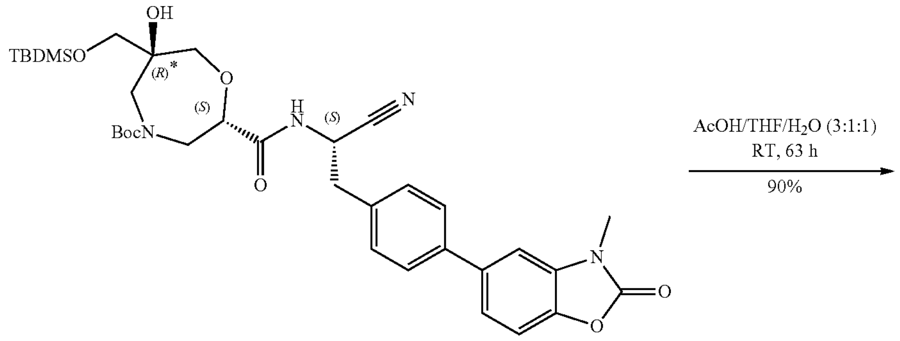
B1-78-7-(R)*
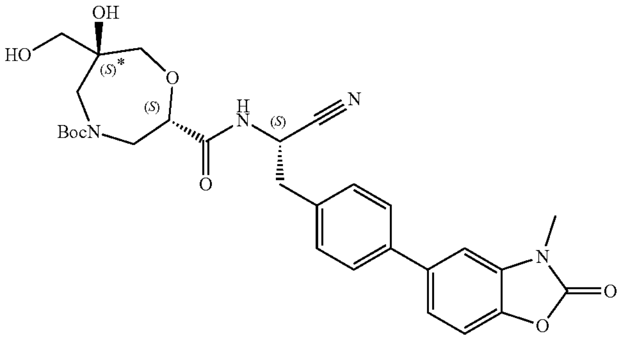
B1-78-10-(S)*

-continued

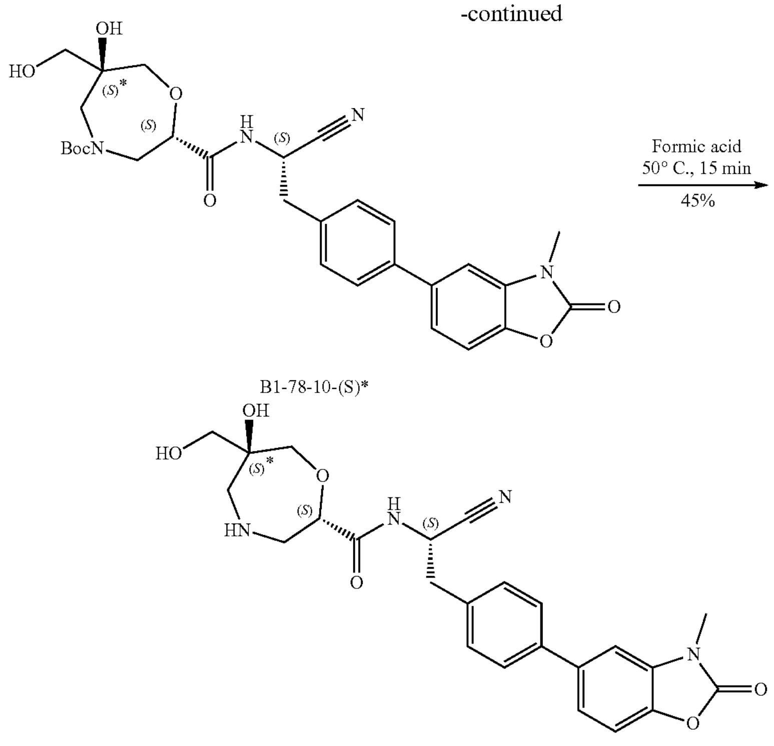

B1-78-10-(S)*

Compound 13 tert-butyl (2S,6R*)-2-[(benzyloxy)methyl]-6-{[(tert-butyldimethylsilyl)oxy]methyl}-6-hydroxy-1,4-oxazepane-4-carboxylate B1-78-3-(R)*

To a solution of B1-78-(S)* (1 eq., 238 mg, 0.65 mmol) in DCM (5 mL) were added imidazole (2 eq., 88.19 mg, 1.3 mmol) and DMAP (0.1 eq., 7.91 mg, 0.065 mmol) at room temperature. The resulting mixture was stirred at room temperature for 5 min then cooled to 0° C. before the dropwise addition of a solution of TBDMSCl (2 eq., 195.25 mg, 0.22 mL, 1.3 mmol) in DCM (1 mL). The resulting mixture was allowed to warm to room temperature and stirred for 18 h. The reaction mixture was concentrated under reduced pressure then diluted with water (30 mL) and EtOAc (40 mL). The layers were separated and the aqueous layer was extracted with EtOAc (3×40 mL). The combined organic layers were washed with brine (60 mL), dried over $Na_2SO_4$, filtered and concentrated under reduced pressure. The resulting crude was purified by flash chromatography over silica gel (15 μm, 40 g, Cyclohexane/EtOAc from 100:0 to 8:2 over 42 min, revealed with PMA) to afford B1-78-3-(R)* (243 mg, 78%) as colorless oil.

LC/MS (AN01_001_012): Rt=3.26 min, 72.5%, $[M-Boc+H]^+$=382.6.

tert-butyl (2S,6R*)-6-{[(tert-butyldimethylsilyl)oxy]methyl}-6-hydroxy-2-(hydroxymethyl)-1,4-oxazepane-4-carboxylate B1-78-4-(R)*

Starting from B1-78-3-(R)* (1 eq., 365 mg, 0.76 mmol), using general procedure D, B1-78-4-(R)* was obtained as a colorless oil (296 g, 100%).

LC/MS (AN01_001_021): Rt=11.11 min, non-UV active, $[M-Boc+H]^+$=292.13

(2S,6R*)-4-[(tert-butoxy) carbonyl]-6-{[(tert-butyldimethylsilyl)oxy]methyl}-6-hydroxy-1,4-oxazepane-2-carboxylic acid B1-78-5-(R)*

Starting from B1-78-4-(R)* (1 eq., 211.0 mg, 0.54 mmol), using general procedure E, B1-78-5-(R)* was obtained as a colorless gum (218 mg, 100%).

LC/MS (AN01_001_021): Rt=10.84 min, 91%, $[M-Boc+H]^+$=306.1 tert-butyl (2S,6R*)-6-{[(tert-butyldimethylsilyl)oxy]methyl}-2-{[(1S)-1-cyano-2-[4-(3-methyl-2-oxo-2,3-dihydro-1,3-benzoxazol-5-yl)phenyl]ethyl]carbamoyl}-6-hydroxy-1,4-oxazepane-4-carboxylate B1-78-7-(R)*

Starting from BB01 (1 eq., 167.1 mg, 0.51 mmol) and B1-78-5-(R)* (1.05 eq., 260 mg, 0.51 mmol), using general procedure B, B1-78-7-(R)* was obtained as a light yellow solid (220 mg, 70%) after purification by silica gel flash chromatography (regular SiOH, 50 μm, 40 g, cyclohexane/EtOAc from 100:0 to 20:80 over 42 min).

LC/MS (AN01_001_021): Rt=12.38 min, 99.14%, $[M-Boc+H]^+$=581.32 tert-butyl (2S,6S*)-2-{[(1S)-1-cyano-2-[4-(3-methyl-2-oxo-2,3-dihydro-1,3-benzoxazol-5-yl)phenyl]ethyl]carbamoyl}-6-hydroxy-6-(hydroxymethyl)-1,4-oxazepane-4-carboxylate B1-78-10-(S)*

To a solution of B1-78-7-(R)* (1 eq., 130 mg, 0.19 mmol) in a mixture of THF (0.65 mL) and water (0.65 mL) was added AcOH (178.23 eq., 2043.6 mg, 1.95 mL, 34.031 mmol) dropwise at room temperature. The resulting solution was stirred at room temperature for 63 h. The reaction mixture was poured dropwise into a sat. aq. sol. of $NaHCO_3$ (50 mL) at 0° C. (diluted with ~15 mL of EtOAc when bubbling/foaming). The mixture was stirred for 10 minutes (pH ~8) at 0° C. then diluted with water (25 mL) and EtOAc (60 mL). The layers were separated and the aqueous layer was extracted with EtOAc (3×100 mL). The combined organic layers were washed with a sat. aq. sol. of $NaHCO_3$ (75 mL), then with brine (100 mL) dried over $Na_2SO_4$, filtered and concentrated under reduced pressure. The resulting residue was purified by flash chromatography over silica gel (50 μm, 12 g, Cyclohexane/EtOAc from 8:2 to 0:100 over 42 min) to afford B1-78-10-(S)* (97 mg, 90%) as a white solid.

LC/MS (AN01_001_012): Rt=2.27 min, 100%, $[M-tBu+H]^+$=511.2.

(2S,6S*)—N-[(1S)-1-cyano-2-[4-(3-methyl-2-oxo-2,3-dihydro-1,3-benzoxazol-5-yl)phenyl]ethyl]-6-hydroxy-6-(hydroxymethyl)-1,4-oxazepane-2-carboxamide Starting from B1-78-10-(S)* (1 eq., 71 mg, 0.13 mmol), using general procedure C, (2S,6S*)—N-[(1S)-1-cyano-2-[4-(3-methyl-2-oxo-2,3-dihydro-1,3-benzoxazol-5-yl)phenyl]ethyl]-6-hydroxy-6-(hydroxymethyl)-1,4-oxazepane-2-carboxamide was obtained as a white solid (26 mg, 45%) after purification by silica gel flash chromatography (50 μm, 12 g, gradient: DCM/MeOH from 100:0 to 80:20 over 42 min).

LC/MS (AN01_001_026): Rt=6.38 min, 100%, $[M+H]^+$=467.39.

$^1$H NMR (400 MHZ, DMSO) δ 8.55 (d, J=8.5 Hz, 1H), 7.67-7.63 (m, 2H), 7.58-7.55 (m, 1H), 7.43-7.36 (m, 4H), 5.04-4.96 (m, 1H), 4.60-4.50 (m, 1H), 4.44 (s, 1H), 4.00 (dd, J=8.8, 3.8 Hz, 1H), 3.78 (d, J=12.4 Hz, 1H), 3.44 (d, J=12.4 Hz, 1H), 3.40 (s, 3H), 3.33-3.12 (m, 4H), 3.05 (dd, J=14.0, 3.8 Hz, 1H), 2.62 (s, 2H), 2.37 (dd, J=14.0, 8.8 Hz, 1H).

Example 14: Preparation of (2S)-6-allyl-N—((S)-1-cyano-2-(4-(3-methyl-2-oxo-2,3-dihydrobenzo[d]oxazol-5-yl)phenyl)ethyl)-6-hydroxy-1,4-oxazepane-2-carboxamide (Compound 14)

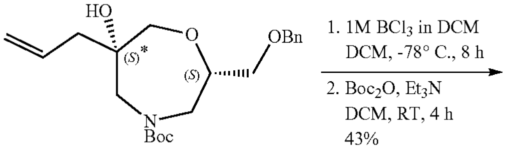

B1-80-1-(S)*

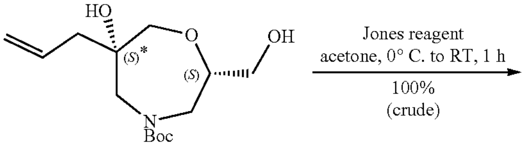

B1-80-2-(S)*

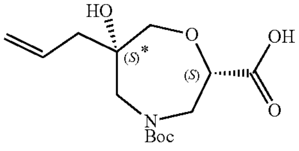

B1-80-3-(S)*

-continued

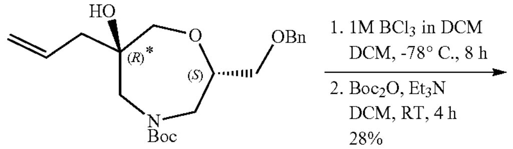

B1-80-1-(R)*

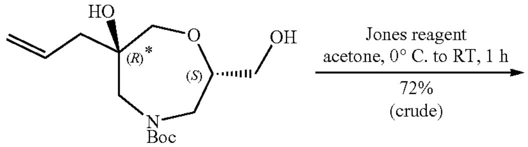

B1-80-2-(R)*

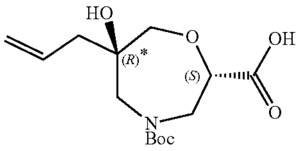

B1-80-3-(R)*

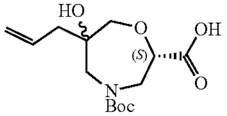

B1-80-3
(diastereomeric ratio:~1:1)

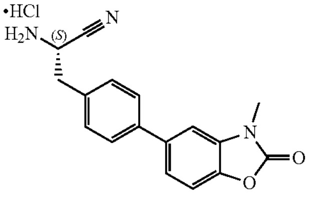

TBTU, DIPEA
DMF, RT, 18 h
36%

BB01
1 eq.

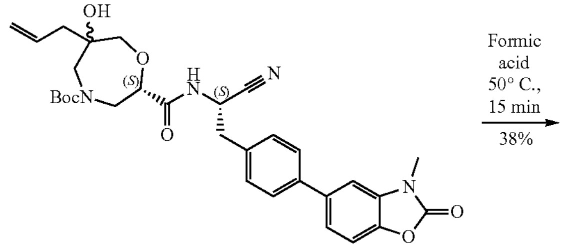

B1-80-5
(diastereomeric ratio: 77:23)

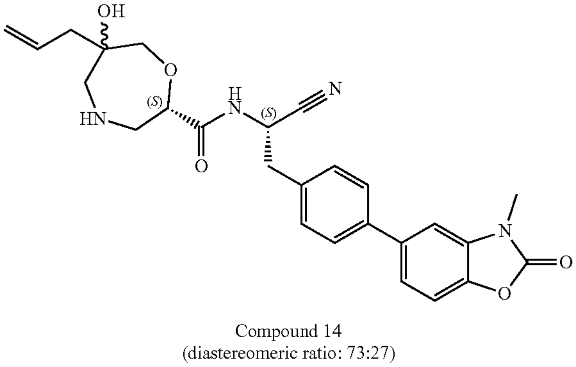

Compound 14
(diastereomeric ratio: 73:27)

tert-butyl (2S,6S*)-6-hydroxy-2-(hydroxymethyl)-6-(prop-2-en-1-yl)-1,4-oxazepane-4-carboxylate B1-80-2-(S)*

To a solution of B1-80-1-(S)* (1 eq., 220 mg, 0.58 mmol) in DCM (2.91 mL) at −78° C. was added $BCl_3$ 1M in DCM (5 eq., 2.91 mL, 2.91 mmol). The reaction mixture was stirred at −78° C. for 6 h. The RM was quenched with MeOH (10 mL), then concentrated under reduced pressure to afford crude material (131 mg) as a colorless gum.

To a solution of crude material (1 eq., 131 mg, 0.53 mmol) and $Et_3N$ (3 eq., 160 mg, 0.22 mL, 1.58 mmol) in DCM (0.6 mL) and MeOH (0.6 mL), was added a solution of $Boc_{20}$ (1 eq., 115.027 mg, 0.11 mL, 0.53 mmol). The reaction mixture was stirred at RT for 18 h. The reaction mixture was diluted with water (25 mL) and extracted with EtOAc (3×25 mL). The combined organic layers were washed with brine (25 mL), dried over $Na_2SO_4$, filtered and concentrated to dryness under reduced pressure to afford the crude (120 mg) as a yellowish oil. The crude was purified by flash chromatography over silica gel (50 μm, 12 g Interchim, dry loading (silica), mobile phase gradient: cyclohexane/EtOAc from 100/0 to 60/40 over 45 min) to afford B1-80-2-(S)* as a colorless oil (105 mg, 43% over two steps)

LC/MS (AN_01_001_012): Not UV active, Rt=2.02 min, ND, $[M-{}^tBu+H]^+$=232.1

(2S,6S*)-4-[(tert-butoxy) carbonyl]-6-hydroxy-6-(prop-2-en-1-yl)-1,4-oxazepane-2-carboxylic acid B1-80-3-(S)*

To a solution of B1-80-2-(S)* (1 eq., 80 mg, 0.28 mmol) in acetone (2.78 mL) was added Jones reagent (2.5 eq., 0.35 mL, 0.7 mmol) at 0° C. The solution was stirred at RT for 1 h, then isopropanol (3 mL) was added at RT and the reaction mixture was stirred at RT for 30 min. DCM (10 mL) and 1 M HCl (5 mL) were added. The two phases were separated, and the aqueous layer was extracted with DCM (2×10 mL). The combined organic layers were dried over $Na_2SO_4$, filtered and concentrated to dryness under reduced pressure to afford crude material B1-80-3-(S)*as a colorless gum (84.0 mg, 100%). The crude was used as such in the next experiment without further purification.

LC/MS (AN_01_001_012): Not UV active, Rt=2.01 min, ND, [M−H]−=300.1 tert-butyl (2S,6R*)-6-hydroxy-2-(hydroxymethyl)-6-(prop-2-en-1-yl)-1,4-oxazepane-4-carboxylate B1-80-2-(R)*

To a solution of B1-80-1-(R)* (1 eq., 200 mg, 0.53 mmol) in DCM (2.60 mL) at −78° C. was added $BCl_3$ 1M in DCM (5 eq., 2.65 mL, 2.65 mmol). The reaction mixture was stirred at −78° C. for 6 h. The reaction mixture was quenched with MeOH (10 mL), then concentrated under reduced pressure to afford crude material (105 mg) as a colorless gum.

To a solution of crude material (1 eq., 100 mg, 0.45 mmol) and $Et_3N$ (3 eq., 136 mg, 0.19 mL, 1.34 mmol) in DCM (0.5 mL) and MeOH (0.5 mL), was added a solution of $Boc_2O$ (1 eq., 97.56 mg, 0.096 mL, 0.45 mmol). The reaction mixture was stirred at RT for 18 h, then was diluted with water (25 mL) and extracted with EtOAc (3×25 mL). The combined organic layers were washed with brine (25 mL), dried over $Na_2SO_4$, filtered and concentrated to dryness under reduced pressure to afford the crude (71 mg) as a yellowish oil. The crude was purified by flash chromatography over silica gel (50 μm, 4 g Interchim, dry loading (silica), mobile phase gradient: cyclohexane/EtOAc from 100/0 to 50/50 over 60 min) to afford B1-80-2-(R)* as a colorless oil (42.2 mg, 28% over two steps).

LC/MS (AN_01_001_012): Not UV active, Rt=2.08 min, ND, $[M-{}^tBu+H]^+$=232.3

(2S,6R*)-4-[(tert-butoxy) carbonyl]-6-hydroxy-6-(prop-2-en-1-yl)-1,4-oxazepane-2-carboxylic acid B1-80-3-(R)*

To a solution of B1-80-2-(R)* (1 eq., 40 mg, 0.14 mmol) in acetone (1.39 mL) was added Jones reagent (2.5 eq., 0.17 mL, 0.35 mmol) at 0° C. The solution was stirred at RT for 1 h, then isopropanol (3 mL) was added at RT and the reaction mixture was stirred at RT for 30 min. DCM (10 mL) and 1 M HCl (5 mL) were added. The two phases were separated, and the aqueous layer was extracted with DCM (2×10 mL). The combined organic layers were dried over $Na_2SO_4$, filtered and concentrated to dryness under reduced pressure to afford B1-80-3-(R)* crude material as a colorless gum (30.2 mg, 72%). The crude was used as such in the next experiment without further purification.

LC/MS (AN_01_001_061): Not UV active, Rt=1.34 min, ND, [M−H]=300.3.

tert-butyl (2S)-2-{[(1S)-1-cyano-2-[4-(3-methyl-2-oxo-2,3-dihydro-1,3-benzoxazol-5-yl)phenyl]ethyl] carbamoyl}-6-hydroxy-6-(prop-2-en-1-yl)-1,4-oxazepane-4-carboxylate B1-80-5

A 50:50 mixture of B1-80-3-(S)* and B1-80-3-(R)* was prepared and used as such in the peptide coupling's step.

Starting from BB01 (1 eq., 52.1 mg, 0.16 mmol) and the mixture of B1-80-3-(S)* and B1-80-3-(R)* (1.05 eq., 50.0 mg, 0.17 mmol), using general procedure B, was obtained B1-80-5 (33.0 mg, 36%) after purification by flash chromatography over silica gel (irregular SiOH, 50 μm, 12 g Interchim, dry loading (silica), mobile phase gradient: cyclohexane/EtOAc from 100/0 to 40/60 over 45 min) as a yellow solid of diastereomers (ratio, 77:23).

LC/MS (AN_01_001_061): Rt=1.63 min, 93.79, $[M-{}^tBu+H]^+$=521.6

(2S)—N-[(1S)-1-cyano-2-[4-(3-methyl-2-oxo-2,3-dihydro-1,3-benzoxazol-5-yl)phenyl]ethyl]-6-hydroxy-6-(prop-2-en-1-yl)-1,4-oxazepane-2-carboxamide Starting from B1-80-5 (1 eq., 30.0 mg, 0.05 mmol) and using general procedure C, (2S)—N-[(1S)-1-cyano-2-[4-(3-methyl-2-oxo-2,3-dihydro-1,3-benzoxazol-5-yl)phenyl] ethyl]-6-hydroxy-6-(prop-2-en-1-yl)-1,4-oxazepane-2-carboxamide was obtained as a white solid of diastereomers (ratio, 73:27) (9.30 mg, 38%) after purification by flash chromatography over silica gel (regular SiOH, 50 μm, 4 g Interchim, dry loading (silica), mobile phase gradient: DCM/MeOH from 100/0 to 92/08 over 40 min), co-evaporation with DCM and vacuum drying at 40° C. for 48 h.

LC/MS (AN_01_001_021): Rt=7.11 and 7.23 min, 20.55 and 73.99%, $[M+H]^+$=477.41

$^1H$ NMR (400 MHZ, DMSO) δ 8.70-8.49 (m, 1H), 7.68-7.61 (m, 2H), 7.59-7.52 (m, 1H), 7.45-7.32 (m, 4H), 5.94-5.79 (m, 1H), 5.11-4.96 (m, 3H), 4.57-4.48 (m, 1H), 4.05-3.93 (m, 1H), 3.63-3.50 (m, 1H), 3.49-3.37 (m, 4H), 3.25-3.12 (m, 2H), 3.12-3.00 (m, 1H), 2.68-2.56 (m, 1H), 2.54-2.46 (m, 1H), 2.43-2.34 (m, 1H), 2.21-2.06 (m, 2H), one missing proton (NH).

Example 15: Preparation of (2S)—N—((S)-1-cyano-2-(4-(3-methyl-2-oxo-2,3-dihydrobenzo[d]oxazol-5-yl)phenyl)ethyl)-6-hydroxy-6-(pyridin-2-ylmethyl)-1,4-oxazepane-2-carboxamide (Compound 15)

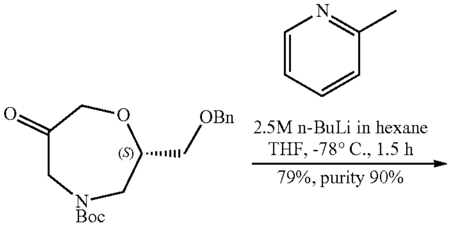

B1-2-14

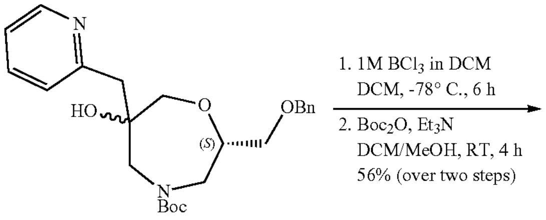

B1-88-2
(diastereomeric ratio: 65:35)

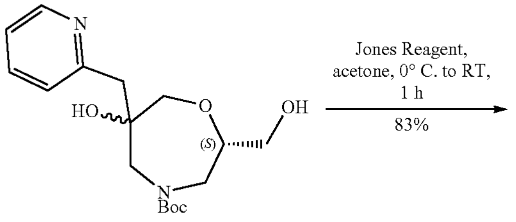

B1-88-3
(diastereomeric ratio: 74:26)

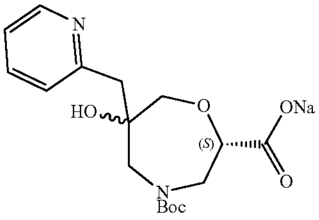

B1-88-4

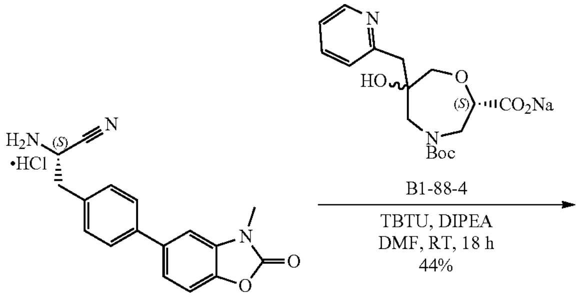

BB01

-continued

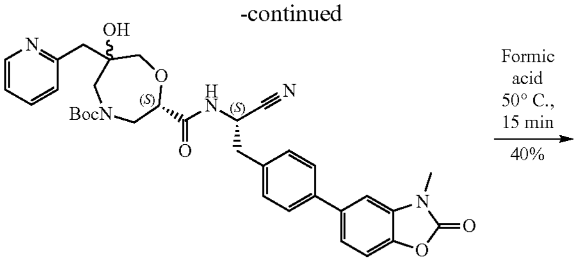

B1-88-5
(diastereomeric ratio: 82:18)

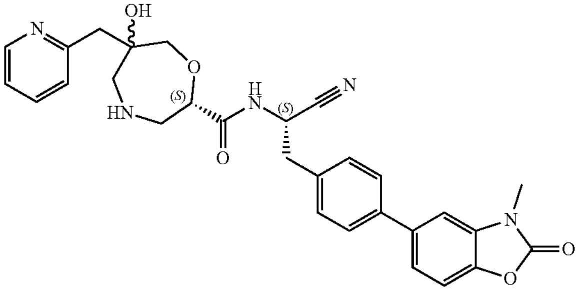

Compound 15
(diastereomeric ratio: 82:18)

tert-butyl (2S)-2-[(benzyloxy)methyl]-6-hydroxy-6-(pyridin-2-ylmethyl)-1,4-oxazepane-4-carboxylate B1-88-2

To a solution of 2-picoline (1 eq., 55.53 mg, 0.059 mL, 0.6 mmol) in THF (3.86 mL) was added butyllithium 2.5 M in hexane (0.85 eq., 0.203 mL, 0.507 mmol) at −78° C. The solution was stirred at −78° C. for 0.5 h. A solution of I1-2-14 (1.25 eq., 250 mg, 0.75 mmol) in THF (1.54 mL) was added and the reaction mixture was stirred at −78° C. for 1 h. The reaction mixture was quenched with sat. $NH_4Cl$ (50 mL) and extracted with EtOAc (3×50 mL). The combined organic layers were washed with brine (50 mL), dried over $Na_2SO_4$, filtered and concentrated to dryness under reduced pressure to afford crude material (288 mg) as a yellowish oil. The crude was purified by flash chromatography over silica gel (irregular SiOH, 50 μm, 12 g Interchim, dry loading (silica), mobile phase gradient: cyclohexane/EtOAc from 100/0 to 50/50 over 40 min) to afford B1-88-2 as a colorless oil (170 mg, 79% based on nBuLi as limiting reagent).

LC/MS (AN_01_001_021_DEDL): Rt=8.00 and 8.37 min, 88.02 and 11.78%, $[M+H]^+$=429.53 tert-butyl (2S)-6-hydroxy-2-(hydroxymethyl)-6-(pyridin-2-ylmethyl)-1,4-oxazepane-4-carboxylate B1-88-3

To a solution of B1-88-2 (1 eq., 300 mg, 0.7001 mmol) in DCM (3.5 mL) at −78° C. was added $BCl_3$ 1M in DCM (5 eq., 3.5 mL, 3.5 mmol). The reaction mixture was stirred at −78° C. for 6 h. The reaction mixture was quenched with MeOH (10 mL), then concentrated under reduced pressure to crude material (253 mg) as a white solid. The crude was used as such without further purification in the next step.

To a solution of crude (1 eq., 210 mg, 0.67 mmol) and $Et_3N$ (5 eq., 341.43 mg, 0.47 mL, 3.37 mmol) in DCM (0.77 mL) and MeOH (0.77 mL), was added a solution of $Boc_{20}$ (1 eq., 147.28 mg, 0.14 mL, 0.67 mmol). The RM was stirred at RT for 4 h. The reaction mixture was diluted with water (20 mL) and extracted with EtOAc (3×20 mL). The combined organic layers were washed with brine (20 mL), dried over $Na_2SO_4$, filtered and concentrated to dryness under reduced pressure to afford crude (193 mg) as a yellowish oil. The crude was purified by flash chromatography over silica gel (50 μm, 12 g Interchim, dry loading (silica), mobile phase gradient: cyclohexane/EtOAc from 100/0 to 0/100 over 50 min) to afford B1-88-3 as a colorless gum (138 mg, 56% over two steps).

LC/MS (AN_01_001_061): Rt=0.96 min, 100%, $[M+H]^+$=339.8

4-tert-butyl 2-sodium (2S)-6-hydroxy-6-(pyridin-2-ylmethyl)-1,4-oxazepane-2,4-dicarboxylate B1-88-4

To a solution of B1-88-3 (1 eq., 50 mg, 0.15 mmol) in acetone (1.48 mL) was added Jones reagent (2.5 eq., 0.18 mL, 0.37 mmol) at 0° C. The solution was stirred at RT for 1 h. Isopropanol (2 mL) was added at RT and the RM was stirred at RT for 30 min. An aqueous solution of 10% $Na_2CO3$ was added until pH~7-8. The solution was concentrated under reduced pressure. The residue was dissolved in DCM (5 mL), sonicated, centrifugated and the supernatant was concentrated under reduced pressure to afford B1-88-4 as a pale-yellow solid (45.7 mg, 83%, crude). The crude was used as such as a sodium salt in the next step.

LC/MS (AN_01_001_061): Rt=0.96 min, 100%, [M−Na+H]=353.6.

tert-butyl (2S)-2-{[(1S)-1-cyano-2-[4-(3-methyl-2-oxo-2,3-dihydro-1,3-benzoxazol-5-yl)phenyl]ethyl]carbamoyl}-6-hydroxy-6-(pyridin-2-ylmethyl)-1,4-oxazepane-4-carboxylate B1-88-5

Starting from BB01 (1 eq., 33.6 mg, 0.102 mmol) and B1-88-4 (1.05 eq., 40.0 mg, 0.107 mmol) and using general procedure B, B1-88-5 was obtained as an orange solid (28.1 mg, 44%) after purification by flash chromatography over silica gel (50 μm, 12 g, cyclohexane/EtOAc from 100:0 to 25:75 in 50 min).

LC/MS (AN_01_001_061): Rt=1.36 min, 76.48%, $[M+H]^+$=628.23

(2S)—N-[(1S)-1-cyano-2-[4-(3-methyl-2-oxo-2,3-dihydro-1,3-benzoxazol-5-yl)phenyl]ethyl]-6-hydroxy-6-(pyridin-2-ylmethyl)-1,4-oxazepane-2-carboxamide Starting from B1-88-5 (1 eq., 50.0 mg, 0.08 mmol) and using general procedure C, (2S)—N-[(1S)-1-cyano-2-[4-(3-methyl-2-oxo-2,3-dihydro-1,3-benzoxazol-5-yl)phenyl]ethyl]-6-hydroxy-6-(pyridin-2-ylmethyl)-1,4-oxazepane-2-carboxamide was obtained as a white solid (16.8 mg, 40%) after purification by flash chromatography over silica gel (regular SiOH, 15 μm, 4 g Interchim, dry loading (silica), mobile phase gradient: DCM/MeOH from 100/0 to 92/8 over 35 min), then vacuum-dried at 40° C. for 18 h.

LC/MS (AN_01_001_021): Rt=6.45 and 6.51 min, 82 and 18%, $[M+H]^+$=528.51

$^1H$ NMR (400 MHZ, DMSO) δ 9.21 (d, J=8.4 Hz, 1H), 8.52-8.43 (m, 1H), 7.75-7.69 (m, 1H), 7.68-7.62 (m, 2H), 7.57-7.53 (m, 1H), 7.44-7.35 (m, 5H), 7.29-7.21 (m, 1H), 5.14-4.88 (m, 2H), 4.06-3.96 (m, 1H), 3.63-3.44 (m, 1H), 3.42-3.35 (m, 4H), 3.28-3.14 (m, 2H), 3.12-2.97 (m, 2H), 2.89-2.79 (m, 1H), 2.78-2.70 (m, 1H), 2.69-2.62 (m, 1H), 2.48-2.44 (m, 1H), one missing proton (NH).

Example 16: Preparation of (8S)—N—((S)-1-cyano-2-(4-(3-methyl-2-oxo-2,3-dihydrobenzo[d]oxazol-5-yl)phenyl)ethyl)-1,7-dioxa-10-azaspiro[4.6]undecane-8-carboxamide (Compound 16)

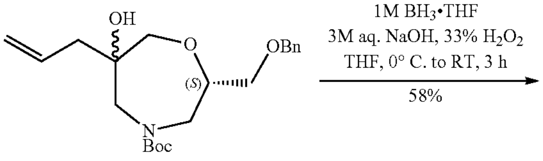

B1-80-1
(diastereomeric ratio: ~1:1)

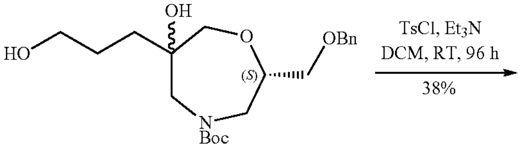

B1-89-3

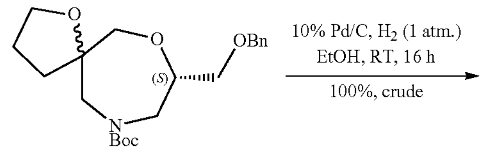

B1-89-1
(diastereomeric ratio: 55:45)

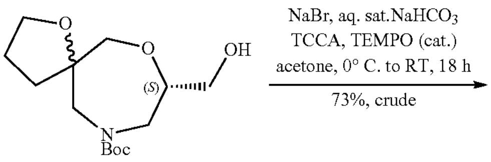

B1-89-5

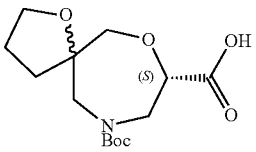

B1-89-6

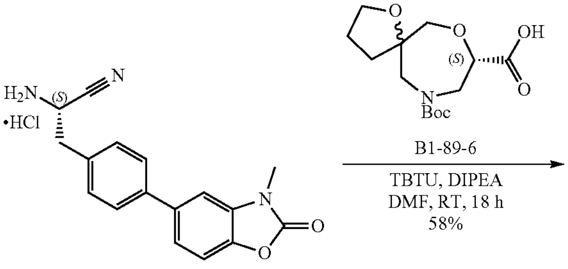

B1-89-6

BB01

-continued

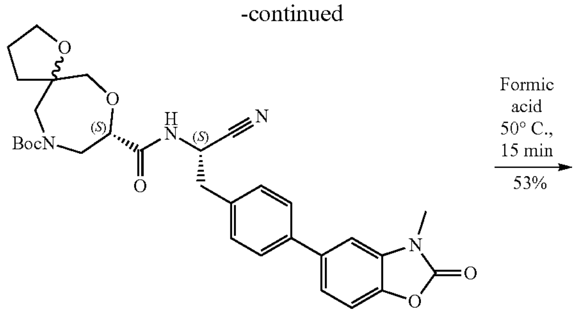

B1-89-7
(diastereomeric ratio: 55:45)

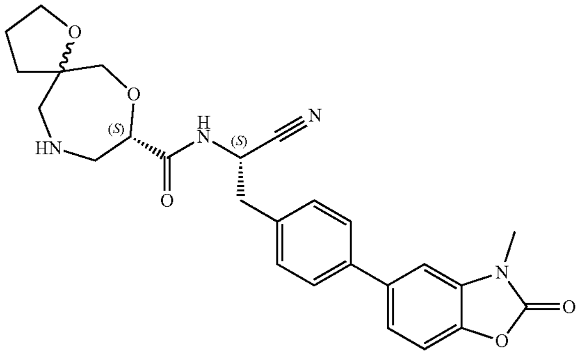

Compound 16
(diastereomeric ratio: 56:44)

tert-butyl (2S)-2-[(benzyloxy)methyl]-6-hydroxy-6-(3-hydroxypropyl)-1,4-oxazepane-4-carboxylate B1-89-3

Starting from a 50:50 mixture of B1-80-1 (1 eq., 300 mg, 0.79 mmol) and using general procedure I, B1-89-3 (182 mg, 0.46 mmol, 58%) was obtained as a yellow oil of diastereomers after purification by flash chromatography over silica gel (regular SiOH, 50 μm, 12 g, dry loading (silica), mobile phase gradient: Cyclo/EtOAc from 10/0 to 0/10 over 40 min).

LC/MS (AN_01_001_012): Rt=2.38 and 2.43 min, 44.08 and 48.96%, $[M-{}^{t}Bu+H]^{+}$=340.7.

tert-butyl (8S)-8-[(benzyloxy)methyl]-1,7-dioxa-10-azaspiro[4.6]undecane-10-carboxylate B1-89-1

To a solution of B1-89-3 (1 eq., 180 mg, 0.46 mmol) and DMAP (0.1 eq., 5.56 mg, 0.046 mmol) in $Et_3N$ (3 eq., 138.17 mg, 0.19 mL, 1.37 mmol) was added a solution of tosyl chloride (1.1 eq., 95.44 mg, 0.5006 mmol) in DCM (3.034 mL). The reaction mixture was stirred at RT for 24 h. The reaction mixture was diluted with water (30 mL) and extracted with DCM (3×30 mL). The combined organic layers were washed with 1M HCl (2×30 mL) and brine (30 mL), dried over $Na_2SO_4$, filtered and concentrated to dryness under reduced pressure to afford crude yellow oil (109 mg). The crude was purified by flash chromatography over $SiO_2$ (50 μm, 12 g, cyclohexane/EtOAc 100:0 to 50:50 over 45 min) to afford B1-89-1 as a colorless oil of diastereomers (ratio 55:45, 66 mg, 38%).

LC/MS (AN_01_001_061): Rt=1.71 min, 100%, $[M+H]^{+}$=378.65 tert-butyl (8S)-8-(hydroxymethyl)-1,7-dioxa-10-azaspiro[4.6]undecane-10-carboxylate B1-89-5

Starting from B1-89-1 (1 eq., 65.0 mg, 0.17 mmol), using general procedure D, crude B1-89-5 was obtained as a colorless oil (49.5 mg, 100%) and was used as such without further purification.

LC/MS (AN01_001_026): Not UV active, Rt=7.15 min, ND, $[M-Boc+H]^{+}$=188.07.

(8S)-10-[(tert-butoxy) carbonyl]-1,7-dioxa-10-azaspiro[4.6]undecane-8-carboxylic acid B1-89-6

Starting from B1-89-5 (1 eq., 45.0 mg, 0.16 mmol), using general procedure E, crude B1-89-6 was obtained as a white solid (34.3 mg, 73%) and was used as such without further purification.

LC/MS (AN01_001_061): Not UV active, Rt=1.37 min, ND, $[M-{}^{t}Bu+H]^{+}$=246.2.

tert-butyl (8S)-8-{[(1S)-1-cyano-2-[4-(3-methyl-2-oxo-2,3-dihydro-1,3-benzoxazol-5-yl)phenyl]ethyl]carbamoyl}-1,7-dioxa-10-azaspiro[4.6]undecane-10-carboxylate B1-89-7

Starting from BB01 (1 eq., 33.5 mg, 0.101 mmol) and B1-89-6 (1.05 eq., 32.0 mg, 0.106 mmol) and using general procedure B, B1-89-7 was obtained as an orange gum of diastereomers (34.0 mg, 58%) after purification by flash chromatography over silica gel (50 μm, 12 g, cyclohexane/EtOAc from 100:0 to 25:75 in 45 min).

LC/MS (AN01_001_026): Rt=9.61 and 9.62 min, 44.69 and 52.14%, $[M-{}^{t}Bu+H]^{+}$=521.41.

(8S)—N-[(1S)-1-cyano-2-[4-(3-methyl-2-oxo-2,3-dihydro-1,3-benzoxazol-5-yl)phenyl]ethyl]-1,7-dioxa-10-azaspiro[4.6]undecane-8-carboxamide Starting from B2-1-1-(R)* (1 eq., 30.0 mg, 0.052 mmol) and using general procedure C, (8S)—N-[(1S)-1-cyano-2-[4-(3-methyl-2-oxo-2,3-dihydro-1,3-benzoxazol-5-yl)phenyl]ethyl]-1,7-dioxa-10-azaspiro[4.6]undecane-8-carboxamide was obtained as a white solid (13.2 mg, 53%) after purification by flash chromatography over silica gel (regular SiOH, 15 μm, 4 g Interchim, dry loading (silica), mobile phase gradient: DCM/MeOH from 100/0 to 95/5 over 40 min), then vacuum-dried at 40° C. for 18 h.

LC/MS (AN_01_001_021): Rt=7.10 and 7.21 min, 55.51 and 43.79%, $[M+H]^{+}$=477.40

$^{1}H$ NMR (400 MHZ, DMSO) § 8.68-8.49 (m, 1H), 7.71-7.61 (m, 2H), 7.60-7.54 (m, 1H), 7.45-7.32 (m, 4H), 5.07-4.95 (m, 1H), 4.07-3.92 (m, 1H), 3.81-3.53 (m, 4H), 3.40 (s, 3H), 3.27-3.13 (m, 2H), 3.13-3.01 (m, 1H), 2.77-2.67 (m, 1H), 2.61-2.53 (m, 1H), 2.48-2.34 (m, 2H), 1.89-1.67 (m, 3H), 1.60-1.41 (m, 1H).

Example 17: Preparation of (2S,6R)—N—((S)-1-cyano-2-(4-(3-methyl-2-oxo-2,3-dihydrobenzo[d]oxazol-5-yl)phenyl)ethyl)-6-hydroxy-6-(hydroxymethyl)-1,4-oxazepane-2-carboxamides (Compound 17)
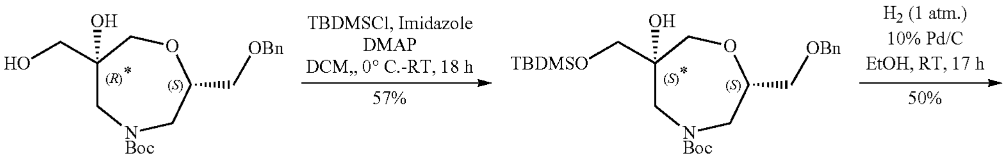
B1-78-1-(R)* B1-78-3-(S)*
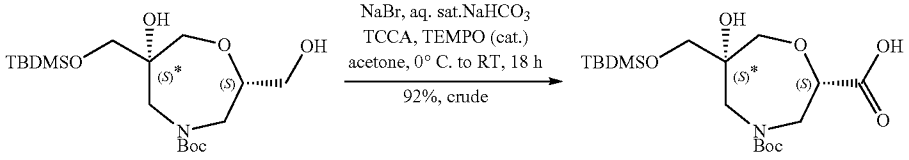
B1-78-4-(S)* B1-78-5-(S)*
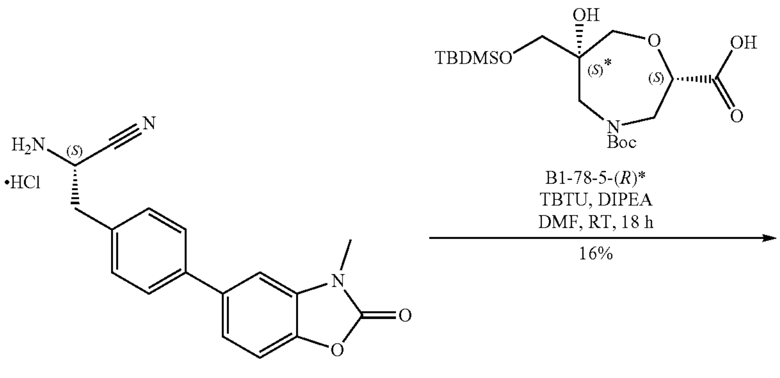
BB01
1 eq.
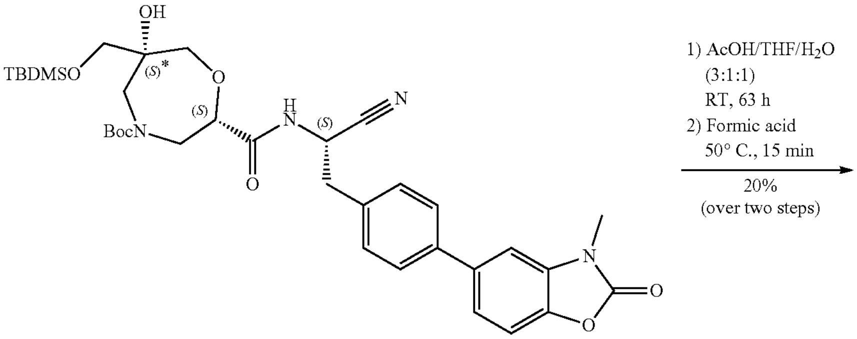
B1-78-7-(S)*

-continued

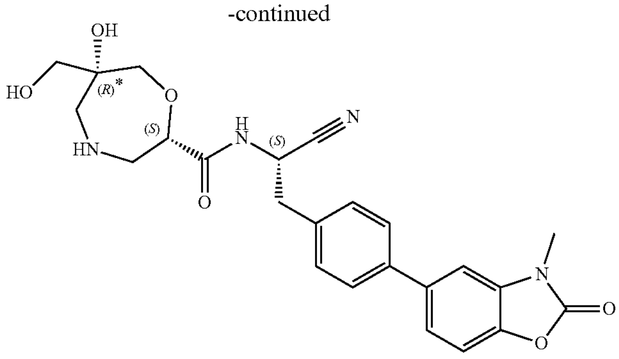

Compound 17 tert-butyl (2S,6S*)-2-[(benzyloxy)methyl]-6-{[(tert-butyldimethylsilyl)oxy]methyl}-6-hydroxy-1,4-oxazepane-4-carboxylate B1-78-3-(S)*

To a solution of B1-78-1-(R)* (1 eq., 345 mg, 0.94 mmol) in DCM (7 mL) were added successively imidazole (2 eq., 127.84 mg, 1.88 mmol), TBDMSCl (2 eq., 283.029 mg, 0.33 mL, 1.88 mmol) and DMAP (0.1 eq., 11.47 mg, 0.094 mmol) at RT. The resulting mixture was stirred for 17 h at RT. The reaction mixture was diluted with water (15 mL) and EtOAc (20 mL). The layers were separated, and the aqueous layer was extracted with EtOAc (2×25 mL). The combined organic layers were washed brine (30 mL), dried over $Na_2SO_4$, filtered and concentrated under reduced pressure to afford crude material (383 mg) as a yellow oil. The crude was purified by flash chromatography over silica gel (15 μm, 25 g, Cyclohexane/EA from 100:0 to 2:8 over 36 min, revealed with PMA) to afford B1-78-3-(S)* as colorless oil (256 mg, 57%).

LC/MS (AN_01_001_021): Rt=3.18 min, 100%, $[M-Boc+H]^+$=477.40.

tert-butyl (2S,6S*)-6-{[(tert-butyldimethylsilyl)oxy]methyl}-6-hydroxy-2-(hydroxymethyl)-1,4-oxazepane-4-carboxylate B1-78-4-(S)*

Starting from B1-78-3-(S)* (1 eq., 165 mg, 0.34 mmol), using general procedure D, crude B1-78-4-(S)* was obtained as a colorless oil (117 mg). The crude mixture was purified by flash chromatography over silica gel (irregular SiOH, 50 μm, 12 g Interchim, dry loading (silica), mobile phase gradient: Cyclo/EtOAc from 10/0 to 6/4 over 45 min). The fractions containing compound were combined, evaporated in vacuo and co-evaporated with DCM affording B1-78-4-(S)* as a white solid (68 mg, 50%).

LC/MS (AN_01_001_012): Not UV active, Rt=2.63 min, ND, $[M-{}^tBu+H]^+$=336.1.

(2S,6S*)-4-[(tert-butoxy) carbonyl]-6-{[(tert-butyldimethylsilyl)oxy]methyl}-6-hydroxy-1,4-oxazepane-2-carboxylic acid B1-78-5-(S)*

Starting from B1-78-4-(S)* (1 eq., 65.0 mg, 0.207 mmol), using general procedure E, crude B1-78-5-(S)* was obtained as a yellow gum (77.0 mg, 92%, crude) and was used as such without further purification.

LC/MS (AN01_001_012): Not UV active, Rt=2.63 min, ND, [M−H]−=404.2.

tert-butyl (2S,6S*)-6-{[(tert-butyldimethylsilyl)oxy]methyl}-2-{[(1S)-1-cyano-2-[4-(3-methyl-2-oxo-2,3-dihydro-1,3-benzoxazol-5-yl)phenyl]ethyl]carbamoyl}-6-hydroxy-1,4-oxazepane-4-carboxylate B1-78-7-(S)*

Starting from BB01 (1 eq., 59.6 mg, 0.18 mmol) and B1-78-5-(S)* (1.05 eq., 75.0 mg, 0.19 mmol) and using general procedure B, B1-78-7-(S)* was obtained as a yellow gum (19.7 mg, 16%) after purification by flash chromatography over silica gel (25 μm, 25 g, cyclohexane/EtOAc from 100:0 to 20:80 in 50 min).

LC/MS (AN01_001_012): Rt=2.92 min, 91.17%, $[M-{}^tBu+H]^+$=625.2.

(2S,6R*)—N-[(1S)-1-cyano-2-[4-(3-methyl-2-oxo-2,3-dihydro-1,3-benzoxazol-5-yl)phenyl]ethyl]-6-hydroxy-6-(hydroxymethyl)-1,4-oxazepane-2-carboxamide To a solution of B1-78-7-(S)* (1 eq., 33.0 mg, 0.0407 mmol) in a mixture of THF (0.14 mL) & H2O (0.14 mL) was added AcOH (178.23 eq., 435.76 mg, 0.42 mL, 7.26 mmol) dropwise at RT. The resulting solution was stirred at RT for 68 h. The reaction mixture was poured dropwise into a sat. aq. sol. of $NaHCO_3$ (50 mL) at 0° C. (diluted with ~15 mL of EtOAc when bubbling/foaming). The mixture was stirred for 10 minutes (pH ~8) at 0° C. then diluted with $H_2O$ (25 mL) and EtOAc (60 mL). The layers were separated, and the aqueous layer was extracted with EtOAc (3×100 mL). The combined organic layers were washed with a sat. aq. sol. of $NaHCO_3$ (75 mL), then with brine (100 mL) dried over $Na_2SO_4$, filtered and concentrated under reduced pressure to afford crude material as a pale-yellow gum (23.1 mg, 100%, crude). The crude was used as such in the next experiment.

Starting from the crude material (23.1 mg, 0.04 mmol) and using general procedure C, the target compound (2S,6R*)—N-[(1S)-1-cyano-2-[4-(3-methyl-2-oxo-2,3-dihydro-1,3-benzoxazol-5-yl)phenyl]ethyl]-6-hydroxy-6-(hydroxymethyl)-1,4-oxazepane-2-carboxamide was obtained as a white solid (5.00 mg, 20%, purity: 77.76%) after purification by preparative HPLC (Method:Eluant:Water+0.1% TFA/Acetonitrile; Gradient: from 15 to 30% acetonitrile in water+0.1% TFA in 20 min; Flow Rate: 43 mL/min over 28 min), column: XBridge C18 (30×150 (5 μm)). The fractions containing compound were combined and ACN was evaporated in vacuo. The resulting solution containing water was basified with solid $NaHCO_3$ until pH~8. The aqueous layer was extracted with DCM (3×200 mL). The combined organic layers were dried over $Na_2SO_4$, filtered, concentrated to dryness under reduced pressure and the residue was freeze-dried using a mixture of ACN/water (1:10).

LC/MS (AN_01_001_026_DEDL): Rt=6.72 min, 77.76%, $[M+H]^+$=467.41

$^1$H NMR (400 MHz, DMSO) δ 8.69 (d, J=8.5 Hz, 1H), 8.09 (s, 0H), 7.69-7.61 (m, 2H), 7.60-7.53 (m, 1H), 7.44-7.28 (m, 4H), 5.05-4.94 (m, 1H), 4.47 (s, 1H), 4.26-4.20 (m, 1H), 3.94 (dd, J=8.5, 4.7 Hz, 1H), 3.73-3.62 (m, 1H), 3.40 (s, 3H), 3.22-3.16 (m, 2H), 3.04 (dd, J=13.9, 4.6 Hz, 1H), 2.80 (d, J=13.5 Hz, 1H), 2.21-2.12 (m, OH), 2.05-1.94 (m, 1H), 0.93-0.80 (m, 5H).

Example 18: Preparation of (2S,6S)—N—((S)-1-cyano-2-(4-(3-methyl-2-oxo-2,3-dihydrobenzo[d]oxazol-5-yl)phenyl)ethyl)-6-hydroxy-1,4-oxazocane-2-carboxamide (Compound 18-A) and (2S,7S)—N—((S)-1-cyano-2-(4-(3-methyl-2-oxo-2,3-dihydrobenzo[d]oxazol-5-yl)phenyl)ethyl)-7-hydroxy-1,4-oxazocane-2-carboxamide (Compound 18-B)

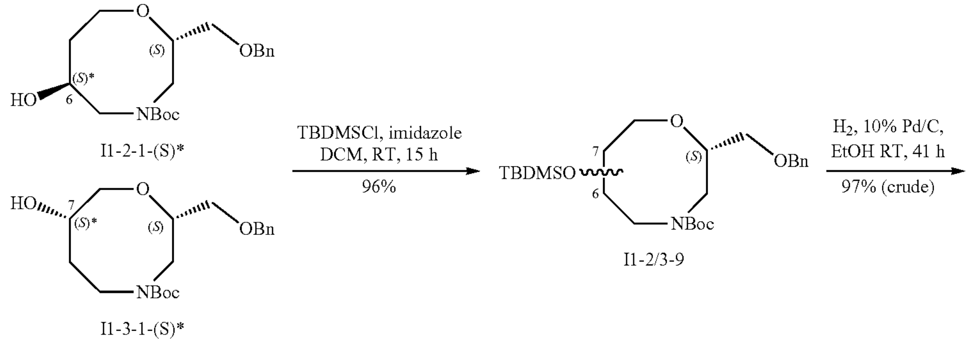

I1-2-1-(S)*
I1-3-1-(S)*
I1-2/3-9

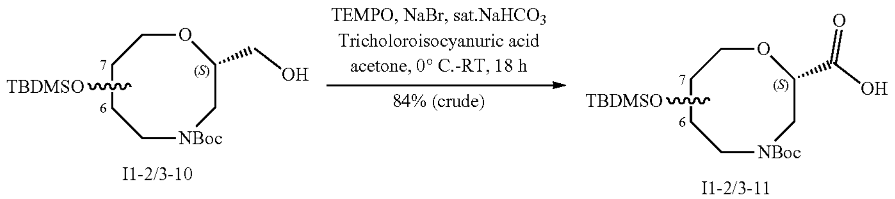

I1-2/3-10
I1-2/3-11

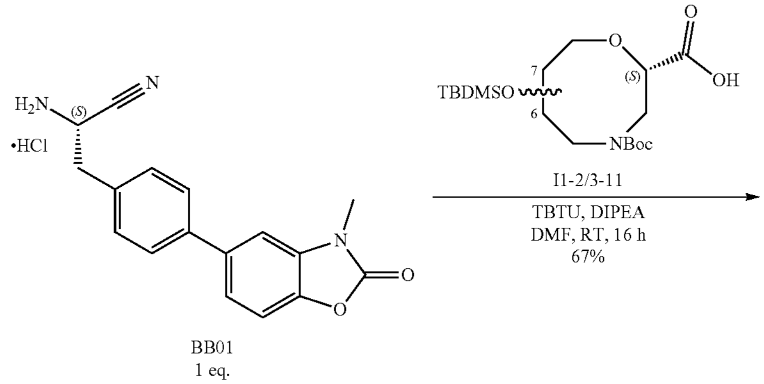

BB01
1 eq.

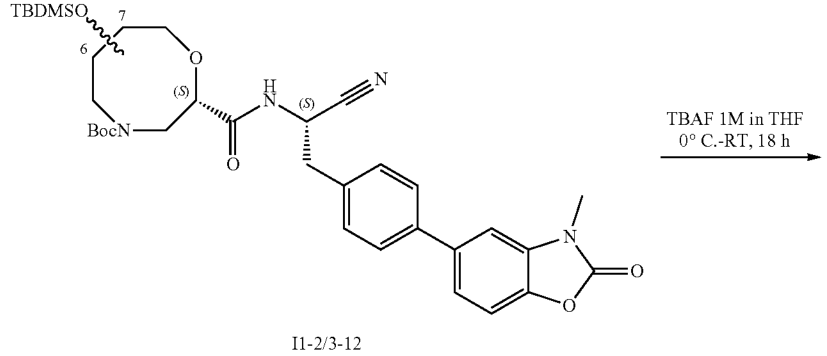

I1-2/3-12

-continued
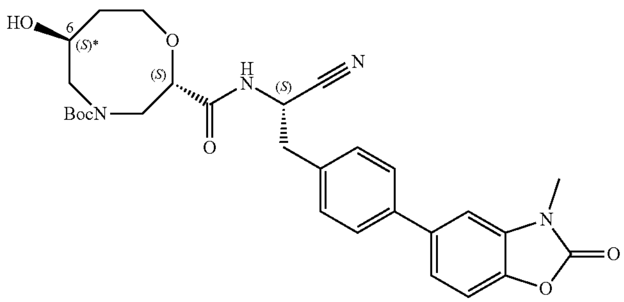
I1-2-13
(47%)
+
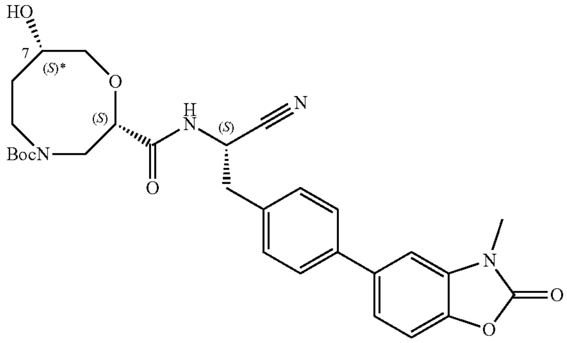
I1-3-1
(47%)
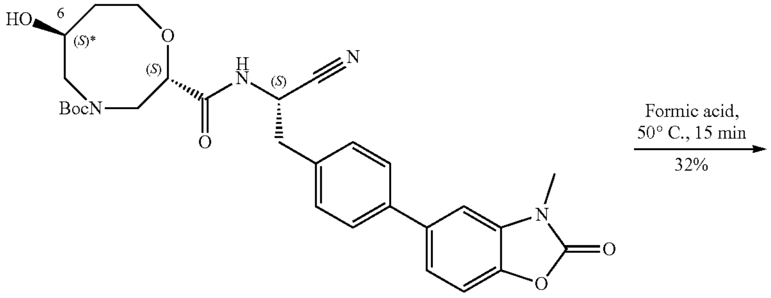
I1-2-13
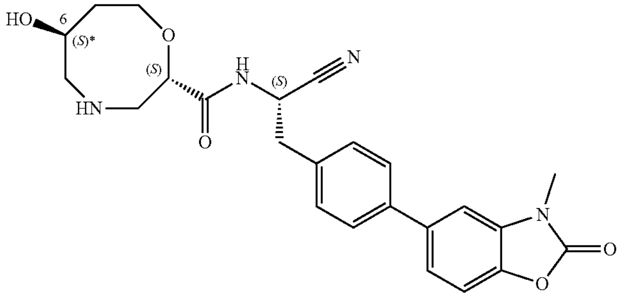
Compound 18-A -continued

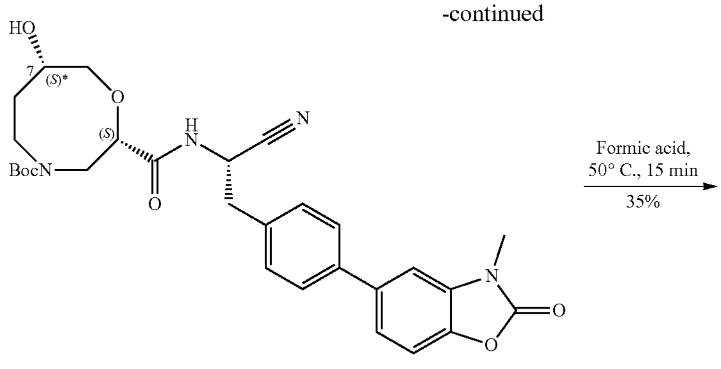

I1-3-1

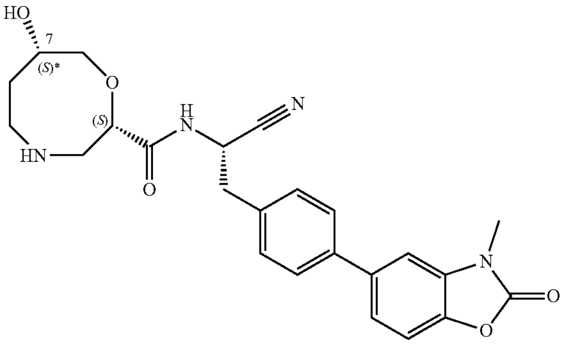

Compound 18-B tert-butyl (2S,6S*)-2-[(benzyloxy)methyl]-6-[(tert-butyldimethylsilyl)oxy]-1,4-oxazocane-4-carboxylate I1-2-9 and tert-butyl (2S,7S)-2-[(benzyloxy)methyl]-7-[(tert-butyldimethylsilyl)oxy]-1,4-oxazocane-4-carboxylate 11-3-9.

To a solution of a mixture of I1-2/3-1-(S)* (1 eq., 0.5 g, 1.303 mmol, 92% of purity) in DCM (7.5 mL) were added TBDMSCl (1.5 eq., 0.29 g, 0.34 mL, 1.95 mmol) and imidazole (3 eq., 0.27 g, 3.91 mmol) at RT. The reaction was stirred at 0° C. for 15 h, then the reaction mixture was diluted with water (40 mL) and extracted with DCM (3×50 mL). The combined organic layers were washed with brine (50 mL), dried over $Na_2SO_4$, filtered and concentrated to dryness under reduced pressure affording the crude as a yellowish gum (0.65 g). The crude was purified by ELSD flash chromatography over silica gel (irregular SiOH, 50 μm, 25 g Interchim, dry loading (silica), mobile phase gradient: cyclohexane/EtOAc from 100/0 to 80/20 over 30 min). The fractions containing compound were combined, evaporated in vacuo and co-evaporated with DCM affording a mixture of I1-2/3-9 as a colorless oil (0.58 g, 1.25 mmol, 95.57%).

LC/MS (AN_01_001_061): Rt=2.16 and 2.20 min, 59.13 and 40.87%, $[M-Boc+H]^+$=366.5.

$^1$H NMR (400 MHZ, DMSO) δ 7.39-7.24 (m, 5H), 4.96-4.60 (m, 1H), 4.54-4.42 (m, 2H), 4.00-3.50 (m, 5H), 3.45-3.32 (m, 2H), 3.21-3.07 (m, 1H), 2.95-2.63 (m, 2H), 2.07-1.59 (m, 2H), 1.45-1.31 (m, 9H).

tert-butyl (2S,6S*)-6-[(tert-butyldimethylsilyl)oxy]-2-(hydroxymethyl)-1,4-oxazocane-4-carboxylate I1-2-10 tert-butyl (2S,7S*)-7-[(tert-butyldimethylsilyl)oxy]-2-(hydroxymethyl)-1,4-oxazocane-4-carboxylate I1-3-10

Starting from a mixture of 11-2/3-9 (1 eq., 0.58 g, 1.25 mmol), using general procedure D, crude 11-2/3-10 was obtained as a white solid (460 mg, 97%) and was used as such without further purification.

LC/MS (AN01_001_026, ELSD): Rt=11.02 and 11.36 min, 55.93 and 42.79%, $[M-{}^tBu+H]^+$=320.61.

(2S,6S*)-4-[(tert-butoxy) carbonyl]-6-[(tert-butyldimethylsilyl)oxy]-1,4-oxazocane-2-carboxylic acid Nov. 2, 2011 (2S,7S*)-4-[(tert-butoxy) carbonyl]-7-[(tert-butyldimethylsilyl)oxy]-1,4-oxazocane-2-carboxylic acid I1-3-11.

Starting from a mixture of I1-2/3-10 (1 eq., 460 mg, 1.21 mmol), using general procedure E, crude 11-2/3-11 was obtained as an orange gum (400 mg, 85%) and was used as such without further purification.

LC/MS (AN01_001_061): Not UV active, Rt=1.92 min, ND, [M−H]−=388.4.

tert-butyl (2S,6S*)-6-[(tert-butyldimethylsilyl)oxy]-2-{[(1S)-1-cyano-2-[4-(3-methyl-2-oxo-2,3-dihydro-1,3-benzoxazol-5-yl)phenyl]ethyl]carbamoyl}-1,4-oxazocane-4-carboxylate I1-2-12 and tert-butyl (2S,7S)-7-[(tert-butyldimethylsilyl)oxy]-2-{[(1S)-1-cyano-2-[4-(3-methyl-2-oxo-2,3-dihydro-1,3-benzoxazol-5-yl)phenyl]ethyl]carbamoyl}-1,4-oxazocane-4-carboxylate I1-3-12

Starting from BB01 (1 eq., 200 mg, 0.61 mmol) and I1-2/3-11 (1.05 eq., 290 mg, 0.64 mmol) and using general procedure B, a mixture of I1-2/3-12 was obtained as an orange gum (270 mg, 68%) after purification by flash chromatography over silica gel (25 μm, 25 g, cyclohexane/EtOAc from 100:0 to 0:100 in 60 min).

LC/MS (AN01_001_061): Rt=2.00 and 2.03 min, 54.21 and 45.79%, $[M-Boc+H]^+$=565.8.

$^1$H NMR (400 MHZ, DMSO) δ 8.87-8.71 (m, 1H), 7.70-7.62 (m, 2H), 7.60-7.52 (m, 1H), 7.44-7.33 (m, 4H), 5.07-4.95 (m, 1H), 4.29-3.96 (m, 2H), 3.96-3.51 (m, 3H), 3.40 (s, 3H), 3.26-2.74 (m, 3H), 2.62-2.37 (m, 1H), 2.11-1.53 (m, 2H), 1.46-1.32 (m, 9H), 0.92-0.78 (m, 9H), 0.13--0.01 (m, 7H).

tert-butyl (2S,6S*)-2-{[(1S)-1-cyano-2-[4-(3-methyl-2-oxo-2,3-dihydro-1,3-benzoxazol-5-yl)phenyl]ethyl]carbamoyl}-6-hydroxy-1,4-oxazocane-4-carboxylate Nov. 2, 2013 and tert-butyl (2S,7S*)-2-{[(1S)-1-cyano-2-[4-(3-methyl-2-oxo-2,3-dihydro-1,3-benzoxazol-5-yl)phenyl]ethyl]carbamoyl}-7-hydroxy-1,4-oxazocane-4-carboxylate I1-3-1

Starting from a mixture of 11-2/3-12 (1 eq., 265 mg, 0.33 mmol) and using general procedure A, Nov. 2, 2013 (89 mg, 47%) and I1-3-1 (89 mg, 47%) were obtained as white solids after purification by flash chromatography over silica gel (50 μm, 25 g, DCM/EtOAc from 70:30 to 0:100 in 35 min).

I1-2-13 (C-6 regioisomer):

LC/MS (AN01_001_026): Rt=8.63 and 8.74 min, 74.03 and 25.97%, $[M-Boc+H]^+$=451.38.

Chiral SFC analysis: Chiralpak IC-3 4.6×100 mm, Mobile phase: CO2/(MeOH+0.3% iPrNH2) 55/45): 3 products at Rt=3.57, 4.22, and 4.63 min, 81.75, 2.23 and 16.02%.

$^1$H NMR (400 MHZ, DMSO) δ 8.85-8.75 (m, 1H), 7.71-7.61 (m, 2H), 7.60-7.54 (m, 1H), 7.45-7.33 (m, 4H), 5.08-4.90 (m, 1H), 4.88-4.72 (m, 1H), 4.25-3.94 (m, 4H), 3.77-3.61 (m, 1H), 3.53-3.42 (m, 1H), 3.40 (s, 3H), 3.27-3.07 (m, 2H), 2.88-2.68 (m, 1H), 2.43-2.34 (m, 1H), 1.91-1.77 (m, 1H), 1.55-1.31 (m, 10H).

I1-3-1 (C-7 regioisomer):

LC/MS (AN01_001_026): Rt=8.69 min, 97.64%, $[M-Boc+H]^+$=451.40.

Chiral SFC analysis:Whelk-04 4.6×100 mm, Mobile phase: CO2/(MeOH/EtOH/iPrOH+0.3% iPrNH2) 60/40): 3 products at Rt=3.22, 3.59 and 4.26 min, 88.86, 3.00 and 7.51%.

$^1$H NMR (400 MHZ, DMSO) δ 8.85-8.70 (m, 1H), 7.71-7.61 (m, 2H), 7.59-7.52 (m, 1H), 7.45-7.31 (m, 4H), 5.09-4.95 (m, 1H), 2.07-1.54 (m, 2H), 4.77-4.65 (m, 1H), 3.98-3.49 (m, 6H), 3.40 (s, 3H), 3.27-2.95 (m, 3H), 1.52-1.30 (m, 10H).

(2S,6S*)—N-[(1S)-1-cyano-2-[4-(3-methyl-2-oxo-2,3-dihydro-1,3-benzoxazol-5-yl)phenyl]ethyl]-6-hydroxy-1,4-oxazocane-2-carboxamide Starting from a mixture of I1-2-13 (1 eq., 85 mg, 0.16 mmol) and using general procedure C, (2S,6S*)—N-[(1S)-1-cyano-2-[4-(3-methyl-2-oxo-2,3-dihydro-1,3-benzoxazol-5-yl)phenyl]ethyl]-6-hydroxy-1,4-oxazocane-2-carboxamide (22.8 mg, 32%) was obtained as an off-white solid after SFC purification (Chiralpak IC 20×250 mm, Mobile phase: CO2/(EtOH+0.3% iPrNH2) 55/45).

The structure of (2S,6S*)—N-[(1S)-1-cyano-2-[4-(3-methyl-2-oxo-2,3-dihydro-1,3-benzoxazol-5-yl)phenyl]ethyl]-6-hydroxy-1,4-oxazocane-2-carboxamide (C-6 regioisomer) was confirmed by 2D NMR analysis.

LC/MS (AN01_001_021): Rt=6.76 min, 97.03%, $[M+H]^+$=451.44.

Chiral SFC analysis: Chiralpak IC-3 4.6×100 mm, Mobile phase: CO2/(EtOH+0.3% iPrNH2) 55/45:1 product at Rt=1.86 min, 100%.

$^1$H NMR (400 MHZ, DMSO) § 8.63 (d, J=8.5 Hz, 1H), 7.68-7.62 (m, 2H), 7.60-7.55 (m, 1H), 7.44-7.33 (m, 4H), 5.04-4.93 (m, 1H), 4.46 (d, J=4.1 Hz, 1H), 4.19-4.09 (m, 1H), 3.85 (dd, J=10.2, 2.6 Hz, 1H), 3.67-3.53 (m, 2H), 3.40 (s, 3H), 3.23-3.16 (m, 2H), 3.10-2.93 (m, 2H), 2.42-2.31 (m, 2H), 2.22 (dd, J=13.6, 10.2 Hz, 1H), 2.17-2.07 (m, 1H), 1.54-1.42 (m, 1H).

(2S,7S*)—N-[(1S)-1-cyano-2-[4-(3-methyl-2-oxo-2,3-dihydro-1,3-benzoxazol-5-yl)phenyl]ethyl]-7-hydroxy-1,4-oxazocane-2-carboxamide Starting from a mixture of I1-3-1 (1 eq., 85 mg, 0.16 mmol) and using general procedure C, (2S,7S*)—N-[(1S)-1-cyano-2-[4-(3-methyl-2-oxo-2,3-dihydro-1,3-benzoxazol-5-yl)phenyl]ethyl]-7-hydroxy-1,4-oxazocane-2-carboxamide (25.7 mg, 35%) was obtained as an off-white solid after SFC purification (Chiralpak AS-H 30×250 mm, Mobile phase: CO2/(MeOH+0.3% iPrNH2) 70/30).

The structure of (2S,7S*)—N-[(1S)-1-cyano-2-[4-(3-methyl-2-oxo-2,3-dihydro-1,3-benzoxazol-5-yl)phenyl]ethyl]-7-hydroxy-1,4-oxazocane-2-carboxamide (C-7 regioisomer) was confirmed by 2D NMR analysis.

LC/MS (AN01_001_021): Rt=6.58 min, 95.17%, $[M+H]^+$=451.42.

Chiral SFC analysis: Chiralpak AS-H 30×250 mm, Mobile phase: CO2/(MeOH+0.3% iPrNH2) 70/30:1 product at Rt=0.85 min, 97.14%.

$^1$H NMR (400 MHZ, DMSO) δ 8.61 (d, J=8.6 Hz, 1H), 7.69-7.62 (m, 2H), 7.59-7.54 (m, 1H), 7.44-7.35 (m, 4H), 5.07-4.98 (m, 1H), 4.58 (s, 1H), 3.86-3.69 (m, 4H), 3.40 (s, 3H), 3.40-3.35 (m, 1H), 3.26-3.13 (m, 2H), 2.92 (dd, J=14.2, 3.2 Hz, 1H), 2.75 (t, J=6.1 Hz, 2H), 2.37-2.27 (m, 1H), 1.80-1.61 (m, 2H).

Example 19: Preparation of (2S,6S)—N—((S)-1-cyano-2-(4-(3-methyl-2-oxo-2,3-dihydrobenzo[d]oxazol-5-yl)phenyl)ethyl)-6-methoxy-1,4-oxazocane-2-carboxamide (Compound 19-A) and (2S,7S)—N—((S)-1-cyano-2-(4-(3-methyl-2-oxo-2,3-dihydrobenzo[d]oxazol-5-yl)phenyl)ethyl)-7-methoxy-1,4-oxazocane-2-carboxamide Compound 19-B

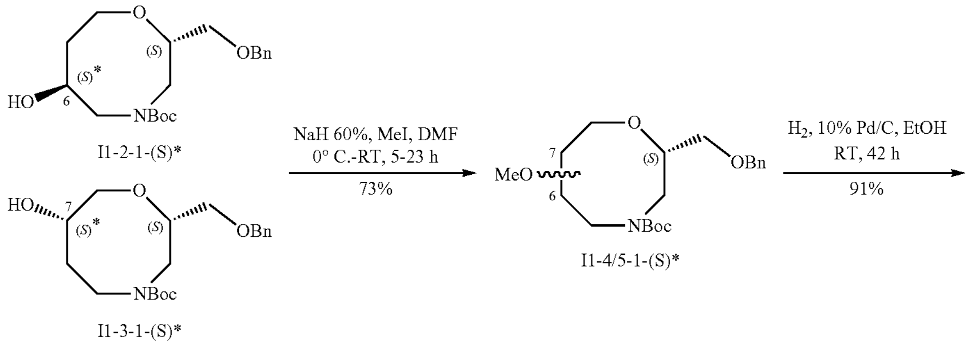

-continued

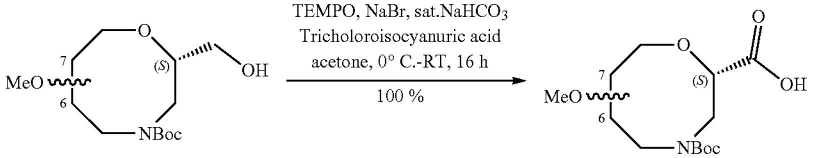

I1-4/5-2-(S)*

I1-4/5-3-(S)*

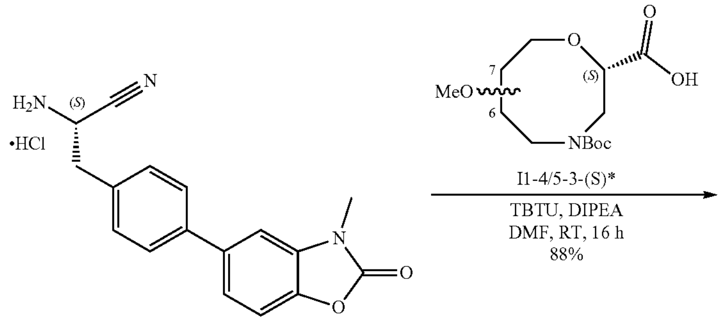

BB01
1 eq.

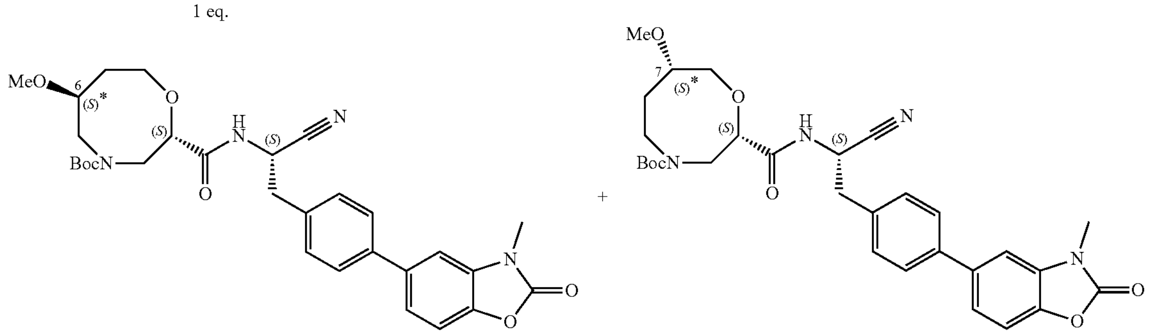

I1-4-4-(S)*

I1-5-4-(S)*

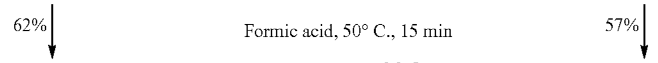

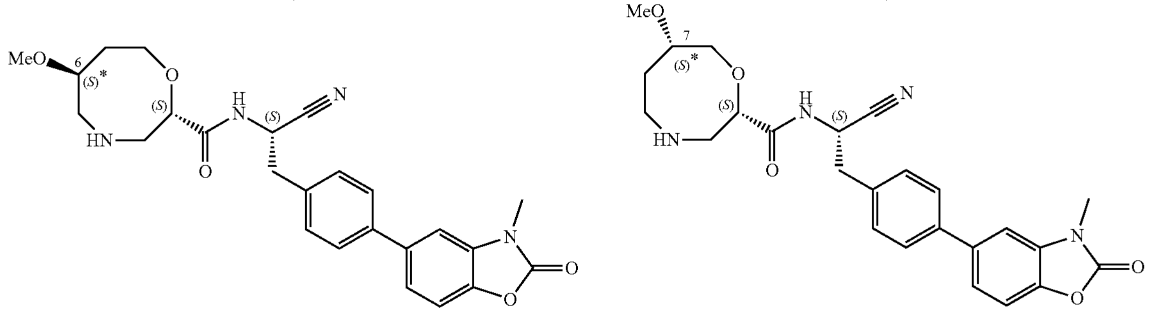

Compound 19-A

Compound 19-B

Mixture of tert-butyl (2S)-2-[(benzyloxy)methyl]-(7S)*-methoxy-1,4-oxazocane-4-carboxylate and tert-butyl (2S)-2-[(benzyloxy)methyl]-(6S)*-methoxy-1,4-oxazocane-4-carboxylate I1-4/5-1-(S)*.

Starting from the mixture I1-2/3-1-(S)* (1 eq., 410 mg, 1.17 mmol) and using general procedure F, I1-4/5-1-(S)* was obtained as a yellowish oil (313 mg, 73%) after purification by flash chromatography over silica gel (irregular SiOH, 50 μm, 25 g Interchim, dry loading (silica), mobile phase gradient: cyclohexane/EtOAc from 100/0 to 60/40 over 25 min) and co-evaporation with DCM.

LC/MS (AN01_001_026): Rt=10.26 min, 52%, $[M-Boc+H]^+$=266.4 & Rt=10.47 min, 45.3%, $[M-Boc+H]^+$=266.4.

$^1$H NMR (400 MHZ, DMSO) δ 7.40-7.24 (m, 5H), 4.56-4.43 (m, 2H), 4.05-3.51 (m, 5H), 3.51-2.97 (m, 6H), 2.92-2.54 (m, 2H), 2.08-1.56 (m, 2H), 1.49-1.31 (m, 9H).

Mixture of tert-butyl (2S)-2-(hydroxymethyl)-(7S)*-methoxy-1,4-oxazocane-4-carboxylate and tert-butyl (2S)-2-(hydroxymethyl)-(6S)*-methoxy-1,4-oxazocane-4-carboxylate I1-4/5-2-(S)*.

Starting from I1-4/5-1-(S)* (1 eq., 320 mg, 0.68 mmol) and using general procedure D, I1-4/5-2-(S)* was obtained as a brownish gum (215 mg, 91%).

LC/MS (AN01_001_026, ELSD): Rt=6.84 min, 74.06%, $[M-Boc+H]^+$=220.08 & Rt =6.93 min, 25.5%, $[M-Boc+H]^+$=220.08

$^1$H NMR (400 MHZ, DMSO) δ 4.71-4.61 (m, 1H), 4.11-3.49 (m, 4H), 3.44-3.32 (m, 1H), 3.28-3.10 (m, 6H), 3.05-2.63 (m, 1H), 2.62-2.44 (m, 1H), 2.09-1.52 (m, 2H), 1.50-1.34 (m, 9H).

Mixture of (2S)-4-[(tert-butoxy) carbonyl]-(7S)*-methoxy-1,4-oxazocane-2-carboxylic acid and (2S)-4-[(tert-butoxy) carbonyl]-(6S)*-methoxy-1,4-oxazocane-2-carboxylic acid I1-4/5-3-(S)*.

Starting from I1-4/5-2 (1 eq., 200 mg, 0.708 mmol) and using general procedure E, I1-4/5-3-(S)* was obtained as a crude orange gum (205 mg, 100%).

LC/MS (AN01_001_012): Rt=2.02 min, 89.6%, [M−H]−=288.1.

tert-butyl (2S,6S*)-2-{[(1S)-1-cyano-2-[4-(3-methyl-2-oxo-2,3-dihydro-1,3-benzoxazol-5-yl)phenyl]ethyl]carbamoyl}-6-methoxy-1,4-oxazocane-4-carboxylate 11-4-4-(S)* & tert-butyl (2S,7S*)-2-{[(1S)-1-cyano-2-[4-(3-methyl-2-oxo-2,3-dihydro-1,3-benzoxazol-5-yl)phenyl]ethyl]carbamoyl}-7-methoxy-1,4-oxazocane-4-carboxylate I1-5-3-(S)*

Starting from BB01 (1 eq., 221.25 mg, 0.67 mmol) and the mixture of I1-4/5-2-(S)* (1.05 eq., 237.00 mg, 0.70 mmol), using general procedure B, was obtained a mixture of I1-4-4-(S)* and I1-5-4-(S)*. The mixture was purified by flash chromatography over silica gel (irregular SiOH, 50 μm, 25 g Interchim, dry loading (silica), mobile phase gradient: cyclohexane/EtOAc from 90/10 to 0/100 over 45 min), both regioisomers were separated as single diastereomer (the stereochemistry was arbitrarily assigned(S)*: 11-4-4-(S)* (150 mg, 40%) as a yellow solid and I1-5-4-(S)* (186 mg, 48%) as an orange solid. The structure of both regioisomers were confirmed by 2D NMR analyses on the final targets.

I1-4-4-(S)*: $C_6$ regioisomer

LC/MS (AN01_001_026): Rt=9.81 min, 86.3%, $[M-Boc+H]^+$=465.4.

$^1$H NMR (400 MHZ, DMSO) δ 8.85-8.72 (m, 1H), 7.70-7.62 (m, 2H), 7.60-7.53 (m, 1H), 7.44-7.33 (m, 4H), 5.09-4.92 (m, 1H), 4.15-3.95 (m, 3H), 3.90-3.76 (m, 1H), 3.76-3.60 (m, 1H), 3.56-3.44 (m, 1H), 3.40 (s, 3H), 3.30-3.24 (m, 3H), 3.24-3.12 (m, 2H), 2.90-2.60 (m, 1H), 2.44-2.28 (m, 1H), 1.86-1.58 (m, 2H), 1.48-1.29 (m, 9H).

I1-5-4-(S)*: $C_7$ regioisomer

LC/MS (AN01_001_026): Rt=9.66 min, 70.8%, $[M-Boc+H]^+$=465.4.

$^1$H NMR (400 MHZ, DMSO) δ 8.82-8.72 (m, 1H), 7.71-7.62 (m, 2H), 7.58-7.51 (m, 1H), 7.44-7.33 (m, 4H), 5.08-4.96 (m, 1H), 4.22-3.75 (m, 4H), 3.75-3.48 (m, 2H), 3.40 (s, 3H), 3.30-2.90 (m, 6H), 2.68-2.48 (m, 1H), 2.10-1.65 (m, 2H), 1.50-1.30 (m, 9H).

(2S,7S*)—N-[(1S)-1-cyano-2-[4-(3-methyl-2-oxo-2,3-dihydro-1,3-benzoxazol-5-yl)phenyl]ethyl]-7-methoxy-1,4-oxazocane-2-carboxamide Starting from I1-5-4-(S)* (1 eq., 80.00 mg, 0.14 mmol) and using general procedure C, (2S,7S*)—N-[(1S)-1-cyano-2-[4-(3-methyl-2-oxo-2,3-dihydro-1,3-benzoxazol-5-yl)phenyl]ethyl]-7-methoxy-1,4-oxazocane-2-carboxamide was obtained as a white solid (29.8 mg, 45%) after purification by flash chromatography over silica gel (regular SiOH, 15 μm, 12 g Interchim, dry loading (silica), mobile phase gradient: DCM/MeOH from 100/0 to 85/15 over 45 min), co-evaporation with DCM and vacuum drying at 40° C. for 48 h.

LC/MS (AN_01_001_021_DEDL): Rt=7.08 min, 98.9%, $[M+H]^+$=465.4.

$^1$H NMR (400 MHZ, DMSO) & 8.60 (d, J=8.6 Hz, 1H), 7.68-7.62 (m, 2H), 7.58-7.55 (m, 1H), 7.43-7.35 (m, 4H), 5.06-4.98 (m, 1H), 4.02-3.83 (m, 2H), 3.81 (dd, J=9.4, 3.0 Hz, 1H), 3.44-3.34 (m, 4H), 3.25 (s, 3H), 3.23-3.14 (m, 2H), 2.94 (dd, J=14.4, 3.0 Hz, 1H), 2.77-2.70 (m, 2H), 2.29 (dd, J=14.4, 9.5 Hz, 1H), 1.91-1.80 (m, 1H), 1.75-1.67 (m, 1H), one missing proton (NH).

(2S,6S*)—N-[(1S)-1-cyano-2-[4-(3-methyl-2-oxo-2,3-dihydro-1,3-benzoxazol-5-yl)phenyl]ethyl]-6-methoxy-1,4-oxazocane-2-carboxamide Starting from I1-4-4 (1 eq., 70.00 mg, 0.12 mmol) and using general procedure C, (2S,6S*)—N-[(1S)-1-cyano-2-[4-(3-methyl-2-oxo-2,3-dihydro-1,3-benzoxazol-5-yl)phenyl]ethyl]-6-methoxy-1,4-oxazocane-2-carboxamide was obtained as a white solid (20.0 mg, 35%) after purification by flash chromatography over silica gel (regular SiOH, 15 μm, 12 g Interchim, dry loading (silica), mobile phase gradient: DCM/MeOH from 100/0 to 90/10 over 40 min), co-evaporation with DCM and vacuum drying at 40° C. for 48 h.

LC/MS (AN_01_001_021_DEDL): Rt=7.14 min, 98.7%, $[M+H]^+$=465.4.

$^1$H NMR (400 MHZ, DMSO) § 8.64 (d, J=8.5 Hz, 1H), 7.69-7.62 (m, 2H), 7.59-7.54 (m, 1H), 7.44-7.34 (m, 4H), 5.04-4.93 (m, 1H), 4.10-4.00 (m, 1H), 3.89 (dd, J=10.3, 2.7 Hz, 1H), 3.61-3.52 (m, 1H), 3.40 (s, 3H), 3.37-3.27 (m, 2H), 3.23 (s, 3H), 3.22-3.13 (m, 3H), 2.97 (dd, J=13.5, 2.7 Hz, 1H), 2.38 (dd, J=13.6, 9.6 Hz, 1H), 2.21 (dd, J=13.5, 10.3 Hz, 1H), 1.67-1.57 (m, 1H), one missing proton (NH).

Example 20: Preparation of (2S,7R)—N—((S)-1-cyano-2-(4-(3-methyl-2-oxo-2,3-dihydrobenzo[d]oxazol-5-yl)phenyl)ethyl)-7-methoxy-1,4-oxazocane-2-carboxamide (Compound 20-A) and (2S,6R)—N—((S)-1-cyano-2-(4-(3-methyl-2-oxo-2,3-dihydrobenzo[d]oxazol-5-yl)phenyl)ethyl)-6-methoxy-1,4-oxazocane-2-carboxamide (Compound 20-B)

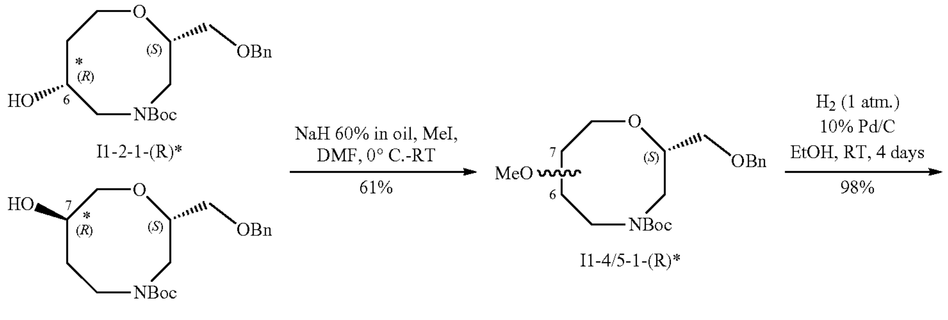

I1-2-1-(R)*

I1-3-1-(R)*

I1-4/5-1-(R)*

-continued

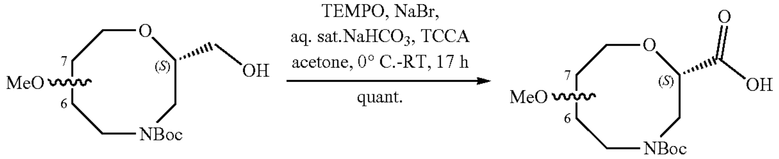

I1-4/5-2-(R)*

I1-4/5-3-(R)*

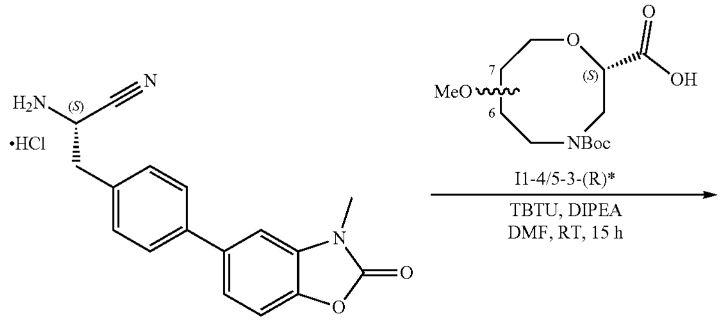

BB01
1 eq.

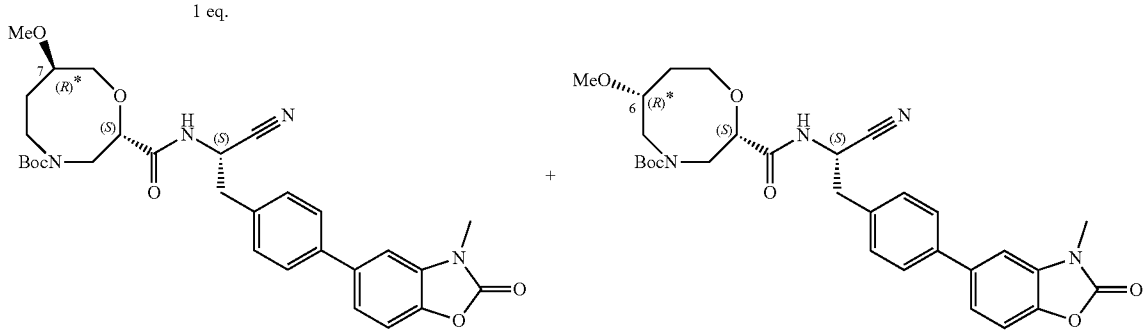

I1-5-4-(R)*
53%

I1-4-4-(R)*
21%

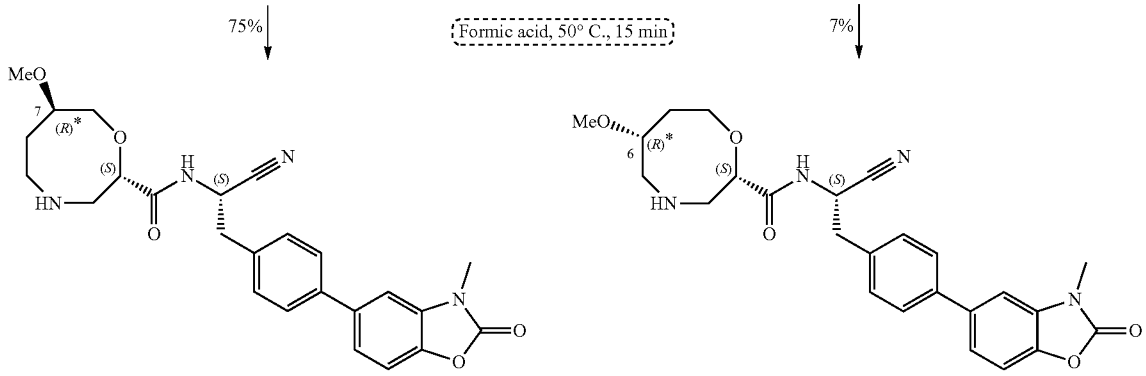

Compound 20-A

Compound 20-B

Mixture of tert-butyl (2S)-2-[(benzyloxy)methyl]-(7R)*-methoxy-1,4-oxazocane-4-carboxylate and tert-butyl (2S)-2-[(benzyloxy)methyl]-(6R)*-methoxy-1,4-oxazocane-4-carboxylate I1-4/5-1-(R)*.

Starting from the mixture I1-2/3-1-(R)* (1 eq., 1.08 g, 3.06 mmol) and using general procedure F, 11-4/5-1-(R)* was obtained as a yellowish oil (680 mg, 61%) after purification by flash chromatography over silica gel (irregular SiOH, 50 μm, 40 g Interchim, dry loading (silica), mobile phase gradient: cyclohexane/EtOAc from 100/0 to 60/40 over 40 min) and co-evaporation with DCM.

LC/MS (AN01_001_026, ELSD): Rt=10.04 and 10.21 min, 28.29 and 71.23%, $[M\text{-}Boc+H]^+$=266.49.

$^1H$ NMR (400 MHZ, DMSO) δ 7.40-7.23 (m, 5H), 4.54-4.43 (m, 2H), 4.03 (dt, J=11.8, 3.5 Hz, 1H), 3.96-3.50 (m, 4H), 3.42 (ddd, J=13.2, 9.0, 5.6 Hz, 1H), 3.36-3.32 (m, 1H), 3.26-3.22 (m, 3H), 3.23-3.14 (m, 1H), 3.05-2.64 (m, 2H), 2.04-1.61 (m, 2H), 1.40 (dd, J=13.6, 3.9 Hz, 9H).

Mixture of tert-butyl (2S)-2-(hydroxymethyl)-(7R)*-methoxy-1,4-oxazocane-4-carboxylate and tert-butyl (2S)-2-(hydroxymethyl)-(6R)*-methoxy-1,4-oxazocane-4-carboxylate I1-4/5-2-(R)*.

Starting from I1-4/5-1-(R)* (1 eq., 670 mg, 1.87 mmol) and using general procedure D, I1-4/5-2-(R)* was obtained as a yellow gum (506 mg, 98%).

LC/MS (AN01_001_026, ELSD): Not UV active, Rt=6.80 min, 100%, [M-Boc+H]$^+$=220.12.

$^1$H NMR (400 MHZ, DMSO) δ 4.73-4.61 (m, 1H), 4.11-3.99 (m, 1H), 3.95-3.60 (m, 2H), 3.55-3.45 (m, 1H), 3.44-3.33 (m, 1H), 3.26-3.23 (m, 3H), 3.20-3.13 (m, 1H), 2.99-2.80 (m, 1H), 2.78-2.60 (m, 1H), 2.06-1.84 (m, 1H), 1.84-1.66 (m, 1H), 1.47-1.34 (m, 11H).

Mixture of (2S)-4-[(tert-butoxy) carbonyl]-(7R)*-methoxy-1,4-oxazocane-2-carboxylic acid and (2S)-4-[(tert-butoxy) carbonyl]-(6R)*-methoxy-1,4-oxazocane-2-carboxylic acid I1-4/5-3-(R)*.

Starting from I1-4/5-2 (1 eq., 500 mg, 1.84 mmol) and using general procedure E, I1-4/5-3-(R)* was obtained as a crude orange gum (530 mg, crude, 100%).

LC/MS (AN01_001_026, ELSD): Rt=6.89 min, 94.01%, [M−Boc+H]$^+$=190.06

$^1$H NMR (400 MHZ, DMSO) & 12.72 (s, 1H), 4.18-3.49 (m, 5H), 3.45-3.37 (m, 1H), 3.26-3.22 (m, 3H), 3.21-2.84 (m, 2H), 2.01-1.67 (m, 2H), 1.45-1.33 (m, 9H).

tert-butyl (2S,6R*)-2-{[(1S)-1-cyano-2-[4-(3-methyl-2-oxo-2,3-dihydro-1,3-benzoxazol-5 yl)phenyl]ethyl]carbamoyl}-6-methoxy-1,4-oxazocane-4-carboxylate 11-4-4-(R)* & tert-butyl (2S,7R*)-2-{[(1S)-1-cyano-2-[4-(3-methyl-2-oxo-2,3-dihydro-1,3-benzoxazol-5-yl)phenyl]ethyl]carbamoyl}-7-methoxy-1,4-oxazocane-4-carboxylate I1-5-3-(R)*

Starting from BB01 (1 eq., 580 mg, 1.74 mmol) and the mixture of I1-4/5-2-(R)* (1.05 eq., 600 mg, 1.83 mmol), using general procedure B, was obtained a mixture of I1-4-4-(R)* and I1-5-4-(R)*. The mixture was purified by flash chromatography over silica gel (irregular SiOH, 15 μm, 40 g Interchim, dry loading (silica), mobile phase gradient: cyclohexane/EtOAc from 90/10 to 0/100 over 45 min), both regioisomers were separated: 11-4-4-(R)* (208 mg, 21%) as a white solid and I1-5-4-(R)* (524 mg, 53%) as a yellow solid.

I1-4-4-(R)*: $C_6$ regioisomer

LC/MS (AN01_001_086): Rt=6.82 min, 67.20%, [M−Boc+H]$^+$=465.41

I1-5-4-(R)*: $C_7$ regioisomer

LC/MS (AN01_001_086): Rt=6.90 min, 92.07%, [M−Boc+H]=465.45

$^1$H NMR (400 MHZ, DMSO) δ 8.81 (dd, J=8.4, 3.6 Hz, 1H), 7.67 (d, J=8.2 Hz, 2H), 7.57 (s, 1H), 7.46-7.33 (m, 4H), 5.09-4.93 (m, 1H), 4.18-3.96 (m, 2H), 3.96-3.66 (m, 2H), 3.49-3.33 (m, 4H), 3.28-3.25 (m, 4H), 3.23-3.05 (m, 2H), 2.96-2.77 (m, 1H), 2.74-2.57 (m, 1H), 2.02-1.69 (m, 2H), 1.45-1.30 (m, 9H).

(2S,7R*)—N-[(1S)-1-cyano-2-[4-(3-methyl-2-oxo-2,3-dihydro-1,3-benzoxazol-5-yl)phenyl]ethyl]-7-methoxy-1,4-oxazocane-2-carboxamide Starting from 11-5-4-(R)* (1 eq., 267 mg, 0.47 mmol) and using general procedure C, (2S,7R*)—N-[(1S)-1-cyano-2-[4-(3-methyl-2-oxo-2,3-dihydro-1,3-benzoxazol-5-yl)phenyl]ethyl]-7-methoxy-1,4-oxazocane-2-carboxamide was obtained as a white solid (160 mg, 75%) after purification by flash chromatography over silica gel (regular SiOH, 50 μm, 25 g Interchim, dry loading (silica), mobile phase gradient: DCM/MeOH from 100/0 to 85/15 over 45 min), co-evaporation with DCM and vacuum drying at 40° C. for 48 h.

LC/MS (AN_01_001_088): Rt=4.78 min, 98.74%, [M+H]$^+$=465.48.

$^1$H NMR (400 MHZ, DMSO) § 8.64 (d, J=8.5 Hz, 1H), 7.69-7.61 (m, 2H), 7.58-7.54 (m, 1H), 7.42-7.34 (m, 4H), 5.06-4.95 (m, 1H), 4.08 (dd, J=11.5, 4.3 Hz, 1H), 3.92 (dd, J=9.0, 3.1 Hz, 1H), 3.58 (dd, J=11.5, 8.4 Hz, 1H), 3.40 (s, 3H), 3.38-3.33 (m, 1H), 3.25 (s, 3H), 3.23-3.13 (m, 2H), 3.03-2.94 (m, 2H), 2.49-2.44 (m, 1H), 2.33 (dd, J=14.5, 9.0 Hz, 1H), 1.96-1.86 (m, 1H), 1.65-1.54 (m, 1H), one missing proton (NH).

The structure of (2S,7R*)—N-[(1S)-1-cyano-2-[4-(3-methyl-2-oxo-2,3-dihydro-1,3-benzoxazol-5-yl)phenyl]ethyl]-7-methoxy-1,4-oxazocane-2-carboxamide (C-7) was confirmed by 2D NMR analysis.

(2S,6R*)—N-[(1S)-1-cyano-2-[4-(3-methyl-2-oxo-2,3-dihydro-1,3-benzoxazol-5-yl)phenyl]ethyl]-6-methoxy-1,4-oxazocane-2-carboxamide Starting from I1-4-4-(R)* (1 eq., 100 mg, 0.18 mmol) and using general procedure C, (2S,6R*)—N-[(1S)-1-cyano-2-[4-(3-methyl-2-oxo-2,3-dihydro-1,3-benzoxazol-5-yl)phenyl]ethyl]-6-methoxy-1,4-oxazocane-2-carboxamide was obtained as a white solid (6.00 mg, 7%) after purification by flash chromatography over silica gel (regular SiOH, 15 μm, 12 g Interchim, dry loading (silica), mobile phase gradient: DCM/MeOH from 100/0 to 90/10 over 40 min), co-evaporation with DCM and vacuum drying at 40° C. for 48 h. N.B: (42 mg, 51%) of (2S,7S)—N—((S)-1-cyano-2-(4-(3-methyl-2-oxo-2,3-dihydrobenzo[d]oxazol-5-yl)phenyl)ethyl)-7-methoxy-1,4-oxazocane-2-carboxamide was also isolated during the purification.

LC/MS (AN_01_001_088): Rt=4.77 min, 85.45%, [M+H]$^+$=465.50.

$^1$H NMR (400 MHZ, $CDCl_3$) δ 7.60-7.51 (m, 2H), 7.42-7.34 (m, 2H), 7.33-7.28 (m, 1H), 7.26-7.20 (m, 1H), 7.18-7.11 (m, 1H), 5.23-5.08 (m, 1H), 4.25-4.08 (m, 1H), 4.01-3.87 (m, 1H), 3.86-3.73 (m, 1H), 3.45 (s, 4H), 3.42-3.35 (m, 2H), 3.34 (s, 2H), 3.23-3.06 (m, 2H), 2.98-2.83 (m, 1H), 2.57 (dd, J=13.9, 10.1 Hz, 1H), 2.29-2.14 (m, 1H), 1.88-1.76 (m, 1H), 1.35-1.16 (m, 1H), 0.93-0.75 (m, 1H).

The structure of (2S,6R*)—N-[(1S)-1-cyano-2-[4-(3-methyl-2-oxo-2,3-dihydro-1,3-benzoxazol-5-yl)phenyl]ethyl]-6-methoxy-1,4-oxazocane-2-carboxamide (C-6) was confirmed by 2D NMR analysis.

Example 21: Preparation of (2S,6R)—N—((S)-1-cyano-2-(2-fluoro-4-(3-methyl-2-oxo-2,3-dihydrobenzo[d]oxazol-5-yl)phenyl)ethyl)-6-hydroxy-6-methyl-1,4-oxazepane-2-carboxamide (Compound 21)

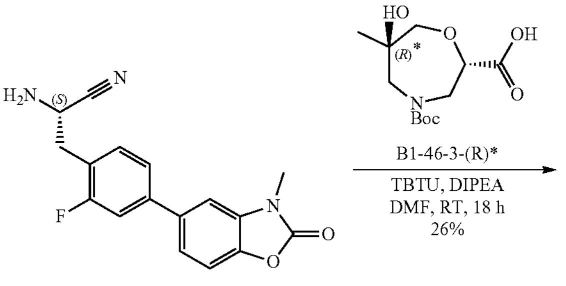

A3-8

-continued

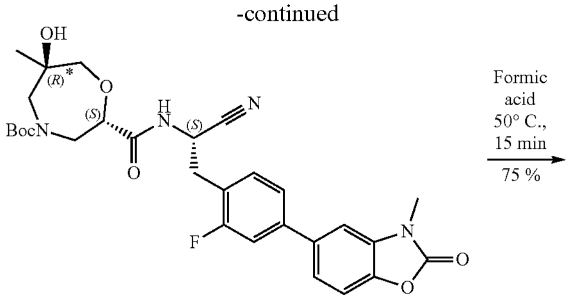

B2-1-1-(R)*

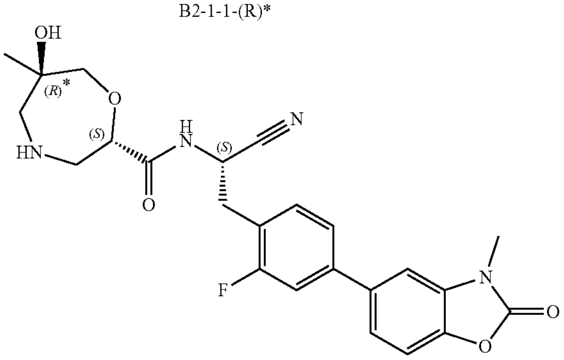

Compound 21 tert-butyl (2S,6R*)-2-{[(1S)-1-cyano-2-[2-fluoro-4-(3-methyl-2-oxo-2,3-dihydro-1,3-benzoxazol-5-yl) phenyl]ethyl]carbamoyl}-6-hydroxy-6-methyl-1,4-oxazepane-4-carboxylate B2-1-1-(R)*

Starting from A3-8 (1 eq., 50.0 mg, 0.16 mmol) and B1-46-3-(R)* (described in Example 1 procedure) (1.47 eq., 65.00 mg, 0.24 mmol), using general procedure B, was obtained B2-1-1-(R)* (42.3 mg, 26%, contaminated by 40 wt. % of remaining A3-8) after purification by flash chromatography over silica gel (irregular SiOH, 50 μm, 25 g Interchim, dry loading (silica), mobile phase gradient: cyclohexane/EtOAc from 100/0 to 25/75 over 45 min).

LC/MS (AN01_001_061): Rt=1.51 min, 56%, $[M-{}^{t}Bu+H]^{+}$=513.1.

(2S,6R*)—N-[(1S)-1-cyano-2-[2-fluoro-4-(3-methyl-2-oxo-2,3-dihydro-1,3-benzoxazol-5-yl)phenyl]ethyl]-6-hydroxy-6-methyl-1,4-oxazepane-2-carboxamide Starting from B2-1-1-(R)* (1 eq., 40 mg, 0.039 mmol, purity 55%) and using general procedure C, (2S,6R*)—N-[(1S)-1-cyano-2-[2-fluoro-4-(3-methyl-2-oxo-2,3-dihydro-1,3-benzoxazol-5-yl)phenyl]ethyl]-6-hydroxy-6-methyl-1,4-oxazepane-2-carboxamide was obtained as a white solid (13.6 mg, 75%) after purification by flash chromatography over silica gel (regular SiOH, 15 μm, 4 g Interchim, dry loading (silica), mobile phase gradient: DCM/MeOH from 100/0 to 90/10 over 35 min), then vacuum-dried at 40° C. for 18 h.

LC/MS (AN_01_001_021): Rt=6.93 min, 97.0%, [M+H]=469.38

$^{1}$H NMR (400 MHZ, DMSO) δ 8.78 (dd, J=13.6, 5.1 Hz, 1H), 7.68-7.63 (m, 1H), 7.63-7.52 (m, 2H), 7.51-7.43 (m, 2H), 7.42-7.37 (m, 1H), 5.06 (q, J=8.2 Hz, 1H), 4.56 (s, 1H), 4.01 (dd, J=8.0, 5.1 Hz, 1H), 3.55 (dd, J=48.9, 12.5 Hz, 2H), 3.41 (s, 3H), 3.35-3.26 (m, 1H), 3.18 (dd, J=13.7, 8.4 Hz, 1H), 3.05 (dd, J=14.0, 5.2 Hz, 1H), 2.66-2.53 (m, 4H), 0.98 (s, 3H). 19F NMR (376 MHZ, DMSO) δ-117.21

Example 22: Preparation of (2S)—N—((S)-1-cyano-2-(4-(3-methyl-2-oxo-2,3-dihydrobenzo[d]oxazol-5-yl)phenyl)ethyl)-6-hydroxy-6-(trifluoromethyl)-1,4-oxazepane-2-carboxamide (Compound 22)

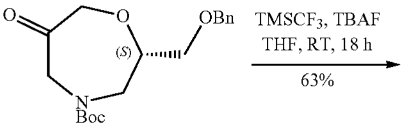

B1-2-14

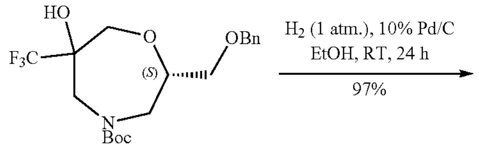

B1-96-1

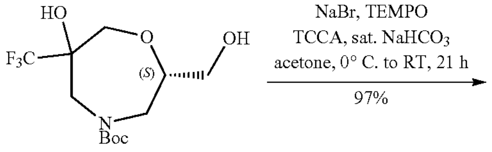

B1-96-2

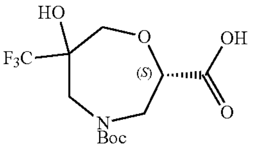

B1-96-3

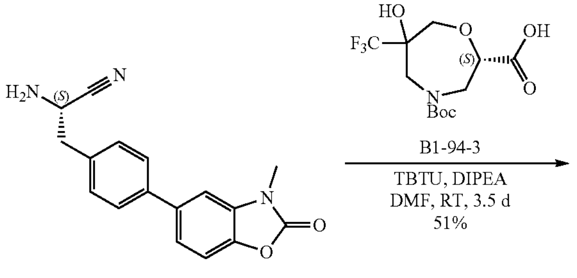

BB01

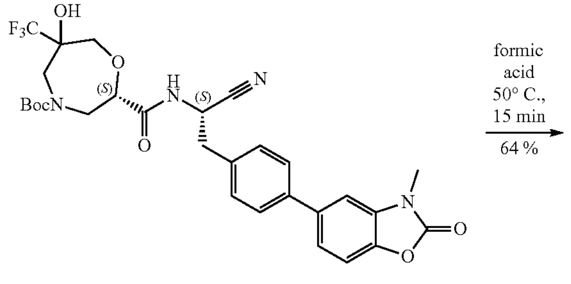

B1-96-4

-continued

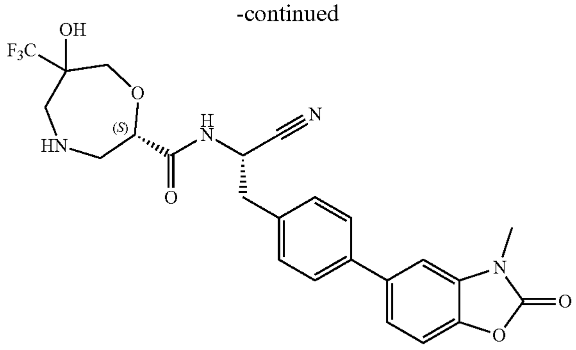

Compound 22 tert-butyl (2S)-2-[(benzyloxy)methyl]-6-hydroxy-6-(trifluoromethyl)-1,4-oxazepane-4-carboxylate B1-96-1

To a solution of I1-2-14 (1 eq., 460 mg, 1.37 mmol) in THF (11.04 mL) were added TFMTMS (1.3 eq., 0.89 mL, 1.78 mmol) and TBAF (2.1 eq., 2.88 mL, 2.88 mmol) dropwise at 0° C. The reaction mixture was stirred at RT for 18 h. The reaction mixture was diluted with EtOAc (50 mL) and water was added (50 mL). The layers were separated, the aqueous layer was extracted with EtOAc (20 mL) and the combined organic layer was washed with an aq. solution of saturated $NH_4Cl$ (60 mL), dried over $Na_2SO_4$, filtered and concentrated under reduced pressure to afford crude (580 mg) as a yellow oil. The crude was purified by ELSD flash chromatography over silica gel (irregular SiOH, 50 μm, 24 g Interchim, dry loading (silica), mobile phase gradient: cyclohexane/EtOAc from 100/0 to 70/30 over 40 min). The fractions containing compound were combined, evaporated in vacuo to afford both diastereomers of B1-96-1 as colorless oils (188 and 160 mg, 63%). Both diastereomers were combined and engaged as such in the next experiment.

B1-96-1 (diasteromer N°1):

LC/MS (AN01_001_061): Rt=1.72 min, 91.01%, $[M-{}^tBu+H]^+$=350.1.

B1-96-1 (diasteromer N°2):

LC/MS (AN01_001_061): Rt=1.65 min, 100%, $[M-{}^tBu+H]^+$=350.1.

tert-butyl (2S)-6-hydroxy-2-(hydroxymethyl)-6-(trifluoromethyl)-1,4-oxazepane-4-carboxylate B1-96-2

Starting from B1-96-1 (1 eq., 345 mg, 0.86 mmol) and using general procedure D, B1-96-2 was obtained as a colorless oil (262 mg, 97%). The crude was used as such without further purification.

LC/MS (AN01_001_061): Not UV active, Rt=1.30 min, ND, $[M-{}^tBu+H]^+$=260.0.

(2S)-4-[(tert-butoxy) carbonyl]-6-hydroxy-6-(trifluoromethyl)-1,4-oxazepane-2-carboxylic acid B1-96-3

Starting from B1-96-2 (1 eq., 277 mg, 0.82 mmol), using general procedure E, B1-96-3 was obtained as a colorless oil (261 mg, 97%). The crude was used as such without further purification.

LC/MS (AN01_001_061): Not UV active, Rt=1.32 min, ND, [M−H]−=328.1.

tert-butyl (2S)-2-{[(1S)-1-cyano-2-[4-(3-methyl-2-oxo-2,3-dihydro-1,3-benzoxazol-5-yl)phenyl]ethyl]carbamoyl}-6-hydroxy-6-(trifluoromethyl)-1,4-oxazepane-4-carboxylate B1-96-4

Starting from BB01 (1 eq., 249 mg, 0.76 mmol) and B1-96-3 (1.05 eq., 261 mg, 0.79 mmol), and using general procedure B, B1-96-4 was obtained as a yellow gum (235 mg, 51%) after purification by flash chromatography over silica gel (50 μm, 24 g, cyclohexane/EtOAc from 90:10 to 0:100 over 45 min).

LC/MS (AN01_001_026): Mixture of two diastereomers at Rt=9.41 and 9.60 min, 32 and 68%, $[M-{}^tBu+H]^+$=549.47

(2S)—N-[(1S)-1-cyano-2-[4-(3-methyl-2-oxo-2,3-dihydro-1,3-benzoxazol-5-yl)phenyl]ethyl]-6-hydroxy-6-(trifluoromethyl)-1,4-oxazepane-2-carboxamide Starting from B1-96-4 (1 eq., 81 mg, 0.13 mmol) and using general procedure C, (2S)—N-[(1S)-1-cyano-2-[4-(3-methyl-2-oxo-2,3-dihydro-1,3-benzoxazol-5-yl)phenyl]ethyl]-6-hydroxy-6-(trifluoromethyl)-1,4-oxazepane-2-carboxamide was obtained as a white solid (43 mg, 64%) after purification by flash chromatography over silica gel (regular SiOH, 15 μm, 12 g Interchim, dry loading (silica), mobile phase gradient: DCM/MeOH from 100/0 to 85/15 over 50 min), then vacuum-dried at 40° C. for 18 h.

LC/MS (AN_01_001_021): Rt=7.03 and 7.19 min, 94.31%, $[M+H]^+$=506.46, diastereomeric ratio: 65:35.

$^1$H NMR (400 MHZ, DMSO, presence of diastereomers) δ 8.72-8.56 (m, 1H), 7.69-7.61 (m, 2H), 7.59-7.54 (m, 1H), 7.43-7.35 (m, 4H), 6.15-6.09 (m, 1H), 5.06-4.94 (m, 1H), 4.12-3.85 (m, 2H), 3.66 (d, J=13.5 Hz, 1H), 3.40 (s, 3H), 3.25-3.11 (m, 3H), 3.01 (d, J=14.2 Hz, 1H), 2.82 (d, J=14.2 Hz, 1H), 2.67-2.58 (m, 1H), 2.31-2.23 (m, 1H). 19F NMR (376 MHz, DMSO) δ-78.75, −79.75.

Example 23: Preparation of (2S,6S)—N—((S)-1-cyano-2-(4-(3-methyl-2-oxo-2,3-dihydrobenzo[d]oxazol-5-yl)phenyl)ethyl)-6-hydroxy-6-methyl-1,4-oxazocane-2-carboxamide (Compound 23-A) and (2S,6R)—N—((S)-1-cyano-2-(4-(3-methyl-2-oxo-2,3-dihydrobenzo[d]oxazol-5-yl)phenyl)ethyl)-6-hydroxy-6-methyl-1,4-oxazocane-2-carboxamide (Compound 23-B)
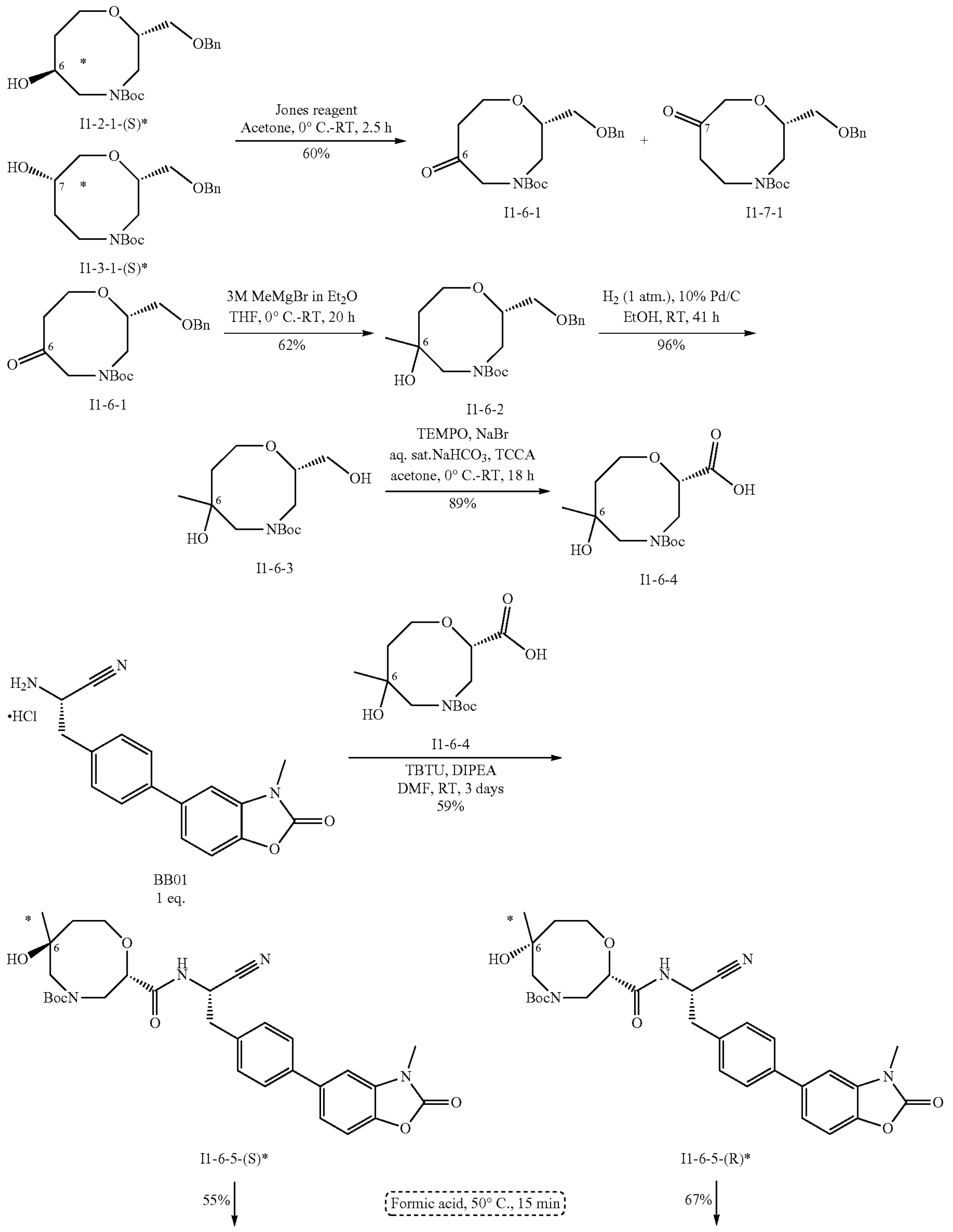

-continued

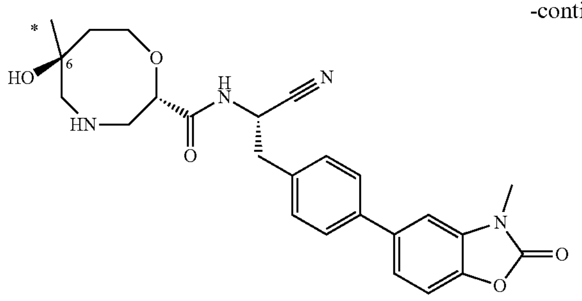

Compound 23-A

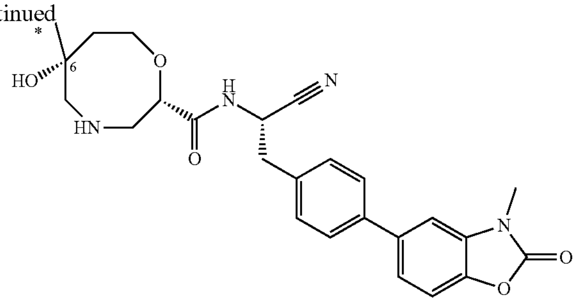

Compound 23-B tert-butyl (2S)-2-[(benzyloxy)methyl]-6-oxo-1,4-oxazocane-4-carboxylate I1-6-1 and tert-butyl (2S)-2-[(benzyloxy)methyl]-7-oxo-1,4-oxazocane-4-carboxylate I1-7-1

To a mixture of I1-2/3-1-(S)* (1 eq., 1.47 g, 3.83 mmol) in acetone (35 mL) was added Jones reagent (1.5 eq., 2.87 mL, 5.75 mmol) at 0° C. The reaction was stirred at 0° C. for 2 h and the reaction mixture was quenched with isopropanol (50 mL), diluted with water (100 mL) and extracted with EtOAc (3×100 mL). The combined organic layers were washed with brine (100 mL), dried over $Na_2SO_4$, filtered and concentrated to dryness under reduced pressure affording the crude (1.43 g) as a yellowish gum. The crude mixture was purified by ELSD flash chromatography over silica gel (irregular SiOH, 50 μm, 40 g Interchim, dry loading (silica), mobile phase gradient: cyclohexane/EtOAc from 100/0 to 60/40 over 35 min). The fractions containing the compound were combined, evaporated in vacuo and co-evaporated with DCM affording a mixture of I1-6/7-1 as a yellowish oil (1.1 g, 3.15 mmol, 82%).

A mixture of I1-6/7-1 (1.3 g) was purified by SFC (SS-Whelk-01 20×250 mm, Mobile phase: CO2/(iPrOH+ 0.3% iPrNH2) 95/5 to afford I1-6-1 (444 mg, 35%) and I1-7-1 (584 mg, 46%, impure) as colorless oils after concentration under reduced pressure.

Impure I1-7-1 was repurified by ELSD flash chromatography over silica gel (regular SiOH, 25 μm, 25 g Interchim, dry loading (silica), mobile phase gradient: cyclohexane/ EtOAc from 100/0 to 60/40 over 45 min). The fractions containing compound were combined, evaporated in vacuo and co-evaporated with DCM affording I1-7-1 as a yellowish oil (320 mg, 25%).

I1-6-1:

SFC analysis: Whelk-04 4.6×100 mm, Mobile phase: CO2/(iPrOH+0.3% iPrNH2) 90/10, Rt=2.49 min, 100%.

LC/MS (AN01_001_026): Rt=9.76 min, 95.43%, $[M-Boc+H]^+$=250.28

The C-6 regiochemistry was confirmed by 2D NMR analysis.

$^1$H NMR (400 MHZ, DMSO) δ 7.41-7.18 (m, 5H), 4.56-4.44 (m, 2H), 4.09-3.95 (m, 1H), 3.94-3.69 (m, 4H), 3.64-3.49 (m, 1H), 3.48-3.39 (m, 2H), 3.04-2.85 (m, 2H), 2.15-2.06 (m, 1H), 1.48-1.33 (m, 9H).

I1-7-1:

SFC analysis: Whelk-04 4.6×100 mm, Mobile phase: CO2/(iPrOH+0.3% iPrNH2) 90/10, Rt=2.10 min, 100%.

LC/MS (AN01_001_026): Rt=9.66 min, 91.66%, $[M-Boc+H]^+$=250.33 The C-7 regiochemistry was confirmed by 2D NMR analysis.

$^1$H NMR (400 MHZ, DMSO) & 7.41-7.25 (m, 5H), 4.58-4.47 (m, 2H), 4.32-4.20 (m, 1H), 4.00-3.83 (m, 1H), 3.81-3.71 (m, 1H), 3.71-3.57 (m, 2H), 3.54-3.42 (m, 2H), 3.30-3.03 (m, 3H), 2.33-2.20 (m, 1H), 1.36 (s, 9H).

tert-butyl (2S)-2-[(benzyloxy)methyl]-6-hydroxy-6-methyl-1,4-oxazocane-4-carboxylate I1-6-2

To a solution of I1-6-1 (1 eq., 0.406 g, 1.16 mmol) in THF (10 mL) was added MeMgBr 3M in $Et_2O$ (3.5 eq., 1.36 mL, 4.067 mmol) at 0° C. The reaction mixture was warmed to RT and stirred for 15 h, then the reaction mixture was quenched with water (20 mL) and a sat. aq. $NH_4Cl$ solution (30 mL) and extracted with EtOAc (3×50 mL). The combined organic layers were washed with brine (50 mL), dried over $Na_2SO_4$, filtered and concentrated to dryness under reduced pressure affording the crude (0.37 g) as a yellow gum. The crude mixture was purified by ELSD flash chromatography over silica gel (irregular SiOH, 50 μm, 25 g Interchim, dry loading (silica), mobile phase gradient: cyclohexane/EtOAc from 100/0 to 30/70 over 50 min). The fractions containing compounds were combined, evaporated in vacuo and co-evaporated with DCM affording both diastereomers (217 mg) and (60.0 mg) as yellow gums. Both fractions were combined together affording 11-6-2 as a yellow gum mixture of diastereomers (ratio, 68:25) (0.26 g, 0.72 mmol, 62%).

tert-butyl (2S)-6-hydroxy-2-(hydroxymethyl)-6-methyl-1,4-oxazocane-4-carboxylate I1-6-3

Starting from a diastereomeric mixture of I1-6-2 (1 eq., 260 mg, 0.72 mmol) and using general procedure D, I1-6-3 was obtained as a colorless oil (190 mg, 96%). The crude was used as such without further purification.

LC/MS (AN01_001_026, ELSD): Not UV active, Rt=6.10 and 6.41 min, 38.70 and 61.30%, $[M-{}^tBu+H]^+$=220.12.

(2S)-4-[(tert-butoxy) carbonyl]-6-hydroxy-6-methyl-1,4-oxazocane-2-carboxylic acid I1-6-4

Starting from a diastereomeric mixture of I1-6-3 (1 eq., 185 mg, 0.69 mmol), using general procedure E, 11-6-4 was obtained as a white solid (179 mg, 89%). The crude was used as such in the next experiment without further purification.

LC/MS (AN01_001_026, ELSD): Not UV active, Rt=6.23 and 6.47 min, 11.18 and 66.82%, $[M+Na]^+$=312.18.

tert-butyl (2S,6S*)-2-{[(1S)-1-cyano-2-[4-(3-methyl-2-oxo-2,3-dihydro-1,3-benzoxazol-5-yl)phenyl]ethyl]carbamoyl}-6-hydroxy-6-methyl-1,4-oxazocane-4-carboxylate 11-6-5-(S)* and tert-butyl (2S,6R*)-2-{[(1S)-1-cyano-2-[4-(3-methyl-2-oxo-2,3-dihydro-1,3-benzoxazol-5-yl)phenyl]ethyl]carbamoyl}-6-hydroxy-6-methyl-1,4-oxazocane-4-carboxylate I1-6-5-(R)*

Starting from BB01 (1 eq., 150 mg, 0.45 mmol) and I1-6-4 (1.05 eq., 140 mg, 0.48 mmol), and using general procedure B, both diastereomers I1-6-5-(S)* (120 mg, 47%) and I1-6-5-(R)* (31 mg, 12%) were obtained as orange gums after purification by flash chromatography over silica gel (50 μm, 24 g, DCM/EtOAc from 100:0 to 0:100 over 40 min). 11-6-5-(S)*:

LC/MS (AN01_001_061): Rt=1.56 min, 100%, $[M-{}^tBu+H]^+$=509.2.

I1-6-5-(R)*:

LC/MS (AN01_001_061): Rt=1.50 min, 85.7%, [M−Boc+H]=465.2.

(2S,6S*)—N-[(1S)-1-cyano-2-[4-(3-methyl-2-oxo-2,3-dihydro-1,3-benzoxazol-5-yl)phenyl]ethyl]-6-hydroxy-6-methyl-1,4-oxazocane-2-carboxamide Starting from 11-6-5-(S)* (1 eq., 115 mg, 0.21 mmol) and using general procedure C, the product was obtained as a white solid (54.4 mg, 55%) after purification by flash chromatography over silica gel (regular SiOH, 15 μm, 12 g Interchim, dry loading (silica), mobile phase gradient: DCM/MeOH from 100/0 to 90/10 over 30 min), then vacuum-dried at 40° C. for 18 h.

LC/MS (AN_01_001_021): Rt=6.92 min, 99.42%, $[M+H]^+$=465.46.

$^1$H NMR (400 MHZ, DMSO) δ 8.63 (d, J=8.5 Hz, 1H), 7.68-7.62 (m, 2H), 7.59-7.55 (m, 1H), 7.43-7.33 (m, 4H), 5.03-4.91 (m, 1H), 4.20 (s, 1H), 3.94-3.81 (m, 2H), 3.69-3.61 (m, 1H), 3.40 (s, 3H), 3.25-3.11 (m, 2H), 3.04 (dd, J=13.7, 2.5 Hz, 1H), 2.80 (d, J=13.9 Hz, 1H), 2.55-2.52 (m, 1H), 2.21 (dd, J=13.8, 10.3 Hz, 1H), 2.14-2.02 (m, 1H), 1.43-1.33 (m, 1H), 1.02 (s, 3H), one missing proton (NH).

(2S,6R*)—N-[(1S)-1-cyano-2-[4-(3-methyl-2-oxo-2,3-dihydro-1,3-benzoxazol-5-yl)phenyl]ethyl]-6-hydroxy-6-methyl-1,4-oxazocane-2-carboxamide Starting from 11-6-5-(R)* (1 eq., 28 mg, 0.06 mmol) and using general procedure C, (2S,6R*)—N-[(1S)-1-cyano-2-[4-(3-methyl-2-oxo-2,3-dihydro-1,3-benzoxazol-5-yl)phenyl]ethyl]-6-hydroxy-6-methyl-1,4-oxazocane-2-carboxamide was obtained as a white solid (17.0 mg, 67%) after purification by flash chromatography over silica gel (regular SiOH, 15 μm, 12 g Interchim, dry loading (silica), mobile phase gradient: DCM/MeOH from 100/0 to 95/5 over 30 min), then vacuum-dried at 40° C. for 18 h.

LC/MS (AN_01_001_021): Rt=6.83 min, 94.77%, $[M+H]^+$=465.42.

$^1$H NMR (400 MHZ, DMSO) § 8.63 (d, J=8.5 Hz, 1H), 7.68-7.61 (m, 2H), 7.58-7.51 (m, 1H), 7.45-7.32 (m, 4H), 5.06-4.90 (m, 1H), 4.18 (s, 1H), 4.07 (td, J=11.9, 2.4 Hz, 1H), 3.91 (dd, J=10.3, 2.4 Hz, 1H), 3.57-3.49 (m, 1H), 3.40 (s, 3H), 3.26-3.13 (m, 2H), 2.97 (dd, J=13.2, 2.4 Hz, 1H), 2.67 (d, J=13.3 Hz, 1H), 2.56 (d, J=13.3 Hz, 1H), 2.28-2.11 (m, 2H), 1.23-1.16 (m, 1H), 1.05 (s, 3H), one missing proton (NH).

Example 24: Preparation of (2S,6S)—N—((S)-1-cyano-2-(4-(3-methyl-2-oxo-2,3-dihydrobenzo[d]oxazol-5-yl)phenyl)ethyl)-6-hydroxy-6-vinyl-1,4-oxazepane-2-carboxamide (Compound 24)

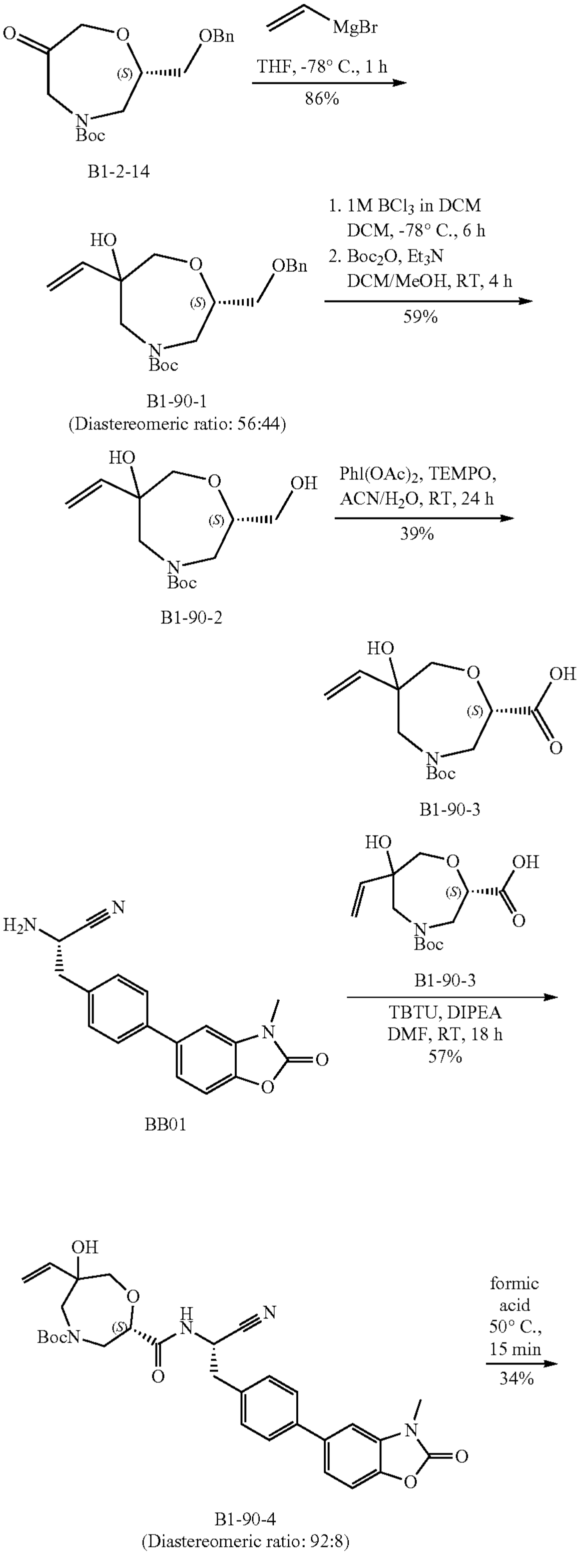

-continued

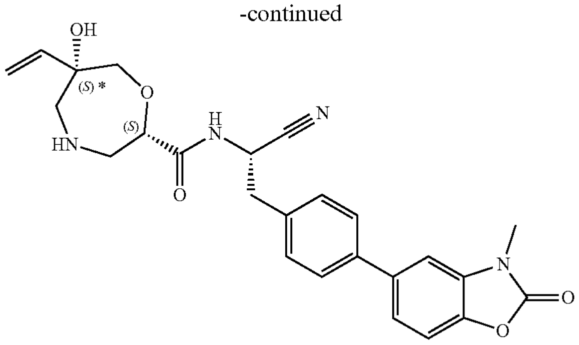

Compound 24
(Diastereomeric ratio: 92:8)

tert-butyl (2S)-2-[(benzyloxy)methyl]-6-ethenyl-6-hydroxy-1,4-oxazepane-4-carboxylate B1-90-1

To a solution of I1-2-14 (1 eq., 1 g, 2.98 mmol) in THF (27 mL) was added a solution of vinylmagnesium bromide 1M in THF (3 eq., 8.94 mL, 8.94 mmol) at −78° C. The RM was stirred at −78° C. for 1 h. The RM was diluted with water (30 mL) and extracted with EtOAc (3×50 mL). The combined organic layers were washed with brine (50 mL), dried over $Na_2SO_4$, filtered and concentrated to afford the crude residue (1.31 g) as a yellowish transparent oil. The crude was purified by flash chromatography over silica gel (regular SiOH, 15 μm, 40 g, dry loading (silica), mobile phase gradient: Cyclo/EtOAc from 10/0 to 4/6 over 50 min). The fractions containing compound were combined, evaporated in vacuo and co-evaporated with DCM affording B1-90-1 as colorless oil (0.93 g, 86%).

LC/MS (AN_01_001_061): Rt=1.58 & 1.62 min, 43.81 & 56.19%, $[M-{}^tBu+H]^+$=308.11.

tert-butyl (2S)-6-ethenyl-6-hydroxy-2-(hydroxymethyl)-1,4-oxazepane-4-carboxylate B1-90-2

To a solution of B1-90-1 (1 eq., 800 mg, 2.201 mmol) in DCM (11.006 mL) at −78° C. was added a solution of $BCl_3$ 1M in DCM (2 eq., 4.402 mL, 4.402 mmol). The reaction mixture was stirred at −78° C. for 4 h. Additional solution of $BCl_3$ 1M in DCM (2 eq., 4.402 mL, 4.402 mmol) was added at −78° C. and the reaction mixture was stirred at −78° C. for 2 h. The RM was quenched with MeOH (10 mL), then concentrated under reduced pressure to afford the crude residue (483 mg) as a colorless gum which was engaged as such in the next step.

To the crude residue (1 eq., 460 mg, 2.19 mmol) and $Et_3N$ (3 eq., 666.029 mg, 0.91 mL, 6.58 mmol) in DCM (3.29 mL) was added a solution of $Boc_{20}$ (1.2 eq., 574.59 mg, 0.56 mL, 2.63 mmol) in MeOH (3 mL). The RM was stirred at RT for 4 h. The RM was concentrated under reduced pressure to the crude residue (888 mg) as a white solid. The crude was purified by flash chromatography over silica gel (50 μm, 24 g, Cyclohexane/EA from 100:0 to 25:75 over 50 min) to afford B1-90-2 as a colorless oil (352 mg, 59% over two steps).

LC/MS (AN_01_001_061): Not UV active, Rt=1.18 min, ND, $[M-{}^tBu+H]^+$=218.1.

(2S)-4-[(tert-butoxy) carbonyl]-6-ethenyl-6-hydroxy-1,4-oxazepane-2-carboxylic acid B1-90-3

To a solution of B1-90-2 (1 eq., 80 mg, 0.29 mmol) in MeCN (1.46 mL) was added TEMPO (0.2 eq., 9.15 mg, 0.059 mmol) and iodobenzene diacetate (2.5 eq., 235.69 mg, 0.73 mmol) at 0° C. The reaction mixture was stirred at RT for 24 h. DCM (15 mL) and 1 M HCl (15 mL) were added. The two phases were separated and the aqueous layer was extracted with DCM (2×15 mL). The combined organic layers were dried over $Na_2SO_4$, filtered and concentrated to dryness under reduced pressure to afford B1-90-3 as a colorless gum (33 mg, 39%). The crude was used as such in the next step without further purification.

LC/MS (AN_01_001_061): Not UV active, Rt=1.20 min, ND, [M−H]=286.1.

tert-butyl (2S)-2-{[(1S)-1-cyano-2-[4-(3-methyl-2-oxo-2,3-dihydro-1,3-benzoxazol-5-yl)phenyl]ethyl]carbamoyl}-6-ethenyl-6-hydroxy-1,4-oxazepane-4-carboxylate B1-90-4

Starting from BB01 (1 eq., 32.8 mg, 0.10 mmol) and B1-90-3 (1.05 eq., 30.0 mg, 0.10 mmol), and using general procedure B, B1-90-4 (32.0 mg, 0.057 mmol, 57%) was obtained as an orange solid after purification by flash chromatography over silica gel (50 μm, 4 g, cyclohexane/EtOAc from 100:0 to 40:60 over 40 min).

LC/MS (AN_01_001_061): Rt=1.54 min, 96.57%, $[M-{}^tBu+H]$=507.2.

(2S,6S)—N-[(1S)-1-cyano-2-[4-(3-methyl-2-oxo-2,3-dihydro-1,3-benzoxazol-5-yl)phenyl]ethyl]-6-ethenyl-6-hydroxy-1,4-oxazepane-2-carboxamide The Stereochemistry(S)* was Arbitrarily Assigned Starting from B1-90-4 (1 eq., 30.0 mg, 0.05 mmol) and using general procedure C, (2S,6S)—N-[(1S)-1-cyano-2-[4-(3-methyl-2-oxo-2,3-dihydro-1,3-benzoxazol-5-yl)phenyl]ethyl]-6-ethenyl-6-hydroxy-1,4-oxazepane-2-carboxamide was obtained as a single diastereomer as a white solid (8.4 mg, 34%) after purification by flash chromatography over silica gel (regular SiOH, 15 μm, 4 g Interchim, dry loading (silica), mobile phase gradient: DCM/MeOH from 100/0 to 95/5 over 35 min), then vacuum-dried at 40° C. for 18 h.

LC/MS (AN_01_001_021): Rt=9.47 min, 99.01%, $[M+H]^+$=463.40

$^1$H NMR (400 MHZ, DMSO) δ 8.58 (d, J=8.5 Hz, 1H), 7.68-7.61 (m, 2H), 7.58-7.53 (m, 1H), 7.44-7.35 (m, 4H), 5.95 (dd, J=17.4, 10.8 Hz, 1H), 5.27 (dd, J=17.4, 2.1 Hz, 1H), 5.08-4.96 (m, 2H), 4.77 (s, 1H), 4.09 (dd, J=9.4, 4.3 Hz, 1H), 3.63 (d, J=12.3 Hz, 1H), 3.49 (d, J=12.3 Hz, 1H), 3.40 (s, 3H), 3.27-3.15 (m, 2H), 3.15-3.07 (m, 1H), 2.62 (d, J=5.6 Hz, 2H), 2.41 (dd, J=14.2, 9.5 Hz, 1H).

Example 25: Preparation of (2S,6S)—N—((S)-1-cyano-2-(4-(3-methyl-2-oxo-2,3-dihydrobenzo[d]oxazol-5-yl)phenyl)ethyl)-6-ethoxy-1,4-oxazocane-2-carboxamide (Compound 25-A) and (2S,7S)—N—((S)-1-cyano-2-(4-(3-methyl-2-oxo-2,3-dihydrobenzo[d]oxazol-5-yl)phenyl)ethyl)-7-ethoxy-1,4-oxazocane-2-carboxamide (Compound 25-B)
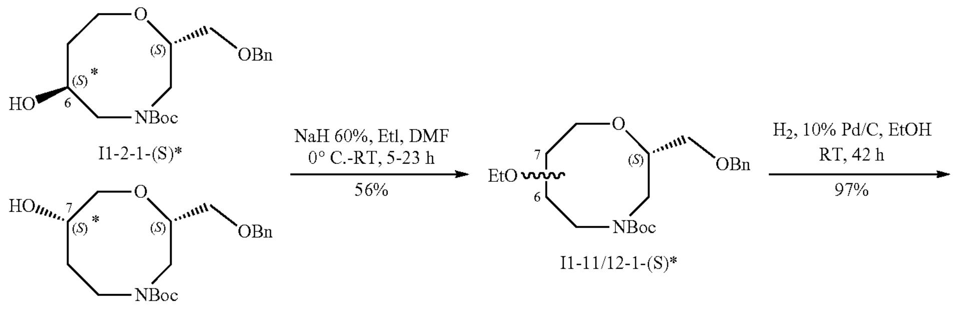
I1-3-1-(S)*
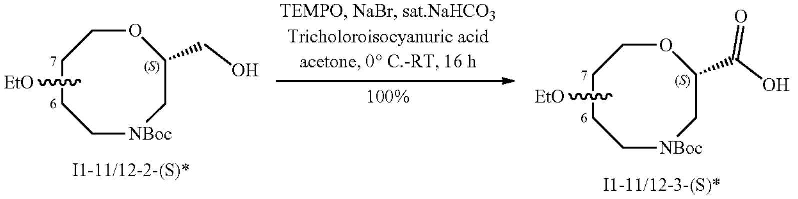
I1-11/12-2-(S)*
I1-11/12-3-(S)*
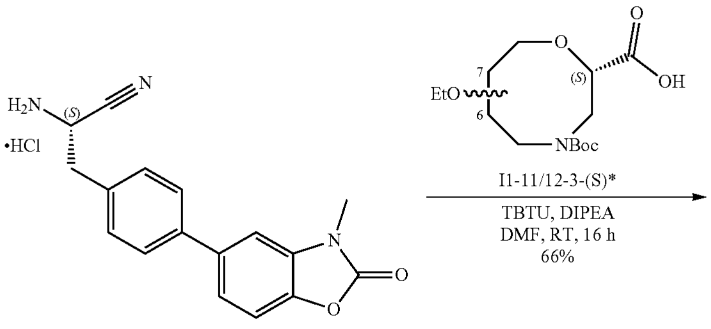
BB01
1 eq.
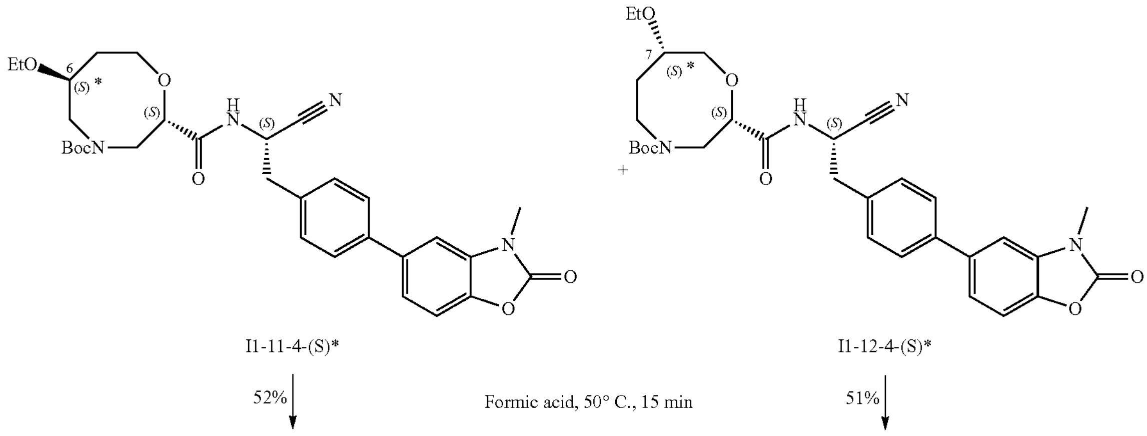

-continued

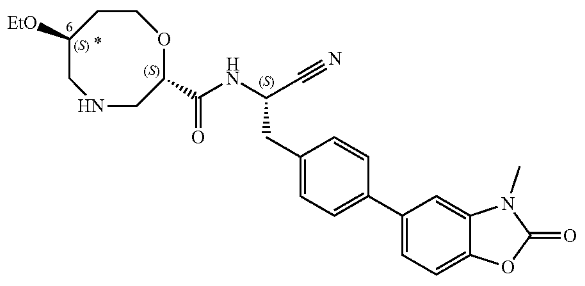

Compound 25-A

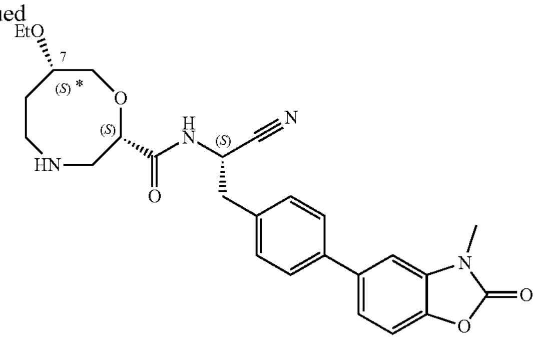

Compound 25-B

Mixture of tert-butyl (2S,6S*)-2-[(benzyloxy)methyl]-7-ethoxy-1,4-oxazocane-4-carboxylate and tert-butyl (2S,7S*)-2-[(benzyloxy)methyl]-7-ethoxy-1,4-oxazocane-4-carboxylate I1-11/12-1-(S)*.

Starting from a mixture of I1-2/3-1-(S)* (1 eq., 81 mg, 0.13 mmol), and using general procedure F with EtI (2 eq. 4.42 mmol), I1-11/12-1-(S)* was obtained as a yellow oil (301 mg, 56%) after purification by flash chromatography over silica gel (regular SiOH, 50 μm, 25 g Interchim, dry loading (silica), mobile phase gradient: Cyclohexane/EtOAc from 100/0 to 60/40 over 45 min).

LC/MS (AN_01_001_026): Rt=10.60 and 10.82 min, 53 and 47%, $[M-Boc+H]^+$=280.57.

Mixture of tert-butyl (2S,6S*)-6-ethoxy-2-(hydroxymethyl)-1,4-oxazocane-4-carboxylate and tert-butyl (2S,7S*)-6-ethoxy-2-(hydroxymethyl)-1,4-oxazocane-4-carboxylate I1-11/12-2-(S)*.

Starting from a mixture of I1-11/12-1-(S)* (1 eq., 300 mg, 0.79 mmol), and using general procedure D), I1-11/12-2-(S)* was obtained as a crude yellow oil (223 mg, 97%) which was used as such in the next experiment.

LC/MS (AN_01_001_026, ELSD): Not UV active, Rt=7.28 and 7.40 min, 61.06 and 38.94%, $[M-Boc+H]^+$=190.26

Mixture of (2S,6S*)-4-[(tert-butoxy) carbonyl]-6-ethoxy-1,4-oxazocane-2-carboxylic acid and (2S,7S*)-4-[(tert-butoxy) carbonyl]-6-ethoxy-1,4-oxazocane-2-carboxylic acid I1-11/12-3-(S)*.

Starting from a mixture of I1-11/12-2-(S)* (1 eq., 220 mg, 0.77 mmol), and using general procedure E), I1-11/12-3-(S)* was obtained as a crude orange gum (233 mg, 100%) which was used as such in the next experiment.

LC/MS (AN_01_001_026, ELSD): Not UV active, Rt=7.48 and 7.61 min, 73.70 and 26.27%, $[M-Boc+H]^+$=204.07.

tert-butyl (2S,6S*)-2-{[(1S)-1-cyano-2-[4-(3-methyl-2-oxo-2,3-dihydro-1,3-benzoxazol-5-yl)phenyl]ethyl]carbamoyl}-6-ethoxy-1,4-oxazocane-4-carboxylate 11-11-4-(S)* and tert-butyl (2S,7S*)-2-{[(1S)-1-cyano-2-[4-(3-methyl-2-oxo-2,3-dihydro-1,3-benzoxazol-5-yl)phenyl]ethyl]carbamoyl}-6-ethoxy-1,4-oxazocane-4-carboxylate I1-12-4-(S)*

Starting from BB01 (1 eq., 200 mg, 0.61 mmol) and I1-11/12-3-(S)* (1.05 eq., 245 mg, 0.64 mmol), and using general procedure B, I1-11-4-(S)* (98.0 mg, 28%) and I1-12-4-(S)* (134 mg, 38%) were obtained as off-white solids after purification by flash chromatography over silica gel (15 μm, 24 g, cyclohexane/EtOAc from 100:0 to 30:70 over 45 min). The C-6 and C-7 regioisomers were confirmed by 2D NMR analyses on final products.

I1-11-4-(S)*:

LC/MS (AN01_001_061): Rt=1.66 min, 100%, $[M-Boc-H]^+$=479.2

I1-12-4-(S)*

LC/MS (AN01_001_061): Rt=1.63 min, 100%, $[M-Boc-H]^+$=479.3

(2S,6S*)—N-[(1S)-1-cyano-2-[4-(3-methyl-2-oxo-2,3-dihydro-1,3-benzoxazol-5-yl)phenyl]ethyl]-6-ethoxy-1,4-oxazocane-2-carboxamide Starting from I1-11-4-(S)* (1 eq., 85 mg, 0.15 mmol) and using general procedure C, (2S,6S*)—N-[(1S)-1-cyano-2-[4-(3-methyl-2-oxo-2,3-dihydro-1,3-benzoxazol-5-yl)phenyl]ethyl]-6-ethoxy-1,4-oxazocane-2-carboxamide was obtained as a white solid (37.0 mg, 52%) after purification by flash chromatography over silica gel (regular SiOH, 50 μm, 12 g Interchim, dry loading (silica), mobile phase gradient: DCM/MeOH from 100/0 to 90/10 over 35 min), then vacuum-dried at 40° C. for 18 h.

LC/MS (AN_01_001_021): Rt=7.23 min, 99.75%, $[M+H]^+$=479.50.

The C-6 regiochemistry was confirmed by 2D NMR analyses.

$^1$H NMR (400 MHZ, DMSO) δ 8.66 (d, J=8.5 Hz, 1H), 7.70-7.61 (m, 2H), 7.60-7.55 (m, 1H), 7.47-7.30 (m, 4H), 5.06-4.91 (m, 1H), 4.14-3.99 (m, 1H), 3.88 (dd, J=10.3, 2.7 Hz, 1H), 3.64-3.52 (m, 1H), 3.51-3.42 (m, 2H), 3.41 (s, 3H), 3.40-3.34 (m, 1H), 3.25-3.12 (m, 3H), 2.97 (dd, J=13.5, 2.7 Hz, 1H), 2.38 (dd, J=13.6, 9.6 Hz, 1H), 2.25-2.11 (m, 2H), 1.66-1.52 (m, 1H), 1.09 (t, J=7.0 Hz, 3H), one missing proton (NH).

(2S,7S*)—N-[(1S)-1-cyano-2-[4-(3-methyl-2-oxo-2,3-dihydro-1,3-benzoxazol-5-yl)phenyl]ethyl]-7-ethoxy-1,4-oxazocane-2-carboxamide Starting from 11-12-4-(S)* (1 eq., 67 mg, 0.12 mmol) and using general procedure C, (2S,7S*)—N-[(1S)-1-cyano-2-[4-(3-methyl-2-oxo-2,3-dihydro-1,3-benzoxazol-5-yl)phenyl]ethyl]-7-ethoxy-1,4-oxazocane-2-carboxamide was obtained as a white solid (28.4 mg, 51%) after purification by flash chromatography over silica gel (regular SiOH, 15 μm, 12 g Interchim, dry loading (silica), mobile phase gradient: DCM/MeOH from 100/0 to 90/10 over 30 min), then vacuum-dried at 40° C. for 18 h.

LC/MS (AN_01_001_021): Rt=7.19 min, 99.65%, $[M+H]^+$=479.53

The C-7 regiochemistry was confirmed by 2D NMR analyses.

$^1$H NMR (400 MHZ, DMSO) & 8.62 (d, J=8.6 Hz, 1H), 7.70-7.61 (m, 2H), 7.59-7.54 (m, 1H), 7.44-7.33 (m, 4H), 5.06-4.97 (m, 1H), 3.97-3.83 (m, 2H), 3.81 (dd, J=9.2, 2.8 Hz, 1H), 3.55-3.42 (m, 3H), 3.40 (s, 3H), 3.26-3.14 (m, 2H), 2.94 (dd, J=14.3, 3.1 Hz, 1H), 2.80-2.72 (m, 2H), 2.35-2.24 (m, 1H), 1.92-1.80 (m, 1H), 1.77-1.65 (m, 1H), 1.10 (t, J=7.0 Hz, 3H), one missing proton (NH).
Example 26: Preparation of (2S,6R)—N—((S)-1-cyano-2-(4-(3-methyl-2-oxo-2,3-dihydrobenzo[d]oxazol-5-yl)phenyl)ethyl)-6-ethoxy-1,4-oxazocane-2-carboxamide (Compound 26-A) and (2S,7R)—N—((S)-1-cyano-2-(4-(3-methyl-2-oxo-2,3-dihydrobenzo[d]oxazol-5-yl)phenyl)ethyl)-7-ethoxy-1,4-oxazocane-2-carboxamide (Compound 26-B)
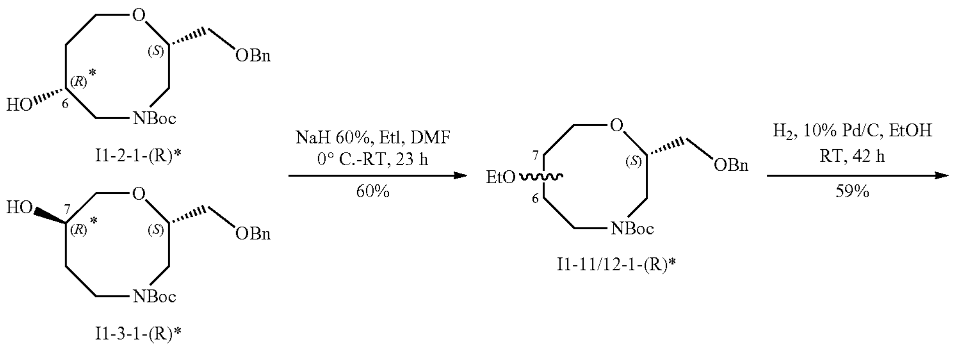
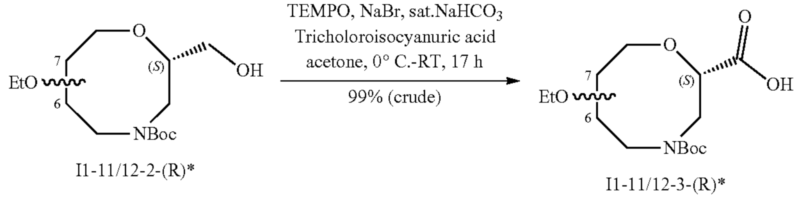
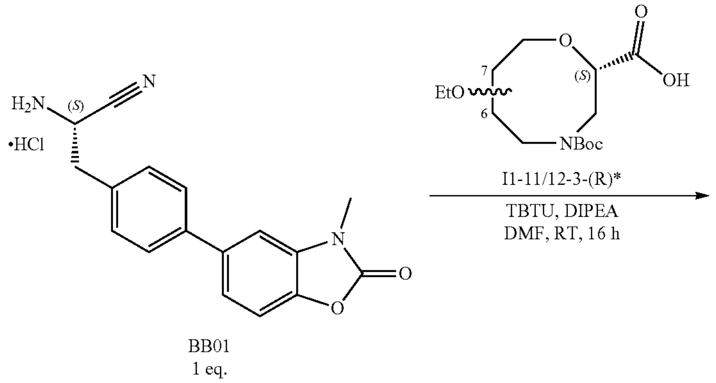
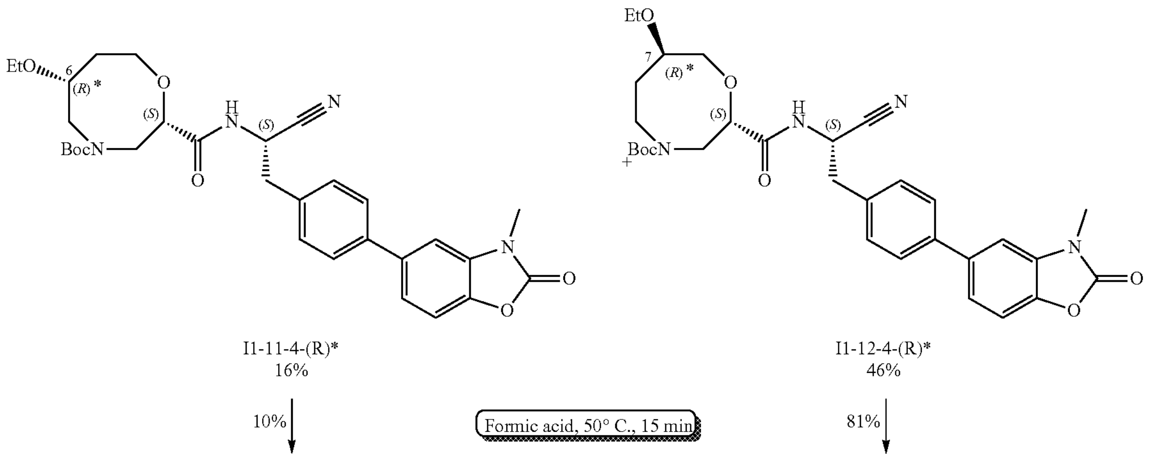

-continued

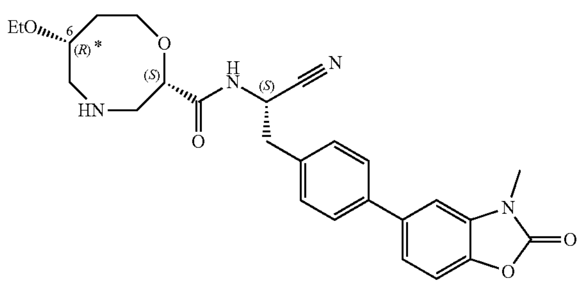

Compound 26-A

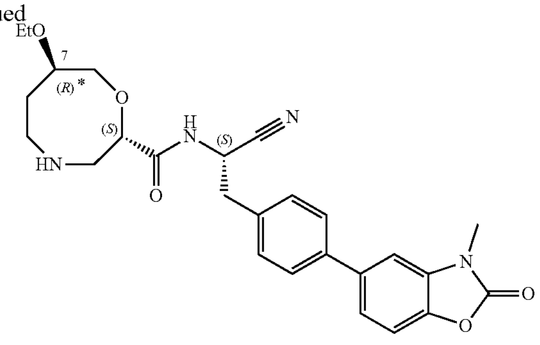

Compound 26-B

Mixture of tert-butyl (2S,6R*)-2-[(benzyloxy)methyl]-7-ethoxy-1,4-oxazocane-4-carboxylate and tert-butyl (2S,7R*)-2-[(benzyloxy)methyl]-7-ethoxy-1,4-oxazocane-4-carboxylate I1-11/12-1-(R)*.

Starting from a mixture of I1-2/3-1-(R)* (1 eq., 850 mg, 2.42 mmol), and using general procedure F with EtI (2 eq. 4.42 mmol), I1-11/12-1-(R)* was obtained as a yellow oil (551 mg, 60%) after purification by flash chromatography over silica gel (regular SiOH, 50 μm, 40 g Interchim, dry loading (silica), mobile phase gradient: Cyclohexane/EtOAc from 100/0 to 80/20 over 35 min).

LC/MS (AN_01_001_061): Rt=1.74 min, 95.34%, $[M-Boc+H]^+$=280.2.

Mixture of tert-butyl (2S,6R*)-6-ethoxy-2-(hydroxymethyl)-1,4-oxazocane-4-carboxylate and tert-butyl (2S,7R*)-6-ethoxy-2-(hydroxymethyl)-1,4-oxazocane-4-carboxylate I1-11/12-2-(R)*.

Starting from a mixture of I1-11/12-1-(R)* (1 eq., 550 mg, 1.45 mmol), and using general procedure D), I1-11/12-2-(R)* was obtained as a crude yellow oil (246 mg, 59%) which was used as such in the next experiment.

LC/MS (AN_01_001_086): Low UV active, Rt=5.37 and 5.42 min, 22.61 and 70.75%, $[M-{}^tBu+H]^+$=220.23.

Mixture of (2S,6R*)-4-[(tert-butoxy) carbonyl]-6-ethoxy-1,4-oxazocane-2-carboxylic acid and (2S,7R*)-4-[(tert-butoxy) carbonyl]-6-ethoxy-1,4-oxazocane-2-carboxylic acid I1-11/12-3-(R)*.

Starting from a mixture of I1-11/12-2-(R)* (1 eq., 245 mg, 0.85 mmol), and using general procedure E), I1-11/12-3-(R)* was obtained as a crude yellow gum (256 mg, 99%) which was used as such in the next experiment.

LC/MS (AN_01_001_086, ELSD): Low UV active, Rt=5.52 min, 98.69%, $[M-Boc+H]^+$=204.17.

tert-butyl (2S,6R*)-2-{[(1S)-1-cyano-2-[4-(3-methyl-2-oxo-2,3-dihydro-1,3-benzoxazol-5-yl)phenyl]ethyl]carbamoyl}-6-ethoxy-1,4-oxazocane-4-carboxylate I1-11-4-(R)* and tert-butyl (2S,7R*)-2-{[(1S)-1-cyano-2-[4-(3-methyl-2-oxo-2,3-dihydro-1,3-benzoxazol-5-yl)phenyl]ethyl]carbamoyl}-6-ethoxy-1,4-oxazocane-4-carboxylate I1-12-4-(R)*

Starting from BB01 (1 eq., 265 mg, 0.80 mmol) and I1-11/12-3-(R)* (1.05 eq., 256 mg, 0.84 mmol), and using general procedure B, 11-11-4-(R)* (86.0 mg, 18%) and I1-12-4-(R)* (223 mg, 48%) were obtained as off-white solids after purification by flash chromatography over silica gel (15 μm, 25 g, cyclohexane/EtOAc from 100:0 to 50:50 over 45 min).

I1-11-4-(R)*:

LC/MS (AN01_001_088, ELSD): Rt=6.98 min, 100%, $[M-Boc-H]^+$=479.48.

I1-12-4-(R)*:

LC/MS (AN01_001_086): Rt=7.09 min, 96.38%, $[M-{}^tBu+H]^+$=523.55.

(2S,6R*)—N-[(1S)-1-cyano-2-[4-(3-methyl-2-oxo-2,3-dihydro-1,3-benzoxazol-5-yl)phenyl]ethyl]-6-ethoxy-1,4-oxazocane-2-carboxamide Starting from I1-11-4-(R)* (1 eq., 85 mg, 0.13 mmol) and using general procedure C, (2S,6R*)—N-[(1S)-1-cyano-2-[4-(3-methyl-2-oxo-2,3-dihydro-1,3-benzoxazol-5-yl)phenyl]ethyl]-6-ethoxy-1,4-oxazocane-2-carboxamide was obtained as a white solid (6.00 mg, 10%) after purification by flash chromatography over silica gel (regular SiOH, 15 μm, 12 g Interchim, dry loading (silica), mobile phase gradient: DCM/MeOH from 100/0 to 90/10 over 35 min), then vacuum-dried at 40° C. for 18 h. N.B: (19.0 mg, 30%) of (2S,7S)—N—((S)-1-cyano-2-(4-(3-methyl-2-oxo-2,3-dihydrobenzo[d]oxazol-5-yl)phenyl)ethyl)-7-ethoxy-1,4-oxazocane-2-carboxamide was also isolated during the purification.

LC/MS (AN_01_001_088): Rt=4.88 min, 88.91%, $[M+H]^+$=479.50

$^1$H NMR (400 MHZ, DMSO) § 8.62 (d, J=8.6 Hz, 1H), 7.69-7.61 (m, 2H), 7.59-7.53 (m, 1H), 7.44-7.32 (m, 4H), 5.06-4.94 (m, 1H), 3.99-3.86 (m, 1H), 3.86-3.75 (m, 1H), 3.67 (dt, J=12.0, 3.9 Hz, 1H), 3.40 (s, 3H), 3.42-3.37 (m, 1H), 3.23-3.15 (m, 2H), 3.14-3.07 (m, 1H), 2.97 (dd, J=13.7, 2.6 Hz, 1H), 2.73-2.64 (m, 1H), 2.59-2.54 (m, 1H), 2.25-2.07 (m, 3H), 1.60 (dd, J=14.6, 3.6 Hz, 1H), 1.11-1.04 (m, 3H), one missing proton (NH).

The structure of (2S,6R)—N—((S)-1-cyano-2-(4-(3-methyl-2-oxo-2,3-dihydrobenzo[d]oxazol-5-yl)phenyl) ethyl)-6-ethoxy-1,4-oxazocane-2-carboxamide (C-6) was confirmed by 2D NMR analysis.

(2S,7R*)—N-[(1S)-1-cyano-2-[4-(3-methyl-2-oxo-2,3-dihydro-1,3-benzoxazol-5-yl)phenyl]ethyl]-7-ethoxy-1,4-oxazocane-2-carboxamide Starting from I1-12-4-(R)* (1 eq., 100 mg, 0.17 mmol) and using general procedure C, (2S,7R*)—N-[(1S)-1-cyano-2-[4-(3-methyl-2-oxo-2,3-dihydro-1,3-benzoxazol-5-yl)phenyl]ethyl]-7-ethoxy-1,4-oxazocane-2-carboxamide was obtained as a white solid (67.0 mg, 81%) after purification by flash chromatography over silica gel (regular SiOH, 15 μm, 12 g Interchim, dry loading (silica), mobile phase gradient: DCM/MeOH from 100/0 to 90/10 over 30 min), then vacuum-dried at 40° C. for 18 h.

LC/MS (AN_01_001_088): Rt=4.90 min, 99.07%, $[M+H]^+$=479.55

The C-7 regiochemistry was confirmed by 2D NMR analyses.

$^1$H NMR (400 MHZ, DMSO) § 8.64 (d, J=8.6 Hz, 1H), 7.68-7.62 (m, 2H), 7.59-7.54 (m, 1H), 7.43-7.34 (m, 4H), 5.01 (td, J=8.7, 7.2 Hz, 1H), 4.07 (dd, J=11.4, 4.3 Hz, 1H), 3.90 (dd, J=9.0, 3.0 Hz, 1H), 3.57 (dd, J=11.4, 8.6 Hz, 1H), 3.52-3.41 (m, 3H), 3.40 (s, 3H), 3.25-3.12 (m, 2H), 3.03-2.93 (m, 2H), 2.59-2.55 (m, 1H), 2.31 (dd, J=14.5, 9.0 Hz, 1H), 1.93-1.84 (m, 1H), 1.64-1.53 (m, 1H), 1.08 (t, J=7.0 Hz, 3H), one missing proton (NH).

Example 27: Preparation of (2S)—N—((S)-1-cyano-2-(4-(3-methyl-2-oxo-2,3-dihydrobenzo[d]oxazol-5-yl)phenyl)ethyl)-7-hydroxy-7-methyl-1,4-oxazocane-2-carboxamide (Compound 27)

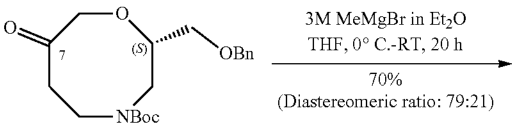

I1-7-1

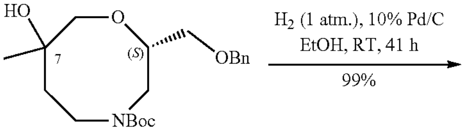

I1-7-2

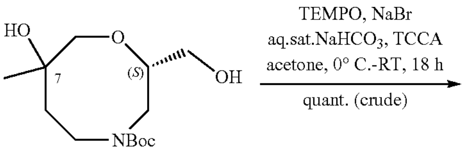

I1-7-3

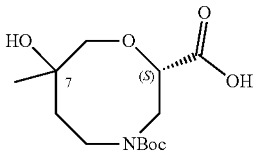

I1-7-4

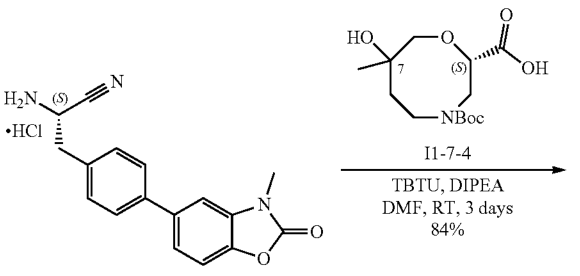

BB01
1 eq.

-continued

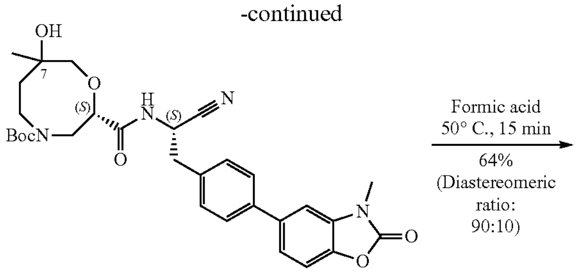

I1-7-5

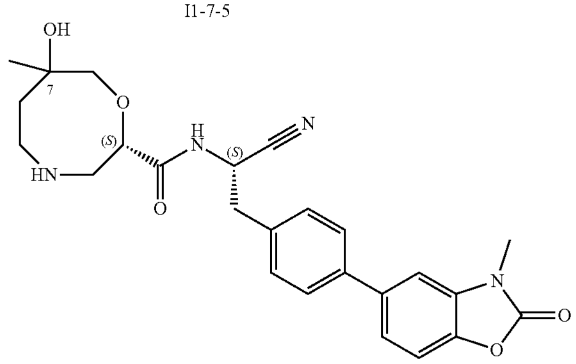

Compound 27 tert-butyl (2S)-2-[(benzyloxy)methyl]-7-hydroxy-7-methyl-1,4-oxazocane-4-carboxylate I1-7-2

To a solution of 11-7-1 (1 eq., 280 mg, 0.801 mmol, previously described) in THF (7 mL) was added MeMgBr 3M in $Et_{20}$ (3.5 eq., 0.93 mL, 2.805 mmol) at 0° C. The reaction mixture was warmed to RT and stirred for 15 h, then the reaction mixture was quenched with water (20 mL) and a sat. aq. $NH_4Cl$ solution (30 mL) and extracted with EtOAc (3×50 mL). The combined organic layers were washed with brine (50 mL), dried over $Na_2SO_4$, filtered and concentrated to dryness under reduced pressure affording the crude (270 mg) as a yellow gum. The crude mixture was purified by ELSD flash chromatography over silica gel (irregular SiOH, 50 µm, 25 g Interchim, dry loading (silica), mobile phase gradient: cyclohexane/EtOAc from 100/0 to 0/100 over 60 min). The fractions containing compounds were combined, evaporated in vacuo and co-evaporated with DCM affording 11-7-2 as a yellow oil (mixture of diastereomers ratio, 68:25) (210 mg, 0.57 mmol, 72%).

LC/MS (AN01_001_026): Rt=8.82 and 9.20 min, 17.30 and 66.98%, $[M\text{-}Boc+H]^+$=266.46.

tert-butyl (2S)-7-hydroxy-2-(hydroxymethyl)-7-methyl-1,4-oxazocane-4-carboxylate I1-7-3

Starting from a diastereomeric mixture of I1-7-2 (1 eq., 210 mg, 0.57 mmol) and using general procedure D, I1-7-3 was obtained as a colorless oil (160 mg, 99%, crude). The crude was used as such without further purification.

LC/MS (AN01_001_026, ELSD): Not UV active, Rt=6.10 min, 92.84%, $[M\text{-}^tBu+H]^+$=220.15.

(2S)-4-[(tert-butoxy) carbonyl]-7-hydroxy-7-methyl-1,4-oxazocane-2-carboxylic acid I1-7-4

Starting from a diastereomeric mixture of I1-7-3 (1 eq., 160 mg, 0.57 mmol), using general procedure E, I1-7-4 was obtained as a white solid (120 mg, 74%, crude). The crude was used as such in the next experiment without further purification.

LC/MS (AN01_001_026, ELSD): Not UV active, Rt=6.16 min, 95.53%, $[M-^{t}Bu+H]^{+}$=234.12.

tert-butyl (2S)-2-{[(1S)-1-cyano-2-[4-(3-methyl-2-oxo-2,3-dihydro-1,3-benzoxazol-5-yl)phenyl]ethyl] carbamoyl}-7-hydroxy-7-methyl-1,4-oxazocane-4-carboxylate I1-7-5

Starting from BB01 (1 eq., 130 mg, 0.40 mmol) and I1-7-4 (1.05 eq., 170 mg, 0.42 mmol), and using general procedure B, I1-7-5 (190 mg, 84%) was obtained as a yellow solid after purification by flash chromatography over silica gel (50 μm, 12 g, DCM/EtOAc from 100:0 to 0:100 over 50 min).

LC/MS (AN01_001_026): Rt=8.92 min, 92.17%, $[M-^{t}Bu+H]^{+}$=509.45

(2S)—N-[(1S)-1-cyano-2-[4-(3-methyl-2-oxo-2,3-dihydro-1,3-benzoxazol-5-yl)phenyl]ethyl]-7-hydroxy-7-methyl-1,4-oxazocane-2-carboxamide Starting from I1-7-5 (1 eq., 90.0 mg, 0.16 mmol) and using general procedure C, (2S)—N-[(1S)-1-cyano-2-[4-(3-methyl-2-oxo-2,3-dihydro-1,3-benzoxazol-5-yl)phenyl] ethyl]-7-hydroxy-7-methyl-1,4-oxazocane-2-carboxamide was obtained as a white solid (47.7 mg, 64%) after purification by flash chromatography over silica gel (regular SiOH, 50 μm, 12 g Interchim, dry loading (silica), mobile phase gradient: DCM/MeOH from 100/0 to 80/20 over 35 min), then vacuum-dried at 40° C. for 18 h.

LC/MS (AN_01_001_088): Rt=4.58 and 4.63 min, 10.31 and 88.84%, $[M+H]^{+}$=465.47.

(2S)—N-[(1S)-1-cyano-2-[4-(3-methyl-2-oxo-2,3-dihydro-1,3-benzoxazol-5-yl)phenyl]ethyl]-7-hydroxy-7-methyl-1,4-oxazocane-2-carboxamide: (Diastereomeric ratio 90:10)

$^{1}$H NMR (400 MHZ, DMSO) δ 8.64-8.49 (m, 1H), 7.69-7.60 (m, 2H), 7.59-7.51 (m, 1H), 7.45-7.34 (m, 4H), 5.13-4.96 (m, 1H), 4.01-3.80 (m, 1H), 3.79-3.55 (m, 2H), 3.40 (s, 3H), 3.28-3.11 (m, 2H), 3.08-2.91 (m, 2H), 2.58-2.52 (m, 2H), 2.41-2.25 (m, 1H), 1.71-1.60 (m, 1H), 1.59-1.43 (m, 1H), 1.11 (s, 3H), one missing proton (NH).

Example 28: Preparation of (R)—N—((S)-1-cyano-2-(2-fluoro-4-(3-methyl-2-oxo-2,3-dihydrobenzo[d] oxazol-5-yl)phenyl)ethyl) azocane-3-carboxamide (Compound 28-A) and(S)—N—((S)-1-cyano-2-(2-fluoro-4-(3-methyl-2-oxo-2,3-dihydrobenzo[d]oxazol-5-yl)phenyl)ethyl) azocane-3-carboxamide (Compound 28-B)

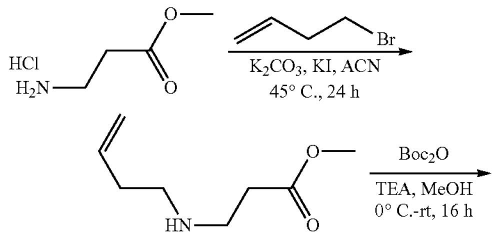

-continued

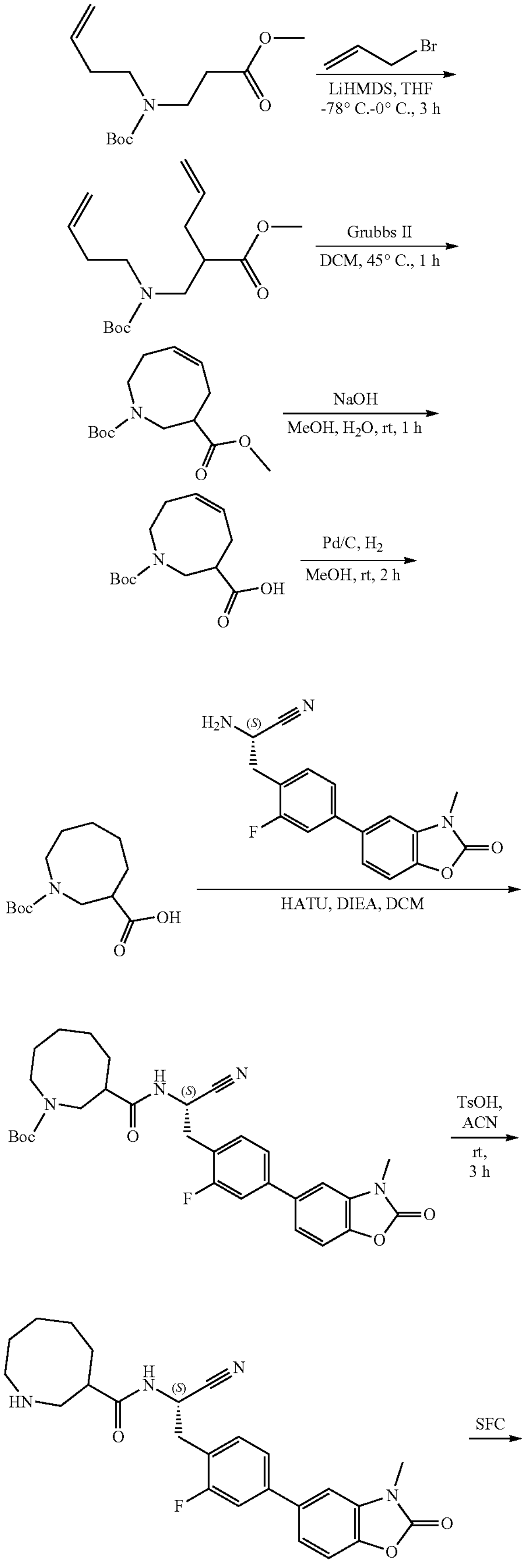

-continued

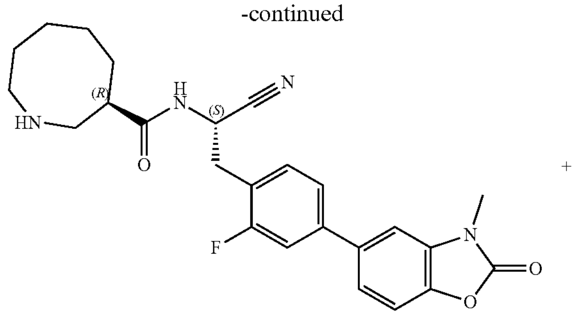

Assumed
Compound 28-A

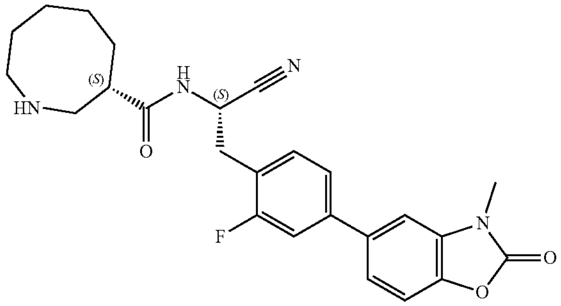

Assumed
Compound 28-B

Synthesis of methyl 3-(but-3-en-1-ylamino) propanoate

To a stirred solution of methyl 3-aminopropanoate hydrochloride (62.03 g, 444.432 mmol, 2.0 equiv) and 4-bromo-1-butene (30 g, 222.216 mmol, 1.0 equiv) in ACN (500 mL) were added $K_2CO_3$ (92.13 g, 666.648 mmol, 3.0 equiv) and KI (36.89 g, 222.216 mmol, 1.0 equiv). The resulting mixture was stirred for 24 h at 45° C. under nitrogen atmosphere. The resulting mixture was filtered, the filter cake was washed with EA (100 mL). The filtrate was concentrated under reduced pressure. The residue was purified by silica gel column chromatography, eluted with $CH_2Cl_2$/MeOH (10:1) to afford methyl 3-(but-3-en-1-ylamino) propanoate (20 g, 57.25%) as a colorless oil. LCMS(ES) [M+1]+m/z: 158.

Synthesis of methyl 3-[but-3-en-1-yl(tert-butoxycarbonyl)amino]propanoate

To a stirred solution of methyl 3-(but-3-en-1-ylamino) propanoate (20 g, 127.216 mmol, 1.0 equiv) in MeOH (400 mL) was added TEA (38.62 g, 381.648 mmol, 3.0 equiv) and di-tert-butyl dicarbonate (41.65 g, 190.824 mmol, 1.5 equiv) in portions at 0° C. . . . The resulting mixture was stirred for 16 h at room temperature. The resulting mixture was concentrated under reduced pressure. The residue was purified by silica gel column chromatography, eluted with PE/THF (1:1) to afford methyl 3-[but-3-en-1-yl(tert-butoxycarbonyl) amino]propanoate (24 g, 73.31%) as a colorless oil. LCMS(ES) [M+1]+m/z: 258.

Synthesis of methyl 2-{[but-3-en-1-yl(tert-butoxycarbonyl)amino]methyl}pent-4-enoate To a stirred solution of methyl 3-[but-3-en-1-yl(tert-butoxycarbonyl)amino]propanoate (24 g, 93.265 mmol, 1.0 equiv) in THF (250 mL) was added LiHMDS (17.17 g, 102.592 mmol, 1.1 equiv) dropwise at −78° C. under nitrogen atmosphere. The resulting mixture was stirred for 1 h at −78° C. under nitrogen atmosphere. To the above mixture was added allyl bromide (12.41 g, 102.592 mmol, 1.1 equiv) dropwise at −78° C. The resulting mixture was slowly warmed to 0° C. during 2 h. The reaction was quenched with sat. $NH_4Cl$ (aq.) at 0° C. The resulting mixture was extracted with EtOAc (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with PE/THF (10:1) to afford methyl 2-{[but-3-en-1-yl(tert-butoxycarbonyl)amino] methyl}pent-4-enoate (14 g, 50.47%) as a colorless oil. LCMS(ES) [M+1]+m/z: 298.

Synthesis of 1-tert-butyl 3-methyl 3,4,7,8-tetrahydro-2H-azocine-1,3-dicarboxylate To a stirred solution of methyl 2-{[but-3-en-1-yl(tert-butoxycarbonyl)amino methyl}pent-4-enoate (14 g, 47.075 mmol, 1.0 equiv) in DCM (1400 mL) was added Grubbs $2^{nd}$ (2.00 g, 2.354 mmol, 0.05 equiv) under nitrogen atmosphere. The resulting mixture was stirred for 1 h at 45° C. under nitrogen atmosphere. The resulting mixture was concentrated under reduced pressure. The residue was purified by silica gel column chromatography, eluted with PE/EA (20:1) to afford 1-tert-butyl 3-methyl 3,4,7,8-tetrahydro-2H-azocine-1,3-dicarboxylate (10 g, 78.87%) as a light brown oil. LCMS(ES) [M+1]+m/z: 270.

Synthesis of 1-(tert-butoxycarbonyl)-3,4,7,8-tetrahydro-2H-azocine-3-carboxylic acid To a stirred solution of 1-tert-butyl 3-methyl 3,4,7,8-tetrahydro-2H-azocine-1,3-dicarboxylate (10 g, 37.128 mmol, 1.0 equiv) in MeOH (100 mL) and $H_2O$ (30 mL) was added caustic soda (2.97 g, 74.256 mmol, 2.0 equiv). The resulting mixture was stirred for 1 h at room temperature. The resulting mixture was extracted with EtOAc (2×30 mL). The aqueous layer was acidified to pH 6 with citric acid. The resulting mixture was extracted with EtOAc (3×40 mL). The combined organic layers were washed with brine (50 mL), dried over anhydrous $Na_2SO_4$. After filtration, the filtrate was concentrated under reduced pressure. This resulted in 1-(tert-butoxycarbonyl)-3,4,7,8-tetrahydro-2H-azocine-3-carboxylic acid (7 g, 73.85%) as a light brown oil. LCMS(ES) [M+1]+m/z: 256.

Synthesis of 1-(tert-butoxycarbonyl) azocane-3-carboxylic acid

To a stirred solution of 1-(tert-butoxycarbonyl)-3,4,7,8-tetrahydro-2H-azocine-3-carboxylic acid (7 g, 27.417 mmol, 1.0 equiv) in methanol (100 mL) was added Pd/C (2 g) The resulting mixture was stirred for 2 h at room temperature under hydrogen atmosphere. The resulting mixture was filtered, the filter cake was washed with MeOH (50 mL). The filtrate was concentrated under reduced pressure. This resulted in 1-(tert-butoxycarbonyl) azocane-3-carboxylic acid (6 g, 85.04%) as a off-white oil. LCMS(ES) [M+1]+m/z: 258.

Synthesis of tert-butyl 3-{[(1S)-1-cyano-2-[2-fluoro-4-(3-methyl-2-oxo-1,3-benzoxazol-5-yl)phenyl]ethyl]carbamoyl}azocane-1-carboxylate To a stirred solution of (2S)-2-amino-3-[2-fluoro-4-(3-methyl-2-oxo-1,3-benzoxazol-5-yl)phenyl]propanenitrile (2.00 g, 6.412 mmol, 1.1 equiv) and 1-(tert-butoxycarbonyl) azocane-3-carboxylic acid (1.5 g, 5.829 mmol, 1.0 equiv) in DCM (20 mL) was added DIEA (1.51 g, 11.658 mmol, 2.0 equiv). To the above mixture was added HATU (2.66 g, 6.995 mmol, 1.2 equiv) in portions at 0° C. The resulting mixture was stirred for additional 1 h at 0° C. The resulting mixture was extracted with EtOAc (3x30 mL). The combined organic layers were washed with brine (50 mL), dried over anhydrous $Na_2SO_4$. After filtration, the filtrate was concentrated under reduced pressure. The residue was purified by silica gel column chromatography, eluted with PE/THF (1:1) to afford tert-butyl 3-{[(1S)-1-cyano-2-[2-fluoro-4-(3-methyl-2-oxo-1,3-benzoxazol-5-yl)phenyl] ethyl]carbamoyl}azocane-1-carboxylate (2.1 g, 65.43%) as a colorless oil. LCMS(ES) $[M+1]^+$ m/z: 551.

Synthesis of 1-azabicyclo[3.2.2]nonane-6-carbonitrile

To a stirred solution of tert-butyl 3-{[(1S)-1-cyano-2-[2-fluoro-4-(3-methyl-2-oxo-1,3-benzoxazol-5-yl)phenyl] ethyl]carbamoyl}azocane-1-carboxylate (2.1 g, 3.814 mmol, 1.0 equiv) in ACN (25 mL) was added TsOH (1.97 g, 11.442 mmol, 3.0 equiv). The resulting mixture was stirred for 3 h at room temperature. The residue was purified by reversed-phase flash chromatography with the following conditions: column, $C_{18}$ silica gel; mobile phase, MeCN in Water (0.1% $NH_3 \cdot H_2O$), 10% to 80% gradient in 20 min; detector, UV 254 nm. This resulted in N-[(1S)-1-cyano-2-[2-fluoro-4-(3-methyl-2-oxo-1,3-benzoxazol-5-yl)phenyl] ethyl]azocane-3-carboxamide (1.4 g, 81.48%) as a white solid. LCMS(ES) $[M+1]^+$ m/z: 451.

Synthesis of 1-azabicyclo[3.2.2]nonane-6-carboxylic acid

The crude product was purified by Chiral-Prep-HPLC with the following conditions (Chiral-Prep-HPLC with the following conditions: MeOH+50% DCM+20 mM $NH_3$; Flow rate: 20 mL/min; Column: DAICEL CHIRALPAK ID, 250*20 mm, 5 μm; Gradient: 50% B in 20 min; Detector, UV) to afford (3S)—N-[(1S)-1-cyano-2-[2-fluoro-4-(3-methyl-2-oxo-1,3-benzoxazol-5-yl)phenyl]ethyl]azocane-3-carboxamide (155 mg, 31.00%) as a white solid and (3R)—N-[(1S)-1-cyano-2-[2-fluoro-4-(3-methyl-2-oxo-1,3-benzoxazol-5-yl)phenyl]ethyl]azocane-3-carboxamide (155 mg, 31.00%) as a white solid.

(R)—N—((S)-1-cyano-2-(2-fluoro-4-(3-methyl-2-oxo-2,3-dihydrobenzo[d]oxazol-5-yl)phenyl)ethyl) azocane-3-carboxamide (stereochemistry assumed)

$^1$H NMR (300 MHZ, DMSO-$d_6$) δ 8.71 (d, J=7.9 Hz, 1H), 7.66 (d, J=1.9 Hz, 1H), 7.64-7.54 (m, 2H), 7.49 (dd, J=8.3, 1.8 Hz, 2H), 7.41 (d, J=8.3 Hz, 1H), 5.01 (q, J=7.8 Hz, 1H), 3.41 (s, 3H), 3.16 (qd, J=13.7, 7.8 Hz, 2H), 2.68 (dtd, J=26.4, 13.7, 7.3 Hz, 4H), 2.37 (s, 2H), 1.75-1.30 (m, 8H). LCMS(ES) $[M+1]^+$ m/z: 451.

(S)—N—((S)-1-cyano-2-(2-fluoro-4-(3-methyl-2-oxo-2,3-dihydrobenzo[d]oxazol-5-yl)phenyl)ethyl) azocane-3-carboxamide (stereochemistry assumed)

$^1$H NMR (300 MHz, DMSO-$d_6$) δ 8.71 (d, J=8.0 Hz, 1H), 7.65 (d, J=1.8 Hz, 1H), 7.63-7.53 (m, 2H), 7.52-7.45 (m, 2H), 7.40 (d, J=8.3 Hz, 1H), 5.02 (q, J=7.8 Hz, 1H), 3.41 (s, 3H), 3.17 (qd, J=13.8, 7.9 Hz, 2H), 2.82 (dd, J=13.7, 5.3 Hz, 1H), 2.76-2.62 (m, 3H), 2.36 (dd, J=9.1, 4.6 Hz, 2H), 1.50 (d, J=52.4 Hz, 8H). LCMS(ES) $[M+1]^+$ m/z: 451.

Example 29: Preparation of (2S)—N-[(1S)-1-cyano-2-[4-(3-methyl-2-oxo-1,3-benzoxazol-5-yl)phenyl] ethyl]-1,4-oxazocane-2-carboxamide (Compound 29)

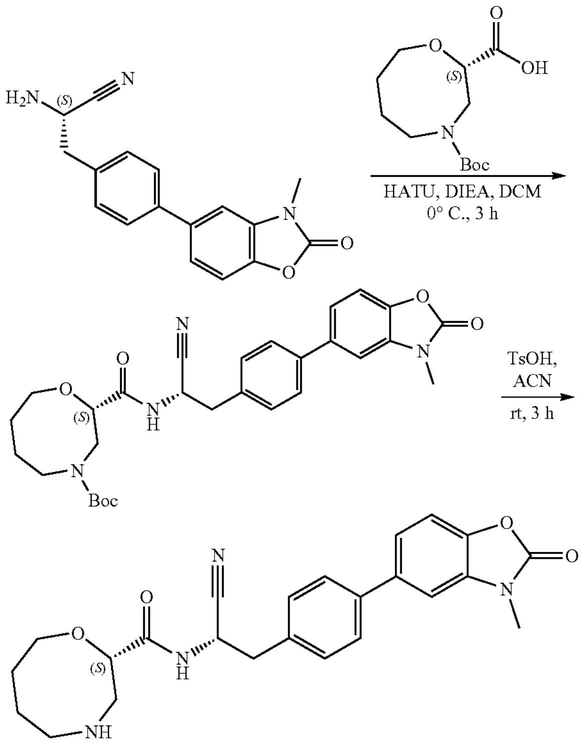

Compound 29

To a stirred solution of (2S)-2-amino-3-[4-(3-methyl-2-oxo-1,3-benzoxazol-5-yl)phenyl]propanenitrile (622 mg, 2.12 mmol, 1.1 equiv), (2S)-4-(tert-butoxycarbonyl)-1,4-oxazocane-2-carboxylic acid (500 mg, 1.92 mmol, 1.0 equiv) and DIEA (748 mg, 5.78 mmol, 3.0 equiv) in DCM (10 mL) was added HATU (879 mg, 2.31 mmol, 1.2 equiv) in portions at 0° C. The resulting mixture was stirred for additional 3 h at 0° C. The residue was purified by silica gel column chromatography, eluted with PE/THF (1:1) to afford tert-butyl (2S)-2-{[(1S)-1-cyano-2-[4-(3-methyl-2-oxo-1,3-benzoxazol-5-yl)phenyl]ethyl]carbamoyl}-1,4-oxazocane-4-carboxylate (1.0 g, 97.0%) as a white oil. LCMS (ES, m/z): $[M+H]^+$: 535.

Synthesis of (2S)—N-[(1S)-1-cyano-2-[4-(3-methyl-2-oxo-1,3-benzoxazol-5-yl)phenyl]ethyl]-1,4-oxazocane-2-carboxamide Into a 100 mL round-bottom flask were added tert-butyl (2S)-2-{[(1S)-1-cyano-2-[4-(3-methyl-2-oxo-1,3-benzoxazol-5-yl)phenyl]ethyl]carbamoyl}-1,4-oxazocane-4-carboxylate (1.0 g, 1.87 mmol, 1.0 equiv) in ACN (30 mL) and TsOH (1.0 g, 5.61 mmol, 3.0 equiv) at room temperature. The resulting mixture was stirred for additional 3 h at room temperature. The residue was purified by reversed-phase flash chromatography with the following conditions: column, $C_{18}$ silica gel; mobile phase, MeCN in Water (0.1% $NH_3 \cdot H_2O$), 10% to 80% gradient in 10 min; detector, UV 254 nm. This resulted in (2S)—N-[(1S)-1-cyano-2-[4-(3-methyl-2-oxo-1,3-benzoxazol-5-yl)phenyl]ethyl]-1,4-oxazocane-2-carboxamide (320 mg, 39.37%) as a white solid.

LCMS (ES, m/z): $[M+H]^+$: 435.2.

$^1H$ NMR (400 MHZ, DMSO-$d_6$) δ 8.63 (d, J=8.6 Hz, 1H), 7.70-7.63 (m, 2H), 7.58 (d, J=1.6 Hz, 1H), 7.45-7.35 (m, 4H), 5.01 (td, J=8.6, 7.2 Hz, 1H), 3.96 (ddd, J=11.2, 7.9, 2.9 Hz, 1H), 3.86 (dd, J=9.7, 2.9 Hz, 1H), 3.66 (dq, J=10.8, 4.0 Hz, 1H), 3.42 (s, 3H), 3.27-3.12 (m, 2H), 2.95 (td, J=14.1, 4.0 Hz, 2H), 2.59 (ddd, J=13.6, 8.8, 4.7 Hz, 1H), 2.23 (dd, J=14.0, 9.7 Hz, 1H), 1.93-1.79 (m, 1H), 1.63-1.47 (m, 3H).

Example 30: Preparation of (4R,7S)—N-[(1S)-1-cyano-2-[4-(3-methyl-2-oxo-1,3-benzoxazol-5-yl)phenyl]ethyl]-1,6-dioxa-9-azaspiro[3.6]decane-7-carboxamide (Compound 30-A) and (4S,7S)—N—((S)-1-cyano-2-(4-(3-methyl-2-oxo-2,3-dihydrobenzo[d]oxazol-5-yl)phenyl)ethyl)-1,6-dioxa-9-azaspiro[3.6]decane-7-carboxamide (Compound 30-B)

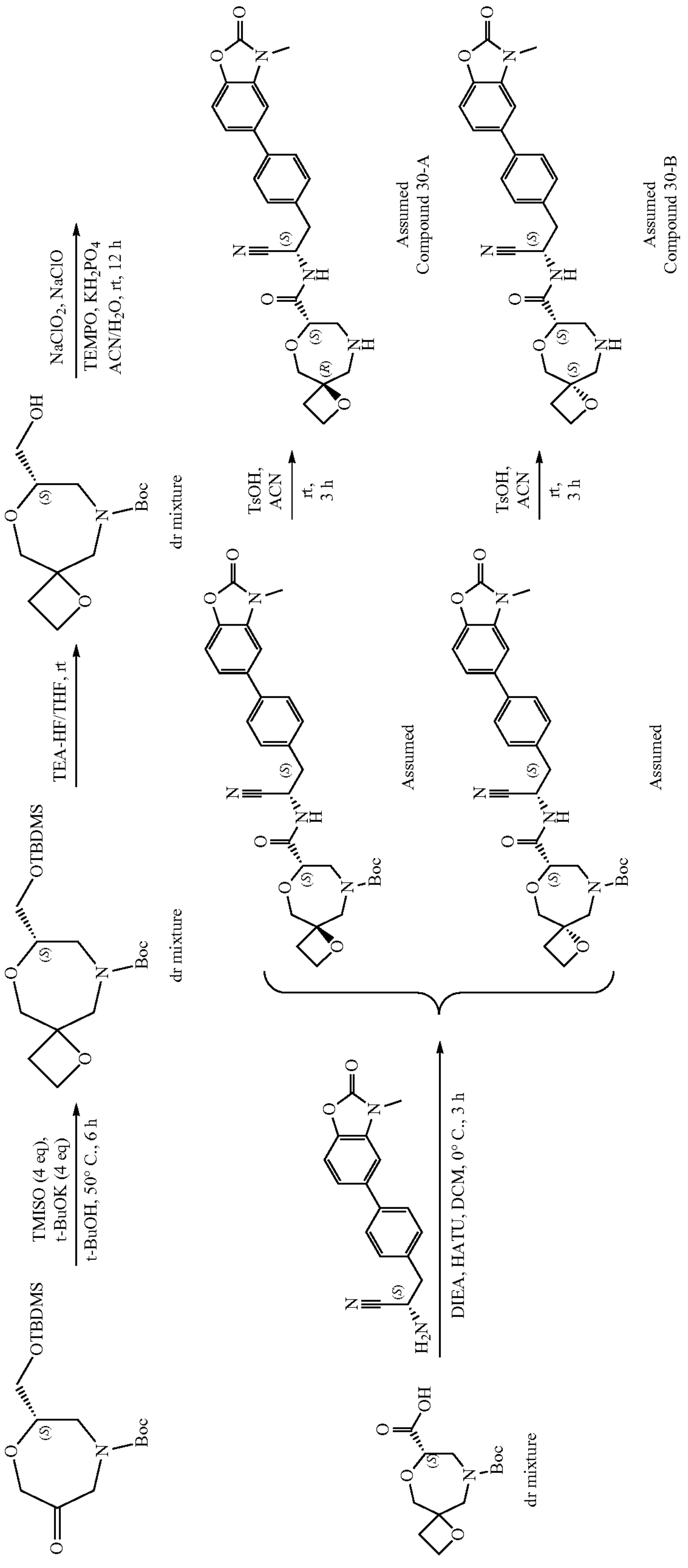
TMISO (4 eq),
t-BuOK (4 eq)
t-BuOH, 50° C., 6 h
dr mixture
TEA-HF/THF, rt
dr mixture
NaClO$_2$, NaClO
TEMPO, KH$_2$PO$_4$
ACN/H$_2$O, rt, 12 h
dr mixture
DIEA, HATU, DCM, 0° C., 3 h
Assumed
Assumed
TsOH,
ACN
rt,
3 h
Assumed
Compound 30-A
TsOH,
ACN
rt,
3 h
Assumed
Compound 30-B Synthesis of tert-butyl (7S)-7-(((tert-butyldimethylsilyl)oxy)methyl)-1,6-dioxa-9-azaspiro[3.6]decane-9-carboxylate Trimethyl(oxo)-lambda6-sulfanylium iodide (12.2 g, 55.63 mmol, 4.0 equiv) was dissolved in t-BuOH (100 mL), t-BuOK (6.24 g, 55.63 mmol, 4.0 equiv) was added at room temperature. The mixture was stirred for 30 min at 60° C., this was followed by the addition of tert-butyl (2S)-2-{[(tert-butyldimethylsilyl)oxy]methyl}-6-oxo-1,4-oxazepane-4-carboxylate (5 g, 13.91 mmol, 1.0 equiv) and stirred for additional 4 h. The reaction was cooled to room temperature, diluted with water (200 mL), extracted with ethyl acetate (200 mL×2). The combined organic phase was washed with brine (100 mL), dried over anhydrous sodium sulfate. After filtration, the filtrate was concentrated and the residue was purified by silica gel column, eluted with ethyl acetate/petroleum ether (1:5), tert-butyl (7S)-7-(((tert-butyldimethylsilyl)oxy)methyl)-1,6-dioxa-9-azaspiro[3.6]decane-9-carboxylate (3.5 g, 65%) was obtained as colorless oil. LCMS (ES, m/z): $[M+H]^+$: 388.

Synthesis of tert-butyl (7S)-7-(hydroxymethyl)-1,6-dioxa-9-azaspiro[3.6]decane-9-carboxylate To a solution of tert-butyl (7S)-7-(((tert-butyldimethylsilyl)oxy)methyl)-1,6-dioxa-9-azaspiro[3.6]decane-9-carboxylate (3.5 g, 9.03 mmol, 1.0 equiv) in THF (70 mL), TEA: 3HF (11 mL, 79.14 mmol, 8.76 equiv) was added at room temperature. The mixture was stirred for 12 h. The reaction was quenched with $NaHCO_3$ (aq) (100 mL), extracted with dichloromethane (150 mL×2), the combined organic phase was dried over anhydrous sodium sulfate. After filtration, the filtrate was concentrated, tert-butyl (7S)-7-(hydroxymethyl)-1,6-dioxa-9-azaspiro[3.6]decane-9-carboxylate (2.2 g, 89%) was obtained as colorless oil and used to the next step without further purification. LCMS (ES, m/z): $[M+H]^+$: 274.

Synthesis of (7S)-9-(tert-butoxycarbonyl)-1,6-dioxa-9-azaspiro[3.6]decane-7-carboxylic acid To a solution of tert-butyl (7S)-7-(hydroxymethyl)-1,6-dioxa-9-azaspiro[3.6]decane-9-carboxylate (2.2 g, 8.05 mmol, 1.0 equiv) in ACN (20 mL), TEMPO (0.13 g, 0.81 mmol, 0.1 equiv), $NaClO_2$ (0.94 g, 16.10 mmol, 2.0 equiv), $KH_2PO_4$ (2.19 g, 16.10 mmol, 2.0 equiv) and NaClO (5% in water) (20 mL) were added at room temperature in sequence. The mixture was stirred for 12 h. The reaction was diluted with water (30 mL), extracted with dichloromethane (50 mL×3). The combined organic phase was dried over anhydrous sodium sulfate. After filtration, the filtrate was concentrated under reduced pressure, (7S)-9-(tert-butoxycarbonyl)-1,6-dioxa-9-azaspiro[3.6]decane-7-carboxylic acid (2.1 g, 90%) was obtained as light brown oil and used to the next step directly without further purification. LCMS (ES, m/z): $[M+H]^+$: 274.

Synthesis of tert-butyl (4R,7S)-7-{[(1S)-1-cyano-2-[4-(3-methyl-2-oxo-1,3-benzoxazol-5-yl)phenyl]ethyl]carbamoyl}-1,6-dioxa-9-azaspiro[3.6]decane-9-carboxylate; tert-butyl (4S,7S)-7-{[(1S)-1-cyano-2-[4-(3-methyl-2-oxo-1,3-benzoxazol-5-yl)phenyl]ethyl]carbamoyl}-1,6-dioxa-9-azaspiro[3.6]decane-9-carboxylate A solution of (7S)-9-(tert-butoxycarbonyl)-1,6-dioxa-9-azaspiro[3.6]decane-7-carboxylic acid (2.1 g, 7.30 mmol, 1.3 equiv) in DCM (20 mL) was treated with (2S)-2-amino-3-[4-(3-methyl-2-oxo-1,3-benzoxazol-5-yl)phenyl]propanenitrile (1.7 g, 5.62 mmol, 1.0 equiv), DIEA (2.2 g, 16.86 mmol, 3.0 equiv). This was followed by the addition of HATU (2.6 g, 6.74 mmol, 1.2 equiv) at 0° C. The resulting mixture was stirred for 3 h at room temperature. Concentrated to remove the solvent, the residue was purified by silica gel column chromatography, eluted with PE/THF (1:1) to afford tert-butyl (4R,7S)-7-{[(1S)-1-cyano-2-[4-(3-methyl-2-oxo-1,3-benzoxazol-5-yl)phenyl]ethyl]carbamoyl}-1,6-dioxa-9-azaspiro[3.6]decane-9-carboxylate (1.0 g 16%); tert-butyl (4S,7S)-7-{[(1S)-1-cyano-2-[4-(3-methyl-2-oxo-1,3-benzoxazol-5-yl)phenyl]ethyl]carbamoyl}-1,6-dioxa-9-azaspiro[3.6]decane-9-carboxylate (2.0 g, 31.6%) as white solid. LCMS (ES, m/z): $[M+H]^+$: 563.

Synthesis of (4R,7S)—N-[(1S)-1-cyano-2-[4-(3-methyl-2-oxo-1,3-benzoxazol-5-yl)phenyl]ethyl]-1,6-dioxa-9-azaspiro[3.6]decane-7-carboxamide Into a 100 mL round-bottom flask were added tert-butyl (4R,7S)-7-{[(1S)-1-cyano-2-[4-(3-methyl-2-oxo-1,3-benzoxazol-5-yl)phenyl]ethyl]carbamoyl}-1,6-dioxa-9-azaspiro[3.6]decane-9-carboxylate (1.0 g, 1.77 mmol, 1.0 equiv), ACN (30 mL) and TsOH (0.9 g, 5.33 mmol, 3.0 equiv) at room temperature. The resulting mixture was stirred for 3 h at room temperature. The reaction solution was purified by reversed-phase flash chromatography with the following conditions: column, $C_{18}$ silica gel-120 g; mobile phase, MeCN in Water (0.1% $NH_3 \cdot H_2O$), 10% to 50% gradient in 10 min; detector, UV 254 nm. This resulted in (4R,7S)—N-[(1S)-1-cyano-2-[4-(3-methyl-2-oxo-1,3-benzoxazol-5-yl)phenyl]ethyl]-1,6-dioxa-9-azaspiro[3.6]decane-7-carboxamide (247 mg, 30%) as white solid.

LCMS (ES, m/z): $[M+H]^+$: 463.2

$^1H$ NMR (400 MHZ, DMSO-$d_6$) δ 8.92-8.88 (m, 1H), 7.70-7.63 (m, 2H), 7.58 (d, J=1.3 Hz, 1H), 7.46-7.36 (m, 4H), 5.04 (q, J=8.3 Hz, 1H), 4.47-4.36 (m, 2H), 4.28-4.21 (m, 2H), 3.72 (d, J=13.5 Hz, 1H), 3.44-3.41 (m, 4H), 3.27-3.08 (m, 4H), 2.70-2.61 (m, 1H), 2.41-2.35 (m, 2H).

Synthesis of (4S,7S)—N-[(1S)-1-cyano-2-[4-(3-methyl-2-oxo-1,3-benzoxazol-5-yl)phenyl]ethyl]-1,6-dioxa-9-azaspiro[3.6]decane-7-carboxamide Into a 100 mL round-bottom flask were added tert-butyl (4S,7S)-7-{[(1S)-1-cyano-2-[4-(3-methyl-2-oxo-1,3-benzoxazol-5-yl)phenyl]ethyl]carbamoyl}-1,6-dioxa-9-azaspiro[3.6]decane-9-carboxylate (1.0 g, 1.77 mmol, 1.0 equiv), ACN (30 mL) and TsOH (0.9 g, 5.33 mmol, 3.0 equiv) at room temperature. The resulting mixture was stirred for 3 h at room temperature. The reaction solution was purified by reversed-phase flash chromatography with the following conditions: column, $C_{18}$ silica gel-120 g; mobile phase, MeCN in Water (0.1% $NH_3 \cdot H_2O$), 10% to 50% gradient in 10 min; detector, UV 254 nm. This resulted in (4S,7S)—N-[(1S)-1-cyano-2-[4-(3-methyl-2-oxo-1,3-benzoxazol-5-yl)phenyl]ethyl]-1,6-dioxa-9-azaspiro[3.6]decane-7-carboxamide (300 mg, 36%) as white solid.

LCMS (ES, m/z): $[M+H]^+$: 463.3.

$^1H$ NMR (400 MHZ, DMSO-$d_6$) δ 8.62 (d, J=8.5 Hz, 1H), 7.69-7.63 (m, 2H), 7.58 (s, 1H), 7.46-7.35 (m, 4H), 5.01 (q, J=8.6 Hz, 1H), 4.37-4.28 (m, 2H), 4.00 (d, J=12.8 Hz, 1H), 3.93 (dd, J=8.9, 3.4 Hz, 1H), 3.79 (d, J=12.9 Hz, 1H), 3.41 (s, 3H), 3.27-3.11 (m, 3H), 3.04 (dd, J=14.0, 3.5 Hz, 1H), 2.75 (d, J=14.3 Hz, 1H), 2.50-2.21 (m, 3H).

Example 31: Preparation of (2S,6R)—N-[(1S)-1-cyano-2-[2-fluoro-4-(3-methyl-2-oxo-1,3-benzoxazol-5-yl)phenyl]ethyl]-6-hydroxy-6-methyl-1,4-oxazepane-2-carboxamide (Compound 31)

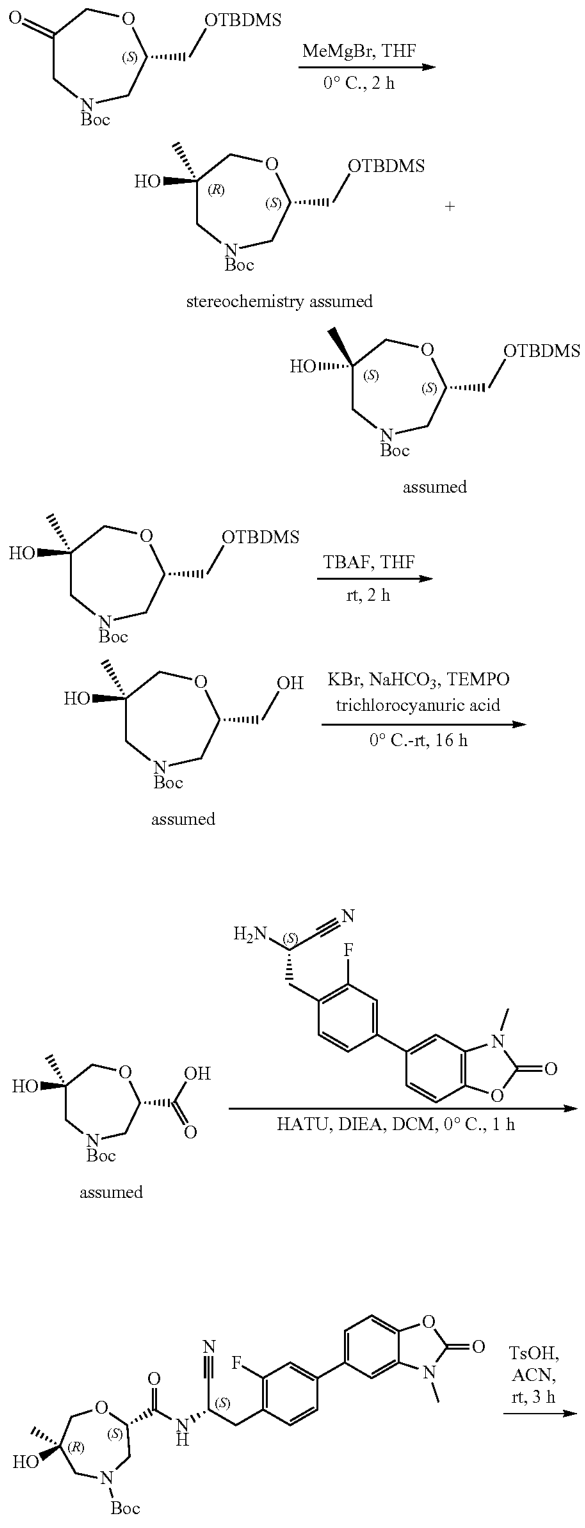

assumed

-continued

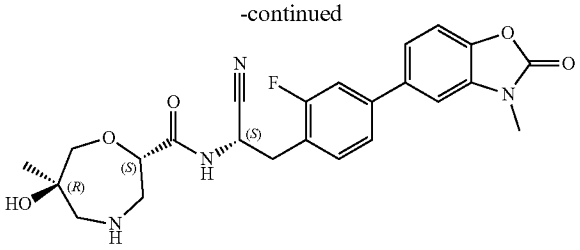

Compound 31
assumed

Synthesis of tert-butyl (2S,6R)-2-{[(tert-butyldimethylsilyl)oxy]methyl}-6-hydroxy-6-methyl-1,4-oxazepane-4-carboxylate and tert-butyl (2S,6S)-2-{[(tert-butyldimethylsilyl)oxy]methyl}-6-hydroxy-6-methyl-1,4-oxazepane-4-carboxylate To a stirred solution of tert-butyl (2S)-2-{[(tert-butyldimethylsilyl)oxy]methyl}-6-oxo-1,4-oxazepane-4-carboxylate (6 g, 16.688 mmol, 1.0 equiv) in THF (100 mL) was added MeMgBr (11.13 mL, 33.376 mmol, 2.0 equiv) dropwise at 0° C. under nitrogen atmosphere. The resulting mixture was stirred for 2 h at 0° C. under nitrogen atmosphere. The reaction was quenched by the addition of sat. $NH_4Cl$ (aq.) (20 mL) at 0° C. The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/THF (9:1) to afford tert-butyl (2S,6R)-2-{[(tert-butyldimethylsilyl)oxy]methyl}-6-hydroxy-6-methyl-1,4-oxazepane-4-carboxylate (3.2 g, 51.06%) as a colorless oil and tert-butyl (2S,6S)-2-{[(tert-butyldimethylsilyl)oxy]methyl}-6-hydroxy-6-methyl-1,4-oxazepane-4-carboxylate (1.7 g, 27.12%) as a colorless oil. LCMS(ES) $[M+H]^+$ m/z: 376.

Synthesis of tert-butyl (2S,6R)-6-hydroxy-2-(hydroxymethyl)-6-methyl-1,4-oxazepane-4-carboxylate To a stirred solution of tert-butyl (2S,6R)-2-{[(tert-butyldimethylsilyl)oxy]methyl}-6-hydroxy-6-methyl-1,4-oxazepane-4-carboxylate (3.2 g, 8.520 mmol, 1.0 equiv) in THF (40 mL) was added TBAF (2.23 g, 8.520 mmol, 1.0 equiv). The resulting mixture was stirred for 2 h at room temperature. The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/THF (2:3) to afford tert-butyl (2S,6R)-6-hydroxy-2-(hydroxymethyl)-6-methyl-1,4-oxazepane-4-carboxylate (2.2 g, 98.81%) as a colorless oil. LCMS(ES) $[M+H]^+$ m/z: 262.

Synthesis of (2S,6R)-4-(tert-butoxycarbonyl)-6-hydroxy-6-methyl-1,4-oxazepane-2-carboxylic acid To a stirred solution of tert-butyl (2S,6R)-6-hydroxy-2-(hydroxymethyl)-6-methyl-1,4-oxazepane-4-carboxylate (2.4 g, 9.184 mmol, 1.0 equiv) in acetone (30 mL) was added $NaHCO_3$ (1.54 g, 18.368 mmol, 2.0 equiv) in $H_2O$ (10 mL)

at 0° C. under nitrogen atmosphere. To the above mixture was added NaBr (0.19 g, 1.837 mmol, 0.2 equiv) and TEMPO (0.14 g, 0.918 mmol, 0.1 equiv) and TCCA (4.27 g, 18.368 mmol, 2.0 equiv) in portions at 0° C. The resulting mixture was stirred for additional 16 h at room temperature. The mixture was basified to pH 9 with saturated $NaHCO_3$ (aq.). The resulting mixture was filtered, the filter cake was washed with $H_2O$ (50 mL). The filtrate was acidified to pH 5 with citric acid. The resulting mixture was extracted with $CH_2Cl_2$ (10×50 mL). The combined organic layers were washed with brine (50 mL), dried over anhydrous $Na_2SO_4$. After filtration, the filtrate was concentrated under reduced pressure. This resulted in (2S,6R)-4-(tert-butoxycarbonyl)-6-hydroxy-6-methyl-1,4-oxazepane-2-carboxylic acid (1.8 g, 71.19%) as a white solid. LCMS(ES) $[M-H]^-$ m/z: 274.

Synthesis of tert-butyl (2S,6R)-2-{[(1S)-1-cyano-2-[2-fluoro-4-(3-methyl-2-oxo-1,3-benzoxazol-5-yl)phenyl]ethyl]carbamoyl}-6-hydroxy-6-methyl-1,4-oxazepane-4-carboxylate To a stirred mixture of (2S,6R)-4-(tert-butoxycarbonyl)-6-hydroxy-6-methyl-1,4-oxazepane-2-carboxylic acid (670 mg, 2.434 mmol, 1.0 equiv) and (2S)-2-amino-3-[2-fluoro-4-(3-methyl-2-oxo-1,3-benzoxazol-5-yl)phenyl]propanenitrile (757 mg, 2.434 mmol, 1.0 equiv) in DCM (8 mL) was added DIEA (943 mg, 7.302 mmol, 3.0 equiv). To the above mixture was added HATU (1110 mg, 2.921 mmol, 1.2 equiv) in portions at 0° C. The resulting mixture was stirred for additional 1 h at 0° C. The resulting mixture was extracted with $CH_2Cl_2$ (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/THF (2:3) to afford tert-butyl (2S,6R)-2-{[(1S)-1-cyano-2-[2-fluoro-4-(3-methyl-2-oxo-1,3-benzoxazol-5-yl)phenyl]ethyl]carbamoyl}-6-hydroxy-6-methyl-1,4-oxazepane-4-carboxylate (1.1 g, 79.49%) as a light yellow solid. LCMS(ES) $[M+H]^+$ m/z: 569.

Synthesis of (2S,6R)—N-[(1S)-1-cyano-2-[2-fluoro-4-(3-methyl-2-oxo-1,3-benzoxazol-5-yl)phenyl]ethyl]-6-hydroxy-6-methyl-1,4-oxazepane-2-carboxamide To a stirred solution of tert-butyl (2S,6R)-2-{[(1S)-1-cyano-2-[2-fluoro-4-(3-methyl-2-oxo-1,3-benzoxazol-5-yl)phenyl]ethyl]carbamoyl}-6-hydroxy-6-methyl-1,4-oxazepane-4-carboxylate (1.1 g, 1.935 mmol, 1.0 equiv) in ACN (15 mL) were added TsOH (1.00 g, 5.805 mmol, 3.0 equiv). The resulting mixture was stirred for 3 h at room temperature. The resulting mixture was purified by reversed-phase flash chromatography with the following conditions: column, $C^{18}$ silica gel; mobile phase, MeCN in Water (0.1% $NH_3 \cdot H_2O$), 5% to 60% gradient in 10 min; detector, UV 254 nm. This resulted in (2S,6R)—N-[(1S)-1-cyano-2-[2-fluoro-4-(3-methyl-2-oxo-1,3-benzoxazol-5-yl)phenyl]ethyl]-6-hydroxy-6-methyl-1,4-oxazepane-2-carboxamide (450 mg, 49.65%) as a white solid.

$^1H$ NMR (400 MHZ, DMSO-$d_6$) δ 8.67 (d, J=8.5 Hz, 1H), 7.65 (d, J=1.8 Hz, 1H), 7.63-7.52 (m, 2H), 7.51-7.37 (m, 3H), 5.05 (q, J=8.2 Hz, 1H), 4.48 (s, 1H), 4.05 (dd, J=8.9, 4.4 Hz, 1H), 3.56-3.44 (m, 2H), 3.41 (s, 3H), 3.32-3.26 (m, 1H), 3.20 (dd, J=13.7, 8.6 Hz, 1H), 3.09 (dd, J=14.2, 4.4 Hz, 1H), 2.64 (d, J=13.7 Hz, 1H), 2.52 (d, J=1.9 Hz, 1H), 2.47 (t, J=7.1 Hz, 1H), 1.05 (s, 3H). LCMS(ES) [M+H]m/z: 469.

Example 32: Preparation of (2S,6S)—N-[(1S)-1-cyano-2-[2-fluoro-4-(3-methyl-2-oxo-1,3-benzoxazol-5-yl)phenyl]ethyl]-6-hydroxy-6-methyl-1,4-oxazepane-2-carboxamide (Compound 32)

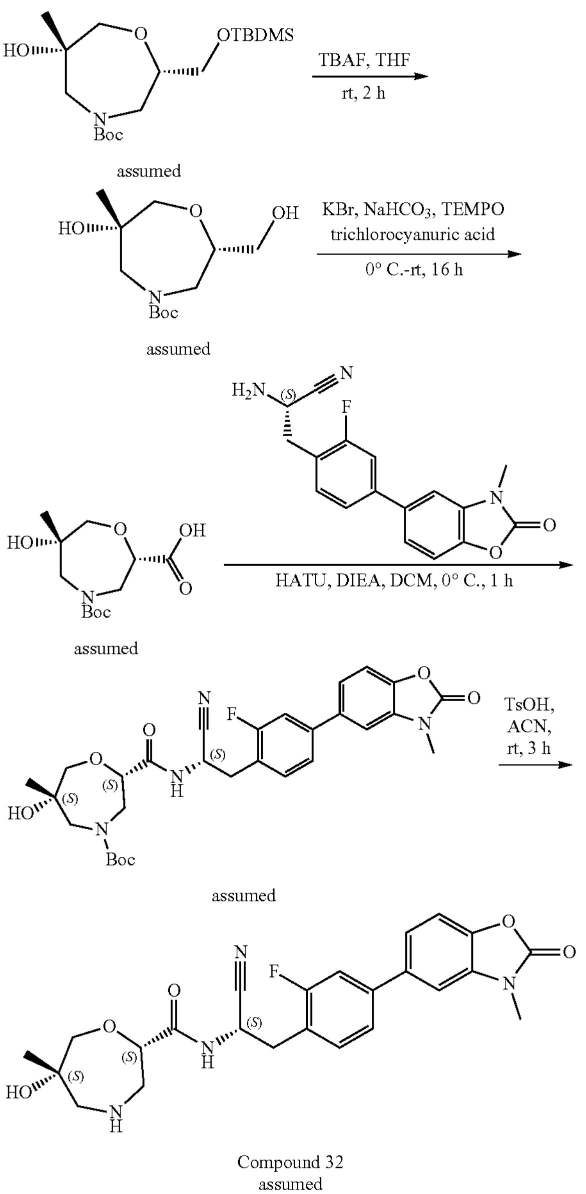

Compound 32
assumed

Synthesis of tert-butyl (2S,6S)-6-hydroxy-2-(hydroxymethyl)-6-methyl-1,4-oxazepane-4-carboxylate To a stirred solution of tert-butyl (2S,6S)-2-{[(tert-butyldimethylsilyl)oxy]methyl}-6-hydroxy-6-methyl-1,4-oxazepane-4-carboxylate (1.7 g, 4.526 mmol, 1.0 equiv) in THF (20 mL) was added TBAF (1.18 g, 4.526 mmol, 1.0 equiv). The resulting mixture was stirred for 2 h at room temperature. The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/THF (2:3) to afford tert-butyl (2S,6S)-6-hydroxy-2-(hydroxymethyl)-6-methyl-1,4-oxazepane-4-carboxylate (1.1 g, 93.00%) as a colorless oil. LCMS(ES) $[M+H]^+$ m/z: 262.

Synthesis of (2S,6S)-4-(tert-butoxycarbonyl)-6-hydroxy-6-methyl-1,4-oxazepane-2-carboxylic acid To a stirred solution of tert-butyl (2S,6S)-6-hydroxy-2-(hydroxymethyl)-6-methyl-1,4-oxazepane-4-carboxylate (1.2 g, 4.592 mmol, 1.0 equiv) in acetone (15 mL) was added a solution of $NaHCO_3$ (0.77 g, 9.184 mmol, 2.0 equiv) in $H_2O$ (5 mL) at 0° C. under nitrogen atmosphere. To the above mixture was added NaBr (0.09 g, 0.918 mmol, 0.2 equiv) and TEMPO (0.07 g, 0.459 mmol, 0.1 equiv) and TCCA (2.13 g, 9.184 mmol, 2.0 equiv) in portions at 0° C. The resulting mixture was stirred for additional 16 h at room temperature. The mixture was basified to pH 9 with saturated $NaHCO_3$ (aq.). The resulting mixture was filtered, the filter cake was washed with $H_2O$ (50 mL). The filtrate was acidified to pH 5 with citric acid. The resulting mixture was extracted with $CH_2Cl_2$ (10×30 mL). The combined organic layers were washed with brine (30 mL), dried over anhydrous $Na_2SO_4$. After filtration, the filtrate was concentrated under reduced pressure. This resulted in (2S,6S)-4-(tert-butoxycarbonyl)-6-hydroxy-6-methyl-1,4-oxazepane-2-carboxylic acid (550 mg, 43.51%) as a white solid. LCMS(ES) $[M-H]^-$ m/z: 274.

Synthesis of tert-butyl (2S,6S)-2-{[(1S)-1-cyano-2-[2-fluoro-4-(3-methyl-2-oxo-1,3-benzoxazol-5-yl)phenyl]ethyl]carbamoyl}-6-hydroxy-6-methyl-1,4-oxazepane-4-carboxylate To a stirred mixture of (2S,6S)-4-(tert-butoxycarbonyl)-6-hydroxy-6-methyl-1,4-oxazepane-2-carboxylic acid (550 mg, 1.998 mmol, 1.0 equiv) and (2S)-2-amino-3-[2-fluoro-4-(3-methyl-2-oxo-1,3-benzoxazol-5-yl)phenyl]propanenitrile (621 mg, 1.998 mmol, 1.0 equiv) in DCM (7 mL) was added DIEA (774 mg, 5.994 mmol, 3.0 equiv). To the above mixture was added HATU (911 mg, 2.398 mmol, 1.2 equiv) in portions at 0° C. The resulting mixture was stirred for additional 1 h at 0° C. The resulting mixture was extracted with $CH_2Cl_2$ (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/THF (2:3) to afford tert-butyl (2S,6S)-2-{[(1S)-1-cyano-2-[2-fluoro-4-(3-methyl-2-oxo-1,3-benzoxazol-5-yl)phenyl]ethyl]carbamoyl}-6-hydroxy-6-methyl-1,4-oxazepane-4-carboxylate (850 mg, 74.83%) as a light yellow solid. LCMS(ES) $[M+H]^+$ m/z: 569.

Synthesis of (2S,6S)—N-[(1S)-1-cyano-2-[2-fluoro-4-(3-methyl-2-oxo-1,3-benzoxazol-5-yl)phenyl]ethyl]-6-hydroxy-6-methyl-1,4-oxazepane-2-carboxamide To a stirred solution of tert-butyl (2S,6S)-2-{[(1S)-1-cyano-2-[2-fluoro-4-(3-methyl-2-oxo-1,3-benzoxazol-5-yl)phenyl]ethyl]carbamoyl}-6-hydroxy-6-methyl-1,4-oxazepane-4-carboxylate (850 mg, 1.495 mmol, 1.0 equiv) in ACN (10 mL) was added TsOH (772 mg, 4.485 mmol, 3.0 equiv). The resulting mixture was stirred for 3 h at room temperature. The resulting mixture was purified by reversed-phase flash chromatography with the following conditions: column, $C^{18}$ silica gel; mobile phase, MeCN in Water (0.1% $NH_3 \cdot H_2O$), 5% to 60% gradient in 10 min; detector, UV 254 nm. This resulted in (2S,6S)—N-[(1S)-1-cyano-2-[2-fluoro-4-(3-methyl-2-oxo-1,3-benzoxazol-5-yl)phenyl]ethyl]-6-hydroxy-6-methyl-1,4-oxazepane-2-carboxamide (350 mg, 49.98%) as a white solid.

$^1$H NMR (400 MHZ, DMSO-$d_6$) δ 8.79 (d, J=8.5 Hz, 1H), 7.66 (d, J=2.0 Hz, 1H), 7.62-7.53 (m, 2H), 7.52-7.43 (m, 2H), 7.41 (d, J=8.3 Hz, 1H), 5.06 (q, J=8.2 Hz, 1H), 4.55 (s, 1H), 4.00 (dd, J=8.0, 5.1 Hz, 1H), 3.62 (d, J=12.7 Hz, 1H), 3.50 (d, J=12.6 Hz, 1H), 3.41 (s, 3H), 3.34-3.26 (m, 1H), 3.19 (dd, J=13.7, 8.3 Hz, 1H), 3.05 (dd, J=14.0, 5.1 Hz, 1H), 2.66-2.57 (m, 2H), 2.55 (d, J=5.6 Hz, 1H), 2.40 (s, 1H), 0.99 (s, 3H). LCMS(ES) $[M+H]^+$ m/z: 469.

Example 33: Preparation of (2S,6R)—N-[(1S)-1-cyano-2-[4-(3-methyl-2-oxo-1,3-benzoxazol-5-yl)phenyl]ethyl]-6-methoxy-1,4-oxazocane-2-carboxamide and (2S,7S)—N-[(1S)-1-cyano-2-[4-(3-methyl-2-oxo-1,3-benzoxazol-5-yl)phenyl]ethyl]-7-methoxy-1,4-oxazocane-2-carboxamide (Compound 33-B)

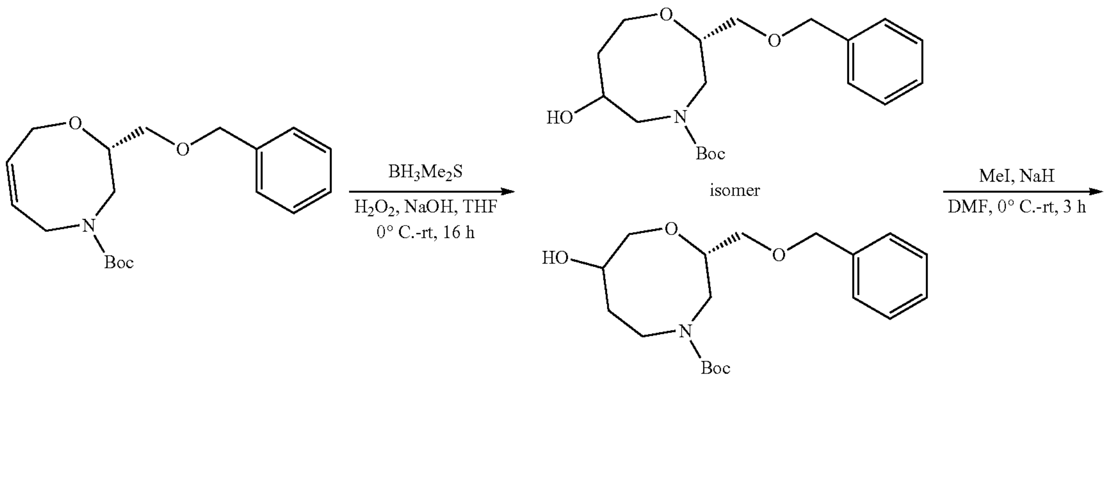

-continued
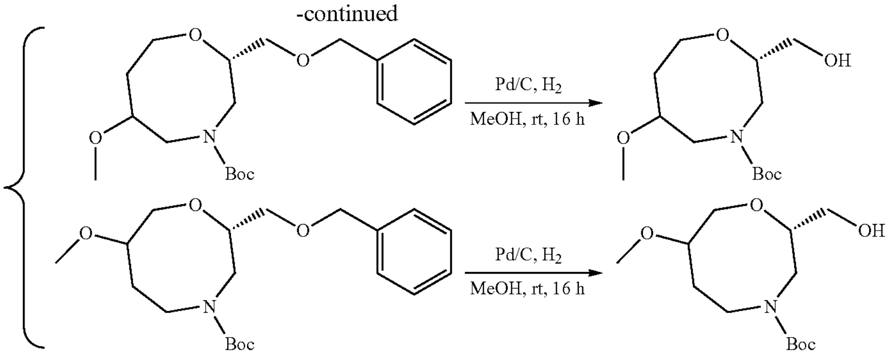
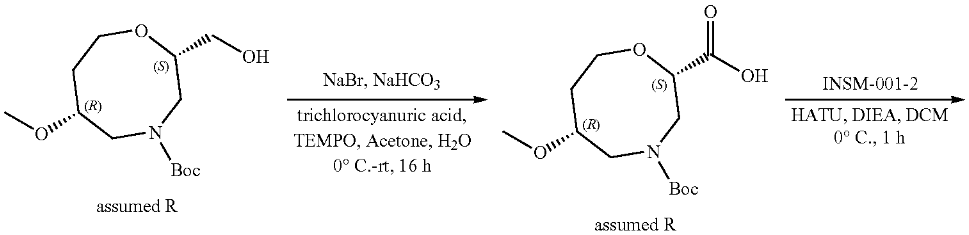
assumed R
assumed R
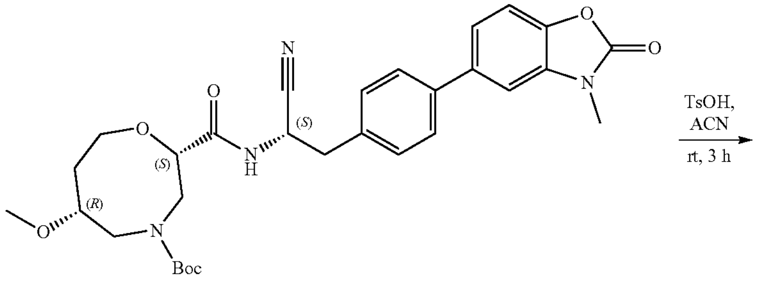
assumed R
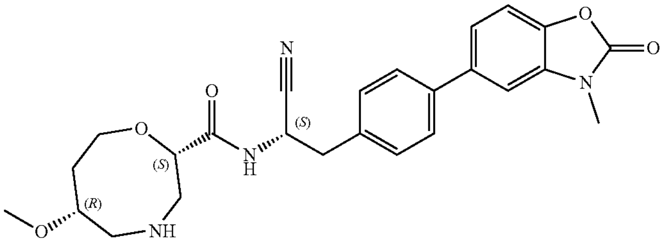
assumed R
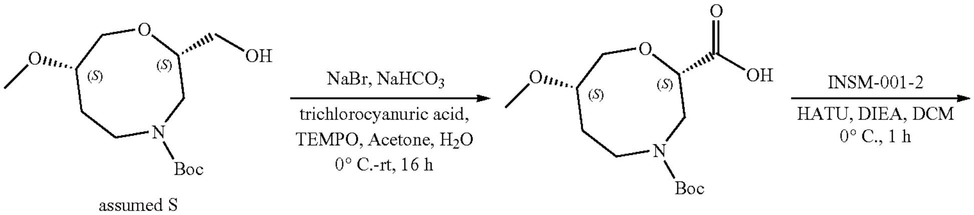
assumed S
assumed S
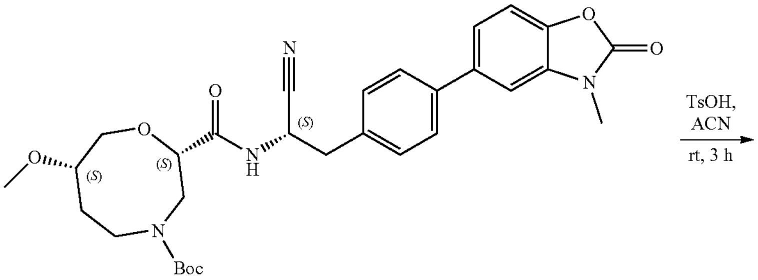
assumed S -continued

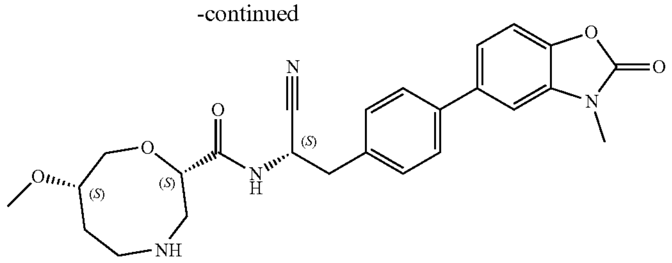

assumed S
Compound 33-B

Synthesis of tert-butyl (2S)-2-[(benzyloxy)methyl]-6-hydroxy-1,4-oxazocane-4-carboxylate & tert-butyl (2S)-2-[(benzyloxy)methyl]-7-hydroxy-1,4-oxazocane-4-carboxylate To a stirred solution of tert-butyl (2S)-2-[(benzyloxy)methyl]-2,3,5,8-tetrahydro-1,4-oxazocine-4-carboxylate (3.0 g, 9.00 mmol, 1.0 equiv) in THF (25 mL) was added $BH_3$-$Me_2S$ (10 M) (2.70 mL, 26.99 mmol, 3.0 equiv) dropwise at 0° C. under nitrogen atmosphere. The resulting mixture was stirred for 12 h at room temperature. To the above mixture was added a stirred solution of NaOH (1.91 g, 47.68 mmol, 5.30 equiv) in $H_2O$ (5 mL) and $H_2O_2$ (5.10 g, 44.98 mmol, 5.0 equiv, 30% in water) dropwise at 0° C. The resulting mixture was stirred for additional 3 h at room temperature. The reaction was quenched by the addition of $Na_2SO_3$ (aq) (20 mL). The resulting mixture was extracted with EtOAc (3×20 mL). The combined organic layer was washed with brine (50 mL), dried over anhydrous $Na_2SO_4$. After filtration, the filtrate was concentrated under reduced pressure. The residue was purified by silica gel column chromatography, eluted with PE/EA (3:1) to afford tert-butyl (2S)-2-[(benzyloxy)methyl]-6-hydroxy-1,4-oxazocane-4-carboxylate and tert-butyl (2S)-2-[(benzyloxy)methyl]-7-hydroxy-1,4-oxazocane-4-carboxylate (1.6 g, 50.6%) as colorless oil. LCMS(ES) $[M+H]^+$ m/z: 352.

Synthesis of tert-butyl (2S,7S)-2-[(benzyloxy)methyl]-7-methoxy-1,4-oxazocane-4-carboxylate and tert-butyl (2S,6R)-2-[(benzyloxy)methyl]-6-methoxy-1,4-oxazocane-4-carboxylate To a stirred mixture of tert-butyl (2S)-2-[(benzyloxy)methyl]-6-hydroxy-1,4-oxazocane-4-carboxylate and tert-butyl (2S)-2-[(benzyloxy)methyl]-7-hydroxy-1,4-oxazocane-4-carboxylate (1.6 g, 4.56 mmol, 1.0 equiv) in dimethylformamide (20 mL) was added NaH (0.22 g, 5.47 mmol, 1.2 equiv, 60% in mineral oil) in portions at 0° C. under nitrogen atmosphere. The resulting mixture was stirred for 30 min at 0° C. under nitrogen atmosphere. To the above mixture was added MeI (0.97 g, 6.84 mmol, 1.5 equiv) dropwise at 0° C. The resulting mixture was stirred for additional 3 h at room temperature. The reaction was quenched by the addition of Water/Ice (20 mL) at 0° C., extracted with EtOAc (3×20 mL). The combined organic layer was washed with brine (20 mL), dried over anhydrous $Na_2SO_4$. After filtration, the filtrate was concentrated under reduced pressure. The residue was purified by silica gel column chromatography, eluted with PE/THF (10:1) to afford tert-butyl (2S,7S)-2-[(benzyloxy)methyl]-7-methoxy-1,4-oxazocane-4-carboxylate (540 mg, 32.4%) as colorless oil and tert-butyl (2S,6R)-2-[(benzyloxy)methyl]-6-methoxy-1,4-oxazocane-4-carboxylate (480 mg, 28.8%) as colorless oil. LCMS(ES) $[M+H]^+$ m/z: 366.

Synthesis of tert-butyl (2S,6R)-2-(hydroxymethyl)-6-methoxy-1,4-oxazocane-4-carboxylate To a stirred solution of tert-butyl (2S,6R)-2-[(benzyloxy)methyl]-6-methoxy-1,4-oxazocane-4-carboxylate (480 mg, 1.31 mmol, 1.0 equiv) in MeOH (8 mL) was added Pd/C (50 mg). The resulting mixture was stirred for 16 h at room temperature under hydrogen atmosphere. The resulting mixture was filtered, the filter cake was washed with MeOH (20 mL). The filtrate was concentrated under reduced pressure. This resulted in tert-butyl (2S,6R)-2-(hydroxymethyl)-6-methoxy-1,4-oxazocane-4-carboxylate (260 mg, 71.9%) as a colorless oil and used to the next step directly without further purification. LCMS(ES) $[M+H]^+$ m/z: 276.

Synthesis of (2S,6R)-4-(tert-butoxycarbonyl)-6-methoxy-1,4-oxazocane-2-carboxylic acid To a stirred solution tert-butyl (2S,6R)-2-(hydroxymethyl)-6-methoxy-1,4-oxazocane-4-carboxylate (260 mg, 0.94 mmol, 1.0 equiv) and NaBr (19 mg, 0.189 mmol, 0.2 equiv) in Acetone (3 mL) and $H_2O$ (1 mL) were added TEMPO (14 mg, 0.09 mmol, 0.1 equiv) and $NaHCO_3$ (158 mg, 1.89 mmol, 2.0 equiv) in portions at 0° C. under nitrogen atmosphere. To the above mixture was added 1,3,5-trichloro-1,3,5-triazinane-2,4,6-trione (438 mg, 1.89 mmol, 2.0 equiv) in portions at 0° C. The resulting mixture was stirred for additional 16 h at room temperature. The reaction was quenched with $NaHCO_3$ (aq). The resulting mixture was filtered, the filter cake was washed with $H_2O$ (10 mL). The filtrate was acidified to pH 6 with citric acid. The resulting mixture was extracted with $CH_2Cl_2$ (3×20 mL). The combined organic layer was washed with brine (10 mL), dried over anhydrous $Na_2SO_4$. After filtration, the filtrate was concentrated under reduced pressure. This resulted in (2S,6R)-4-(tert-butoxycarbonyl)-6-methoxy-1,4-oxazocane-2-carboxylic acid (180 mg, 65.9%) as off-white solid. LCMS(ES) $[M-H]^-$ m/z: 288.

Synthesis of tert-butyl (2S,6R)-2-{[(1S)-1-cyano-2-[4-(3-methyl-2-oxo-1,3-benzoxazol-5-yl)phenyl]ethyl]carbamoyl}-6-methoxy-1,4-oxazocane-4-carboxylate To a stirred solution of (2S,6R)-4-(tert-butoxycarbonyl)-6-methoxy-1,4-oxazocane-2-carboxylic acid (100 mg, 0.35 mmol, 1.0 equiv) and (2S)-2-amino-3-[4-(3-methyl-2-oxo-1,3-benzoxazol-5-yl)phenyl]propanenitrile (101 mg, 0.35 mmol, 1.0 equiv) in DCM (2 mL) was added DIEA (89 mg, 0.69 mmol, 2.0 equiv) and HATU (157 mg, 0.42 mmol, 1.2 equiv) in portions at 0° C. under nitrogen atmosphere. The resulting mixture was stirred for 1 h at 0° C. The resulting mixture was concentrated under reduced pressure. The residue was purified by silica gel column chromatography, eluted with PE/THF (1:1) to afford tert-butyl (2S,6R)-2-{[(1S)-1-cyano-2-[4-(3-methyl-2-oxo-1,3-benzoxazol-5-yl)phenyl]ethyl]carbamoyl}-6-methoxy-1,4-oxazocane-4-carboxylate (140 mg, 72%) as a white solid. LCMS(ES) $[M+H]^+$ m/z: 565.

Synthesis of (2S,6R)—N-[(1S)-1-cyano-2-[4-(3-methyl-2-oxo-1,3-benzoxazol-5-yl)phenyl]ethyl]-6-methoxy-1,4-oxazocane-2-carboxamide To a stirred solution of tert-butyl (2S,6R)-2-{[(1S)-1-cyano-2-[4-(3-methyl-2-oxo-1,3-benzoxazol-5-yl)phenyl]ethyl]carbamoyl}-6-methoxy-1,4-oxazocane-4-carboxylate (120 mg, 0.21 mmol, 1.0 equiv) in ACN (2 mL) was added TsOH (109 mg, 0.64 mmol, 3.0 equiv). The resulting mixture was stirred for 3 h at room temperature. The mixture was purified by reversed-phase flash chromatography with the following conditions: column, C18 silica gel-120 g; mobile phase, MeCN in Water (10 mmol/L $NH_4HCO_3$), 10% to 50% gradient in 10 min; detector, UV 254 nm. This resulted in (2S,6R)—N-[(1S)-1-cyano-2-[4-(3-methyl-2-oxo-1,3-benzoxazol-5-yl)phenyl]ethyl]-6-methoxy-1,4-oxazocane-2-carboxamide (30 mg, 30.4%) as white solid. LCMS(ES) $[M+H]^+$ m/z: 465.2.

$^1H$ NMR (300 MHz, DMSO-$d_6$) δ 8.67 (d, J=8.6 Hz, 1H), 7.71-7.62 (m, 2H), 7.58 (d, J=1.5 Hz, 1H), 7.47-7.33 (m, 4H), 5.07-4.92 (m, 1H), 4.05 (t, J=10.2 Hz, 1H), 3.90 (dd, J=10.3, 2.6 Hz, 1H), 3.62-3.50 (m, 1H), 3.41 (s, 3H), 3.30-3.09 (m, 6H), 2.98 (dd, J=13.6, 2.6 Hz, 1H), 2.38 (dd, J=13.5, 9.6 Hz, 1H), 2.28-2.11 (m, 2H), 1.68-1.56 (m, 1H).

Synthesis of (2S,7S)-2-(hydroxymethyl)-7-methoxy-1,4-oxazocane-4-carboxylate To a stirred solution of tert-butyl (2S,7S)-2-[(benzyloxy)methyl]-7-methoxy-1,4-oxazocane-4-carboxylate (520 mg, 1.43 mmol, 1.0 equiv) in MeOH (10 mL) was added Pd/C (60 mg). The resulting mixture was stirred for 16 h at room temperature under hydrogen atmosphere. The resulting mixture was filtered, the filter cake was washed with MeOH (10 mL). The filtrate was concentrated under reduced pressure. This resulted in tert-butyl (2S,7S)-2-(hydroxymethyl)-7-methoxy-1,4-oxazocane-4-carboxylate (300 mg, 76.6%) as colorless oil. LCMS(ES) $[M+H]^+$ m/z: 276.

Synthesis of (2S,7S)-4-(tert-butoxycarbonyl)-7-methoxy-1,4-oxazocane-2-carboxylic acid To a stirred solution tert-butyl (2S,7S)-2-(hydroxymethyl)-7-methoxy-1,4-oxazocane-4-carboxylate (300 mg, 1.09 mmol, 1.0 equiv) and NaBr (22 mg, 0.22 mmol, 0.2 equiv) in Acetone (3 mL) and $H_2O$ (1 mL) were added TEMPO (17 mg, 0.11 mmol, 0.1 equiv) and $NaHCO_3$ (183 mg, 2.18 mmol, 2.0 equiv) in portions at 0° C. under nitrogen atmosphere. To the above mixture was added 1,3,5-trichloro-1,3,5-triazinane-2,4,6-trione (506 mg, 2.18 mmol, 2.0 equiv) in portions at 0° C. The resulting mixture was stirred for additional 16 h at room temperature. The reaction was quenched with $NaHCO_3$ (aq). The resulting mixture was filtered, the filter cake was washed with $H_2O$ (10 mL). The filtrate was acidified to pH 6 with citric acid. The resulting mixture was extracted with $CH_2Cl_2$ (3×20 mL). The combined organic layer was washed with brine (10 mL), dried over anhydrous $Na_2SO_4$. After filtration, the filtrate was concentrated under reduced pressure. This resulted in (2S,7S)-4-(tert-butoxycarbonyl)-7-methoxy-1,4-oxazocane-2-carboxylic acid (200 mg, 63.4%) as off-white solid. LCMS(ES) $[M-H]^-$ m/z: 288.

Synthesis of tert-butyl (2S,7S)-2-{[(1S)-1-cyano-2-[4-(3-methyl-2-oxo-1,3-benzoxazol-5-yl)phenyl]ethyl]carbamoyl}-7-methoxy-1,4-oxazocane-4-carboxylate To a stirred solution of (2S,7S)-4-(tert-butoxycarbonyl)-7-methoxy-1,4-oxazocane-2-carboxylic acid (100 mg, 0.35 mmol, 1.0 equiv) and (2S)-2-amino-3-[4-(3-methyl-2-oxo-1,3-benzoxazol-5-yl)phenyl]propanenitrile (101 mg, 0.35 mmol, 1.0 equiv) in DCM (2 mL) was added DIEA (89 mg, 0.69 mmol, 2.0 equiv) and HATU (157 mg, 0.42 mmol, 1.2 equiv) in portions at 0° C. under nitrogen atmosphere. The resulting mixture was stirred for 1 h at 0° C. under nitrogen atmosphere. The resulting mixture was concentrated under reduced pressure. The residue was purified by silica gel column chromatography, eluted with PE/THF (1:1) to afford tert-butyl (2S,7S)-2-{[(1S)-1-cyano-2-[4-(3-methyl-2-oxo-1,3-benzoxazol-5-yl)phenyl]ethyl]carbamoyl}-7-methoxy-1,4-oxazocane-4-carboxylate (150 mg, 76.9%) as white solid. LCMS(ES) $[M+H]^+$ m/z: 565.

Synthesis of (2S,7S)—N-[(1S)-1-cyano-2-[4-(3-methyl-2-oxo-1,3-benzoxazol-5-yl)phenyl]ethyl]-7-methoxy-1,4-oxazocane-2-carboxamide To a stirred solution of tert-butyl (2S,7S)-2-{[(1S)-1-cyano-2-[4-(3-methyl-2-oxo-1,3-benzoxazol-5-yl)phenyl]ethyl]carbamoyl}-7-methoxy-1,4-oxazocane-4-carboxylate (120 mg, 0.21 mmol, 1.0 equiv) in ACN (2 mL) was added TsOH (109 mg, 0.64 mmol, 3.0 equiv). The resulting mixture was stirred for 3 h at room temperature. The mixture was purified by reversed-phase flash chromatography with the following conditions: column, $C_{18}$ silica gel-120 g; mobile phase, MeCN in Water (10 mmol/L $NH_4HCO_3$), 10% to 50% gradient in 10 min; detector, UV 254 nm. This resulted in (2S,7S)—N-[(1S)-1-cyano-2-[4-(3-methyl-2-oxo-1,3-benzoxazol-5-yl)phenyl]ethyl]-7-methoxy-1,4-oxazocane-2-carboxamide (30 mg, 30%) as a white solid. LCMS(ES) $[M+H]^+$ m/z: 465.

$^1H$ NMR (300 MHz, DMSO-$d_6$) δ 8.61 (d, J=8.6 Hz, 1H), 7.71-7.61 (m, 2H), 7.57 (t, J=1.1 Hz, 1H), 7.47-7.34 (m, 4H), 5.10-4.95 (m, 1H), 3.99 (dd, J=12.6, 3.9 Hz, 1H), 3.87 (dd, J=12.6, 3.8 Hz, 1H), 3.80 (dd, J=9.4, 3.0 Hz, 1H), 3.40 (s, 3H), 3.39-3.36 (m, 1H), 3.25 (s, 3H), 3.26-3.16 (m, 2H), 2.93 (dd, J=14.4, 3.0 Hz, 1H), 2.81-2.65 (m, 2H), 2.26 (dd, J=14.4, 9.5 Hz, 1H), 1.95-1.76 (m, 1H), 1.78-1.65 (m, 1H).

Example 34: Preparation of (2S)—N-[(1S)-1-cyano-2-(4-{1-methyl-3'-oxospiro[azetidine-3,1'-[2]benzofuran]-6'-yl}phenyl)ethyl]-1,4-oxazocane-2-carboxamide (Compound 34)

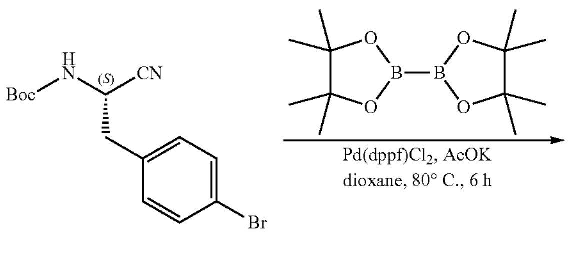

-continued

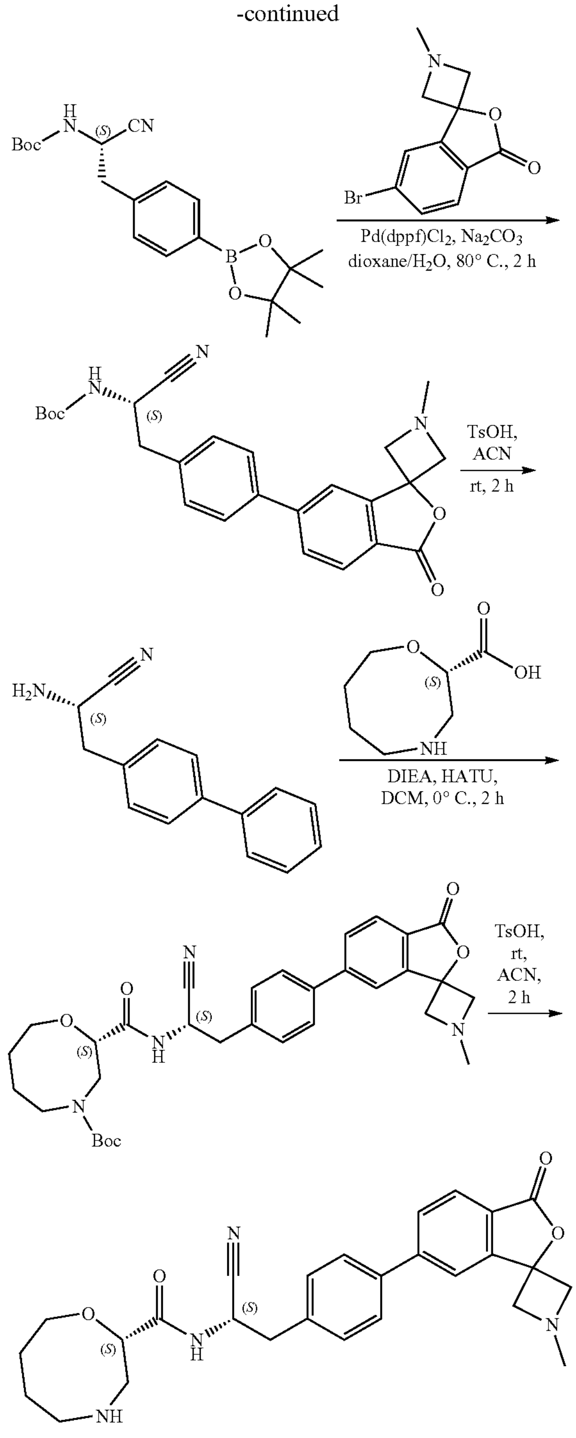

Compound 34

Synthesis of tert-butyl N-[(1S)-1-cyano-2-[4-(4,4,5,5-tetramethyl-1,3,2-dioxaborolan-2-yl)phenyl]ethyl] carbamate To a stirred solution of tert-butyl N-[(1S)-2-(4-bromophenyl)-1-cyanoethyl]carbamate (5 g, 15.38 mmol, 1.0 equiv), bis(pinacolato)diboron (4.29 g, 16.91 mmol, 1.1 equiv) and AcOK (3.02 g, 30.75 mmol, 2.0 equiv) in dioxane (50 mL) was added Pd (dppf) $C_{12}$ (1.25 g, 1.54 mmol, 0.1 equiv) in portions at room temperature under nitrogen atmosphere. The resulting mixture was stirred for 6 h at 80° C. under nitrogen atmosphere. The reaction was cooled to room temperature, the resulting mixture was filtered, the filter cake was washed with DCM (3x30 mL). The filtrate was concentrated under reduced pressure. The residue was purified by silica gel column chromatography, eluted with PE/EA (1:1) to afford tert-butyl N-[(1S)-1-cyano-2-[4-(4,4,5,5-tetramethyl-1,3,2-dioxaborolan-2-yl)phenyl]ethyl]carbamate (5.4 g, 94%) as white solid. LCMS(ES) $[M+H]^+$ m/z: 373.

Synthesis of tert-butyl N-[(1S)-1-cyano-2-(4-{1-methyl-3'-oxospiro[azetidine-3,1'-[2]benzofuran]-6'-yl}phenyl)ethyl]carbamate To a stirred solution of tert-butyl N-[(1S)-1-cyano-2-[4-(4,4,5,5-tetramethyl-1,3,2-dioxaborolan-2-yl)phenyl]ethyl] carbamate (1.5 g, 4.03 mmol, 1.0 equiv), 6'-bromo-1-methylspiro[azetidine-3,1'-[2]benzofuran]-3'-one (1.19 g, 4.43 mmol, 1.1 equiv) and $Na_2CO_3$ (0.85 g, 8.06 mmol, 2.0 equiv) in dioxane (16 mL) and $H_2O$ (2 mL) was added Pd (dppf) $C_{12}$ (0.33 g, 0.40 mmol, 0.1 equiv) in portions at room temperature under nitrogen atmosphere. The resulting mixture was stirred for 2 h at 80° C. under nitrogen atmosphere. The reaction was cooled to room temperature, concentrated under vacuum to remove the solvent. The residue was purified by silica gel column chromatography, eluted with PE/EA (1:1) to afford tert-butyl N-[(1S)-1-cyano-2-(4-{1-methyl-3'-oxospiro[azetidine-3,1'-[2]benzofuran]-6'-yl}phenyl)ethyl]carbamate (800 mg, 46%) as light yellow solid. LCMS(ES) $[M+H]^+$ m/z: 434.

Synthesis of (2S)-2-amino-3-(4-{1-methyl-3'-oxospiro[azetidine-3,1'-[2] benzofuran]-6'-yl}phenyl) propanenitrile A solution of tert-butyl N-[(1S)-1-cyano-2-(4-{1-methyl-3'-oxospiro[azetidine-3,1'-[2]benzofuran]-6'-yl}phenyl) ethyl]carbamate (800 mg, 1.85 mmol, 1.0 equiv) and TsOH (953 mg, 5.54 mmol, 3.0 equiv) in ACN (10 mL) was stirred for 2 h at room temperature. The mixture was neutralized to pH 8 with saturated $NaHCO_3$ (aq.). The resulting mixture was extracted with EtOAc (3x20 mL). The combined organic layer was washed with water (2x20 mL), dried over anhydrous $Na_2SO_4$. After filtration, the filtrate was concentrated under reduced pressure. This resulted in (2S)-2-amino-3-(4-{1-methyl-3'-oxospiro[azetidine-3,1'-[2]benzofuran]-6'-yl}phenyl) propanenitrile (580 mg, 94%) as a light yellow solid. LCMS(ES) $[M+H]^+$ m/z: 334.

Synthesis of tert-butyl (2S)-2-{[(1S)-1-cyano-2-(4-{1-methyl-3'-oxospiro[azetidine-3,1'-[2]benzofuran]-6'-yl}phenyl)ethyl]carbamoyl}-1,4-oxazocane-4-carboxylate To a stirred solution of (2S)-2-amino-3-(4-{1-methyl-3'-oxospiro[azetidine-3,1'-[2] benzofuran]-6'-yl}phenyl) propane nitrile (130 mg, 0.39 mmol, 1.0 equiv), (2S)-1,4-oxazocane-2-carboxylic acid (62 mg, 0.39 mmol, 1.0 equiv) and DIEA (151 mg, 1.17 mmol, 3.0 equiv) in DCM (2 mL) was added HATU (177 mg, 0.47 mmol, 1.2 equiv) in portions at 0° C. The resulting mixture was stirred for 2 h at 0° C. Concentrated under reduced pressure to remove the solvent, the residue was purified by silica gel column chromatography, eluted with PE/EA (1:1) to afford tert-butyl (2S)-2-{[(1S)-1-cyano-2-(4-{1-methyl-3'-oxospiro[azetidine-3,1'-[2]benzofuran]-6'-yl}phenyl)ethyl]carbamoyl}-1,4-oxazocane-4-carboxylate (90 mg, 40%) as white solid. LCMS(ES) $[M+H]^+$ m/z: 575.

Synthesis of (2S)—N-[(1S)-1-cyano-2-(4-{1-methyl-3'-oxospiro[azetidine-3,1'-[2]benzofuran]-6'-yl}phenyl)ethyl]-1,4-oxazocane-2-carboxamide A solution of tert-butyl (2S)-2-{[(1S)-1-cyano-2-(4-{1-methyl-3'-oxospiro[azetidine-3,1'-[2]benzofuran]-6'-yl}phenyl)ethyl]carbamoyl}-1,4-oxazocane-4-carboxylate (90 mg, 0.16 mmol, 1.0 equiv) and TsOH (80 mg, 0.47 mmol, 3.0 equiv) in ACN (1.5 mL) was stirred for 2 h at room temperature. The reaction solution was purified by reversed-phase flash chromatography with the following conditions: column, $C_{18}$ silica gel-120 g; mobile phase, MeCN in Water (0.1% $NH_3 \cdot H_2O$), 10% to 60% gradient in 10 min; detector, UV 254 nm. This resulted in (2S)—N-[(1S)-1-cyano-2-(4-{1-methyl-3'-oxospiro[azetidine-3,1'-[2]benzofuran]-6'-yl}phenyl)ethyl]-1,4-oxazocane-2-carboxamide (30 mg, 40.4%) as white solid. LCMS(ES) $[M+H]^+$ m/z: 475.4

$^1$H NMR (400 MHZ, DMSO-$d_6$) § 8.64 (d, J=8.6 Hz, 1H), 8.16 (t, J=1.1 Hz, 1H), 8.00-7.84 (m, 2H), 7.83-7.75 (m, 2H), 7.49-7.42 (m, 2H), 5.08-5.01 (m, 1H), 3.99-3.94 (m, 1H), 3.86 (dd, J=9.7, 2.9 Hz, 1H), 3.73 (d, J=8.1 Hz, 2H), 3.70-3.61 (m, 3H), 3.27-3.18 (m, 2H), 2.98-2.91 (m, 2H), 2.62-2.56 (m, 1H), 2.44 (s, 3H), 2.21 (dd, J=14.0, 9.7 Hz, 1H), 1.91-1.84 (m, 1H), 1.61-1.49 (m, 3H).

Example 35: Preparation of (2S,7R)—N—((S)-1-cyano-2-(4-(3-methyl-2-oxo-2,3-dihydrobenzo[d]oxazol-5-yl)phenyl)ethyl)-7-hydroxy-1,4-oxazocane-2-carboxamide (Compound 35)

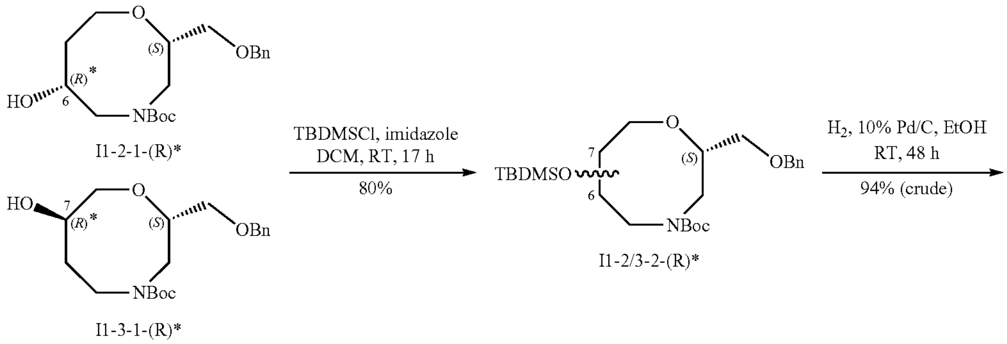

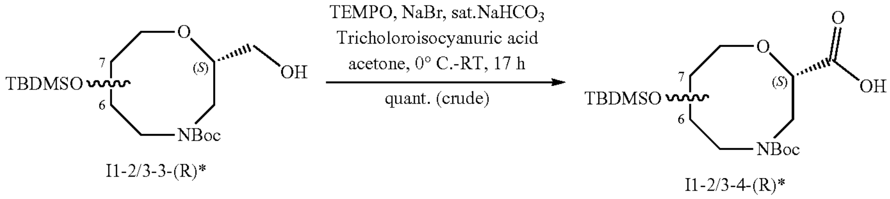

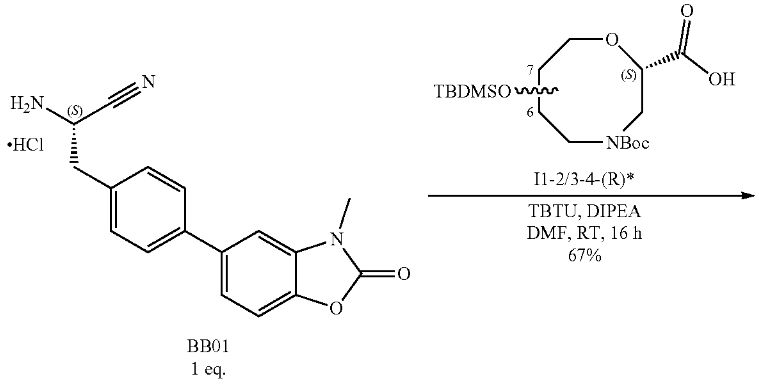

-continued
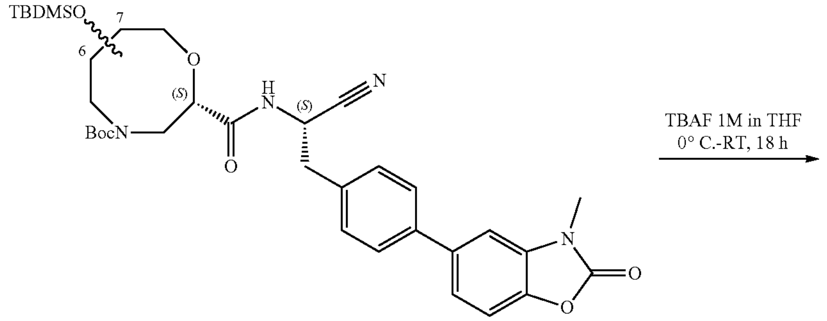
I1-2/3-5-(R)*
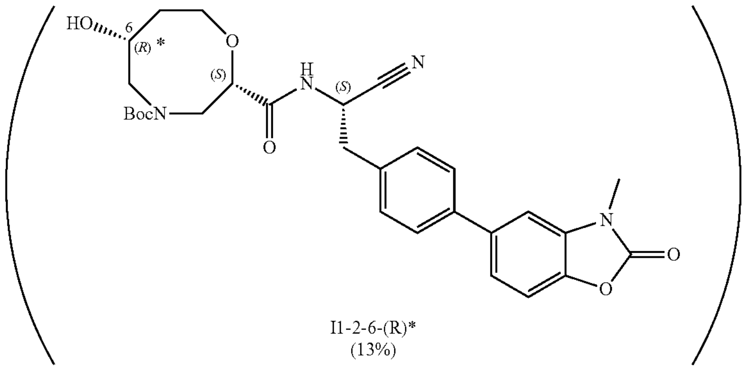
I1-2-6-(R)*
(13%)
+
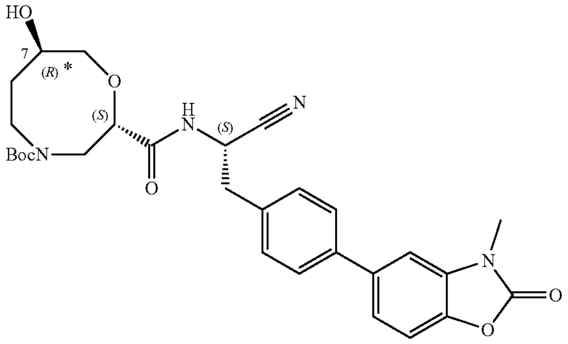
I1-3-6-(R)*
(65%)
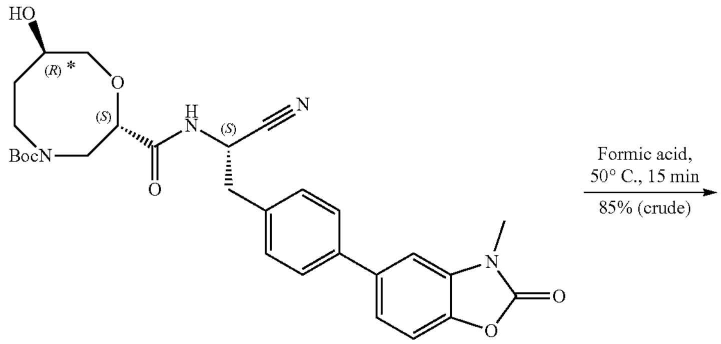
I1-3-6-(R)*

-continued

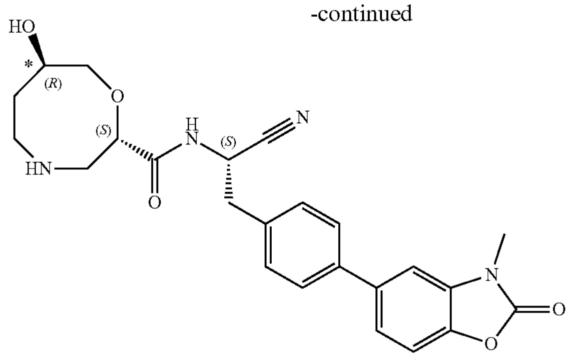

Compound 35 tert-butyl (2S,6R*)-2-[(benzyloxy)methyl]-6-[(tert-butyldimethylsilyl)oxy]-1,4-oxazocane-4-carboxylate 11-2-2-(R)* and tert-butyl (2S,7R*)-2-[(benzyloxy)methyl]-7-[(tert-butyldimethylsilyl)oxy]-1,4-oxazocane-4-carboxylate I1-3-2-(R)*

To a solution of a mixture of I1-2/3-1-(R)* (1 eq., 942 mg, 2.68 mmol) in DCM (15 mL) were added TBDMSCl (1.5 eq., 606 mg, 0.7 mL, 4.02 mmol) and imidazole (3 eq., 0.55 g, 8.04 mmol) at RT. The reaction was stirred at 0° C. for 15 h, then the reaction mixture was diluted with water (60 mL) and extracted with DCM (3×60 mL). The combined organic layers were washed with brine (50 mL), dried over $Na_2SO_4$, filtered and concentrated to dryness under reduced pressure affording the crude as a yellowish gum (1.35 g). The crude was purified by ELSD flash chromatography over silica gel (irregular SiOH, 50 μm, 40 g Interchim, dry loading (silica), mobile phase gradient: cyclohexane/EtOAc from 100/0 to 80/20 over 30 min). The fractions containing compound were combined, evaporated in vacuo and co-evaporated with DCM affording a mixture of I1-2/3-2-(R)* as a colorless oil (1.00 g, 2.15 mmol, 80%).

LC/MS (AN_01_001_087): Rt=8.32 and 8.39 min, 25.09 and 71.32%, [M−Boc+H]=366.34.

tert-butyl (2S,6R*)-6-[(tert-butyldimethylsilyl)oxy]-2-(hydroxymethyl)-1,4-oxazocane-4-carboxylate I1-2-3-(R)* tert-butyl (2S,7R*)-7-[(tert-butyldimethylsilyl)oxy]-2-(hydroxymethyl)-1,4-oxazocane-4-carboxylate I1-3-(R)*

Starting from a mixture of I1-2/3-(R)* (1 eq., 1.00 g, 2.15 mmol), using general procedure D, crude I1-2/3-3-(R)* was obtained as a white solid (760 mg, crude, 94%) and was used as such without further purification.

LC/MS (AN01_001_086, ELSD): Rt=7.96 min, 98.87%, $[M-{}^{t}Bu+H]^+$=320.39.

(2S,6R*)-4-[(tert-butoxy) carbonyl]-6-[(tert-butyldimethylsilyl)oxy]-1,4-oxazocane-2-carboxylic acid I1-2-4-(R)* (2S,7R*)-4-[(tert-butoxy) carbonyl]-7-[(tert-butyldimethylsilyl)oxy]-1,4-oxazocane-2-carboxylic acid I1-3-4-(R)*

Starting from a mixture of I1-2/3-3-(R)* (1 eq., 755 mg, 2.01 mmol), using general procedure E, crude I1-2/3-4-(R)* was obtained as yellow gum (780 mg, crude, quant.) and was used as such without further purification.

LC/MS (AN01_001_088): Rt=7.11 min, 57.93%, $[M-{}^{t}Bu+H]^+$=334.61.

tert-butyl (2S,6R*)-6-[(tert-butyldimethylsilyl)oxy]-2-{[(1S)-1-cyano-2-[4-(3-methyl-2-oxo-2,3-dihydro-1,3-benzoxazol-5-yl)phenyl]ethyl]carbamoyl}-1,4-oxazocane-4-carboxylate I1-2-5-(R)* and tert-butyl (2S,7R*)-7-[(tert-butyldimethylsilyl)oxy]-2-{[(1S)-1-cyano-2-[4-(3-methyl-2-oxo-2,3-dihydro-1,3-benzoxazol-5-yl)phenyl]ethyl]carbamoyl}-1,4-oxazocane-4-carboxylate I1-3-5-(R)*

Starting from BB01 (1 eq., 400 mg, 1.21 mmol) and I1-2/3-4-(R)* (1.05 eq., 520 mg, 1.27 mmol) and using general procedure B, a mixture of I1-2/3-5-(R)* was obtained as an orange gum (540 mg, 67%) after purification by flash chromatography over silica gel (25 μm, 25 g, cyclohexane/EtOAc from 100:0 to 0:100 in 60 min).

LC/MS (AN01_001_086): Rt=8.41 and 8.46 min, 15.71 and 75.12%, $[M-{}^{t}Bu+H]^+$=609.62.

tert-butyl (2S,7R*)-2-{[(1S)-1-cyano-2-[4-(3-methyl-2-oxo-2,3-dihydro-1,3-benzoxazol-5-yl)phenyl]ethyl]carbamoyl}-7-hydroxy-1,4-oxazocane-4-carboxylate 11-3-6-(R)*

Starting from a mixture of I1-2/3-5-(R)* (1 eq., 540 mg, 0.81 mmol) and using general procedure A, 11-3-6-(R)* (294 mg, 65%) was obtained as a yellow solid after purification by flash chromatography over silica gel (15 μm, 25 g, DCM/EtOAc from 80:20 to 0:100 in 50 min).

LC/MS (AN01_001_086): Rt=6.26 min, 98.28%, $[M-{}^{t}Bu+H]^+$=495.48.

(2S,7R*)—N-[(1S)-1-cyano-2-[4-(3-methyl-2-oxo-2,3-dihydro-1,3-benzoxazol-5-yl)phenyl]ethyl]-7-hydroxy-1,4-oxazocane-2-carboxamide Starting from a mixture of I1-3-6-(R)* (1 eq., 100 mg, 0.18 mmol) and using general procedure C, (2S,7R*)—N-[(1S)-1-cyano-2-[4-(3-methyl-2-oxo-2,3-dihydro-1,3-benzoxazol-5-yl)phenyl]ethyl]-7-hydroxy-1,4-oxazocane-2-carboxamide (18.8 mg, 23%) was obtained as an off-white solid after SFC purification (Chiralpak Chiralpak AD-H 20×250 mm, Mobile phase: $CO_2$/(iPrOH+0.3% iPrNH2) 70/30).

LC/MS (AN01_001_088): Rt=4.52 min, 97.92%, $[M+H]^+$=451.59.

Chiral SFC analysis: Chiralpak AD-3 4.6×100 mm, Mobile phase: $CO_2$/(iPrOH+0.3% iPrNH2) 70/30: Rt=3.41 min, 88.14%.

$^1$H NMR (400 MHZ, DMSO) δ 8.64 (d, J=8.5 Hz, 1H), 7.69-7.62 (m, 2H), 7.58-7.52 (m, 1H), 7.43-7.33 (m, 4H), 5.32-4.81 (m, 1H), 4.74 (s, 1H), 4.05-3.90 (m, 2H), 3.71-3.60 (m, 1H), 3.51-3.42 (m, 1H), 3.40 (s, 3H), 3.27-3.11 (m, 2H), 3.11-2.96 (m, 2H), 2.57-2.52 (m, 1H), 2.37-2.27 (m, 1H), 1.90-1.80 (m, 1H), 1.62-1.49 (m, 1H), one missing proton (NH).

Example 36: IC50 Assays

Mouse DPP1 Enzyme IC50 Assay

Test articles were applied to active mouse DPP1 enzyme (R&D Systems; Minneapolis, MN) in Assay Buffer (50 mM MES pH 5.5, 50 mM NaCl, 5 mM DTT) in a total reaction volume of 125 μL. 25 μL of compound in Assay Buffer plus 5% DMSO was first added to 50 μL of active mouse DPP1 enzyme at a concentration of 62.5 pg/μL and allowed to pre-incubate for 10 minutes at 37° C. after which 50 μL of 1000 μM H-Gly-Arg-AMC substrate (Bachem; St. Torrance, CA) was added, giving final substrate concentration of 400 M and a final DMSO concentration of 1%. Substrate cleavage was measured for 90 minutes at 37° C., with fluorescence at Excitation/Emission 350/450 nm measured every 5 minutes. DPP1 concentration was interpolated based on its activity relative to a standard curve of recombinant active mouse DPP1 enzyme. IC50 values for each compound were calculated via the XLFit (IDBS Version 5.3.1.3) Add-On to Microsoft Excel using the four parameter fit equation y=(A+((B−A)/(1+((C/x)^D)))), which appears as equation number 205 (4 Parameter Logistic Model or Sigmoidal Dose-Response Model) in XLFit. Default constraints were used for each Parameter. IC50 was defined as the compound concentration at which 50% of enzyme activity was inhibited when compared to the no-compound control.

Results are provided in Table 2 below. The absolute stereochemistry of each compound was not conclusively determined but assigned as shown below.

TABLE 2

Mouse DPP1 enzyme IC50 values

| No. | Mouse DPP1 IC50 (nM) |
|---|---|
| 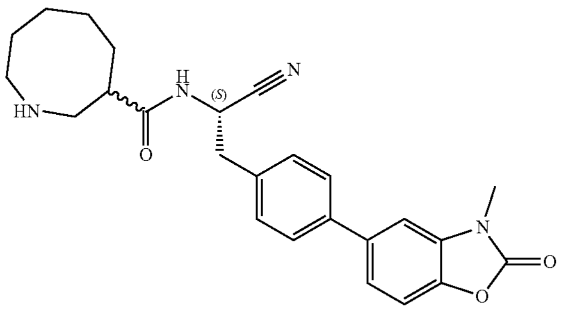 IA | 63.4 |
| 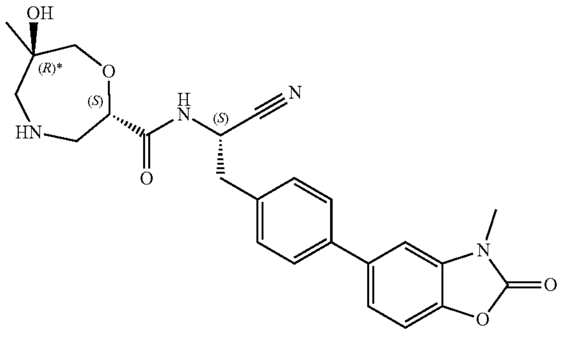 2-A | 51.7 |

TABLE 2-continued
| Mouse DPP1 enzyme IC50 values | |
|---|---|
| No. | Mouse DPP1 IC50 (nM) |
| 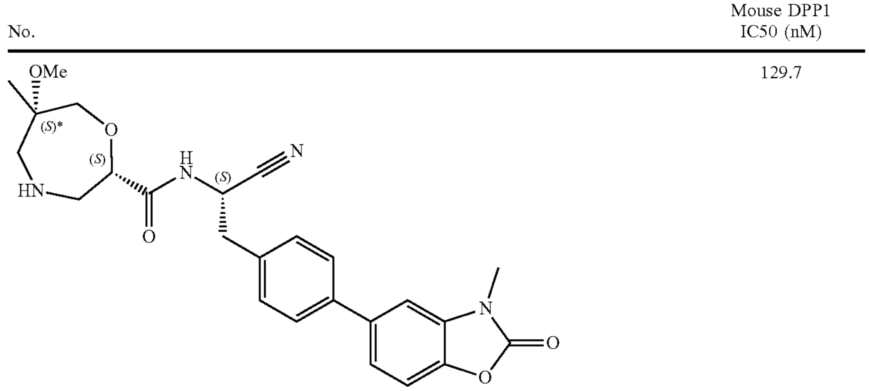 3-A | 129.7 |
| 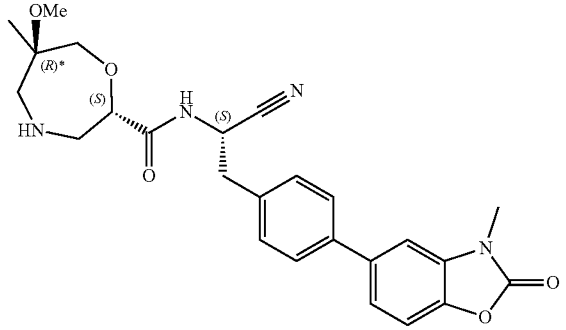 3-B | 251 |
| 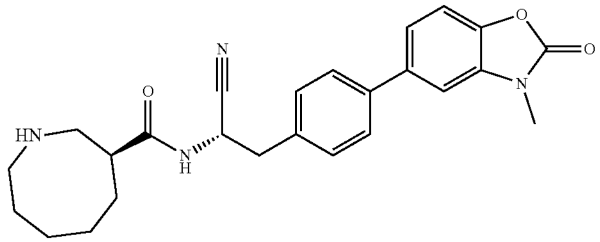 [SMILES: Cn1c(=O)oc2ccc(-c3ccc(C[C@@H](C#N)NC(=O)[C@H]4CCCCCNC4)cc3)cc21] | 54 |
| 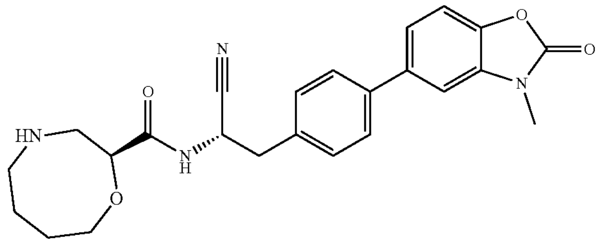 [SMILES: Cn1c(=O)oc2ccc(-c3ccc(C[C@@H](C#N)NC(=O)[C@@H]4CNCCCCO4)cc3)cc21] | 41.4 ± 4.5 (n = 3) |
| 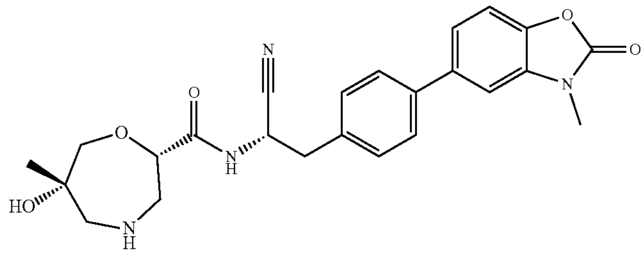 [SMILES: Cn1c(=O)oc2ccc(-c3ccc(C[C@@H](C#N)NC(=O)[C@@H]4CNC[C@](C)(O)CO4)cc3)cc21] | 351.3 ± 222.8 (n = 3) |

TABLE 2-continued
| Mouse DPP1 enzyme IC50 values | | |
|---|---|---|
| No. | | Mouse DPP1 IC50 (nM) |
| | 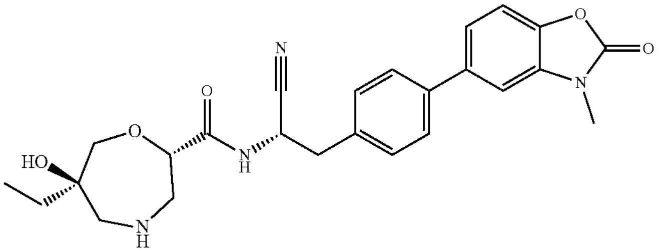 [SMILES: CC[C@@]1(O)CNC[C@@H](C(=O)N[C@H](C#N)Cc2ccc(-c3ccc4oc(=O)n(C)c4c3)cc2)OC1] | 36.9 |
| | 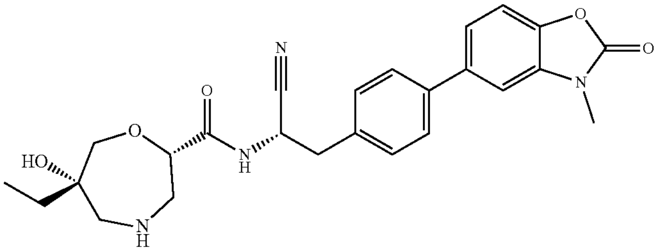 [SMILES: CC[C@]1(O)CNC[C@@H](C(=O)N[C@H](C#N)Cc2ccc(-c3ccc4oc(=O)n(C)c4c3)cc2)OC1] | 4037.6 |
| | 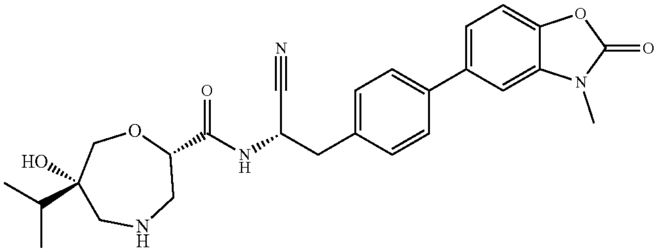 [SMILES: CC(C)[C@]1(O)CNC[C@@H](C(=O)N[C@H](C#N)Cc2ccc(-c3ccc4oc(=O)n(C)c4c3)cc2)OC1] | >5000 |
| | 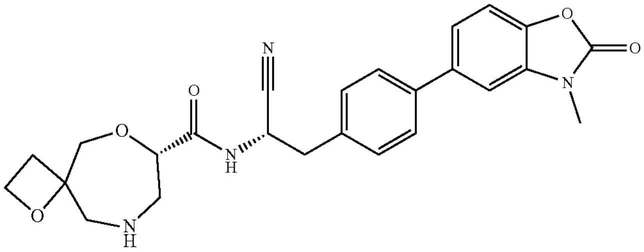 | 4.2 ± 0.8 (n = 3) |
| | 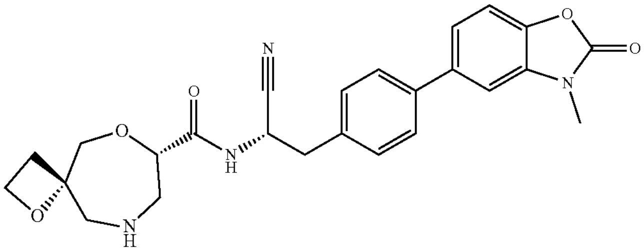 [SMILES: Cn1c(=O)oc2ccc(-c3ccc(C[C@@H](C#N)NC(=O)[C@@H]4CNC[C@@]5(CCO5)CO4)cc3)cc21] | 2.36 ± 0.3 (n = 3) |
| | 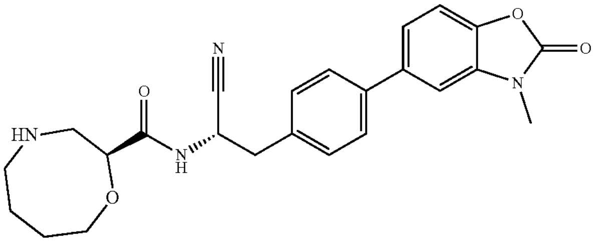 [SMILES: Cn1c(=O)oc2ccc(-c3ccc(C[C@@H](C#N)NC(=O)[C@@H]4CNCCCCO4)cc3)cc21] | 33.9 ± 4 (n = 3) |

TABLE 2-continued
| Mouse DPP1 enzyme IC50 values | |
|---|---|
| No. | Mouse DPP1 IC50 (nM) |
| 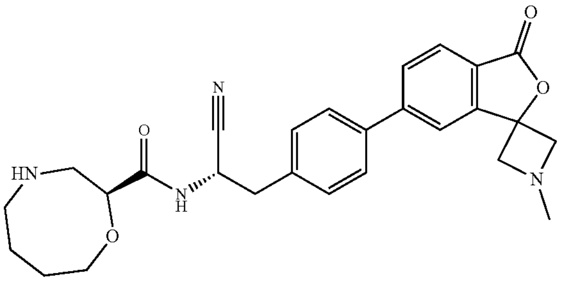 [SMILES: CN1CC2(C1)OC(=O)c1ccc(-c3ccc(C[C@@H](C#N)NC(=O)[C@@H]4CNCCCCO4)cc3)cc12] | 17.8 ± 2 (n = 3) |
| 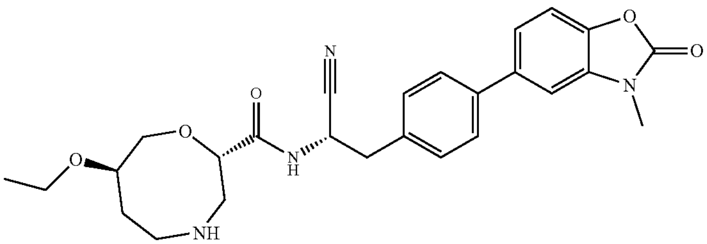 [SMILES: CCO[C@@H]1CCNC[C@@H](C(=O)N[C@H](C#N)Cc2ccc(-c3ccc4oc(=O)n(C)c4c3)cc2)OC1] | 6.05 ± 2 (n = 3) |
| 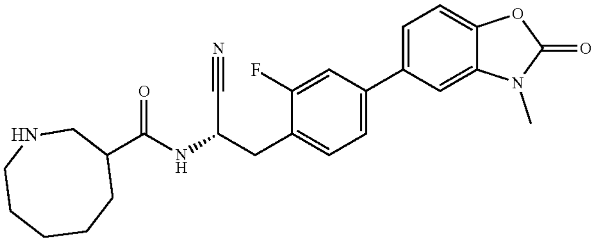 [SMILES: Cn1c(=O)oc2ccc(-c3ccc(C[C@@H](C#N)NC(=O)C4CCCCCNC4)c(F)c3)cc21] | 13.1 ± 3.7 (n = 3) |
| 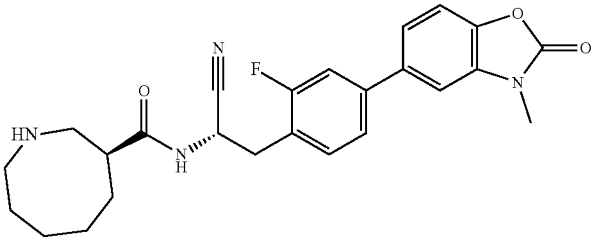 [SMILES: Cn1c(=O)oc2ccc(-c3ccc(C[C@@H](C#N)NC(=O)[C@H]4CCCCCNC4)c(F)c3)cc21] | 147.6 ± 16 (n = 2) |
| 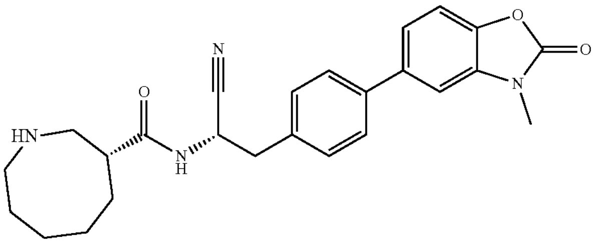 [SMILES: Cn1c(=O)oc2ccc(-c3ccc(C[C@@H](C#N)NC(=O)[C@@H]4CCCCCNC4)cc3)cc21] | 628.6 |

TABLE 2-continued

Mouse DPP1 enzyme IC50 values

| No. | Mouse DPP1 IC50 (nM) |
| --- | --- |
| 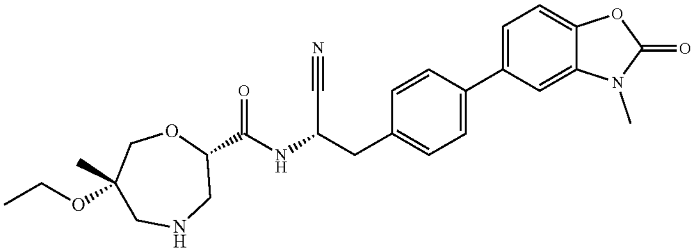 [SMILES: CCO[C@@]1(C)CNC[C@@H](C(=O)N[C@H](C#N)Cc2ccc(-c3ccc4oc(=O)n(C)c4c3)cc2)OC1] | >5000 |
| 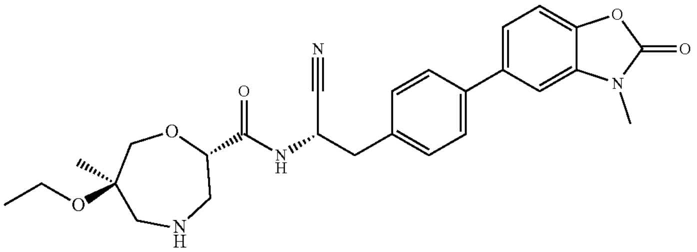 [SMILES: CCO[C@]1(C)CNC[C@@H](C(=O)N[C@H](C#N)Cc2ccc(-c3ccc4oc(=O)n(C)c4c3)cc2)OC1] | 1642.1 |
| 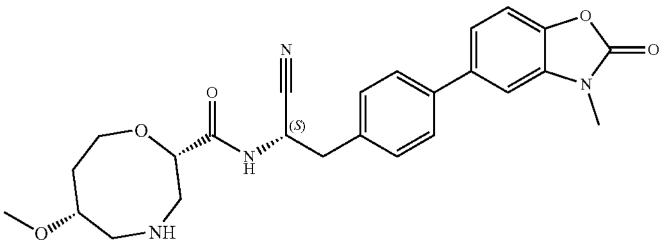 | 7.04 |

Human DPP 1 Enzyme IC50 Assay

Recombinant human DPP1 enzyme (R&D Systems; Minneapolis, MN) was first proteolytically processed into its mature form using recombinant human cathepsin L (R&D Systems) in a buffer consisting of 20 mM citric acid pH 4.5, 150 mM NaCl, 1 mM EDTA and 10 mM DTT. Test articles were applied to activated human DPP1 enzyme in Assay Buffer (25 mM MES pH 6.0, 50 mM NaCl, 5 mM DTT) in a total reaction volume of 125 μL. 25 μL of compound in Assay Buffer plus 5% DMSO was first added to 50 μL of activated human DPP1 enzyme at a concentration of 1 ng/μL and allowed to pre-incubate for 10 minutes at 37° C. after which 50 μL of 1000 μM H-Gly-Arg-AMC substrate (Bachem; St. Torrance, CA) was added, giving final substrate concentration of 400 M and a final DMSO concentration of 1%. Substrate cleavage was measured for 90 minutes at 37° C., with fluorescence at Excitation/Emission 350/450 nm measured every 5 minutes. DPP1 concentration was interpolated based on its activity relative to a standard curve of activated human recombinant DPP1 enzyme. IC50 values for each compound were calculated via the XLFit (IDBS Version 5.3.1.3) Add-On to Microsoft Excel using the four parameter fit equation y={A+[(B−A)]/[1+((C/x)^D)]}, which appears as equation number 205 (4 Parameter Logistic Model or Sigmoidal Dose-Response Model) in XLFit. Default constraints were used for each Parameter. IC50 was defined as the compound concentration at which 50% of enzyme activity was inhibited when compared to the no-compound control.

Results are provided in Table 3 below. The absolute stereochemistry of each compound was not conclusively determined but assigned as shown below.

TABLE 3
| Human DPP1 enzyme IC50 values | | |
|---|---|---|
| No. | | Human DPP1 IC50 (nM) |
| I-A | 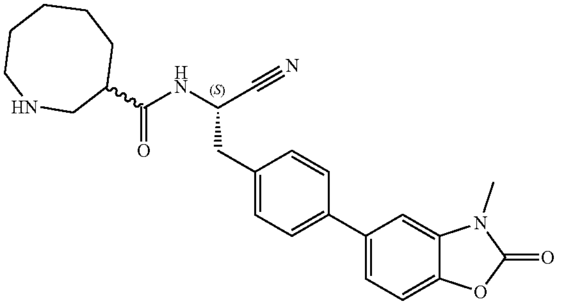 | 72.6 |
| 2-A | 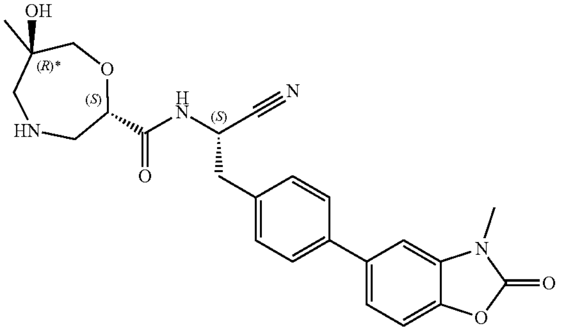 | 39.6 |
| 3-A | 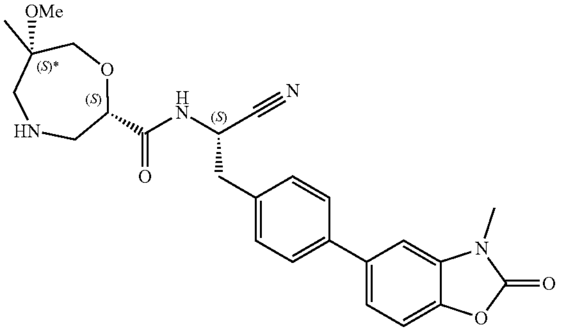 | 144.8 |
| 3-B | 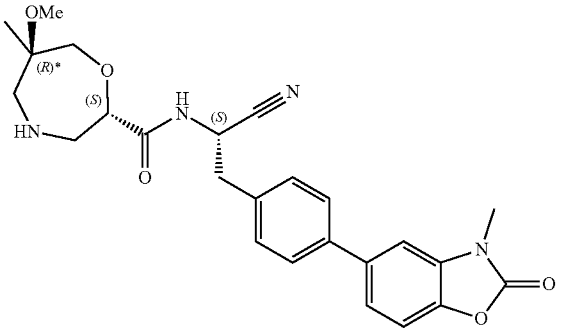 | 205.5 |

TABLE 3-continued
| Human DPP1 enzyme IC50 values | | |
|---|---|---|
| No. | | Human DPP1 IC50 (nM) |
| | 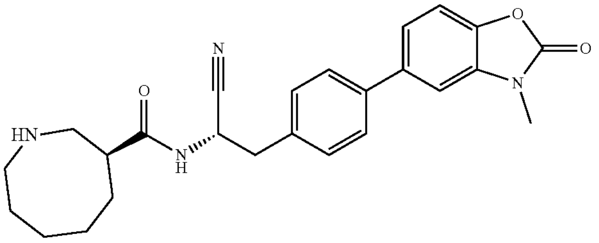 [SMILES: Cn1c(=O)oc2ccc(-c3ccc(C[C@@H](C#N)NC(=O)[C@H]4CCCCCNC4)cc3)cc21] | 49.8 |
| | 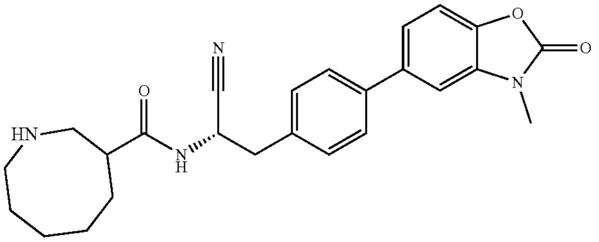 | 85.6 ± 19.5 (n = 3) |
| | 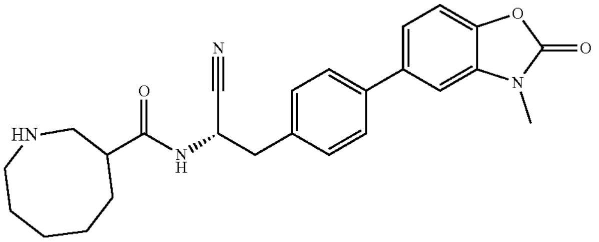 [SMILES: Cn1c(=O)oc2ccc(-c3ccc(C[C@@H](C#N)NC(=O)C4CCCCCNC4)cc3)cc21] | 61.3 ± 9.9 (n = 3) |
| | 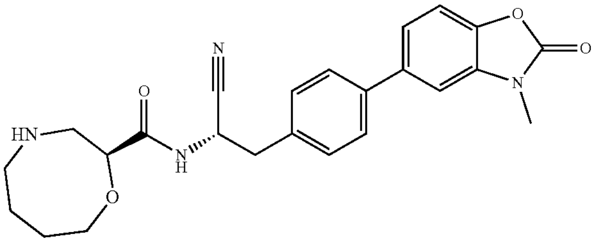 [SMILES: Cn1c(=O)oc2ccc(-c3ccc(C[C@@H](C#N)NC(=O)[C@@H]4CNCCCCO4)cc3)cc21] | 25.1 ± 3.1 (n = 3) |
| | 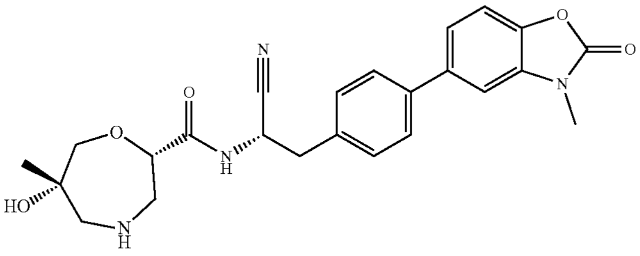 [SMILES: Cn1c(=O)oc2ccc(-c3ccc(C[C@@H](C#N)NC(=O)[C@@H]4CNC[C@](C)(O)CO4)cc3)cc21] | 314.5 ± 201.3 (n = 3) |
| | 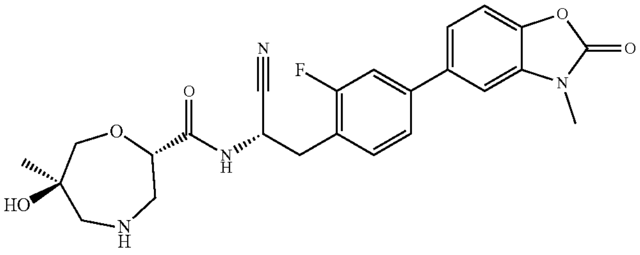 [SMILES: Cn1c(=O)oc2ccc(-c3ccc(C[C@@H](C#N)NC(=O)[C@@H]4CNC[C@@](C)(O)CO4)c(F)c3)cc21] | 14.1 ± 3 (n = 3) |

TABLE 3-continued
| Human DPP1 enzyme IC50 values | |
|---|---|
| No. | Human DPP1 IC50 (nM) |
| 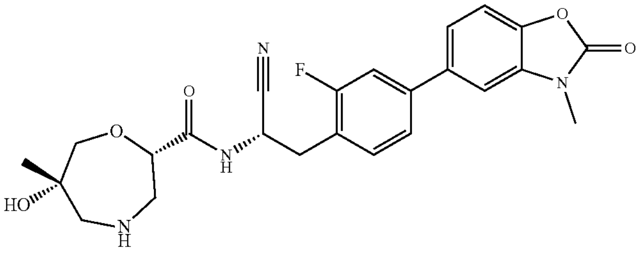 [SMILES: Cn1c(=O)oc2ccc(-c3ccc(C[C@@H](C#N)NC(=O)[C@@H]4CNC[C@](C)(O)CO4)c(F)c3)cc21] | 13.6 ± 2.1 (n = 3) |
| 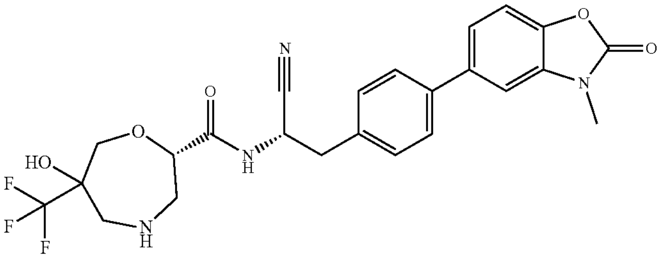 [SMILES: Cn1c(=O)oc2ccc(-c3ccc(C[C@@H](C#N)NC(=O)[C@@H]4CNCC(O)(C(F)(F)F)CO4)cc3)cc21] | 3752.1 |
| 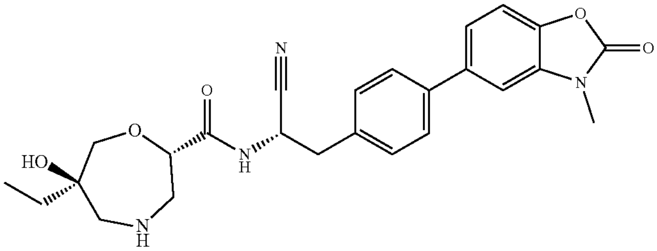 [SMILES: CC[C@@]1(O)CNC[C@@H](C(=O)N[C@H](C#N)Cc2ccc(-c3ccc4oc(=O)n(C)c4c3)cc2)OC1] | 25.1 |
| 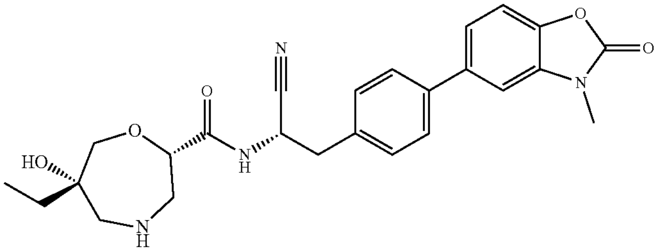 [SMILES: CC[C@]1(O)CNC[C@@H](C(=O)N[C@H](C#N)Cc2ccc(-c3ccc4oc(=O)n(C)c4c3)cc2)OC1] | 2737.1 |
| 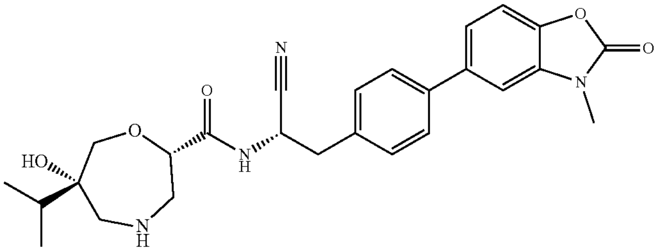 [SMILES: CC(C)[C@]1(O)CNC[C@@H](C(=O)N[C@H](C#N)Cc2ccc(-c3ccc4oc(=O)n(C)c4c3)cc2)OC1] | >5000 |

TABLE 3-continued
| Human DPP1 enzyme IC50 values | | |
|---|---|---|
| No. | | Human DPP1 IC50 (nM) |
| | 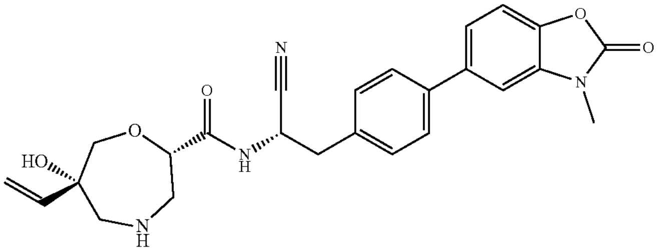 [SMILES: C=C[C@]1(O)CNC[C@@H](C(=O)N[C@H](C#N)Cc2ccc(-c3ccc4oc(=O)n(C)c4c3)cc2)OC1] | 1470 |
| | 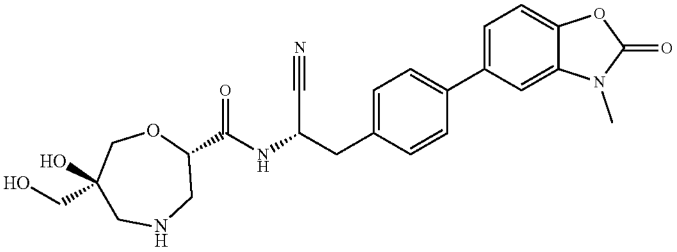 [SMILES: Cn1c(=O)oc2ccc(-c3ccc(C[C@@H](C#N)NC(=O)[C@@H]4CNC[C@](O)(CO)CO4)cc3)cc21] | 780.7 |
| | 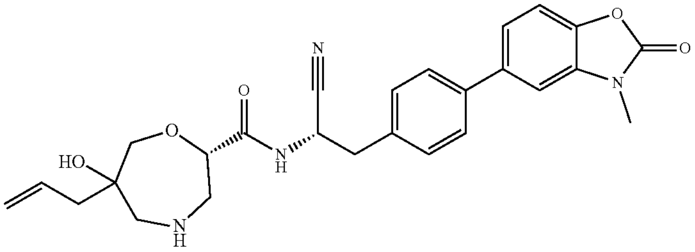 | 1022 |
| | 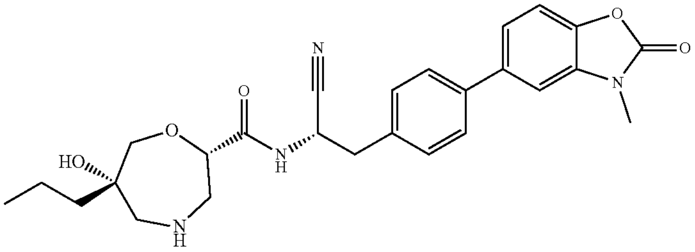 [SMILES: CCC[C@]1(O)CNC[C@@H](C(=O)N[C@H](C#N)Cc2ccc(-c3ccc4oc(=O)n(C)c4c3)cc2)OC1] | >5000 |
| | 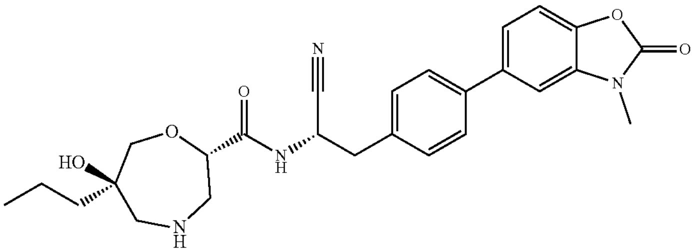 [SMILES: CCC[C@@]1(O)CNC[C@@H](C(=O)N[C@H](C#N)Cc2ccc(-c3ccc4oc(=O)n(C)c4c3)cc2)OC1] | 768.6 |

TABLE 3-continued
| Human DPP1 enzyme IC50 values | |
|---|---|
| No. | Human DPP1 IC50 (nM) |
| 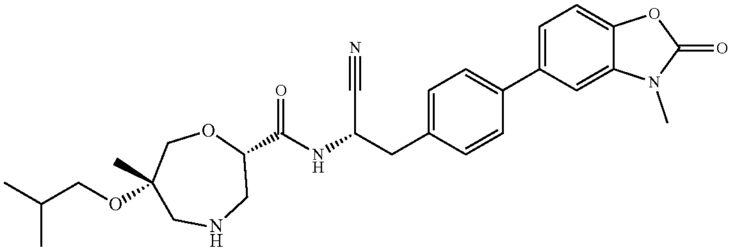 [SMILES: CC(C)CO[C@@]1(C)CNC[C@@H](C(=O)N[C@H](C#N)Cc2ccc(-c3ccc4oc(=O)n(C)c4c3)cc2)OC1] | >5000 |
| 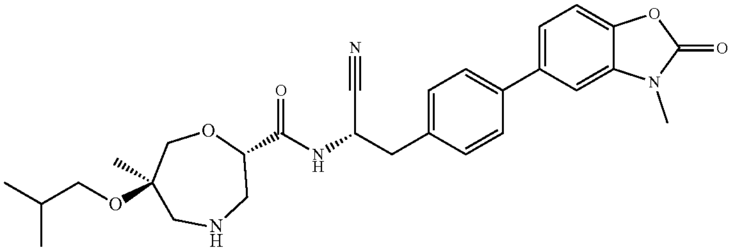 [SMILES: CC(C)CO[C@]1(C)CNC[C@@H](C(=O)N[C@H](C#N)Cc2ccc(-c3ccc4oc(=O)n(C)c4c3)cc2)OC1] | >5000 |
| 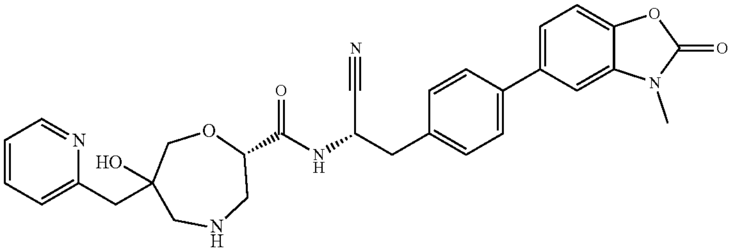 [SMILES: Cn1c(=O)oc2ccc(-c3ccc(C[C@@H](C#N)NC(=O)[C@@H]4CNCC(O)(Cc5ccccn5)CO4)cc3)cc21] | >5000 |
| 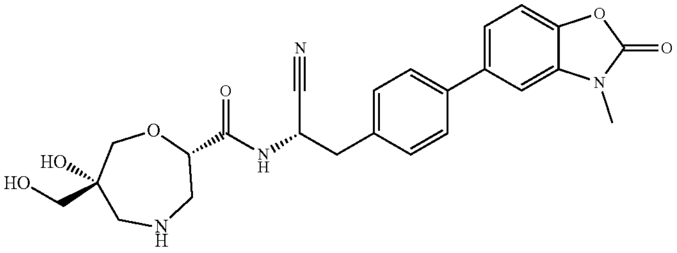 [SMILES: Cn1c(=O)oc2ccc(-c3ccc(C[C@@H](C#N)NC(=O)[C@@H]4CNC[C@@](O)(CO)CO4)cc3)cc21] | 234.2 |
| 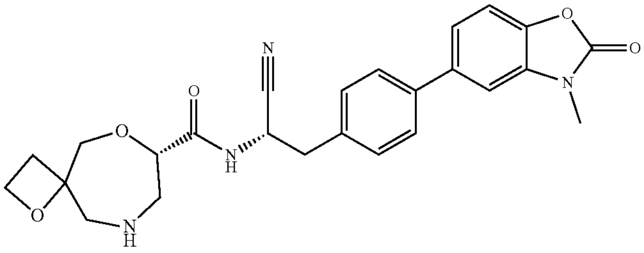 | 4.2 ± 0.8 |
| 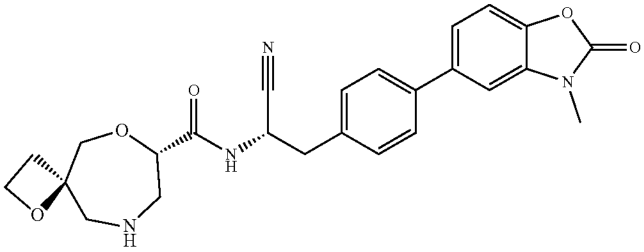 [SMILES: Cn1c(=O)oc2ccc(-c3ccc(C[C@@H](C#N)NC(=O)[C@@H]4CNC[C@]5(CCO5)CO4)cc3)cc21] | 729.1 |

TABLE 3-continued
| Human DPP1 enzyme IC50 values | |
|---|---|
| No. | Human DPP1 IC50 (nM) |
| 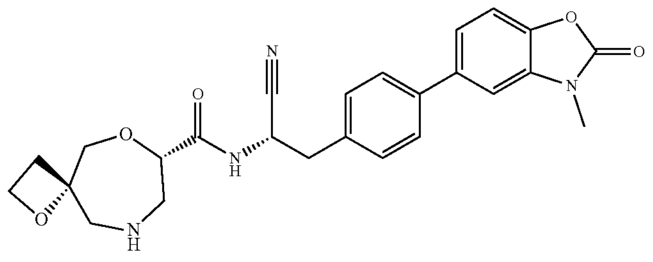 [SMILES: Cn1c(=O)oc2ccc(-c3ccc(C[C@@H](C#N)NC(=O)[C@@H]4CNC[C@@]5(CCO5)CO4)cc3)cc21] | 3.04 ± 0.8 (n = 3) |
| 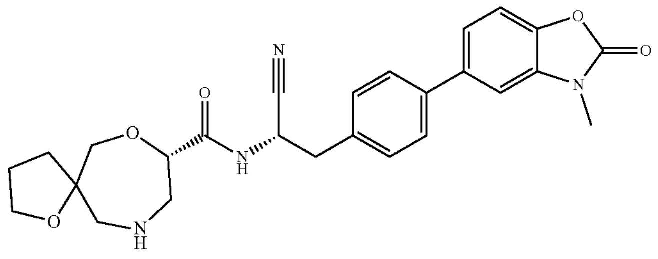 [SMILES: Cn1c(=O)oc2ccc(-c3ccc(C[C@@H](C#N)NC(=O)[C@@H]4CNCC5(CCCO5)CO4)cc3)cc21] | 95.9 ± 4.4 (n = 3) |
| 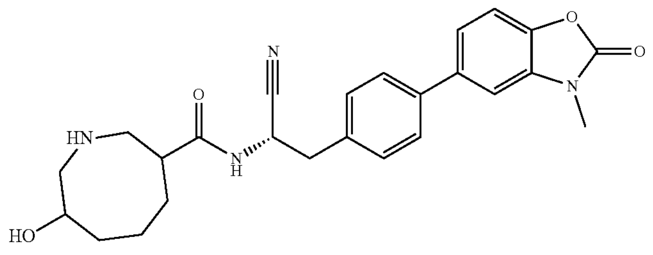 [SMILES: Cn1c(=O)oc2ccc(-c3ccc(C[C@@H](C#N)NC(=O)C4CCCC(O)CNC4)cc3)cc21] | 229.9 |
| 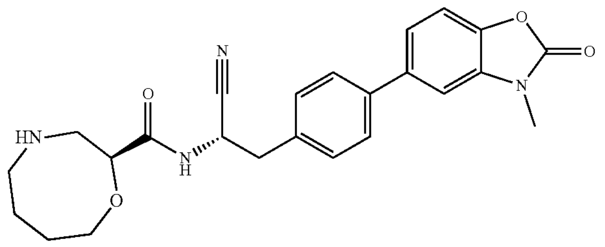 [SMILES: Cn1c(=O)oc2ccc(-c3ccc(C[C@@H](C#N)NC(=O)[C@@H]4CNCCCCO4)cc3)cc21] | 22.3 ± 2 (n = 3) |
| 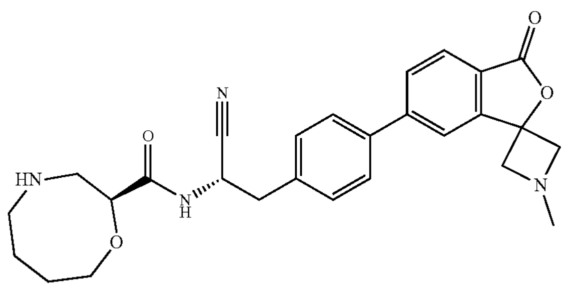 [SMILES: CN1CC2(C1)OC(=O)c1ccc(-c3ccc(C[C@@H](C#N)NC(=O)[C@@H]4CNCCCCO4)cc3)cc12] | 30.9 ± 2 (n = 3) |

TABLE 3-continued
| Human DPP1 enzyme IC50 values | |
|---|---|
| No. | Human DPP1 IC50 (nM) |
| 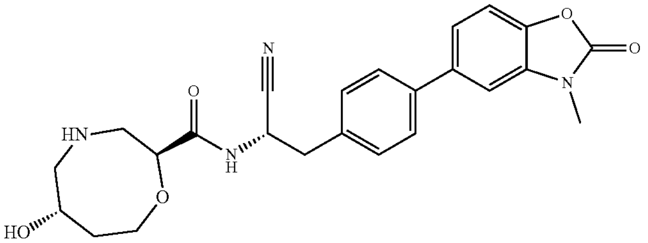 [SMILES: Cn1c(=O)oc2ccc(-c3ccc(C[C@@H](C#N)NC(=O)[C@@H]4CNC[C@@H](O)CCO4)cc3)cc21] | 198.2 |
| 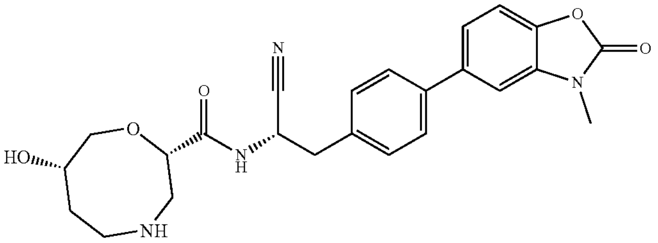 | 67.4 |
| 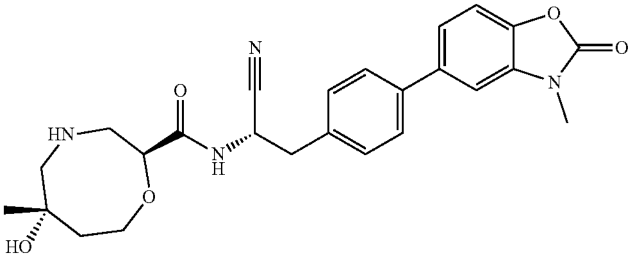 [SMILES: Cn1c(=O)oc2ccc(-c3ccc(C[C@@H](C#N)NC(=O)[C@@H]4CNC[C@@](C)(O)CCO4)cc3)cc21] | 243 |
| 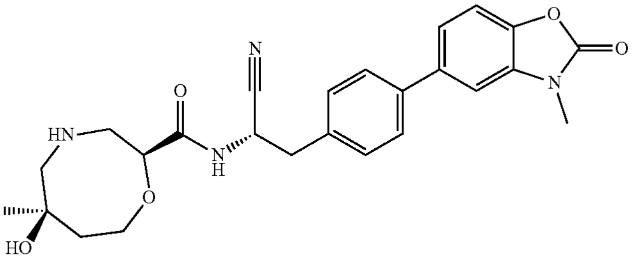 [SMILES: Cn1c(=O)oc2ccc(-c3ccc(C[C@@H](C#N)NC(=O)[C@@H]4CNC[C@](C)(O)CCO4)cc3)cc21] | 23.2 ± 2 (n = 3) |
| 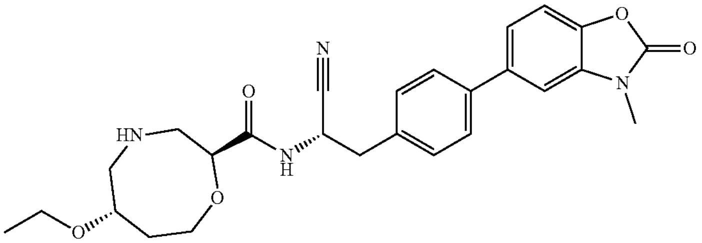 [SMILES: CCO[C@H]1CCO[C@H](C(=O)N[C@H](C#N)Cc2ccc(-c3ccc4oc(=O)n(C)c4c3)cc2)CNC1] | >5000 |
| 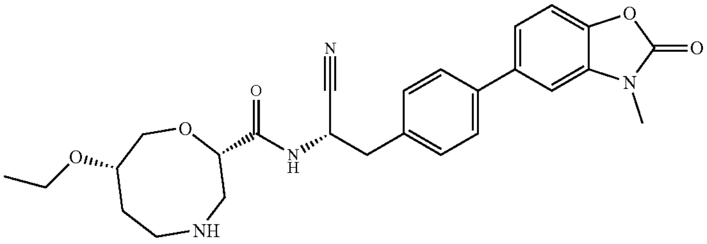 [SMILES: CCO[C@H]1CCNC[C@@H](C(=O)N[C@H](C#N)Cc2ccc(-c3ccc4oc(=O)n(C)c4c3)cc2)OC1] | 457 |

TABLE 3-continued
| Human DPP1 enzyme IC50 values | |
|---|---|
| No. | Human DPP1 IC50 (nM) |
| 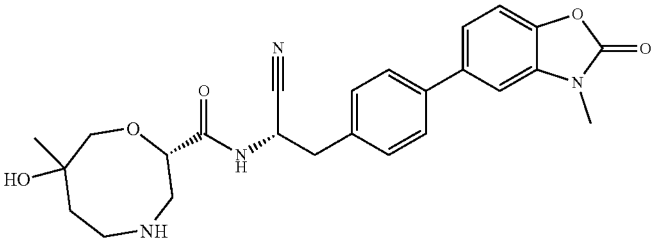 [SMILES: Cn1c(=O)oc2ccc(-c3ccc(C[C@@H](C#N)NC(=O)[C@@H]4CNCCC(C)(O)CO4)cc3)cc21] | 2240 |
| 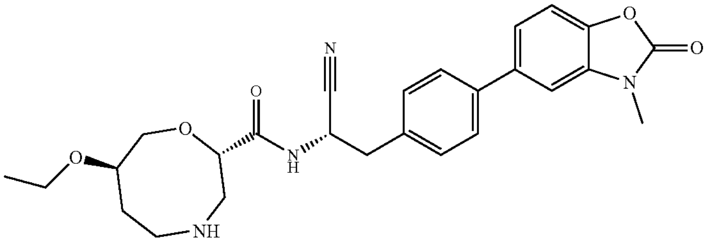 [SMILES: CCO[C@@H]1CCNC[C@@H](C(=O)N[C@H](C#N)Cc2ccc(-c3ccc4oc(=O)n(C)c4c3)cc2)OC1] | 4.91 ± 0.9 (n = 3) |
| 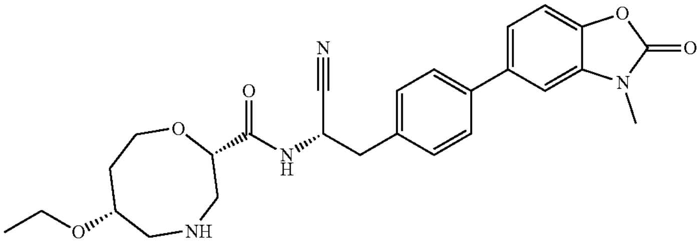 [SMILES: CCO[C@@H]1CCO[C@H](C(=O)N[C@H](C#N)Cc2ccc(-c3ccc4oc(=O)n(C)c4c3)cc2)CNC1] | 27 |
| 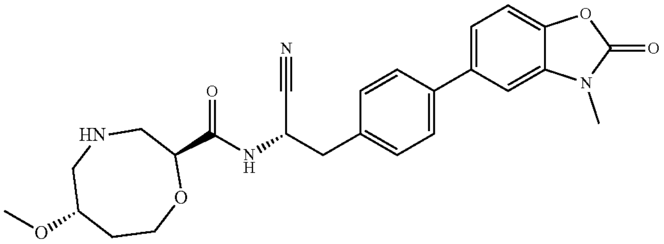 [SMILES: CO[C@H]1CCO[C@H](C(=O)N[C@H](C#N)Cc2ccc(-c3ccc4oc(=O)n(C)c4c3)cc2)CNC1] | 1141.3 |
| 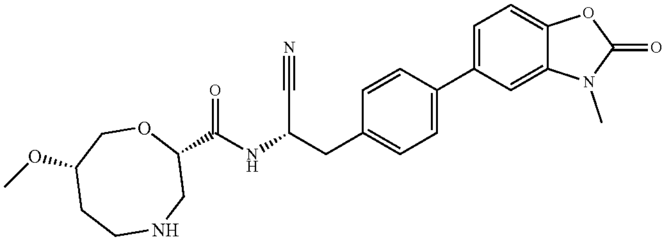 [SMILES: CO[C@H]1CCNC[C@@H](C(=O)N[C@H](C#N)Cc2ccc(-c3ccc4oc(=O)n(C)c4c3)cc2)OC1] | 74.7 |
| 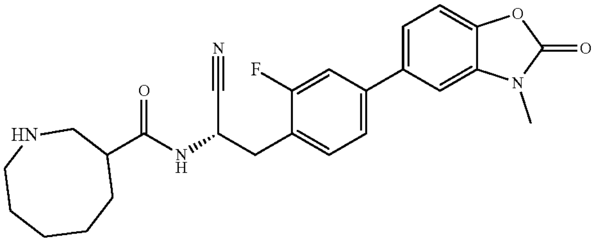 [SMILES: Cn1c(=O)oc2ccc(-c3ccc(C[C@@H](C#N)NC(=O)C4CCCCCNC4)c(F)c3)cc21] | 15.8 ± 6.8 (n = 3) |

TABLE 3-continued
Human DPP1 enzyme IC50 values
| No. | | Human DPP1 IC50 (nM) |
| --- | --- | --- |
| | 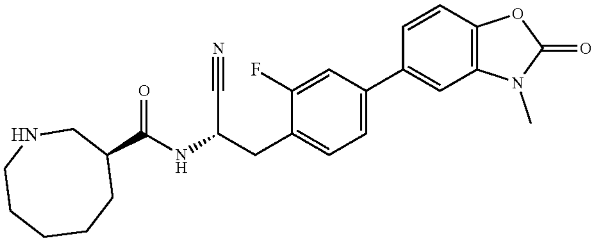 [SMILES: Cn1c(=O)oc2ccc(-c3ccc(C[C@@H](C#N)NC(=O)[C@H]4CCCCCNC4)c(F)c3)cc21] | 139.7 ± 59.3 (n = 3) |
| | 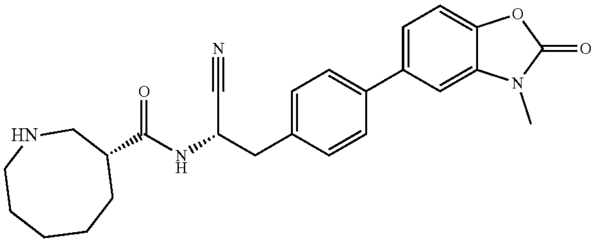 | 602.8 |
| | 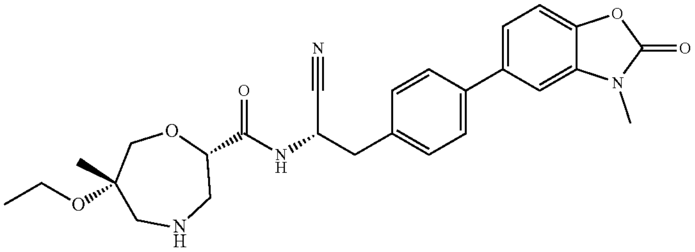 [SMILES: CCO[C@@]1(C)CNC[C@@H](C(=O)N[C@H](C#N)Cc2ccc(-c3ccc4oc(=O)n(C)c4c3)cc2)OC1] | >5000 |
| | 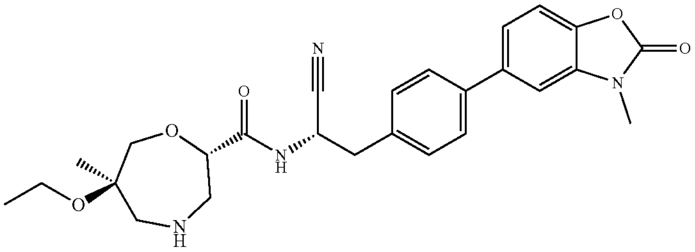 [SMILES: CCO[C@]1(C)CNC[C@@H](C(=O)N[C@H](C#N)Cc2ccc(-c3ccc4oc(=O)n(C)c4c3)cc2)OC1] | 1675.2 |
| | 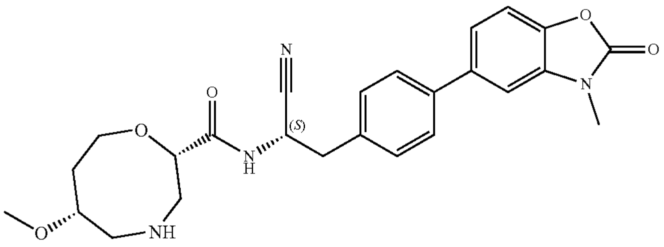 | 6.82 ± 0.5 (n = 3) |
| | 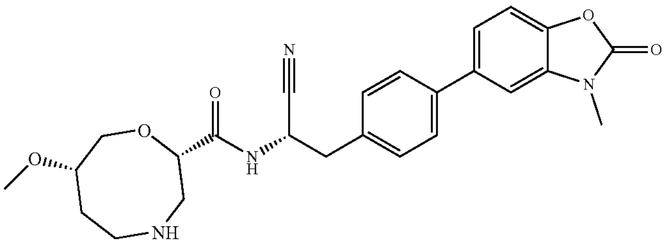 | 17.4 ± 6 (n = 3) |

The invention claimed is:

1. A compound of formula (I)

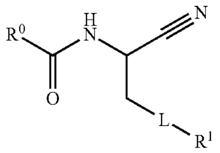

(I)

or a pharmaceutically acceptable salt or deuterated form thereof, wherein:

$R^0$ is

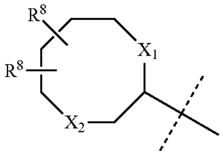

,

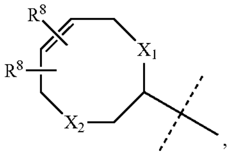

,

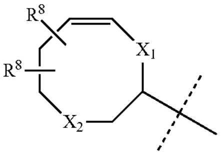

, or

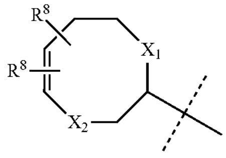

;

$X_1$ and $X_2$ are independently O, S, NH, $N(C_{1-6}$ alkyl), or $CR^{12}R^{13}$, wherein at least one of $X_1$ and $X_2$ are not $CR^{12}R^{13}$;

L is aryl, heterocyclyl, heteroaryl, or

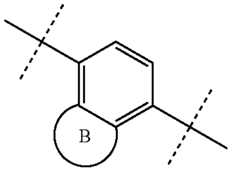

;

wherein L is independently substituted by 0-4 $R^{10}$ and wherein ring B is a carbocycle, or a heterocycle;

$R^1$ is

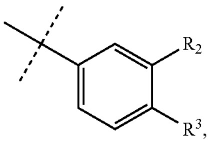

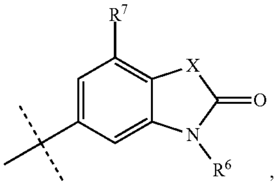

,

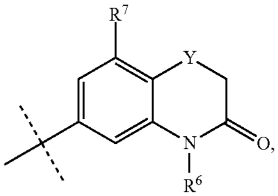

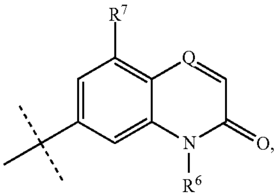

-continued

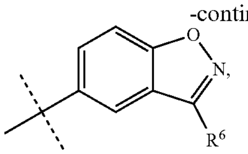

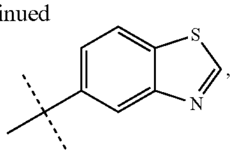

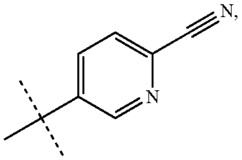

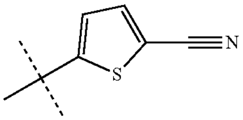

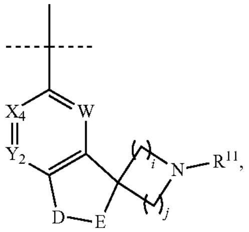

or

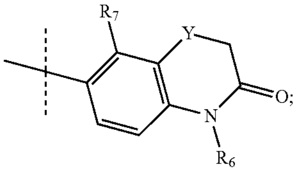

$R^2$ is H, F, Cl, Br, $OSO_2C_{1-6}$ alkyl, or $C_{1-6}$ alkyl;

$R^3$ is H, F, Cl, Br, CN, $C_{1-6}$haloalkyl, $SO_2C_{1-6}$ alkyl, $CONH_2$, or $SO_2NR^4R^5$, wherein $R^4$ and $R^5$ together with the nitrogen atom to which they are attached form a heterocyclyl;

X is O, S, CHF, or $CF_2$;

Y is O, S, or $CH_2$;

Q is CH or N;

$R^6$ is $C_{1-6}$ alkyl optionally substituted by 1, 2 or 3 F, or optionally substituted by OH, $OC_{1-6}$ alkyl, $N(C_{1-6}$ alkyl$)_2$, $N(C_{1-6}$ alkyl)($C_{1-6}$alkylene-O—$C_{1-6}$ alkyl), cycloalkyl, or heterocyclyl;

$R^7$ is H, F, Cl, Br, or $C_{1-6}$ alkyl;

each $R^8$ and $R^{12}$ are independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$alkylene-carbocyclyl, $C_{1-6}$alkylene-heteroaryl, halogenated $C_{1-6}$ alkyl, halogenated $C_{1-6}$alkoxy, heteroaryl, or carbocyclyl;

each $R^{13}$ is independently H, F, Cl, Br, I, or $C_1$-$C_6$ alkyl;

each $R^{10}$ is independently oxo, halogen, $C_{1-6}$ alkyl, $C_{1-6}$alkoxy, S-$C_{1-6}$ alkyl, $C_{2-6}$alkenyl, $C_{2-6}$alkynyl, $C_{3-6}$cycloalkyl, cyano, hydroxy, $NH_2$, —NH—$C_{1-6}$ alkyl, $N(C_{1-6}$ alkyl$)_2$, COOH, $COC_{1-6}$ alkyl, $COOC_{1-6}$ alkyl, $CON_{1-6}$ alkyl, $CON(C_{1-6}$ alkyl$)_2$, $NHCOC_{1-6}$ alkyl, or heterocycle; wherein each alkyl, alkoxy, alkenyl, alkynyl, cycloalkyl, and heterocycle are independently optionally substituted with 1-3 substituents selected from halogen, cyano, hydroxy, $NH_2$, and COOH;

W, $X_4$, and $Y_2$ are each independently CH or N, provided that a maximum of one of W, $X_4$, and $Y_2$ can be N;

D-E is N(H)—C(O), $N(C_{1-6}$ alkyl)-C(O), $CH_2CH_2$, C(O)—O, or $CH_2$—O;

$R^{11}$ is H, $C_{1-6}$ alkyl, alkylene-O-alkyl, or heterocyclyl; and i and j are each independently 1, 2 or 3, provided that the sum of i+j is 2, 3, or 4.

2. The compound of claim 1, wherein the compound is of Formula (II):

(II)

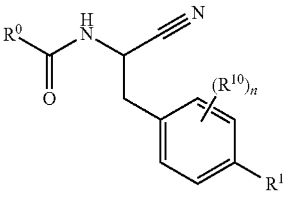

or a pharmaceutically acceptable salt or deuterated form thereof, wherein n is 0, 1, or 2, and $R^{10}$ is halogen.

3. The compound of claim 2, or a pharmaceutically acceptable salt thereof or deuterated form thereof, wherein the halogen is F.

4. The compound of claim 2, or a pharmaceutically acceptable salt thereof or deuterated form thereof, wherein n is 0 or 1.

5. The compound of claim 1, or a pharmaceutically acceptable salt or deuterated form thereof, wherein, $R^1$ is

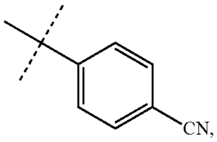

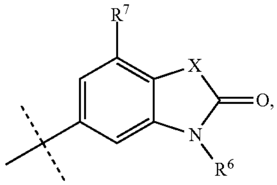

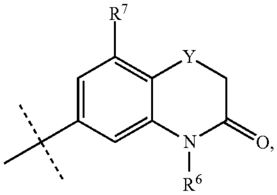

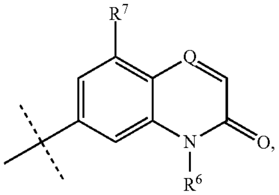

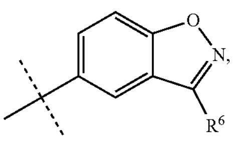

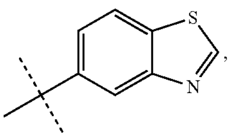

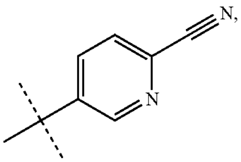

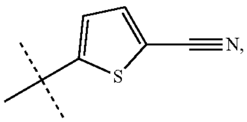

-continued

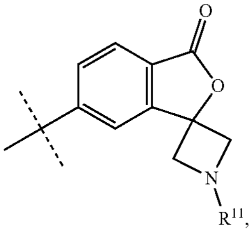

or

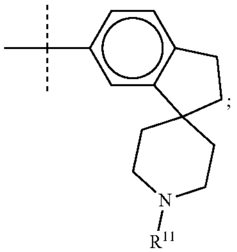

X is O, S, or $CF_2$;

Y is O or S;

Q is CH or N;

$R^6$ is $C_{1-3}$ alkyl, wherein said $C_{1-3}$ alkyl is optionally substituted by 1, 2, or 3 F, OH, $OC_{1-3}$ alkyl, $N(C_{1-3}$ alkyl$)_2$, $N(C_{1-3}$ alkyl$)(C_{1-3}$alkylene-O—$C_{1-3}$ alkyl), cyclopropyl, or tetrahydropyran;

$R^7$ is H, F, $C_1$, or $CH_3$; and $R^{11}$ is H, $C_{1-6}$ alkyl, alkylene-O-alkyl, or heterocyclyl.

6. The compound of claim 1, or a pharmaceutically acceptable salt or deuterated form thereof, wherein, $R^1$ is

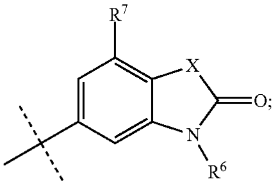

X is O;

$R^6$ is $C_{1-3}$ alkyl; and $R^7$ is H.

7. The compound of claim 2, or a pharmaceutically acceptable salt or deuterated form thereof, wherein $R^6$ is methyl.

8. The compound of claim 2, or a pharmaceutically acceptable salt or deuterated form thereof, wherein $R^6$ is ethyl.

9. The compound of claim 2, or a pharmaceutically acceptable salt or deuterated form thereof, wherein $R^1$ is

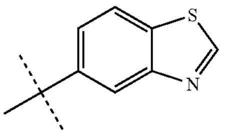

,

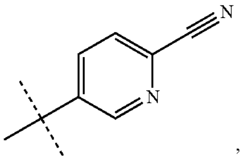

,

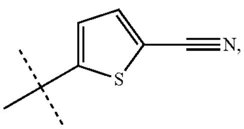

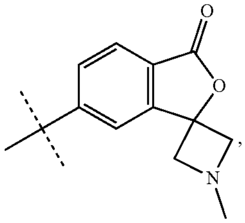

, or

-continued

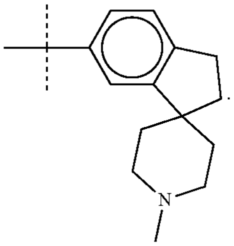

10. The compound of claim 1, wherein the compound is of Formula (III):

(III)

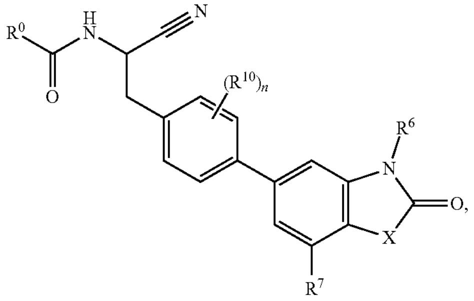

or a pharmaceutically acceptable salt or deuterated form thereof, wherein n is 0 or 1.

11. The compound of claim 1, wherein the compound is of Formula (III-B):

(III-B)

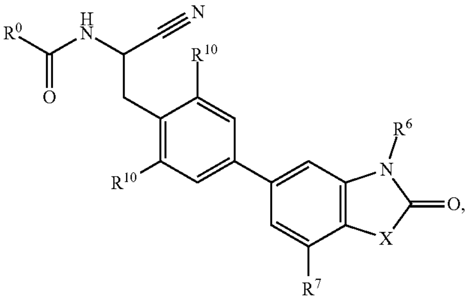

or a pharmaceutically acceptable salt or deuterated form thereof, wherein $R^{10}$ is —F.

12. The compound of claim 11, or a pharmaceutically acceptable salt or deuterated form thereof, wherein X is O.

13. The compound of claim 2, or a pharmaceutically acceptable salt or deuterated form thereof, wherein $R^0$ is

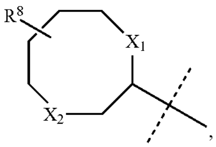

,

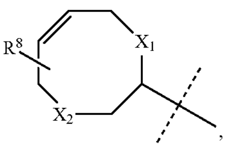

,

-continued

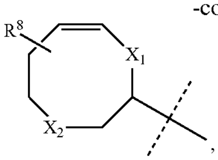

, or

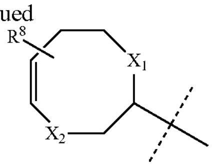

.

14. The compound of claim 13, or a pharmaceutically acceptable salt or deuterated form thereof, wherein $R^0$ is

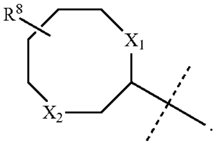

15. The compound of claim 14, or a pharmaceutically acceptable salt or deuterated form thereof, wherein $R^0$ is

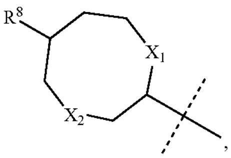

,

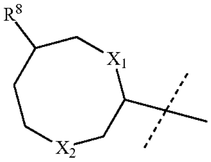

, or

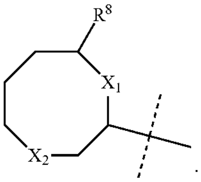

16. The compound of claim 15, or a pharmaceutically acceptable salt or deuterated form thereof, wherein $X_1$ is O and $X_2$ is NH.

17. The compound of claim 15, or a pharmaceutically acceptable salt or deuterated form thereof, wherein $X_1$ is $CH_2$ and $X_2$ is NH.

18. The compound of claim 15, or a pharmaceutically acceptable salt or deuterated form thereof, wherein one $R^8$ is OH, unsubstituted $C_{1-6}$alkoxy, or O-cycloalkyl.

19. The compound of claim 2, or a pharmaceutically acceptable salt or deuterated form thereof, wherein each occurrence of $R^8$ is methoxy, ethoxy, or OH.

20. The compound of claim 15, or a pharmaceutically acceptable salt or deuterated form thereof, wherein $R^8$ is H.

21. The compound of claim 1, or a pharmaceutically acceptable salt or deuterated form thereof, wherein $R^0$ is

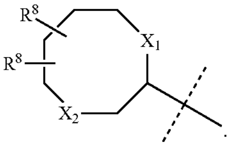

22. The compound of claim 21, or a pharmaceutically acceptable salt or deuterated form thereof, wherein:

$R^0$ is

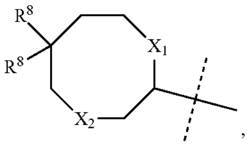

,

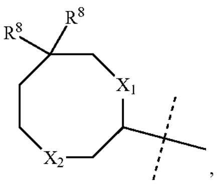

, or

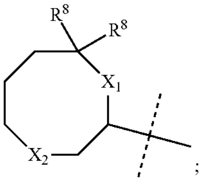

;

$X_1$ is O and $X_2$ is NH, or $X_1$ is $CH_2$ and $X_2$ is NH; and each $R^8$ is independently H, OH, halogen, $NH_2$, COOH, $C_{1-6}$ alkyl, $C_{1-6}$ alkyl-OH, $C_{2-6}$alkenyl, $C_{1-6}$alkoxy, O-cycloalkyl, cycloalkyl, $C_{1-6}$ alkylene-heteroaryl, halogenated $C_{1-6}$ alkyl, or halogenated $C_{1-6}$ alkoxy, provided that one $R^8$ is not H.

23. The compound of claim 13, or a pharmaceutically acceptable salt or deuterated form thereof, wherein $R^0$ is:

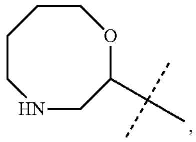

,

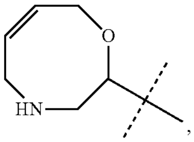

,

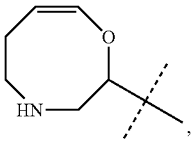

, or

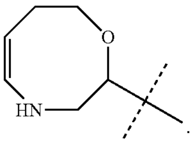

.

24. A compound having the structure:

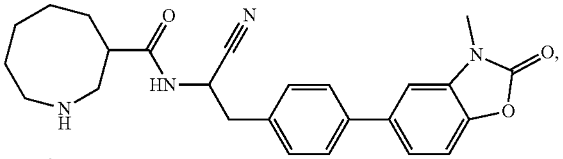

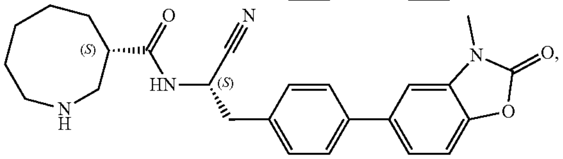

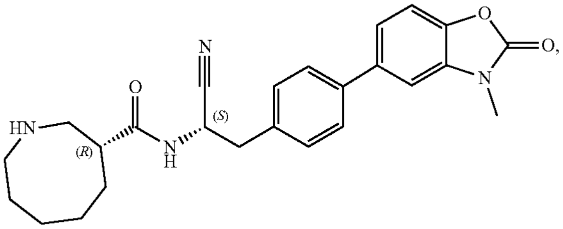

-continued

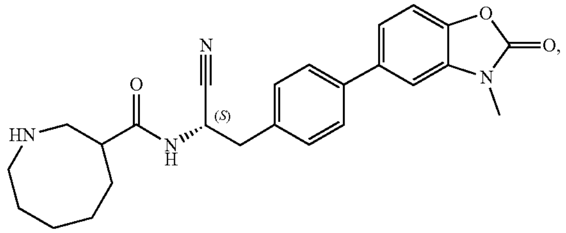

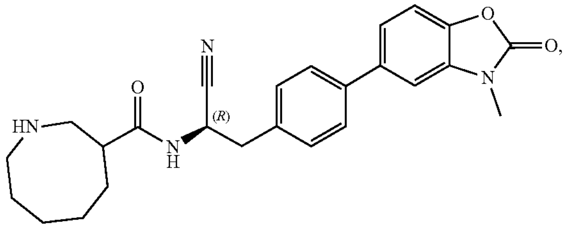

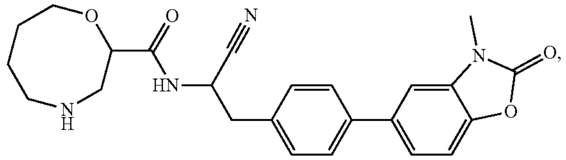

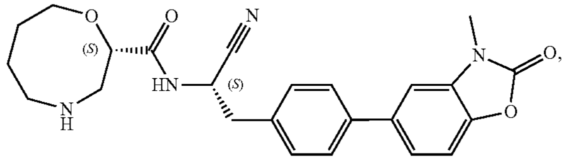

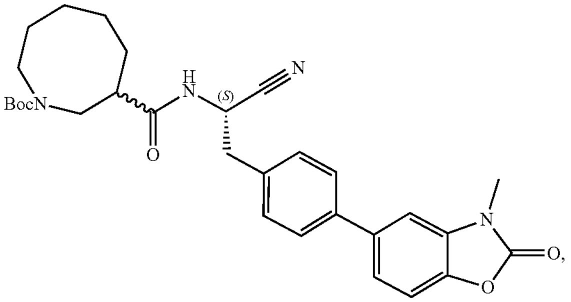

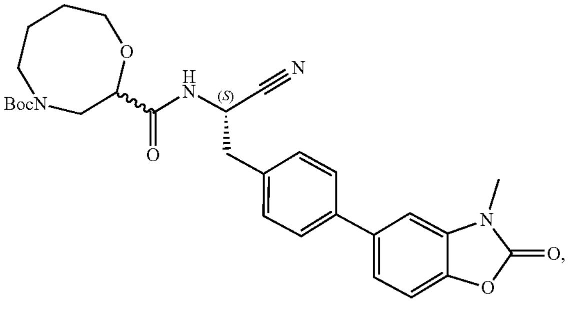

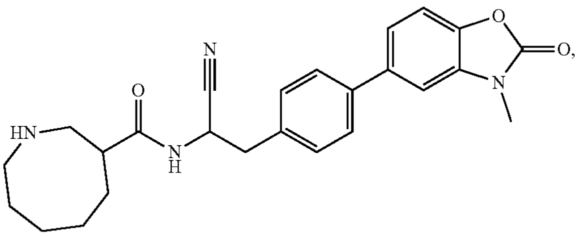

-continued
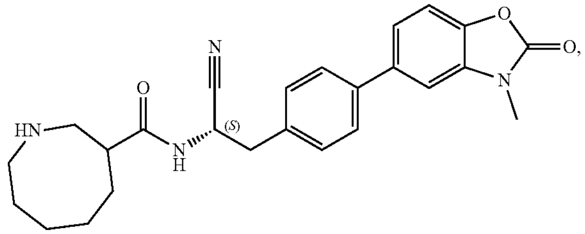,
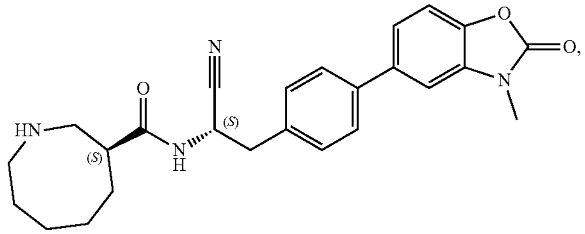,
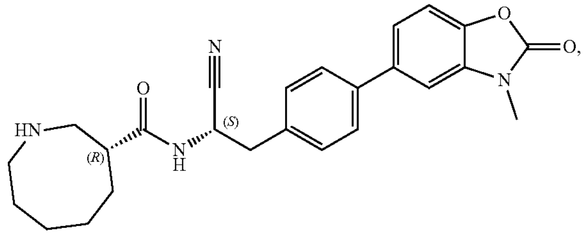,
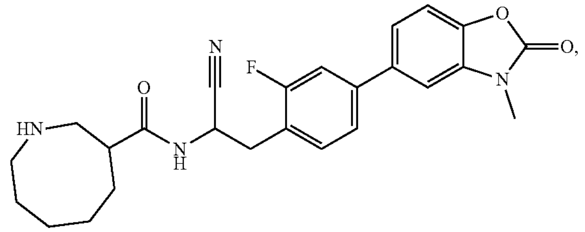,
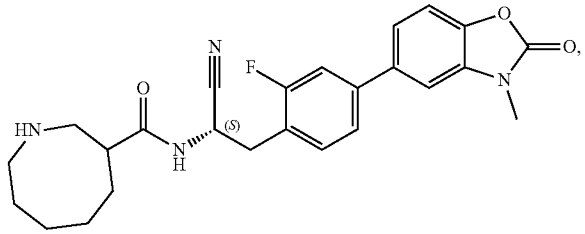,
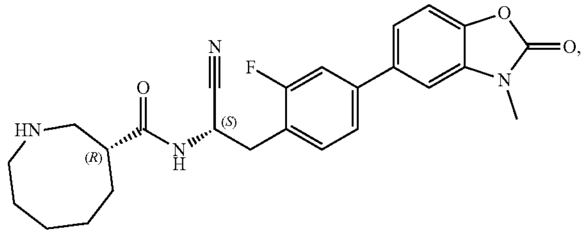,
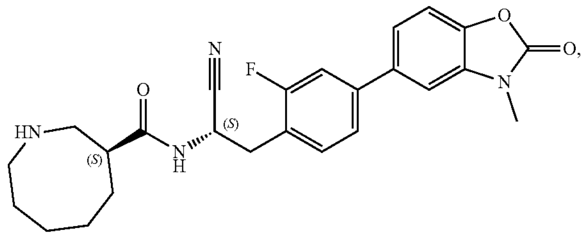,
-continued
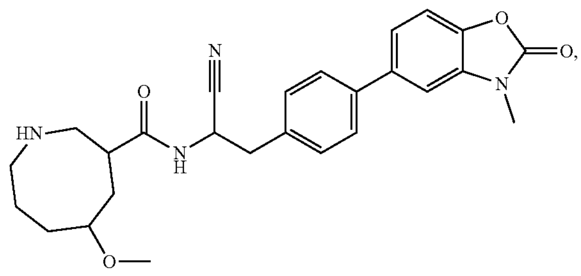,
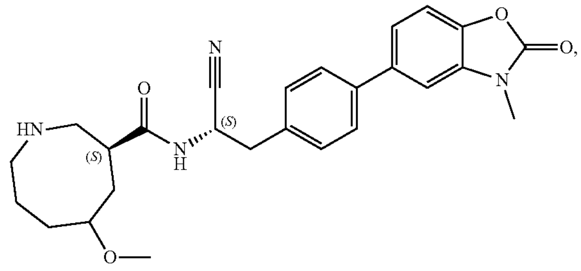,
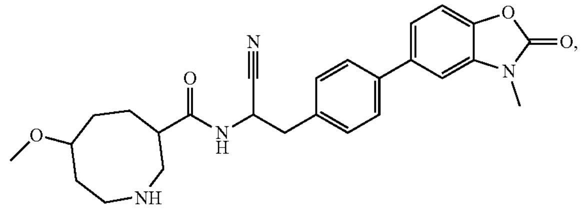,
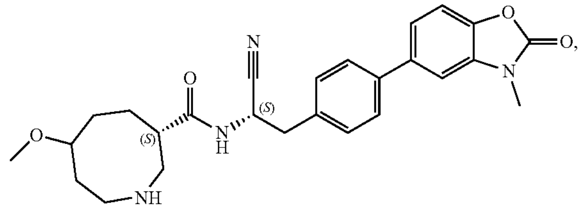,
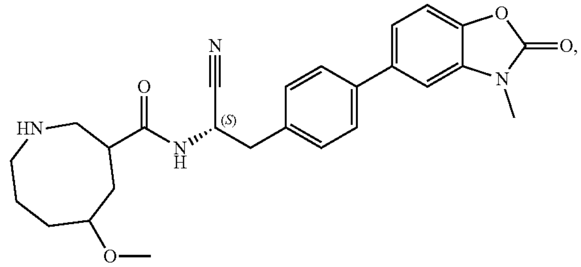,
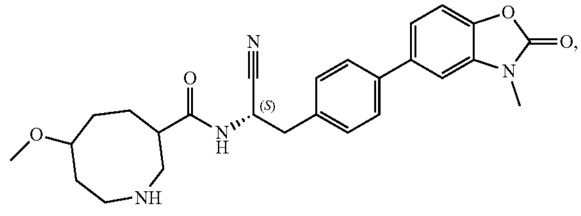,
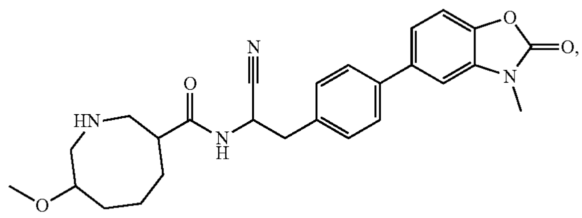, -continued
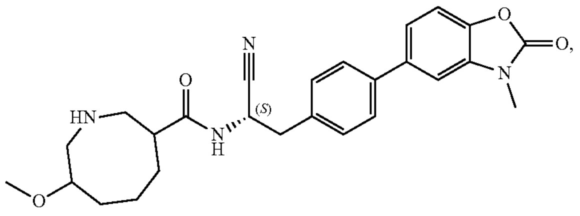
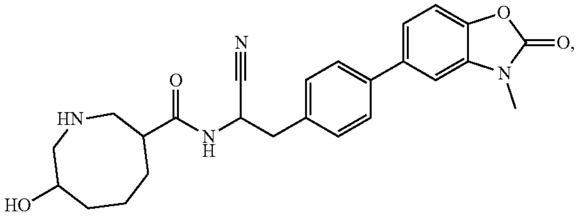
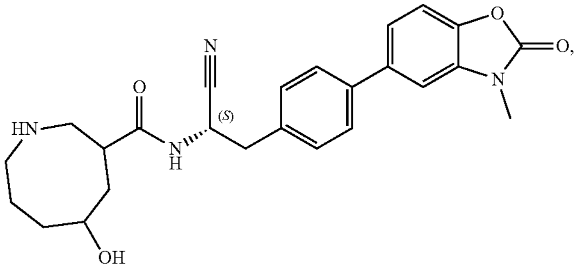
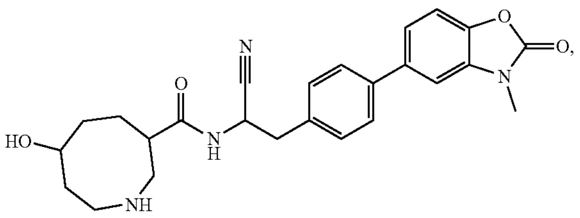
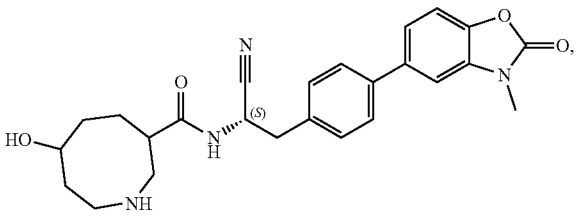
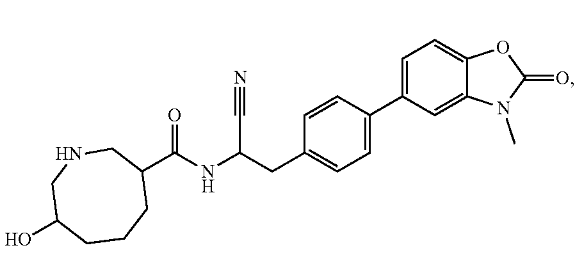
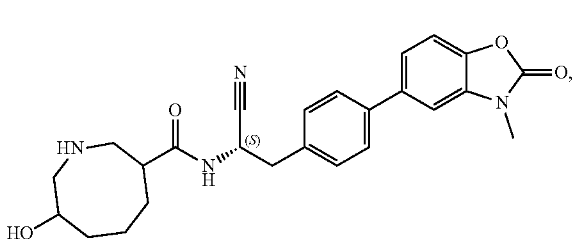
-continued
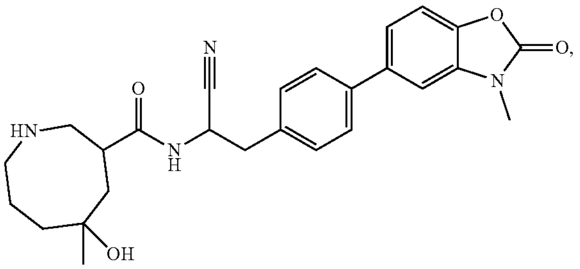
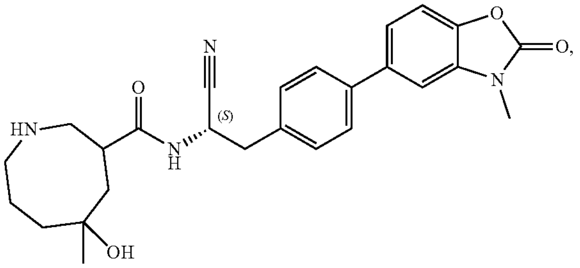
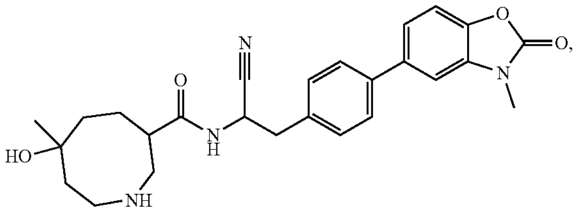
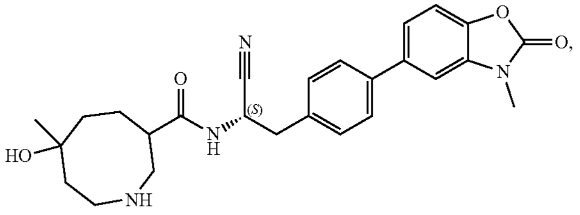
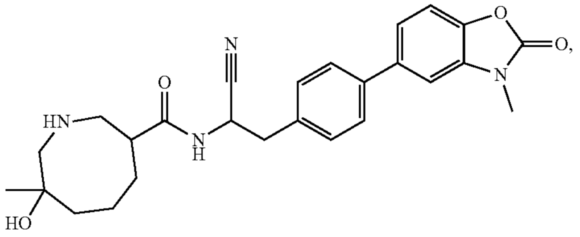
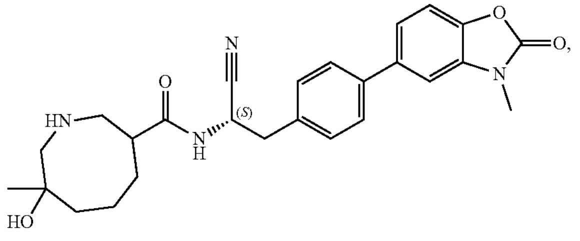
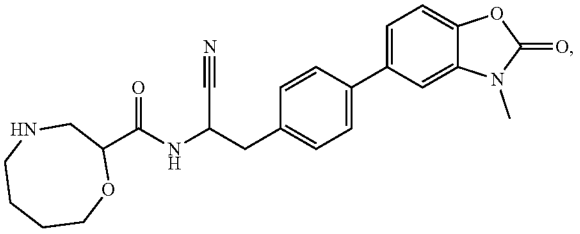

-continued
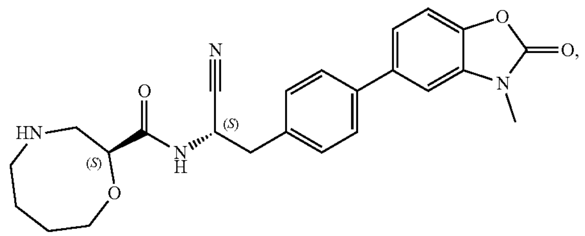
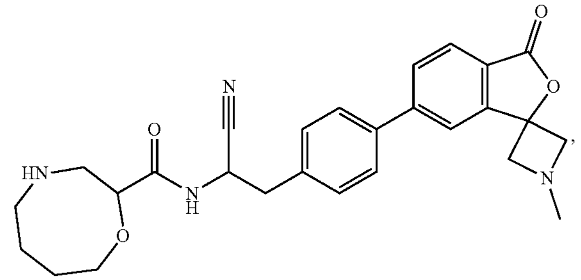
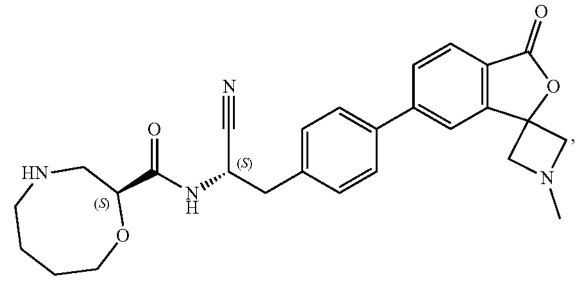
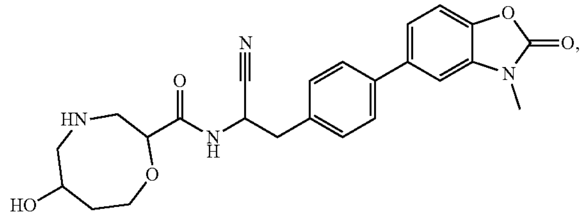
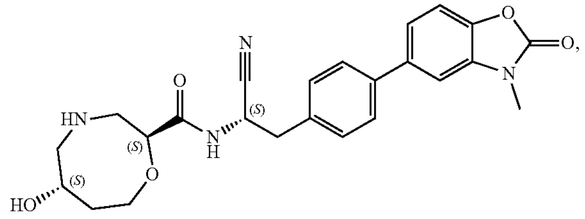
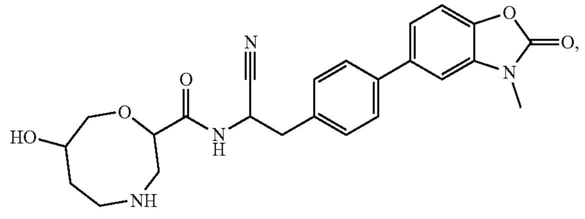
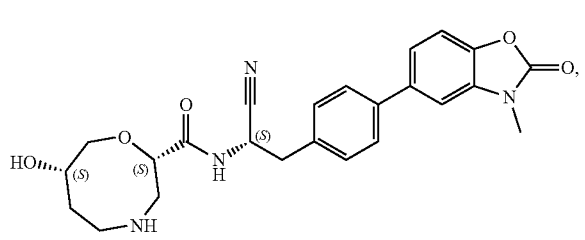
-continued
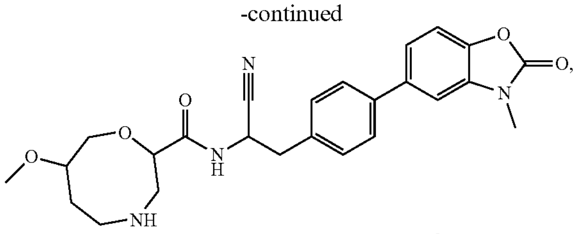
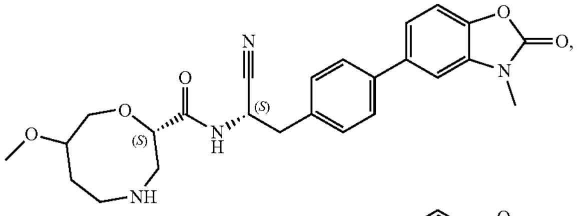
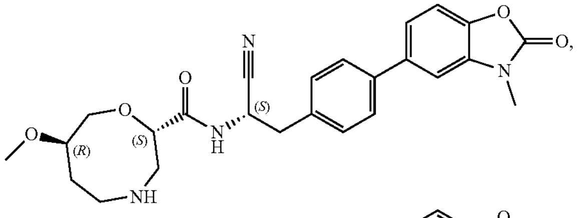
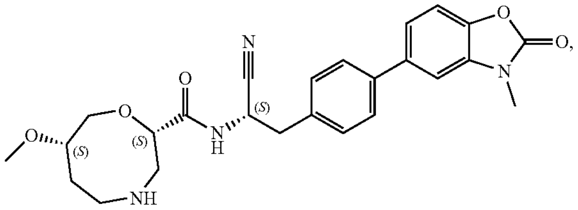
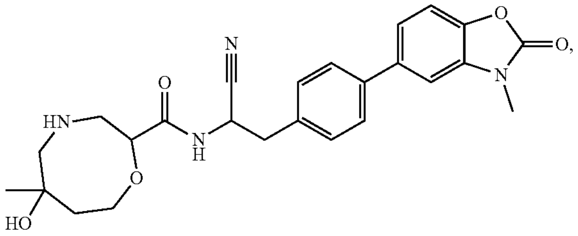
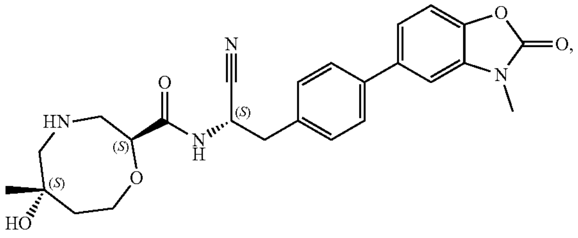
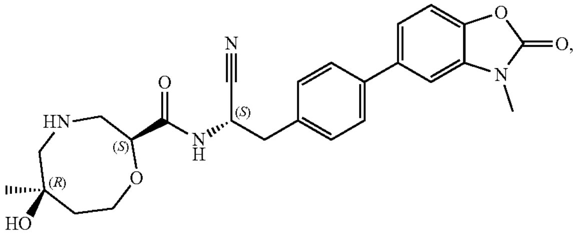
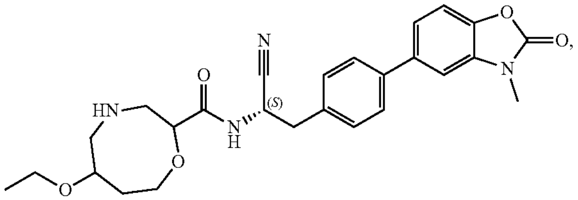

-continued
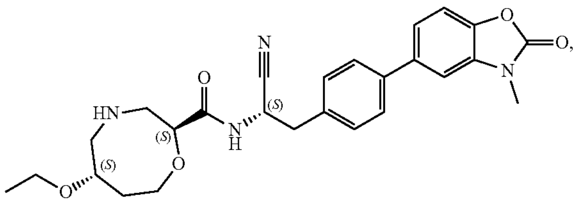
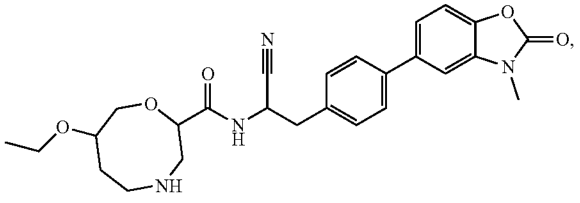
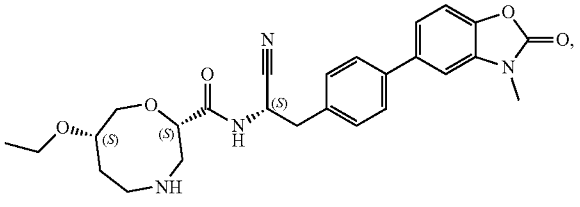
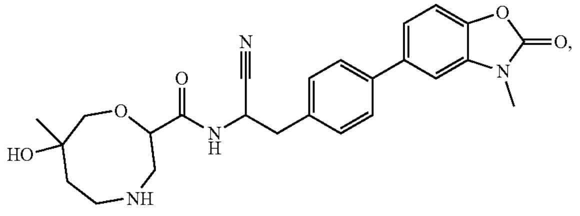
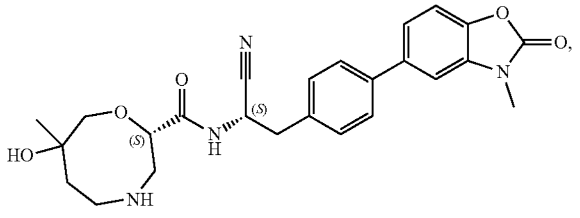
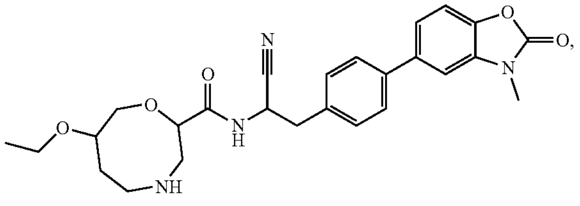
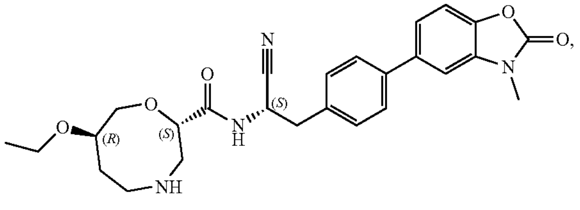
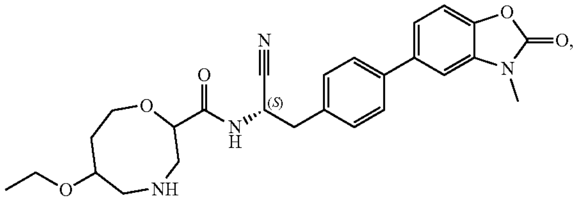
-continued
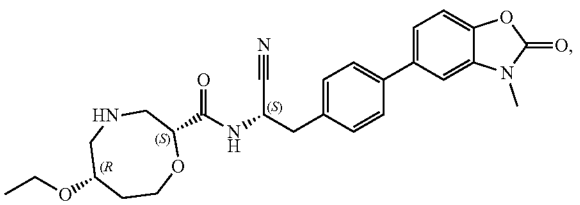
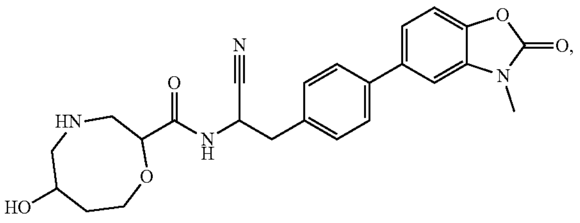
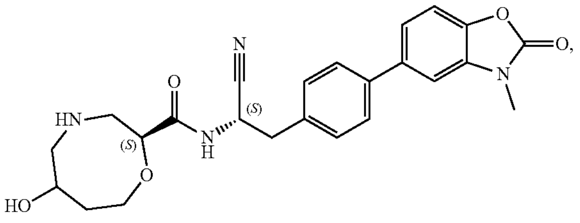
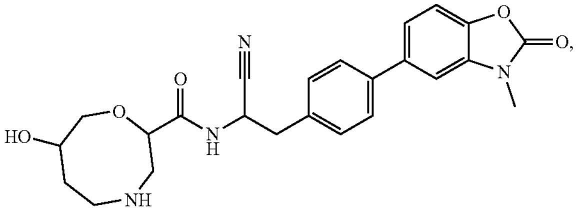
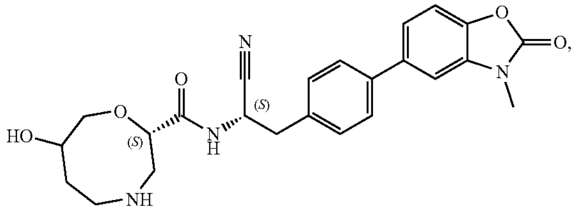
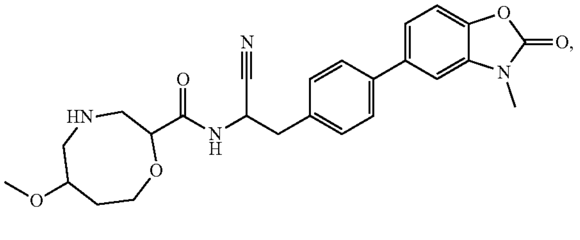
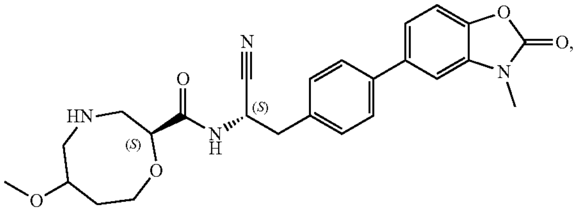

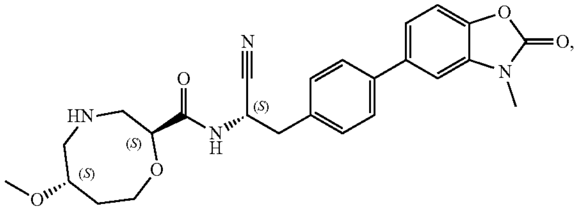
,
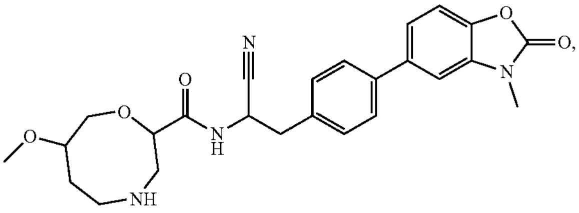
,
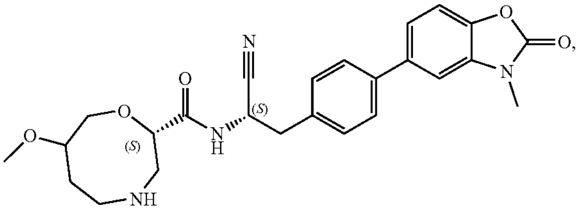
,
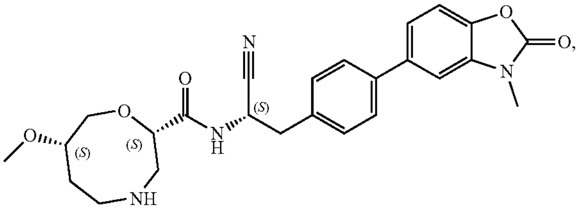
,
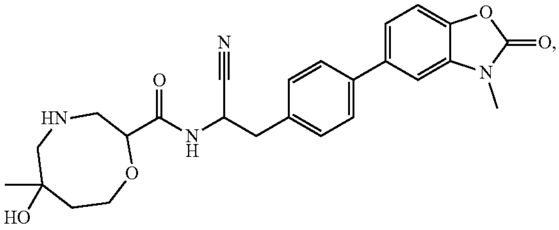
,
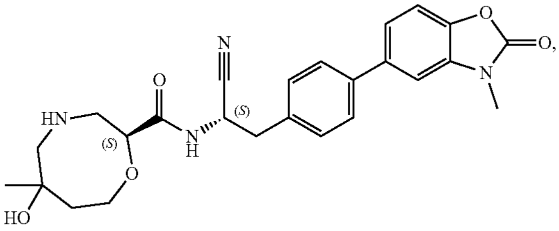
,
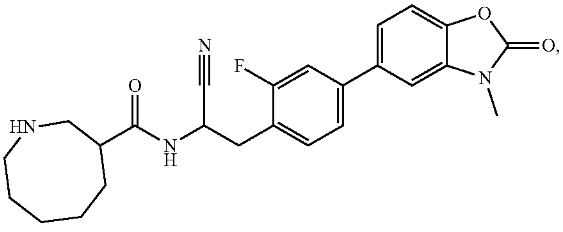
,
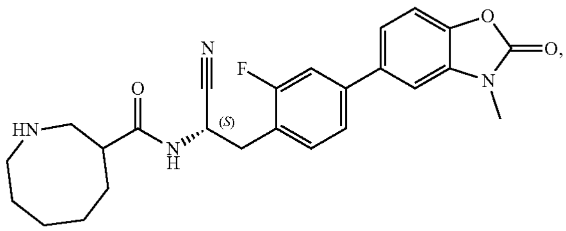
,
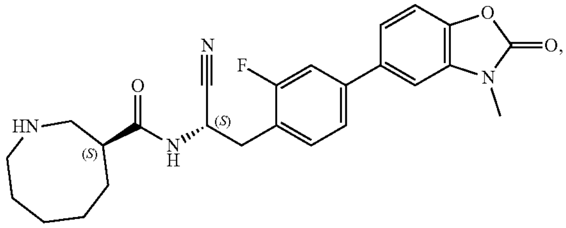
,
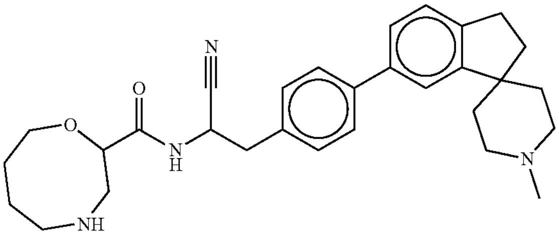
,
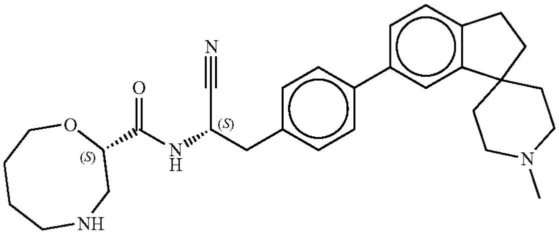
,
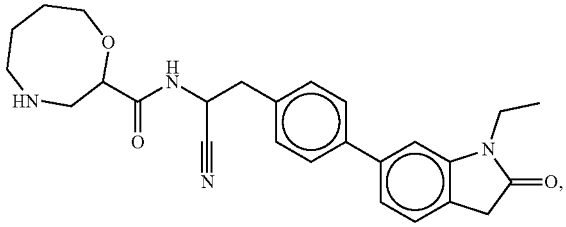
,
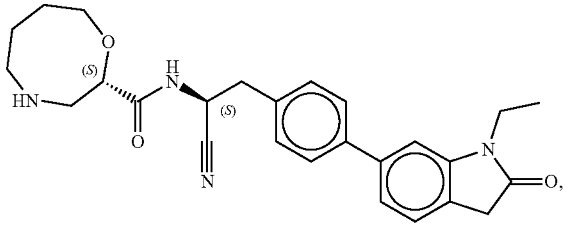
,
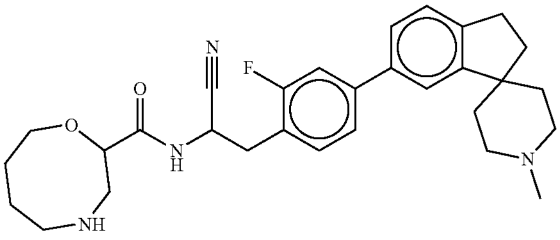
, -continued
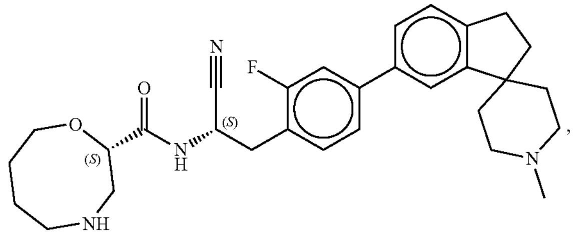
,
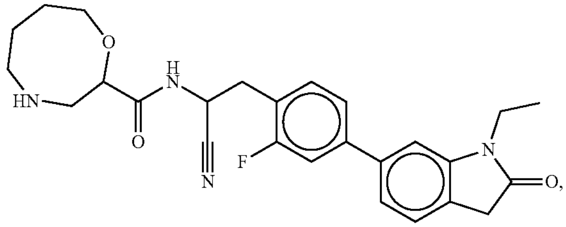
,
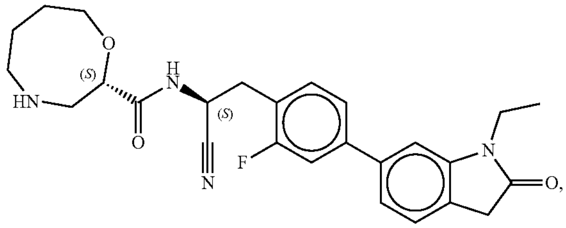
,
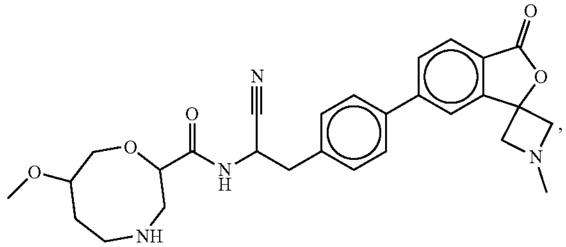
,
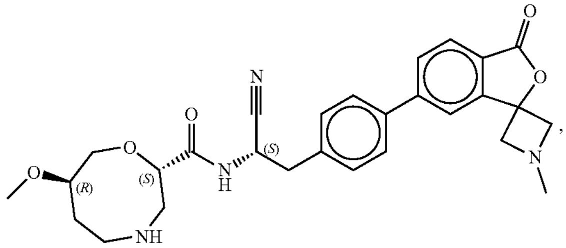
,
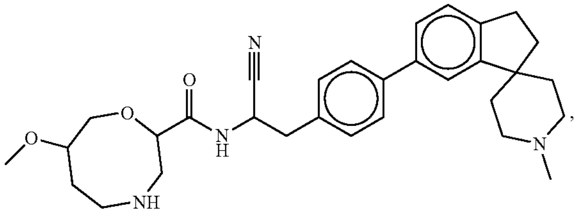
,
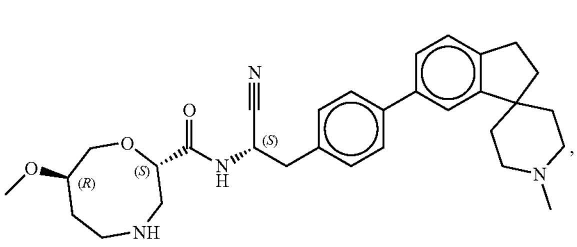
,
-continued
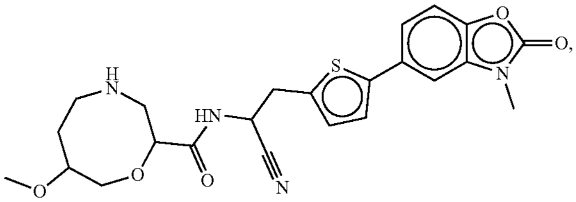
,
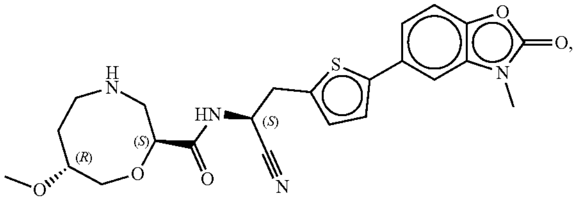
,
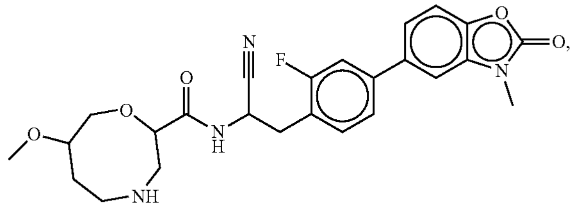
,
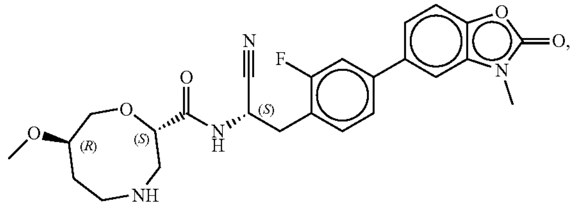
,
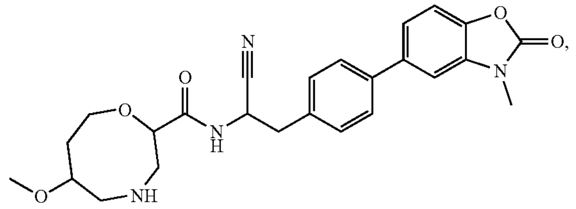
,
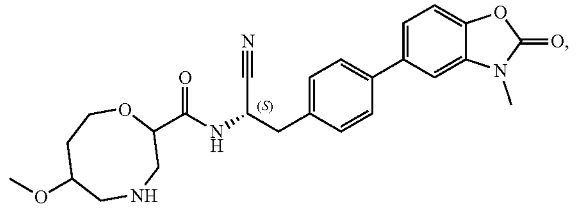
,
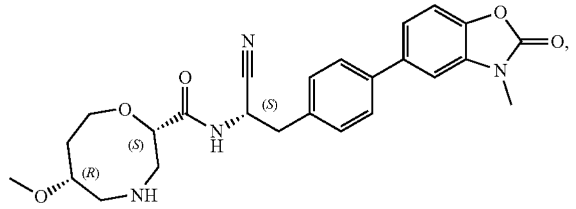
,
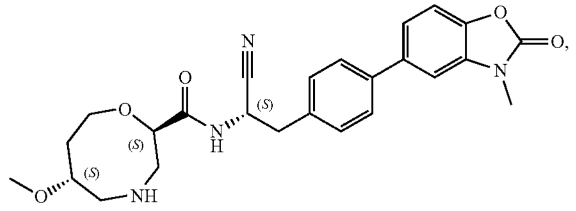
, -continued
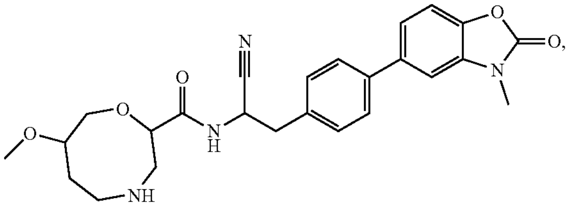
,
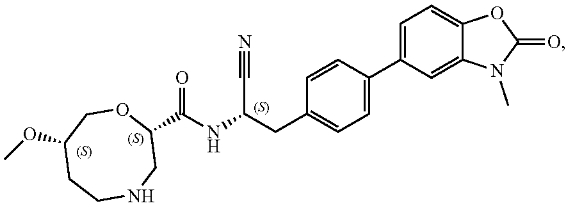
,
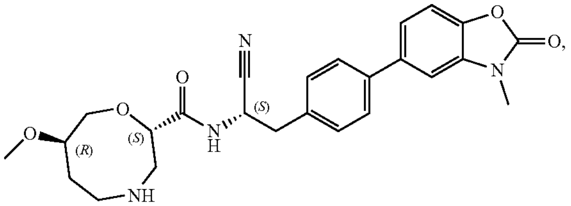
,
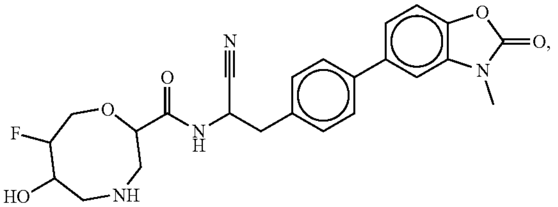
,
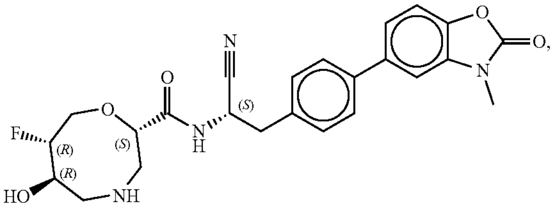
,
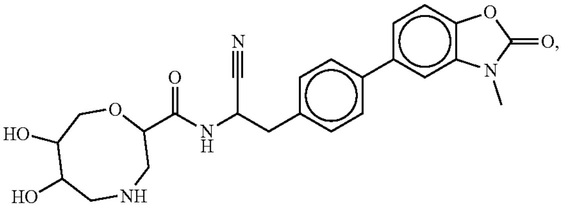
,
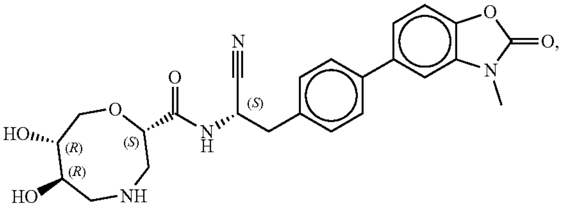
,
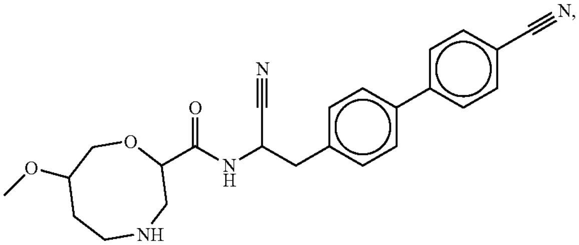
,
-continued
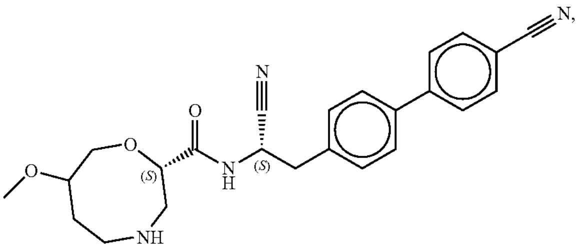
,
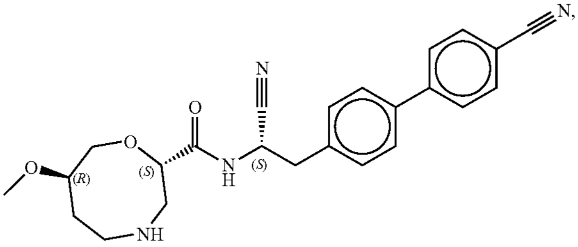
,
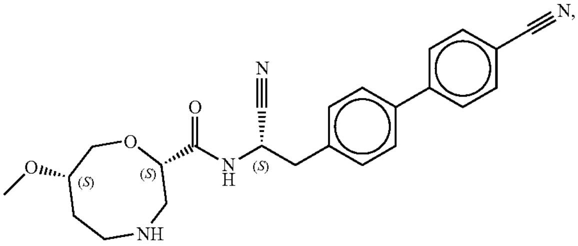
,
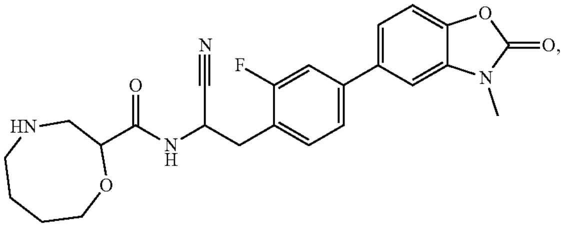
,
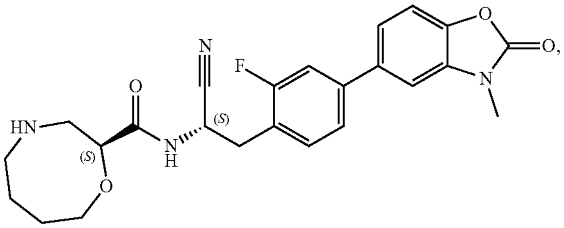
,
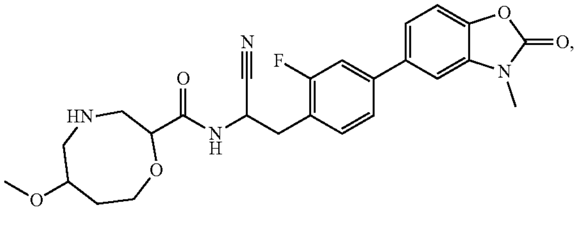
,
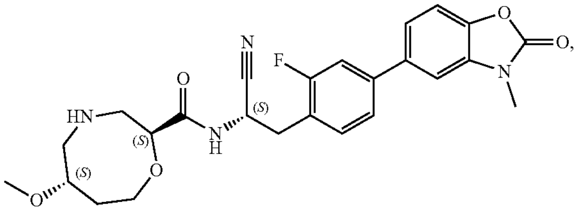
, -continued

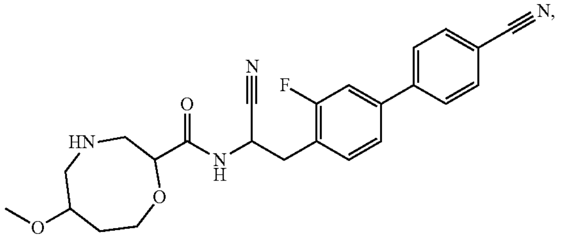

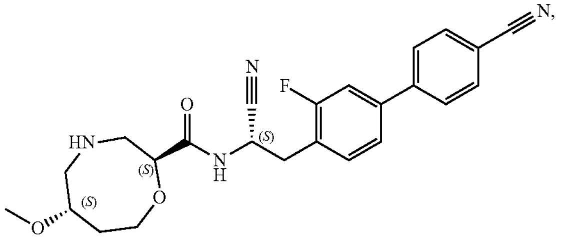

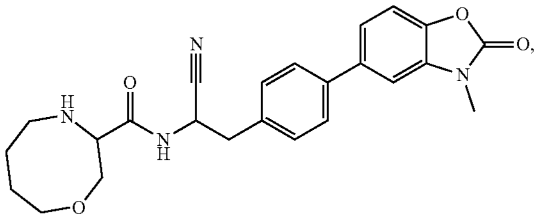

or

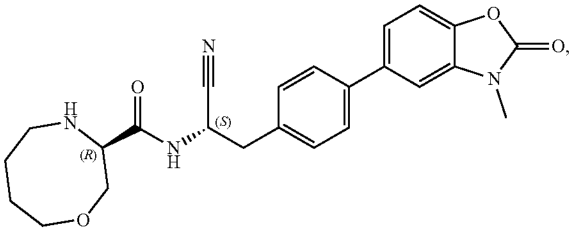

or a pharmaceutically acceptable salt thereof.

25. The compound of claim 24, having the structure:

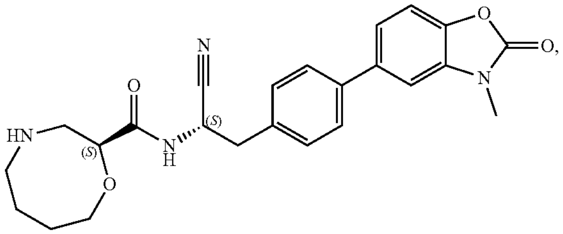

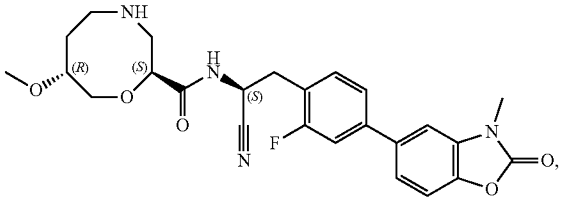

or

-continued

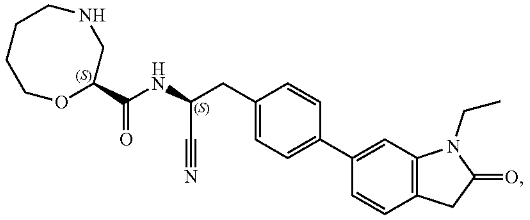

or a pharmaceutically acceptable salt thereof.

26. The compound of claim 10, or a pharmaceutically acceptable salt or deuterated form thereof, wherein n is 0.

27. The compound of claim 26, or a pharmaceutically acceptable salt or deuterated form thereof, wherein X is O.

28. The compound of claim 24, having the structure:

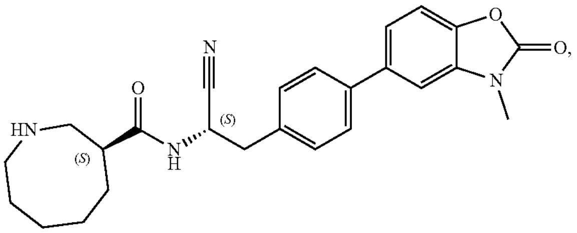

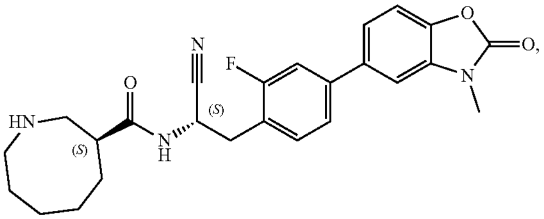

or

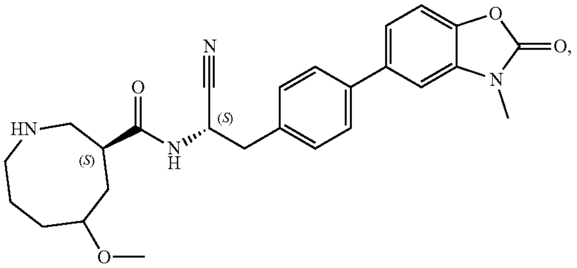

or a pharmaceutically acceptable salt thereof.

29. The compound of claim 24, having the structure:

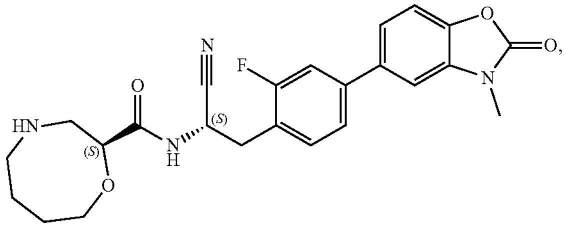

-continued

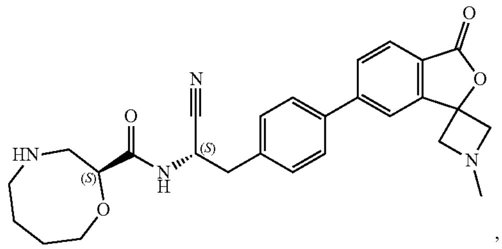

, or

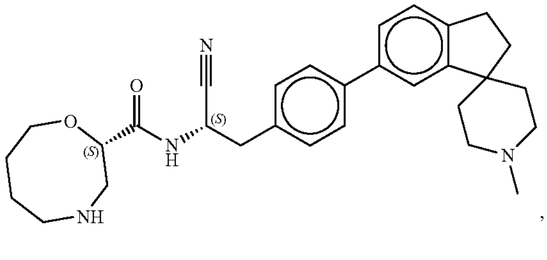

, or a pharmaceutically acceptable salt thereof.

30. The compound of claim 24, having the structure:

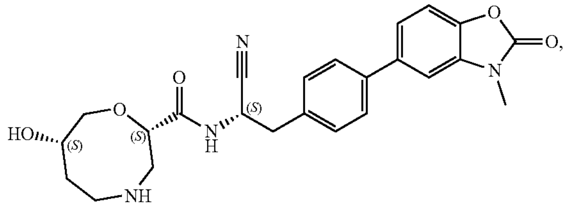

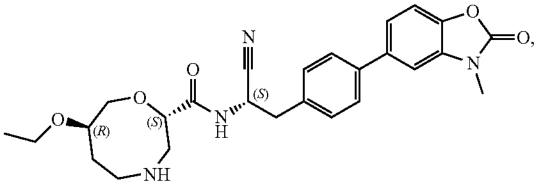

or

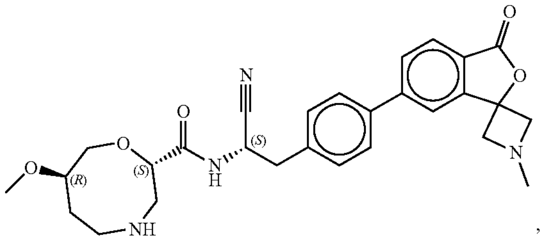

, or a pharmaceutically acceptable salt thereof.

31. The compound of claim 1, having the structure:

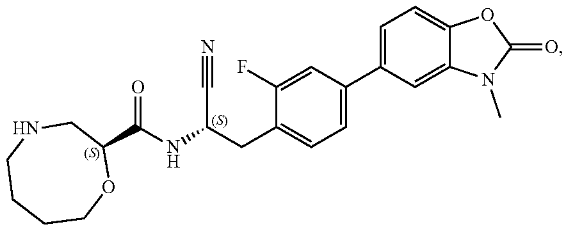

or a pharmaceutically acceptable salt thereof.

32. The compound of claim 1, having the structure:

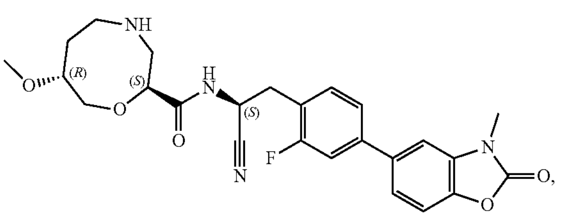

or a pharmaceutically acceptable salt thereof.

33. The compound of claim 1, having the structure:

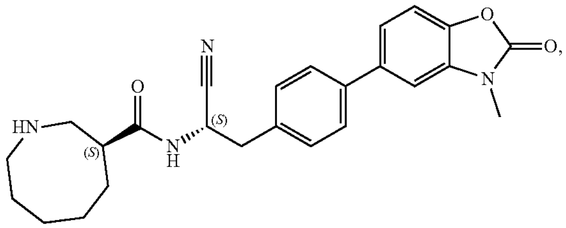

or a pharmaceutically acceptable salt thereof.

34. The compound of claim 1, having the structure:

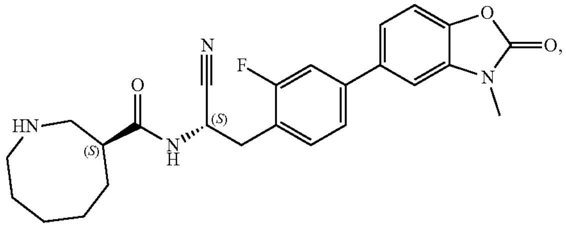

or a pharmaceutically acceptable salt thereof.

35. The compound of claim 1, having the structure:

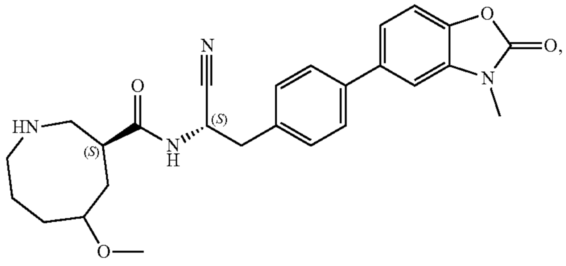

or a pharmaceutically acceptable salt thereof.

36. The compound of claim 1, having the structure:

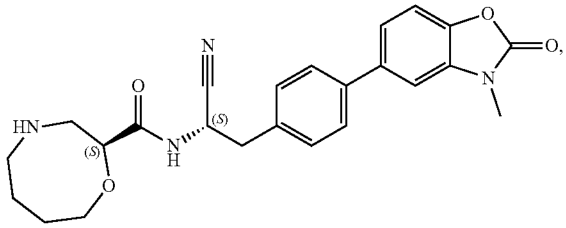

or a pharmaceutically acceptable salt thereof.

37. The compound of claim 1, having the structure:

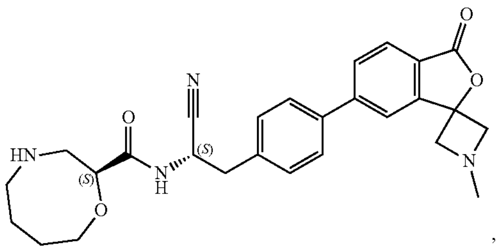

, or a pharmaceutically acceptable salt thereof.

38. The compound of claim 1, having the structure:

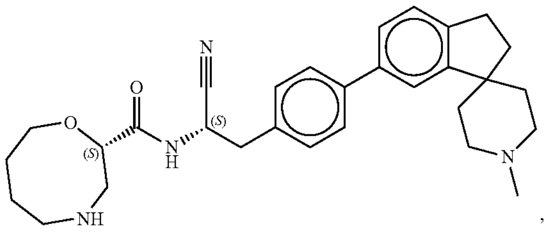

, or a pharmaceutically acceptable salt thereof.

39. The compound of claim 1, having the structure:

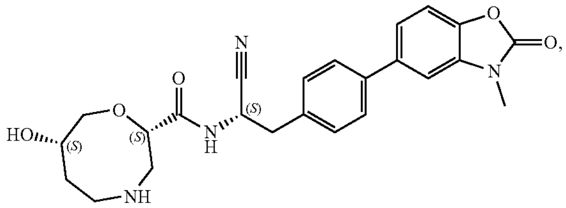

or a pharmaceutically acceptable salt thereof.

40. The compound of claim 1, having the structure:

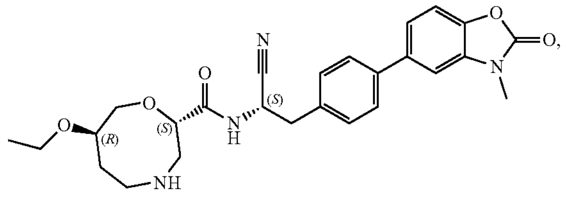

or a pharmaceutically acceptable salt thereof.

41. The compound of claim 1, having the structure:

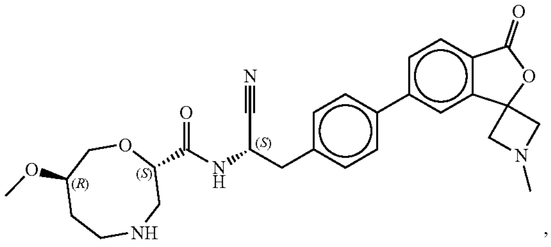

, or a pharmaceutically acceptable salt thereof.

* * * * *